(12) United States Patent
Gross et al.

(10) Patent No.: US 11,369,469 B2
(45) Date of Patent: Jun. 28, 2022

(54) METHOD FOR USE AT A HEART VALVE

(71) Applicant: CARDIOVALVE LTD., Or Yehuda (IL)

(72) Inventors: Yossi Gross, Moshav Mazor (IL); Gil Hacohen, Ramat Gan (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 17/394,807

(22) Filed: Aug. 5, 2021

(65) Prior Publication Data
US 2021/0361422 A1 Nov. 25, 2021

Related U.S. Application Data

(63) Continuation of application No. 16/881,350, filed on May 22, 2020, which is a continuation of application (Continued)

(51) Int. Cl.
*A61F 2/24* (2006.01)
*A61F 2/848* (2013.01)

(52) U.S. Cl.
CPC .......... *A61F 2/2418* (2013.01); *A61F 2/2409* (2013.01); *A61F 2/2436* (2013.01); (Continued)

(58) Field of Classification Search
CPC .... A61F 2/2418; A61F 2/2409; A61F 2/2436; A61F 2/2439; A61F 2/2433; (Continued)

(56) References Cited

U.S. PATENT DOCUMENTS

| 3,874,388 A | 4/1975 | King et al. |
| 4,222,126 A | 9/1980 | Boretos et al. |

(Continued)

FOREIGN PATENT DOCUMENTS

| CA | 2822801 | 8/2006 |
| CN | 103974674 | 8/2014 |

(Continued)

OTHER PUBLICATIONS

An invitation to pay additional fees dated May 19, 2021, which issued during the prosecution of Applicant's PCT/IL2021/050132.
(Continued)

*Primary Examiner* — Alvin J Stewart
(74) *Attorney, Agent, or Firm* — Sughrue Mion, PLLC

(57) ABSTRACT

A method includes advancing apparatus including a core toward a patient's heart valve. The core tapers in a distal direction toward the smallest perimeter of the core. The apparatus includes a first ventricular arm, which is articulatable with respect to a first atrial arm at a first articulation site, and a second ventricular arm, which is articulatable with respect to a second atrial arm at a second articulation site. The articulation sites are adjacent to the smallest perimeter. The tapering of the core defines a minimum nonzero angle of the atrial arms with respect to a central longitudinal axis of the core. The method also includes clamping the first and second leaflets between the respective atrial arms and the respective ventricular arms. Other embodiments are also described.

18 Claims, 113 Drawing Sheets

Related U.S. Application Data

No. 16/460,313, filed on Jul. 2, 2019, now Pat. No. 10,695,173, which is a continuation of application No. 16/045,059, filed on Jul. 25, 2018, now Pat. No. 10,376,361, which is a continuation of application No. 15/213,791, filed on Jul. 19, 2016, now Pat. No. 10,245,143, which is a continuation of application No. 14/237,264, filed as application No. PCT/IL2012/000292 on Aug. 5, 2012, now abandoned, which is a continuation-in-part of application No. 13/412,814, filed on Mar. 6, 2012, now Pat. No. 8,852,272.

(60) Provisional application No. 61/588,892, filed on Jan. 20, 2012, provisional application No. 61/555,160, filed on Nov. 3, 2011, provisional application No. 61/537,276, filed on Sep. 21, 2011, provisional application No. 61/525,281, filed on Aug. 19, 2011, provisional application No. 61/515,372, filed on Aug. 5, 2011.

(52) U.S. Cl.
CPC .......... *A61F 2/2439* (2013.01); *A61F 2/2433* (2013.01); *A61F 2/2442* (2013.01); *A61F 2/848* (2013.01); *A61F 2220/0016* (2013.01); *A61F 2220/0025* (2013.01); *A61F 2220/0091* (2013.01); *A61F 2230/005* (2013.01); *A61F 2230/0013* (2013.01); *A61F 2230/0054* (2013.01); *A61F 2230/0078* (2013.01); *A61F 2250/006* (2013.01); *A61F 2250/0015* (2013.01); *A61F 2250/0069* (2013.01); *A61F 2250/0071* (2013.01)

(58) Field of Classification Search
CPC ............ A61F 2/2442; A61F 2220/0016; A61F 2220/0025; A61F 2230/0054; A61F 2250/006; A61F 2250/0069
See application file for complete search history.

(56) References Cited

U.S. PATENT DOCUMENTS

| | | |
|---|---|---|
| 4,261,342 A | 4/1981 | Aranguren |
| 4,340,091 A | 7/1982 | Skelton et al. |
| 4,423,525 A | 1/1984 | Vallana et al. |
| 4,853,986 A | 8/1989 | Allen |
| 4,892,541 A | 1/1990 | Alonso |
| 4,972,494 A | 11/1990 | White et al. |
| 5,108,420 A | 4/1992 | Marks |
| 5,314,473 A | 5/1994 | Godin |
| 5,405,378 A | 4/1995 | Strecker |
| 5,443,500 A | 8/1995 | Sigwart |
| 5,607,444 A | 3/1997 | Lam |
| 5,607,470 A | 3/1997 | Milo |
| 5,647,857 A | 7/1997 | Anderson et al. |
| 5,702,397 A | 12/1997 | Goble et al. |
| 5,713,948 A | 2/1998 | Uflacker |
| 5,716,417 A | 2/1998 | Girard et al. |
| 5,741,297 A | 4/1998 | Simon |
| 5,765,682 A | 6/1998 | Bley et al. |
| 5,776,140 A | 7/1998 | Cottone |
| 5,868,777 A | 2/1999 | Lam |
| 5,873,906 A | 2/1999 | Lau et al. |
| 5,954,766 A | 9/1999 | Zadno-Azizi et al. |
| 5,957,949 A | 9/1999 | Leonhardt et al. |
| 5,980,565 A | 11/1999 | Jayaraman |
| 6,010,530 A | 1/2000 | Goicoechea |
| 6,019,787 A | 2/2000 | Richard et al. |
| 6,042,607 A | 3/2000 | Williamson, IV |
| 6,074,417 A | 6/2000 | Peredo |
| 6,113,612 A | 9/2000 | Swanson et al. |
| 6,120,534 A | 9/2000 | Ruiz |
| 6,126,686 A | 10/2000 | Badylak et al. |
| 6,152,937 A | 11/2000 | Peterson et al. |
| 6,165,183 A | 12/2000 | Kuehn et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vasquez et al. |
| 6,312,465 B1 | 11/2001 | Griffin et al. |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,454,799 B1 | 9/2002 | Schreck |
| 6,458,153 B1 | 10/2002 | Bailey et al. |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,569,196 B1 | 5/2003 | Vesely |
| 6,582,464 B2 | 6/2003 | Gabbay |
| 6,602,263 B1 | 8/2003 | Swanson et al. |
| 6,616,675 B1 | 9/2003 | Evard et al. |
| 6,629,534 B1 | 10/2003 | St. Goar et al. |
| 6,652,556 B1 | 11/2003 | VanTessel et al. |
| 6,669,724 B2 | 12/2003 | Park et al. |
| 6,682,558 B2 | 1/2004 | Tu et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,752,813 B2 | 6/2004 | Goldfarb et al. |
| 6,764,514 B1 | 7/2004 | Li et al. |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Artof et al. |
| 6,830,638 B2 | 12/2004 | Boylan et al. |
| 6,893,460 B2 | 5/2005 | Spenser et al. |
| 6,926,715 B1 | 8/2005 | Hauck et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,974,476 B2 | 12/2005 | McGuckin et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,336 B2 | 9/2006 | Miller |
| 7,101,395 B2 | 9/2006 | Tremulis et al. |
| 7,101,396 B2 | 9/2006 | Artof et al. |
| 7,112,207 B2 | 9/2006 | Allen et al. |
| 7,137,184 B2 | 11/2006 | Schreck |
| 7,172,625 B2 | 2/2007 | Shu et al. |
| 7,198,646 B2 | 4/2007 | Figulla et al. |
| 7,201,772 B2 | 4/2007 | Schwammenthal |
| 7,226,467 B2 | 6/2007 | Lucatero et al. |
| 7,226,477 B2 | 6/2007 | Cox |
| 7,261,686 B2 | 8/2007 | Couvillon, Jr. |
| 7,288,097 B2 | 10/2007 | Séguin |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,571 B2 | 5/2008 | Pease et al. |
| 7,374,573 B2 | 5/2008 | Gabbay |

(56) References Cited

U.S. PATENT DOCUMENTS

| | | |
|---|---|---|
| 7,377,938 B2 | 5/2008 | Sarac et al. |
| 7,381,218 B2 | 6/2008 | Schreck |
| 7,381,219 B2 | 6/2008 | Salahieh et al. |
| 7,404,824 B1 | 7/2008 | Webler et al. |
| 7,422,603 B2 | 9/2008 | Lane |
| 7,429,269 B2 | 9/2008 | Schwammenthal |
| 7,442,204 B2 | 10/2008 | Schwammenthal |
| 7,445,630 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,556,632 B2 | 7/2009 | Zadno |
| 7,556,646 B2 | 7/2009 | Yang et al. |
| 7,563,267 B2 | 7/2009 | Goldfarb et al. |
| 7,563,273 B2 | 7/2009 | Goldfarb et al. |
| 7,582,111 B2 | 9/2009 | Krolik et al. |
| 7,585,321 B2 | 9/2009 | Cribier |
| 7,597,711 B2 | 10/2009 | Drews et al. |
| 7,608,091 B2 | 10/2009 | Goldfarb et al. |
| 7,611,534 B2 | 11/2009 | Kapadia et al. |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,635,329 B2 | 12/2009 | Goldfarb et al. |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,002,826 B2 | 8/2011 | Seguin |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,592 B2 | 11/2011 | Goldfarb et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,075,611 B2 | 12/2011 | Milwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Randert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,256 B2 | 7/2012 | Raschdorf, Jr. et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |

(56) References Cited

U.S. PATENT DOCUMENTS

| | | |
|---|---|---|
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,529,431 B2 | 9/2013 | Baker et al. |
| 8,539,662 B2 | 9/2013 | Stacchino et al. |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,119,719 B2 | 9/2015 | Zipory et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,659 B2 | 11/2015 | Bodewadt et al. |
| 9,173,738 B2 | 11/2015 | Murray et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,277,994 B2 | 3/2016 | Miller et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keranen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |

(56) References Cited

U.S. PATENT DOCUMENTS

| | | |
|---|---|---|
| 9,566,152 B2 | 2/2017 | Schweich et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,987,132 B1 | 6/2018 | Hariton et al. |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,245,143 B2 | 4/2019 | Gross et al. |
| 10,258,471 B2 | 4/2019 | Lutter et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,376,361 B2 | 8/2019 | Gross et al. |
| 10,456,256 B2 | 10/2019 | Braido et al. |
| 10,512,456 B2 | 12/2019 | Hacohen et al. |
| 10,517,719 B2 | 12/2019 | Miller et al. |
| 10,531,866 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,695,173 B2 | 6/2020 | Gross et al. |
| 10,702,385 B2 | 7/2020 | Hacohen |
| 10,835,377 B2 | 11/2020 | Hacohen et al. |
| 10,888,644 B2 | 1/2021 | Ratz et al. |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0056295 A1 | 12/2001 | Solem |
| 2002/0013571 A1 | 1/2002 | Goldfarb et al. |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0009236 A1 | 1/2003 | Godin |
| 2003/0036791 A1 | 2/2003 | Bonhoeffer et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0120340 A1 | 6/2003 | Liska et al. |
| 2003/0158578 A1 | 8/2003 | Pantages et al. |
| 2004/0010272 A1 | 1/2004 | Manetakis et al. |
| 2004/0030382 A1 | 2/2004 | St. Goar et al. |
| 2004/0039414 A1 | 2/2004 | Carley et al. |
| 2004/0039442 A1 | 2/2004 | St. Goar et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright et al. |
| 2005/0085900 A1 | 4/2005 | Case et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0203618 A1 | 9/2005 | Sharkawy et al. |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256566 A1 | 11/2005 | Gabbay |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0116750 A1 | 6/2006 | Herbert et al. |
| 2006/0135964 A1 | 6/2006 | Vesley |
| 2006/0155357 A1 | 7/2006 | Melsheimer |
| 2006/0047297 A1 | 8/2006 | Case |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0229708 A1 | 10/2006 | Powell et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0282150 A1 | 12/2006 | Olson et al. |
| 2006/0287719 A1 | 12/2006 | Rowe et al. |
| 2007/0016286 A1 | 1/2007 | Herrmann et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038293 A1 | 2/2007 | St. Goar et al. |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtian |

(56) References Cited

U.S. PATENT DOCUMENTS

| | | |
|---|---|---|
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0239273 A1 | 10/2007 | Allen |
| 2007/0244546 A1 | 10/2007 | Francis |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe et al. |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0200980 A1 | 8/2008 | Robin et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1 | 5/2009 | Chuter |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quardi |
| 2009/0319037 A1 | 12/2009 | Rowe et al. |
| 2010/0022823 A1 | 1/2010 | Goldfarb et al. |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben-Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004227 A1 | 1/2011 | Goldfarb et al. |
| 2011/0004296 A1 | 1/2011 | Lutter et al. |
| 2011/0004299 A1 | 1/2011 | Navia et al. |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0029067 A1 | 2/2011 | Mcguckin, Jr. et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066233 A1 | 3/2011 | Thornton et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |

(56) References Cited

U.S. PATENT DOCUMENTS

| | | |
|---|---|---|
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0165930 A1 | 6/2012 | Gifford, III et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041451 A1 | 2/2013 | Patterson et al. |
| 2013/0046373 A1 | 2/2013 | Cartledge et al. |
| 2013/0066342 A1 | 3/2013 | Dell et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0289740 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0000112 A1 | 1/2014 | Braido et al. |
| 2014/0005778 A1 | 1/2014 | Buchbinder et al. |
| 2014/0018911 A1 | 1/2014 | Zhou et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0142688 A1 | 5/2014 | Duffy et al. |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |

(56) References Cited

U.S. PATENT DOCUMENTS

| | | |
|---|---|---|
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277358 A1 | 9/2014 | Slazas |
| 2014/0277409 A1 | 9/2014 | Bortlein et al. |
| 2014/0277411 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0350662 A1 | 11/2014 | Vaturi |
| 2014/0350670 A1 | 11/2014 | Keränen |
| 2014/0358222 A1 | 12/2014 | Gorman, III et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0272734 A1 | 10/2015 | Sheps et al. |
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0157862 A1 | 6/2016 | Hernandez et al. |
| 2016/0175095 A1 | 6/2016 | Dienno et al. |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0333183 A1 | 11/2017 | Backus |
| 2017/0333187 A1 | 11/2017 | Hariton et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014932 A1 | 1/2018 | Hammer et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0098850 A1 | 4/2018 | Rafiee et al. |
| 2018/0125644 A1 | 5/2018 | Conklin |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0177594 A1 | 6/2018 | Patel et al. |
| 2018/0206983 A1 | 7/2018 | Noe et al. |
| 2018/0214263 A1 | 8/2018 | Rolando et al. |
| 2018/0250126 A1 | 9/2018 | O'connor et al. |
| 2018/0250147 A1 | 9/2018 | Syed |
| 2018/0296336 A1 | 10/2018 | Cooper et al. |
| 2018/0296341 A1 | 10/2018 | Noe et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0021857 A1 | 1/2019 | Hacohen et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0183639 A1 | 6/2019 | Moore |

(56) References Cited

U.S. PATENT DOCUMENTS

| | | |
|---|---|---|
| 2019/0183644 A1 | 6/2019 | Hacohen |
| 2019/0192295 A1 | 6/2019 | Spence et al. |
| 2019/0216602 A1 | 7/2019 | Lozonschi |
| 2019/0321172 A1 | 10/2019 | Gross et al. |
| 2019/0336280 A1 | 11/2019 | Naor |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0060818 A1 | 2/2020 | Geist et al. |
| 2020/0078002 A1 | 3/2020 | Hacohen et al. |
| 2020/0163761 A1 | 5/2020 | Hariton et al. |
| 2020/0246140 A1 | 8/2020 | Hariton et al. |
| 2020/0261094 A1 | 8/2020 | Goldfarb et al. |
| 2020/0330221 A1 | 10/2020 | Hacohen |
| 2020/0330227 A1 | 10/2020 | Hacohen |
| 2021/0093449 A1 | 4/2021 | Hariton et al. |
| 2021/0113331 A1 | 4/2021 | Quadri et al. |

FOREIGN PATENT DOCUMENTS

| | | |
|---|---|---|
| EP | 0170262 | 2/1986 |
| EP | 1264582 | 12/2002 |
| EP | 1768630 | 1/2015 |
| EP | 2739214 | 10/2018 |
| EP | 3417813 | 12/2018 |
| JP | S3152790 | 12/1978 |
| KR | 20010046894 | 6/2001 |
| WO | 1998/043557 | 10/1998 |
| WO | 1999/030647 | 6/1999 |
| WO | 2000-047139 | 8/2000 |
| WO | 2001-062189 | 8/2001 |
| WO | 01/82832 | 11/2001 |
| WO | 2003/020179 | 3/2003 |
| WO | 2003/028558 | 4/2003 |
| WO | 2004/108191 | 12/2004 |
| WO | 2005/107650 | 11/2005 |
| WO | 2006/007401 | 1/2006 |
| WO | 06/054930 | 5/2006 |
| WO | 2006/070372 | 7/2006 |
| WO | 2006/086434 | 8/2006 |
| WO | 2006/089236 | 8/2006 |
| WO | 2006/116558 | 11/2006 |
| WO | 2006/128193 A2 | 11/2006 |
| WO | 2007/059252 | 5/2007 |
| WO | 08/013915 | 1/2008 |
| WO | 2008/029296 | 3/2008 |
| WO | 2008/070797 | 6/2008 |
| WO | 2008/103722 | 8/2008 |
| WO | 09/033469 | 3/2009 |
| WO | 09/053497 | 4/2009 |
| WO | 2009/091509 | 7/2009 |
| WO | 2010/005827 | 1/2010 |
| WO | 2010/006627 | 1/2010 |
| WO | 2010/037141 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/121076 | 10/2010 |
| WO | 2011/025972 | 3/2011 |
| WO | 2011/069048 | 6/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/154942 | 12/2011 |
| WO | 2012/011108 | 1/2012 |
| WO | 2012/024428 | 2/2012 |
| WO | 2012/036740 | 3/2012 |
| WO | 2012/048035 | 4/2012 |
| WO | 2012/127309 | 9/2012 |
| WO | 2012/177942 | 12/2012 |
| WO | 2013/021374 | 2/2013 |
| WO | 2013/021375 | 2/2013 |
| WO | 2013/021384 | 2/2013 |
| WO | 2013/059747 | 4/2013 |
| WO | 2013/072496 | 5/2013 |
| WO | 2013/078497 | 6/2013 |
| WO | 2013114214 | 8/2013 |
| WO | 2013/128436 | 9/2013 |
| WO | 2013/175468 | 11/2013 |
| WO | 2014/022124 | 2/2014 |
| WO | 2014/076696 | 5/2014 |
| WO | 2014/115149 | 7/2014 |
| WO | 2014/145338 | 9/2014 |
| WO | 2014/164364 | 10/2014 |
| WO | 2014/194178 | 12/2014 |
| WO | 2015/173794 | 11/2015 |
| WO | 2015/191923 | 12/2015 |
| WO | 2016/016899 | 2/2016 |
| WO | 2016/093877 | 6/2016 |
| WO | 2016/125160 | 8/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |
| WO | 2019/030753 | 2/2019 |
| WO | 2019027507 | 2/2019 |
| WO | 2019/077595 | 4/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |

OTHER PUBLICATIONS

An Office Action dated Aug. 18, 2021, which issued during the prosecution of U.S. Appl. No. 17/210,183.
Office Action dated Nov. 4, 2021 in U.S. Appl. No. 17/366,711.
Extended European Search Report dated Oct. 11, 2021 in European Application No. 21176010.3.
Fann et al., "Beating Heart Catheter-Based Edge-to-Edge Mitral Valve Procedure in a Porcine Model", Circulation, 2004, vol. 110, pp. 988-993, Cardiovalve Exhibit 2006 (6 pages total).
Feldman et al., "Percutaneous Mitral Leaflet Repair: MitralClip Therapy for Mitral Regurgitation", Informa Healthcare, 2012, CRC Press, pp. 31-44, Cardiovalve Exhibit 2009 (8 pages total).
Feldman et al., "Percutaneous Mitral Valve Repair Using the Edge-to-Edge Technique", Journal of the American College of Cardiology, 2005, vol. 46, No. 11, pp. 2134-2140 (7 pages total).
IPR2021-00383 "Patent Owner's Contingent Motion to Amend", dated Oct. 13, 2021 (35 pages total).
IPR2021-00383 "Patent Owner's Response", dated Oct. 13, 2021 (75 pages total).
Maisano et al., "The Evolution From Surgery to Percutaneous Mitral Valve Interventions", Journal of the American College of Cardiology, 2011, vol. 58, No. 21, pp. 2174-2182 (9 pages total).
Notice of Allowance dated Sep. 15, 2021 in U.S. Appl. No. 16/135,599.
Office Action dated Oct. 14, 2021 in U.S. Appl. No. 16/680,739.
Office Action dated Oct. 21, 2021 in U.S. Appl. No. 17/306,231.
Office Action dated Oct. 21, 2021 in U.S. Appl. No. 17/335,845.
Office Action dated Sep. 9, 2021 in U.S. Appl. No. 16/768,909.
Second Declaration of Dr. Michael Sacks, Oct. 13, 2021, IPR2021-00383, U.S. Pat. No. 10,226,341, United States Patent and Trademark Office, Before the Patent Trial and Appeal Board, Cardiovalve Exhibit 2014 (28 pages total).

(56) References Cited

OTHER PUBLICATIONS

Transcript of Dr. Vesely, Sep. 22, 2021, Case No. IPR2021-00383, U.S. Pat No. 10,226,341 United States Patent and Trademark Office Before the Patent Trial and Appeal Board, Cardiovalve Exhibit 2010 (170 pages total).

An Office Action dated Nov. 23, 2012, which issued during the prosecution of U.S. Appl. No. 13/033,852.

An Office Action dated Dec. 31, 2012, which issued during the prosecution of U.S. Appl. No. 13/044,694.

An Office Action dated Feb. 6, 2013, which issued during the prosecution of U.S. Appl. No. 13/412,814.

Langer F et al., "RING plus STRING: Papillary muscle repositioning as an adjunctive repair technique for ischemic mitral regurgitation," J Thorac Cardiovasc Surg 133:247-9, Jan. 2007.

Langer F et al., "RING+STRING: Successful repair technique for ischemic mitral regurgitation with severe leaflet tethering," Circulation 120[suppl 1]: S85-S91, Sep. 2009.

"Transcatheter Valve-in-Valve Implantation for Failed Bioprosthetic Heart Valves", J Webb et al., Circulation. Apr. 2010; 121: 1848-1857.

Jansen, J., Willeke, S., Reul, H. and Rum, G. (1992), Detachable Shape-Memory Sewing Ring for Heart Valves. Artificial Organs, 16:294-297. 1992 (an abstract).

Alexander S. Geha, et al., Replacement of degenerated mitral and aortic bioprostheses without explanation Ann Thorac Surg. Jun. 2001; 72:1509-1514.

An International Search Report and a Written Opinion both dated Oct. 13, 2011 which issued during the prosecution of Applicant's PCT/IL11/00231.

An Office Action dated Jul. 1, 2016, which issued during the prosecution of U.S. Appl. No. 14/161,921.

An International Search Report and a Written Opinion both dated Dec. 5, 2011, which issued during the prosecution of Applicant's PCT/IL11/00582.

An Office Action dated May 29, 2012, which issued during the prosecution of U.S. Appl. No. 12/840,463.

U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.

An International Search Report and a Written Opinion both dated Feb. 6, 2013, which issued during the prosecution of Applicant's PCT/IL12/00292.

An International Search Report and a Written Opinion both dated Feb. 6, 2013, which issued during the prosecution of Applicant's PCT/IL12/00293.

An Office Action dated Nov. 28, 2012, which issued during the prosecution of U.S. Appl. No. 12/961,721.

An Office Action dated Feb. 15, 2013, which issued during the prosecution of U.S. Appl. No. 12/840,463.

An Office Action dated Feb. 10, 2014, which issued during the prosecution of U.S. Appl. No. 13/033,852.

An Office Action dated Sep. 19, 2014, which issued during the prosecution of U.S. Appl. No. 13/044,694.

An International Search Report and a Written Opinion both dated Sep. 4, 2014 which issued during the prosecution of Applicant's PCT/IL2014/050087.

Invitation to Pay Additional Fees dated Jun. 12, 2014 PCT/IL2014/050087.

An Office Action dated Jun. 17, 2014, which issued during the prosecution of U.S. Appl. No. 12/961,721.

An Office Action dated Jul. 3, 2014, which issued during the prosecution of U.S. Appl. No. 13/033,852.

An Office Action dated May 23, 2014, which issued during the prosecution of U.S. Appl. No. 13/412,814.

Dominique Himbert; Mitral Regurgitation and Stenosis from Bioprosthesis and Annuloplasty Failure: Transcatheter approaches and outcomes, 24 pages Oct. 28, 2013.

An International Search Report and a Written Opinion both dated Mar. 17, 2014 which issued during the prosecution of Applicant's PCT/IL2013/050937.

An International Preliminary Report on patentabilty dated Dec. 2, 2013, which issued during the prosecution of Applicant's PCT/IL11/00582.

An Office Action dated Sep. 12, 2013, which issued during the prosecution of U.S. Appl. No. 13/412,814.

An Office Action dated Aug. 2, 2013, which issued during the prosecution of U.S. Appl. No. 13/033,852.

An International Preliminary Report on patentabilty dated Sep. 11, 2012, which issued during the prosecution of Applicant's PCT/IL2011/000231.

An Office Action dated Jul. 2, 2014, which issued during the prosecution of U.S. Appl. No. 13/811,308.

An Office Action dated Jan. 20, 2016, which issued during the prosecution of U.S. Appl. No. 14/161,921.

An Office Action dated Jul. 23, 2013, which issued during the prosecution of U.S. Appl. No. 12/961,721.

An Office Action dated Jul. 18, 2013, which issued during the prosecution of U.S. Appl. No. 13/044,694.

An Office Action dated Nov. 8, 2013, which issued during the prosecution of U.S. Appl. No. 12/840,463.

An Office Action dated Jun. 4, 2014, which issued during the prosecution of U.S. Appl. No. 12/840,463.

An Office Action dated Aug. 13, 2012, which issued during the prosecution of U.S. Appl. No. 13/044,694.

An Office Action dated Jul. 2, 2012, which issued during the prosecution of U.S. Appl. No. 13/033,852.

An Office Action dated Feb. 3, 2014, which issued during the prosecution of U.S. Appl. No. 13/811,308.

An International Preliminary Report on patentabilty dated Feb. 11, 2014, which issued during the prosecution of Applicant's PCT/IL12/00292.

An International Preliminary Report on patentabilty dated Feb. 11, 2014, which issued during the prosecution of Applicant's PCT/IL12/00293.

A Notice of Allowance dated Aug. 15, 2014, which issued during the prosecution of U.S. Appl. No. 13/412,814.

An Office Action dated Aug. 14, 2012, which issued during the prosecution of U.S. Appl. No. 12/961,721.

U.S. Appl. No. 61/283,819, filed Dec. 8, 2009.

Notice of Allowance dated Apr. 8, 2016, which issued during the prosecution of U.S. Appl. No. 14/237,258.

U.S. Appl. No. 61/756,034, filed Jan. 24, 2013.
U.S. Appl. No. 61/756,049, filed Jan. 24, 2013.

An International Preliminary Report on Patentability dated Jan. 31, 2017, which issued during the prosecution of Applicant's PCT/IL2015/050792.

U.S. Appl. No. 61/312,412, filed Mar. 10, 2010.
U.S. Appl. No. 62/139,854, filed Mar. 30, 2015.

Notice of Allowance dated Apr. 20, 2018, which issued during the prosecution of U.S. Appl. No. 15/878,206.

An Office Action dated Dec. 10, 2015, which issued during the prosecution of U.S. Appl. No. 14/237,258.

An International Preliminary Report on Patentability dated Jul. 28, 2015, which issued during the prosecution of Applicant's PCT/IL2014/050087.

An Office Action dated Nov. 27, 2015, which issued during the prosecution of U.S. Appl. No. 14/626,267.

An Office Action dated Jan. 21, 2016, which issued during the prosecution of U.S. Appl. No. 14/237,264.

An Office Action dated Jan. 30, 2015, which issued during the prosecution of UK Patent Application No. 1413474.6.

An International Search Report and a Written Opinion both dated May 30, 2016, which issued during the prosecution of Applicant's PCT/IL2016/050125.

An Office Action dated Sep. 26, 2016, which issued during the prosecution of U.S. Appl. No. 14/763,004.

An Office Action dated Jan. 18, 2017, which issued during the prosecution of U.S. Appl. No. 14/626,267.

An Office Action dated Feb. 7, 2017, which issued during the prosecution of U.S. Appl. No. 14/689,608.

(56) References Cited

OTHER PUBLICATIONS

An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of Design U.S. Appl. No. 29/635,658.
An Office Action dated Jun. 28, 2018, which issued during the prosecution of Design U.S. Appl. No. 29/635,661.
U.S. Appl. No. 62/030,715, filed Jul. 30, 2014.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
An Office Action dated Sep. 29, 2017, which issued during the prosecution of U.S. Appl. No. 15/197,069.
Notice of Allowance dated Oct. 30, 2018, which issued during the prosecution of U.S. Appl. No. 15/197,069.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
An Office Action dated Apr. 21, 2017, which issued during the prosecution of U.S. Appl. No. 15/213,791.
Maisano (2015) TCR presentation re Cardiovalve.
Notice of Allowance dated Nov. 19, 2018, which issued during the prosecution of U.S. Appl. No. 15/197,069.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
Notice of Allowance dated Jul. 6, 2017, which issued during the prosecution of U.S. Appl. No. 14/689,608.
Notice of Allowance dated Aug. 18, 2017, which issued during the prosecution of U.S. Appl. No. 14/689,608.
Notice of Allowance dated May 22, 2017, which issued during the prosecution of U.S. Appl. No. 14/689,608.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Mar. 18, 2020, which issued during the prosecution of U.S. Appl. No. 16/284,331.
An Office Action dated Jan. 14, 2020, which issued during the prosecution of U.S. Appl. No. 16/284,331.
Notice of Allowance dated May 7, 2020, which issued during the prosecution of U.S. Appl. No. 16/637,166.
An International Search Report and a Written Opinion both dated Nov. 9, 2018, which issued during the prosecution of Applicant's PCT/IL2018/050869.
An Office Action dated Jan. 9, 2020, which issued during the prosecution of U.S. Appl. No. 15/600,190.
An International Search Report and a Written Opinion both dated May 13, 2019, which issued during the prosecution of Applicant's PCT/IL2018/051350.
An International Search Report and a Written Opinion both dated Apr. 25, 2019, which issued during the prosecution of Applicant's PCT/IL2019/050142.
An International Search Report and a Written Opinion both dated Jan. 25, 2019, which issued during the prosecution of Applicant's PCT/IL2018/051122.
An International Search Report and a Written Opinion both dated Dec. 5, 2018, which issued during the prosecution of Applicant's PCT/IL2018/050725.
An International Preliminary Report on Patentability dated Feb. 12, 2019, which issued during the prosecution of Applicant's PCT/IL2017/050873.
An International Preliminary Report on Patentability dated Feb. 5, 2019, which issued during the prosecution of Applicant's PCT/IL2017/050849.
An Office Action dated Nov. 26, 2019, which issued during the prosecution of U.S. Appl. No. 16/532,945.
An Office Action dated Nov. 1, 2019, which issued during the prosecution of U.S. Appl. No. 15/872,501.
An Office Action dated Mar. 25, 2019, which issued during the prosecution of European Patent Application No. 14710060.6.

(56) References Cited

OTHER PUBLICATIONS

An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Jun. 25, 2019, which issued during the prosecution of U.S. Appl. No. 15/329,920.
An Office Action dated Aug. 23, 2019, which issued during the prosecution of U.S. Appl. No. 15/600,190.
An Office Action dated May 16, 2019, which issued during the prosecution of U.S. Appl. No. 15/433,547.
An Office Action dated Aug. 1, 2019, which issued during the prosecution of U.S. Appl. No. 15/668,559.
An Office Action dated Aug. 16, 2019, which issued during the prosecution of U.S. Appl. No. 15/668,659.
An Office Action dated Jun. 19, 2019, which issued during the prosecution of U.S. Appl. No. 15/682,789.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An Office Action dated Sep. 13, 2019, which issued during the prosecution of U.S. Appl. No. 16/460,313.
Notice of Allowance dated Sep. 10, 2020, which issued during the prosecution of U.S. Appl. No. 15/600,190.
An International Search Report and a Written Opinion both dated Jun. 24, 2020, which issued during the prosecution of Applicant's PCT/IL2019/051398.
Sündermann, Simon H., et al. "Feasibility of the Engager™ aortic transcatheter valve system using a flexible over-the-wire design." European Journal of Cardio-Thoracic Surgery 42.4 (2012): e48-e52.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#v=onepage&q=%22Edwards%20SAPIEN%22&f=false ; Downloaded on Jun. 18, 2020.
Tchetche, D. and Nicolas M. Van Mieghem: "New-generation TAVI devices: description and specifications" EuroIntervention, 2014, No. 10:U90-U100.
Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol No. 2015-01, Vs. No. 2, 2015:1-76.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
An Office Action summarized English translation and Search Report dated Jul. 3, 2020, which issued during the prosecution of Chinese Patent Application No. 201780061210.3.
An Office Action dated Aug. 7, 2020, which issued during the prosecution of U.S. Appl. No. 15/668,659.
Notice of Allowance dated Jul. 29, 2020, which issued during the prosecution of U.S. Appl. No. 16/132,937.
Notice of Allowance dated Apr. 24, 2019, which issued during the prosecution of U.S. Appl. No. 16/045,959.
Notice of Allowance dated Mar. 12, 2020, which issued during the prosecution of U.S. Appl. No. 16/460,313.
An International Preliminary Report on Patentability dated Oct. 20, 2020, which issued during the prosecution of Applicant's PCT/IL2019/050142.
An Office Action dated Oct. 5, 2020, which issued during the prosecution of Canadian Patent Application No. 2,973,940.
Notice of Allowance dated Nov. 19, 2020, which issued during the prosecution of U.S. Appl. No. 16/318,025.
An Office Action dated Sep. 24, 2020, which issued during the prosecution of U.S. Appl. No. 16/811,732.
An Office Action summarized English translation and Search Report dated Nov. 25, 2020, which issued during the prosecution of Chinese Patent Application No. 201910449820.1.
An Office Action dated Nov. 30, 2020, which issued during the prosecution of U.S. Appl. No. 16/138,129.
Condado, José Antonio, et al. "Percutaneous edge-to-edge mitral valve repair: 2-year follow-up in the first human case." Catheterization and cardiovascular interventions 67.2 (2006): 323-325.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
Maisano, F., et al. "The edge-to-edge technique: a simplified method to correct mitral insufficiency." European journal of cardio-thoracic surgery 13.3 (1998): 240-246.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.
An Office Action together with an English summary dated Mar. 3, 2021, which issued during the prosecution of Chinese Patent Application No. 201780047391.4.
Fucci, C., et al. "Improved results with mitral valve repair using new surgical techniques." European journal of cardio-thoracic surgery 9.11 (1995): 621-627.
An Office Action dated Sep. 6, 2018, which issued during the prosecution of U.S. Appl. No. 15/213,791.
Declaration of Ivan Vesely, Ph.D., in Support of Petition for Inter Partesreview of U.S. Pat. No. 7,563,267—dated May 29, 2019.
U.S. Appl. No. 60/128,690, filed Apr. 9, 1999.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Kalbacher, D., et al. "1000 MitraClip™ procedures: Lessons learnt from the largest single-centre experience worldwide." (2019): 3137-3139.
U.S. Appl. No. 60/613,867, filed Sep. 27, 2004.
Mitral Valve Academic Research Consortium. "Clinical Trial Design Principles and Endpoint Definitions for Transcatheter Mitral Valve Repair and Replacement: Part 1: Clinical Trial Design Principles A Consensus Document from the Mitral Valve Academic Research Consortium." Journal of the American College of Cardiology 66.3 (2015): 278-307.
Notice of Allowance dated Oct. 3, 2019, which issued during the prosecution of U.S. Appl. No. 15/691,032.
Notice of Allowance dated Mar. 29, 2017, which issued during the prosecution of U.S. Appl. No. 14/161,921.
Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.

(56) References Cited

OTHER PUBLICATIONS

Notice of Allowance dated Nov. 21, 2018, which issued during the prosecution of U.S. Appl. No. 15/213,791.
Notice of Allowance dated Jul. 3, 2019, which issued during the prosecution of U.S. Appl. No. 15/691,032.
An Office Action dated Jan. 6, 2020, which issued during the prosecution of U.S. Appl. No. 16/660,231.
Notice of Allowance dated Jan. 13, 2020, which issued during the prosecution of U.S. Appl. No. 15/956,956.
European Search Report dated Mar. 5, 2020 which issued during the prosecution of Applicant's European App No. 17752184.6.
An Office Action dated Dec. 31, 2019, which issued during the prosecution of U.S. Appl. No. 16/183,140.
An Office Action dated Feb. 6, 2020, which issued during the prosecution of U.S. Appl. No. 15/668,659.
European Search Report dated Mar. 4, 2020 which issued during the prosecution of Applicant's European App No. 16706913.7.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An Office Action dated Mar. 29, 2021, which issued during the prosecution of U.S. Appl. No. 16/738,516.
An Office Action dated Jan. 3, 2020, which issued during the prosecution of U.S. Appl. No. 16/678,355.
Ando, Tomo, et al. "Iatrogenic ventricular septal defect following transcatheter aortic valve replacement: a systematic review." Heart, Lung and Circulation 25.10 (2016): 968-974.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated May 4, 2021, which issued during the prosecution of U.S. Appl. No. 16/636,204.
Notice of Allowance dated May 17, 2021, which issued during the prosecution of U.S. Appl. No. 16/138,129.
Petition for Inter Partes Review of U.S. Pat. No. 10,702,385—dated Jun. 4, 2021.
Declaration of Ivan Vesely, Ph.D. in Support of Petition for Inter Partes Review of U.S. Pat. No. 10,702,385—dated Jun. 4, 2021.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 12, 2021, which issued during the prosecution of Canadian Patent Application No. 2,973,940.
Notice of Allowance dated Jun. 4, 2021, which issued during the prosecution of U.S. Appl. No. 16/802,353.
IPR2021-00383 "Petitioners' Authorized Reply to Patent Owner's Preliminary Response", dated May 27, 2021, 9 pages.
Exhibit 1014, "Transcript of proceedings" held May 20, 2021, 15 pages.
Exhibit 1015, "Facilitate", Meriam-Webster.com, https://www.merriamwebster.com/dictionary/facilitate, retrieved May 26, 2021, 5 pages.
IPR2021-00383, "Patent Owner's Authorized Surreply to Petitioner's Reply to Patent Owner's Preliminary Response", dated Jun. 4, 2021, 8 pages.
IPR2021-00383, "Institution decision" dated Jul. 20, 2021, 51 pages.
An extended European search report dated Jun. 10, 2021 in application No. 21157988.3.
International Search Report and Written Opinion dated Jul. 12, 2021 from the International Searching Authority in International Application No. PCT/IL2021/050132.
Decision Granting Institution of Inter Partes Review dated Dec. 10, 2021 in IPR2021-01051 (42 pages total).
Petitioner's Opposition to Patent Owner's Contingent Motion to Amend dated Jan. 5, 2022 in IPR2021-00383.
Petitioner's Reply to Patent Owner's Response dated Jan. 5, 2022 in IPR2021-00383.
Notice of Allowance dated Dec. 29, 2021 in U.S. Appl. No. 17/210,183.
A Non-Final Office Action dated Apr. 11, 2022 in U.S. Appl. No. 17/473,472.

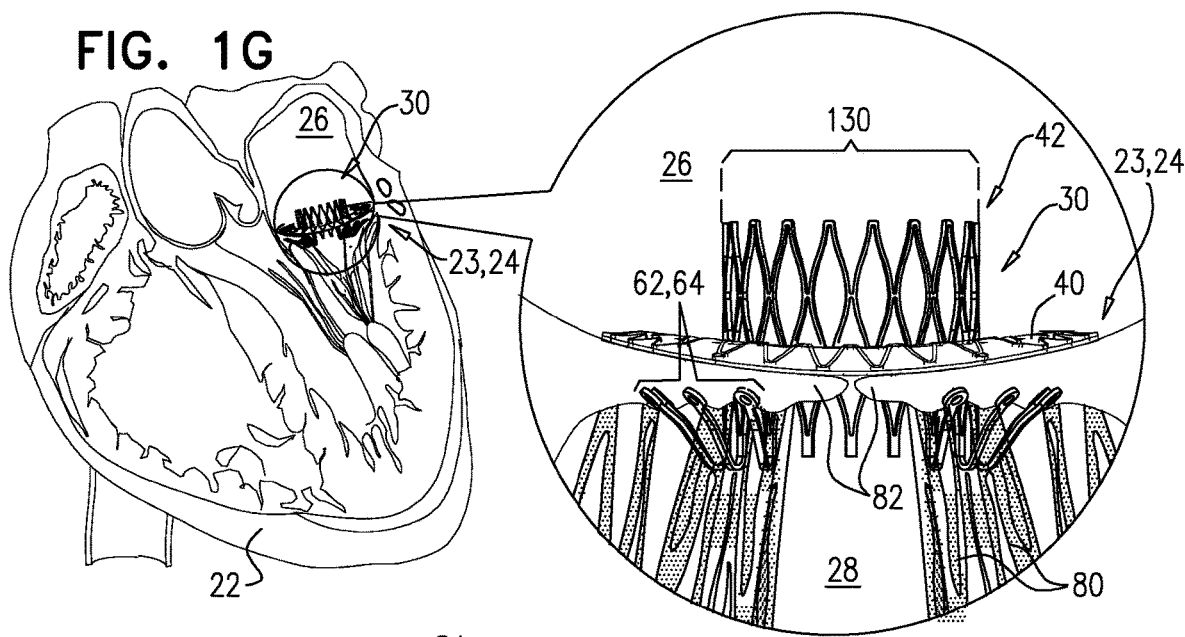
FIG. 1G
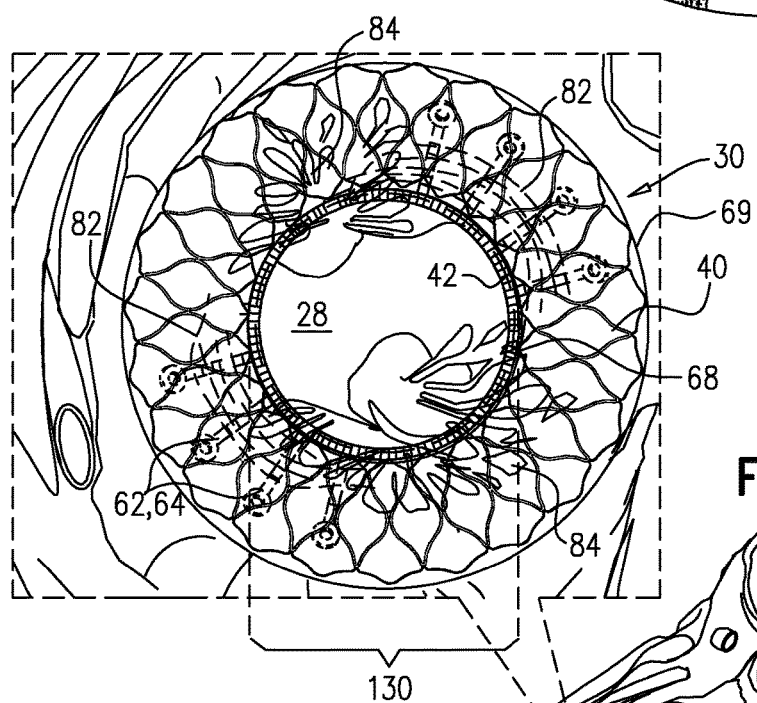
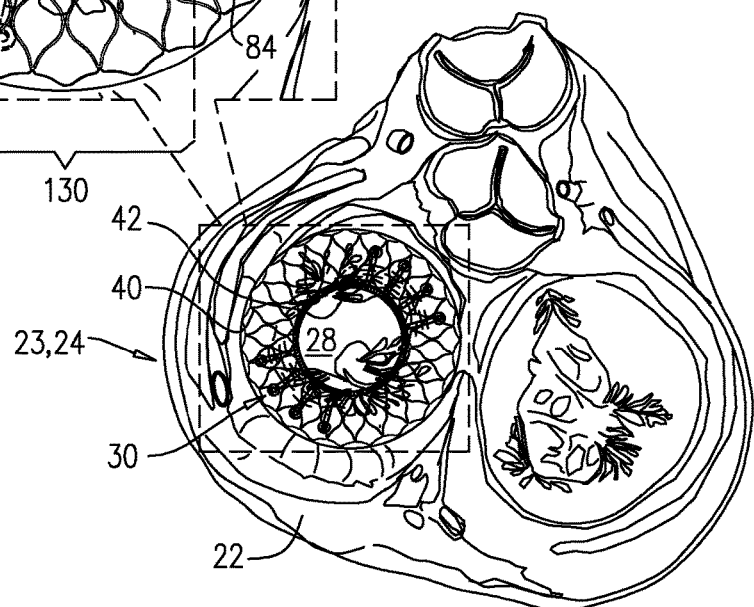
FIG. 1H

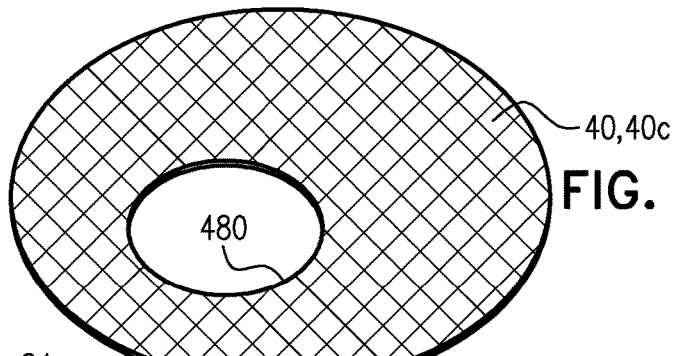
FIG. 13A
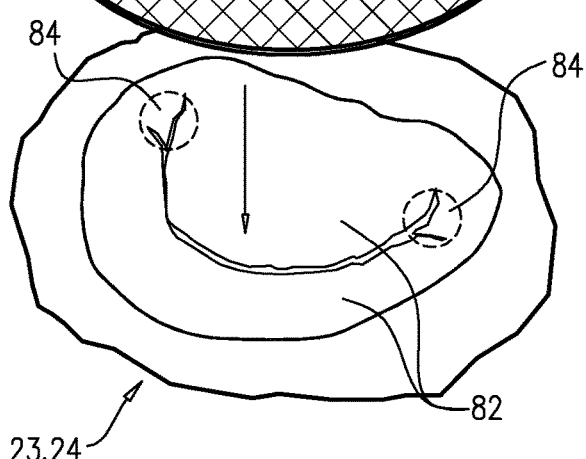
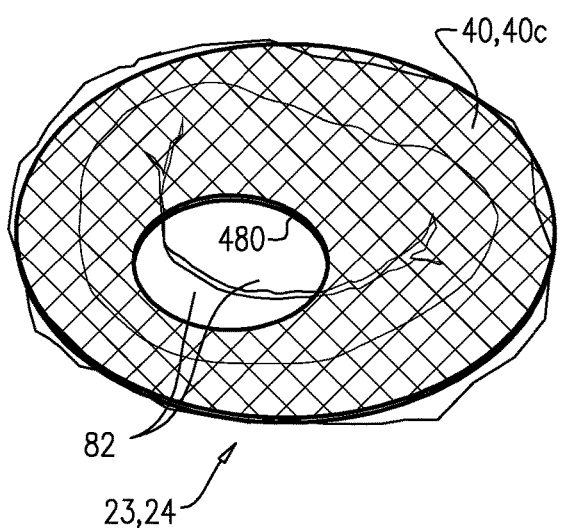
FIG. 13B
FIG. 13C
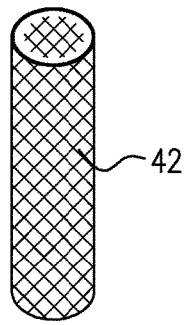
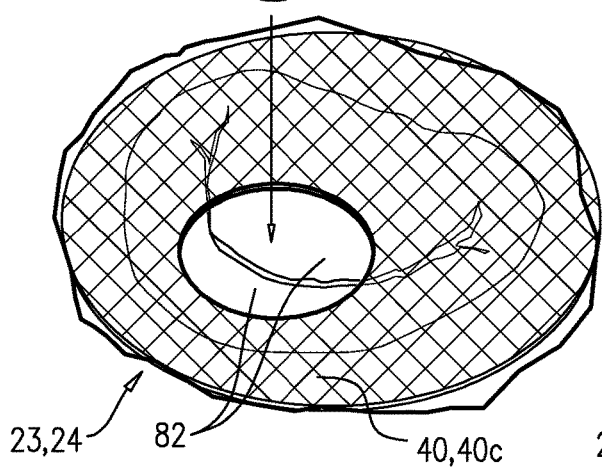
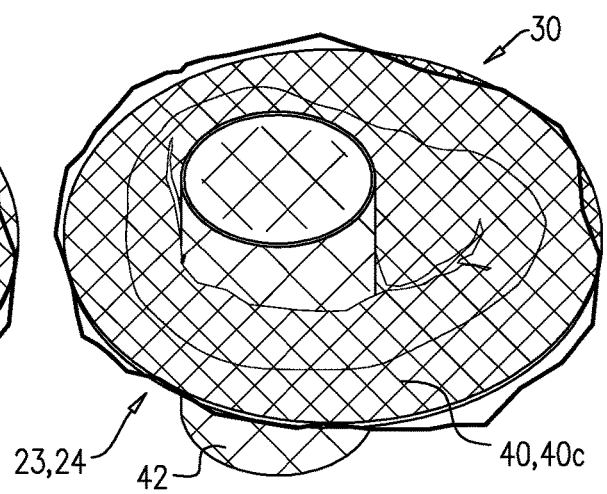
FIG. 13D

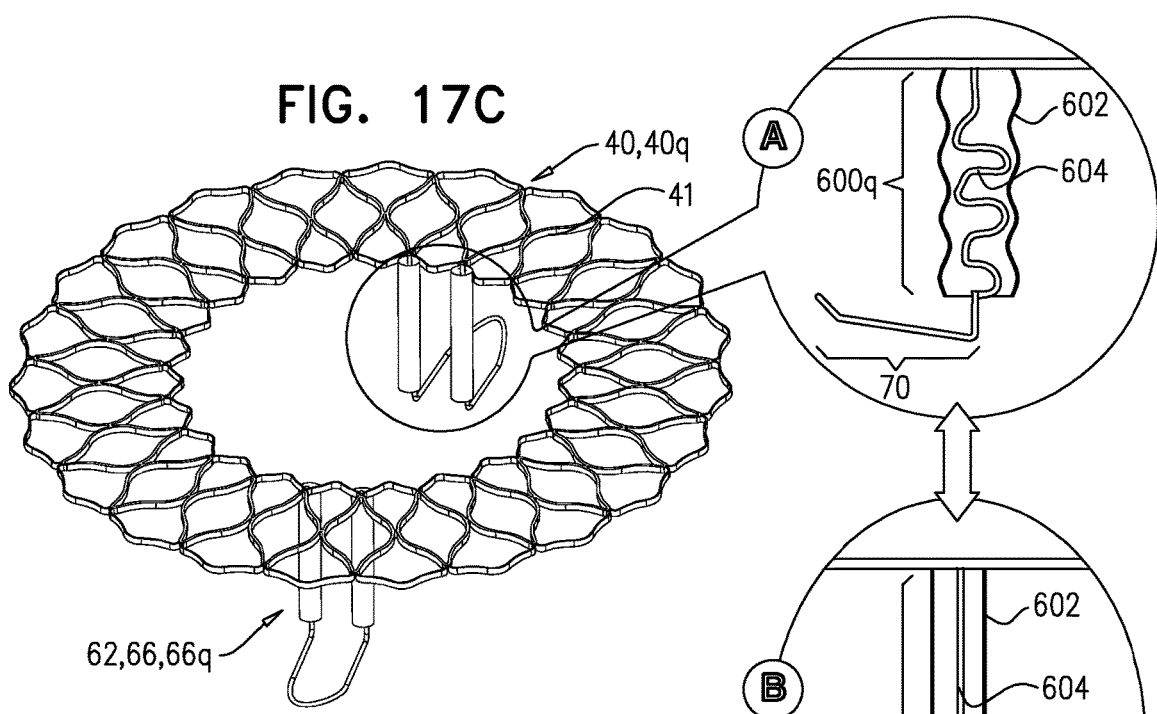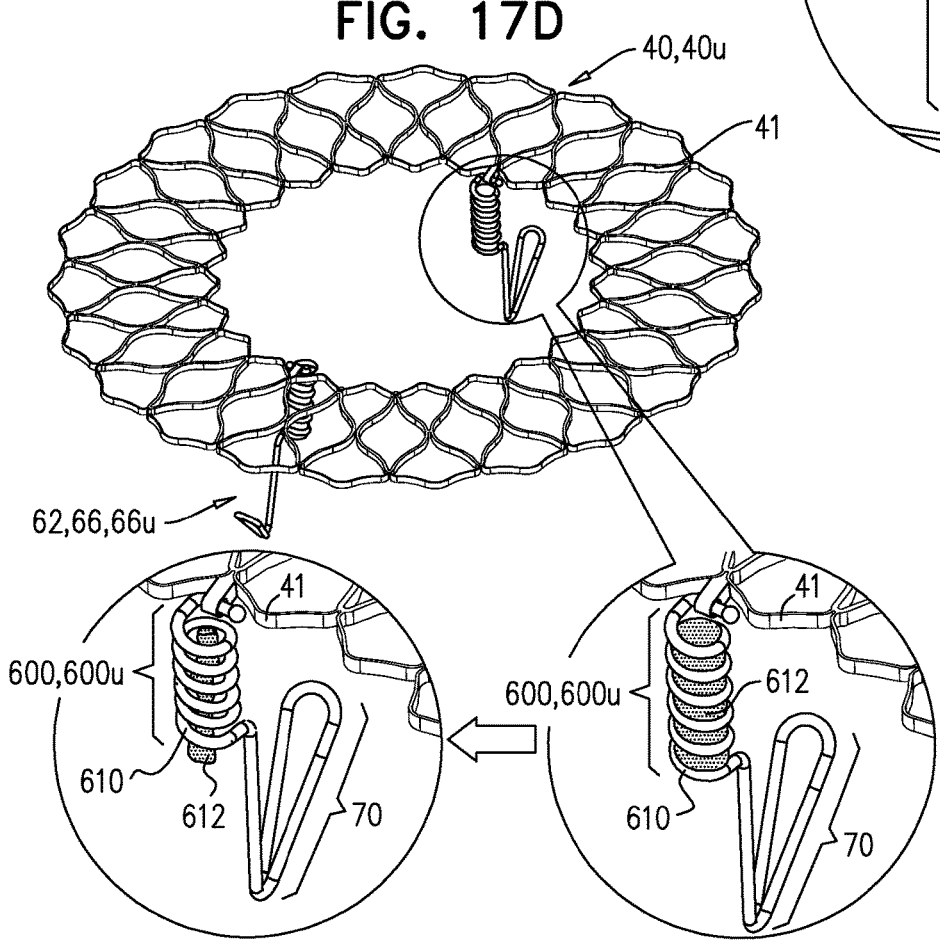

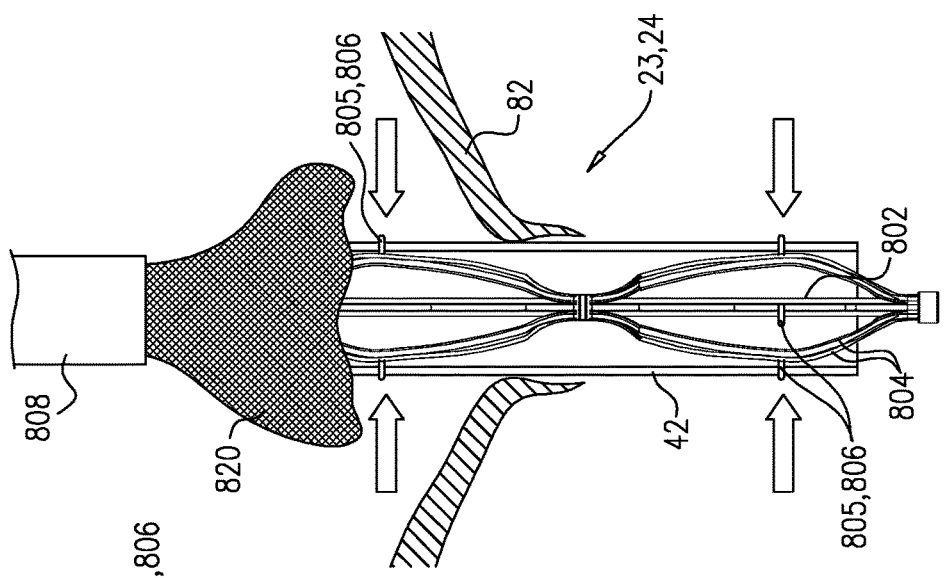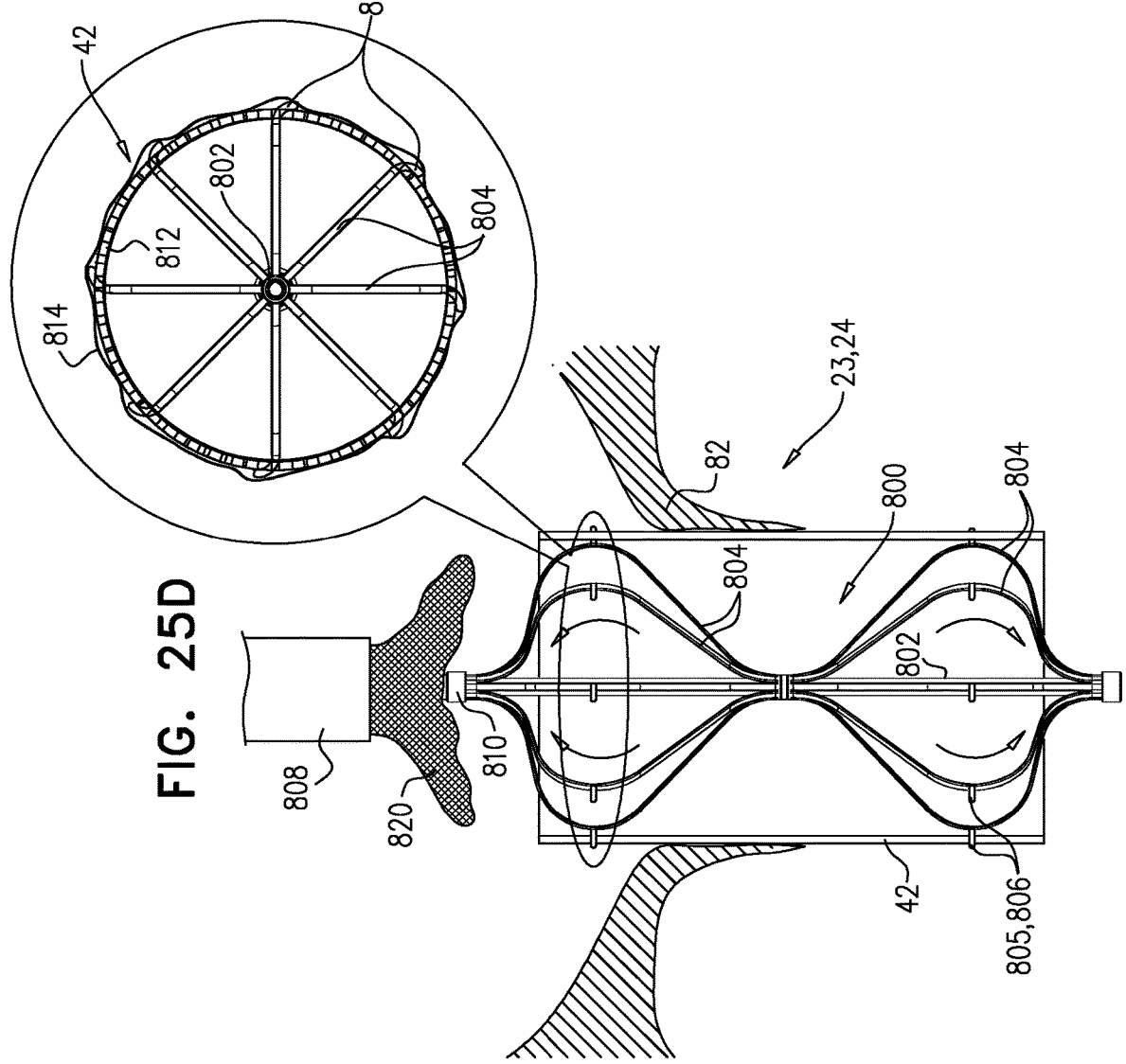

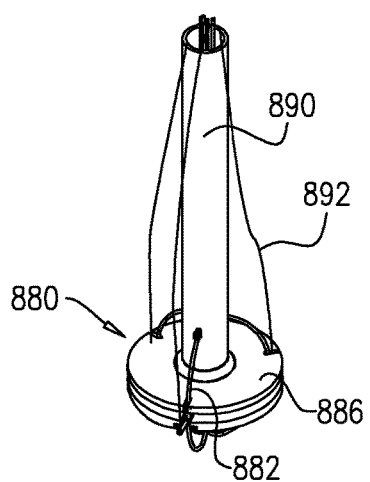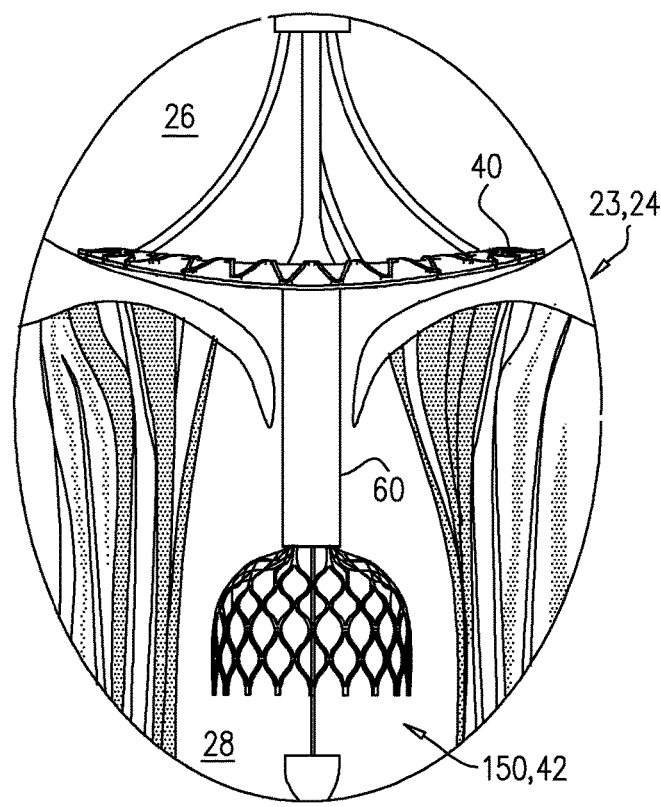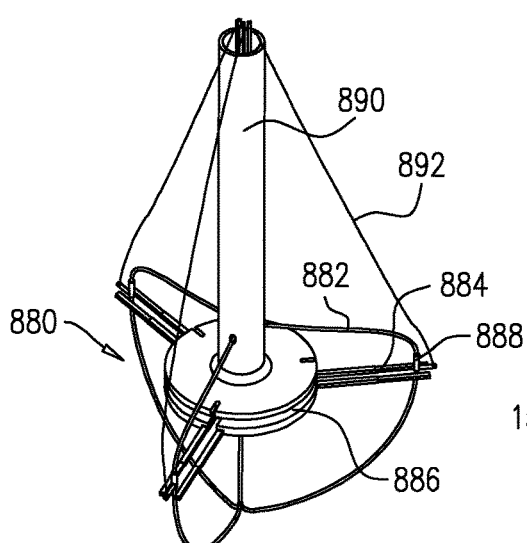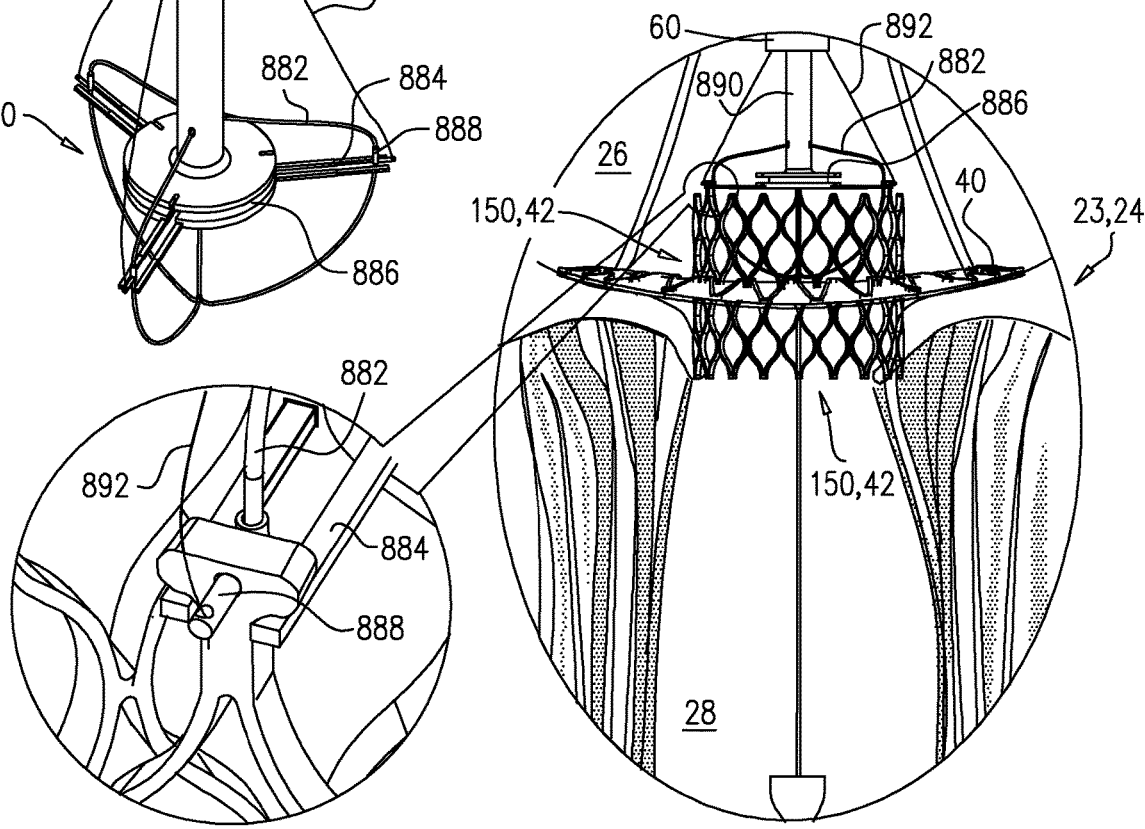
FIG. 27A
FIG. 27B
FIG. 27C
FIG. 27D

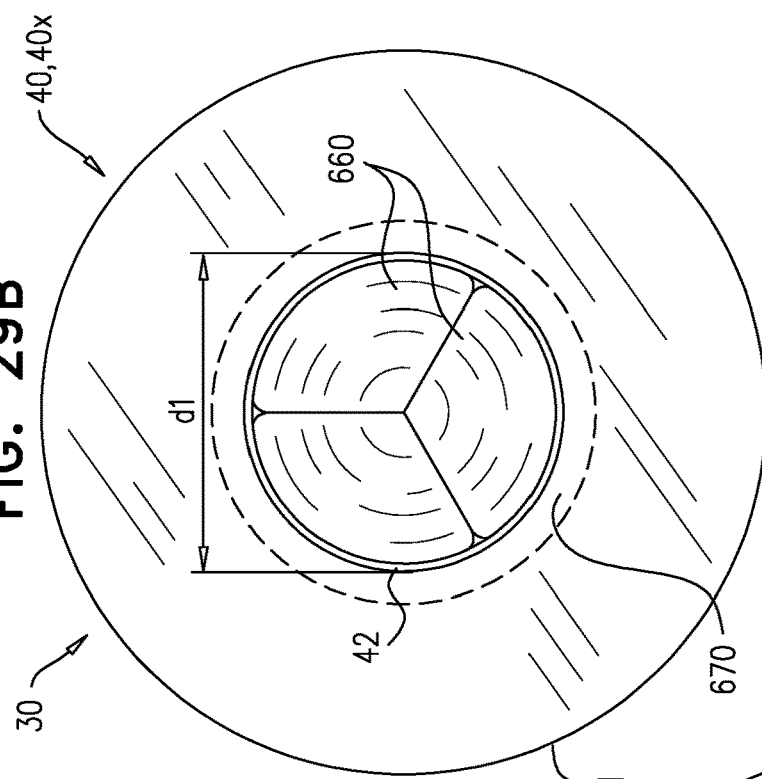
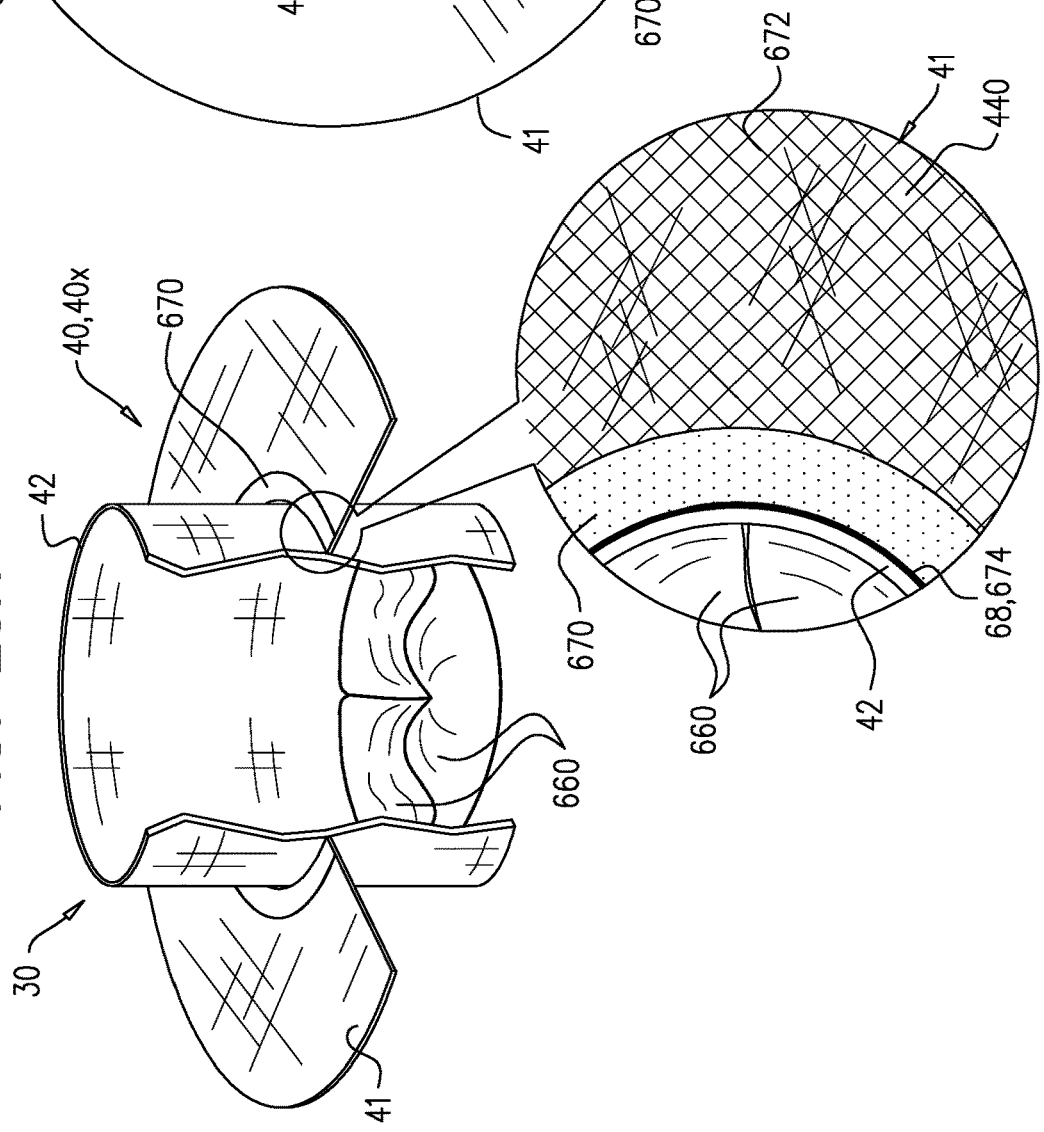

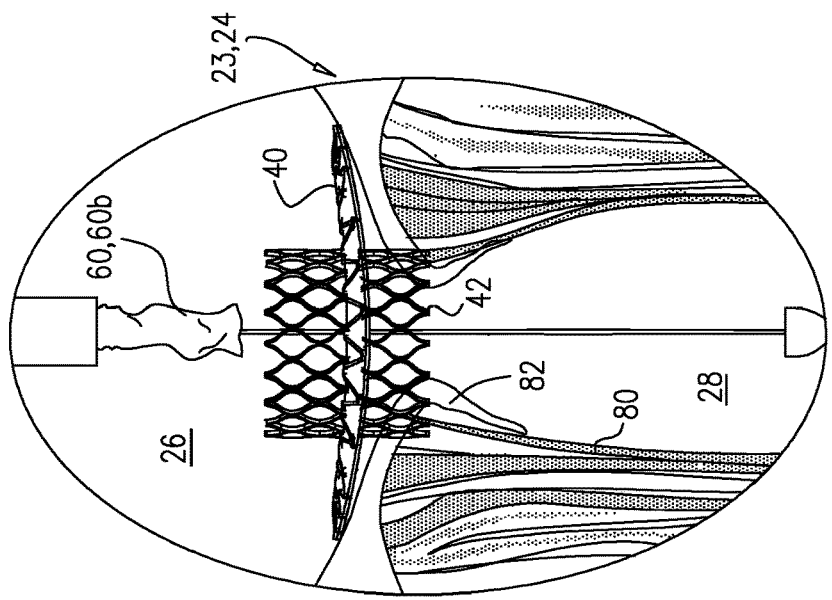
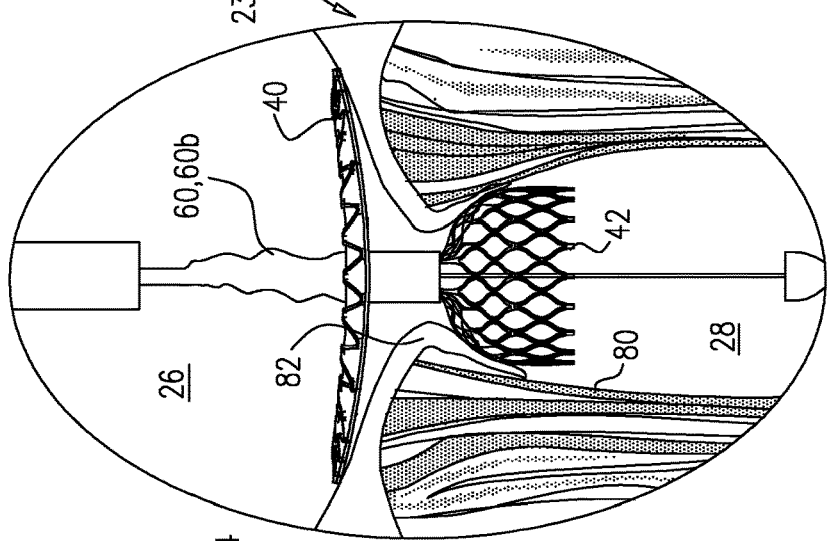
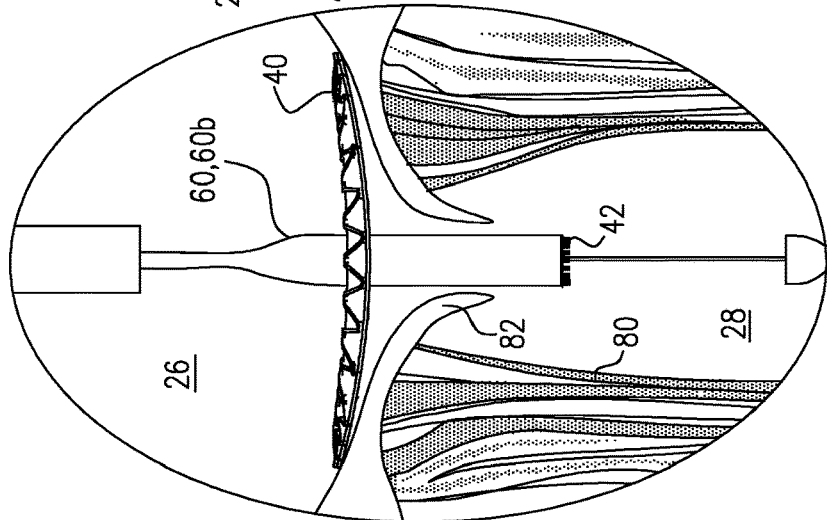

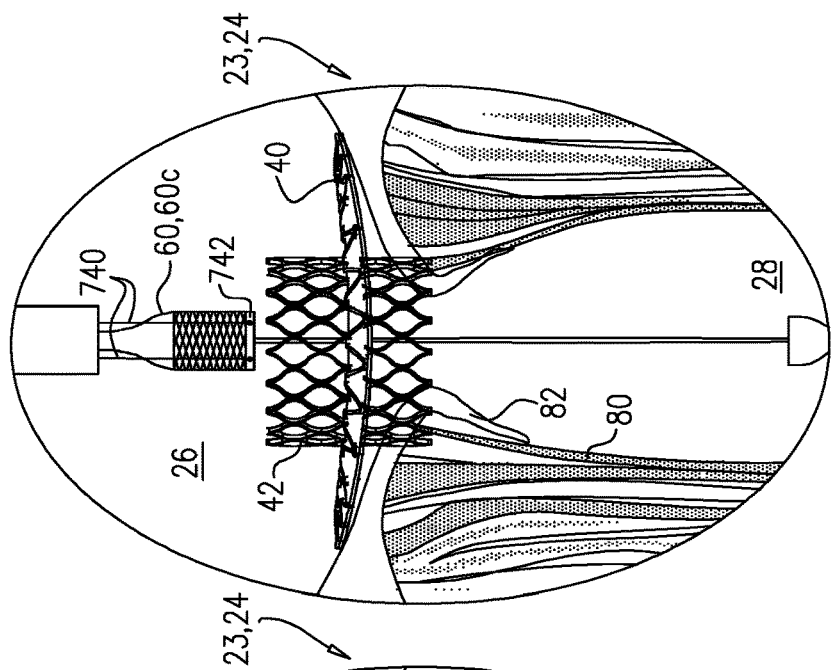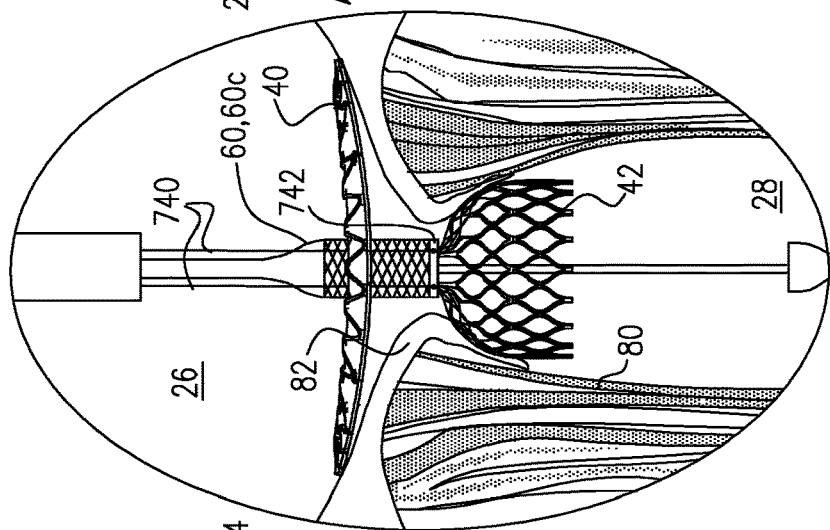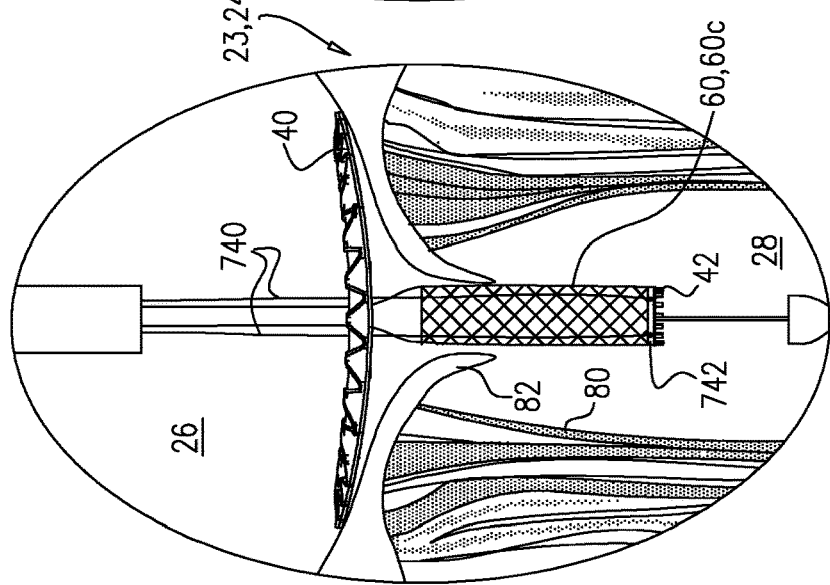

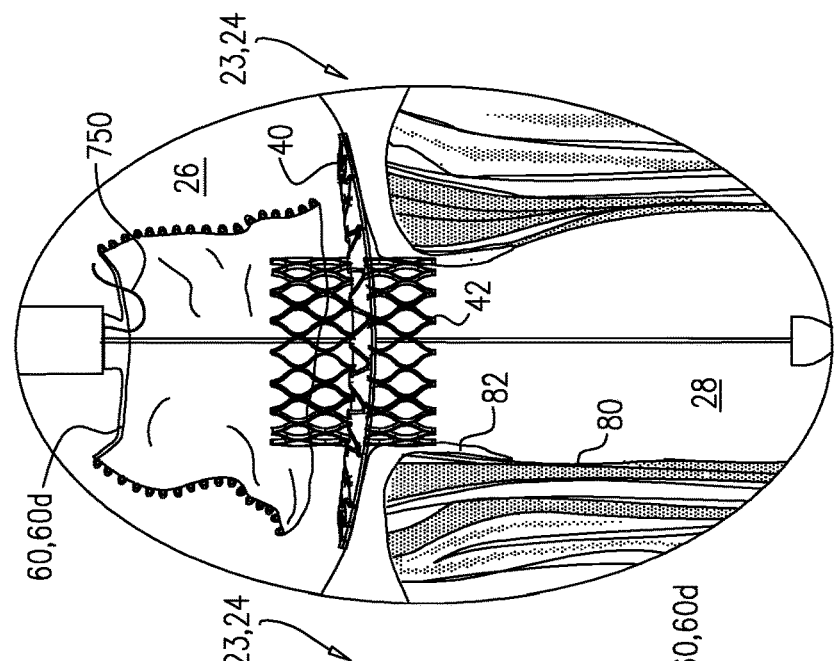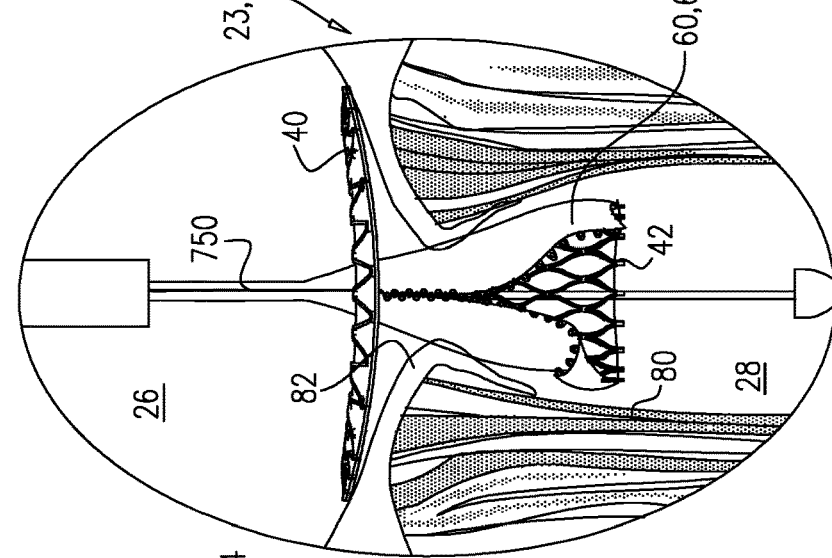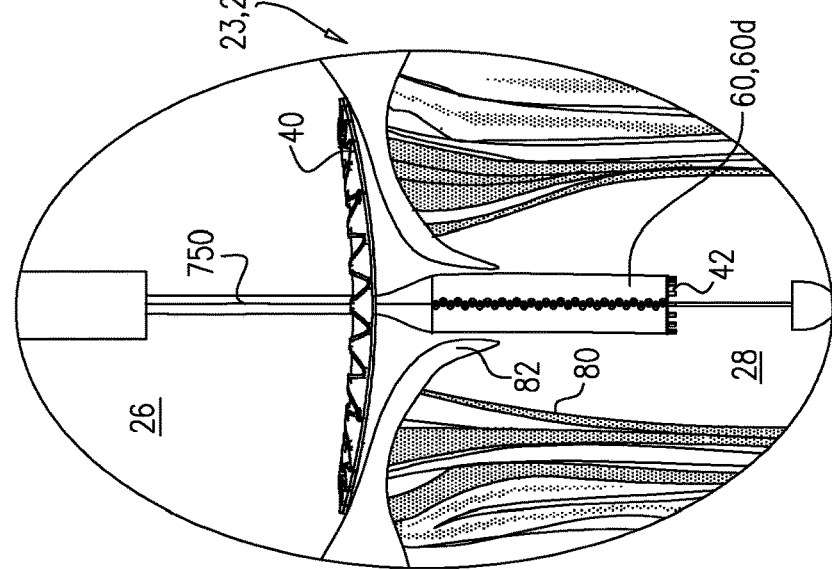

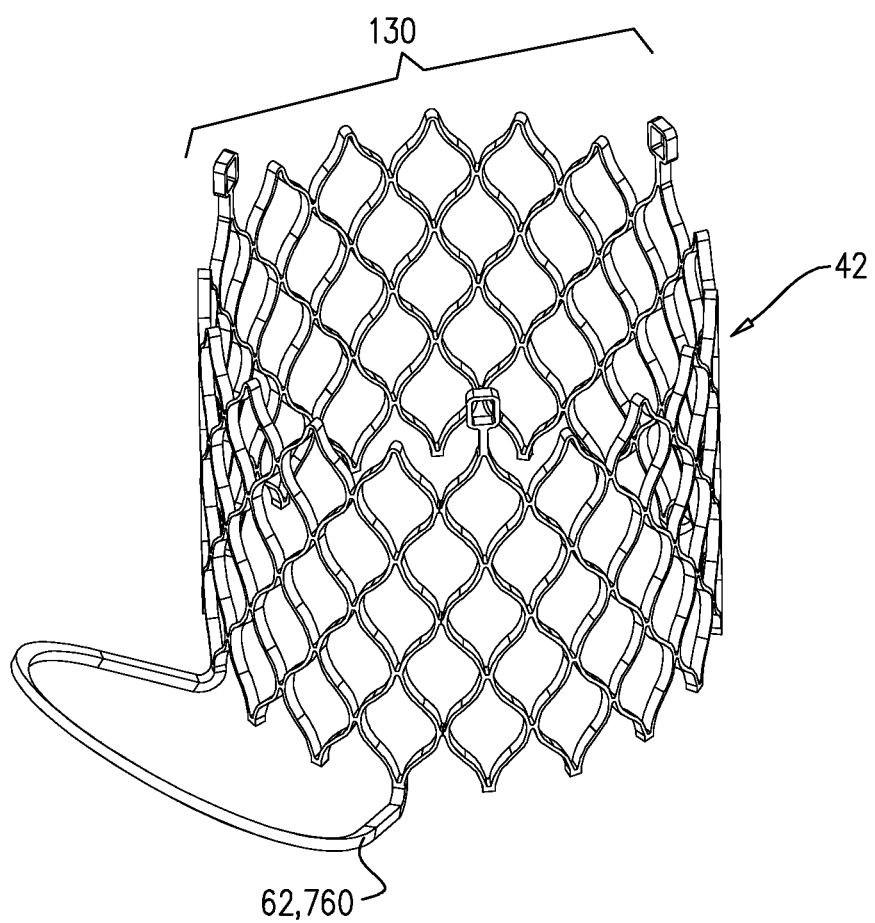

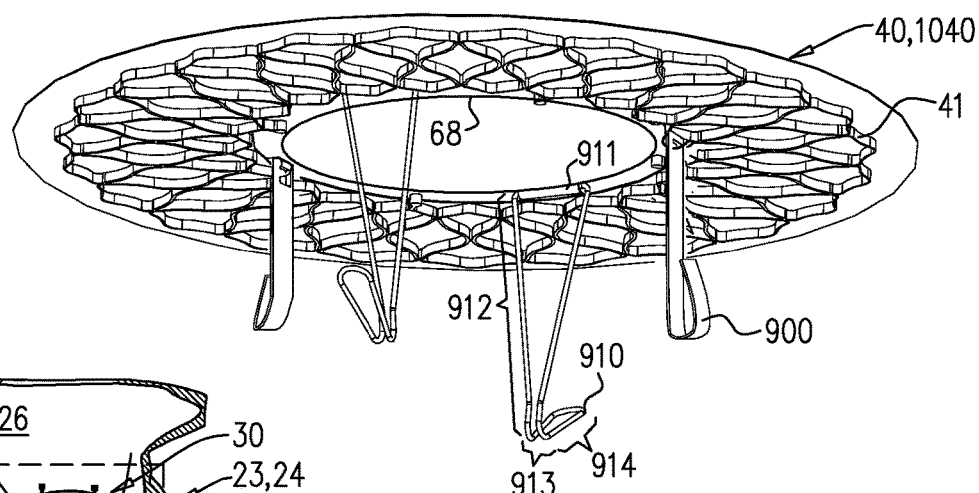
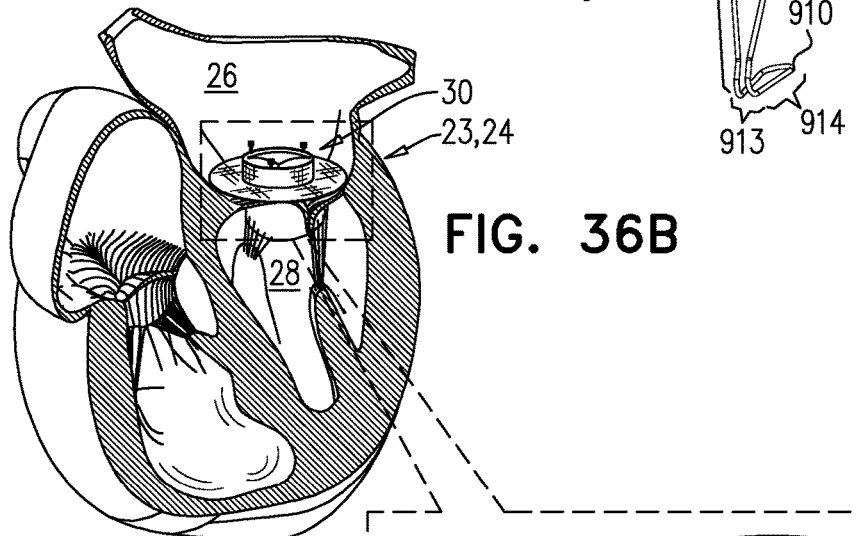
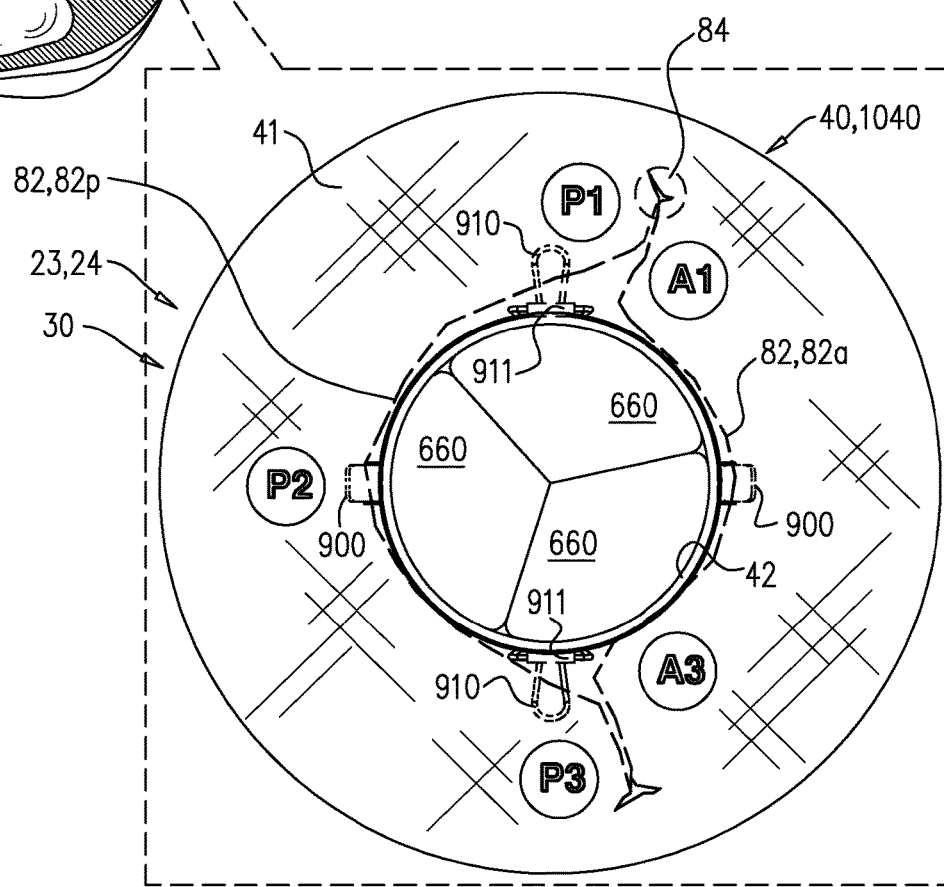

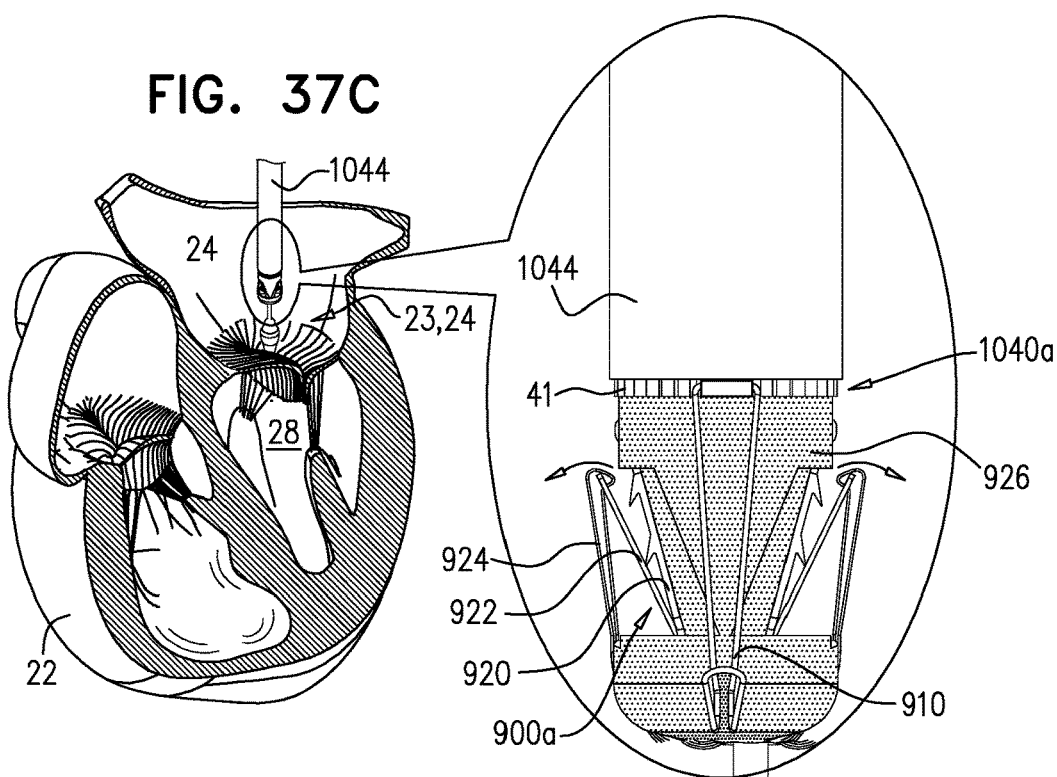
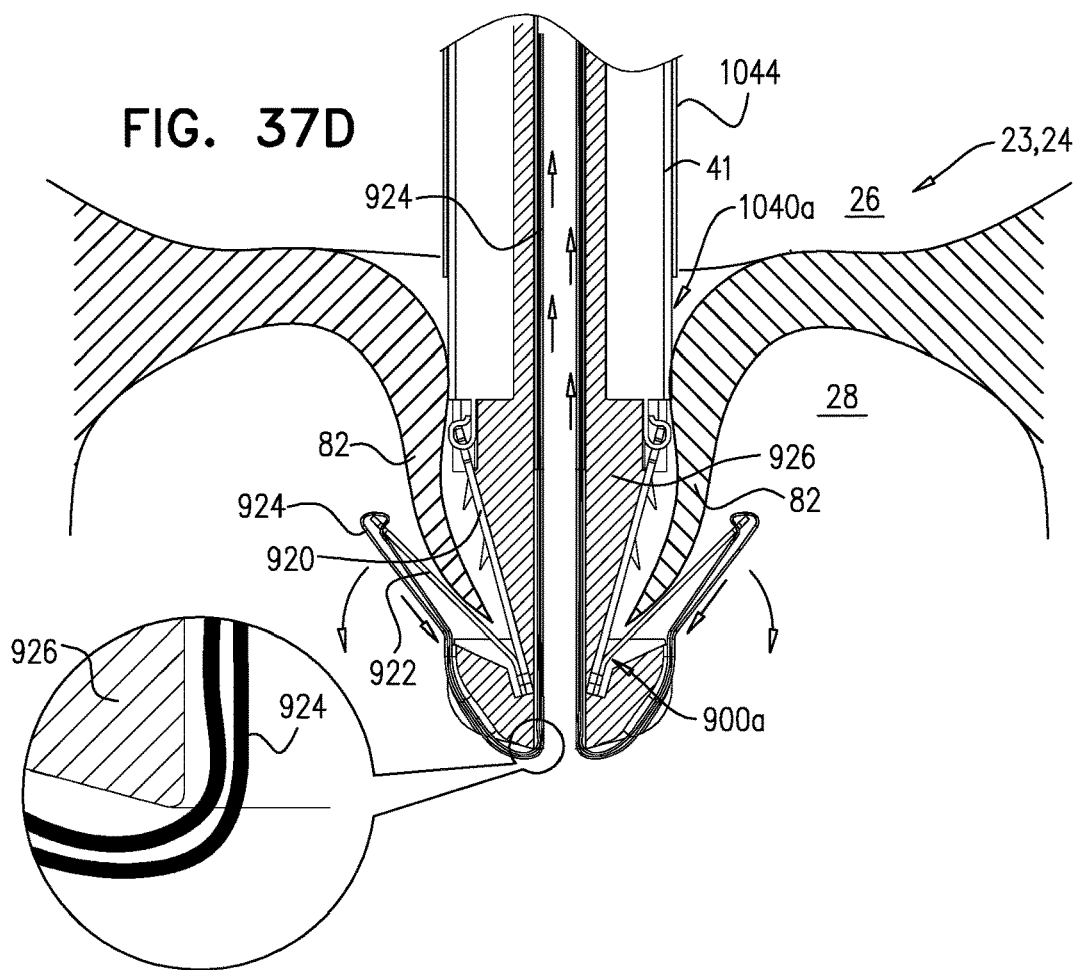

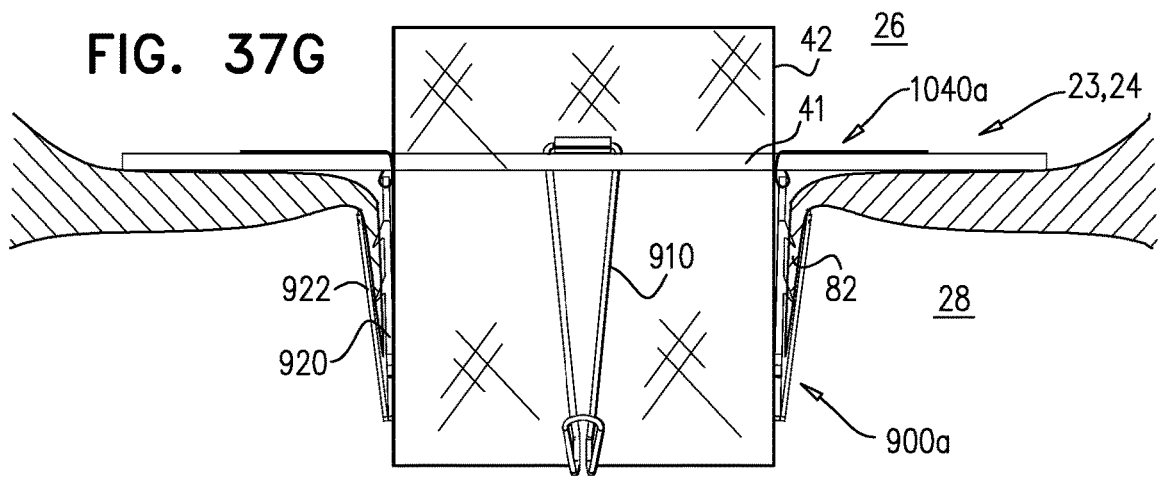
FIG. 37G
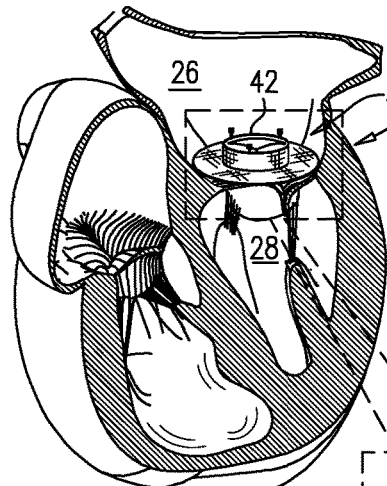
FIG. 37H
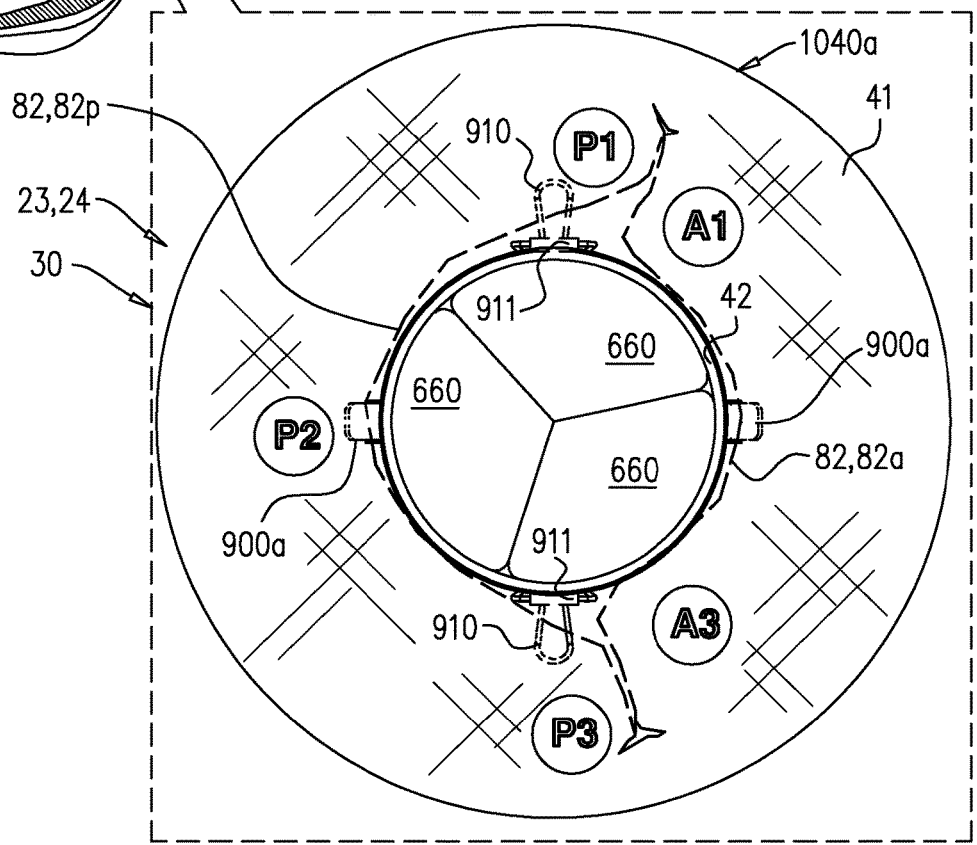

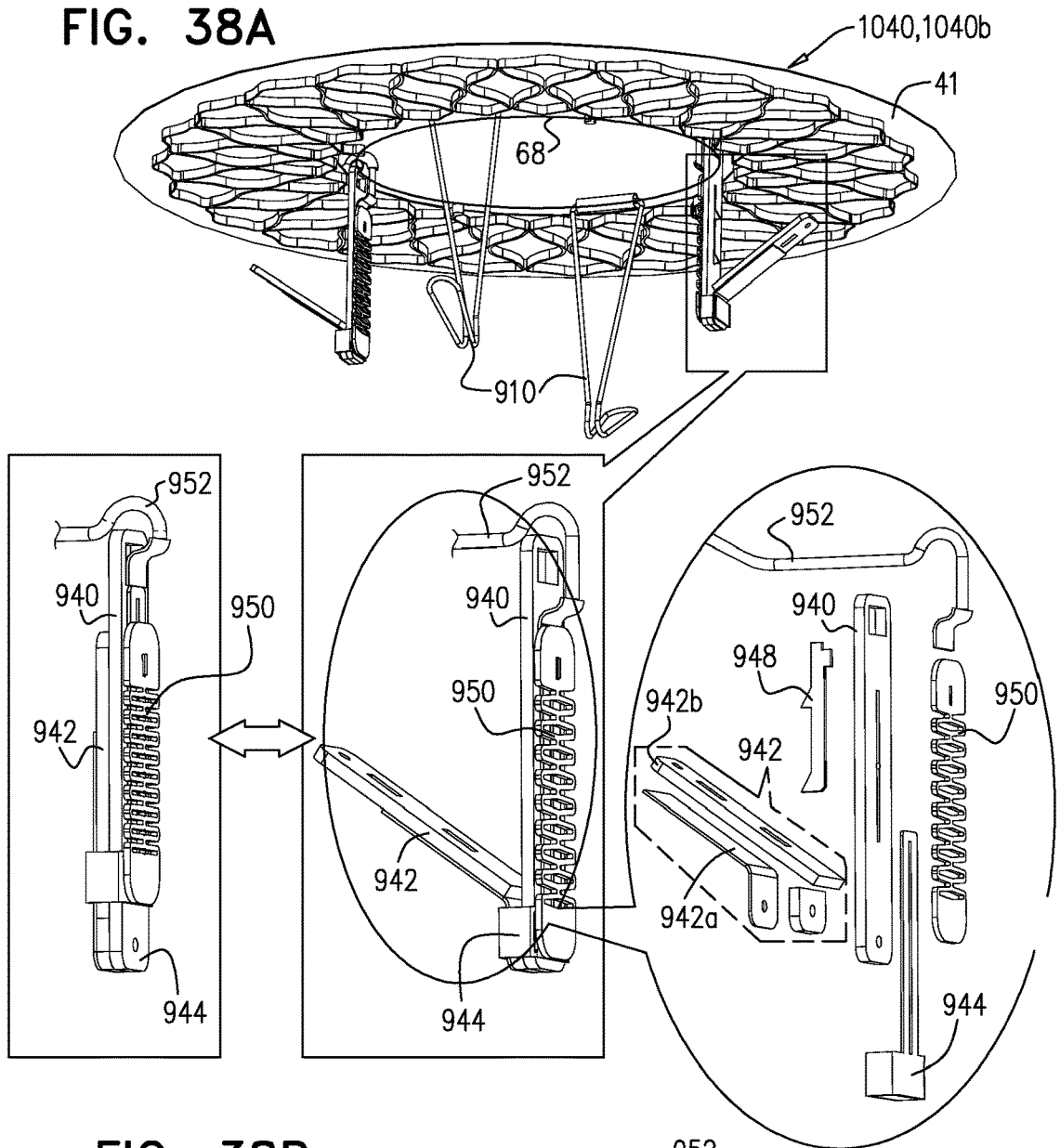
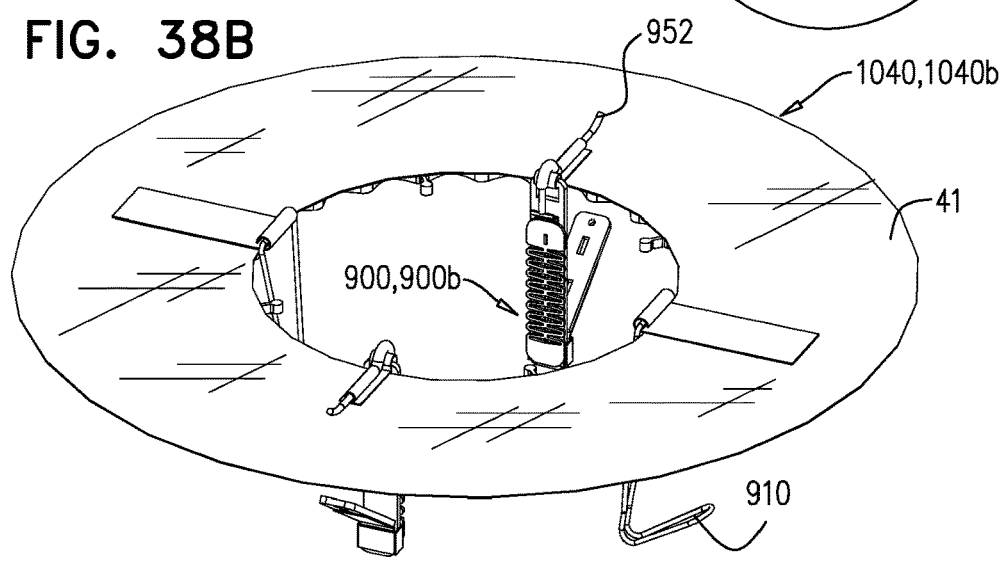

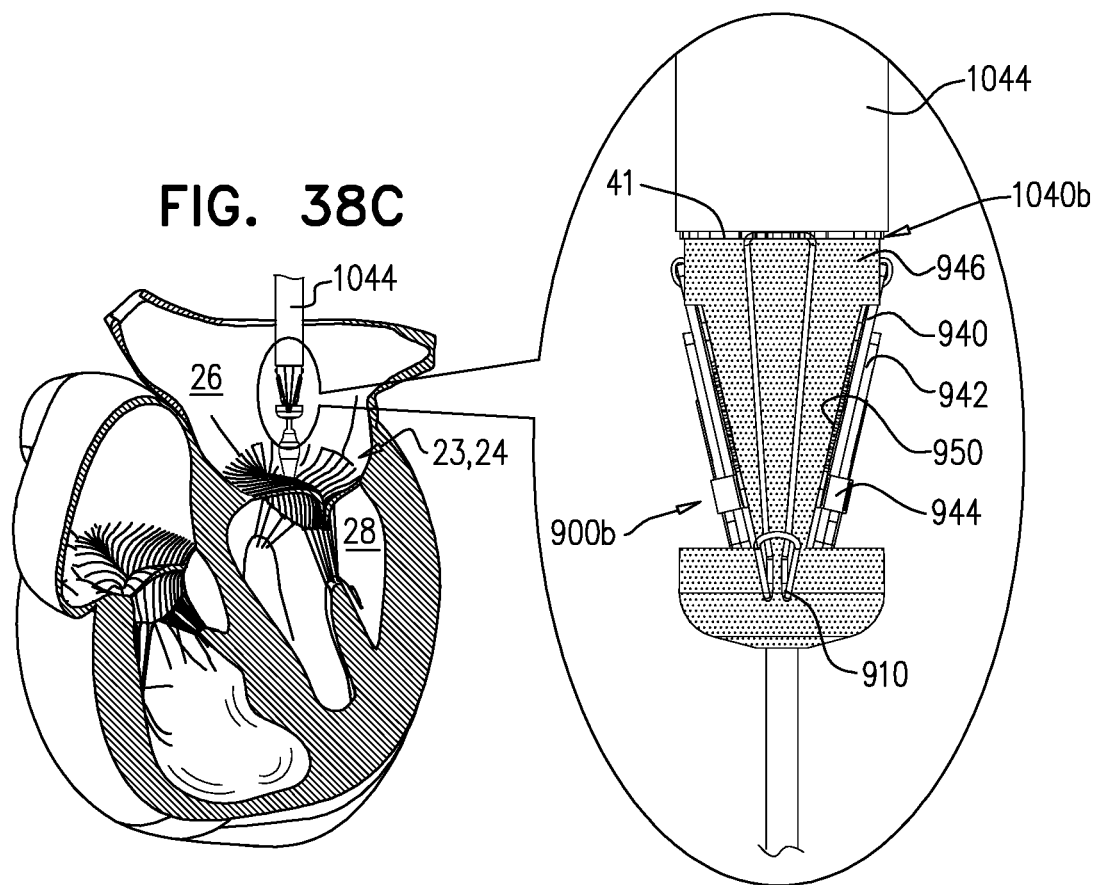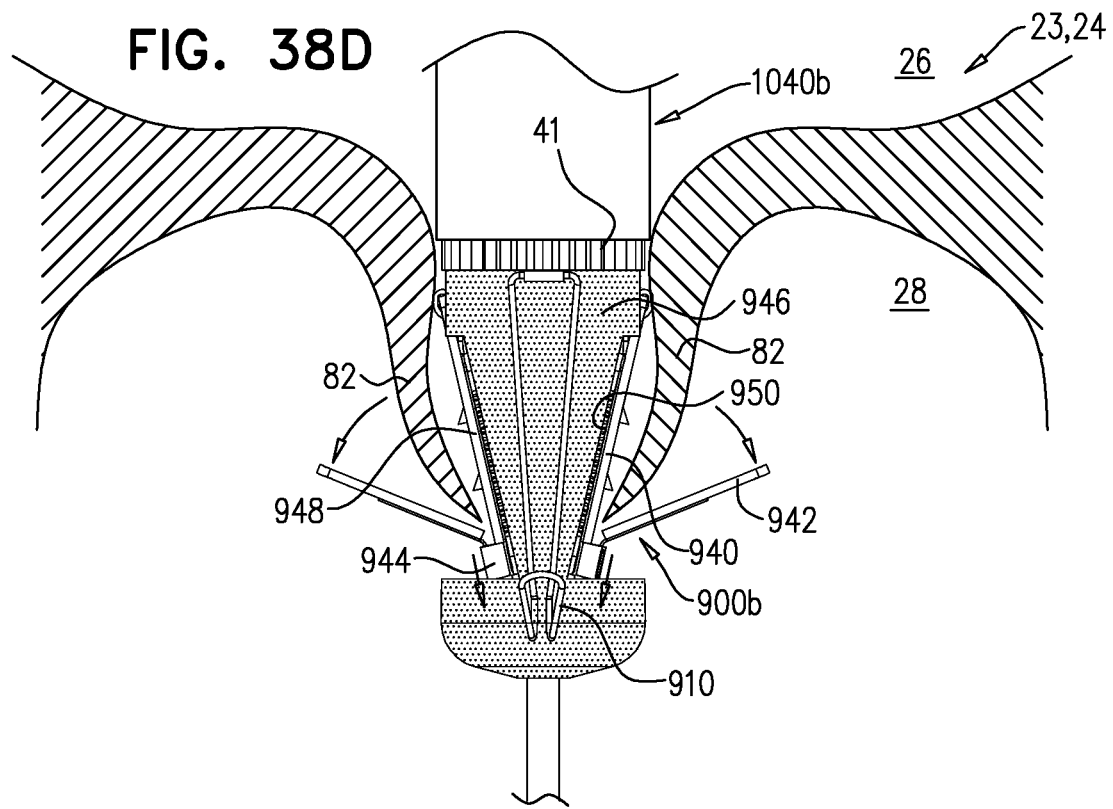

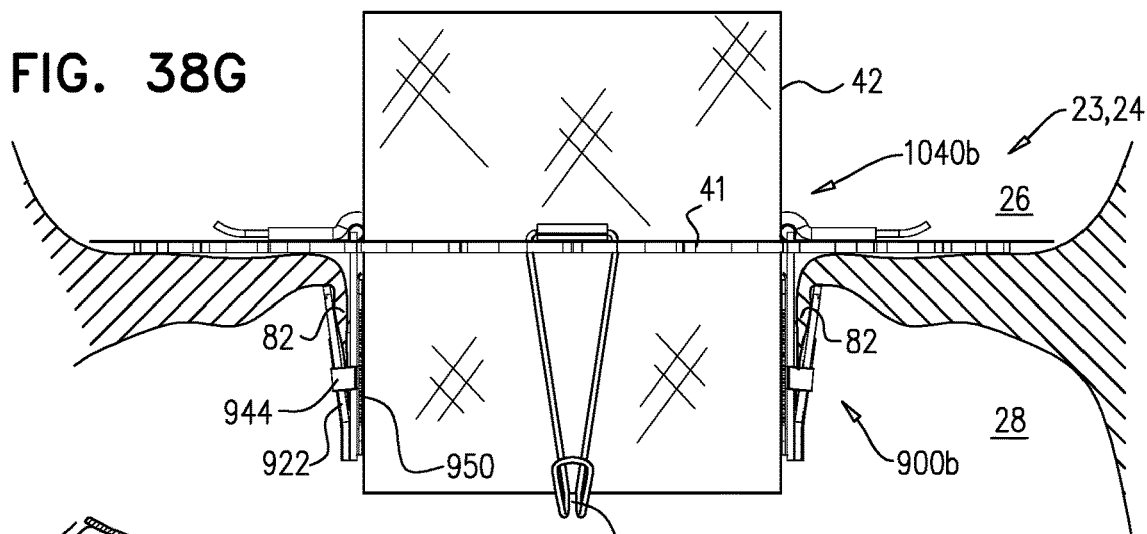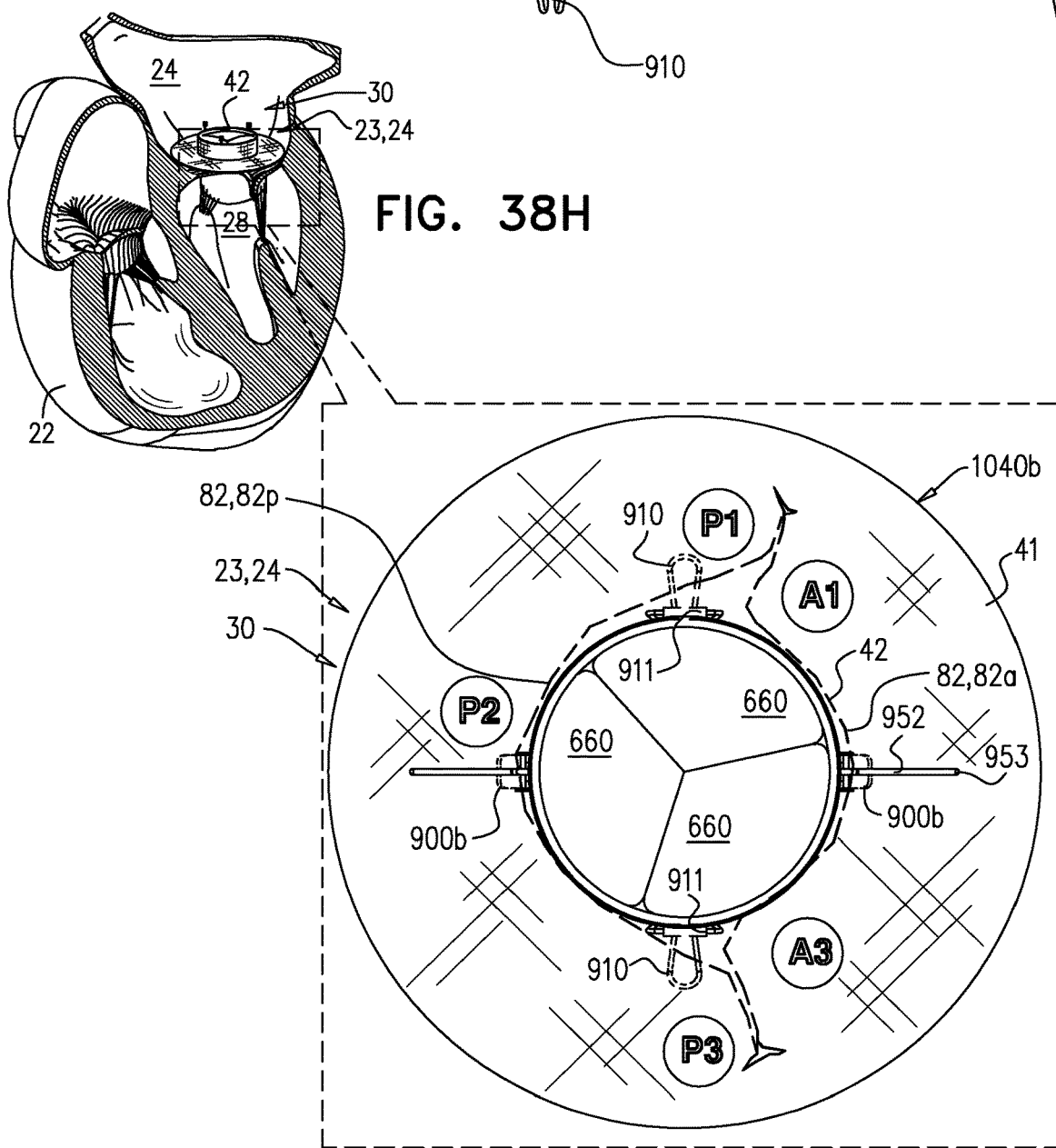

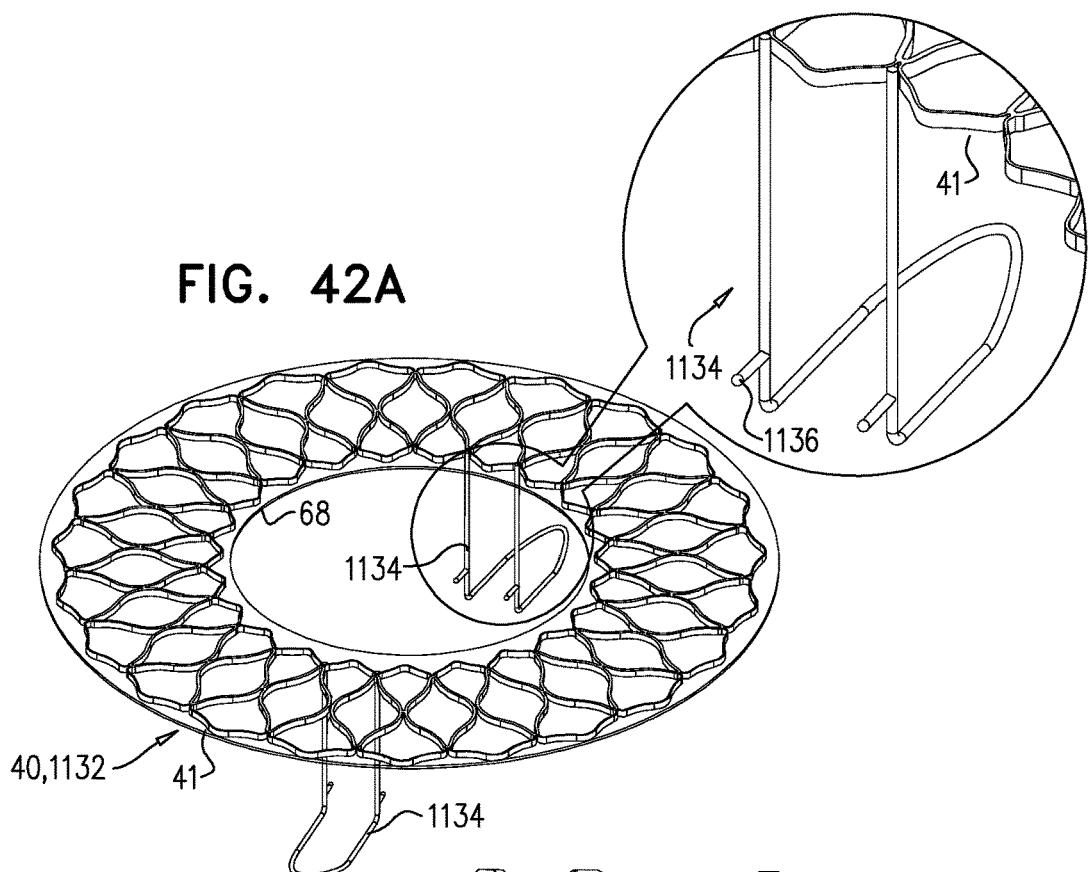
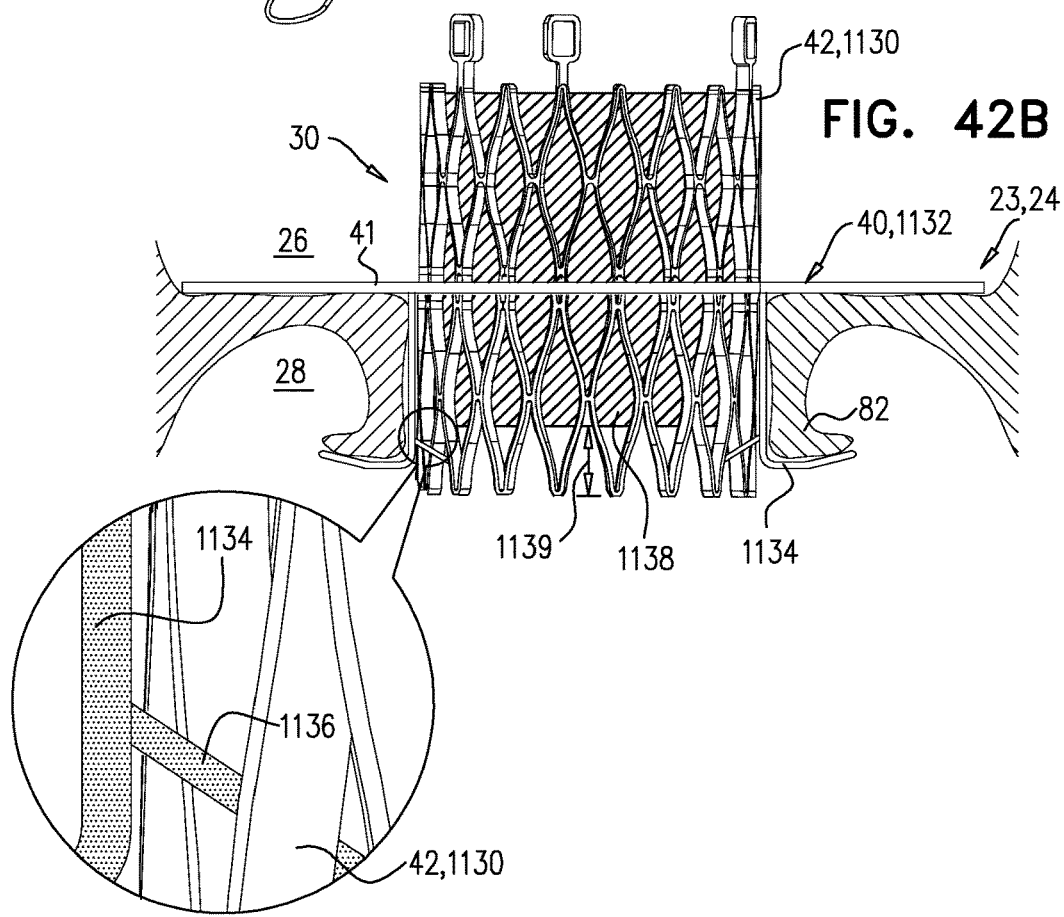

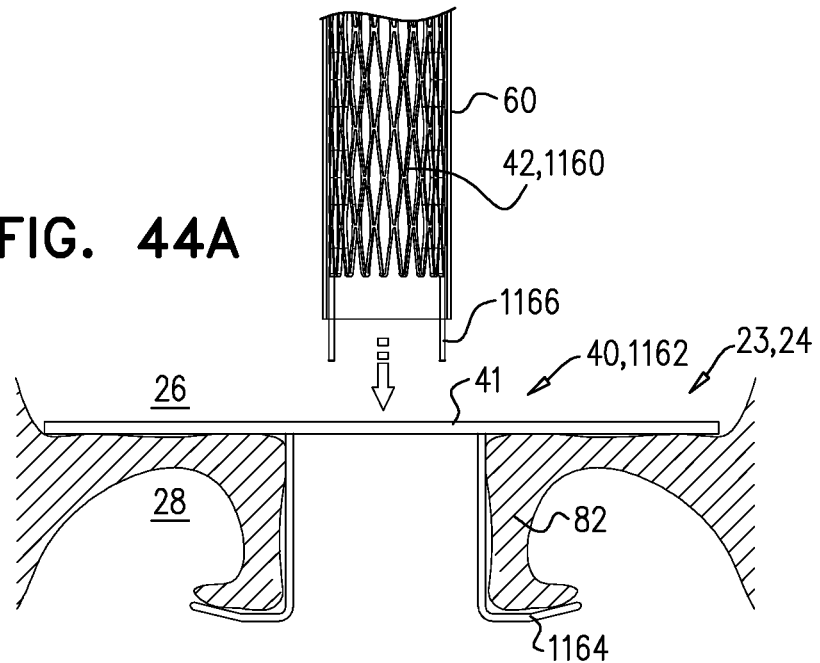
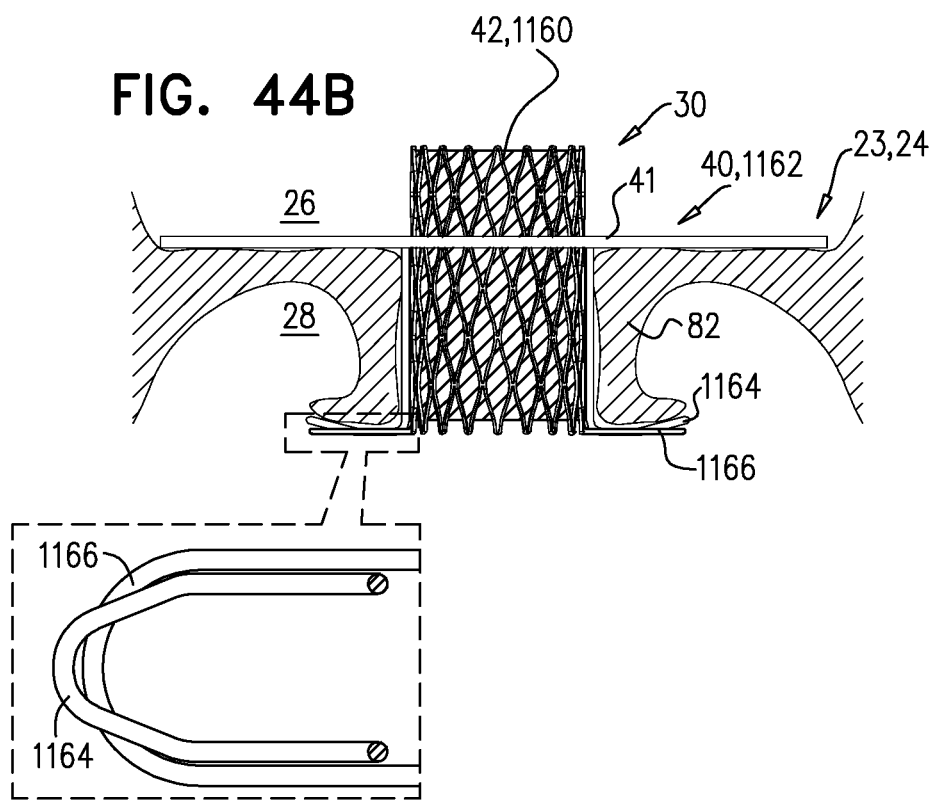

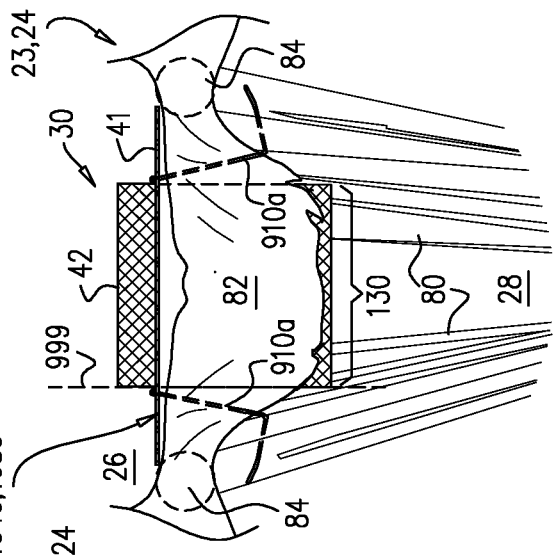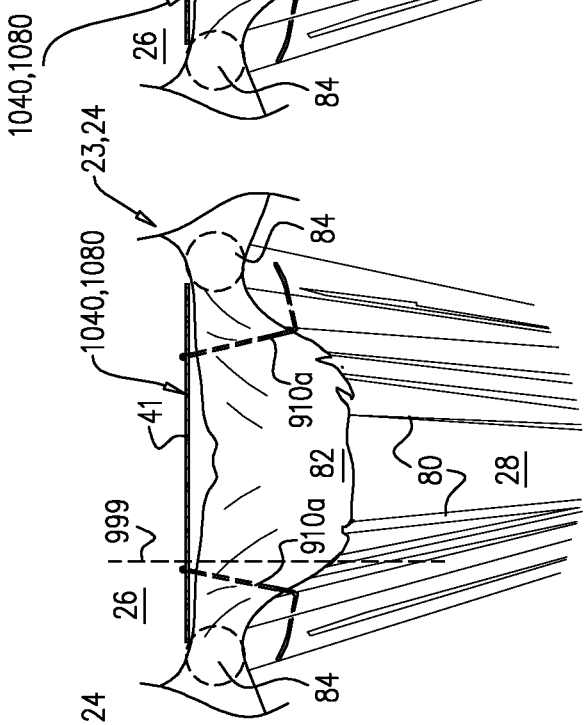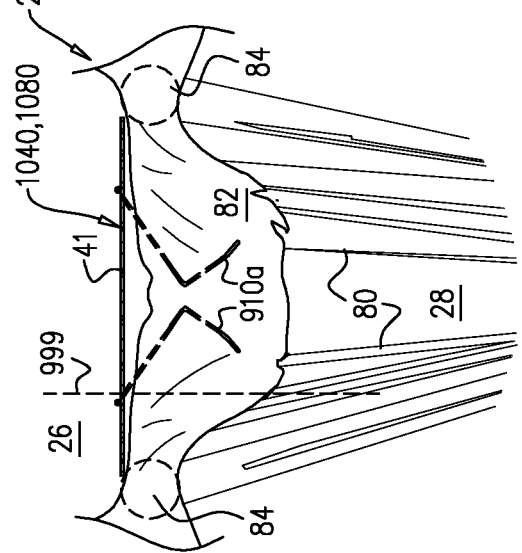

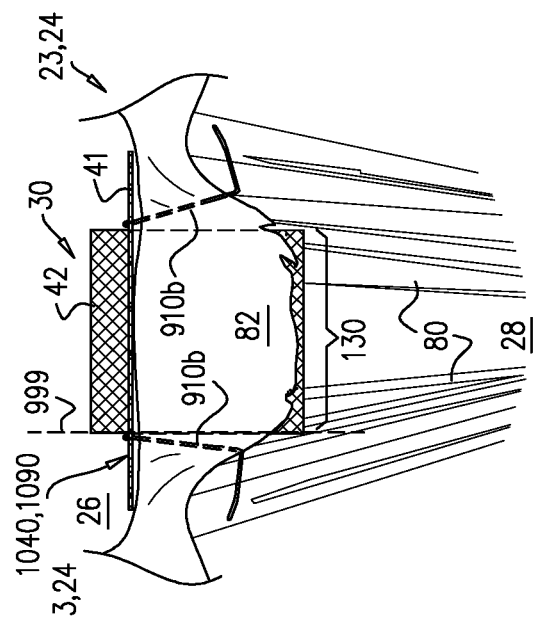
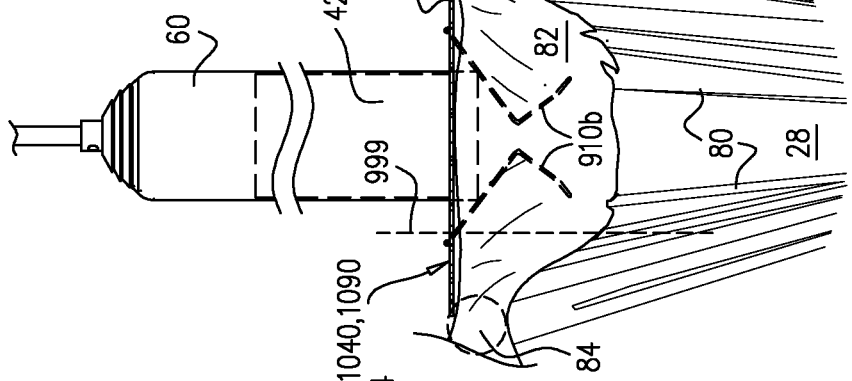
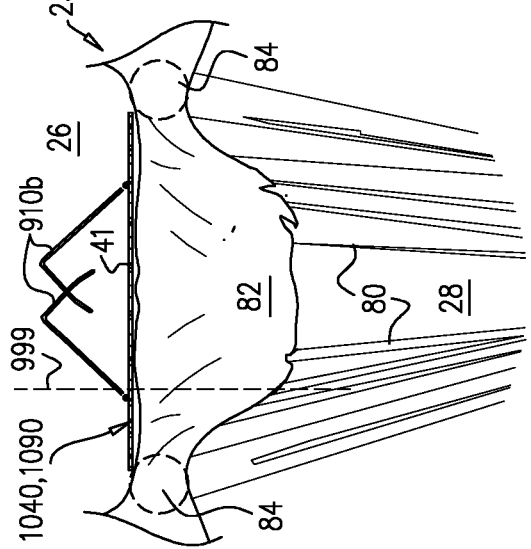

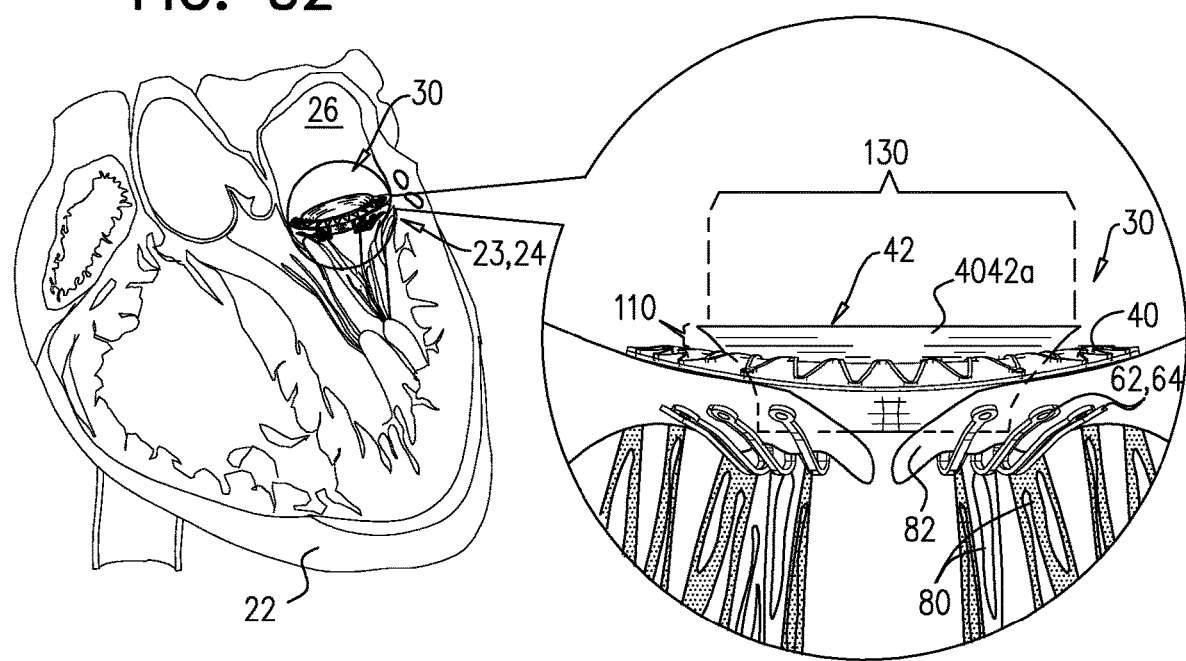

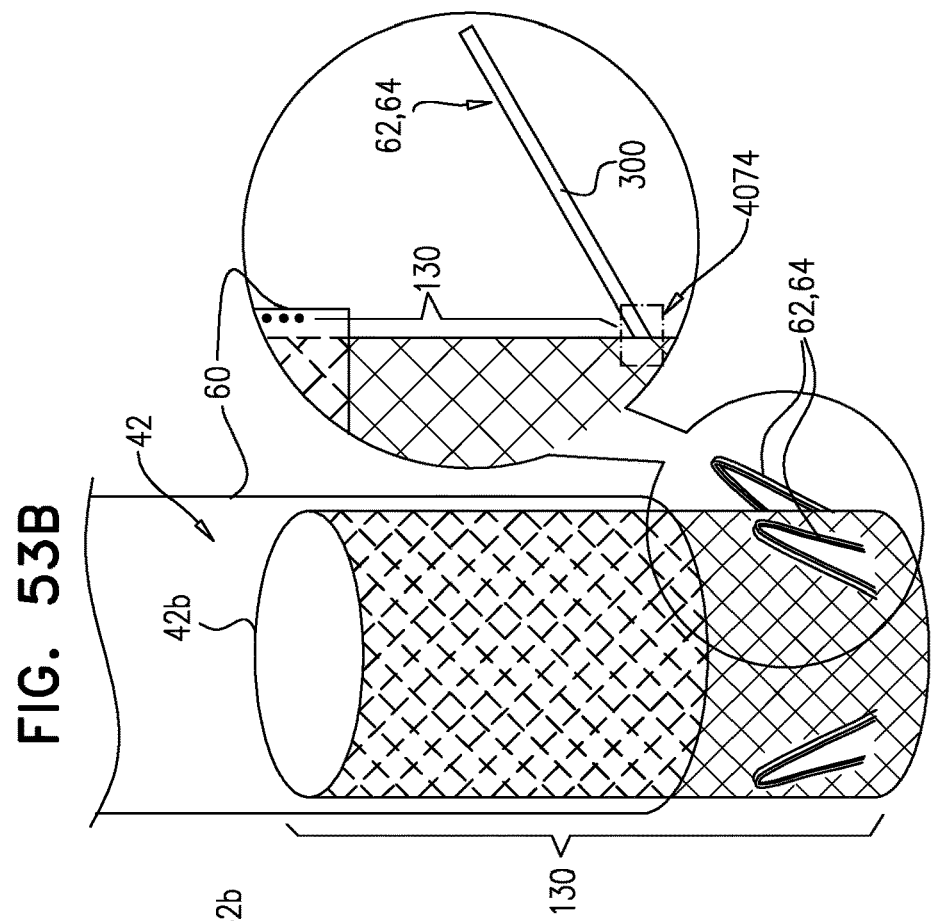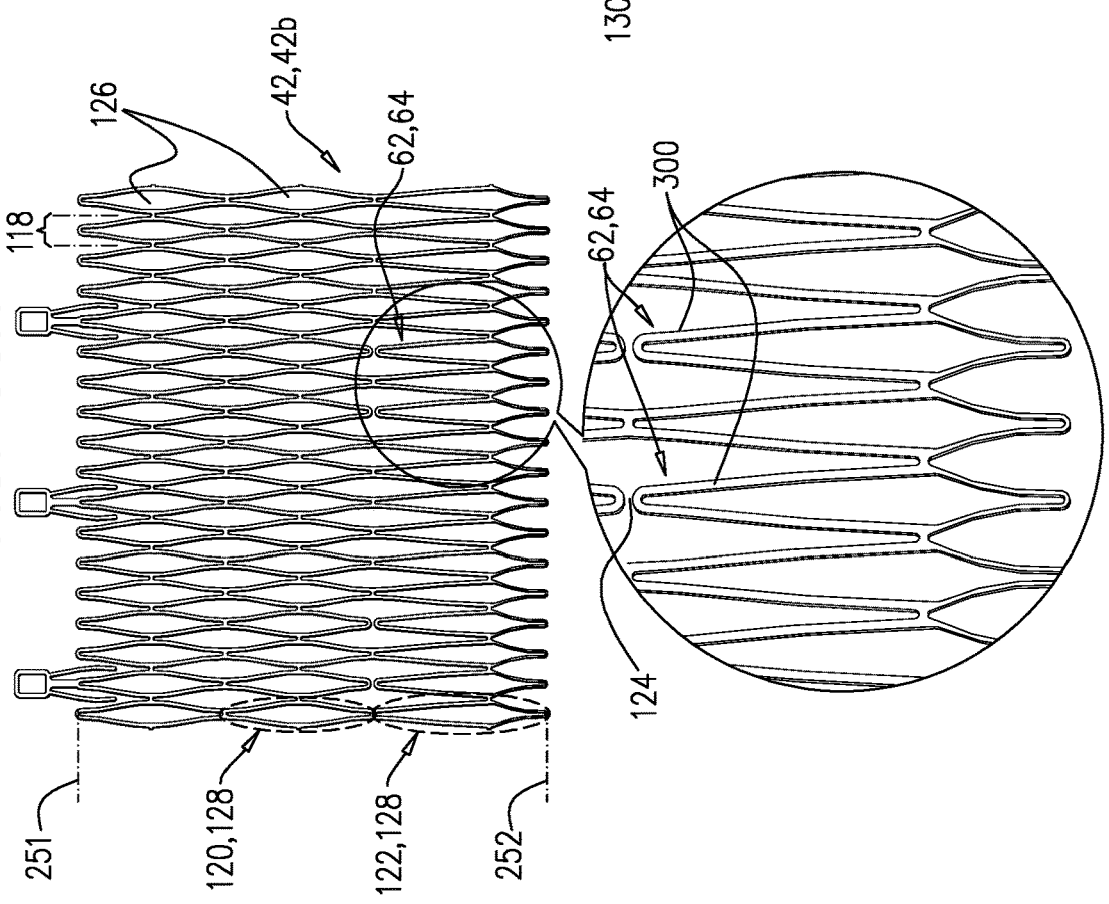

FIG. 57B
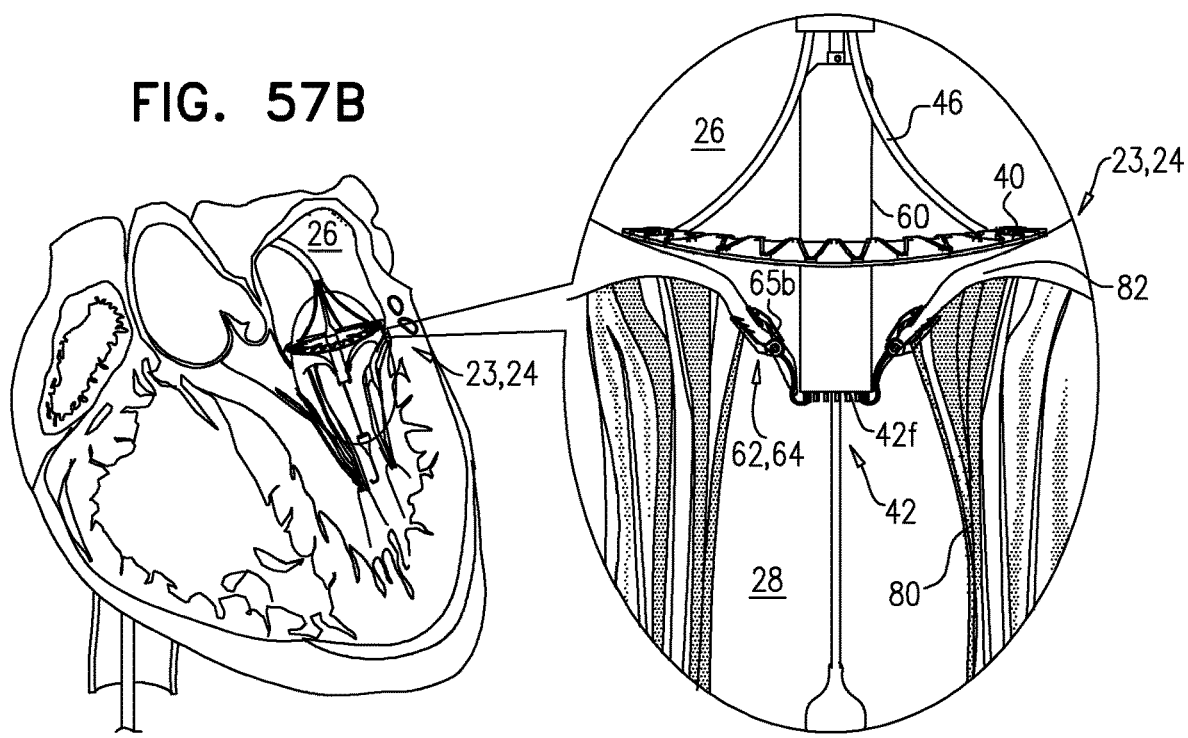
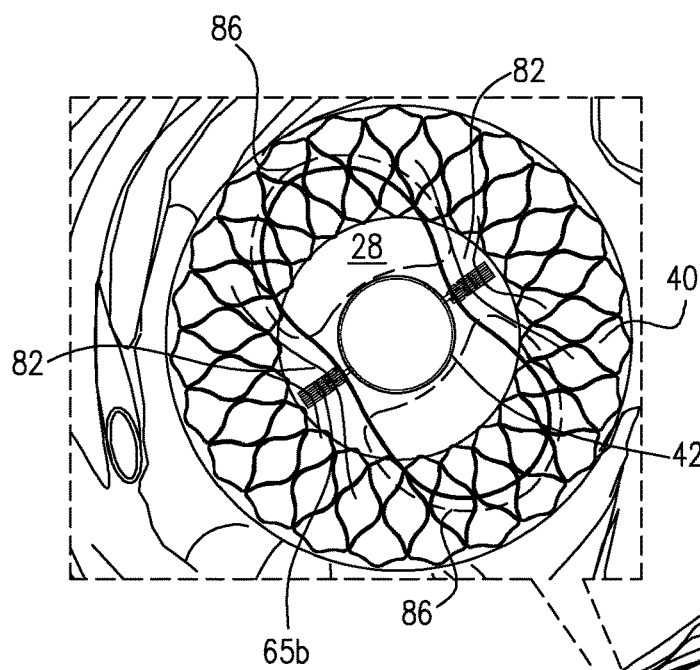
FIG. 57C
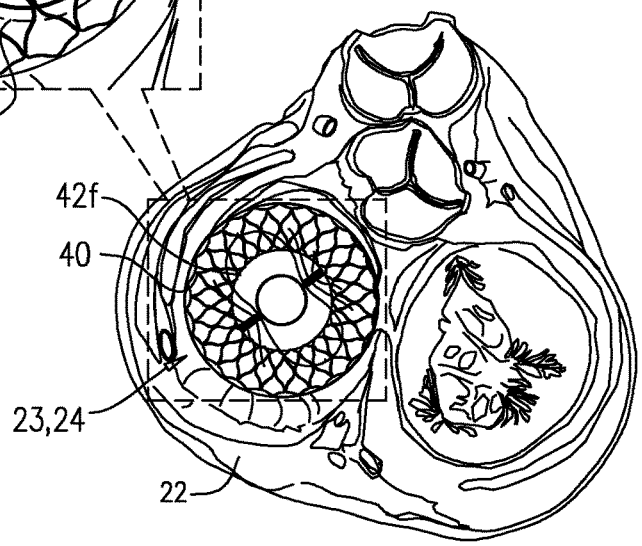

FIG. 59A
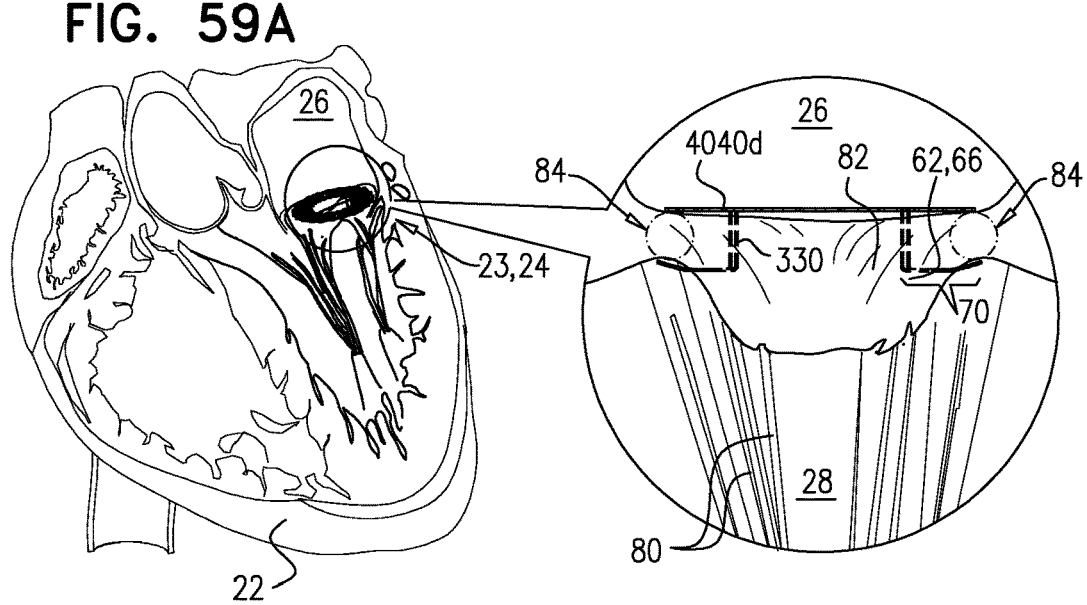
FIG. 59B
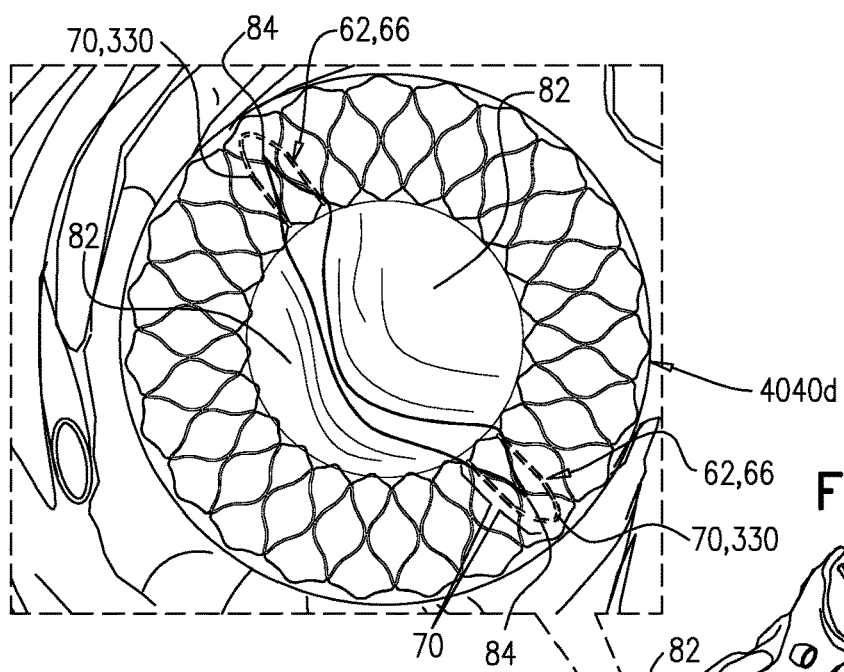
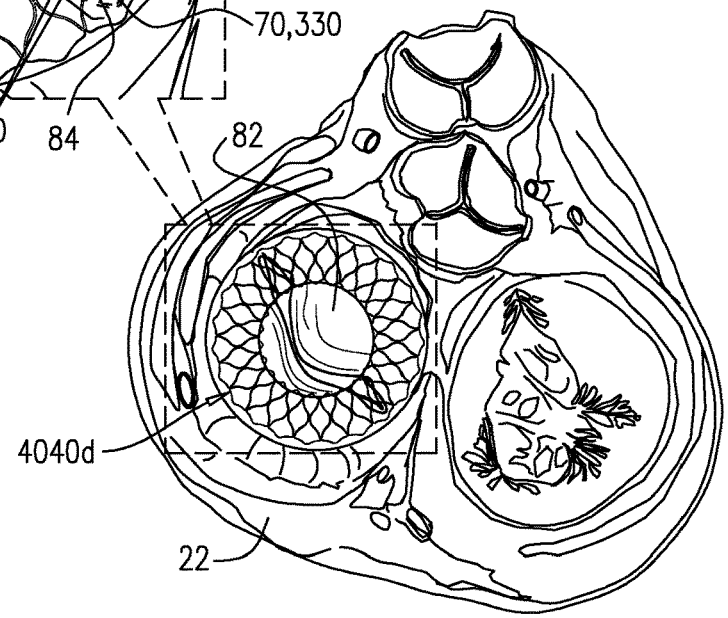

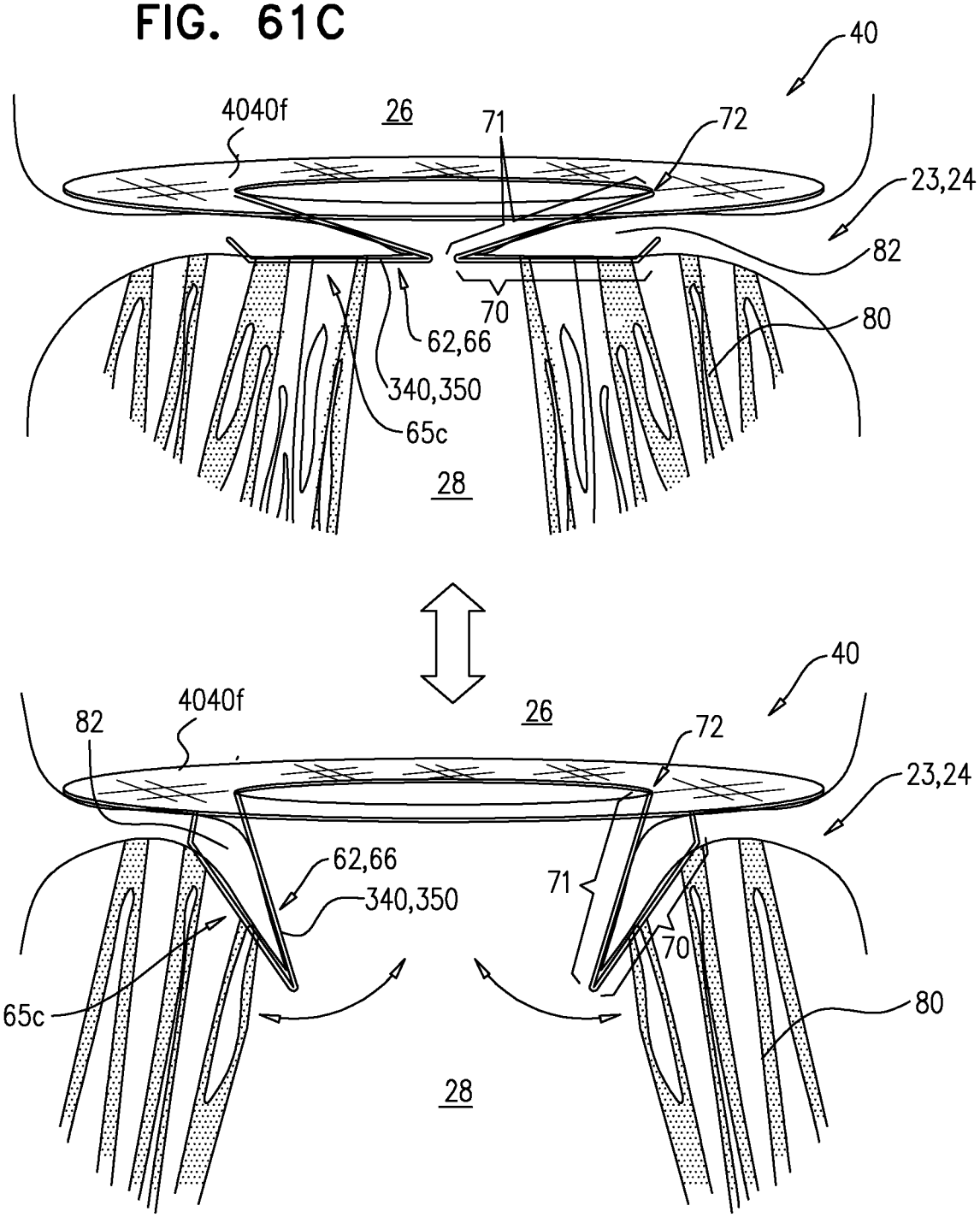

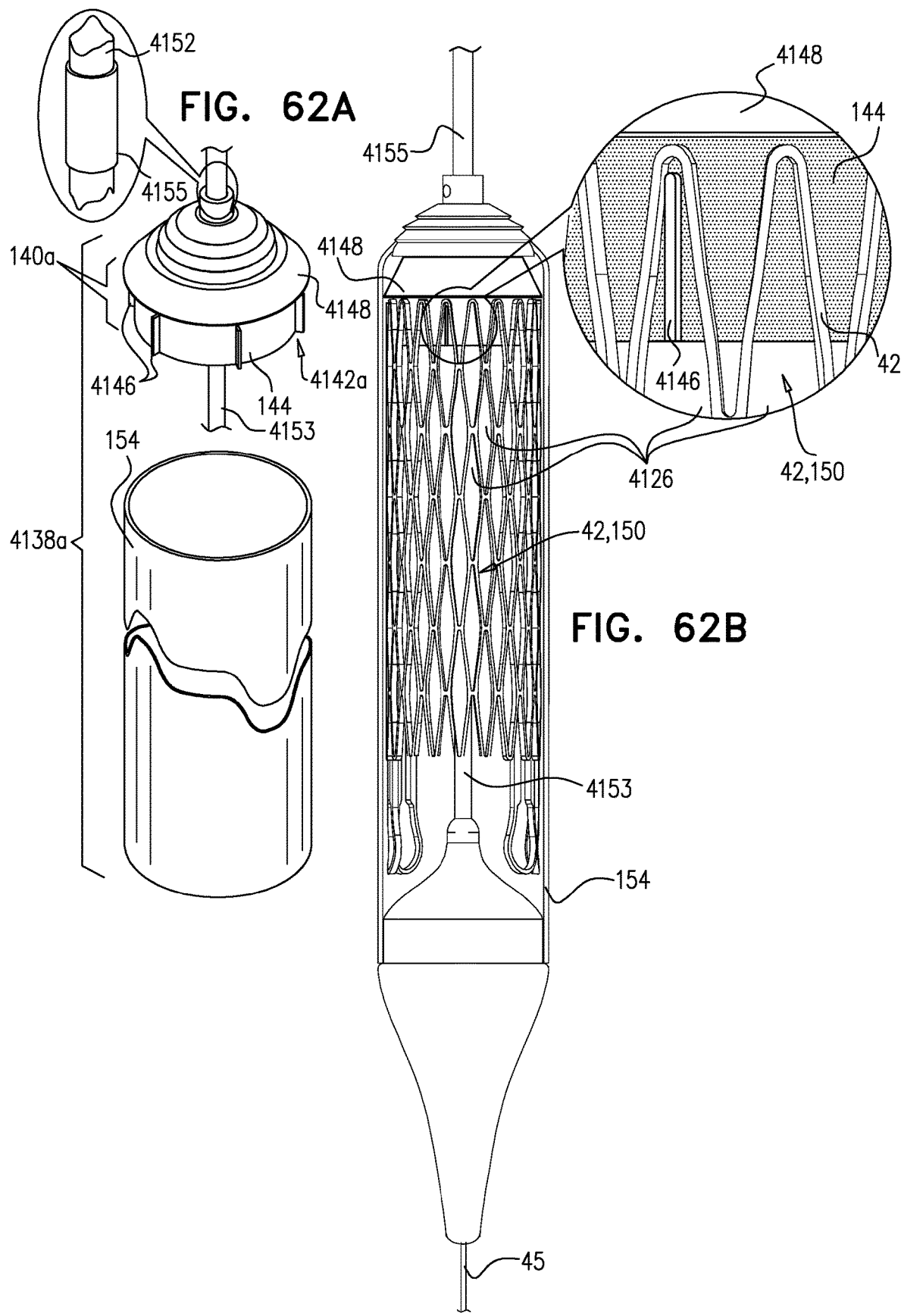

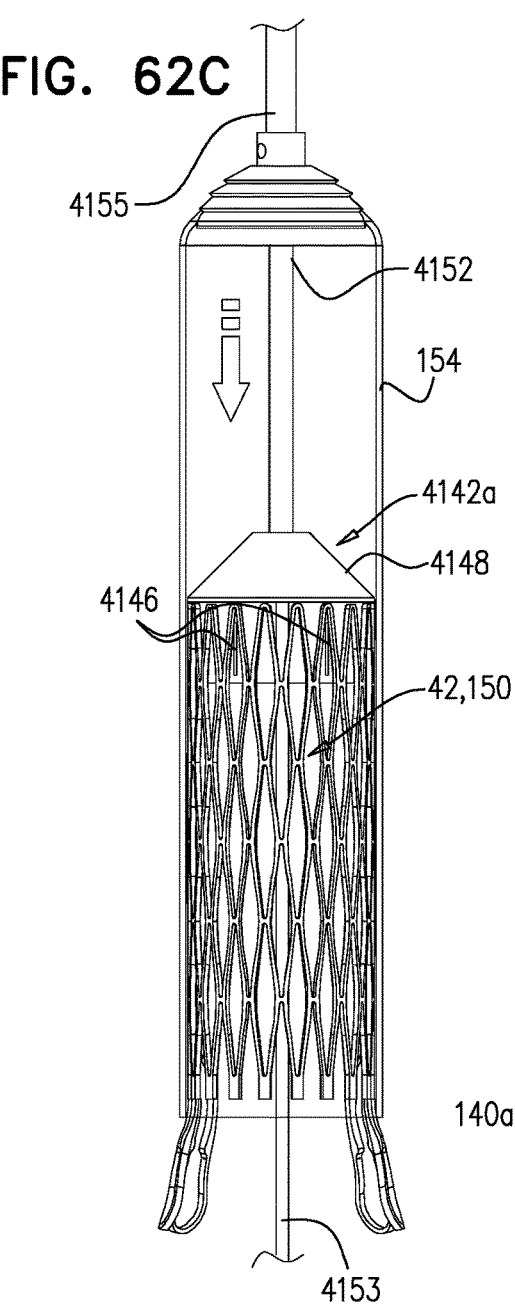
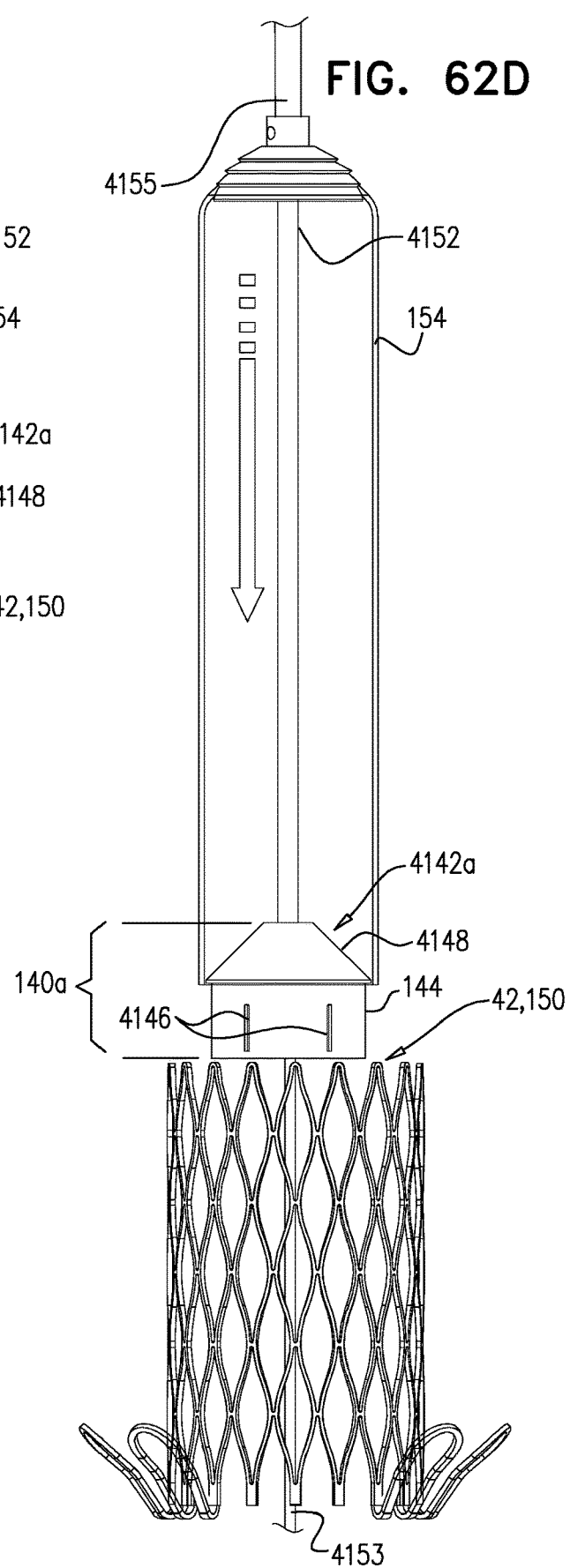

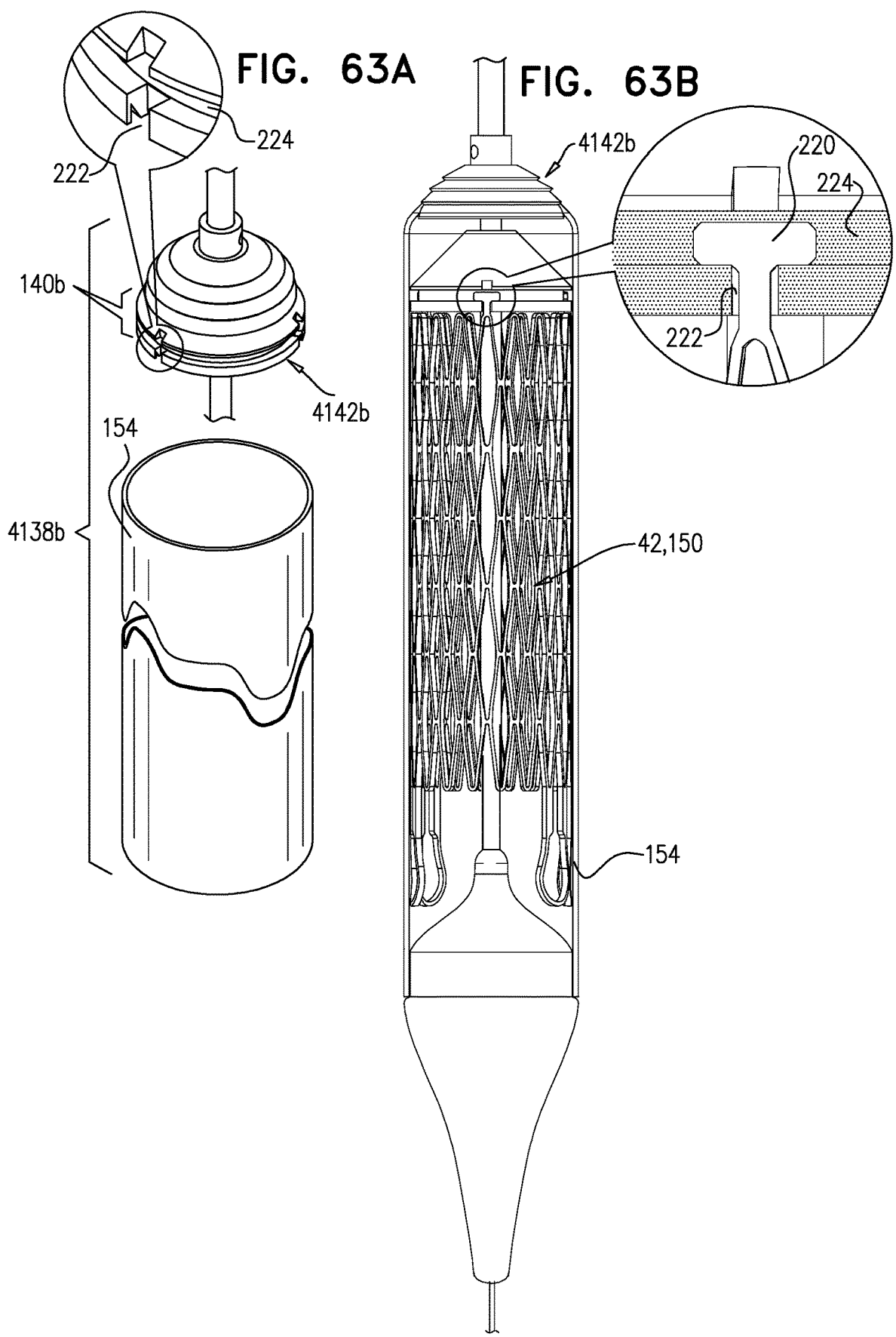

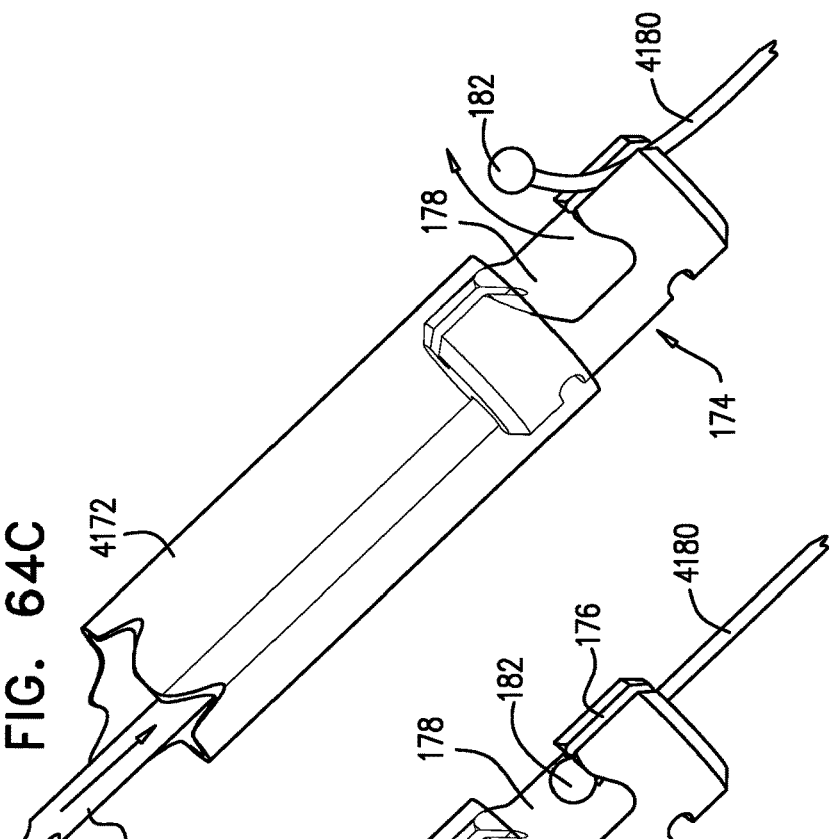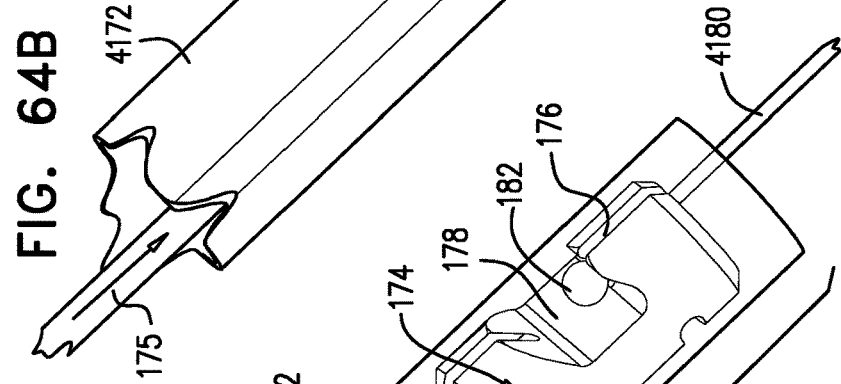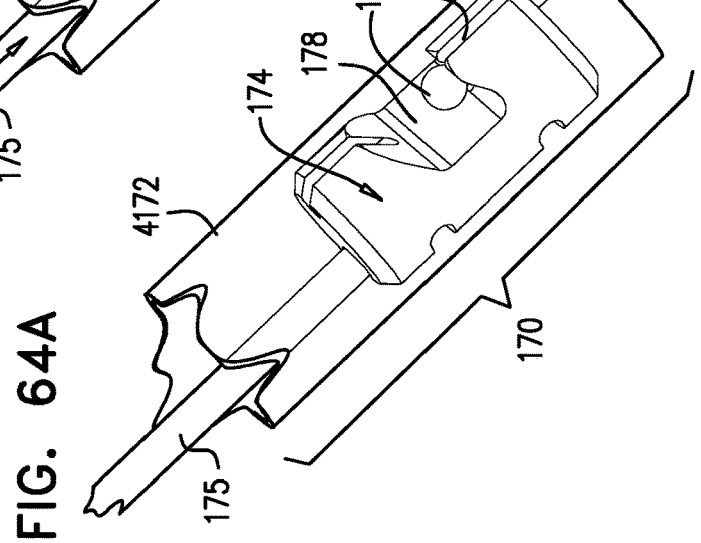

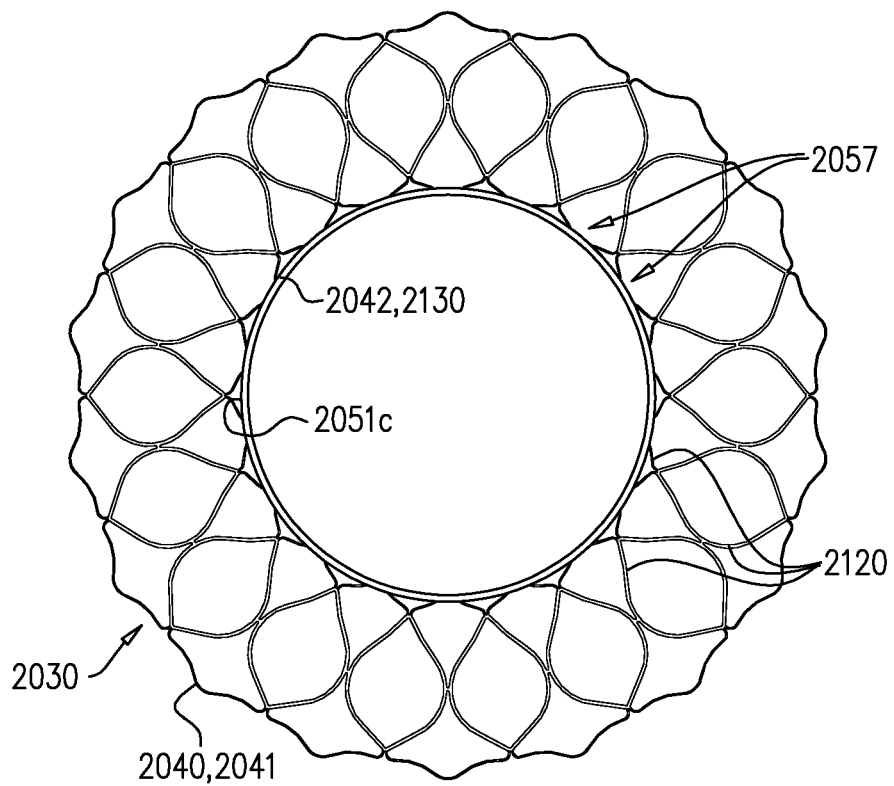
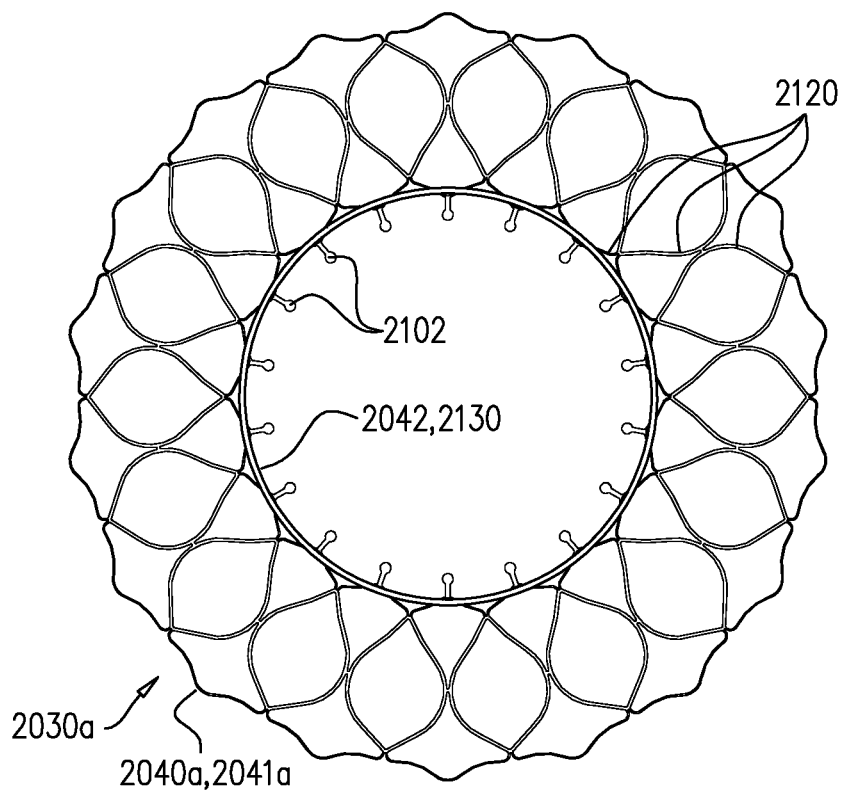

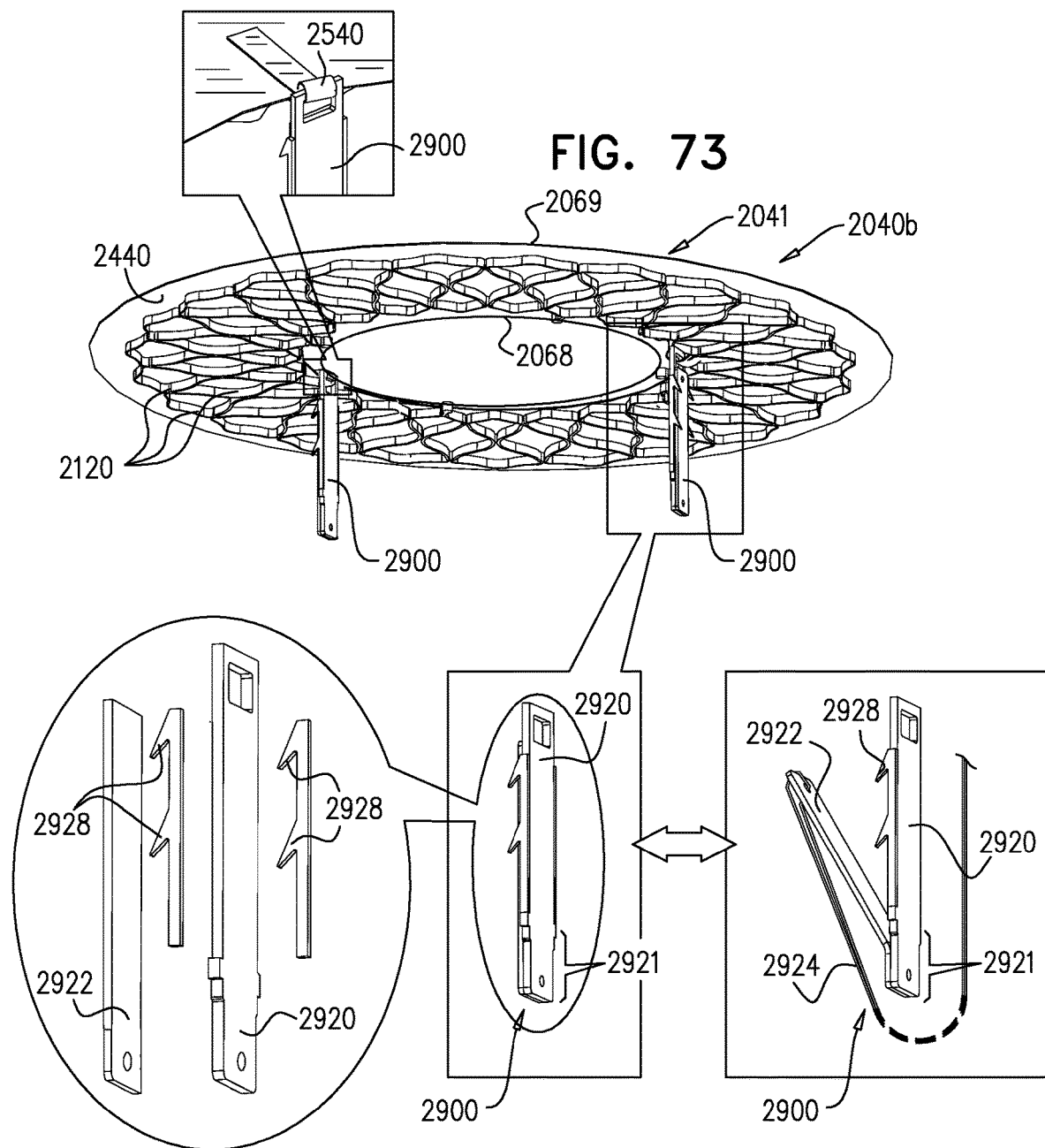

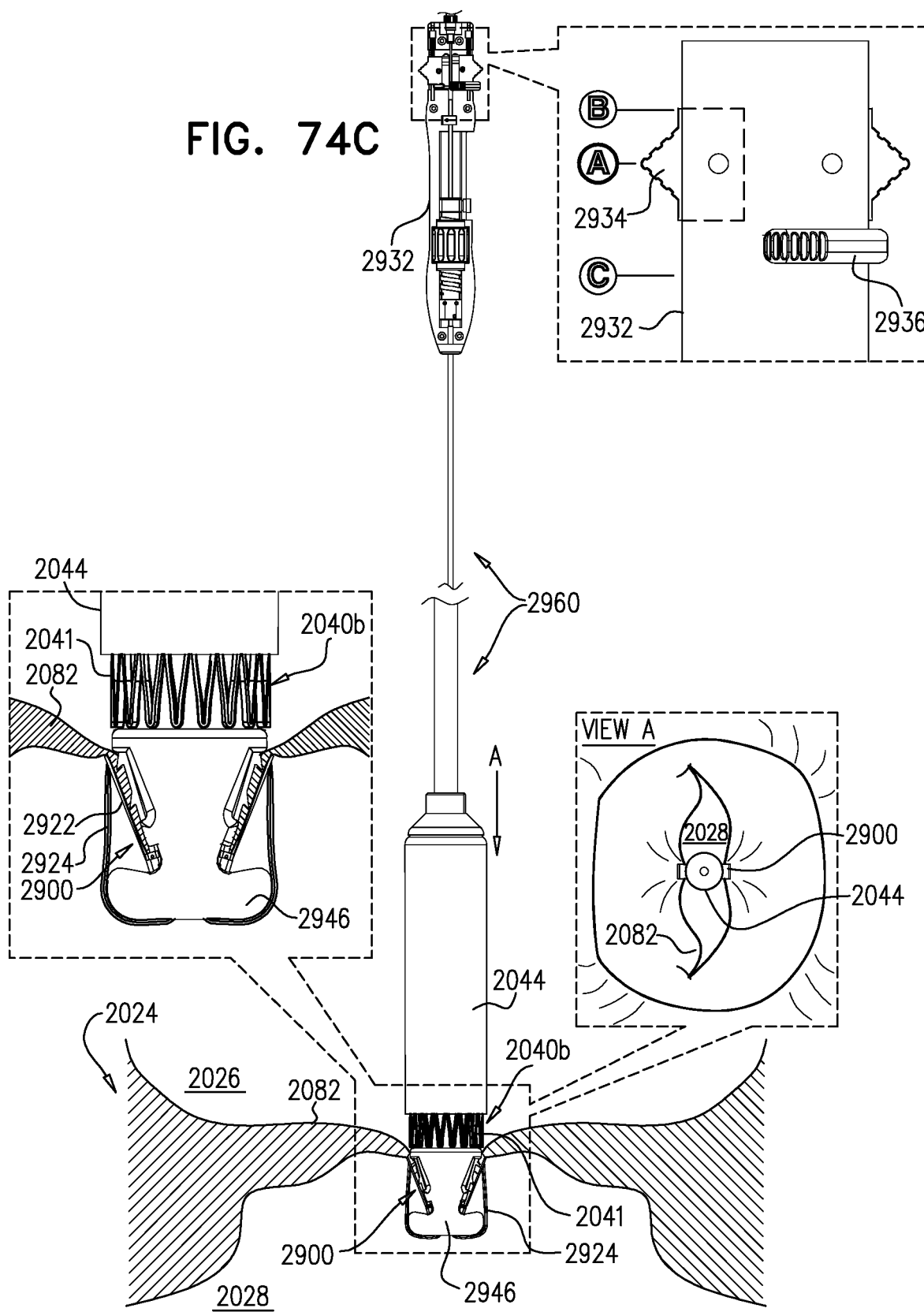

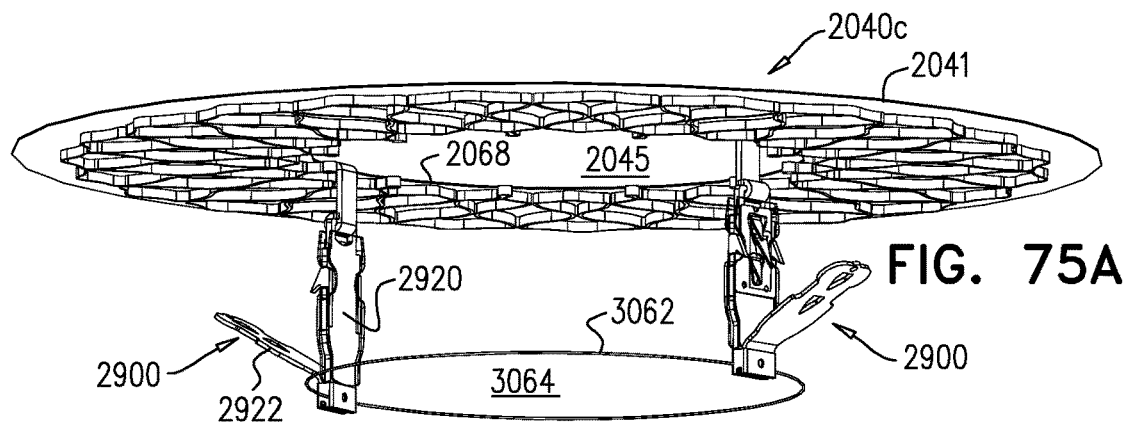
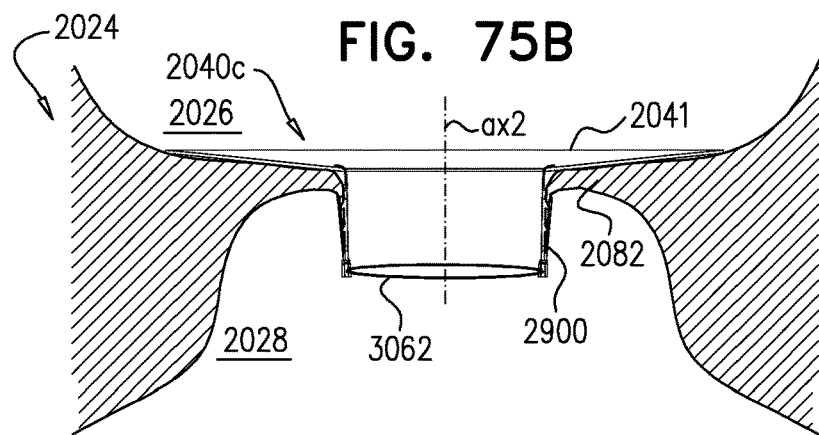
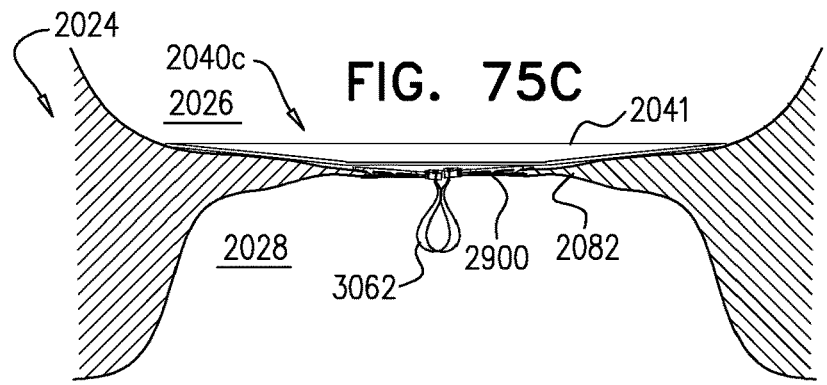
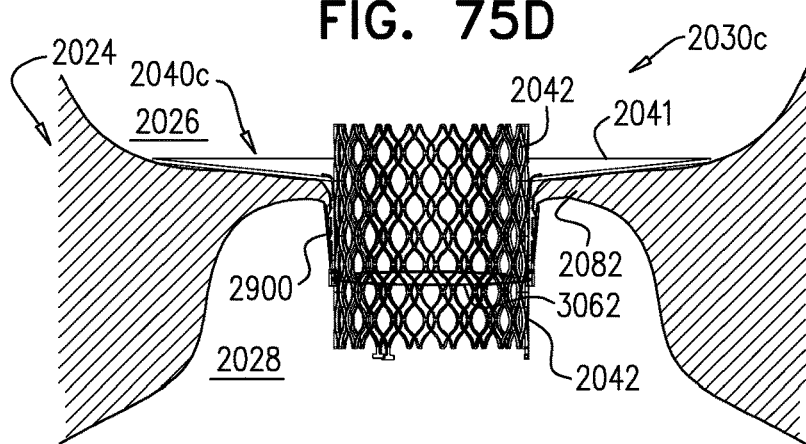

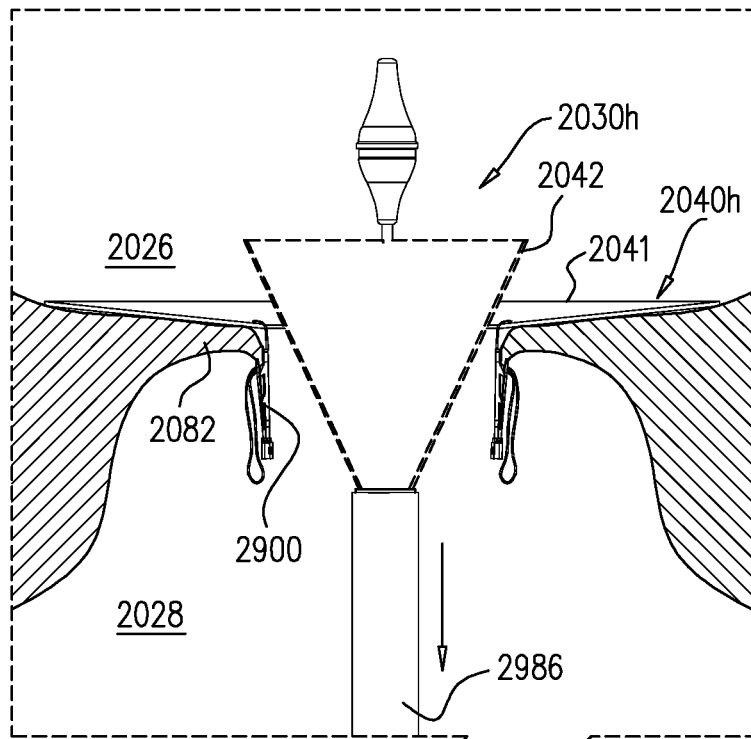
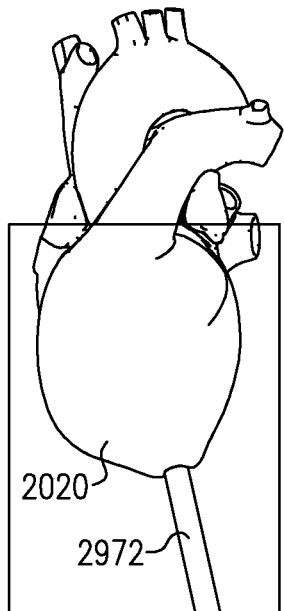
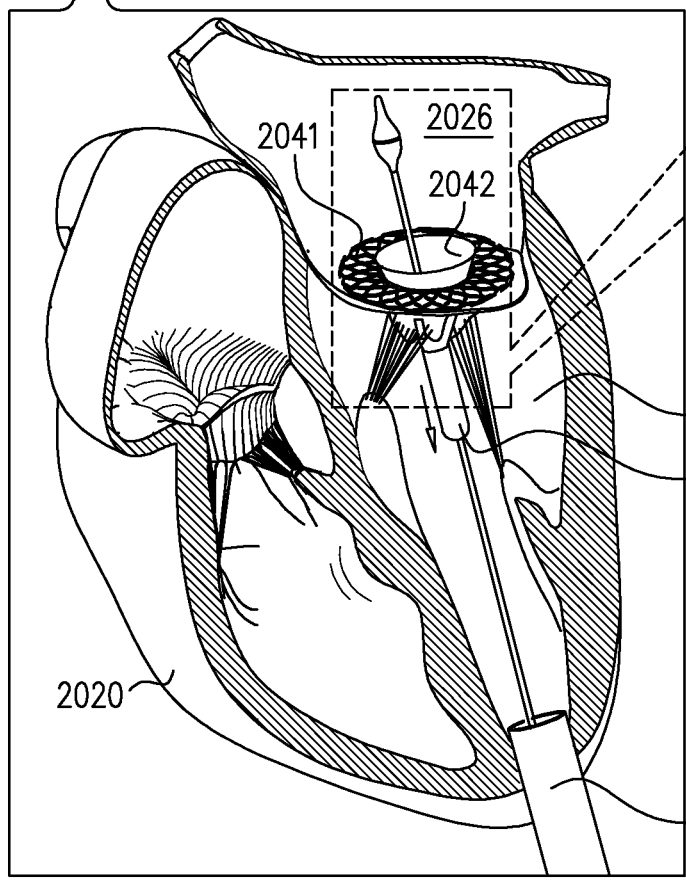
FIG. 76E

FIG. 76F
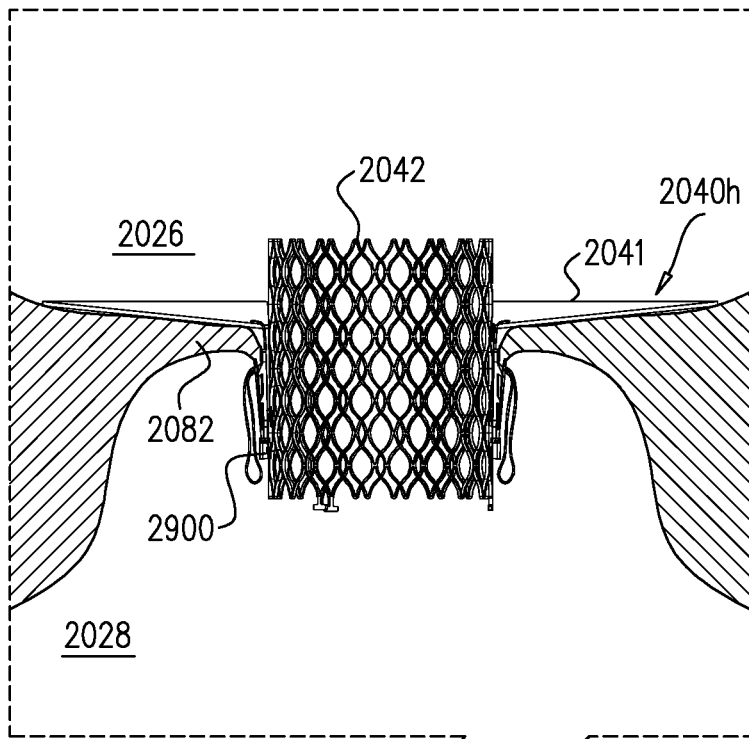
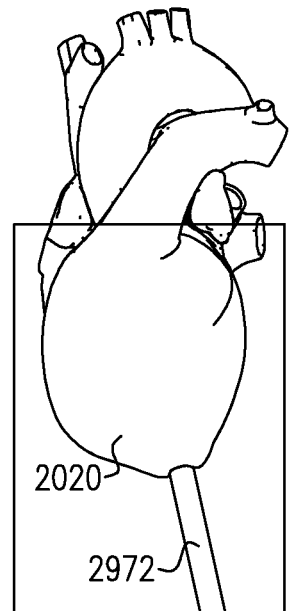
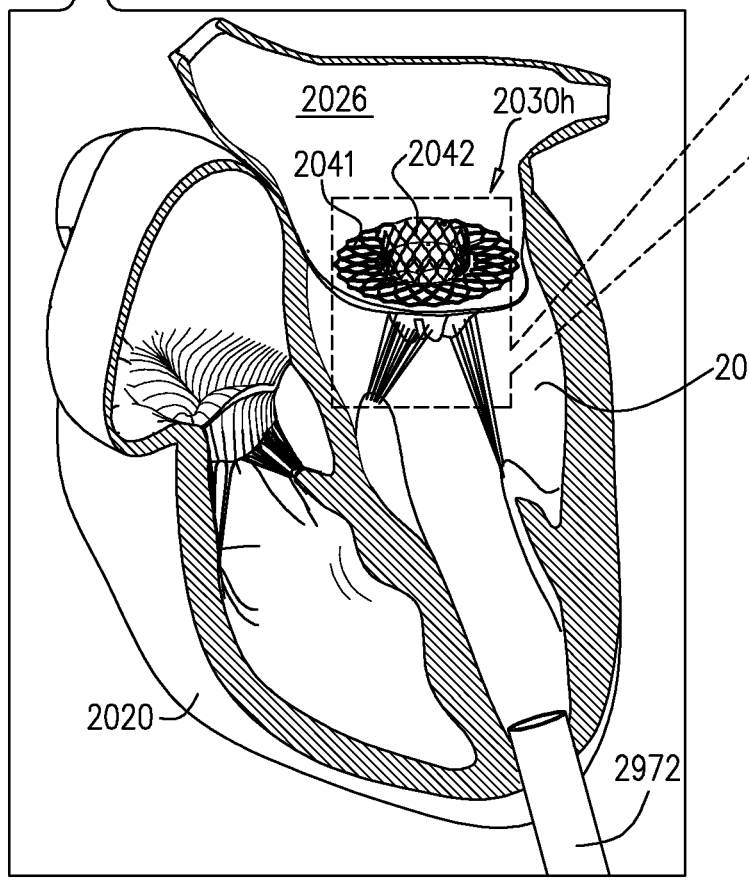

METHOD FOR USE AT A HEART VALVE

CROSS-REFERENCES TO RELATED APPLICATIONS

This application is a Continuation of U.S. Ser. No. 16/881,350 to HaCohen, filed May 22, 2020, which published as US 2020/0330221 and which is a Continuation of U.S. Ser. No. 16/460,313 to Gross et al., filed Jul. 2, 2019 (now U.S. Pat. No. 10,695,173), which is a Continuation of U.S. Ser. No. 16/045,059 to Gross et al., filed Jul. 25, 2018 (now U.S. Pat. No. 10,376,361), which is a Continuation of U.S. Ser. No. 15/213,791 to Gross et al., filed Jul. 19, 2016 (now U.S. Pat. No. 10,245,143), which is a Continuation of U.S. Ser. No. 14/237,264 to Gross et al., filed May 23, 2014 (now abandoned), which published as US 2014/0324164 and which is the US National Phase of PCT Application IL2012/000292 to Gross et al., filed Aug. 5, 2012, which published as WO 2013/021374 and which:
  (1) claims priority from:
    U.S. 61/515,372 to Gross et al., filed Aug. 5, 2011;
    U.S. 61/525,281 to Gross et al., filed Aug. 19, 2011;
    U.S. 61/537,276 to Gross et al., filed Sep. 21, 2011;
    U.S. 61/555,160 to Gross et al., filed Nov. 3, 2011;
    U.S. 61/588,892 to Gross et al., filed Jan. 20, 2012; and
    U.S. Ser. No. 13/412,814 to Gross et al., filed Mar. 6, 2012, (now U.S. Pat. No. 8,852,272) all of which are incorporated herein by reference; and
  (2) is a Continuation-In-Part of U.S. Ser. No. 13/412,814 to Gross et al., filed Mar. 6, 2012 (now U.S. Pat. No. 8,852,272).

This application is related to International Patent Application IL2012/000293 to Gross et al., entitled, "Percutaneous mitral valve replacement and sealing," filed Aug. 5, 2012, which published as WO 2013/021375.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications of the invention, a prosthetic valve support is provided for facilitating transluminal implantation of a prosthetic valve at a native valve (e.g., a native heart valve) of a subject. The prosthetic valve support is configured to be placed at the native valve, such as by placing an upstream support portion (e.g., an annular portion) of the prosthetic valve support against an upstream surface of the native valve (e.g., against a native valve annulus). The prosthetic valve is subsequently implanted at the native valve by coupling the prosthetic valve to the prosthetic valve support, such as by expanding the prosthetic valve in an opening defined by the prosthetic valve support. For some applications, the prosthetic valve support is couplable to the native valve, independently of the prosthetic valve. The implantation of the prosthetic valve at the native valve replaces native check valve functionality of the native valve with substitute check valve functionality of the prosthetic valve. For some applications, the prosthetic valve support and/or the prosthetic valve comprise tissue-engaging elements (e.g., support-anchoring elements, and valve-anchoring elements, respectively), such as anchors or clips.

Typically, the prosthetic valve is expanded within one or more openings defined by the prosthetic valve support, and coupling of the prosthetic valve to the prosthetic valve support is facilitated by radially-expansive force applied by the prosthetic valve against the prosthetic valve support. For some applications, additional coupling techniques, such as support-engaging elements, coupling leads, ratchet mechanisms, protrusions, and/or pockets are used.

For some applications, the prosthetic valve support is configured to receive, at different periods, more than one prosthetic valve. For example, a first prosthetic valve may be removed from the prosthetic valve support, and replaced with a second prosthetic valve. Alternatively, the first prosthetic valve may be left in place when the second prosthetic valve is implanted. For example, the prosthetic valve support may define more than one lumen, each lumen configured to receive a respective prosthetic valve. Alternatively, the prosthetic valve support may define a lumen that is configured (e.g., shaped) to receive a first valve at a first period, and a second valve at a second period.

For some applications, the prosthetic valve support comprises support-anchoring elements that are flexibly-coupled to the upstream support portion. For some such applications, the support-anchoring elements are configured to anchor the prosthetic valve support to the native valve, while allowing the leaflets of the native valve to continue to function, at least in part. For some applications, the prosthetic valve support comprises support-anchoring elements whose length is variable (e.g., adjustable).

For some applications of the invention, a cross-sectional area of the opening defined by the prosthetic valve support is adjustable.

For some applications of the invention, delivery apparatus for implantation of a medical device (e.g., a prosthetic valve and/or a prosthetic valve support) is provided, the delivery apparatus and/or the medical device being configured to allow retrievability of the medical device during one or more stages of delivery and/or deployment of the medical device.

There is therefore provided, in accordance with an application of the present invention, apparatus for use with a first prosthetic valve and a second prosthetic valve at a native heart valve of a subject, the apparatus including:
  a prosthetic valve support, shaped to define at least one lumen, and configured:
    to be implanted at the native valve,
    to facilitate, at a first period, implantation at the native valve of the first prosthetic valve, and
    to facilitate, at a second period, implantation at the native valve of the second prosthetic valve without removal of the first valve.

In an application, the prosthetic valve support is configured to facilitate the implantation of the first prosthetic valve by being configured to receive the first prosthetic valve in the at least one lumen.

In an application, the prosthetic valve support includes a seal, which:
does not cover at least a first region of the at least one lumen,
covers at least a second region of the at least one lumen, and
is configured to be openable at least the second region, and the prosthetic valve support is configured:
to facilitate the implantation of the first prosthetic valve by being configured to receive the first prosthetic valve in the first region, and
to facilitate the implantation of the second prosthetic valve by being configurable, by opening of the seal, to receive the second prosthetic valve in the second region.

In an application, the at least one lumen is shaped to define at least a first lumen and a second lumen, and the seal covers the second lumen.

In an application, the first region and the second region are defined by the same lumen.

In an application, the apparatus includes a covering that covers the prosthetic valve support, and the seal is defined by a portion of the covering.

In an application, the prosthetic valve support is configured to receive the first prosthetic valve in the lumen, and is configured to facilitate the implantation of the second prosthetic valve by being configured to receive the second prosthetic valve in the same lumen.

In an application, the apparatus further includes the first and second prosthetic valves, the first prosthetic valve defines a lumen therethrough, and the second prosthetic valve is configured to be implanted in the lumen of the first prosthetic valve.

In an application:
the second prosthetic valve defines a lumen therethrough,
after the first period, and before the second period, the lumen of the first prosthetic valve has a first diameter, and
the prosthetic valve support is configured such that, after the second period, the lumen of the second prosthetic valve has a diameter that is at least as great as the first diameter.

In an application, the prosthetic valve support is configured such that, after the second period, the lumen of the second prosthetic valve has a diameter that is greater than the first diameter.

In an application, the prosthetic valve support includes a weak zone that circumscribes and defines the lumen, and is configured to facilitate enlarging of the lumen.

In an application, the prosthetic valve support is configured to facilitate enlarging of the lumen by being configured to be deformed by a radially-expansive force applied from within the lumen.

In an application, the prosthetic valve support includes a cylindrical element:
shaped to define the lumen,
configured to receive the first prosthetic valve at a first portion of the lumen, and
configured to receive the second prosthetic valve support at a second portion of the lumen.

In an application, the cylindrical element is configured to receive the first prosthetic valve at a first longitudinal portion of the lumen, and to receive the second prosthetic valve at a second longitudinal portion of the lumen.

There is further provided, in accordance with an application of the present invention, apparatus for use with a prosthetic heart valve for implantation at a native heart valve of a subject, the apparatus including:
a core, shaped to define at least one conduit therethrough; and
one or more control filaments, slidable through the conduit, and reversibly couplable to the prosthetic valve,
the apparatus being configured such that sliding the control filaments in a first direction through the conduit facilitates expansion of the prosthetic valve, and sliding the control filaments in a second direction through the conduit facilitates compression of the prosthetic valve.

In an application, the apparatus is configured such that sliding the control filaments in the first direction through the conduit facilitates radial expansion of the prosthetic valve away from the core.

In an application, the apparatus further includes the prosthetic valve, a delivery tube and a pushing member, and:
the prosthetic valve has an expanded configuration and a compressed configuration,
the delivery tube is configured to be transluminally delivered to the native valve,
the pushing member includes the core,
the pushing member is configured:
to be disposed within the delivery tube,
to be fixedly coupled, within the delivery tube, to the prosthetic valve in the compressed configuration thereof,
when fixedly coupled to the prosthetic valve, to facilitate movement of the prosthetic valve with respect to the delivery tube, and
to be decouplable from the prosthetic valve.

In an application, the apparatus further includes one or more release wires, configured to facilitate decoupling of the control filaments from the prosthetic valve.

In an application, the apparatus further includes one or more guide elements, radially extendable from the core, and configured to guide expansion of the prosthetic valve away from the core.

In an application, the guide elements are configured to automatically radially retract when the control filaments are decoupled from the prosthetic valve.

There is further provided, in accordance with an application of the present invention, apparatus for use at a native heart valve of a subject, the apparatus including:
a prosthetic valve, configured to be transluminally delivered to, and implantable at, the native valve of the subject;
a prosthetic valve support, configured to be transluminally delivered to the native valve of the subject, and to facilitate implantation of the prosthetic valve;
at least one coupling lead, extending between the prosthetic valve and the prosthetic valve support; and
a ratchet housing, slidably coupled to the coupling lead, and configured to be slidable over the coupling lead in a first direction, and inhibited from sliding over the coupling lead in an opposite direction,
the apparatus being configured such that sliding of the ratchet housing over the coupling lead in the first direction facilitates coupling of the prosthetic valve to the prosthetic valve support.

In an application, the coupling lead extends between a proximal portion of the prosthetic valve, and the prosthetic valve support.

In an application, the prosthetic valve support includes one or more support-anchoring elements, configured to couple the prosthetic valve support to the native valve, and the coupling lead extends between the prosthetic valve and the support-anchoring elements.

There is further provided, in accordance with an application of the present invention, apparatus for use with a native heart valve of a subject, the apparatus including:

a first expandable prosthetic valve component, including a crimpable frame, and configured to be transcatheterally advanceable toward the native valve while the first prosthetic valve component is in a crimped state thereof;

a second expandable prosthetic valve component, including a crimpable frame, and configured to be transcatheterally advanceable toward the native valve, placeable in the native valve while the second prosthetic valve component is in a crimped state thereof, and couplable to the first prosthetic valve component, expansion of the second prosthetic valve component facilitating coupling of the second prosthetic valve component to the first prosthetic valve component; and one or more tissue-engagement elements, coupled to at least one of the prosthetic valve components, the tissue-engagement elements configured, when the prosthetic valve component is in an expanded state thereof, to extend from the prosthetic valve component, and to inhibit a proximal movement of the prosthetic valve component.

There is further provided, in accordance with an application of the present invention, apparatus for use with a prosthetic valve for implantation at a native valve of a subject, the native valve (1) defining an orifice, (2) including at least one native leaflet, having a native beating, and (3) having a native blood flow regulation functionality, the apparatus including:

a prosthetic valve support, including:
an upstream support portion, configured to be placed against an upstream side of the native valve, to have an inner perimeter that defines an opening that is configured to receive the prosthetic valve, and
at least one clip, configured to be coupled to a native leaflet of the native valve, the clip including a plurality of clip arms, at least one clip arm coupled to a clip-controller interface; and
a clip controller, couplable to the clip-controller interface, and configured to control a relative angular disposition between the clip arms.

For some applications, techniques described herein are practiced in combination with techniques described in one or more of the references cited in the Background section and Cross-references section of the present patent application.

BRIEF DESCRIPTION OF THE DRAWINGS

FIGS. 1A-H are schematic illustrations of sequential steps in the implantation of an implant comprising a prosthetic valve and a prosthetic valve support, in accordance with some applications of the present invention;

FIGS. 13A-D are schematic illustrations of a prosthetic valve support, comprising an asymmetric prosthetic valve support, in accordance with an application of the invention;

FIGS. 17A-D are schematic illustrations of prosthetic valve supports, comprising tissue-engaging elements, which comprise support-anchoring elements, comprising length-adjustable holding elements, in accordance with some applications of the invention;

FIGS. 25A-E are schematic illustrations of a retrieval device, and sequential steps in the use thereof, in accordance with some applications of the invention;

FIGS. 27A-D are schematic illustrations of delivery apparatus, in accordance with some applications of the invention;

FIGS. 29A-F are schematic illustrations of the deployment of a prosthetic valve in the lumen of another prosthetic valve, and of a prosthetic valve support configured to facilitate such deployment, in accordance with some applications of the invention;

FIGS. 31A-C are schematic illustrations of a flexible delivery tube, configured to facilitate removal thereof from a subject, in accordance with some applications of the invention;

FIGS. 32A-C are schematic illustrations of a compressible delivery tube, configured to facilitate removal thereof from a subject, in accordance with some applications of the invention;

FIGS. 33A-C are schematic illustrations of a dismantling delivery tube, configured to facilitate removal thereof from a subject, in accordance with some applications of the invention;

FIG. 34 is a schematic illustration of a prosthetic valve, comprising a leaflet-engaging element, in accordance with some applications of the invention;

FIGS. 36A-D are schematic illustrations of a prosthetic valve support, comprising support-anchoring elements and stabilizing legs, in accordance with some applications of the invention;

FIGS. 37A-H are schematic illustrations of a prosthetic valve support, comprising support-anchoring elements and stabilizing legs, and sequential steps in the implantation thereof, in accordance with some applications of the invention;

FIGS. 38A-H are schematic illustrations of a prosthetic valve support, comprising support-anchoring elements and stabilizing legs, and sequential steps in the implantation thereof, in accordance with some applications of the invention;

FIGS. 42A-B are schematic illustrations of a prosthetic valve, and a prosthetic valve support, comprising support-anchoring elements that are couplable to the prosthetic valve, in accordance with some applications of the invention;

FIGS. 44A-B are schematic illustrations of a prosthetic valve support, comprising support-anchoring elements, and a prosthetic valve, comprising valve-anchoring elements that are couplable to the tissue-engaging elements of the prosthetic valve support, in accordance with some applications of the invention;

FIGS. 47A-C are schematic illustrations of sequential steps in the implantation of an implant, comprising a prosthetic valve and a prosthetic valve support, in accordance with some applications of the invention;

FIGS. 48A-C are schematic illustrations of sequential steps in the implantation of an implant, comprising a prosthetic valve and a prosthetic valve support, in accordance with some applications of the invention;

FIG. 52 is a schematic illustration of the prosthetic valve, in accordance with some applications of the invention;

FIGS. 53A-C are schematic illustrations of the prosthetic valve, comprising tissue-engaging elements, in accordance with some applications of the invention;

FIGS. 57A-D are schematic illustrations of the prosthetic valve, comprising tissue-engaging elements, in accordance with some applications of the invention;

FIGS. 59A-B are schematic illustrations of the prosthetic valve support, comprising tissue-engaging elements, in accordance with some applications of the invention;

FIGS. 61A-C are schematic illustrations of the prosthetic valve support, comprising tissue-engaging elements, in accordance with some applications of the invention;

FIGS. 62A-D are schematic illustrations of a delivery device for the delivery and deployment of an expandable medical device, in accordance with some applications of the invention;

FIGS. 63A-B are schematic illustrations of the delivery device for the delivery and deployment of an expandable medical device, in accordance with some applications of the invention;

FIGS. 64A-C, 65A-B, 66A-B, and 67A-B are schematic illustrations of a locking mechanism for delivery of an expandable medical device, in accordance with some applications of the invention;

FIGS. 72A-D are schematic illustrations of an implant, comprising a prosthetic valve support and a prosthetic valve, in accordance with some applications of the invention;

FIG. 73 is a schematic illustration of a prosthetic valve support, for use with a prosthetic valve, in accordance with some applications of the invention;

FIGS. 74A-L are schematic illustrations of steps in the implantation of an implant, comprising a prosthetic valve and a prosthetic valve support, in a native valve of a subject, in accordance with some applications of the invention;

FIGS. 75A-D are schematic illustrations of an implant, comprising a prosthetic valve support and a prosthetic valve, and steps in the implantation thereof, in accordance with some applications of the invention;

FIGS. 76A-F are schematic illustrations of steps in the implantation of an implant, comprising a prosthetic valve and a prosthetic valve support, in a native valve of a subject, in accordance with some applications of the invention;

DETAILED DESCRIPTION OF EMBODIMENTS

Figure 1A:
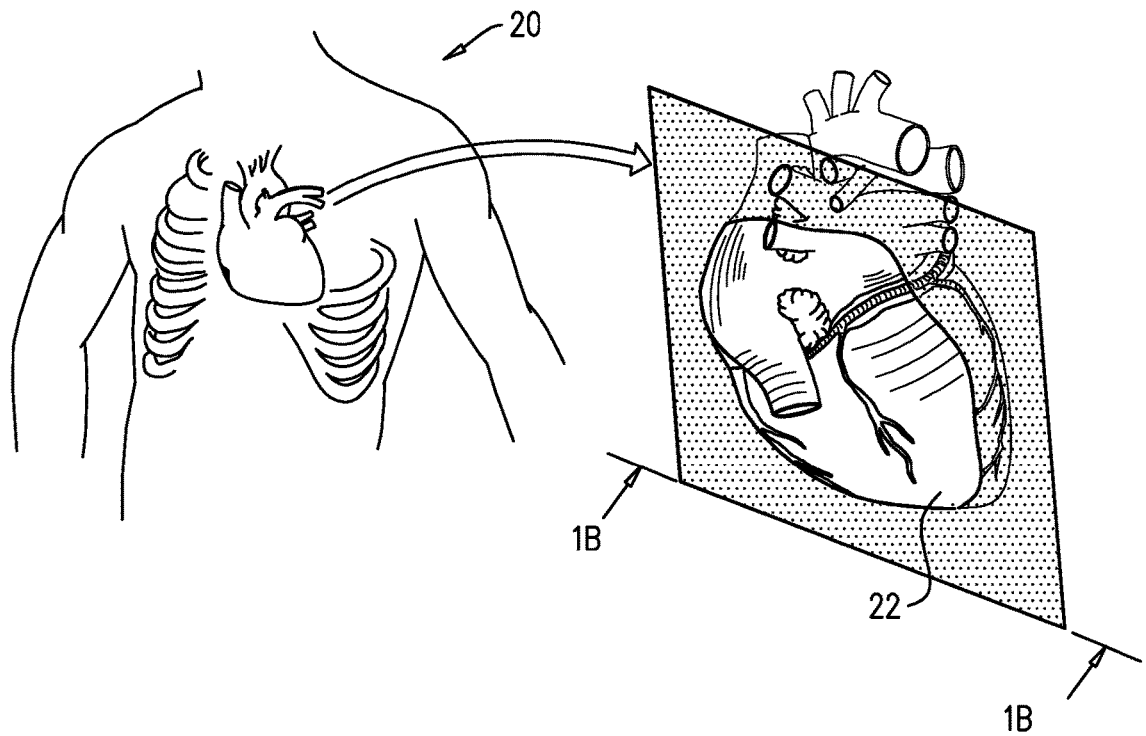

Reference is made to FIGS. 1A-H, which are schematic illustrations of sequential steps in the implantation in a native heart valve 23 of the heart 22 of a subject 20 of an implant 30, comprising (1) a first prosthetic valve component, i.e., prosthetic valve support 40, and (2) a second prosthetic valve component, i.e., a prosthetic valve 42, in accordance with some applications of the present invention. For such applications of the present invention, native valve 23 includes a native mitral valve 24 by way of illustration and not limitation; the scope of the present invention includes implanting implant 30 in other valves of the heart (e.g., the tricuspid valve, the pulmonary valve, or the aortic valve). FIG. 1A illustrates a cross-section through heart 22 of the subject which is used throughout FIGS. 1B-G to illustrate the implantation procedure. As shown in the cross-sectional illustration, native mitral valve 24 includes native leaflets 82, which are supported by native chordae tendineae 80.

Figure 1B:
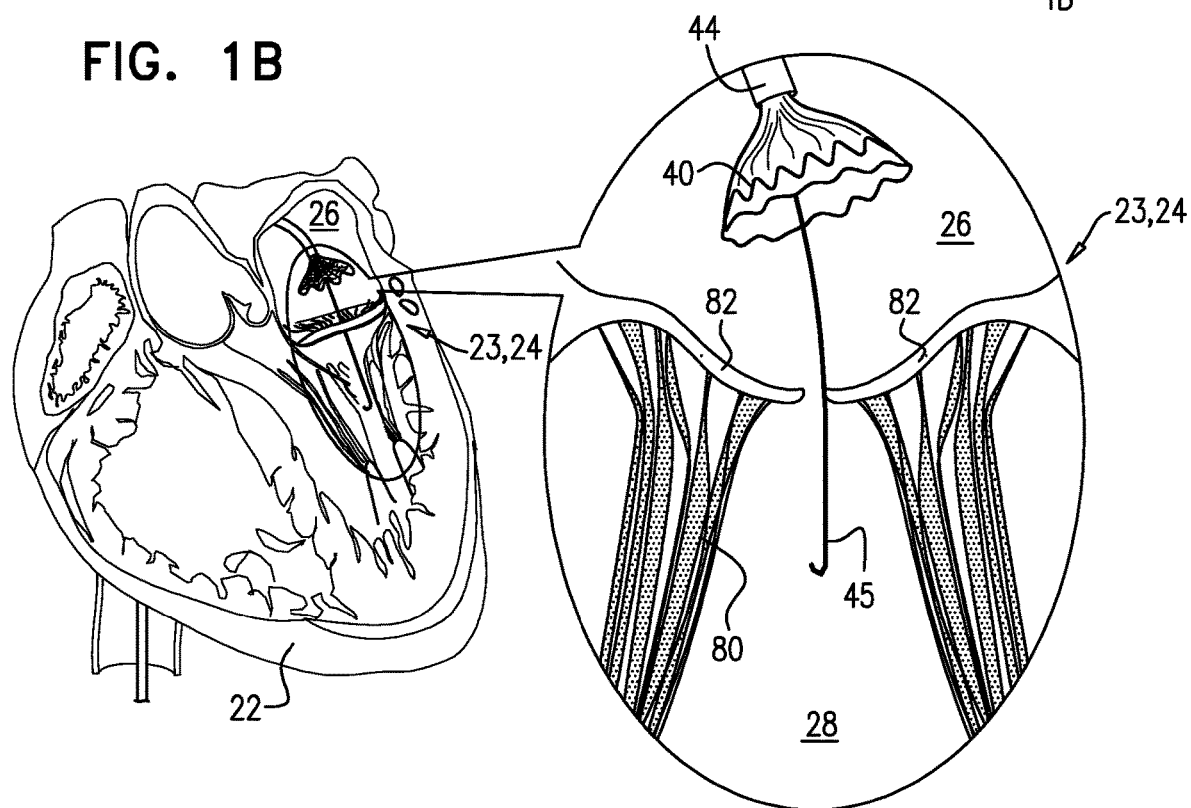

FIG. 1B shows prosthetic valve support 40 being deployed in a left atrium 26. Prior to deployment, support 40 is percutaneously (e.g., transcatheterally) advanced into left atrium 26, typically via overtube 44. In some applications of the present invention, the advancement of overtube 44 toward heart valve 23 is preceded by advancement of a guidewire 45 through vasculature of the subject. Typically, guidewire 45 is used to guide overtube 44 through the vasculature. During its deployment, support 40 is moved distally (e.g., by a pushing coupling element, not shown for clarity of illustration and described hereinbelow), such that support 40 emerges from the distal end of overtube 44. Support 40 is typically expandable, and typically comprises a wire frame which comprises a shape-memory material such as, but not limited to, nickel titanium (nitinol). For some applications of the invention, support 40 comprises nickel cobalt, stainless steel and/or titanium. As support 40 gradually emerges from overtube 44, it gradually expands to assume an expanded configuration.

Figure 1C:
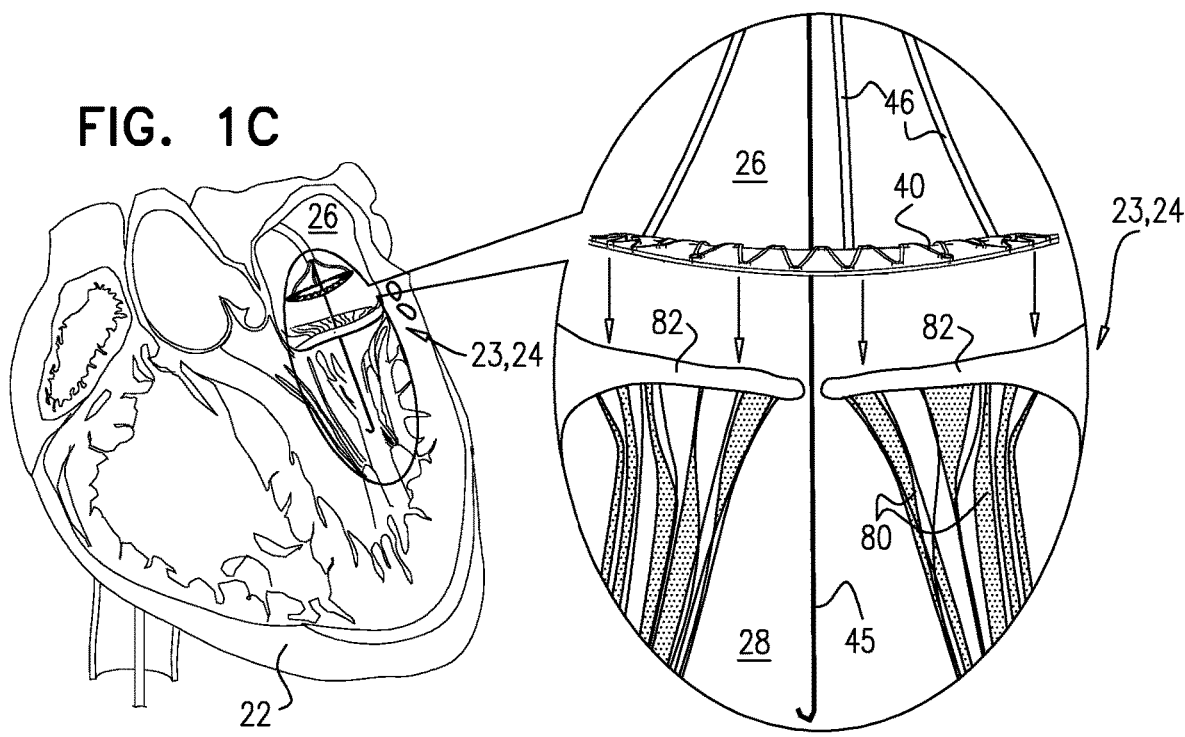

FIG. 1C shows support 40 reversibly coupled to one or more holding members 46, which exert a distal pushing force that causes support 40 to emerge from within overtube 44. Once fully exposed from within overtube 44, support 40 expands to assume the expanded configuration, as shown. In its expanded state, support 40 is annular and is shaped so as to define a lumen therethrough. Typically, prosthetic valve support 40 is shaped to define an outer edge 69 and an inner edge 68 (see FIG. 1H). Outer edge 69 typically defines the diameter of the annular prosthetic valve support, and inner edge 68 typically defines the diameter of the lumen in which prosthetic valve 42 is typically disposed. As shown in FIG. 1C, once support 40 is fully exposed from within overtube 44, holding members 46 continue to push support 40 distally (i.e., in the direction as indicated by the arrows) until support 40 is positioned against an annulus of native heart valve 23.

Support 40 is held against the annulus of native valve 23 (e.g., by holding members 46) such that the lumen of support 40 aligns with the lumen of the native valve, and such that atrium 26 and ventricle 28 remain in fluid communication.

Figure 1D:
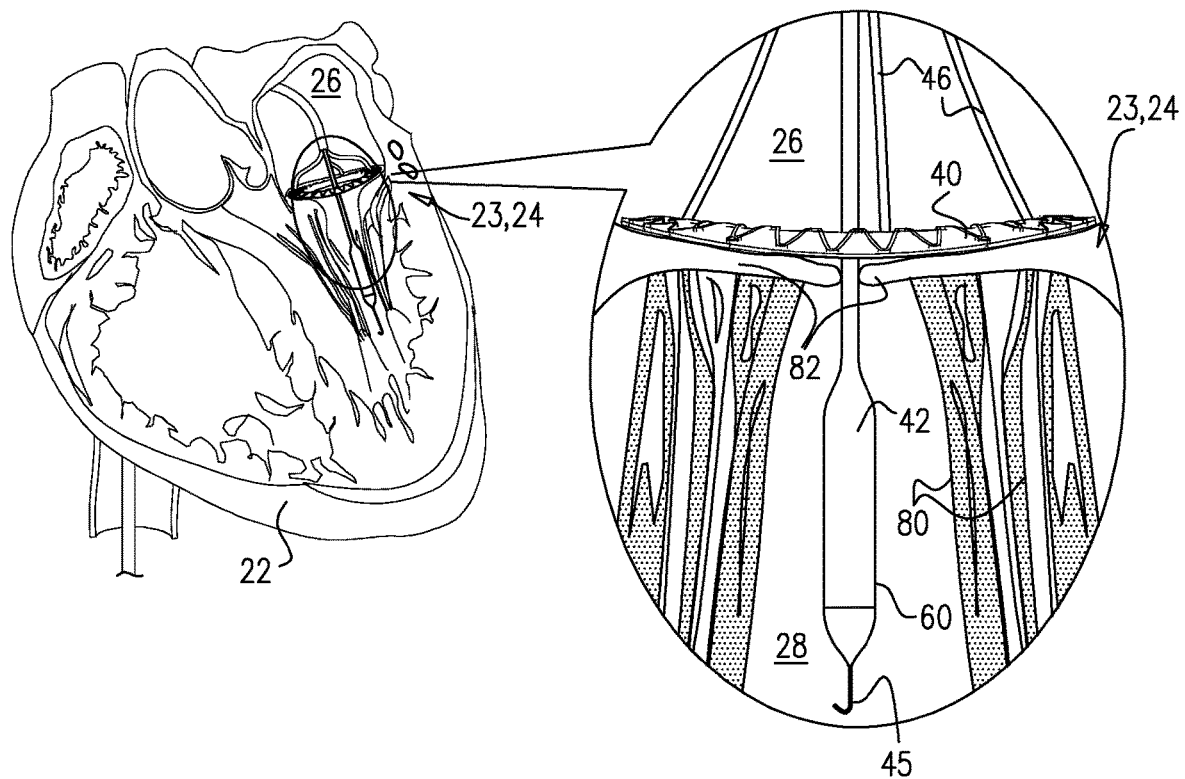

Following the positioning of support 40 against the annulus of the native valve, prosthetic valve 42 is percutaneously (e.g., transcatheterally) advanced and delivered toward the native valve, typically along guidewire 45, as shown in FIG. 1D.

Prosthetic valve 42 is typically expandable, and typically comprises a wire frame which comprises a shape-memory material such as, but not limited to, nickel titanium (nitinol). For some applications of the invention, prosthetic valve 42 comprises nickel cobalt, stainless steel and/or titanium. During the advancing, prosthetic valve 42 is disposed in a distal portion of a delivery tube 60, which holds the prosthetic valve in a compressed (e.g., crimped) configuration. Delivery tube 60 is slidably advanceable within overtube 44. Prosthetic valve 42 is typically delivered through the native valve and into ventricle 28, as shown in FIG. 1D. Typically, prosthetic valve 42 is delivered to the native valve while support 40 is held against the annulus of native valve 23 by holding members 46.

Figure 1E:
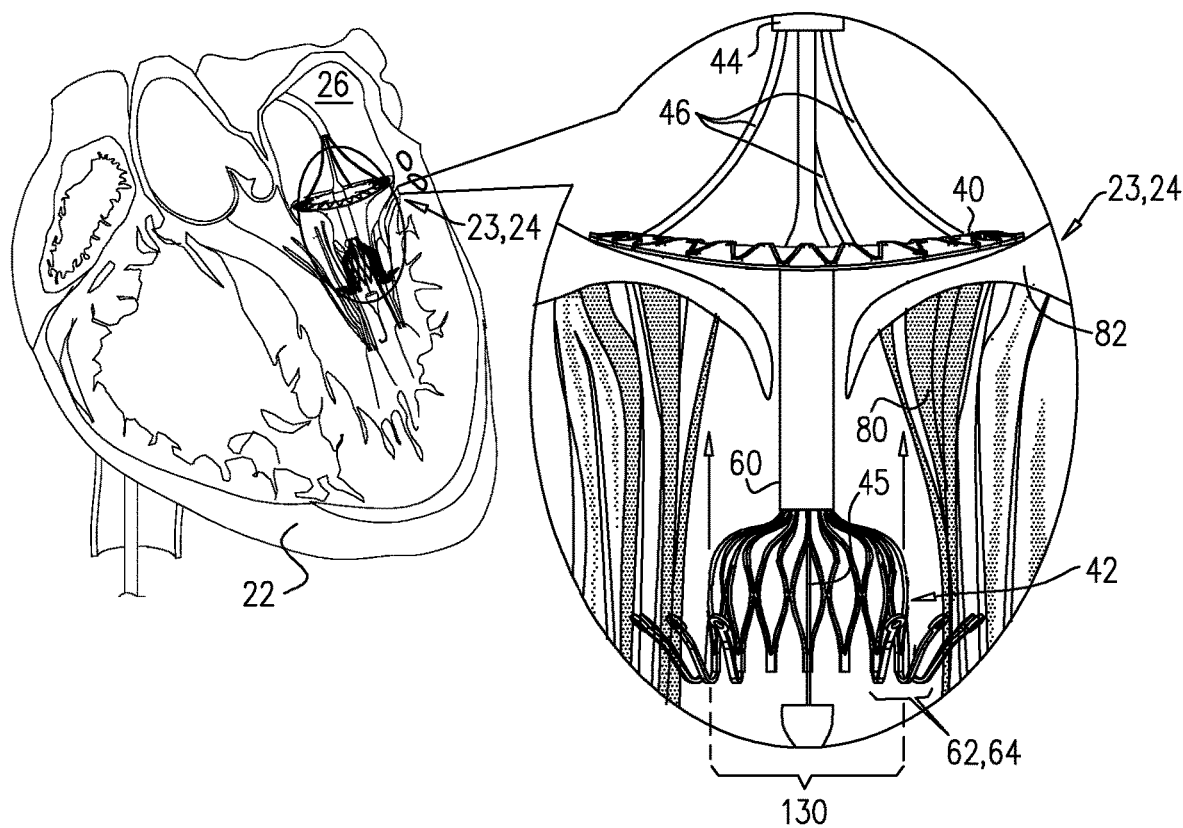

FIG. 1E shows prosthetic valve 42 being partially deployed from within delivery tube 60. As prosthetic valve 42 expands, prosthetic valve 42 expands toward assuming an expanded configuration. Prosthetic valve 42 comprises a primary structural element 130, which is typically cylindrical, prismatic, or any other suitable shape, and is shaped so to define a lumen. Prosthetic valve components (e.g., leaflets; not shown for clarity of illustration) are typically disposed within the lumen of the prosthetic valve, are coupled to a surface of structural element 130 defining the lumen, and regulate blood flow therethrough.

Typically, a plurality of tissue-engaging elements 62 are disposed at a distal portion of the primary structural element 130 of prosthetic valve 42. For applications in which prosthetic valve 42 comprises tissue-engaging elements 62, tissue-engaging elements 62 comprise valve-anchoring elements 64. For such applications of the present invention, primary structural element 130 of prosthetic valve 42 is generally cylindrical (e.g., shaped so as to define a right circular cylinder), and anchoring elements 64 protrude radially from a surface of the cylinder. It is to be noted that although prosthetic valve 42 is shown comprising tissue-engaging elements 62, the scope of the present application includes prosthetic valves with no tissue-engaging elements 62.

Figure 1F:
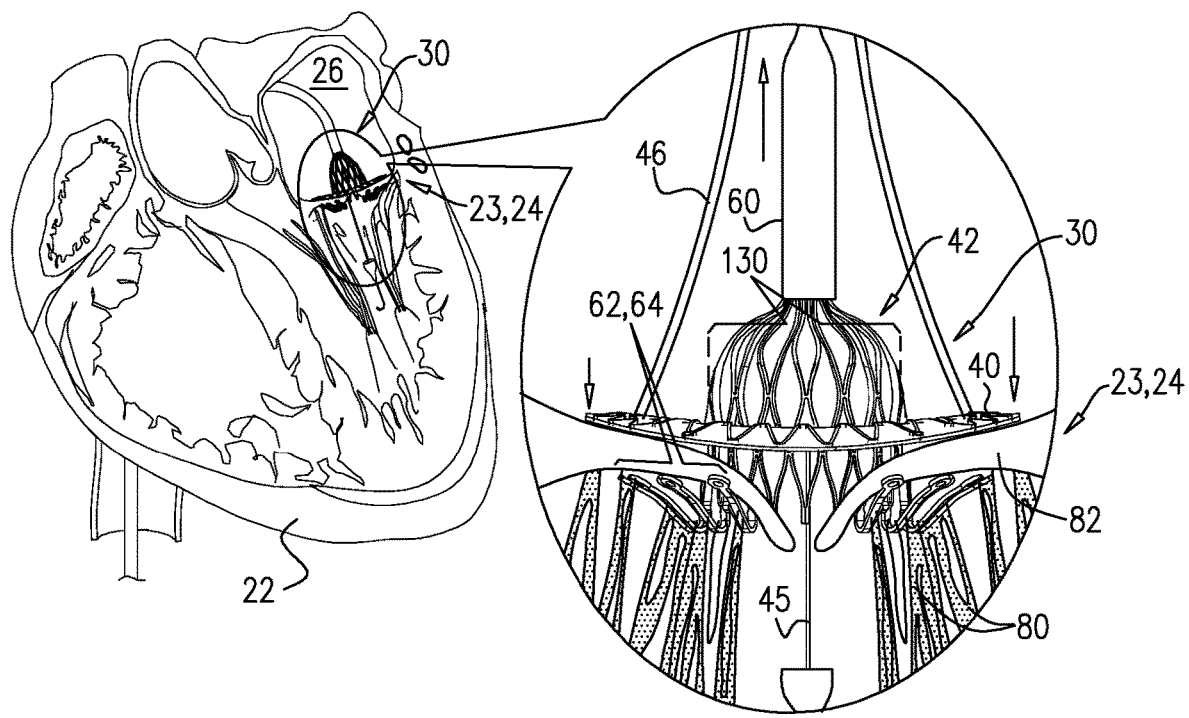

FIG. 1F shows prosthetic valve 42 being moved proximally, such that at least part of primary structural element 130 is disposed in the respective lumens of native valve 23 and prosthetic valve support 40, and such that valve-anchoring elements 64 contact the ventricular side of the native valve. Such contacting of elements 64 with the ventricular side of the native valve restricts further undesired atrial (i.e., proximal) movement of the prosthetic valve. Typically, the contact between valve-anchoring elements 64 and the ventricular side of the native valve occurs by valve-anchoring elements 64 protruding between chordae tendineae 80 and capturing leaflets 82 of the native valve. Responsively to the capturing by valve-anchoring elements 64, leaflets 82 are typically pushed proximally and/or outward by the prosthetic valve. In some applications of the invention, leaflets 82 are held against the outer surface of primary structural element 130 by valve-anchoring elements 64, so as to reduce blood flow between native leaflets 82 and prosthetic valve 42. In an alternative application of the invention, rather than being partially deployed in the ventricle and subsequently moved proximally (as described with reference to FIGS. 1E-F), prosthetic valve 42 is deployed directly in the lumen of the native valve.

Following the capturing of native leaflets 82, prosthetic valve 42 is then fully exposed from within delivery tube 60 (by pushing valve 42 relative to delivery tube 60 or by retracting delivery tube 60 with respect to valve 42) and is allowed to expand further. FIG. 1G shows prosthetic valve 42 in a deployed and expanded configuration after being fully exposed from within delivery tube 60. The expansion of prosthetic valve 42 exerts a radial force against support 40, thereby facilitating coupling of prosthetic valve 42 to support 40. Implant 30, comprising prosthetic valve 42 and support 40, is secured in place by sandwiching the native valve by the components of implant 30. That is, (1) implant 30 is inhibited from ventricular (i.e., distal) movement by support 40 and the radial force of prosthetic valve 42 exerted on support 40, and (2) implant 30 is inhibited from atrial (i.e., proximal) movement by valve-anchoring elements 64.

For some applications of the present invention, support 40 prevents valve 42 from expanding to assume a fully-expanded configuration (i.e., a configuration to which valve 42 would otherwise expand without being impeded by support 40 or tissue). In such applications, the radial force exerted by support 40 on valve 42 facilitates coupling and sealing between support 40 and valve 42 (for example, by increasing friction between support 40 and valve 42), and facilitates implantation of implant 30 at native valve 23.

FIG. 1H shows implant 30 following implantation in the mitral valve of the subject. This figure is a transverse atrial cross-section, showing prosthetic valve support 40 in contact with the atrial side of the native valve. Prosthetic valve 42 is expanded, and is disposed in, and coupled to, prosthetic valve support 40. Tissue-engaging elements 62, comprising valve-anchoring elements 64, are disposed on the ventricular side of the native valve (as described hereinabove with reference to FIGS. 1F-G), and are therefore illustrated in phantom. Valve-anchoring elements 64 are typically arranged in two clusters, each cluster being disposed on opposite sides of prosthetic valve 42.

Typically, when deployed as shown, prosthetic valve 42 is configured to be aligned with the native valve such that valve-anchoring elements 64 protrude toward, and engage leaflets 82 of the native valve. In some applications of the present invention, valve-anchoring elements 64 protrude toward, and engage, commissures 84 of the native valve. In some applications of the invention, a single valve-anchoring element 64 is disposed on each side of the prosthetic valve. It is to be noted that the scope of the present application includes any other suitable arrangement of valve-anchoring elements 64 with respect to valve 42. Typically, valve-anchoring elements 64 capture leaflets 82 of the native valve, holding them clear of the flow of blood through the prosthetic valve and the left ventricular outflow tract (LVOT).

For clarity of illustration, the lumen defined by prosthetic valve 42 is shown as being empty, such that ventricle 28 is visible. However, as described hereinabove, prosthetic valve 42 typically comprises valve components (e.g., prosthetic valve leaflets, not shown in FIG. 1H), that are disposed in the lumen of prosthetic valve 42, coupled to structural element 130, and configured to regulate blood flow through prosthetic valve 42.

Reference is again made to FIGS. 1A-H. For some applications, as described hereinabove, valve-anchoring elements 64 function so as to (1) prevent proximal migration of prosthetic valve 42 into the subject's atrium, while (2) creating a seal between the native valve 23 and prosthetic valve 42 by generally clamping native leaflets 82 between valve-anchoring elements 64 and primary structural element 130, valve support 40, and/or native valve annulus.

For other applications, prevention of proximal migration of valve 42 is maintained, while movement of native leaflets 82 with respect to prosthetic valve 42 is allowed. For example, valve-anchoring elements 64 may have the aforementioned functionalities by having lengths of less than 5 mm, and/or by having a total width of each cluster of valve-anchoring elements (corresponding to respective leaflets of the native valve) being less than 5 mm. For example, the valve may include a single valve-anchoring element 64 corresponding to each leaflet of the native valve, the width of each of the single valve-anchoring elements being less than 1 mm. Thus, the valve may be stopped from proximally migrating into the atrium by the valve-coupling elements preventing the distal end of the valve from migrating further proximally than edges of native leaflets of the valve. Furthermore, the valve-anchoring elements may allow movement of the native leaflets with respect to the prosthetic valve by not generally squeezing the native leaflets between the valve-coupling elements and primary structural element 130 of the prosthetic valve. In other applications of the invention, prosthetic valve support 40 comprises support-anchoring elements (such as clips), and is directly coupled to the native valve. For some such applications, no valve-anchoring elements are used; rather, implant 30 is coupled to the native valve via prosthetic valve support 40 (e.g., as described hereinbelow, such as with reference to FIGS. 37A-H and 38A-H). For some applications, both valve-anchoring elements and support-anchoring elements are used. For some applications, by allowing movement of the native leaflets with respect to the prosthetic valve, sealing of the native leaflets against the outer surface of the primary structural element of the prosthetic valve is facilitated, in accordance with the techniques described herein.

For some applications of the invention, the implantation of implant 30 follows an alternative order to that described with reference to FIGS. 1A-H. For these applications of the invention, prosthetic valve 42 is initially delivered to ventricle 28. Subsequently, prosthetic valve support 40 is deployed within atrium 26. In these applications of the invention, following deployment and positioning of prosthetic valve support 40 against the annulus of native valve 23, prosthetic valve 42 is moved atrially (i.e., proximally) into the respective lumens of the native valve and prosthetic valve support 40, and is deployed, as described hereinabove.

For some applications of the invention, valve-anchoring elements 64 anchor prosthetic valve 42 to the native valve in a manner that restricts both proximal and distal movement of the prosthetic valve. For such applications of the invention, deployment of prosthetic valve 42 may occur in the reverse orientation, such that, following positioning in the native valve of prosthetic valve 42 compressed in delivery tube 60, the delivery tube is moved distally (i.e., ventricularly) as prosthetic valve 42 is deployed from the delivery tube. Delivery tube 60 is then removed from the subject via the lumen of the deployed prosthetic valve. It is hypothesized that this approach facilitates maneuvering of implant components and delivery apparatus, both for delivery of implant 30 and for withdrawal of delivery apparatus. For example, this approach is hypothesized to require less space on the proximal side of the native valve (e.g., in the atrium), compared to techniques whereby the prosthetic valve is deployed from the proximal side of the native valve. An example of this approach is described with reference to FIGS. 15A-E.

For some applications of the invention, surfaces of one or more components of implant 30 are covered at least in part with a covering (not shown). For example, surfaces of prosthetic valve support 40 and prosthetic valve 42 may be covered so as to direct substantially all blood flowing through the valve, to flow through the lumen of prosthetic valve 42. For some applications, the surface of prosthetic valve support 40 (or another component) that is placed in contact with the native valve is covered; the covering is configured to facilitate coupling of support 40 to the native valve, by enhancing fibrosis at the interface between the prosthetic valve support and the native valve.

The covering may comprise polyethylene terephthalate (e.g., polyester), polytetrafluoroethylene (e.g., Teflon, ePTFE), or pericardial tissue. Typically, a thickness of the covering is less than 0.2 mm, e.g., less than 0.1 mm, or less than 0.05 mm.

For some applications, one or more dimensions of native valve 23 (e.g., of leaflets 82, and/or of the annulus of the native valve) is measured (e.g., by using imaging techniques) prior to deployment of valve 42. Taking this measuring into account, a suitably-sized prosthetic valve is chosen to be placed in the annulus, in a manner in which a cross-sectional area of the prosthetic valve in its deployed state is less than 90% (e.g., less than 80%, or less than 60%) of the area defined by the annulus.

For some applications, the cross-sectional area of the prosthetic valve in its deployed state has a longest length of less than 25 mm, e.g., less than 20 mm, and/or more than 15 mm, e.g., 15-25 mm. For some applications, placing a prosthetic valve inside the native valve, with the dimensions of the native valve annulus and the prosthetic valve as described, facilitates sealing of the prosthetic valve with respect to the native valve, by the native valve leaflets closing around the outer surface of the prosthetic valve. In such applications, prosthetic valve 42 is implanted directly within native valve 23 (i.e., without support 40).

For some applications, prosthetic valve support 40, that is shaped to define a lumen, is placed against the annulus of native valve 23 (e.g., as described with reference to FIGS. 1A-H). The lumen of support 40 has a cross-sectional area that is less than 90% (e.g., less than 80%, or less than 60%) of an area defined by native valve 23 (e.g., area A1, FIG. 71). As described hereinabove, prosthetic valve 42 is typically coupled to prosthetic valve support 40 and, thereby, to native valve 23, at least in part by expansion of the prosthetic valve such that primary structural element 130 exerts a radial force against inner edge 68 of prosthetic valve support 40. The cross-sectional area defined by the primary structural element 130 of the prosthetic valve, upon expansion of the prosthetic valve, is limited by the cross-sectional area of the lumen of the prosthetic valve support 40 to less than 90% (e.g., less than 80%, or less than 60%) of the area defined by the annulus of the native valve. For some applications, placing a prosthetic valve support 40 at the native valve, as described, facilitates sealing of the prosthetic valve with respect to the native valve, by the native valve leaflets closing around the outer surface of the prosthetic valve.

Typically, placing a prosthetic valve inside the native valve with the dimensions of the native valve annulus, the prosthetic valve 42, and/or valve support 40 as described in the above paragraphs, facilitates sealing of the prosthetic valve with respect to the native valve. For some applications, the sealing is facilitated by the native leaflets being pushed against, and closing against, the outer surface of the frame of the valve during systole, in a similar manner to the manner in which native valve leaflets coapt during systole, in a healthy mitral valve.

Typically, as the diameter of the prosthetic valve is increased, the proportion of the native leaflets that is pushed against the outer surface of the valve during systole is increased, thereby enhancing the sealing of the native leaflets with respect to the frame of the prosthetic valve. However, beyond a given diameter, as the diameter of the prosthetic valve is increased, the native valve leaflets are pushed apart at the commissures, thereby causing retrograde leakage of blood through the commissures. Therefore, in accordance with some applications of the present invention, prosthetic valve 42, and/or valve support 40 are chosen such that the cross-sectional area of the prosthetic valve (when expanded inside the valve support) is less than 90% (e.g., less than 80%, or less than 60%) of the area defined by the annulus of native valve 23. Thus, the valve support facilitates additional sealing of the prosthetic valve with respect to the native valve, by the native valve leaflets closing around the outer surface of the prosthetic valve, while not causing retrograde leakage of blood through the commissures.

For some applications, in order to facilitate the sealing of the native valve around the outer surface of the prosthetic valve, a material is placed on the outer surface of the prosthetic valve in order to provide a sealing interface between the prosthetic valve and the native valve. For example, a smooth material that prevents tissue growth (e.g., polytetrafluoroethylene (PTFE), and/or pericardium) may be placed on the outer surface of the prosthetic valve. Alternatively or additionally, a material that facilitates tissue growth (such as polyethylene terephthalate; PET) may be placed on the outer surface of the prosthetic valve, in order to (a) act as a sealing interface between the native valve and the prosthetic valve, and (b) facilitate tissue growth around the prosthetic valve to facilitate anchoring and/or sealing of the prosthetic valve.

For some applications, one or more dimensions of native valve 23 (e.g., of leaflets 82, and/or of the annulus of the native valve) are measured (e.g., by using imaging techniques) prior to deployment of prosthetic valve 42 and/or prosthetic valve support 40. Taking this measuring into account, a suitably-sized and/or suitably-configured prosthetic valve and/or prosthetic valve support is selected for implantation. For example, a prosthetic valve or prosthetic valve support comprising tissue-engaging elements 62 with appropriate configurations and/or dimensions may be selected.

Figure 2:
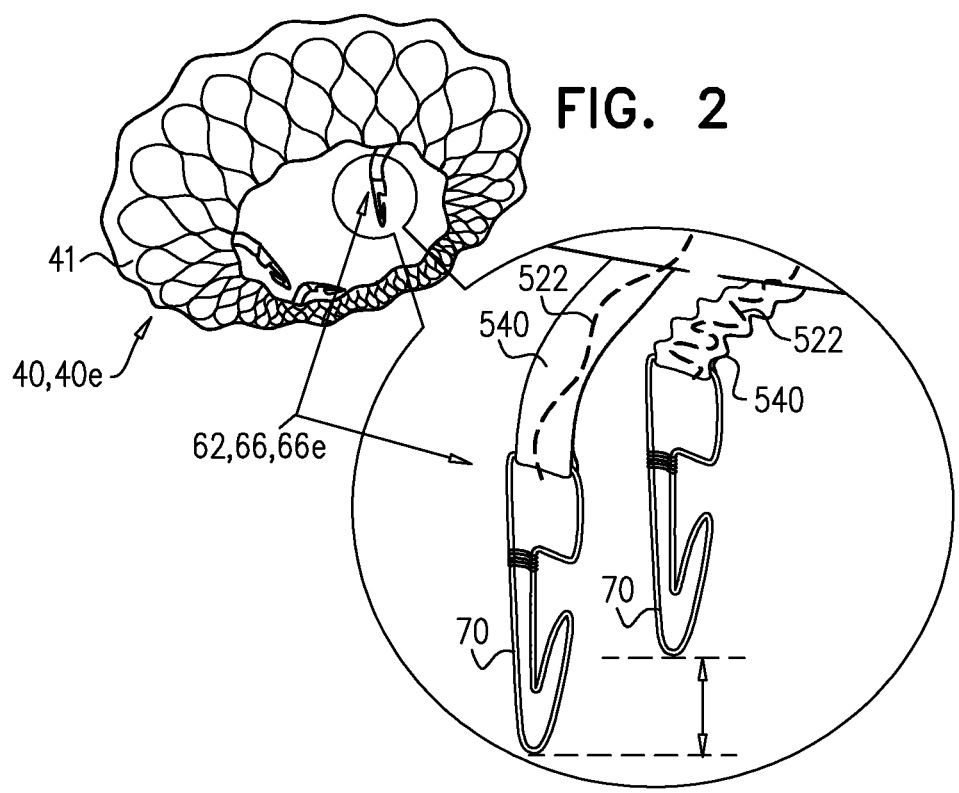
FIG. 2 is a schematic illustration of a prosthetic valve support, comprising adjustable prosthetic valve support, in accordance with some applications of the invention.

Reference is made to FIG. 2, which is a schematic illustration of prosthetic valve support 40, comprising adjustable prosthetic valve support 40e, which comprises tissue-engaging elements 62, comprising support-anchoring elements 66e, in accordance with some applications of the invention. Each support anchoring element 66e comprises, or is coupled to, a holding wire 522, which is slidably coupled to an upstream support portion 41 (e.g., an annular portion) of support 40e. During implantation, support 40e is anchored to native valve 23 via support-anchoring elements 66e. For example, elements 66e may engage commissures 84 or leaflets 82 of the native valve, as described hereinabove. The distance between upstream support portion 41 of support 40e and a coupling portion 70 of anchoring element 66e, is adjustable by adjusting the length of the portion of holding wire 522 that couples the upstream support portion to the coupling portion. Some examples of techniques for adjusting this length are described hereinbelow, with reference to FIGS. 3 and 4.

For some applications of the invention, at least part of holding wire 522 is disposed in a connector 540, which further couples coupling portion 70 to upstream support portion 41. Holding wire 522 may be slidable through connector 540. For some applications, connector 540 is more rigid than holding wire 522.

Figure 3:
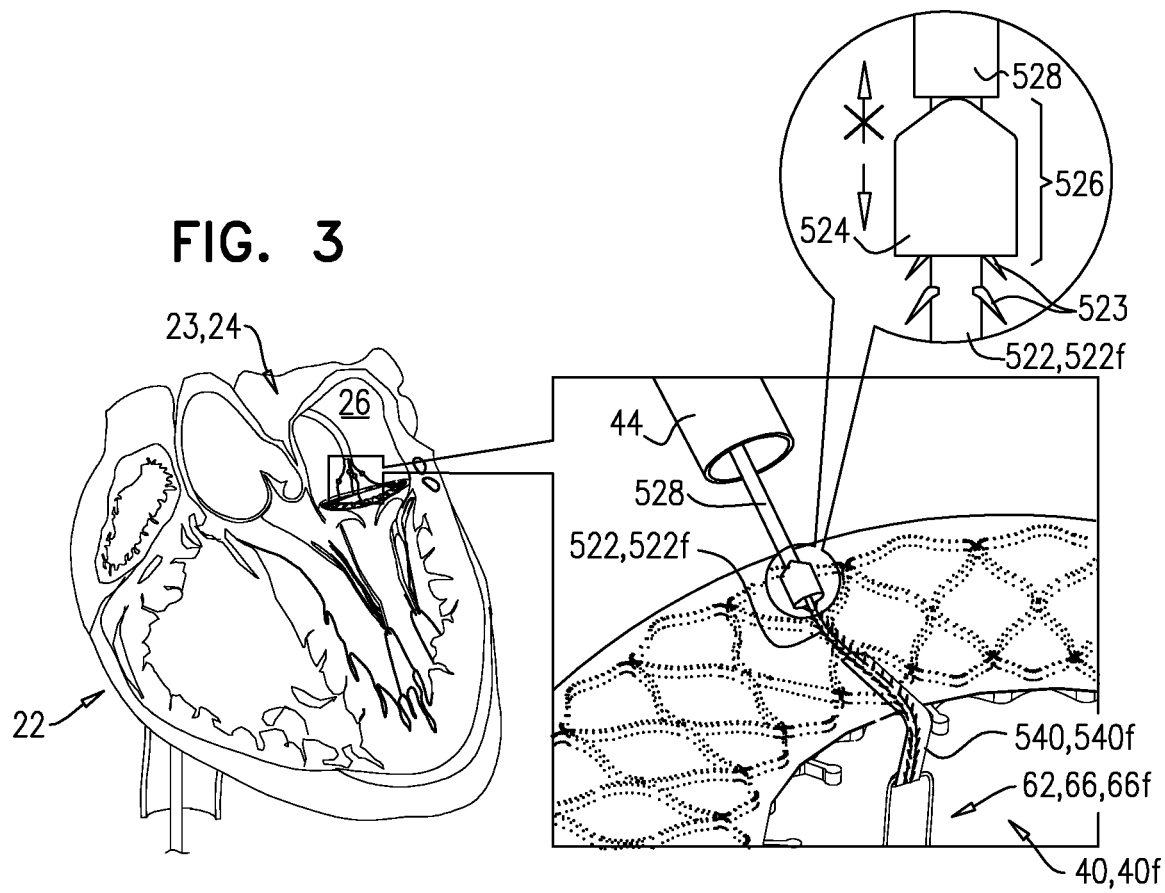
FIG. 3 is a schematic illustration of a prosthetic valve support, comprising an adjustable prosthetic valve support, in accordance with some applications of the invention.

Reference is made to FIG. 3, which is a schematic illustration of prosthetic valve support 40, comprising adjustable prosthetic valve support 40f, which comprises tissue-engaging elements 62, comprising support-anchoring elements 66f, in accordance with some applications of the invention. Each support anchoring element 66f comprises, or is coupled to, a holding wire 522f, which is slidably coupled to upstream support portion 41 of support 40f. During implantation, support 40f is anchored to native valve 23 via support-anchoring elements 66f. For example, elements 66f may engage commissures 84 or leaflets 82 of the native valve, as described herein. The distance between upstream support portion 41 of support 40f and a coupling portion of anchoring element 66f, is adjustable by adjusting the length of holding wire 522f. Typically, holding wire 522f is slidably coupled to upstream support portion 41 of support 40f via a ratchet 526, wherein holding wire 522f is slidable through a ratchet housing 524, and comprises a plurality of teeth 523 which allow the holding wire to slide through the ratchet housing in one direction, and restrict such sliding in another direction. Such adjustment of holding wire 522f may be performed while support 40f is partially deployed, or after the support has been fully deployed.

FIG. 3 shows ratchet housing 524 being slidable over holding wire 522f, such that the ratchet housing is movable with respect to upstream support portion 41 of support 40f. For this application of the invention, a controller tube 528 is typically used to slide (e.g., push) ratchet housing 524 over holding wire 522f, so as to adjust the distance between upstream support portion 41 of support 40f and the coupling portion. For other applications of the invention, ratchet housing 524 is substantially stationary with respect to upstream support portion 41 (e.g., ratchet housing 524 is attached to and/or embedded in portion 41), and holding wire 522 is slid (e.g., pulled) through housing 524, so as to adjust the distance between upstream support portion 41 of support 40f and coupling portion 70.

As described with reference to FIG. 2, for some applications of the invention, at least part of holding wire 522 (e.g., wire 522f) is disposed in a connector 540 (e.g., connector 540f), which further couples coupling portion 70 to upstream support portion 41 of support 40f. Holding wire 522f may be slidable through connector 540f. Connector 540f is typically more rigid that holding wire 522f.

It is hypothesized that adjusting the position of coupling portion 70 of support-anchoring elements 66f, with respect to upstream support portion 41 of prosthetic valve support 40f, allows prosthetic valve support 40f to be adapted to the anatomy of the subject during and/or subsequent to the implantation procedure.

Figure 4:
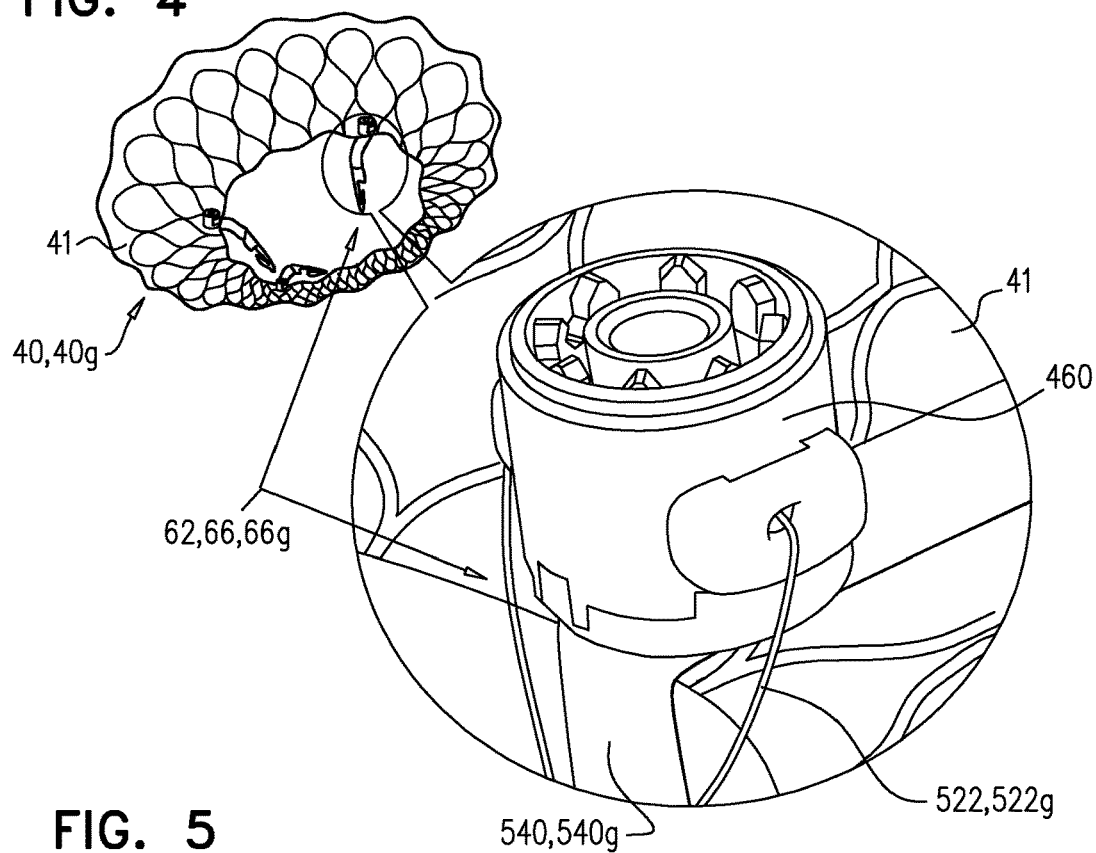
FIG. 4 is a schematic illustration of a prosthetic valve support, comprising an adjustable prosthetic valve support, in accordance with some applications of the invention.

Reference is made to FIG. 4, which is a schematic illustration of prosthetic valve support 40, comprising adjustable prosthetic valve support 40g, which comprises tissue-engaging elements 62, comprising support-anchoring elements 66g, in accordance with some applications of the invention. Each support anchoring element 66g comprises, or is coupled to, a holding wire 522, which is slidably coupled to upstream support portion 41 of support 40g. During implantation, support 40g is anchored to native valve 23 via support-anchoring elements 66g. For example, elements 66g may engage commissures 84 or leaflets 82 of the native valve, as described herein. The distance between upstream support portion 41 of support 40g and a coupling portion 70 (not shown) of anchoring element 66g, is adjustable by adjusting the length of holding wire 522g. Holding wire 522g is coupled to a spool 460, such that operation (e.g., turning) of spool 460 withdraws and/or ejects portions of the holding wire, thereby adjusting the length of holding wire 522g that couples the upstream support portion to the coupling portion, thereby adjusting the distance between upstream support portion 41 and coupling portion 70. Such adjustment of holding wire 522g may be performed while support 40g is partially deployed, or after the support has been fully deployed.

As described with reference to FIG. 2, for some applications of the invention, at least part of holding wire 522 (e.g., wire 522g) is disposed in a connector 540 (e.g., connector 540), which further couples coupling portion 70 to upstream support portion 41 of support 40g. Holding wire 522g may be slidable through connector 540g. In some applications, connector 540g is more rigid that holding wire 522g.

It is hypothesized that adjusting the position of coupling portion 70 of support-anchoring elements 66g, with respect to upstream support portion 41 of prosthetic valve support 40g, allows prosthetic valve support 40g to be adapted to the anatomy of the subject during and/or subsequent to the implantation procedure.

Figure 5:
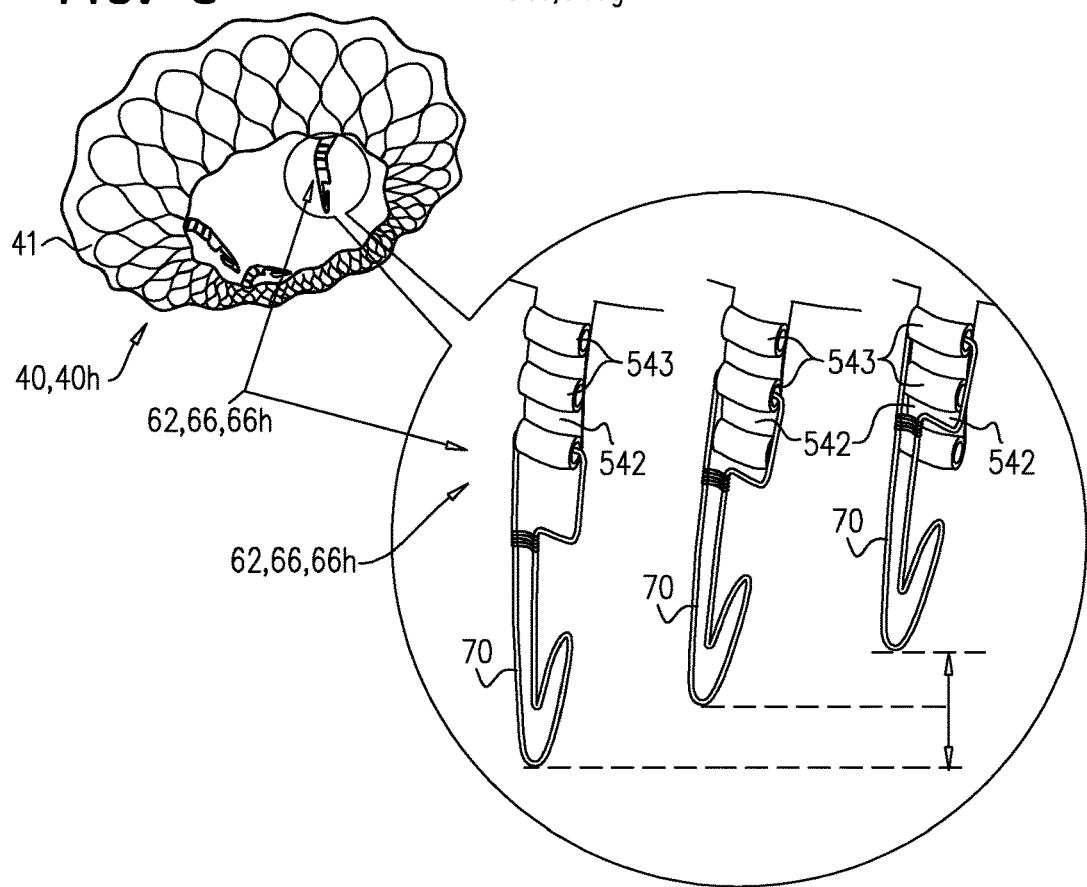
FIG. 5 is a schematic illustration of a prosthetic valve support, comprising a graduated prosthetic valve support, in accordance with some applications of the invention.

Reference is made to FIG. 5, which is a schematic illustration of prosthetic valve support 40, comprising graduated prosthetic valve support 40h, which comprises tissue-engaging elements 62, comprising support-anchoring elements 66h, in accordance with some applications of the invention. Each support-anchoring element 66h is coupled to upstream support portion 41 of support 40h via a graduated connector 542. Graduated connector 542 comprises a plurality of coupling points 543, to which coupling portion 70 of element 66h is couplable. Prior to implantation of prosthetic valve support 40h, the distance between upstream support portion 41 of support 40h and coupling portion 70 is adjustable, by selecting the coupling point 543 to which each coupling portion 70 is coupled.

It is hypothesized that adjusting the position of coupling portion 70 of support-anchoring elements 66h, with respect to upstream support portion 41 of prosthetic valve support 40h, allows prosthetic valve support 40h to be adapted to the anatomy of the subject during and/or subsequent to the implantation procedure.

Figure 6:
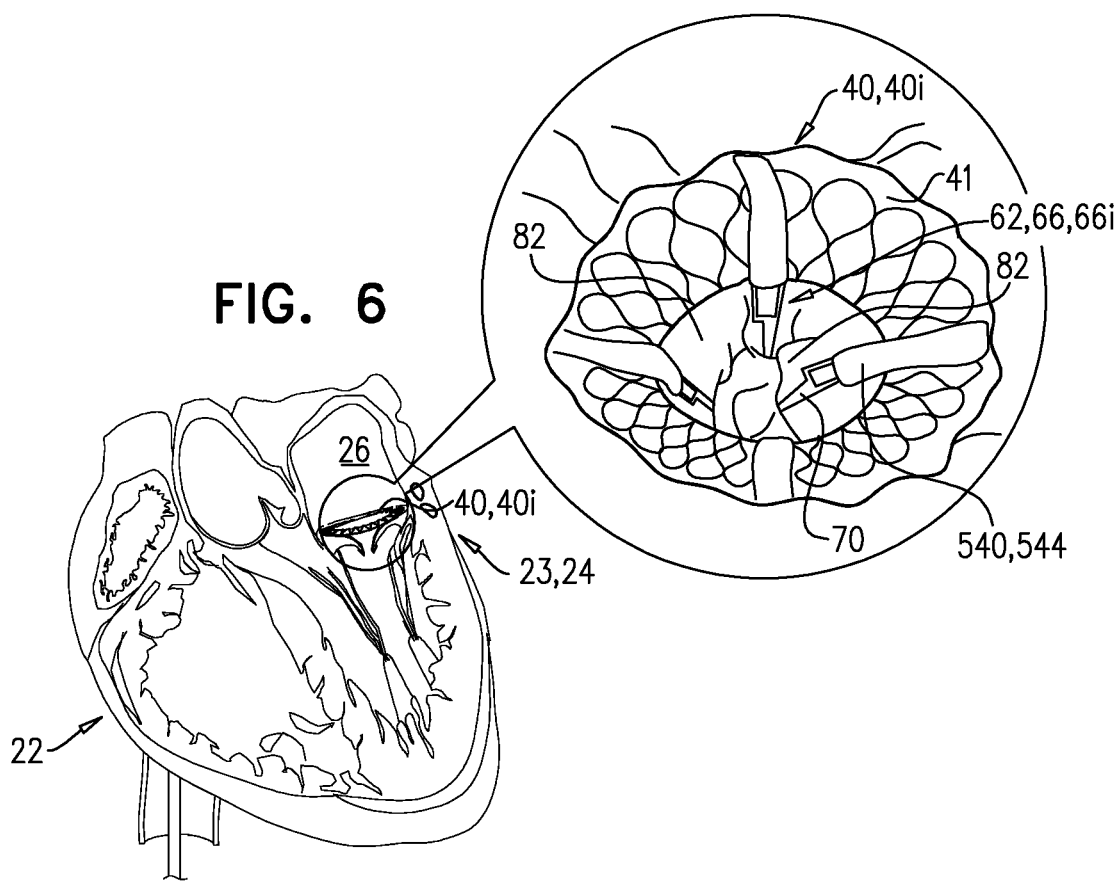
FIG. 6 is a schematic illustration of a prosthetic valve support, comprising a flexibly-anchored prosthetic valve support, in accordance with some applications of the invention.

Reference is made to FIG. 6, which is a schematic illustration of prosthetic valve support 40, comprising flexibly-anchored prosthetic valve support 40i, which comprises tissue-engaging elements 62, comprising support-anchoring elements 66i, in accordance with some applications of the invention. Each support-anchoring element 66i is coupled to upstream support portion 41 of support 40i via a connector 540, such as flexible connector 544. Flexible connector 544 typically comprises a flexible material which typically, but not necessarily, comprises polyethylene terephthalate (e.g., polyester), polytetrafluoroethylene (e.g., Teflon, ePTFE), silicone (e.g., silicone rubber), and/or or pericardial tissue. Flexible connector 544 facilitates movement of coupling portion 70 of elements 66i to move with respect to upstream support portion 41 of support 40i. It is hypothesized that this flexibility allows elements 66i to anchor prosthetic valve support 40i to the native valve (e.g., by coupling to leaflets 82), whilst allowing leaflets 82 to continue to function, at least in part.

Figure 7:
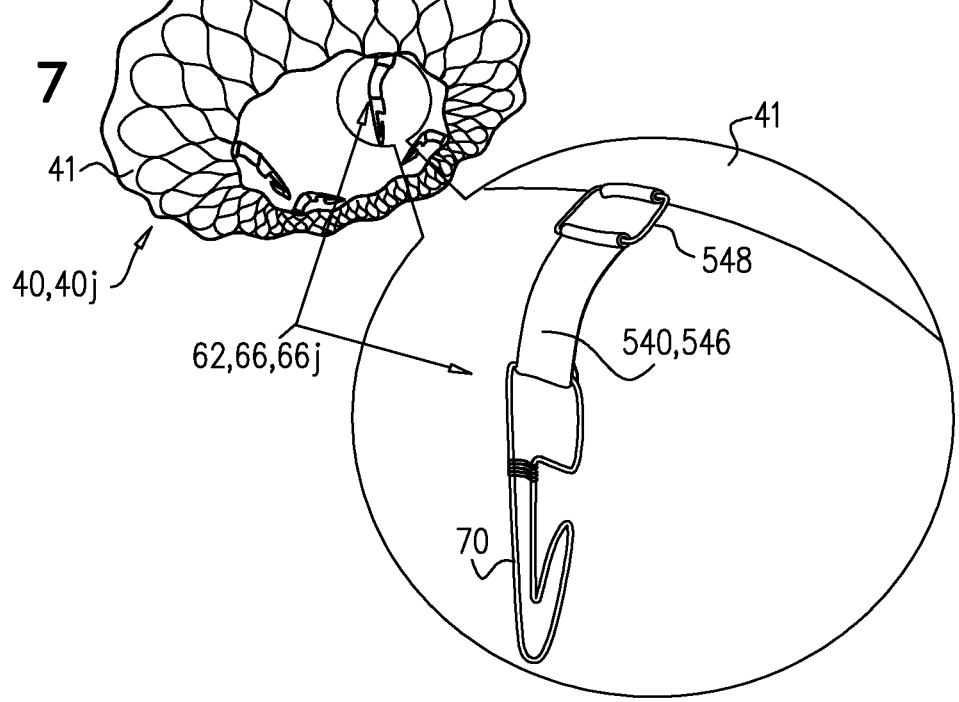
FIG. 7 is a schematic illustration of a prosthetic valve support, comprising a flexibly-anchored prosthetic valve support, in accordance with some applications of the invention.

Reference is made to FIG. 7, which is a schematic illustration of prosthetic valve support 40, comprising flexibly-anchored prosthetic valve support 40j, which comprises tissue-engaging elements 62, comprising support-anchoring elements 66j, in accordance with some applications of the invention. Coupling portion 70 of each element 66j is coupled to upstream support portion 41 of support 40j via at least one connector ring 548. Connector ring 548 typically facilitates movement of coupling portion 70 with respect to upstream support portion 41. Each support-anchoring element 66j typically comprises a connector 540, such as flexible connector 546. Flexible connector 546 typically comprises a flexible material which typically, but not necessarily, comprises polyethylene terephthalate (e.g., polyester), polytetrafluoroethylene (e.g., Teflon, ePTFE), silicone (e.g., silicone rubber), and/or or pericardial tissue. Flexible connector 546 typically further facilitates coupling portion 70 to move with respect to upstream support portion 41 of support 40j. It is hypothesized that this flexibility allows elements 66j to anchor prosthetic valve support 40j to the native valve (e.g., by coupling to leaflets 82), whilst allowing leaflets 82 to continue to function, at least in part.

Figure 8A:
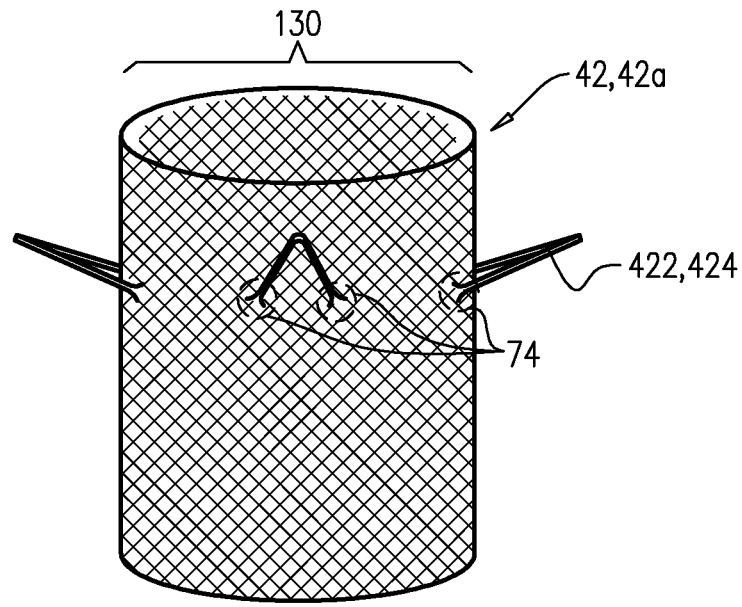
FIGS. 8A-B are schematic illustrations of a prosthetic valve support, and a prosthetic valve, the prosthetic valve comprising an integrally-anchoring prosthetic valve, in accordance with some applications of the invention.
Figure 8B:
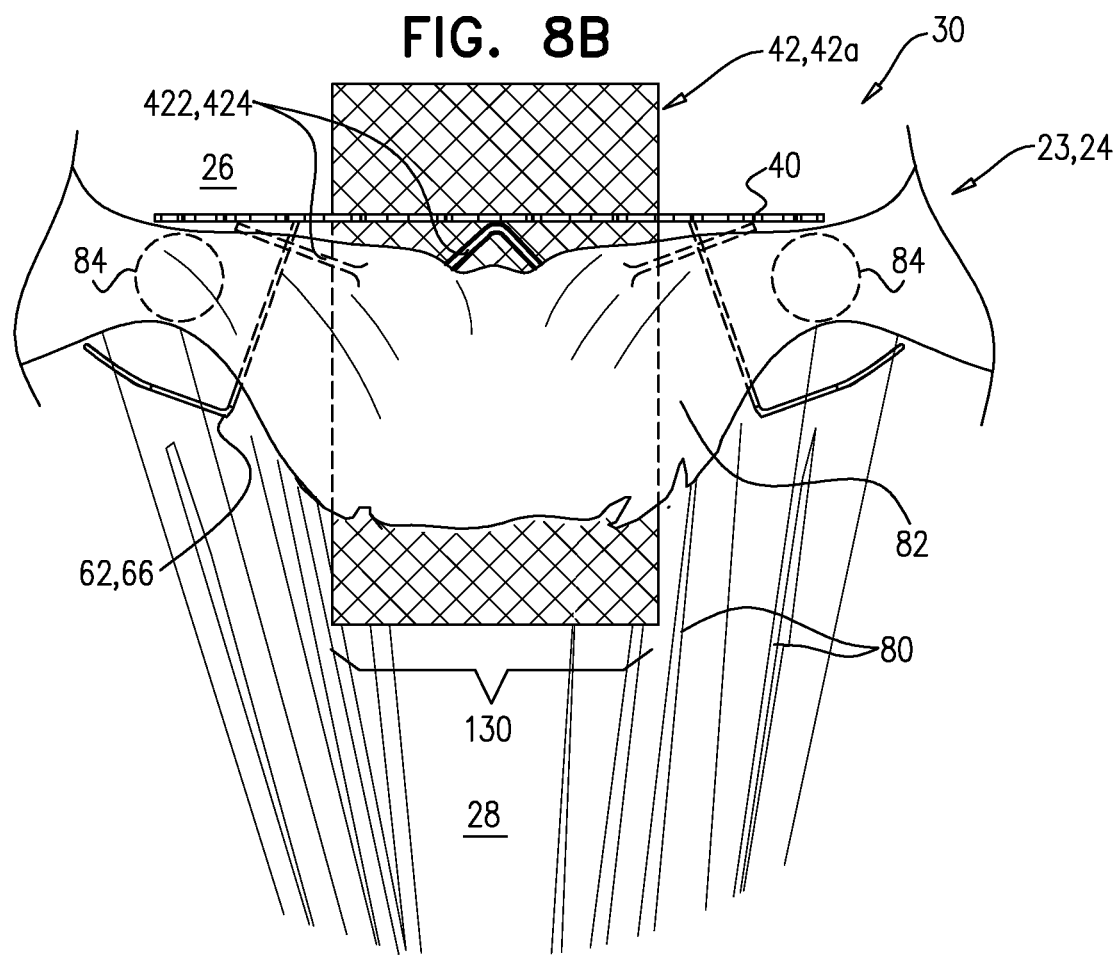

Reference is made to FIGS. 8A-B, which are schematic illustrations of prosthetic valve support 40, and prosthetic valve 42, the prosthetic valve comprising an integrally-anchoring prosthetic valve 42a, which comprises support-engaging elements 422 comprising a plurality of integral support-engaging elements 424, in accordance with some applications of the invention. For some applications of the invention, support-engaging elements 422 comprise other valve-anchoring elements described herein, such as valve-anchoring elements 64.

Reference is now made to FIG. 8A. Prosthetic valve 42a comprises a lattice structure, comprising a plurality of struts which typically collectively define a tessellation of shapes and voids. In some regions of the prosthetic valve, there is a separation between adjacent shapes. This separation allows a portion of the shape to move or be moved out of the plane of the lattice, thereby protruding from primary structural element 130 of prosthetic valve 42a when the prosthetic valve is expanded. The protruding portion of the shapes thereby form integral support-engaging elements 424, which are typically configured to anchor prosthetic valve 42a to the distal side of prosthetic valve support 40.

Reference is made to FIG. 8B, which shows implant 30, comprising prosthetic valve 42a and prosthetic valve support 40, implanted in native valve 23. FIG. 8B shows implant 30, comprising prosthetic valve support 40 and prosthetic valve 42a, implanted in native valve 23, comprising mitral valve 24. Prosthetic valve support 40 typically comprises a plurality of tissue-engaging elements 62, comprising support-anchoring elements 66, which engage leaflets 82 and/or chordae tendineae 80, and/or commissures 84, thereby anchoring support 40 to the native valve. Prosthetic valve 42a is compressible (e.g., crimpable) and expandable, and typically comprises a shape-memory material, as described hereinabove with reference to prosthetic valve 42. Prosthetic valve 42a is configured (e.g., shape-set) such that support-engaging elements 422, comprising integral support-engaging elements 424, are biased to protrude from the surface of primary structural element 130. In this application of the present invention, primary structural element 130 of prosthetic valve 42a is generally cylindrical, and integral support-engaging elements 424 protrude radially from the surface of the cylinder. Because integral support-engaging elements 424 are formed from the regular repeating structure of the lattice that forms prosthetic valve 42a, support-engaging elements 424 fit back into the plane of structural element 130 when valve 42a is crimped into delivery tube 60, prior to and even during implantation. Integral support-engaging elements 424, thereby typically do not increase the length nor the transverse cross-sectional longest dimension of the crimped configuration of prosthetic valve 42, as compared to those of any other prosthetic valves that do not comprise support-engaging elements 422, or that comprise elements 422 at a proximal end thereof.

As described hereinabove, prosthetic valve 42 is deployed by distal movement out of delivery tube 60. FIG. 8B shows prosthetic valve 42a in a fully-deployed state, such that integral support-engaging elements 424 have emerged from delivery tube 60, and have assumed an unconstrained, expanded, resting configuration in which the integral support-engaging elements 424 protrude radially from the surface of primary structural element 130 of the prosthetic valve. In an expanded state of at least the proximal portion of valve 42a, as shown in FIG. 8B, integral support-engaging elements 424 typically protrude up to and including 110 degrees (e.g., between 10 and 60 degrees, such as between 15 and 30 degrees) from the surface of primary structural element 130, in a resting state of support-engaging elements 424. That is, in the protruded state, the proximal portions of support-engaging elements 424 are distanced further from structural element 130 than the distal portions of support-engaging elements 424 which function as the pivot joints 74 between support-engaging elements 424 and structural element 130, as shown in FIG. 8A.

In the expanded state of support-engaging elements 424, the radially-protruding proximal portions thereof typically define a cross-sectional area, the longest dimension of which is typically longer than a transverse cross-sectional longest dimension of the lumen defined by prosthetic valve support 40. That is, in the expanded state, support-engaging elements 424 increase a longest transverse cross-sectional length of prosthetic valve 42a, such that the longest transverse cross-sectional length is longer than a longest transverse cross-sectional length of the lumen defined by prosthetic valve support 40. Thereby, the radially-protruding support-engaging elements 424 restrict proximal movement of prosthetic valve 42a with respect to prosthetic valve support 40, thereby anchoring prosthetic valve 42a to the distal side of prosthetic valve support 40, and to native valve 23.

Reference is made to FIGS. 9A-E, which are schematic illustrations of delivery apparatus 438, used to deploy a medical device 150, in accordance with some applications of the invention. Delivery apparatus 438 comprises a delivery tube 154 and a pushing member 140. Pushing member 140 comprises a support 142 and one or more coupling tabs 146, extending from the support. In the application of the invention shown in FIG. 9A, support 142 comprises a core 144, and coupling tabs 146 extend radially from the core.

In some applications of the invention, support 142 is shaped to define a plate 148 at the proximal end of support 142. The dimensions and relative positions of support 142, tabs 146, and plate 148 may be adjusted for the specific medical device 150 to be deployed using delivery apparatus 438. Support 142 is shaped to define a plurality of conduits 492 (e.g., holes). Delivery apparatus 438 further comprises one or more control filaments, such as retrieval wires 490, slidably disposed in conduits 492. Typically, conduits 492 provide communication between a proximal side of support 142 and a circumference of the support, such that a proximal end of each retrieval wire 490 is disposed at a site proximal to delivery tube 154, and a distal end of each wire is reversibly coupled to medical device 150, retrieval wires 490 extending through conduits 492.

Figure 9A:
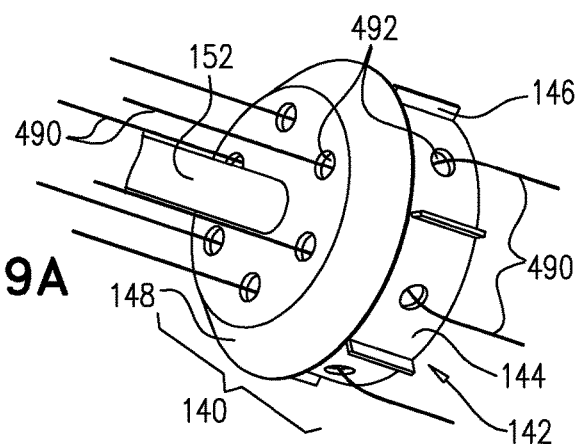
FIGS. 9A-E are schematic illustrations of delivery apparatus, used to deploy a medical device, in accordance with some applications of the invention.
Figure 9B:
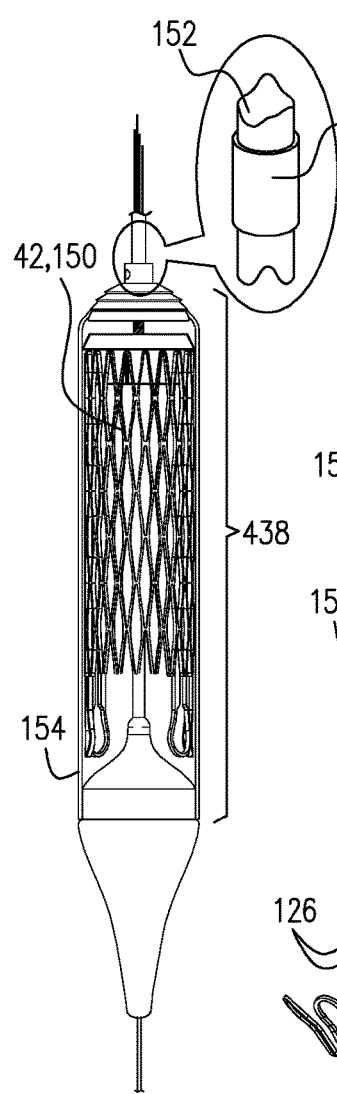
Figure 9C:
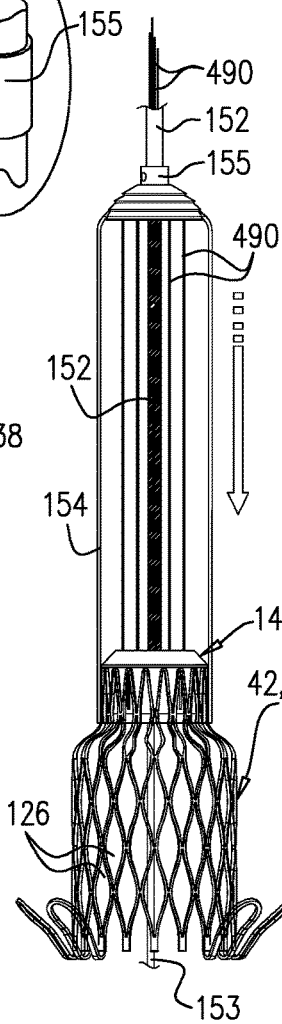
Figure 9D:
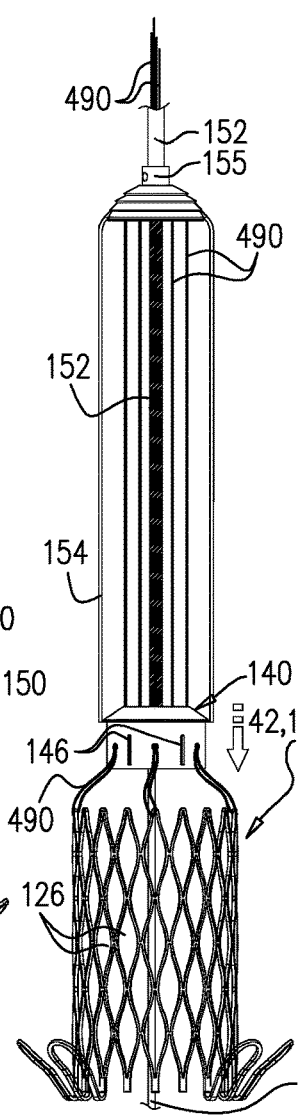

For some applications of the invention, retrieval wires 490 are coupled to medical device 150 by being looped around parts of the medical device (e.g., looped around a strut of the lattice structure, as shown in FIG. 9D), and are uncouplable from the medical device by being unlooped. For some applications of the invention, retrieval wires 490 are coupled to medical device 150 via a lock, such as a lock comprising a plug disposed in a tubular member (e.g., as described with reference to FIGS. 45A-C and/or 64A-C, mutatis mutandis). It is to be noted that the scope of the present application includes other techniques for coupling retrieval wires 490 to medical device 150, and decoupling the retrieval wires. In the application of the invention described with reference to FIGS. 9A-E, medical device 150 comprises prosthetic valve 42.

FIG. 9B shows prosthetic valve 42 in a compressed (i.e., crimped) configuration for delivery and deployment using delivery apparatus 438. Prosthetic valve 42 typically has a lattice structure that defines a plurality of shapes, and respective voids 126 (FIG. 9C), and has shape memory (described in more detail hereinbelow, such as with reference to FIGS. 53A-C and 62A-D, mutatis mutandis). Prosthetic valve 42 is shown in a compressed (e.g., crimped) configuration, and as shown in the enlarged image, a proximal portion of valve 42 is disposed around (e.g., against) core 144 of pushing member 140 such that each of coupling tabs 146 is disposed within a respective void 126 defined by the lattice structure of the prosthetic valve.

Prosthetic valve 42 and pushing member 140 are disposed within the lumen of delivery tube 154. Delivery tube 154 restricts expansion of prosthetic valve 42, thereby holding the proximal portion of prosthetic valve 42 around core 144 of pushing member 140, in the configuration described herein. Coupling tabs 146 restrict movement of prosthetic valve 42 with respect to pushing member 140. Delivery tube 154 therefore facilitates coupling of prosthetic valve 42 to pushing member 140 via coupling tabs 146. In applications of the invention where pushing member 140 is shaped to define plate 148, the plate typically further facilitates this coupling by restricting proximal movement of prosthetic valve 42 with respect to the pushing member (i.e., by functioning as a cap). Thereby, in the compressed configuration thereof, prosthetic valve 42 is configured to be fixedly coupled to pushing member 140.

A control tube 152 is typically coupled at a distal end thereof to pushing member 140 (e.g., control tube 152 is coupled to support 142). Control tube 152 is shaped so as to define a lumen through which a guidewire tube 153 passes, and control tube 152 is slidable with respect to and along guidewire tube 153. Guidewire tube 153 houses guidewire 45 described hereinabove. Control tube 152 is slidably disposed within a lumen of an overtube 155.

FIG. 9C shows prosthetic valve 42 partially deployed from delivery tube 154. Pushing member 140, and, thereby, prosthetic valve 42, are moved distally through delivery tube 154.

Reference is again made to FIG. 9C. Pushing member 140 is pushed distally by pushing control tube 152 along guidewire tube 153 such that pushing member 140 pushes prosthetic valve 42. As pushing member 140 pushes valve 42 distally, distal portions of the prosthetic valve expand toward the expanded configuration as they become exposed from delivery tube 154, while the proximal end of valve 42 remains coupled to pushing member 140 via tabs 146.

FIG. 9D shows prosthetic valve 42 having been fully deployed from within delivery tube 154. Pushing member 140 and prosthetic valve 42 are moved further distally through delivery tube 154 by control tube 152. When the proximal portion of prosthetic valve 42 emerges from within delivery tube 154, expansion of the proximal portion of prosthetic valve 42 uncouples the prosthetic valve from coupling tabs 146 by expanding voids 126 away from tabs 146, thereby releasing the prosthetic valve from pushing member 140. For some applications, retrieval wires 490 are generally loose, such that expansion of prosthetic valve 42 pulls the wires through conduits 492, and radially outward from core 144. For some applications, retrieval wires 490 are under tension, and are released gradually, so as to control expansion of prosthetic valve 42. That is, for some applications, the expansion of prosthetic valve 42 is restricted (e.g., controlled) by the distal advancement of retrieval wires 490.

Should it be necessary and/or desirable during deployment, until medical device 150 (e.g., prosthetic valve 42) is released from pushing member 140 (i.e., while the proximal portion of medical device 150 is crimped within delivery tube 154), the deployed, expanded portions of medical device 150 (i.e., the portions of medical device 150 that are exposed from delivery tube 154) may be drawn back into delivery tube 154 (e.g., for repositioning or withdrawal of the medical device).

Subsequent to deployment of prosthetic valve 42, should it be necessary and/or desirable, the prosthetic valve may be drawn back against support 142 (e.g., radially inward) by proximally pulling retrieval wires 490. Subsequently, prosthetic valve 42 may be drawn back, along with pushing member 140, into delivery tube 154. That is, for some applications, prosthetic valve 42 is recompressible (i.e., the expansion of prosthetic valve 42 is at least in part reversible) by proximal retraction of retrieval wires 490.

Figure 9E:
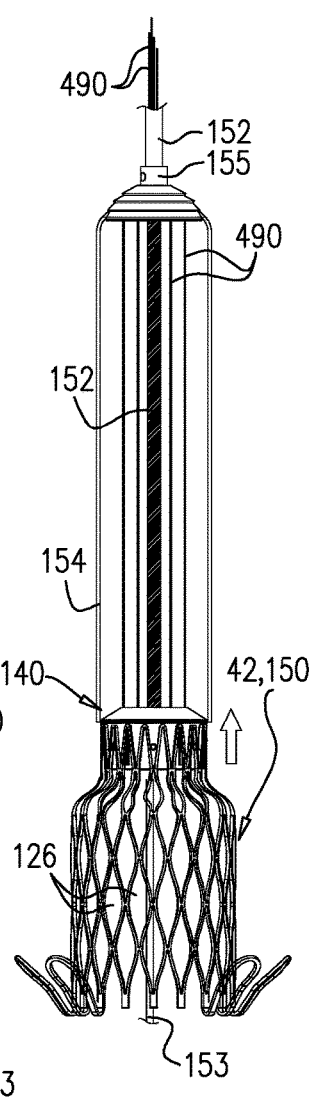

FIG. 9E shows retrieval wires 490 having been pulled proximally (e.g., by a user), such that wires 490 pull at least part of prosthetic valve 42 into a compressed configuration around and against support 142. Prosthetic valve 42 is thereby recoupled to pushing member 140. Pushing member 140 and prosthetic valve 42 are moved proximally and drawn into delivery tube 154. Prosthetic valve 42 may subsequently redeployed, or removed from the subject along with delivery tube 154.

That is, (1) retrieval wires 490 are slidable through conduits 492 of core 144, and reversibly couplable to prosthetic valve 42, and (2) delivery apparatus 438 is configured to control and/or facilitate (a) expansion of prosthetic valve 42, by the retrieval wires being advanced distally through the conduits, and (b) recompression of prosthetic valve 42, by the retrieval wires being retracted proximally through the conduits.

Reference is now made to FIGS. 9A-E and 1D-F. It is to be noted that delivery tube 154 of FIGS. 9A-E is similar to, and/or may comprise, delivery tube 60 of FIGS. 1D-F.

Figure 10:
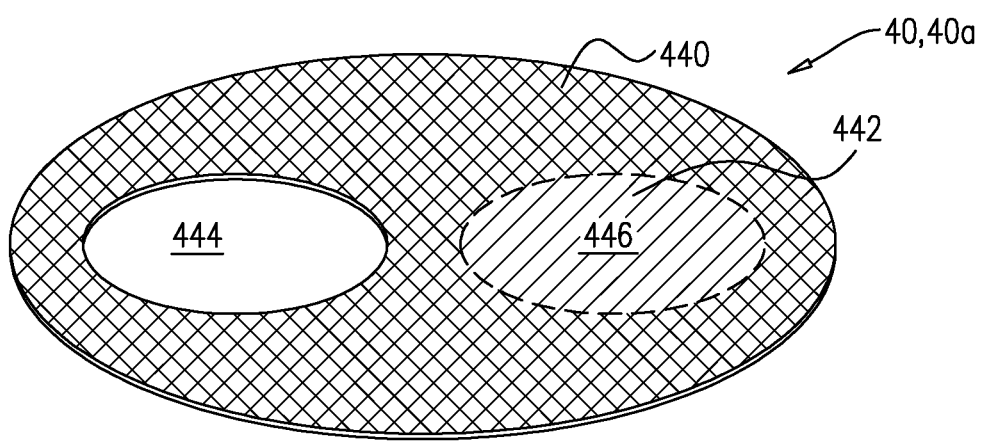
FIG. 10 is a schematic illustration of a prosthetic valve support, comprising a multi-lumen prosthetic valve support, in accordance with some applications of the invention.

Reference is made to FIG. 10, which is a schematic illustration of prosthetic valve support 40, comprising multi-lumen prosthetic valve support 40a, in accordance with some applications of the invention. As described hereinabove, prosthetic valve support 40 is generally annular and shaped to define a lumen, in which prosthetic valve 42 is deployed and expanded. In the application of the invention illustrated in FIG. 10, prosthetic valve support 40, comprising multi-lumen prosthetic valve support 40a, is shaped to define two or more lumens. That is, the wire frame of support 40a defines two or more lumens. Prosthetic valve support 40a is typically couplable to the native valve using techniques described herein for coupling other prosthetic valve supports to the native valve. For example, prosthetic valve support 40a may comprise tissue-engaging elements (e.g., support-anchoring elements). Similarly, other prosthetic valve supports described herein may comprise prosthetic valve support 40a.

Prosthetic valve support 40a is typically covered with a covering 440, such as a fabric. Covering 440 may comprise polyethylene terephthalate (e.g., polyester), polytetrafluoroethylene (e.g., Teflon, ePTFE), or pericardial tissue. Typically, a thickness of covering 440 is less than 0.2 mm, e.g., less than 0.1 mm, or less than 0.05 mm. When support 40a is supplied and/or implanted, covering 440 typically covers support 40a such that only a first lumen 444 is open and configured to receive a prosthetic valve, and the second lumen 446 is closed. That is, the wire frame of support 40a defines two or more lumens but the covering defines only one lumen, thereby covering 440 functions as a seal 442.

In some applications of the invention, covering 440 is not disposed over second lumen 446; rather a different element functions as seal 442. For example, a weaker and/or softer material (e.g., pericardial tissue) or a removable plug may be coupled to prosthetic valve support 40a, and disposed over second lumen 446 to function as seal 442.

Implant 30, comprising prosthetic valve 42 and prosthetic valve support 40a, is implanted in native valve 23 (e.g., as described with reference to FIGS. 1A-H, mutatis mutandis), whereby prosthetic valve prosthetic valve 42 is deployed in first lumen 444 of the support. At a later time, a second prosthetic valve may be introduced by deploying the second prosthetic valve in second lumen 446. That is, at a first period, prosthetic valve support 40a facilitates implantation of a first prosthetic valve at the native valve, and at a second period, the prosthetic valve support facilitates implantation of a second prosthetic valve at the native valve. In some applications of the invention, seal 442 is opened, and thereby configured to receive a prosthetic valve (e.g., by being broken, cut and/or torn) by the introduction of the second prosthetic valve. In other applications, seal 442 is opened with a cutting tool (not shown) prior to deployment of the second prosthetic valve. In some applications of the invention, seal 442 is uncoupled from support 40a, prior to deployment of the second prosthetic valve.

For some applications of the invention, following the deployment of the second prosthetic valve, the first prosthetic valve (i.e., prosthetic valve 42) is disabled (e.g., sealed). For example, an expandable plug may be expanded in the lumen of the first prosthetic valve.

Prosthetic cardiac valves typically require replacement after several years (e.g., after 2-20 years, such as after 5-10 years). For example, the condition of the subject may change and/or components of the prosthetic valve (e.g., prosthetic valve leaflets) may suffer fatigue. It is hypothesized that multi-lumen prosthetic valve support 40a allows a second prosthetic valve to be implanted in the native valve, the second prosthetic valve being supported by the originally-implanted prosthetic valve support 40a. The first prosthetic valve may be sealed, for example, if the original prosthetic valve allows, or is predicted to allow, retrograde leakage. Implantation of a second prosthetic valve is hypothesized to increase the lifespan of implant 30.

Figure 11:
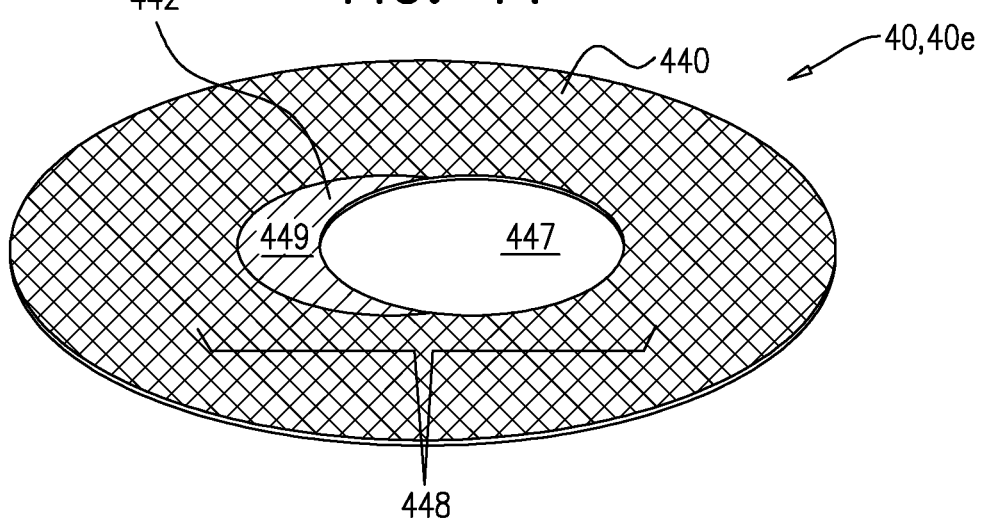
FIG. 11 is a schematic illustration of a prosthetic valve, comprising an extended-lumen prosthetic valve support, in accordance with some applications of the invention.

Reference is made to FIG. 11, which is a schematic illustration of prosthetic valve support 40, comprising extended-lumen prosthetic valve support 40e, in accordance with some applications of the invention. As described hereinabove, prosthetic valve support 40 is generally annular and shaped to define a lumen, in which prosthetic valve 42 is deployed and expanded. Extended-lumen prosthetic valve support 40e is shaped to define a lumen 448, which has an extended dimension. That is, the wire frame of support 40e typically defines lumen 448, which has (1) a primary region 447, and (2) a secondary region 449 that is generally not filled by expansion of prosthetic valve 42 in the lumen. Typically, lumen 448 has a first length that is longer than, and generally orthogonal to, a second length, and has one or more concave portions. For example, lumen 448 may be generally shaped to define an oval or ellipse with one or more concave portions generally midway along the first length (e.g., a Cassini oval or a hippopede). Prosthetic valve support 40e is typically couplable to the native valve using techniques described herein for coupling other prosthetic valve supports to the native valve. For example, prosthetic valve support 40e may comprise tissue-engaging elements (e.g., support-anchoring elements). Similarly, other prosthetic valve supports described herein may comprise prosthetic valve support 40e.

Prosthetic valve support 40e is typically covered with a covering 440, such as a fabric. Covering 440 may comprise polyethylene terephthalate (e.g., polyester), polytetrafluoroethylene (e.g., Teflon, ePTFE), or pericardial tissue. Typically, a thickness of covering 440 is less than 0.2 mm, e.g., less than 0.1 mm, or less than 0.05 mm. When support 40e is supplied and/or implanted, covering 440 typically covers support 40e such that secondary region 449 is closed. That is, the wire frame of support 40e defines a generally elongated lumen 448, whilst covering 440 defines a generally round primary region 447. In this manner, covering 440 functions as a seal 442 over secondary region 449.

In some applications of the invention, covering 440 is not disposed over secondary region 449; rather a different element functions as seal 442. For example, a weaker and/or softer material (e.g., pericardial tissue) or a removable plug may be coupled to prosthetic valve support 40e, and disposed over secondary region 449, so as to function as seal 442.

Implant 30, comprising prosthetic valve 42 and prosthetic valve support 40e, is implanted in native valve 23 (e.g., as described with reference to FIGS. 1A-H), whereby prosthetic valve 42 is deployed in primary region 447 of the support. At a later time, a second prosthetic valve may be introduced by deploying the second prosthetic valve in secondary region 449. That is, at a first period, prosthetic valve support 40e facilitates implantation of a first prosthetic valve at the native valve, and at a second period, the prosthetic valve support facilitates implantation of a second prosthetic valve at the native valve. In some applications of the invention, seal 442 is opened (e.g., broken, cut and/or torn) by the introduction of the second prosthetic valve. In other applications, seal 442 is opened with a cutting tool (not shown) prior to deployment of the second prosthetic valve. In some applications of the invention, seal 442 is uncoupled from support 40e, prior to deployment of the second prosthetic valve.

Typically, expansion of the second prosthetic valve during deployment deforms the first prosthetic valve (i.e., a radially-expansive force of the second prosthetic valve is stronger than that of the first prosthetic valve). For example, following deployment of the second valve, the first valve may assume a lune shape or a generally semicircular shape. In some applications of the invention, the second prosthetic valve is shaped to fit into secondary region 449 without deforming the first prosthetic valve.

Prosthetic cardiac valves typically require replacement after several years (e.g., after 2-20 years, such as after 5-10 years). For example, the condition of the subject may change and/or components of the prosthetic valve (e.g., prosthetic valve leaflets) may suffer fatigue. It is hypothesized that extended-lumen prosthetic valve support 40 allows a second prosthetic valve to be implanted in the native valve, the second prosthetic valve being supported by the originally-implanted prosthetic valve support 40. The first prosthetic valve may be sealed, as described hereinabove, for example, if the original prosthetic valve allows, or is predicted to allow, retrograde leakage. Implantation of a second prosthetic valve is hypothesized to increase the lifespan of implant 30.

Figure 12A:
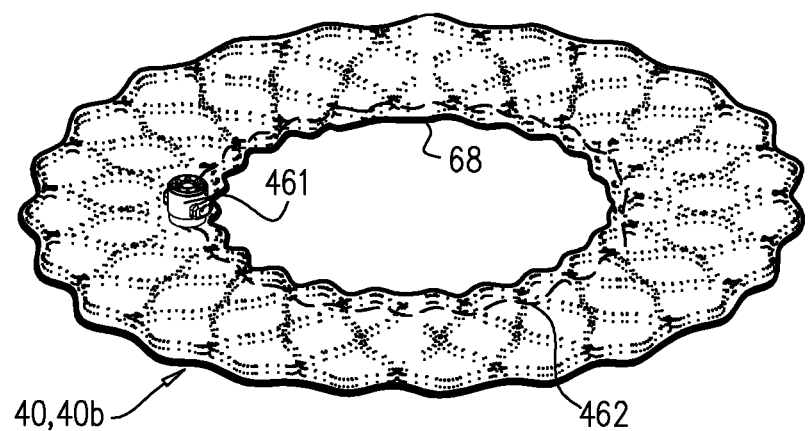
FIGS. 12A-B are schematic illustrations of a prosthetic valve support, comprising an adjustable-lumen prosthetic valve support, in accordance with some applications of the invention.
Figure 12B:
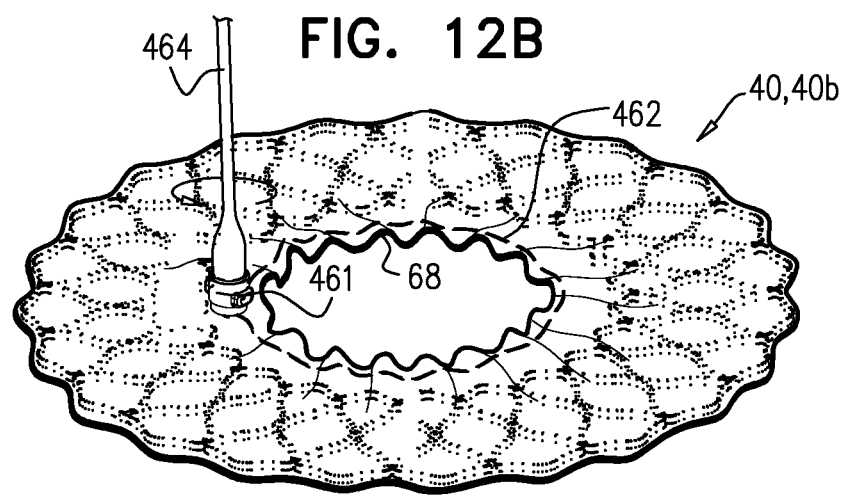

Reference is made to FIGS. 12A-B, which are schematic illustrations of prosthetic valve support 40, comprising adjustable-lumen prosthetic valve support 40b, in accordance with some applications of the invention. As described hereinabove, expansion of prosthetic valve 42 is restricted by the lumen of prosthetic valve support 40. As further described hereinabove, the optimum lumen size may depend on the individual subject and/or condition being treated. Adjusting the size of the lumen of prosthetic valve 42 is hypothesized to alter the flow of blood through the prosthetic valve, and the sealing of leaflets 82 of the native valve against the outer surface of the prosthetic valve. In some applications of the invention, the size of the area defined by the annulus of the native valve is measured (e.g., using a measuring ring and/or using imaging techniques), and appropriately-sized prosthetic valve 42 and prosthetic valve support 40 are selected for implantation. FIGS. 12A-B show adjustable-lumen prosthetic valve support 40b, which comprises a spool 461 and a tightening wire 462. Tightening wire 462 typically forms a loop around a central portion of support 40b (e.g., threadedly coupled around an inner edge 68), and is coupled to spool 461 such that the tightening wire can be tightened (i.e., shortened) via spool 461. FIG. 12A shows support 40b with a larger lumen (i.e., when tightening wire 462 is relatively loose) and FIG. 12B shows support 40b with a smaller lumen, following tightening of tightening wire 462 with a tightening tool 464.

For some applications, prosthetic valve support 40b and prosthetic valve 42 are implanted as described herein (e.g., with reference to FIGS. 1A-H), and tightening wire 462 is subsequently tightened. For some applications, the annulus of the native valve is measured, and tightening wire 462 is responsively adjusted, prior to implantation. For some applications, following measurement of the native valve, and prior to implantation, a support 40b of appropriate size is selected from a range.

Reference is made to FIGS. 13A-D, which are schematic illustrations of prosthetic valve support 40, comprising asymmetric prosthetic valve support 40c, in accordance with an application of the invention. As described hereinabove, support 40 is generally annular, and shaped to define a lumen. FIG. 13A shows that the lumen defined by support 40c (i.e., oblique lumen 480) is typically not central with respect to the support. That is, support 40c is typically rotationally asymmetric. Support 40c typically defines a total cross-sectional area of between 16 cm^2 and 38 cm^2 (e.g., between 22 cm^2 and 28 cm^2). Typically, the cross-sectional area of lumen 480 is less than 70% (e.g., less than 60%, or less than 40%) of the cross-sectional area of area of support 40c. For example, for some applications, the cross-sectional area of lumen 480 has a longest length of less than 25 mm, e.g., less than 20 mm, and/or more than 15 mm, e.g., 15-25 mm. As described hereinabove, for some applications, surfaces of prosthetic valve support 40 are covered with a covering so as to direct substantially all blood to flow through the lumen of prosthetic valve 42. Asymmetric prosthetic valve support 40c is typically not covered, i.e., the lattice structure of which the support is comprised, is exposed.

FIG. 13B shows prosthetic valve support 40c having been deployed to the annulus of native valve 23, as described herein (e.g., with reference to FIGS. 1A-H). For the applications of the invention described with reference to FIGS. 13A-D, prosthetic valve support typically comprises a plurality of tissue-engaging elements (e.g., support-anchoring elements), such as those described herein (not shown in FIGS. 13A-D). Support-anchoring elements 66 are typically configured and oriented to engage commissures 84 of the native valve, so as to anchor support 40 to the native valve whilst allowing leaflets 82 to continue to function. Prosthetic valve support 40c is typically deployed to native valve 23 such that lumen 480 is positioned over (i.e., proximal to) a place of coaptation of the two leaflets 82 of the native valve. Subsequently, prosthetic valve 42 is deployed in lumen 480 (as described hereinabove; e.g., with reference to FIGS. 1A-H), such that, in the expanded state, prosthetic valve 42 is disposed between leaflets 82.

FIG. 13C shows implant 30, comprising prosthetic valve support 40c and prosthetic valve 42, implanted in native valve 23, in accordance with an application of the invention. Typically, but not necessarily, prosthetic valve 42 does not comprise valve-anchoring elements 64. Rather, prosthetic valve 42 is typically anchored to native valve 23 by being coupled to support 40c, which is, itself, anchored to the native valve, as described hereinabove. Prosthetic valve 42 is positioned between leaflets 82 of the native valve, due to the oblique position of lumen 480 of support 40c. Typically, leaflets 82 are generally free to move with respect to the prosthetic valve, and move proximally and distally with the beating of the heart, coapting and sealing around prosthetic valve 42. This movement of leaflets 82 is facilitated by support 40c being uncovered and fluid communication being maintained between atrium 26 and ventricle 28 through the lattice structure of support 40c. For example, when native valve 23 comprises mitral valve 24, during diastole, leaflets 82 open, and left atrial blood moves into the left ventricle, both through and around prosthetic valve 42 (i.e., through the lumen of prosthetic valve 42 and through the exposed lattice structure of support 40c). During systole, leaflets 82 close, i.e., coapt together, and seal around prosthetic valve 42, restricting retrograde movement of blood.

It is hypothesized that over a period of time (e.g., a week, e.g., a month, e.g., a year) following implantation of implant 30 comprising support 40c, movement of leaflets 82 is reduced (e.g., due to tissue growth and/or calciferous deposits), such that the functionality of native valve 23 is gradually reduced, and the proportion of blood that flow through prosthetic valve 42, relative to that which flows around the prosthetic valve, is increased. That is, over time, prosthetic valve 42 takes over the function of native valve 23.

Figure 14:
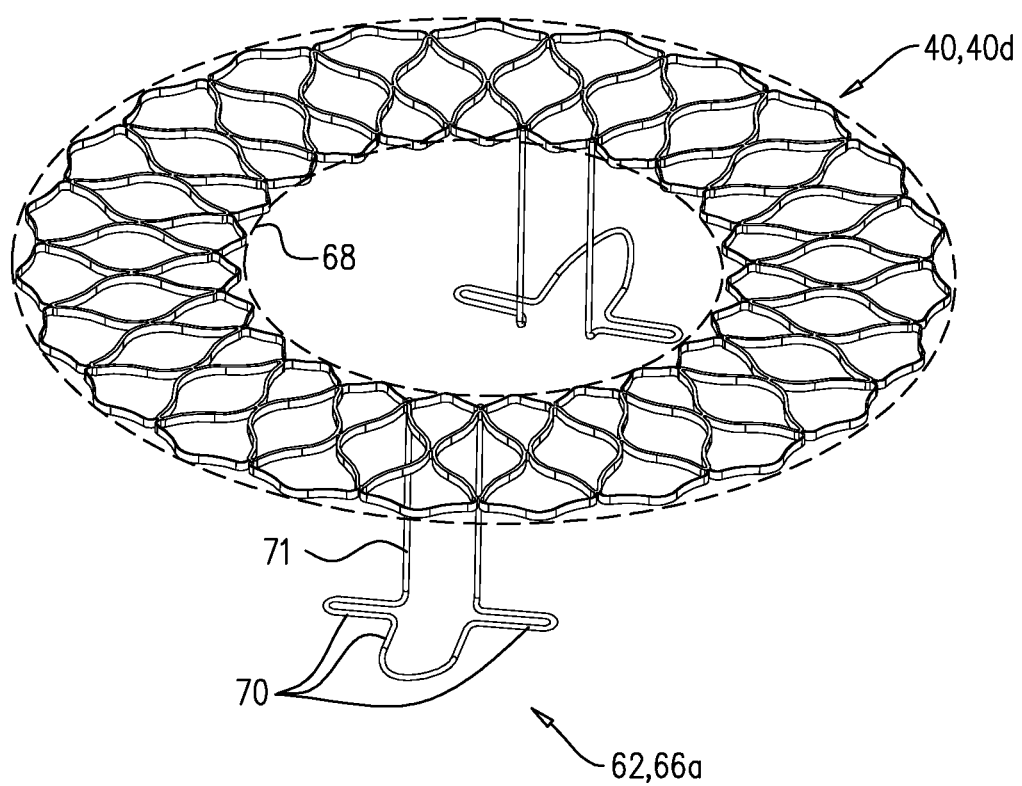
FIG. 14 is a schematic illustration of a prosthetic valve support, in accordance with some applications of the invention.

Reference is made to FIG. 14, which is a schematic illustration of prosthetic valve support 40, comprising prosthetic valve support 40d, which comprises tissue-engaging elements 62, comprising a plurality of support-anchoring elements 66a, in accordance with some applications of the invention. Typically, support 40d comprises two elements 66a, typically coupled to inner edge 68, and positioned generally opposite each other. Elements 66a typically comprise two or more (e.g., three) coupling portions 70, which extend radially from a structural component 71. FIG. 14 shows elements 66a comprising three coupling portions 70, arranged in a T-shape. Support 40d is typically deployed in the native valve such that elements 66a are oriented toward commissures 84 of the native valve, and engage both the commissures and the closest regions of leaflets 82. It is hypothesized that this structure and positioning of elements 66a anchor support 40d to the native valve, whilst allowing leaflets 82 to move, thereby allowing native valve 23 to continue to function, at least partly, until prosthetic valve 42 is deployed.

Figure 15A:
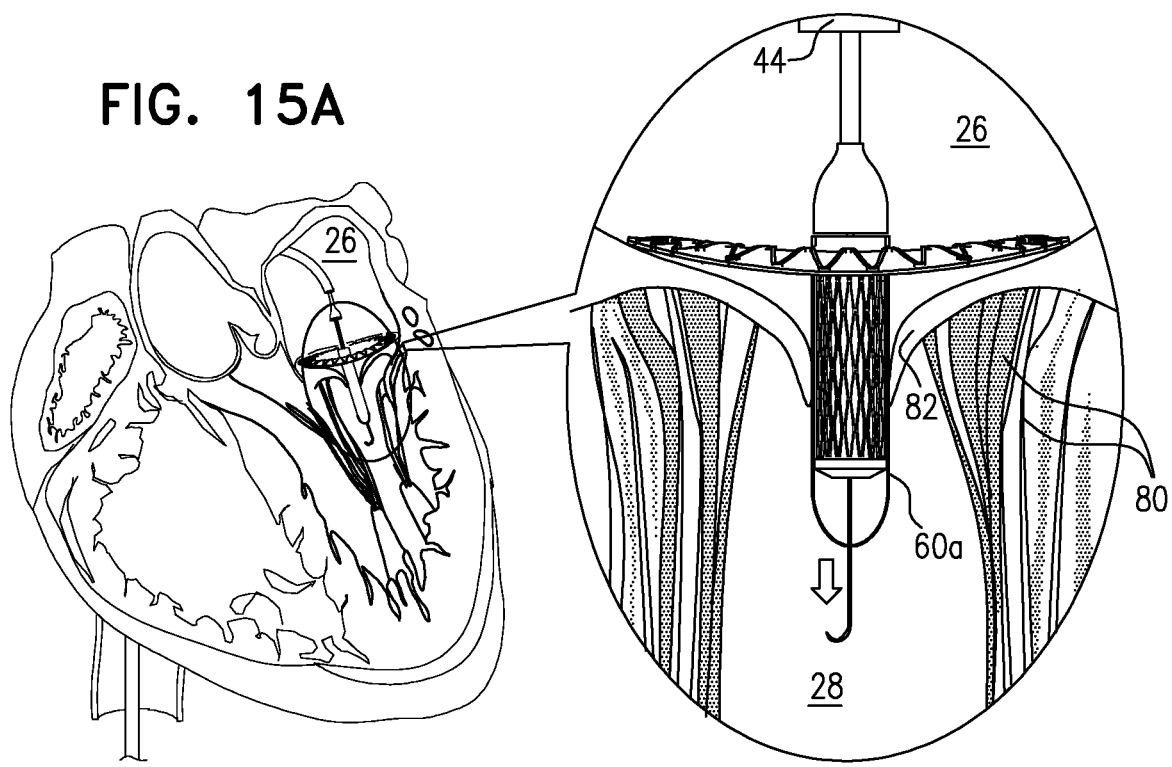
FIGS. 15A-E are schematic illustrations of the implantation of a prosthetic valve support and a prosthetic valve, in accordance with some applications of the invention.

Reference is made to FIGS. 15A-E, which are schematic illustrations of the implantation of prosthetic valve support 40 and prosthetic valve 42, in accordance with some applications of the invention. Prosthetic valve 42 is compressible (e.g., crimpable) and expandable, and typically comprises a shape-memory material, as described hereinabove. FIG. 15A shows prosthetic valve support 40 having been deployed to the annulus of native valve 23, and prosthetic valve 42 having been delivered, in the crimped configuration thereof, within delivery tube 60a, to the native valve. Prosthetic valve 42 and delivery tube 60a are disposed in the lumen of native valve 23. Leaflets 82 of the native valve typically coapt and seal around delivery tube 60a. The proximal end of delivery tube 60a is shown open.

Figure 15B:
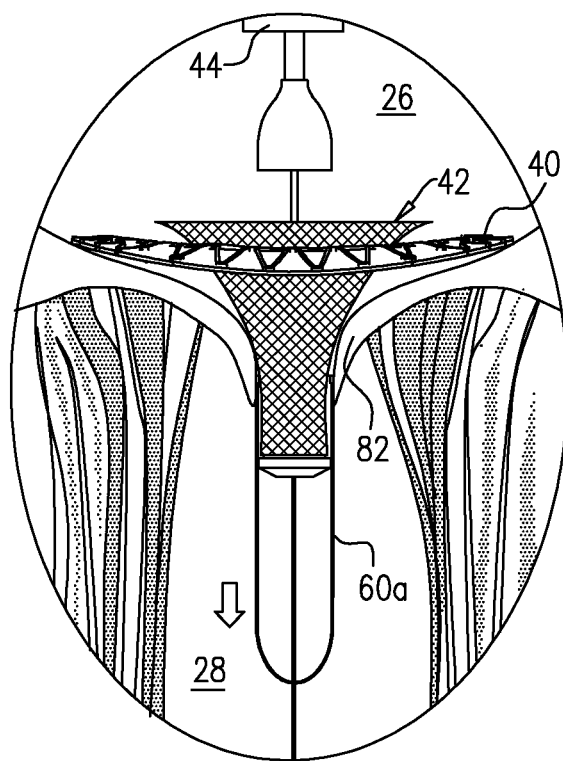

FIG. 15B shows delivery tube 60a being moved distally while prosthetic valve 42 remains relatively stationary, thereby exposing the prosthetic valve from the delivery tube. As portions of prosthetic valve 42 are exposed, they expand from the crimped configuration to an expanded configuration. Typically, expansion of the proximal portion of prosthetic valve 42 facilitates coupling of the prosthetic valve to prosthetic valve support 40. In the application of the invention illustrated by FIGS. 15A-E, prosthetic valve 42 is shaped to define a widened proximal end, which facilitates coupling of prosthetic valve 42 to prosthetic valve support 40. It is to be noted that the scope of the present application includes other configurations of prosthetic valve 42, such as those included herein.

Figure 15C:
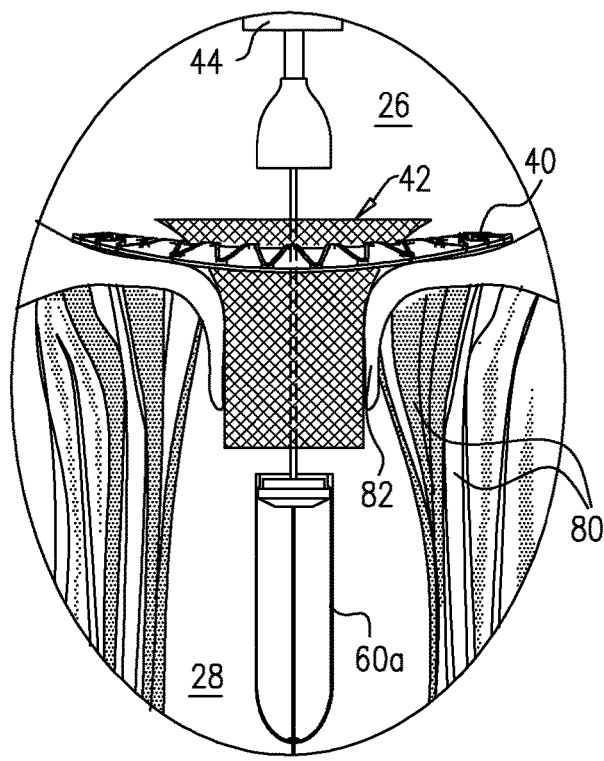

FIG. 15C shows delivery tube 60a having been removed entirely from prosthetic valve 42, and prosthetic valve 42 having expanded to its expanded configuration, the expansion facilitating coupling of the prosthetic valve to support 40 and, thereby, native valve 23. Delivery tube 60a is shown in left ventricle 28 of the heart.

Figure 15D:
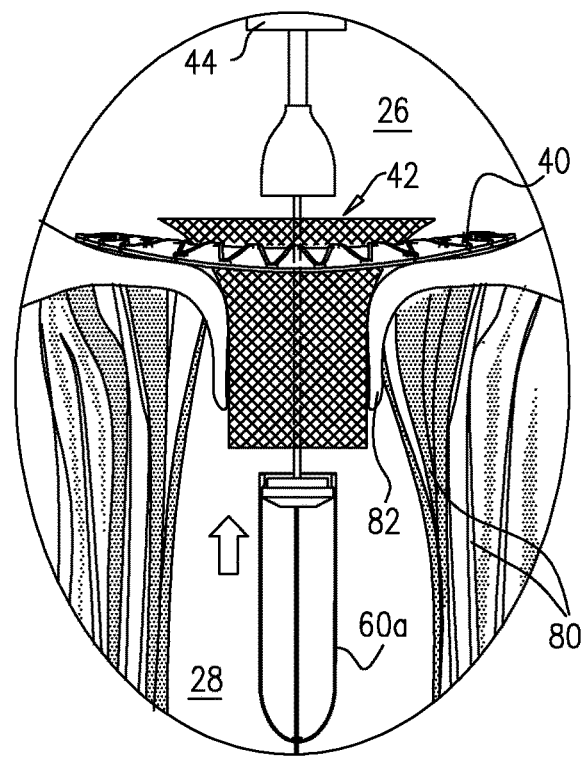
Figure 15E:
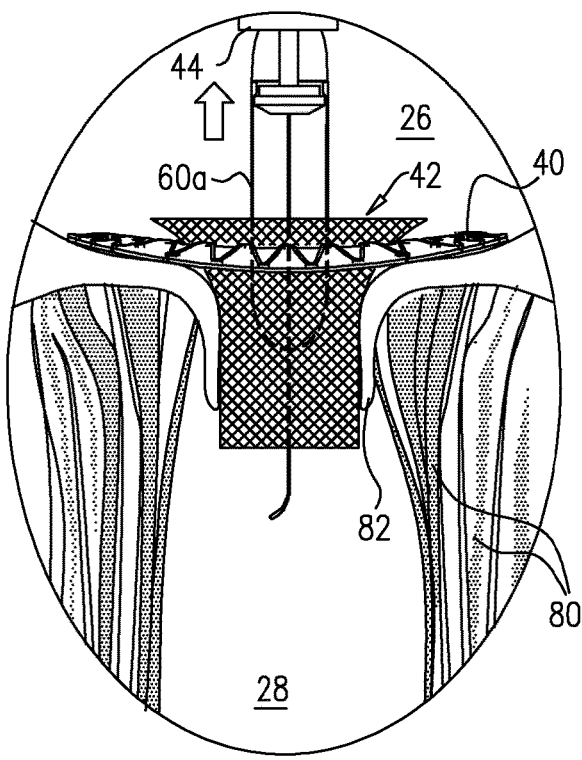

FIGS. 15D and 15E show delivery tube 60a being withdrawn proximally, through the lumen of prosthetic valve 42. Delivery tube 60a is subsequently removed from the subject. Typically, delivery tube 60a is withdrawn between leaflets of prosthetic valve 42 (not shown), which are typically disposed in the lumen of the prosthetic valve. Typically, delivery tube 60a is withdrawn into overtube 44 prior to removal from the subject. It is to be noted that the scope of the present application includes deployment of the prosthetic valve from the distal (i.e., ventricular) side of native valve 23, and the withdrawal of the delivery tube via the lumen of the prosthetic valve. It is hypothesized that this approach facilitates maneuvering of implant components and delivery apparatus, both for delivery of implant 30 and for withdrawal of delivery apparatus. For example, this approach is hypothesized to require less space on the proximal side of the native valve (e.g., in atrium 26), compared to techniques whereby the prosthetic valve is deployed from the proximal side of the native valve.

Figure 16:
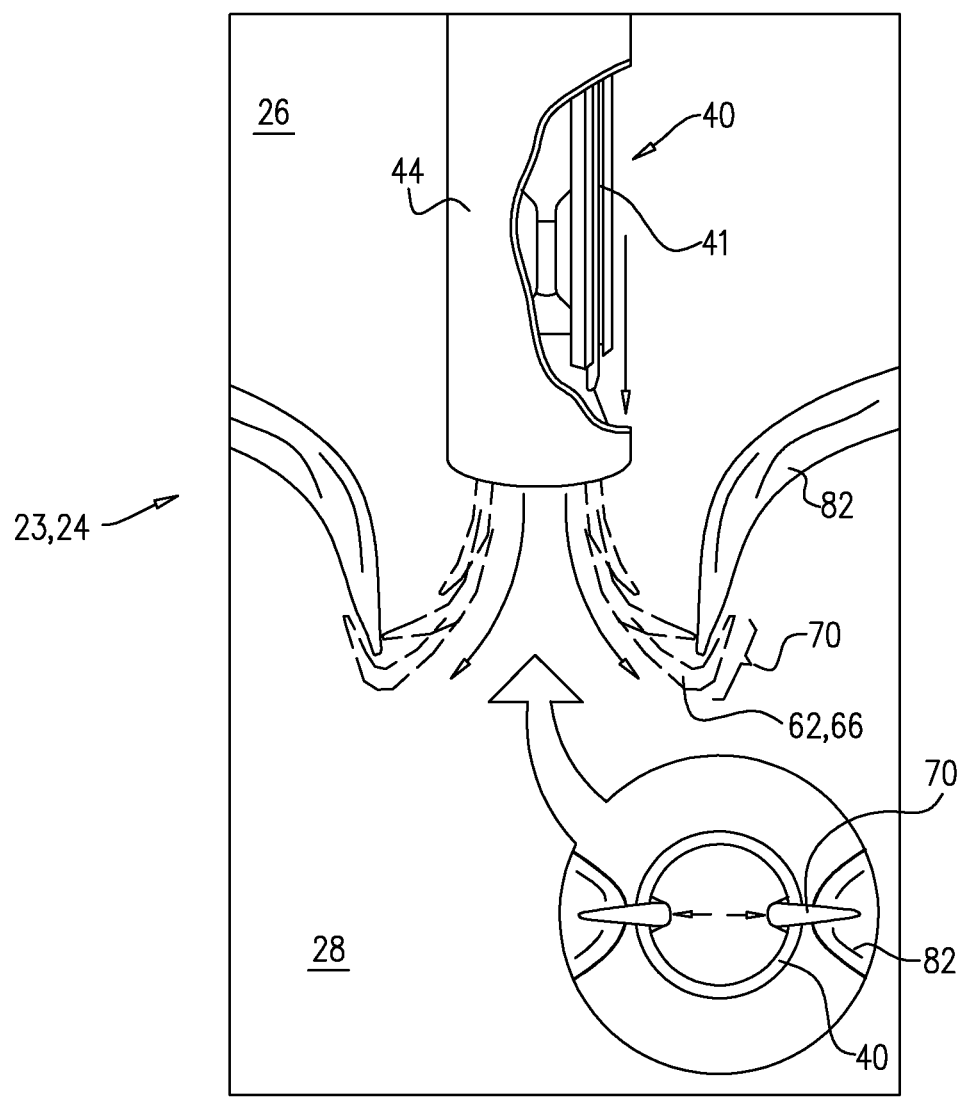
FIG. 16 is a schematic illustration of a prosthetic valve support being deployed in a native heart valve, in accordance with some applications of the invention.

Reference is made to FIG. 16, which is a schematic illustration of prosthetic valve support 40 being deployed in native valve 23, comprising mitral valve 24, in accordance with some applications of the invention. Support 40 is typically delivered to the native valve in a compressed (e.g., crimped) configuration, within overtube 44. In the compressed configuration, support 40 typically assumes a tubular shape, having a proximal end and a distal end. Typically, the distal end is defined by inner edge 68 (described hereinabove), and tissue-engaging elements 62, comprising support-anchoring elements 66, extend distally from the distal end. To deploy support 40, the support is moved (e.g., pushed) through overtube 44, such that support-anchoring elements 66 emerge from the overtube. Support-anchoring elements 66 engage native valve 23, typically by grasping leaflets 82, commissures 84, and/or chordae tendineae 80 of the native valve. Subsequently, the remaining portions of support 40 (e.g., upstream support portion 41) are moved out of overtube 44, and support 40 expands to assume its expanded, generally annular, shape. Prosthetic valve support 40 is thereby anchored to the native valve, typically with upstream support portion 41 held against the annulus of the native valve, by support-anchoring elements 66 (e.g., as described hereinabove).

In some applications of the invention, support-anchoring elements 66 are configured and/or arranged so as to anchor prosthetic valve support 40 to the native valve (e.g., by engaging leaflets 82, and/or commissures 84, and/or chordae tendineae 80), whilst allowing leaflets 82 to continue to function, at least in part.

In some applications of the invention, should it be necessary and/or desirable, support 40 is retrievable before it is fully deployed, by withdrawing the support proximally, back into overtube 44.

In some applications, should it be necessary and/or desirable, support 40 is retrievable after it has been fully deployed. For example, support 40 may be drawn back around and against a pushing member of delivery apparatus, recompressing support 40 for withdrawal into a delivery tube, in a similar way to the technique described with reference to FIGS. 9A-E, mutatis mutandis. Prosthetic valve support 40 may subsequently be removed from the subject, and/or repositioned, and/or redeployed.

Reference is made to FIGS. 17A-D, which are schematic illustrations of support 40, comprising tissue-engaging elements 62, which comprise support-anchoring elements 66, comprising length-adjustable holding elements 600, in accordance with some applications of the invention. Native heart valves vary naturally in various dimensions, such as, but not limited to, the length, width and/or thickness of leaflets 82, the distance between commissures 84, and/or the distance between fibrous trigones. In this context, in the specification and in the claims, these varying parameters are referred to as "dimensions." Length-adjustable holding elements 600 are configured such that the distance between coupling portion 70 and upstream support portion 41 of prosthetic valve support 40 is adjustable. This adjustability typically facilitates placement (i.e., implantation) of the prosthetic valve support at native valves of different dimensions, such that (1) upstream support portion 41 is placeable against the proximal (i.e., atrial) side of the prosthetic valve, and (2) coupling portion 70 is placeable on the distal (i.e., ventricular) side of the native valve (e.g., to engage the native leaflets and/or commissures, as described hereinabove).

For some applications, coupling portions 70 engage (e.g., are coupled to) leaflets 82 and/or commissures 84 of native valve 23 while prosthetic valve support 40 is still in a partially-deployed configuration (e.g., as described with reference to FIGS. 1B and 16). For some applications, support 40 is first expanded, upstream support portion 41 is then placed against the annulus of the native valve, and coupling portions 70 subsequently engage (e.g., are coupled to) the leaflets and/or commissures.

In the applications of the invention described with reference to FIGS. 17A-D, holding elements 600 are typically biased to assume a contracted configuration, and are typically expanded (e.g., stretched) so as to couple portions 70 to the native valve. This bias thereby provides a pulling force, which is hypothesized to facilitate coupling of prosthetic valve support 40 to native valve 23 by sandwiching the native valve between upstream support portion 41 and coupling portion 70, in some applications of the invention.

Typically, adjustment and/or other manipulation of support-anchoring elements 66, comprising length-adjustable holding elements 600, may be performed prior to the implantation procedure, e.g., following imaging-based sizing of one or more dimensions of native valve 23 (e.g., of leaflets 82, and/or of the annulus of the native valve), and/or during the implantation procedure (e.g., when the prosthetic valve support is at the site of implantation).

Figure 17A:
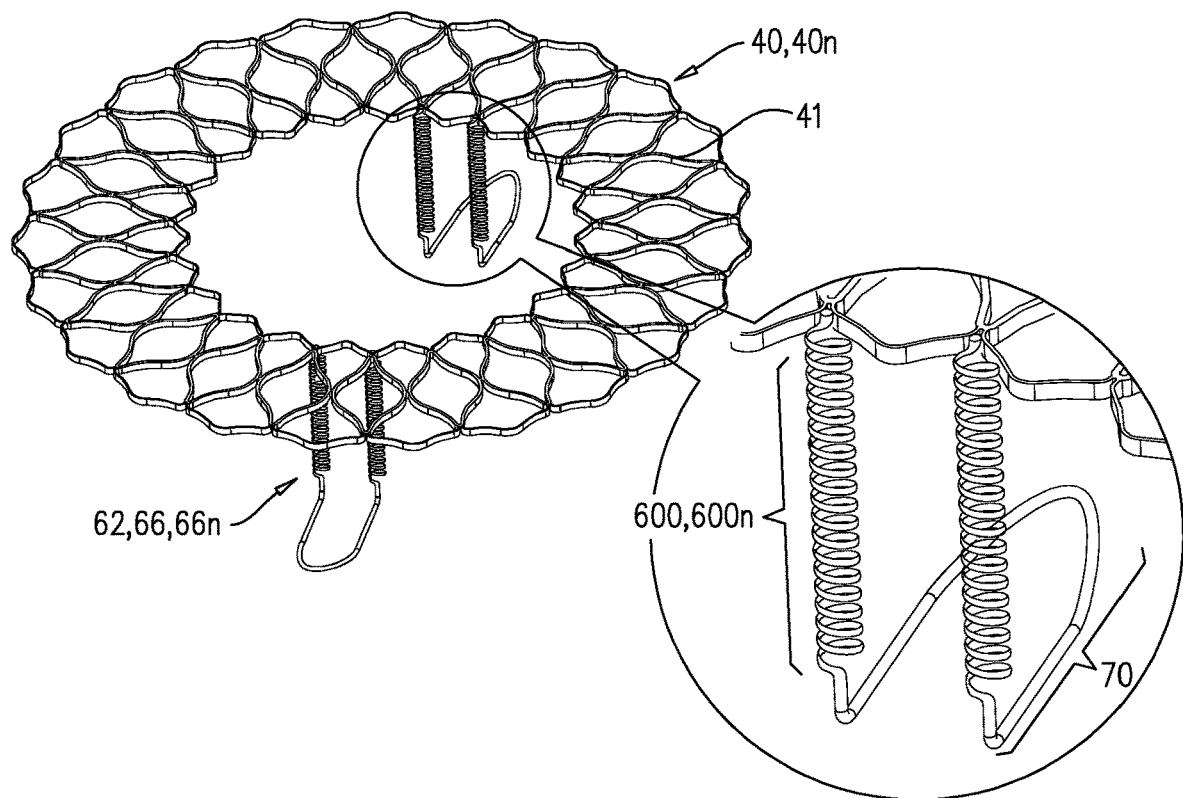
Figure 17B:
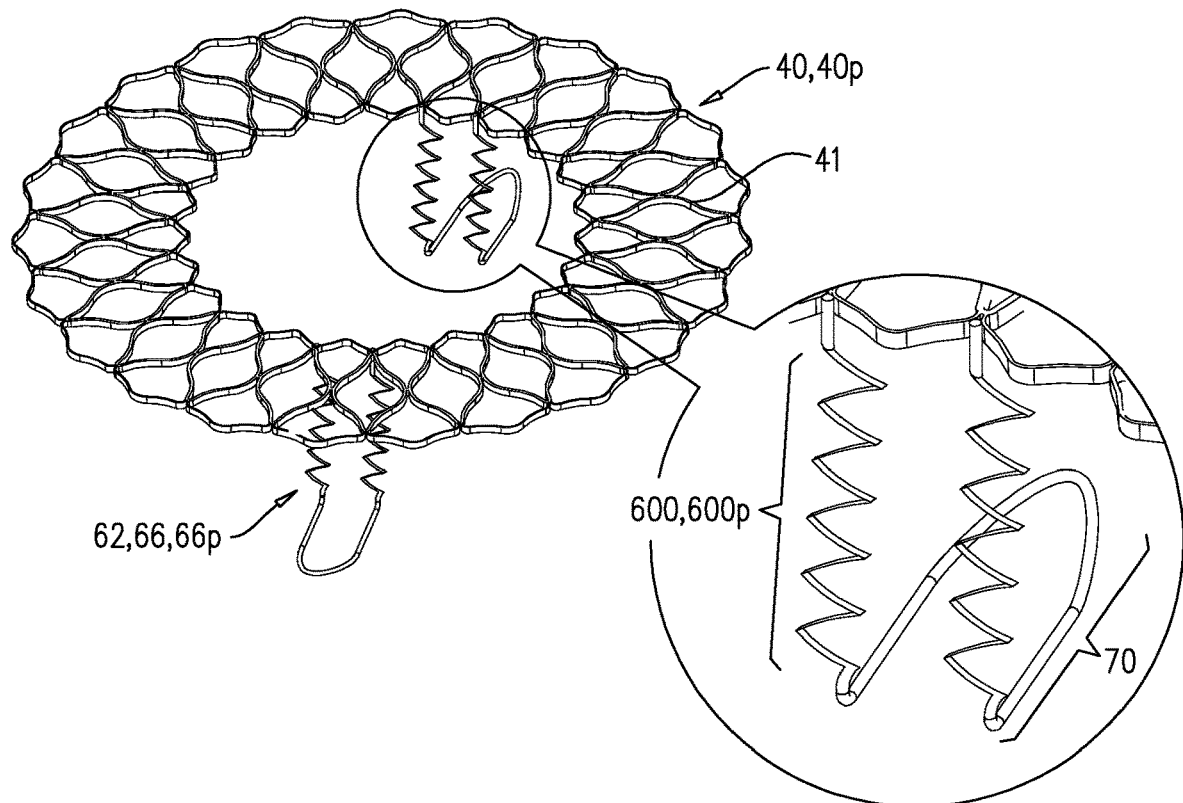

FIG. 17A shows prosthetic valve support 40, comprising prosthetic valve support 40n, which comprises support-anchoring elements 66, comprising support-anchoring elements 66n. Each support-anchoring element 66n comprises a coupling portion 70, coupled to upstream support portion 41 of support 40n via a length-adjustable holding element 600, comprising a stretchable holding element 600n. Stretchable holding element 600n comprises a tension spring, typically comprising a coil spring. Stretchable holding element 600n facilitates adjusting the distance between coupling portion 70 and upstream support portion 41 such that, for native valves of different dimensions, (1) upstream support portion 41 is placeable against the proximal (i.e., atrial) side of the prosthetic valve, and (2) coupling portion 70 is placeable on the distal (i.e., ventricular) side of the native valve (e.g., to engage the native leaflets and/or commissures, as described hereinabove).

FIG. 1713 shows prosthetic valve support 40, comprising prosthetic valve support 40p, which comprises support-anchoring elements 66, comprising support-anchoring elements 66p. Each support-anchoring element 66p comprises a coupling portion 70, coupled to upstream support portion 41 of support 40p via length-adjustable holding element 600, comprising a stretchable holding element 600p. Stretchable holding element 600p comprises a tension spring, typically comprising a zigzag-shaped piece of material, such as a shape-memory material, e.g., nitinol. Stretchable holding element 600p facilitates adjusting the distance between coupling portion 70 and upstream support portion 41 such that, for native valves of different dimensions, (1) upstream support portion 41 is placeable against the proximal (i.e., atrial) side of the prosthetic valve, and (2) coupling portion 70 is placeable on the distal (i.e., ventricular) side of the native valve (e.g., to engage the native leaflets and/or commissures, as described hereinabove).

FIG. 17C shows prosthetic valve support 40, comprising prosthetic valve support 40q, which comprises support-anchoring elements 66, comprising support-anchoring elements 66q. Each support-anchoring element 66q comprises a coupling portion 70, coupled to upstream support portion 41 of support 40q via length-adjustable holding element 600, comprising a stretchable holding element 600q. Stretchable holding element 600q comprises a tension spring, typically comprising an elastic tube 602, such as a tube of elastic silicone. Stretchable holding element 600q facilitates adjusting the distance between coupling portion 70 and upstream support portion 41 such that, for native valves of different dimensions, (1) upstream support portion 41 is placeable against the proximal (i.e., atrial) side of the prosthetic valve, and (2) coupling portion 70 is placeable on the distal (i.e., ventricular) side of the native valve (e.g., to engage the native leaflets and/or commissures, as described hereinabove).

For some applications of the invention, stretchable holding element 600q further comprises a limiting wire 604, typically coupled to upstream support portion 41 and coupling portion 70. Limiting wire 604 is generally non-elastic, and is configured to limit the expansion (i.e., stretching) of holding element 600q. For example, limiting wire may be configured to prevent overstretching of holding element 600q, e.g., to prevent failure of the holding element. Typically, limiting wire 604 is longer than the length of elastic tube 602 in the relaxed (i.e., contracted) configuration thereof, and is shorter than the length of elastic tube 602 in a maximally-expanded (i.e., maximally-stretched) configuration thereof. In the relaxed (i.e., contracted) configuration of elastic tube 602, limiting wire 604 is typically loose (e.g., generally bent, crumpled, flexed). When elastic tube 602 is expanded (i.e., stretched), limiting wire 604 typically becomes taut (e.g., generally straight), thereby limiting the expansion of elastic tube 602 to generally the length of limiting wire 604.

It is to be noted that the scope of the present invention includes the use of limiting wire 604 in combination with other length-adjustable holding elements including, but not limited to, stretchable holding element 600n, described with reference to FIG. 17A.

FIG. 17D shows prosthetic valve support 40, comprising prosthetic valve support 40u, which comprises support-anchoring elements 66, comprising support-anchoring elements 66u. Each support-anchoring element 66u comprises a coupling portion 70, coupled to upstream support portion 41 of support 40u via a length-adjustable holding element 600, comprising a stretchable holding element 600u. Stretchable holding element 600u facilitates adjusting the distance between coupling portion 70 and upstream support portion 41 such that, for native valves of different dimensions, (1) upstream support portion 41 is placeable against the proximal (i.e., atrial) side of the prosthetic valve, and (2) coupling portion 70 is placeable on the distal (i.e., ventricular) side of the native valve (e.g., to engage the native leaflets and/or commissures, as described hereinabove). Stretchable holding element 600u comprises a tension spring, typically comprising a coil spring 610. For some applications of the invention, coil spring 610 is generally similar to the coil spring of stretchable holding element 600n, as described hereinabove. Stretchable holding element 600u further comprises, or is coupled to, a restrictor 612. Restrictor 612 typically holds spring 610 in an expanded (i.e., stretched) configuration. Typically, restrictor 612 is decouplable from spring 610. For some applications, restrictor 612 may be mechanically removed by the user. For some applications, restrictor 612 may comprise a material that disintegrates in the body (e.g., a material that is at least in part soluble and/or biodegradable and/or bioresorbable). For these applications, restrictor 612 typically disintegrates over a predictable period of time e.g., between 15 minutes and 1 week, such as between 30 minutes and 3 days, for example, between 1 h and 1 day. For some applications, restrictor 612 is configured to decouple from (i.e., release) spring 610 gradually, e.g., in stages. For some applications, restrictor 612 is coupled to spring 610 and/or another part of prosthetic valve support 40u, such that, following the release of spring 610, the restrictor is retained so as not to enter the vasculature of the subject.

When spring 610 is released from restrictor 612, the spring relaxes (i.e., contracts), and provides a pulling force that sandwiches the native valve between support 40u and coupling portion 70, e.g., as described hereinabove, mutatis mutandis.

Figure 18A:
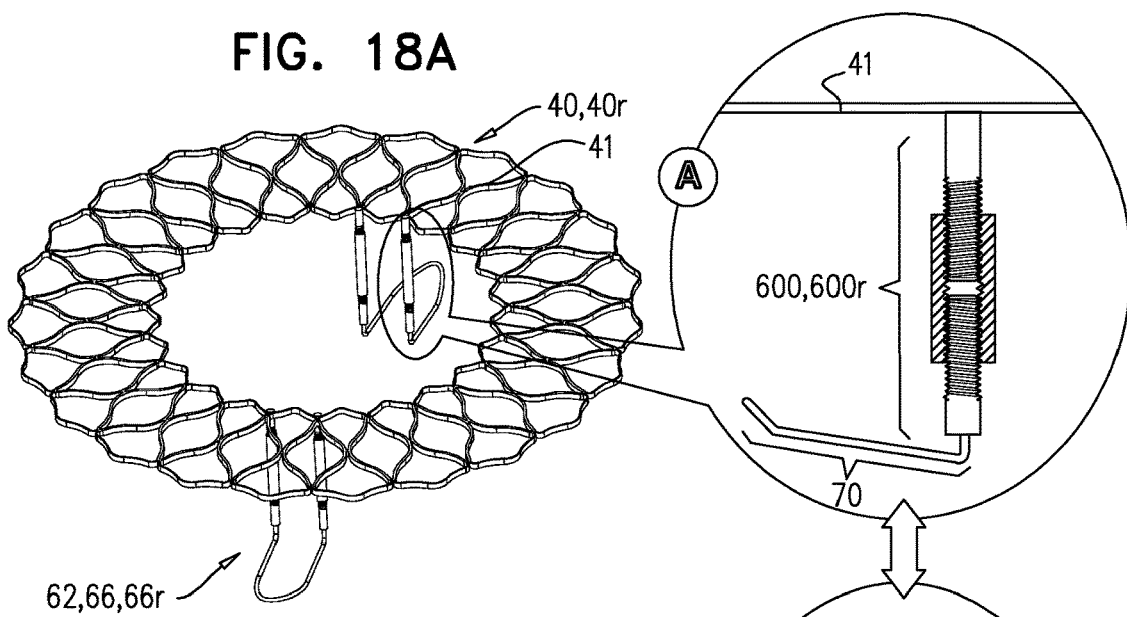
FIGS. 18A-B are schematic illustrations of prosthetic valve supports, comprising tissue-engaging elements, which comprise support-anchoring elements, comprising length-adjustable holding elements, in accordance with some applications of the invention.
Figure 18B:
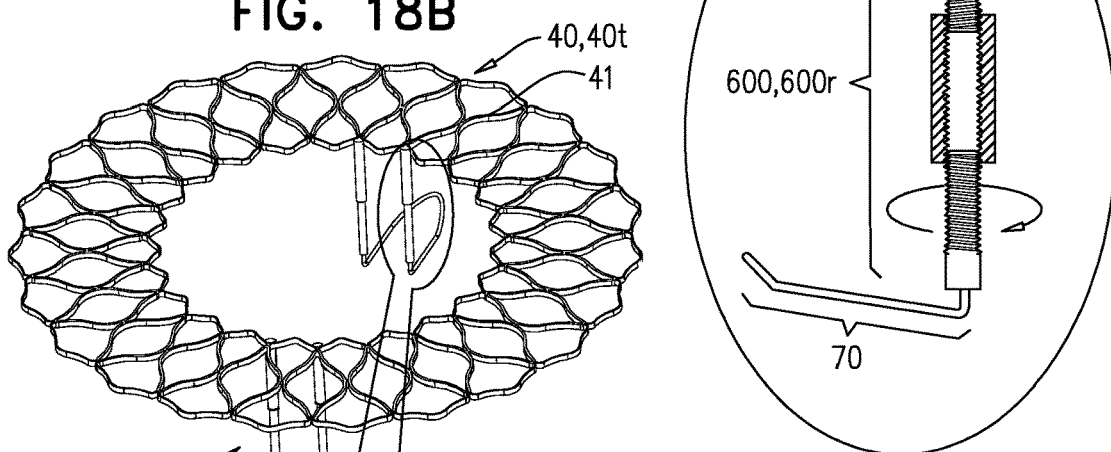

Reference is made to FIGS. 18A-B, which are schematic illustrations of prosthetic valve support 40, which comprises support-anchoring elements 66, comprising length-adjustable holding elements 600, in accordance with some applications of the invention.

FIG. 18A shows prosthetic valve support 40, comprising prosthetic valve support 40r, which comprises support-anchoring elements 66, comprising support-anchoring elements 66r. Each support-anchoring element 66r comprises a coupling portion 70, coupled to upstream support portion 41 of support 40r via length-adjustable holding element 600, comprising a telescopic holding element 600r. Telescopic holding element 600r comprises a plurality of portions, typically cylinders, which are slidable over and/or through each other. FIG. 18A shows telescopic holding element 600r comprising two externally-threaded cylinders connected by an internally-threaded cylinder, and configured such that rotation of the internally-threaded cylinder with respect to the externally-threaded cylinders adjusts the distance between the externally-threaded cylinders. Thereby, rotation of the internally-threaded cylinder adjusts the distance between coupling portion 70 and upstream support portion 41. Adjustment of this distance may be performed prior to implantation of prosthetic valve support 40r, and/or during the implantation procedure (e.g., after deployment of support 40r).

Reference is again made to FIGS. 17A-D, and 18A-B. The applications of the invention described with reference to FIGS. 17A-D, comprise support-anchoring elements 66 that comprise length-adjustable holding elements 600, such as stretchable holding elements 600n, 600p, and 600q. In addition to being axially stretchable, these holding elements are typically laterally flexible. This flexibility is hypothesized to be advantageous in some applications of the invention. For example, in some applications, leaflets 82 of the native valve may continue to function, at least in part, after support-anchoring elements 66 are coupled to the leaflets. In contrast, the adjustable holding elements 600 described with reference to FIGS. 18A-B (i.e., elements 600r and 600t) are typically laterally rigid.

Reference is again made to FIG. 18B, which shows prosthetic valve support 40, comprising prosthetic valve support 40t, which comprises support-anchoring elements 66, comprising support-anchoring elements 66t, in accordance with some applications of the invention. Each support-anchoring element 66t comprises a coupling portion 70, coupled to upstream support portion 41 of support 40t via length-adjustable holding element 600, comprising a telescopic holding element 600t. Telescopic holding element 600r comprises a plurality of portions, typically cylinders, which are slidable over and/or through each other. FIG. 18B shows telescopic holding element 600t comprising two overlapping cylinders. Sliding of the cylinders over each other adjusts the distance between coupling portion 70 and upstream support portion 41. Adjustment of this distance may be performed prior to implantation of prosthetic valve support 40t, and/or during the implantation procedure (e.g., after deployment of support 40t).

Typically, telescopic holding element 600t further comprises another element (not shown), which controls and/or adjusts the sliding of the cylinders described hereinabove. For example, element 600t may comprise a tension spring, such as those described with reference to FIGS. 17A-D, typically disposed inside the lumen defined by the overlapping cylinders. The combination of the tension spring with the overlapping cylinders combines the stretchability described with reference to FIGS. 17A-D, with the rigidity described with reference to FIGS. 18A-B.

Figure 19:
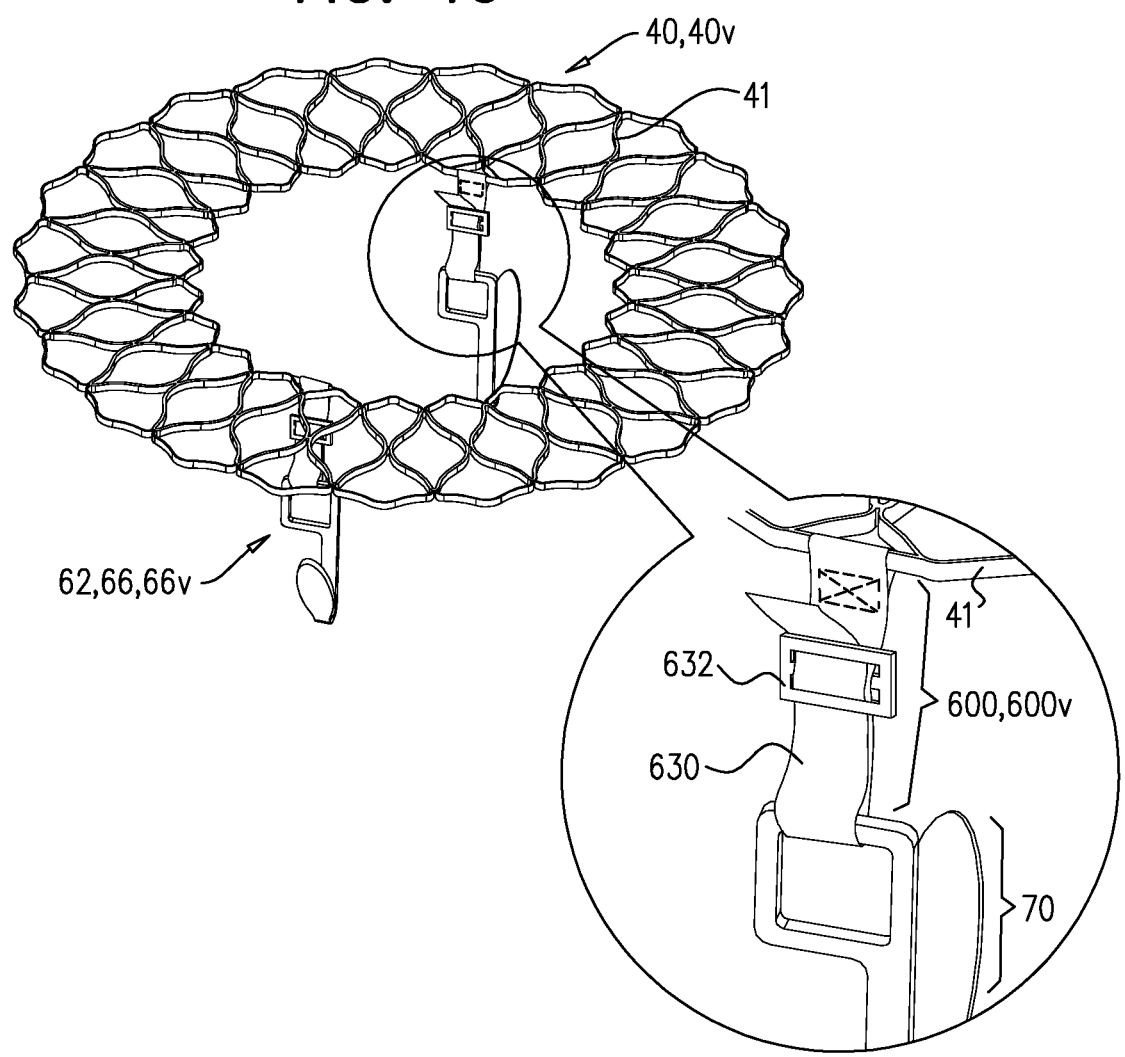
FIG. 19 is a schematic illustration of a prosthetic valve support, comprising tissue-engaging elements, which comprise support-anchoring elements, comprising length-adjustable holding elements, in accordance with some applications of the invention.
Figure 20A:
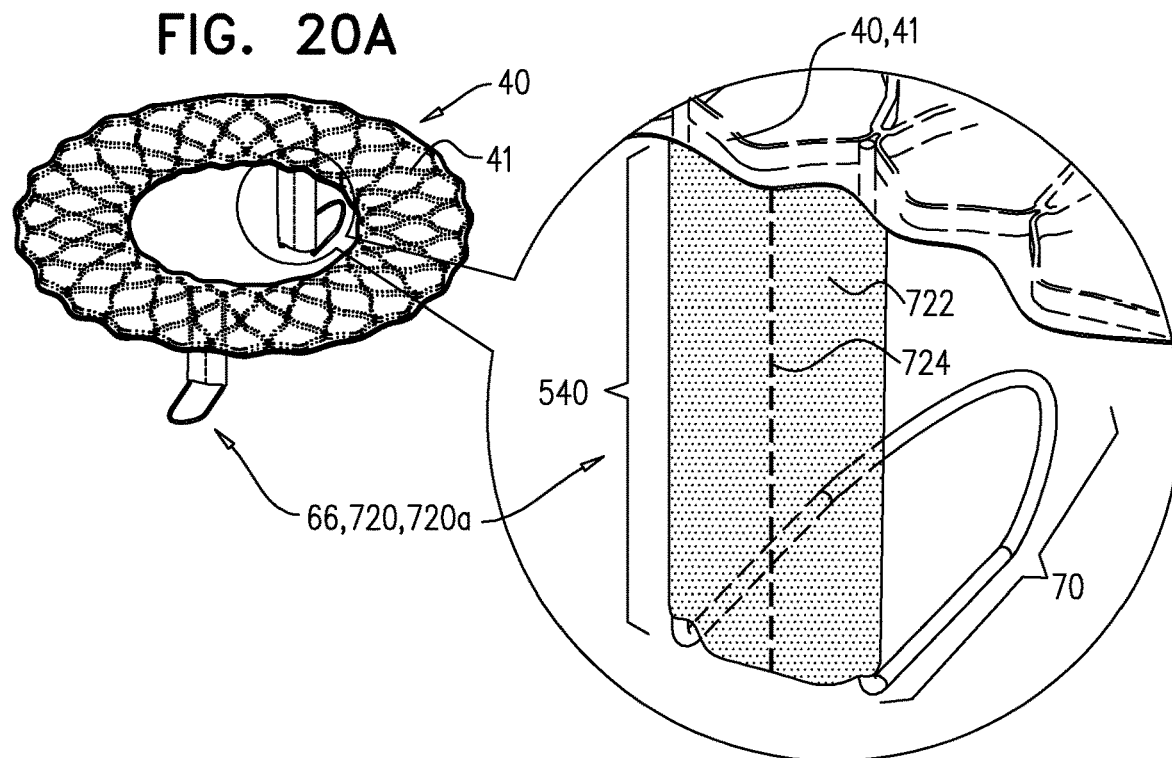
FIGS. 20A-F are schematic illustrations of prosthetic valve supports, comprising tissue-engaging elements, which comp support-anchoring elements, comprising flexible support-anchoring elements, in accordance with some applications of the invention.
Figure 20B:
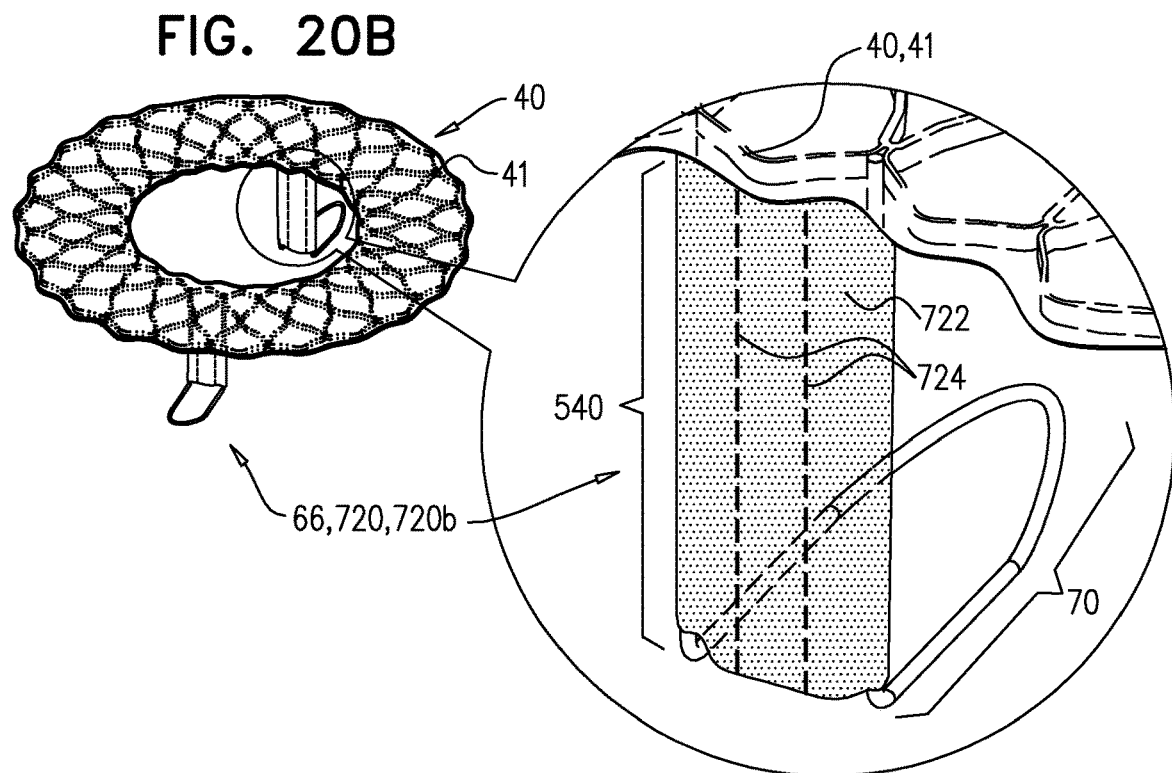
Figure 20C:
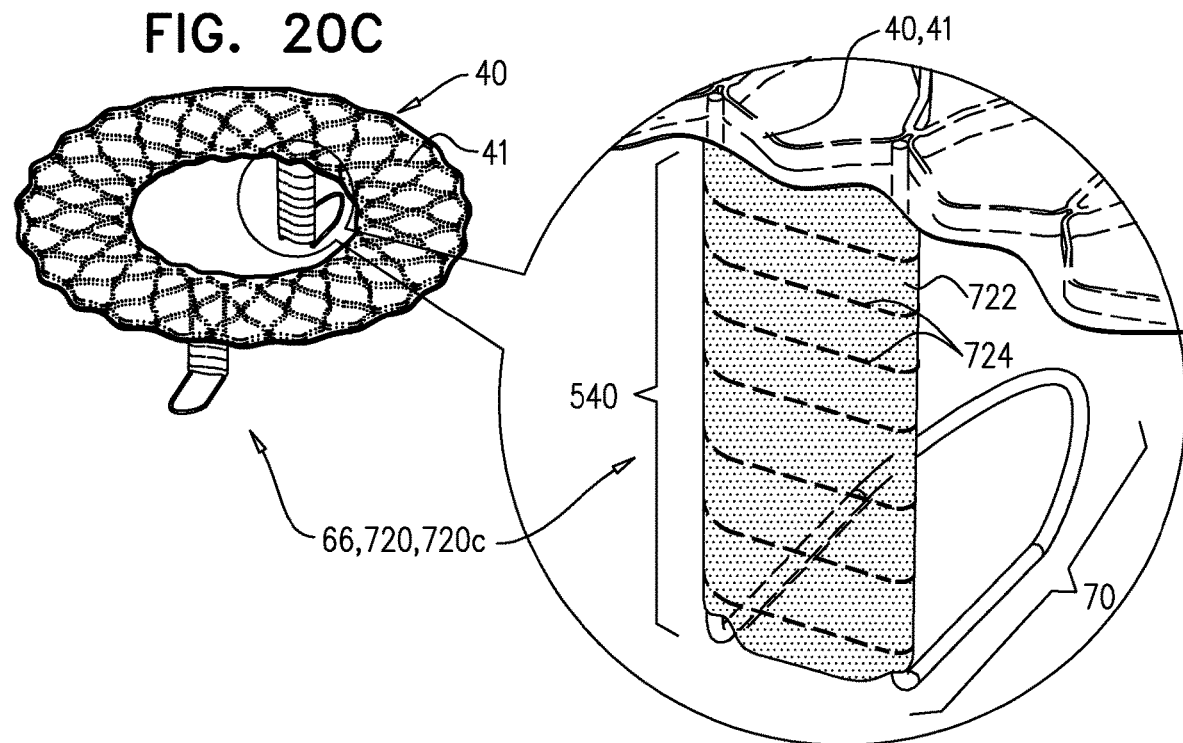
Figure 20D:
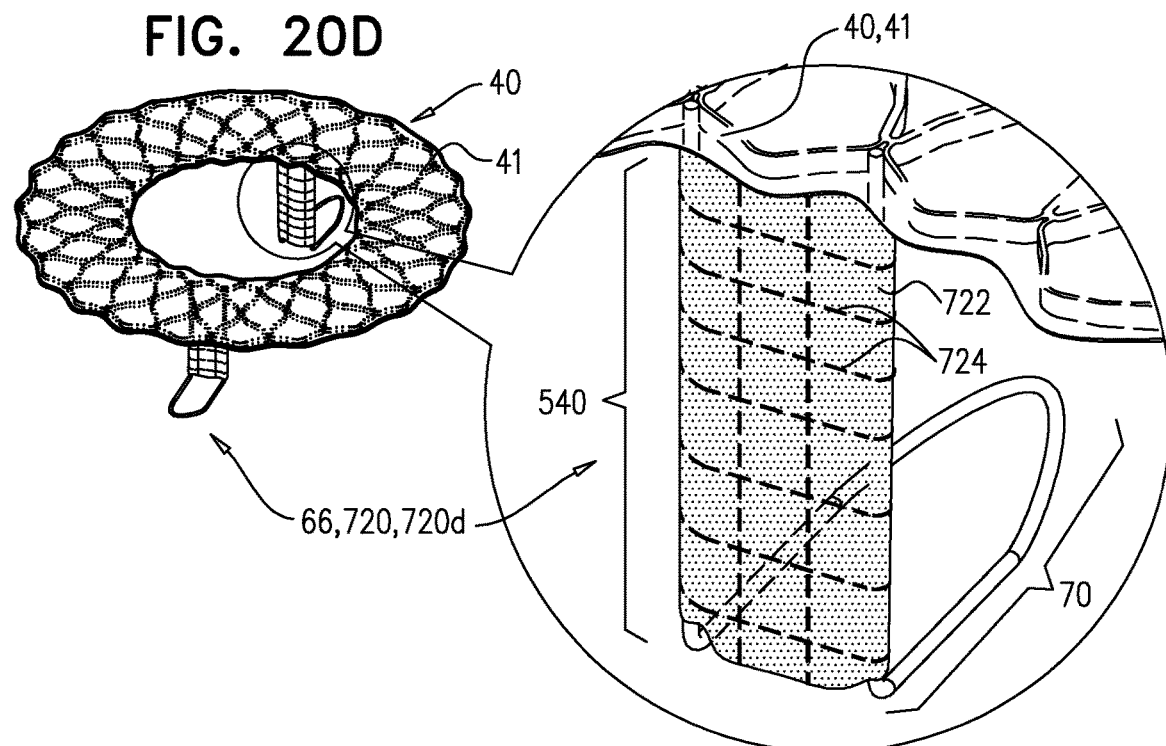
Figure 20E:
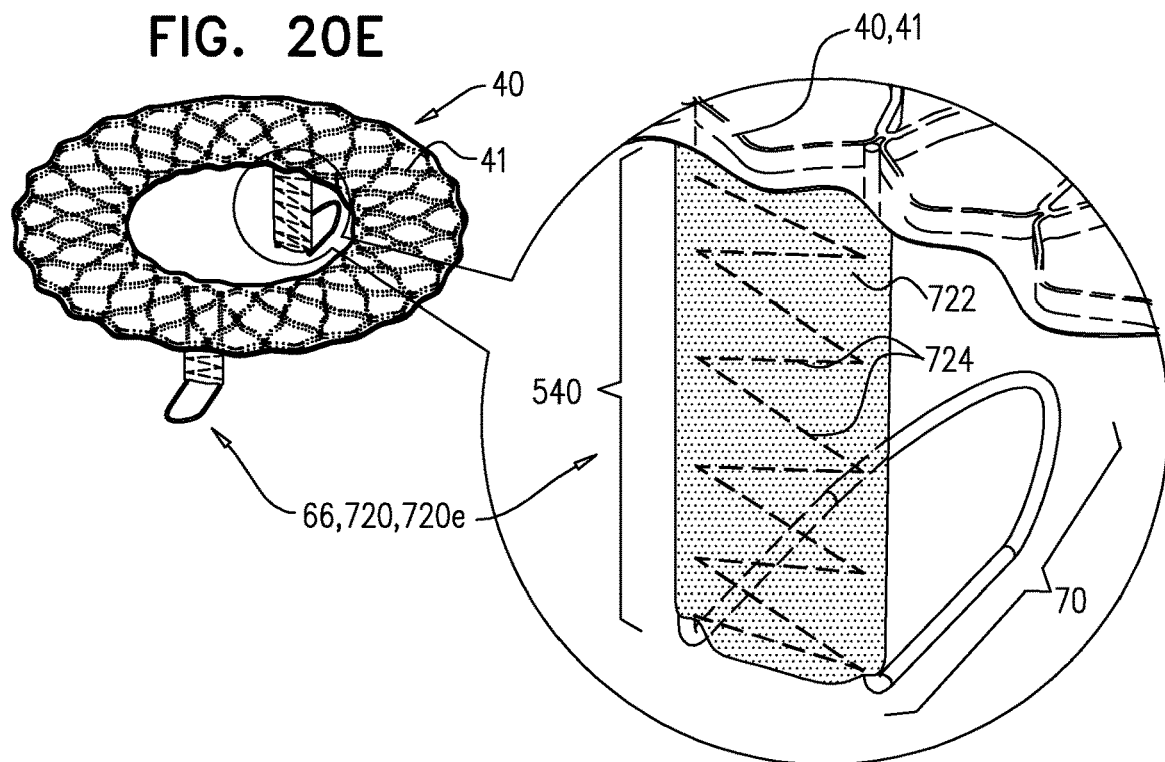
Figure 20F:
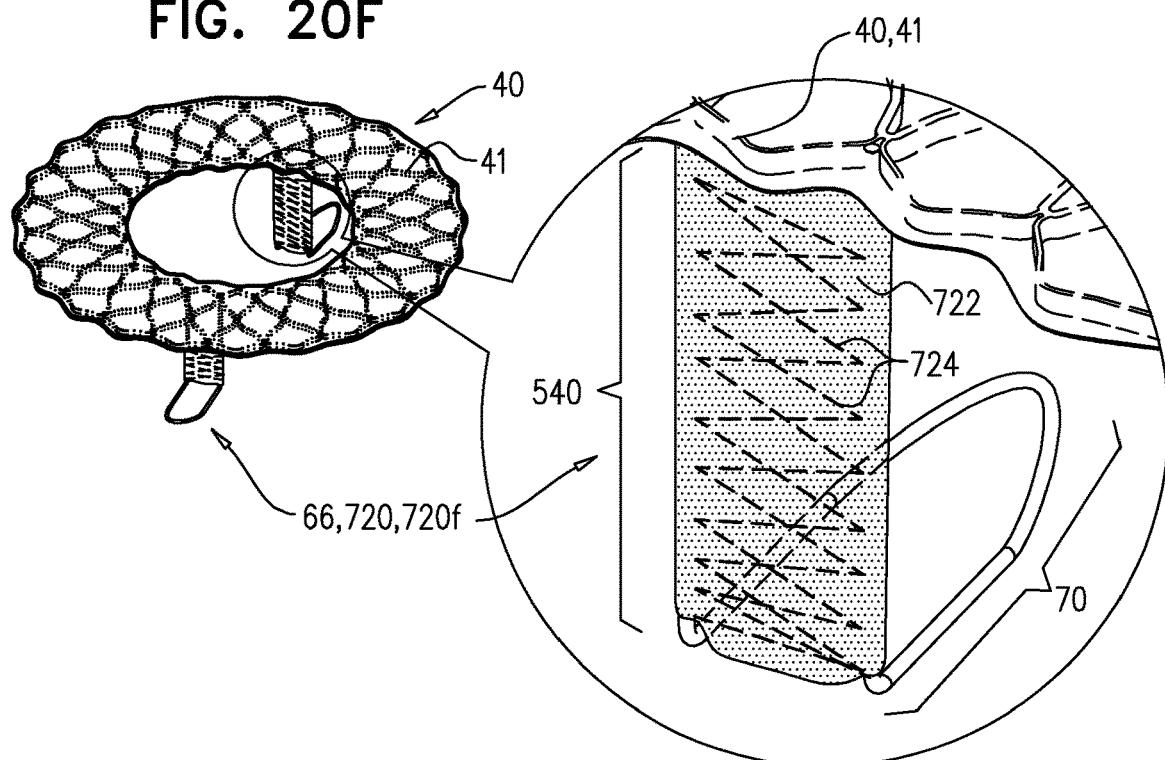

Reference is made to FIG. 19, which is a schematic illustration of prosthetic valve support 40, comprising prosthetic valve support 40v, which comprises support-anchoring elements 66, comprising support-anchoring elements 66v, in accordance with some applications of the invention. Each support-anchoring element 66v comprises a coupling portion 70, coupled to upstream support portion 41 of support 40v via length-adjustable holding element 600, comprising length-adjustable holding element 600v. Element 600v comprises a strap 630 and a strap adjuster 632

(e.g., a buckle, a ladder lock, a tri-glide). Strap 630 and adjuster 632 are configured and arranged such that the distance between coupling portion 70 and upstream support portion 41 is adjustable by sliding adjuster 632 along strap 630, and/or by sliding at least part of strap 630 through adjuster 632. That is, strap 630 and strap adjuster 632 are generally similar to the strap and adjustor of a bag, such as a backpack. Adjustment of element 600*v* may be performed prior to implantation of prosthetic valve support 40*v*, and/or during the implantation procedure (e.g., after deployment of support 40*v*).

Non-limiting examples of materials which strap 630 and/or strap adjuster 632 may comprise, include polyester, PTFE (e.g., ePTFE), nylon, cotton, nitinol, stainless steel, nickel cobalt, and cobalt chrome.

Reference is made to FIGS. 20A-F, which are schematic illustrations of prosthetic valve support 40, comprising support-anchoring elements 66, comprising flexible support-anchoring elements 720, in accordance with some applications of the invention. Elements 720 comprise a coupling portion 70 and a connector 540, which comprises (1) a flexible material 722, such as a fabric (e.g., covering 440), pericardial tissue, and/or a polymer, and (2) one or more stiffening filaments 724. Filaments 724 typically comprise a material that is stiffer and/or more resilient than flexible material 722. For example, filaments 724 may comprise a metallic or plastic wire. Filaments 724 are coupled to material 722, such as by weaving and/or by gluing. The absolute and relative quantities and configurations of material 722 and filaments 724, may be generated and/or selected so as to provide a desired stiffness of an element 720. For example, an element 720 that comprises more and/or more densely-woven stiffening filaments 724 may be selected for applications that require a stiffer element 720. Conversely, an element 720 that comprises fewer and/or less densely-woven stiffening filaments 724 may be selected for applications that require a more flexible element 720. FIGS. 20A-F show elements 720 comprising flexible support-anchoring elements 720*a-f*, comprising various relative quantities of material 722 and filaments 724, in accordance with respective applications of the invention. These figures are not intended to limit the scope of the invention but, rather, to illustrate the variability of the invention as a whole, and of elements 720 in particular.

For some applications, a kit is provided, containing a plurality of prosthetic valve supports 40, each prosthetic valve support comprising a flexible support-anchoring element 720 having a different configuration of material 722 and filaments 724, and thereby a different flexibility (e.g., elements 720*a*-720*f*). A user typically selects a support 40 that comprises a support-anchoring element 720 of a desired configuration for a particular application.

For some applications, a kit is provided, containing (1) at least one prosthetic valve support 40 (i.e., upstream support portion 41), and (2) a plurality of flexible support-anchoring elements 720, each element 720 having a different configuration of material 722 and filaments 724, and thereby a different flexibility. A user typically (1) selects a support-anchoring element 720 of a desired configuration for a particular application, and (2) couples the selected element 720 to the upstream support portion 41.

For some applications, a kit is provided, containing (1) at least one prosthetic valve support 40 (i.e., upstream support portion 41), (2) at least one coupling portion 70, and (3) a plurality of connectors 540, each connector 540 having a different configuration of material 722 and filaments 724, and thereby a different flexibility. A user typically (1) selects a connector 540 of a desired configuration for a particular application, and (2) couples the selected connector 540 to the coupling portion 70, and to the upstream support portion 41.

Figure 21A:
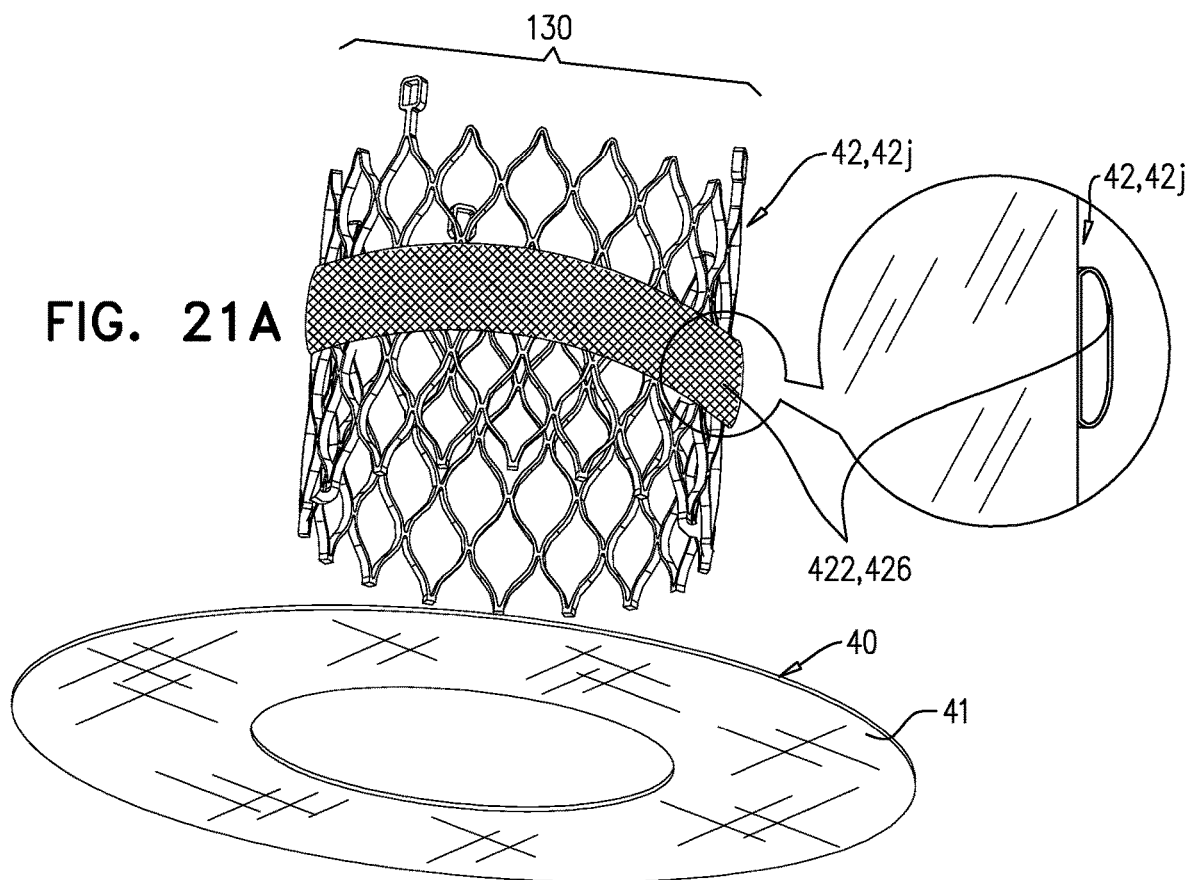
FIGS. 21A-C are schematic illustrations of a prosthetic valve support, comprising an inflatable support-engaging element, in accordance with some applications of the invention.
Figure 21B:
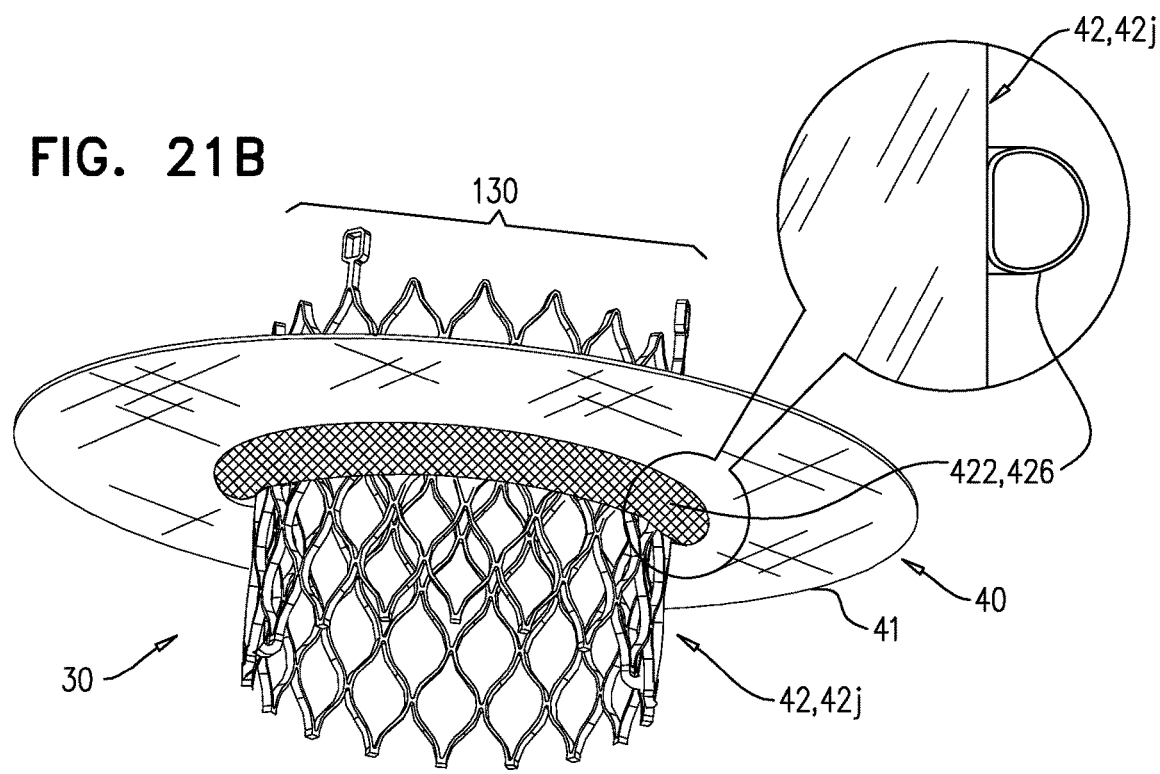
Figure 21C:
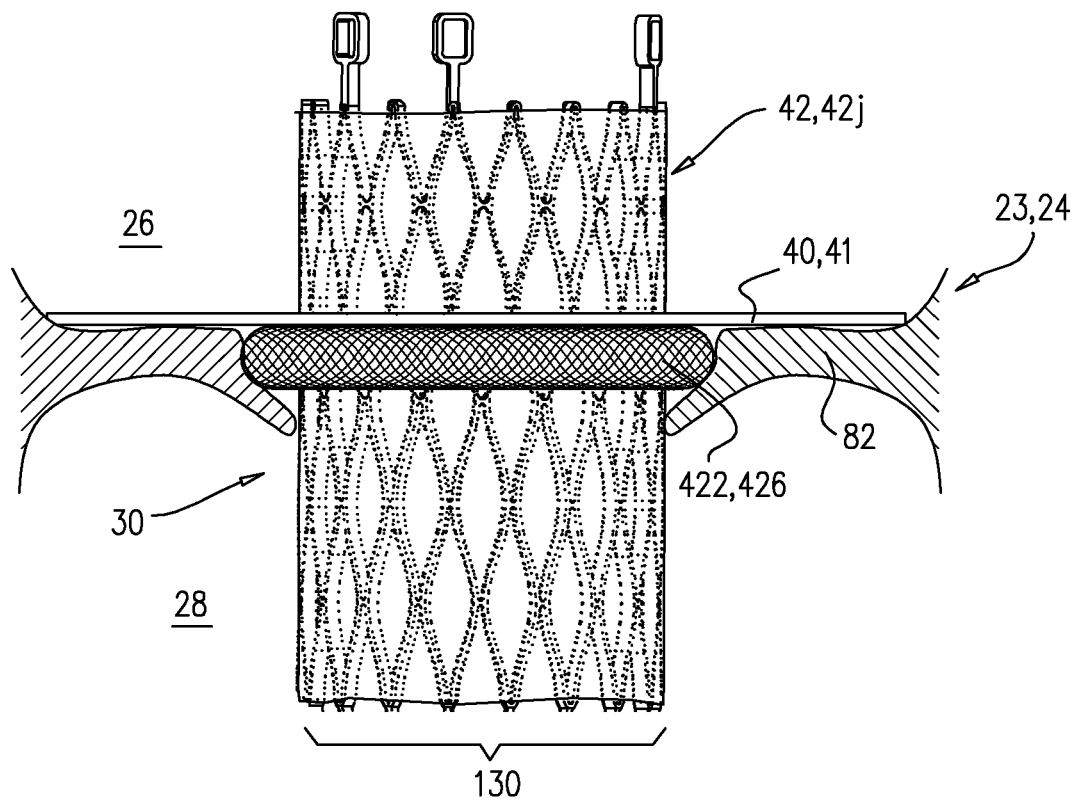

Reference is made to FIGS. 21A-C, which are schematic illustrations of prosthetic valve 42, comprising prosthetic valve 42*j*, in accordance with some applications of the invention. Prosthetic valve 42*j* comprises at least one support-engaging element 422, comprising inflatable support-engaging element 426, disposed on the outer surface of primary structural element 130 of prosthetic valve 42*j*. FIGS. 21A-B show prosthetic valve 42*j* comprising one annular inflatable support-engaging element 426, disposed circumferentially around primary structural element 130. Typically, prosthetic valve support 40 comprises one or more support-anchoring elements (not shown; e.g., support-anchoring elements 66, as described herein) which anchor the prosthetic valve support to native valve 23.

FIG. 21A shows prosthetic valve 42*j* and prosthetic valve support 40. Following the deployment of prosthetic valve support 40 against the annulus of native valve 23, prosthetic valve 42*j* is passed through the lumen of the prosthetic valve support as described hereinabove (e.g., with reference to FIGS. 1A-H). As described hereinabove, prosthetic valve 42*j* is typically less than fully expanded (e.g., prosthetic valve 42*j* is partially expanded) when it is passed through the lumen of the prosthetic valve. Accordingly, FIG. 21A shows prosthetic valve 42*j* in a partially-expanded configuration.

FIG. 21B shows prosthetic valve 42*j* having been expanded in the lumen of prosthetic valve support 40, such that inflatable support-engaging element 426 is disposed distal (e.g., ventricularly) to prosthetic valve support 40. Element 426 is inflated (e.g., with saline) and thereby expands, thereby increasing a longest transverse cross-sectional length of prosthetic valve 42*j*, such that the transverse cross-sectional length is longer than a longest transverse cross-sectional length of the lumen defined by prosthetic valve support 40. Thereby, inflatable support-engaging element 426 restricts proximal movement of prosthetic valve 42*j* with respect to prosthetic valve support 40, thereby anchoring prosthetic valve 42*j* to the distal side of prosthetic valve support 40, and to native valve 23.

Inflatable support-engaging element 426 is typically coupled to prosthetic valve 42 such that the prosthetic valve is compressible (i.e., crimpable) for delivery, as described hereinabove. For some applications, inflatable support-engaging element 426 is coupled to the prosthetic valve using sutures. Typically, such sutures are arranged in a single circumferential suture line, so as to facilitate deformation (e.g., flattening) of element 426 during crimping of the prosthetic valve for delivery. For some applications, element 426 is coupled to the prosthetic valve using an adhesive.

FIG. 21C shows implant 30, comprising prosthetic valve support 40 and prosthetic valve 42*j*, implanted at native valve 23, comprising mitral valve 24. Support 40 is deployed against the proximal (i.e., atrial) surface of the annulus of the native valve, and is typically coupled to the valve via support-anchoring elements 66 (not shown). Prosthetic valve 42*j* is deployed in the lumen of support 40 such that, when inflated, element 426 restricts proximal movement of the prosthetic valve with respect to support 40. This restriction, combined with the coupling of support 40 to the native valve, couples implant 30 to the native valve.

For some applications of the invention, prosthetic valve 42*j* is deployed in the lumen of support 40, such that element 426 is disposed on the proximal side of support 40. It is hypothesized that, when in this position and inflated, element 426 restricts distal movement of the prosthetic valve with respect to the support.

For some applications of the invention, prosthetic valve 42j is deployed in the lumen of support 40, such that element 426 is planar with upstream support portion 41 of the support, and such that at least part of element 426 is disposed proximal to portion 41, and at least part of element 426 is disposed distal to portion 41. It is hypothesized that, when in this position and inflated, element 426: (1) applies a radially-expansive force on support 40 (i.e., supplements radially-expansive forces applied by prosthetic valve 42 on support 40), and (2) restricts proximal and distal movement of the prosthetic valve with respect to the support.

Figure 22A:
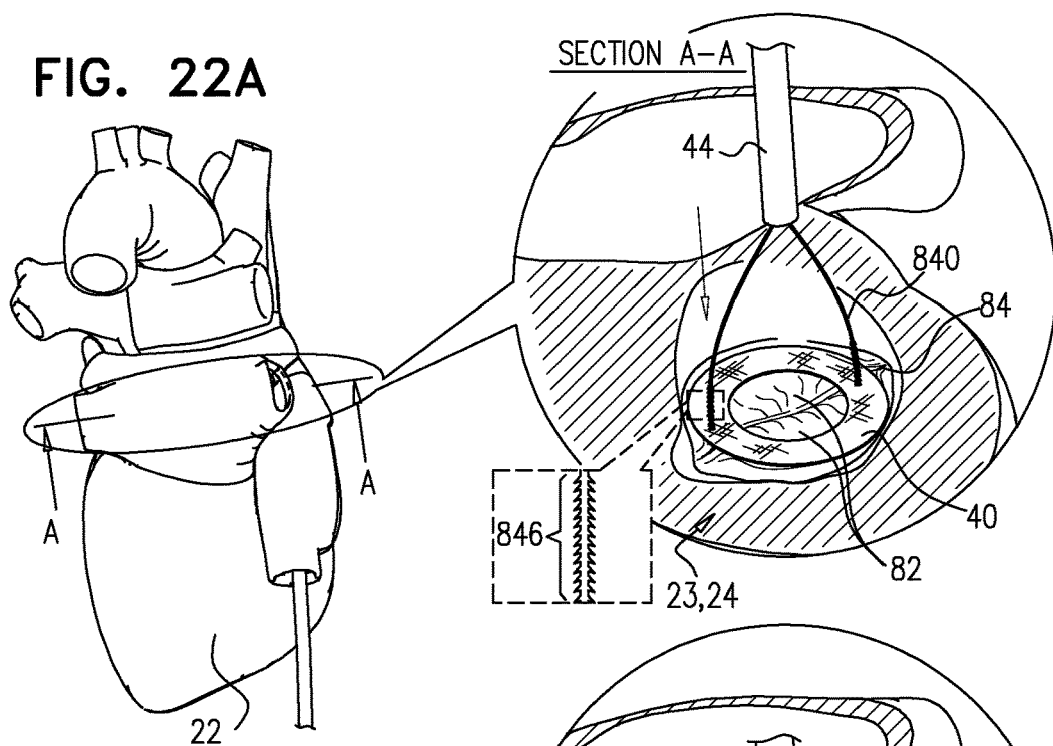
FIGS. 22A-C are schematic illustrations of sequential steps in the implantation of an implant, comprising a prosthetic valve and a prosthetic valve support, coupled via coupling leads.
Figure 22B:
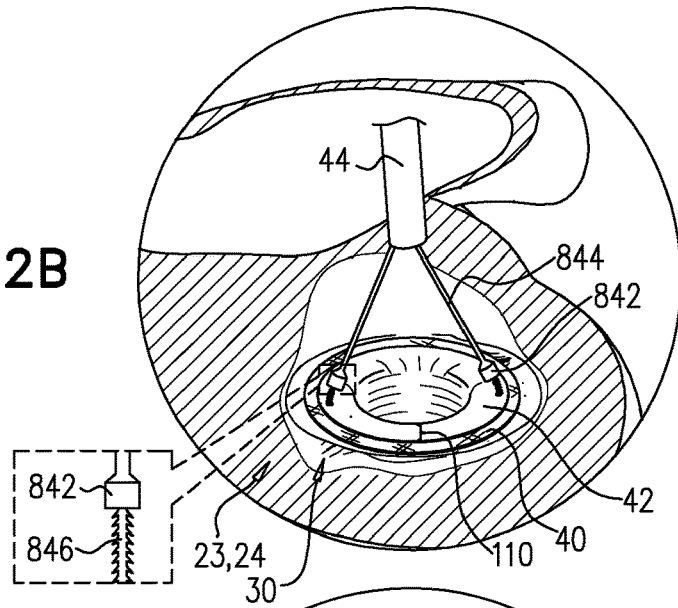
Figure 22C:
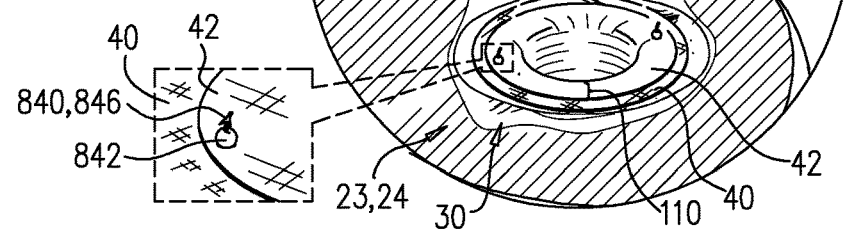

Reference is made to FIGS. 22A-C, which are schematic illustrations of the implantation of implant 30, comprising prosthetic valve support 40 and prosthetic valve 42, coupled by one or more (e.g., 2 or more, such as 4) coupling leads 840 (e.g., coupling wires), in accordance with some applications of the invention. For delivery, coupling leads 840 are coupled to prosthetic valve support 40 and prosthetic valve 42. For some applications, coupling leads 840 are slidably coupled to support 40 and/or prosthetic valve 42. For example, within overtube 44, prosthetic valve 42 may be disposed proximally to support 40, and coupled to support 40 by being slidably coupled to coupling leads 840.

FIG. 22A shows prosthetic valve support 40, having been coupled to native valve 23, comprising mitral valve 24. For example, support 40 may be coupled to the native valve using techniques described herein (e.g., via support-anchoring elements 66). Support 40 is coupled to coupling leads 840, which extend from support 40 to at least prosthetic valve 42, which remains disposed within overtube 44.

FIG. 22B shows prosthetic valve 42 having been deployed in the lumen of support 40, and in the lumen of native valve 23, as described herein, mutatis mutandis. Coupling leads 840 extend from support 40, through a proximal portion (e.g., an upstream portion and/or proximal portion 110) of prosthetic valve 42, and into overtube 44. Typically, coupling lead 840 comprises a plurality of teeth 846, typically disposed at a distal end of the coupling lead. A controller tube 844 is typically used to slide (e.g., push) ratchet housing 842 over coupling lead 840, and over teeth 846, such that the proximal portion of prosthetic valve 42 is pushed against support 40. Teeth 846 allow ratchet housing 842 to slide over coupling lead 840 in one direction, and inhibit (e.g., restrict) such sliding in another (e.g., the opposite) direction. Pushing prosthetic valve 42 against support 40 using controller tube 844 and ratchet housing 842, thereby facilitates coupling of prosthetic valve 42 to support 40. Thereby, sliding of ratchet housing 842 over coupling lead 840 facilitates coupling of the prosthetic valve to the prosthetic valve support.

Reference is made to FIG. 22C. Following the coupling of prosthetic valve 42 to prosthetic valve support 40, and thereby the implantation of implant 30 in native valve 23, coupling leads are typically cut at a point proximal to ratchet housing 842, and overtube 44 is withdrawn from the subject.

Figure 23A:
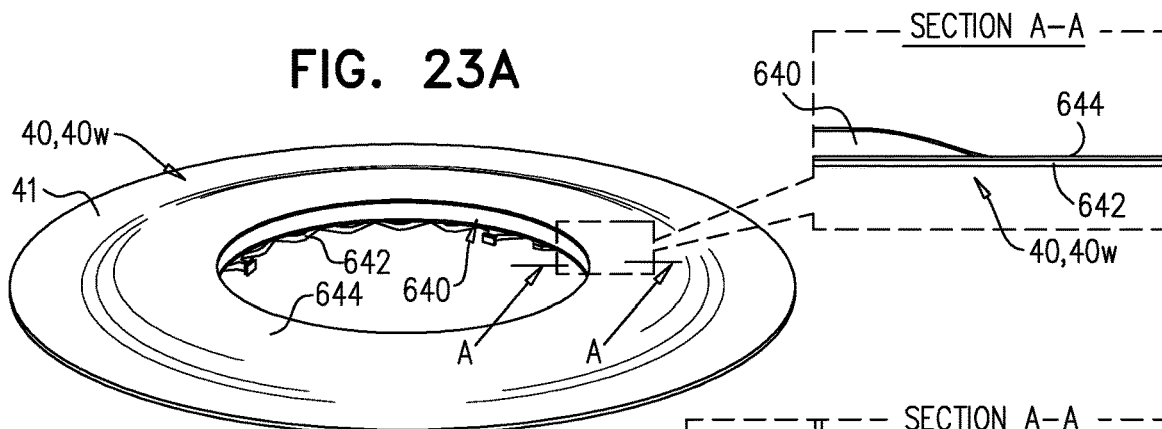
FIGS. 23A-B are schematic illustrations of a prosthetic valve support, shaped to define at least one pocket, and the coupling thereto of a prosthetic valve, in accordance with some applications of the invention.
Figure 23B:
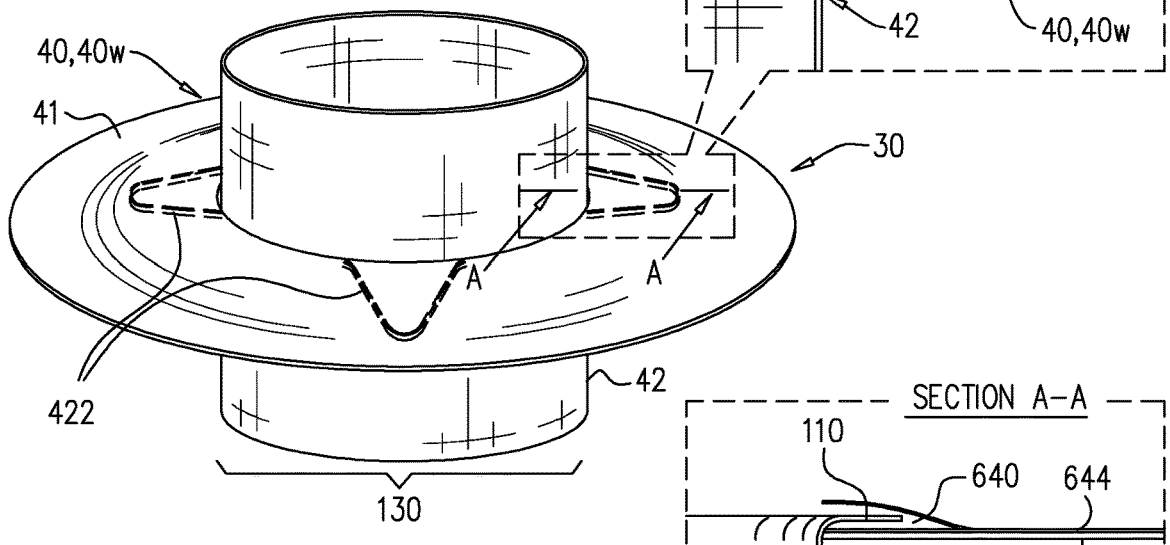
Figure 24:
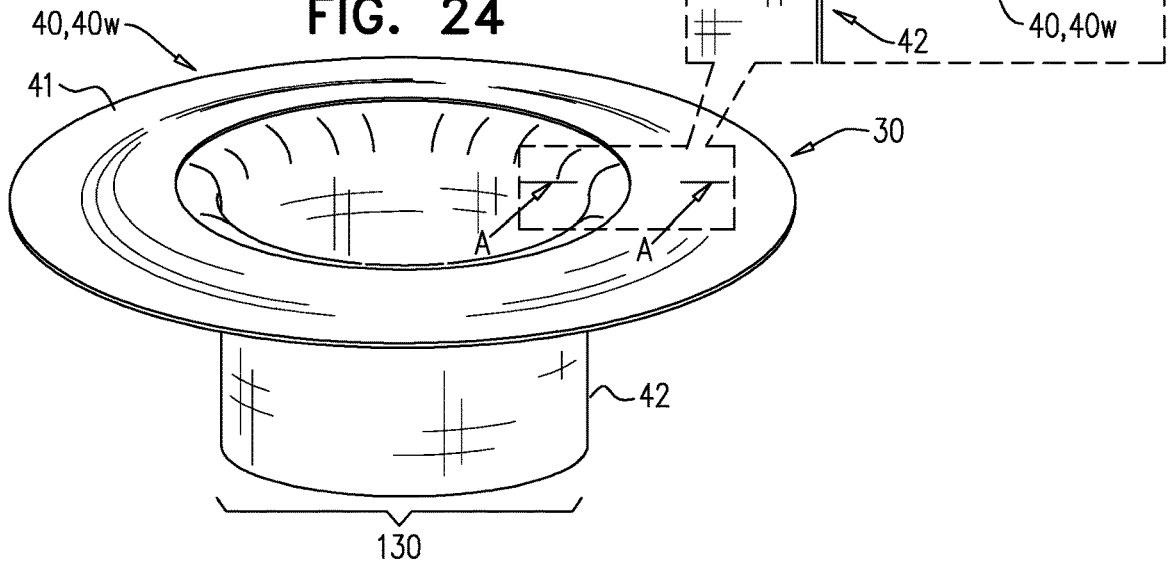
FIG. 24 is a schematic illustration of a prosthetic valve support, shaped to define at least one pocket, and the coupling thereto of a prosthetic valve, in accordance with some applications of the invention.

Reference is made to FIGS. 23A-24, which are schematic illustrations of prosthetic valve support 40, comprising prosthetic valve support 40w, which is shaped to define at least one pocket 640, in accordance with some applications of the invention. Prosthetic valve support 40 (i.e., support 40w) typically comprises a wire frame, such as an expandable wire frame. For some applications, the wire frame of support 40w is shaped to define pocket 640. For some applications, the wire frame of prosthetic valve support 40 (i.e., support 40w) is generally covered with a covering (such as a fabric, e.g., as described herein). For some applications, the covering may form at least one wall of pocket 640.

FIG. 23A shows an application of support 40w, comprising upstream support portion 41 that comprises a wire frame 642, generally covered with a covering 644. In this application, pocket 640 is generally annular, and circumscribes the lumen defined by support 40w (i.e., the lumen defined by upstream support portion 41 of support 40w). That is, the lumen defined by support 40w can be considered to be defined by two holes: (1) a proximal (i.e., upper) hole defined by a proximal (i.e., upper) wall of pocket 640, and (2) a distal (i.e., lower) hole defined by a distal (i.e., lower) wall of pocket 640. FIGS. 23A-24 show both walls of pocket 640 as having a generally similar depth. That is, a longest dimension of the distal hole is generally equal to the longest dimension of the proximal hole. For some applications, the two holes are generally not equally dimensioned. For example, to facilitate deployment of prosthetic valve 42 and/or coupling of prosthetic valve 42 to support 40w, one of the holes that defines the lumen of support 40w may have a smaller longest dimension than the other hole.

FIG. 23B shows prosthetic valve 42 comprising support-engaging elements 422 (e.g., prosthetic valve 42a comprising integral support-engaging elements 424, as described with reference to FIG. 8A), coupled to prosthetic valve support 40w. Elements 422 typically define a cross-sectional area, the longest dimension of which is typically longer than a transverse cross-sectional longest dimension of the lumen defined by prosthetic valve support 40w (i.e., of the upper and/or lower holes described with reference to FIG. 23A). During deployment, elements 422 are placed within pocket 640. Thereby, in addition to the radially-expansive force that typically couples prosthetic valve 42 to support 40, the radially-protruding support-engaging elements 422 restrict axial (i.e., proximal and distal) movement of prosthetic valve 42 with respect to support 40w, thereby anchoring prosthetic valve 42 to support 40w, and to native valve 23.

For some applications, prosthetic valve is provisionally expanded (1) sufficiently such that elements 422 protrude into pocket 420 and prevent axial movement of prosthetic valve 42, but (2) insufficiently for radially-expansive forces to fixedly couple the prosthetic valve to prosthetic valve support 40w. In this configuration, a user may rotate the prosthetic valve to a desired orientation, before finally allowing the prosthetic valve to expand and become coupled to support 40w.

FIG. 24 shows prosthetic valve 42, configured to comprise an expanded proximal portion 110 of primary structural element 130. Proximal portion 110 defines a cross-sectional area with a longest length that is longer than a transverse cross-sectional longest dimension of the lumen defined by prosthetic valve support 40w (i.e., of the upper and/or lower holes described with reference to FIG. 23A). During deployment, portion 110 is placed within pocket 640. Thereby, in addition to the radially-expansive force that typically couples prosthetic valve 42 to support 40, portion 110 restricts axial (i.e., proximal and distal) movement of prosthetic valve 42 with respect to support 40w, thereby anchoring prosthetic valve 42 to support 40w, and to native valve 23.

Reference is made to FIGS. 25A-E, which are schematic illustrations of sequential steps in the use of a retrieval device 800, in accordance with some applications of the invention. Retrieval device 800 comprises a plurality of struts 804, and typically comprises a shaft 802, with which struts 804 are axially aligned, and around which the struts are circumferentially disposed. A coupling element 805, such as a hook 806, is coupled to a middle portion of each strut.

Figure 25C:
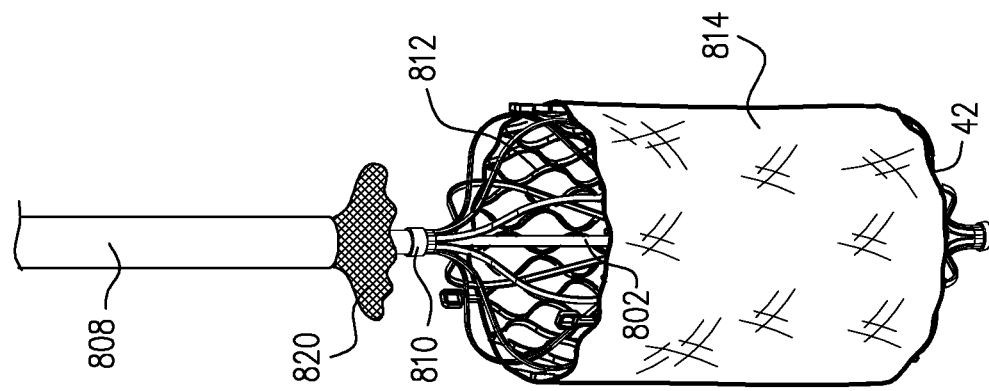
Figure 25B:
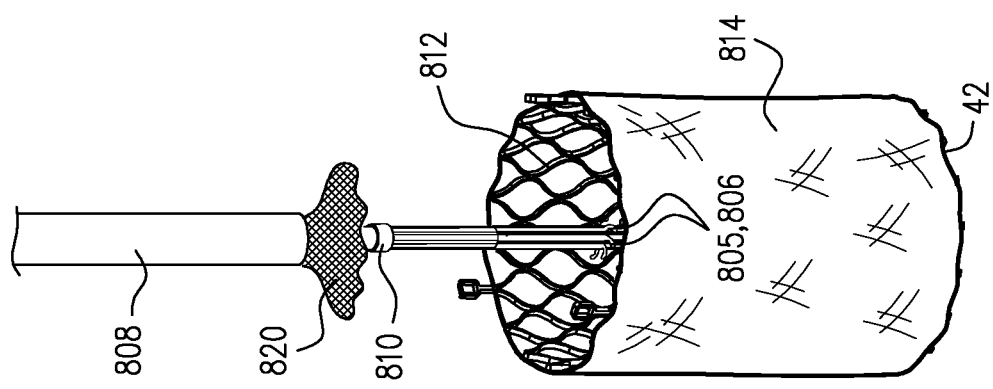
Figure 25A:
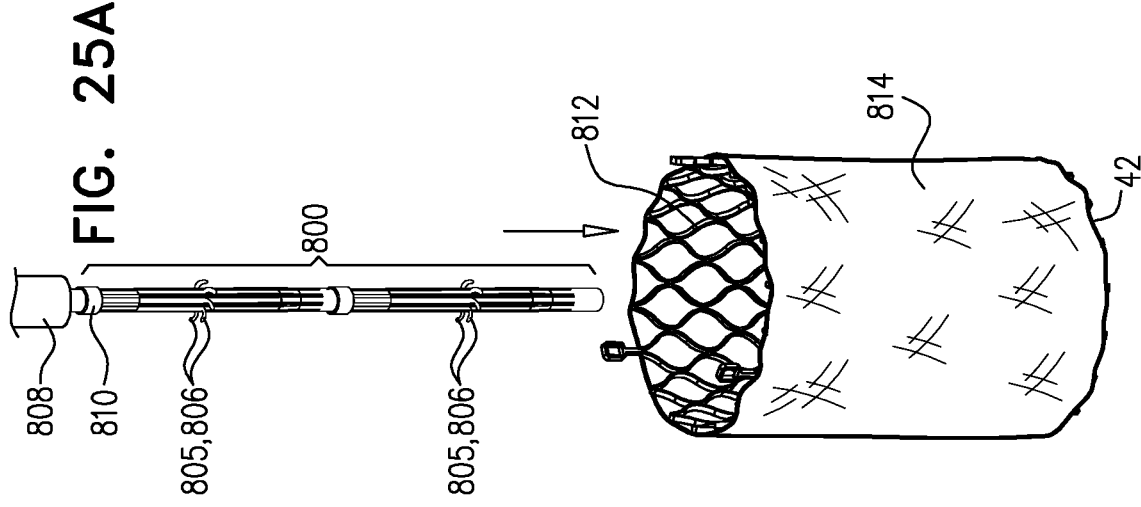

Reference is made to FIGS. 25A-B. At some time subsequent to implantation of a prosthetic valve (i.e., prosthetic valve 42), it may be necessary and/or desirable to retrieve the prosthetic valve (i.e., to remove the prosthetic valve from the subject). Typically, retrieval device 800 is delivered to the site of the prosthetic valve (i.e., to the native valve) in and/or using an overtube 808. Retrieval device 800 is advanced toward prosthetic valve 42, and into the lumen defined by the prosthetic valve.

FIG. 25C shows middle portions of struts 804 being extended radially outward from shaft 802. Typically, one or more middle portions of struts 804 are extended radially outward by reducing the distance between the proximal end and the distal end of each strut. For example, struts 804 may be bent and/or folded. In the application of the invention shown in FIGS. 25A-E, retrieval device further comprises a cuff 810, coupled to the proximal ends of struts 804, and slidably coupled to shaft 802. Movement of cuff 810 distally, reduces the distance between the proximal and distal ends of struts 804, thereby extending the middle portions of the struts radially outward.

FIG. 25D shows two, respectively orthogonal, cross-sectional views of retrieval device 800 in the lumen of prosthetic valve 42. The middle portions of struts 804 have been extended radially outward, and typically make contact with prosthetic valve 42. Prosthetic valve 42 is typically covered with a covering, which facilitates the desired flow of blood through the prosthetic valve. The covering may comprise polyethylene terephthalate (e.g., polyester), polytetrafluoroethylene (e.g., Teflon, ePTFE), pericardial tissue, or any other suitable material. Hooks 806 protrude through wire frame 812 of prosthetic valve 42, and typically do not extend through covering 814. Following the extension of the middle portions of struts 804, coupling element 805 is coupled to (e.g., hooks 806 are hooked around) wire frame 812 of prosthetic valve 42. For example, hooks 806 are arranged to point in the same direction as each other (e.g., such that all hooks point clockwise, or all hooks point anticlockwise). Following extension of the middle portions of struts 804, retrieval device 800 is rotated, such that hooks 806 hook around wire frame 812, between the wire frame and covering 814.

Reference is made to FIG. 25E. Following coupling of coupling elements 805 (i.e., hooks 806) to wire frame 812 of prosthetic valve 42, the middle portions of struts 804 are retracted radially inward, i.e., toward shaft 802. For example, the distance between proximal and distal ends of struts 804 is increased, e.g., by sliding cuff 810 proximally. Because struts 804 are coupled to the wire frame, prosthetic valve 42 is drawn radially inward. That is, prosthetic valve 42 is compressed (i.e., re-crimped). Retrieval device 800 and prosthetic valve 42 are drawn into overtube 808, and subsequently removed from the subject.

FIGS. 25A-E illustrate each strut 804 having two outwardly-extendable middle portions, in order to couple to, and compress prosthetic valve 42 at/from two sites (i.e., a proximal site and a distal site). It is hypothesized that the use of device 800 comprising struts 804 with different numbers and/or configurations of outwardly-extendable middle portions, allows the compression and/or retrieval of prosthetic valve of different dimensions and/or configurations.

Reference is again made to FIGS. 25A-E. For some applications, a hem 820 is disposed within, and slidable through overtube 808. Hem 820 is advanced out of the overtube during or after the advancement of retrieval apparatus, and expands, such that a distal portion of the hem defines a lumen that has a longer transverse cross-sectional area than that of overtube 808 (e.g., as shown in FIGS. 25B-C). When retrieval device 800 and prosthetic valve 42 are drawn into overtube 808, at least proximal portions of the retrieval apparatus and prosthetic valve are first drawn into hem 820. Hem 820 facilitates the drawing in of the retrieval apparatus and prosthetic valve, by widening the effective open end of the overtube, and/or by reducing resistance between the prosthetic valve 42 and overtube 808. Although hem 820 is described herein with respect to the use of retrieval device 800, it is to be noted that the scope of the present invention includes the use of hem 820 in combination with any retrieval apparatus.

Figure 26A:
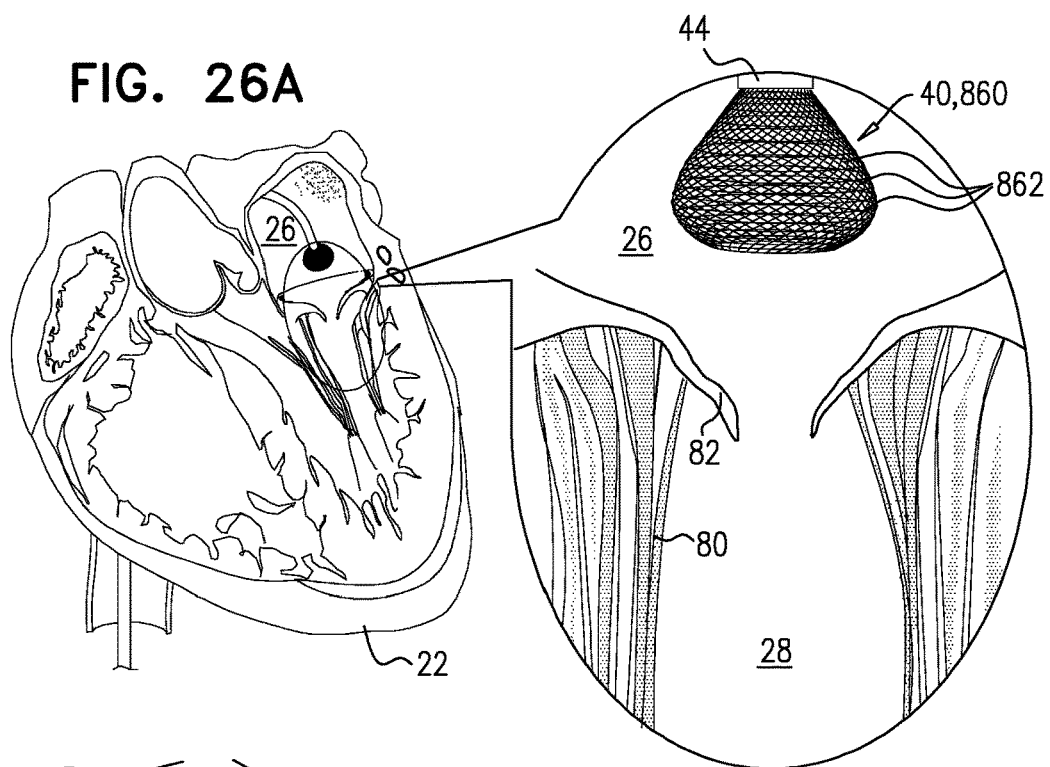
FIGS. 26A-C are schematic illustrations of a prosthetic valve support comprising a braided structure, and the deployment thereof, in accordance with some applications of the invention.
Figure 26B:
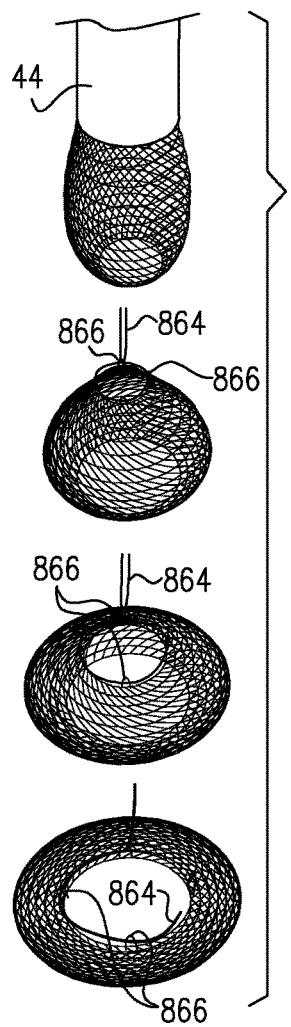
Figure 26C:
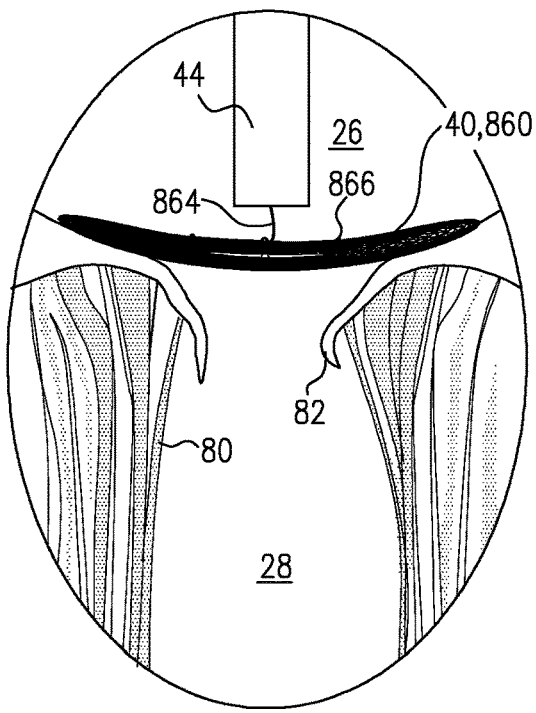

Reference is made to FIGS. 26A-C, which are schematic illustrations of prosthetic valve support 40, comprising a braided prosthetic valve support 860, in accordance with some applications of the invention. As described hereinabove, support 40 is typically expandable, and typically comprises a shape-memory material. Support 860 typically further comprises a braided structure, comprising a plurality of intertwining strands 862. At least some regions of strands 862 are slidable past (e.g., over, under) each other. Typically, strands 862 comprise a shape-memory material such as, but not limited to, nitinol. In an expanded state (i.e., uncompressed), support 40 is annular, and is shaped to define a lumen therethrough. For delivery, support 860 is typically advanced through the vasculature of the subject in a compressed configuration, e.g., within an overtube 44. FIG. 26A shows support 860 being deployed from overtube 44 at native valve 23 (i.e., proximal to the native valve). Typically, support 860 is deployed proximal to the native valve.

FIG. 26B shows sequential illustrations of the expansion of support 860 as it is deployed from overtube 44. Support 860 is typically coupled to a restricting element, such as drawstring 864, in a manner that at least partly restricts expansion of the support. FIG. 26B shows drawstring 864 threaded through a plurality of rings 866, disposed at the proximal end of support 860, whereby both ends of drawstring 864 are disposed proximal to the open distal end of overtube 44 (e.g., within overtube 44, and/or outside the body of the subject). Drawstring 864 thereby forms a closed loop that is coupled to rings 866 and, thereby, to support 860. Once support 860 has been fully ejected from overtube 44, tension on drawstring 864 typically restricts expansion of support 860. Subsequently, at least one end of drawstring 864 is moved distally (i.e., the drawstring is at least partially loosened), such that support 860 moves toward its uncompressed, expanded shape. When support 860 is successfully positioned (i.e., when a user determines that the support is in the desired position), one end of drawstring 864 is released, typically in combination with drawing (i.e., retracting) the other end of drawstring 864 proximally, thereby releasing support 860 from the drawstring.

FIG. 26C shows prosthetic valve support 860 in its fully-expanded configuration, against the proximal (i.e., atrial) side of the annulus of native valve 23. One end of drawstring 864 has been released, and the drawstring is shown being retracted proximally.

Throughout the deployment of prosthetic valve support 860, until the release of one end of drawstring 864, support 860 may be retrieved by moving drawstring 864 proximally (i.e., pulling the drawstring). Pulling the drawstring (1) tightens the loop formed by the drawstring, thereby bringing rings 866 closer to each other, and compressing the proximal portion of support 860, and (2) draws support 860 into overtube 44. Thus, a user can determine if and/or when to release support 860, throughout the deployment procedure.

Reference is made to FIGS. 27A-D, which are schematic illustrations of delivery apparatus 880, and the use thereof, in accordance with some applications of the invention. FIGS. 27A-D show apparatus 880 being used to deliver and deploy a medical device 150, comprising prosthetic valve 42, to native valve 23. Apparatus 880 comprises a plurality of control filaments 882, disposed and slidable within respective guide elements, such as rail-pairs 884 (e.g., between individual rails thereof). Rail-pairs 884 are typically extendable. For example, rail-pairs 884 may comprise sections that are slidable over and/or through each other, such that the rail-pairs are telescopically extendable. Apparatus 880 typically comprises a core 886, from which rail-pairs 884 typically protrude radially, such that extension of rail-pairs 884 comprises outwardly-radial extension of the rail-pairs from core 886.

Apparatus 880 has a contracted configuration and an extended configuration, is typically reversibly movable between these two configurations, and is further typically movable into continuous configurations between the contracted and extended configurations. FIG. 27A shows apparatus 880 in the contracted configuration. In the contracted configuration, rail-pairs 884 are typically telescopically retracted, such that apparatus 880 is disposable in delivery tube 60. That is, in the contracted configuration, a longest length of a transverse cross-section of apparatus 880 is smaller than a longest length of a transverse cross-section of delivery tube 60.

FIG. 27B shows medical device 150, comprising prosthetic valve 42, being deployed from delivery tube 60, at native valve 23, using apparatus 880. Apparatus 880 is coupled to a portion (e.g., a proximal portion) of prosthetic valve 42, and is disposed within delivery tube 60. Apparatus 880 is thereby not visible in FIG. 27B. A distal portion of prosthetic valve 42 has been exposed from delivery tube 60, and has begun to expand toward its expanded configuration. Typically, prosthetic valve 42 is moved with respect to delivery tube 60 (e.g., is pushed out of the delivery tube) by core 886, which thereby acts as a pushing member.

As described hereinabove, prosthetic valve 42 typically comprises a shape-memory material, and expands toward its expanded configuration as it is exposed from delivery tube 60. In the application of the invention described with reference to FIGS. 27A-D, apparatus 880 typically controls this expansion. Control filaments 882 are typically coupled (e.g., slidably coupled) to prosthetic valve 42, e.g., via respective coupling pins 888, which are couplable to prosthetic valve 42, and slidably couplable to control filaments 882. Release wires 892 facilitate the coupling of control filaments 882 to prosthetic valve 42, e.g., by facilitating the coupling of coupling pins 888 to prosthetic valve 42.

Control filaments 882 (e.g., proximal portions thereof) are distally advanceable, and proximally retractable, through a control tube 890, e.g., using a control unit external to the subject. Control filaments 882 are slidably couplable to core 886 and/or control tube 890, such as being slidable through respective conduits (e.g., holes) in the core or the control tube. The expansion of apparatus 880, and thereby that of prosthetic valve 42, is restricted and/or facilitated (e.g., controlled) by the distal advancement and/or proximal retraction of control filaments 882. In the application of the invention illustrated in FIGS. 27A-D, control filaments 882 form respective loops. The size of the loops is increased when the control filaments are distally advanced, and reduced when the control filaments are proximally retracted. When the loops are small, control filaments 882 restrict expansion of prosthetic valve 42. Distal advancement of control filaments 882, and the resulting enlargement of the loops formed thereof, facilitates the expansion of prosthetic valve 42.

FIG. 27C shows apparatus 880 in its expanded configuration. FIG. 27D shows apparatus 880 in its expanded configuration, coupled to prosthetic valve 42, during the deployment of the prosthetic valve. Rail-pairs 884 protrude radially from core 886, and control filaments 882 remain coupled to the prosthetic valve, facilitated by release wires 892, as described hereinabove. Rail-pairs 884 typically facilitate (e.g., guide) the expansion of prosthetic valve 42.

When prosthetic valve 42 is successfully positioned (i.e., when a user determines that the prosthetic valve is in the desired position), prosthetic valve 42 is released from control filaments 882, e.g., by pulling release wires 892 proximally. Release of prosthetic valve 42 allows (1) the prosthetic valve to expand further (e.g., until it couples to, and is restricted by, support 40), and/or (2) control filaments 882 to be retracted, and rail-pairs 884 to be telescopically retracted, such that apparatus 880 is retractable into delivery tube 60.

For some applications, rail-pairs 884 are biased toward moving into the contracted configuration thereof, are pulled radially outward by the expansion of prosthetic valve 42, and automatically return to the contracted configuration upon release of the prosthetic valve. For example, the rail-pairs may provide a contractive force, and the prosthetic valve may provide an expansive force that is sufficient to overcome the contractive force, and thereby to pull the rail-pairs radially outward. Upon release of the prosthetic valve, the contractive force automatically returns the rail-pairs to the contracted configuration thereof. Alternatively or additionally, rail-pairs 884 may be actively controllable (e.g., extracorporeally) by a user.

For some applications of the invention, proximal portions of control filaments 882 are coupled to each other (e.g., fixedly coupled to each other, such as adhered and/or welded to each other), such that the plurality of control filaments are synchronously distally advanceable, and synchronously proximally retractable, e.g., via a control rod and/or control unit.

For some applications of the invention, proximal portions of release wires 892 are coupled to each other (e.g., fixedly coupled to each other, such as adhered and/or welded to each other), such that the plurality of release wires are pullable synchronously, e.g., via a control rod and/or control unit, thereby facilitating synchronous release of control filaments 882.

Throughout the deployment of prosthetic valve 42 using apparatus 880, until the release of the prosthetic valve from control filaments 882, prosthetic valve 42 may be re-compressed (e.g., for repositioning and/or retrieval into delivery tube 60) by proximally retracting control filaments 882. Thus, a user can determine if and/or when to release prosthetic valve 42, throughout the deployment procedure. That is, prosthetic valve 42 is recompressible (i.e., the expansion of prosthetic valve 42 is at least in part reversible) by proximal retraction of control filaments 882.

That is, (1) control filaments 882 are slidable through conduits of core 886, and reversibly couplable to prosthetic valve 42, and (2) delivery apparatus 880 is configured to control and/or facilitate (a) expansion of prosthetic valve 42, by the control filaments being advanced distally through the conduits, and (b) recompression of prosthetic valve 42, by the control filaments being retracted proximally through the conduits.

Reference is made to FIGS. 28A-30B, which are schematic illustrations of techniques for replacement of a prosthetic valve, in accordance with some applications of the invention. It is noted that in the context of the present patent application, the term "replacement" with respect to a prosthetic valve includes both (a) placement at a valve site of a new prosthetic valve while removing or disabling a prosthetic valve that was already at the valve site, as well as (b) placement of a new prosthetic valve at the valve site without removing or disabling a prosthetic valve that was already at the site.

Prosthetic cardiac valves typically require replacement after a duration (e.g., after between 1 month and 10 years, such as after between 1 and 5 years). For example, the condition of the subject may change, components of the prosthetic valve (e.g., prosthetic valve leaflets, sutures, frame) may suffer fatigue, and/or tissue growth may block blood flow or otherwise interfere with prosthetic valve function.

The prosthetic valve supports described with reference to FIGS. 28A-30B are typically couplable to the native valve using techniques described herein for coupling other prosthetic valve supports to the native valve. For example, the prosthetic valve supports described with reference to FIGS. 28A-30B may comprise tissue-engaging elements (e.g., support-anchoring elements), such as those described herein. Similarly, other prosthetic valve supports described herein may comprise the upstream support portions and/or the cylindrical elements of the prosthetic valve supports described with reference to FIGS. 28A-30B.

Figure 28A:
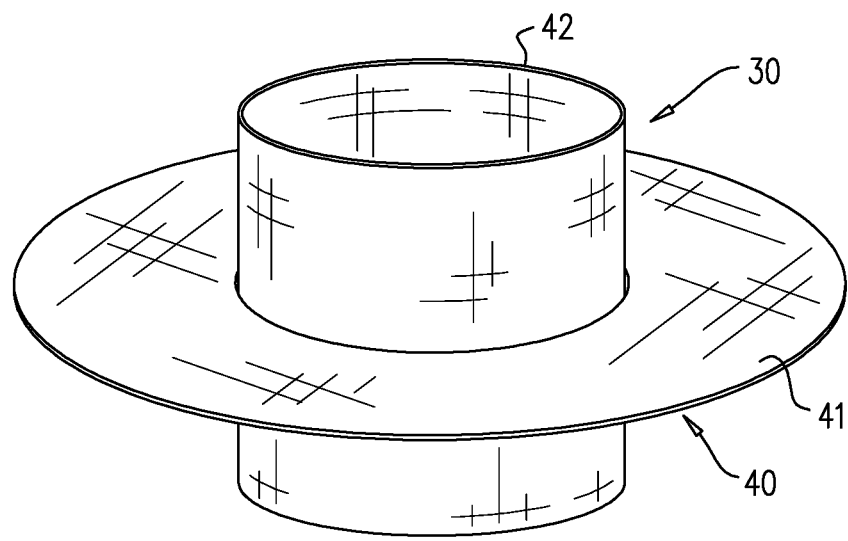
FIGS. 28A-D are schematic illustrations of the deployment of a prosthetic valve in the lumen of another prosthetic valve, in accordance with some applications of the invention.
Figure 28B:
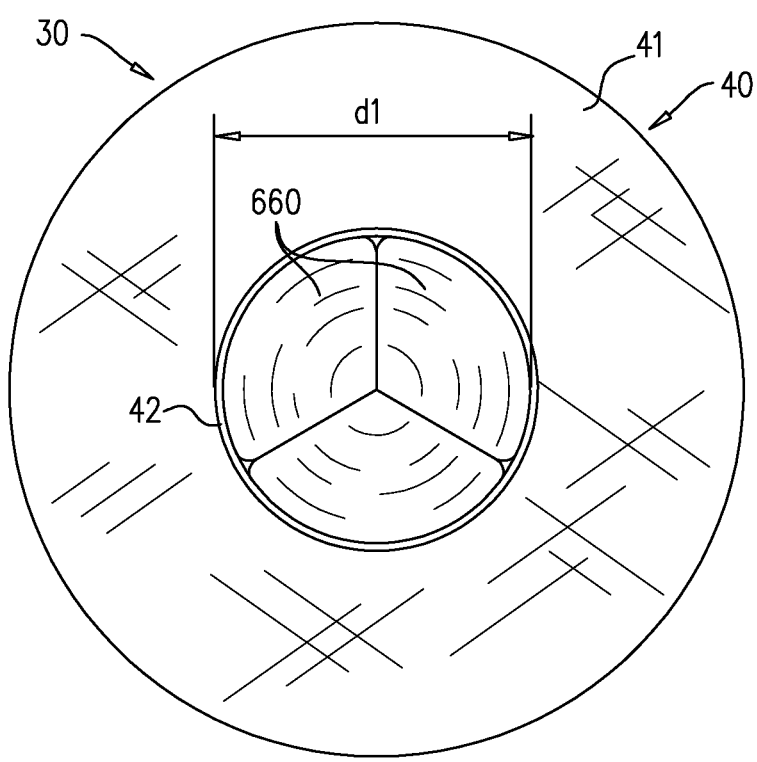

Reference is now made to FIGS. 28A-D. FIGS. 28A-B show implant 30, comprising prosthetic valve 42 coupled to prosthetic valve support 40, such as described hereinabove with reference to the implantation of implant 30 (e.g., with reference to FIGS. 1A-H). FIG. 28A shows a side view and FIG. 28B shows a top view. At such a time that it is deemed necessary and/or desirable to replace prosthetic valve 42, a second prosthetic valve 42' is delivered to the lumen of the first prosthetic valve, and deployed therein. Generally, delivery and deployment of prosthetic valve 42' is performed using similar techniques to those used to deploy prosthetic valve 42.

Figure 28C:
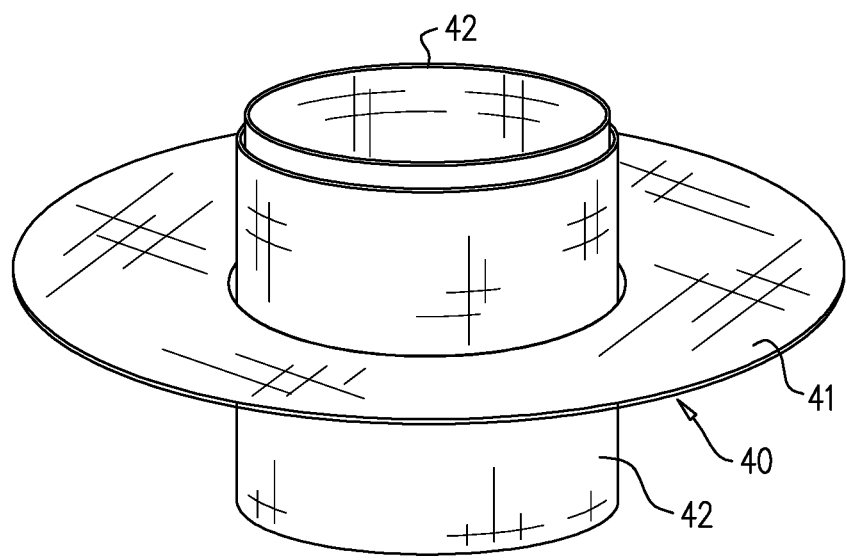
Figure 28D:
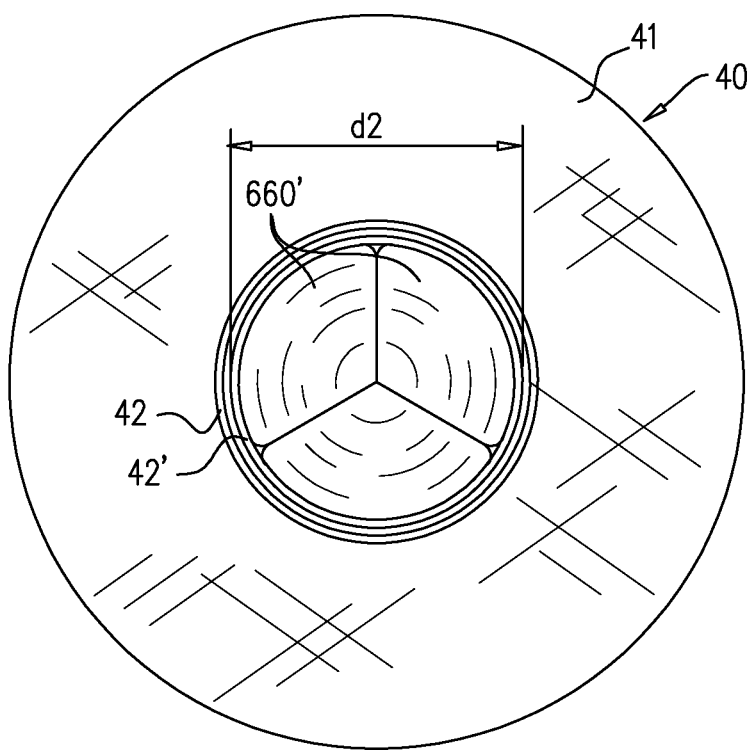

FIGS. 28C-D show second prosthetic valve 42' in an expanded configuration within the lumen of prosthetic valve 42. FIG. 28C shows a side view and FIG. 28D shows a top view. Both prosthetic valve 42 and prosthetic valve 42' comprise valve components, typically valve leaflets 660, disposed in the lumen of the prosthetic valve. As it expands, prosthetic valve 42' typically pushes aside leaflets 660 of prosthetic valve 42. Prosthetic valve 42' exerts radially-expansive forces against the inner surface of prosthetic valve 42, thereby coupling prosthetic valve 42' to prosthetic valve 42. In some applications, leaflets 660 are sandwiched between prosthetic valve 42 and prosthetic valve 42' (i.e., between the primary structural elements 130 of the prosthetic valves). In some applications, leaflets 660 facilitate sealing between the two prosthetic valves. Following the deployment of prosthetic valve 42', leaflets 660' of prosthetic valve 42' begin to function, thereby replacing the function of leaflets 660. Typically, diameter d2 of deployed prosthetic valve 42' is smaller than diameter d1 of deployed prosthetic valve 42. Typically, the difference in diameter is caused at least in part by prosthetic valve 42 restricting the expansion of prosthetic valve 42'.

Figure 29C:
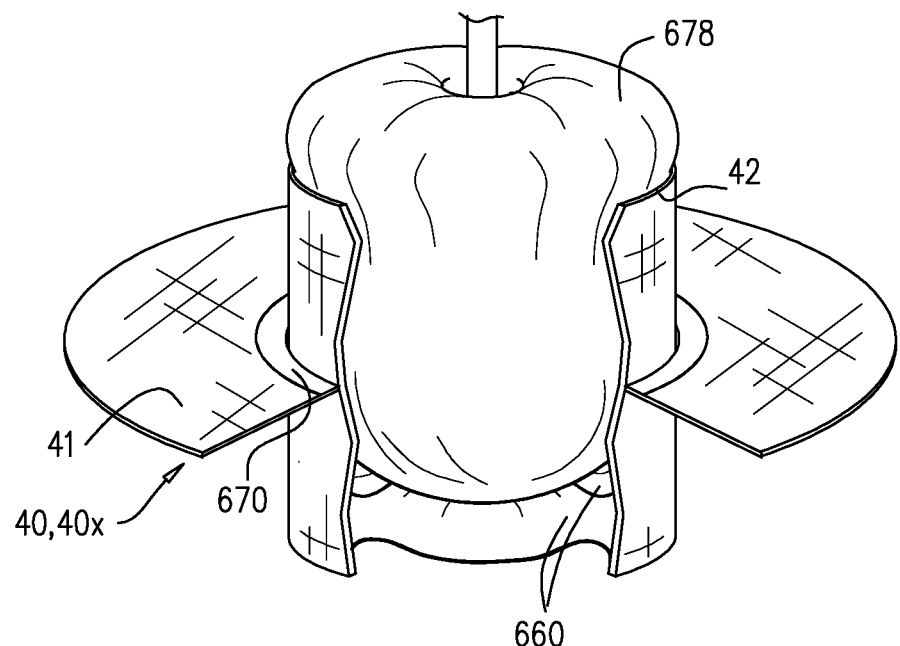

Reference is now made to FIGS. 29A-F. FIGS. 29A-B show implant 30, comprising prosthetic valve 42 coupled to prosthetic valve support 40, comprising prosthetic valve support 40x. FIG. 29A shows a side view and FIG. 29B shows a top view. As described hereinabove, prosthetic valve support 40 is generally annular, and typically comprises a wire frame and/or a shape-memory material. For some applications, the wire frame of prosthetic valve support 40 (i.e., wire frame 672 of support 40x) is generally covered with covering 440 (such as a fabric, e.g., as described herein). Support 40x typically comprises a weak zone 670 that circumscribes the lumen defined by the support (i.e., the lumen defined by upstream support portion 41 of support 40x).

For some applications, wire frame 672 does not extend into weak zone 670; rather the weak zone only comprises covering 440. For some applications, a stretchable and/or breakable reinforcing-wire 674 is disposed at or near inner edge 68 of upstream support portion 41 of support 40x. For some applications, wire frame 672 has a different structure in weak zone 670 than in other regions of upstream support portion 41 of support 40x. For example, wire frame 672 may comprise fewer struts in weak zone 670.

Figure 29D:
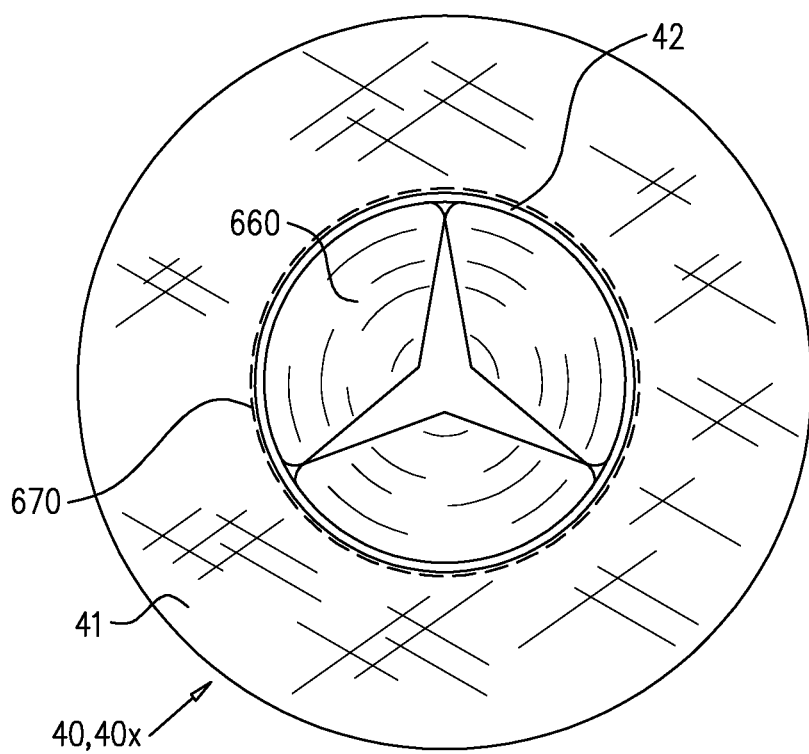

FIG. 29C shows an expanding device, such as a balloon 678, having been delivered to the lumen of prosthetic valve 42, and being used to expand (e.g., to enlarge) the lumen of the prosthetic valve and the lumen of prosthetic valve support 40x. FIG. 29D shows a transverse cross-sectional view of support 40x and prosthetic valve 42, following the expansion of the lumen of the prosthetic valve with balloon 678. At such a time that it is deemed necessary and/or desirable to replace prosthetic valve 42, balloon 678 is delivered to the prosthetic valve and inflated (e.g., using saline), such that it applies a radially-expansive force, from within the lumen of prosthetic valve 42, to the prosthetic valve and support 40x. Typically, the radially-expansive force applied by the balloon is greater than the radially-expansive force applied by prosthetic valve 42 on support 40 (i.e., support 40x), that typically couples prosthetic valve 42 to support 40. For some applications, balloon 678 is shaped to define a lumen, so that blood can continue to flow while the balloon is expanded. For some such applications, balloon 678 comprises a temporary prosthetic valve (i.e., one or more temporary prosthetic valve leaflets), disposed in the lumen of the balloon, and configured to further facilitate continued blood flow while the balloon is expanded.

The radially-expansive force applied by balloon 678 increases the lumen of prosthetic valve 42, typically by increasing the lumen of support 40x by deforming (e.g., crushing) weak zone 670. For example, a material which weak zone 670 comprises may be compressed, broken, bent, stretched and/or torn (e.g., reinforcing wire 674 may be broken and/or covering 440 may be stretched and/or torn). Balloon 678 is subsequently removed from the subject. Typically, leaflets 660 continue to function at least in part until second prosthetic valve 42' is deployed.

For some applications, leaflets 660 are disposed in a portion of prosthetic valve 42 that is distal (i.e., ventricular) to the portion of prosthetic valve 42 that is coupled to prosthetic valve support 40x. For these applications, balloon 678 is typically disposable in a proximal portion of valve 42, and thereby may be used to increase the lumen of prosthetic valve 42, without damaging (e.g., crushing) leaflets 660.

Figure 29E:
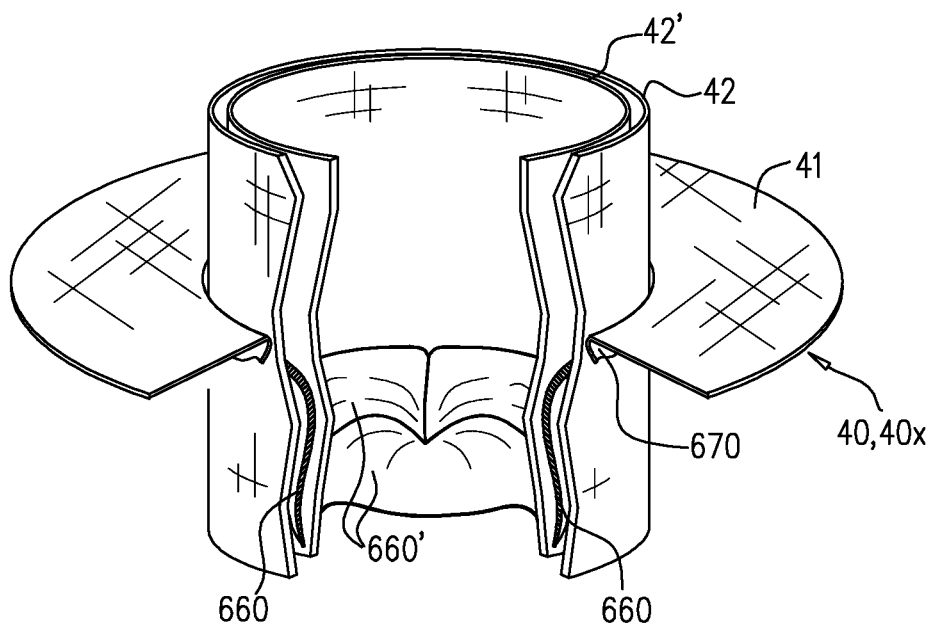
Figure 29F:
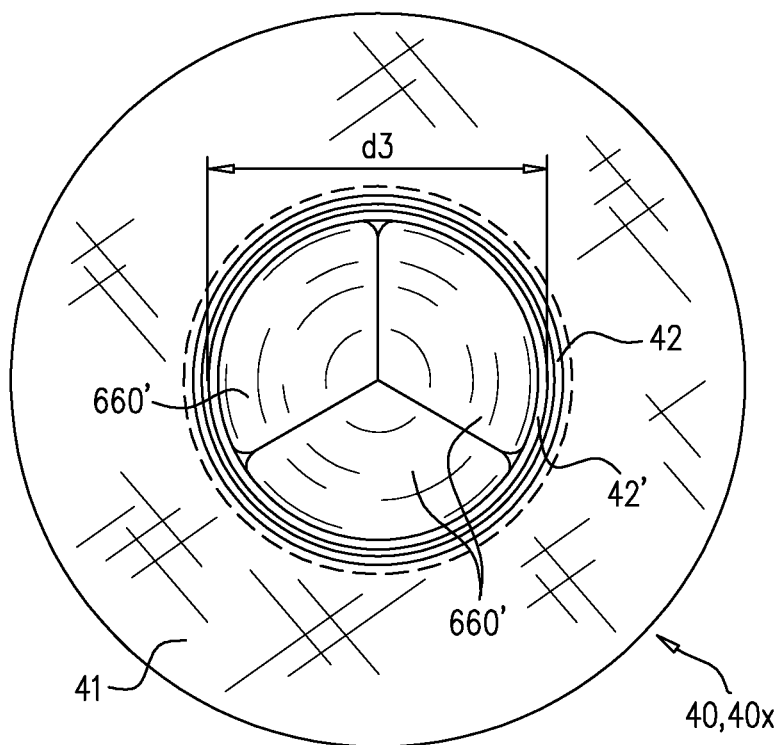

FIGS. 29E-F show second prosthetic valve 42' in an expanded configuration within the lumen of prosthetic valve 42. FIG. 29E shows a side view and FIG. 29F shows a top view. Prosthetic valve 42' exerts radially-expansive forces against the inner surface of prosthetic valve 42, thereby coupling prosthetic valve 42' to prosthetic valve 42. Because the lumen of prosthetic valve 42 is initially expanded, as described hereinabove, a diameter d3 of the lumen defined by prosthetic valve 42' may not be smaller than the diameter d1 of the lumen originally defined by prosthetic valve 42 (i.e., d3 may be at least as great as d1). For example, diameter d3 may be equal to, or larger than, diameter d1.

Reference is again made to FIGS. 28A-29F. For some applications of the invention, prosthetic valve 42' comprises a second prosthetic valve 42. That is, a second (i.e., new) prosthetic valve 42 is used to replace a first prosthetic valve 42. Alternatively, prosthetic valve 42' may be different to prosthetic valve 42. For some applications, prosthetic valve 42' may comprise a sealing element, such as a circumferential seal (e.g., a soft material and/or a balloon), that facilitates sealing and/or coupling between prosthetic valve 42' and prosthetic valve 42. For some applications, prosthetic valve 42' comprises protruding barbs, which facilitate coupling between the two prosthetic valves.

For some applications, a distal portion of prosthetic valve 42' defines a cross-sectional area with a longest length that is longer than a transverse cross-sectional longest dimension of the lumen defined by prosthetic valve 42 (i.e., defined by primary structural element 130 of prosthetic valve 42). During deployment of prosthetic valve 42', the distal portion is placed distal to the open distal end of prosthetic valve 42 (i.e., in the ventricle). Thereby, in addition to the radially-expansive force that typically couples prosthetic valve 42' to prosthetic valve 42, the distal portion restricts proximal movement of prosthetic valve 42' with respect to prosthetic valve 42, thereby anchoring prosthetic valve 42' to prosthetic valve 42, and to native valve 23.

Figure 30A:
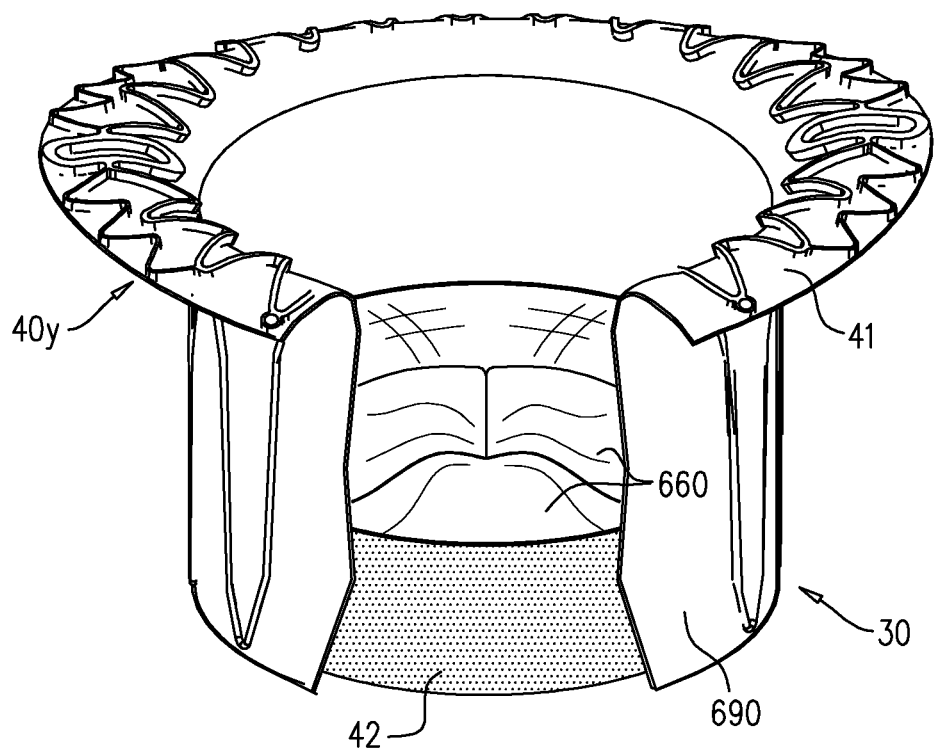
FIGS. 30A-B are schematic illustrations of the deployment of a second prosthetic valve in the lumen of a prosthetic valve support, in which a first prosthetic valve is already disposed, in accordance with some applications of the invention.
Figure 30B:
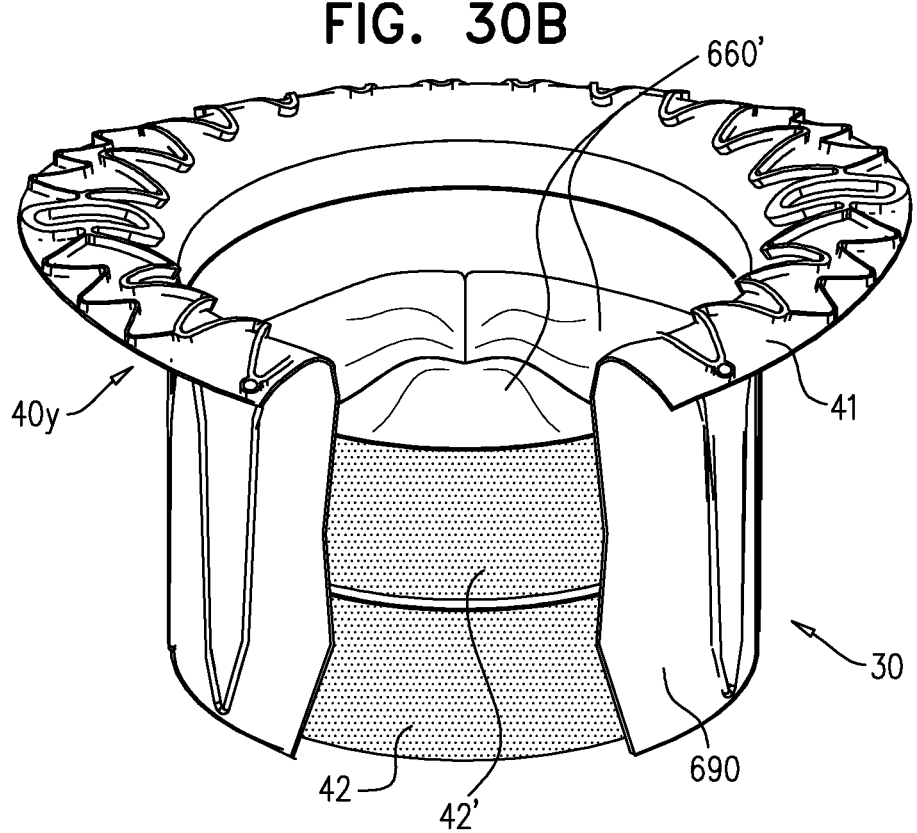

Reference is made to FIGS. 30A-B, which are schematic illustrations of implant 30, comprising prosthetic valve 42 and prosthetic valve support 40y, being restored by the addition of a second prosthetic valve 42', in accordance with some applications of the invention. Prosthetic valve support 40y comprises upstream support portion 41 coupled to a cylindrical element 690 that is typically configured to extend distally through native valve 23. Alternatively, cylindrical element 690 may be configured to extend away from the native valve. Prosthetic valve support 40y is typically couplable to the native valve using techniques described herein for coupling other prosthetic valve supports to the native valve. For example, prosthetic valve support 40y may comprise tissue-engaging elements (e.g., support-anchoring elements). Cylindrical element 690 is typically configured to (1) facilitate coupling of prosthetic valve support 40y to the native valve, and/or sealing therebetween, (2) to facilitate coupling of prosthetic valves to prosthetic valve support 40y, and/or sealing therebetween, and/or (3) to push aside native leaflets 82 of native valve 23.

FIG. 30A shows prosthetic valve 42 having been deployed in the lumen of prosthetic valve support 40y. Typically, prosthetic valve 42 is deployed in a distal (i.e., more ventricular and/or downstream) portion of the lumen.

FIG. 30B shows prosthetic valve 42' having been deployed in the lumen of prosthetic valve support 40y. At such a time that it is deemed necessary and/or desirable to perform a replacement of prosthetic valve 42, prosthetic valve 42' is delivered to, and deployed in, another portion of prosthetic valve support 40y. Typically, prosthetic valve 42' is deployed in a portion of the lumen that is proximal to (e.g., upstream of) prosthetic valve 42. That is, prosthetic valve support 40y is configured to receive, at a first period, a first prosthetic valve at a first longitudinal portion of the lumen of cylindrical element 690, and to receive, at a second period, a second prosthetic valve at a second longitudinal portion of the lumen.

For some applications, prosthetic valve 42 continues to function at least in part, and at least temporarily. That is, prosthetic valve 42 and prosthetic valve 42' operate generally simultaneously. For some applications, prosthetic valve 42 is disabled in conjunction with deployment of prosthetic valve 42'. For example, leaflets 660 of prosthetic valve 42 may be disabled, removed and/or restrained, by using a separate device (not shown) and/or by using a part (e.g., an extending element; not shown) of prosthetic valve 42'.

For some applications, the primary structural element 130 of prosthetic valve 42' is longer than the primary structural element of prosthetic valve 42, and the leaflets of prosthetic valve 42' are disposed in a proximal portion of the primary structural element thereof. A distal portion of the primary structural element of prosthetic valve 42' is deployed in the lumen of prosthetic valve 42, such that the leaflets of prosthetic valve 42 are crushed upon expansion of prosthetic valve 42'.

Reference is made to FIGS. 31A-33C, which are schematic illustrations of delivery tube 60, in accordance with some applications of the invention. Deployment of a medical device 150, such as prosthetic valve 42, as described with reference to FIGS. 1A-H, typically comprises proximal movement of delivery tube 60 relative to prosthetic valve 42, as described hereinabove. Immediately prior to the release of prosthetic valve 42 from the delivery tube, the length of the delivery tube-plus-prosthetic valve may be double or more than that of the delivery tube or prosthetic valve alone. For some applications, this extra length can hinder the movement of, and removal of, the delivery tube from the body. A delivery tube that takes up less room during and/or following deployment of prosthetic valve 42 would thereby be advantageous.

FIGS. 31A-C show delivery tube 60, comprising a flexible delivery tube 60b being used to deliver prosthetic valve 42, in accordance with some applications of the invention. Delivery tube 60b comprises a flexible material, such as a fabric or polymer. FIG. 31A shows prosthetic valve 42 in a compressed (i.e., crimped) configuration within delivery tube 60b. Prosthetic valve 42 exerts an expansive force on tube 60b, and tube 60b provides a reciprocal compressive force on prosthetic valve 42. Delivery tube 60b is typically not rigid; rather prosthetic valve 42 provides (i.e., dictates) the shape to which the delivery tube conforms. That is, prosthetic valve 42 functions as a scaffold on which delivery tube 60b is disposed.

FIG. 31B shows prosthetic valve 42 partially deployed from delivery tube 60b. For example, prosthetic valve 42 may be pushed distally out of the delivery tube using a pushing member (e.g., pushing member 140). FIG. 31C shows prosthetic valve 42 fully deployed from delivery tube 60b. Prosthetic valve 42 has expanded toward its expanded configuration. The reciprocal expansive and compressive forces are thereby no longer exerted, and delivery tube 60b no longer conforms to a rigid shape. That is, delivery tube 60b becomes flaccid, facilitating its removal from the subject. For example, delivery tube 60b may be moved around corners and/or into an overtube such as a catheter.

FIGS. 32A-C show delivery tube 60, comprising a compressible delivery tube 60c being used to deliver prosthetic valve 42, in accordance with some applications of the invention. Delivery tube 60c comprises a flexible material, such as a fabric or polymer, and one or more pulling wires 740. Delivery tube 60c typically further comprises an aperture ring 742. FIG. 32A shows prosthetic valve 42 in a compressed (i.e., crimped) configuration within delivery tube 60c. Prosthetic valve 42 exerts an expansive force on tube 60c, and tube 60c provides a reciprocal compressive force on prosthetic valve 42. Delivery tube 60c is typically not rigid; rather prosthetic valve 42 provides (i.e., dictates) the shape to which the delivery tube conforms. That is, prosthetic valve 42 functions as a scaffold on which delivery tube 60c is disposed. Pulling wires 740 extend from a proximal site (e.g., outside the subject) and are coupled to a distal portion of delivery tube 60c (e.g., to aperture ring 742).

FIG. 32B shows prosthetic valve 42 partially deployed from delivery tube 60c. Typically, following placement of delivery tube 60c (and thereby prosthetic valve 42) in the lumen of native valve 23, pulling wires 740 are pulled, drawing the distal portion of the delivery tube (e.g., aperture ring 742) proximally. Delivery tube 60c is thereby compressed (i.e., shortened) and a distal portion of prosthetic valve 42 is exposed, and typically expands at least in part responsively. For example, a proximal end of delivery tube 60c may be generally closed, such that compressing (i.e., shortening) of the delivery tube, exposes the distal portion of prosthetic valve 42 from the distal end of the delivery tube. FIG. 32C shows prosthetic valve 42 fully deployed from delivery tube 60c. Prosthetic valve 42 has expanded toward its expanded configuration. Delivery tube 60c is generally compressed such that it has a length of less than 50% (e.g., less than 30%, such as less than 10%) of its length when containing prosthetic valve 42, thereby facilitating its removal from the subject. For example, delivery tube 60c may be moved around corners and/or into an overtube such as a catheter.

FIGS. 33A-C show delivery tube 60, comprising a dismantling delivery tube 60d being used to deliver prosthetic valve 42, in accordance with some applications of the invention. Delivery tube 60d comprises a flexible material, such as a fabric or polymer, and a pullstring 750. FIG. 33A shows prosthetic valve 42 in a compressed (i.e., crimped) configuration within delivery tube 60d. Prosthetic valve 42 exerts an expansive force on tube 60d, and tube 60d provides a reciprocal compressive force on prosthetic valve 42. Delivery tube 60d is typically not rigid; rather prosthetic valve 42 provides (i.e., dictates) the shape to which the delivery tube conforms. That is, prosthetic valve 42 functions as a scaffold on which delivery tube 60d is disposed. Pullstring 750 is coupled to the flexible material of delivery tube 60d, typically along the length of the delivery tube. Typically, delivery tube 60d comprises a sheet of the flexible material, held in a generally cylindrical shape by pullstring 750. For example, pullstring 750 may weave between two parts of the flexible material, stitching them together. Alternatively, pullstring 750 may be coupled to the two parts of the flexible material via a weakened (e.g., perforated) join.

FIG. 33B shows prosthetic valve 42 partially deployed from delivery tube 60d. Typically, following placement of delivery tube 60d (and thereby prosthetic valve 42) in the lumen of native valve 23, pullstring 750 is pulled, decoupling the two parts of the flexible material, and thereby opening delivery tube 60d. Typically, regions of prosthetic valve 42 expand as regions of delivery tube 60d are opened. FIG. 33C shows prosthetic valve 42 fully deployed from delivery tube 60d. Prosthetic valve 42 has expanded toward its expanded configuration. Pullstring 750 has been pulled sufficiently, such that the flexible material of delivery tube 60d becomes a generally open sheet. That is, delivery tube 60d typically loses its cylindrical shape and becomes flaccid, thereby facilitating its removal from the subject. For example, delivery tube 60d may be moved around corners and/or into an overtube such as a catheter.

Reference is made to FIG. 34, which is a schematic illustration of prosthetic valve 42, comprising a tissue-engaging element 62, comprising a leaflet-engaging element 760, coupled to a distal portion of primary structural element 130 of the prosthetic valve, in accordance with some applications of the invention. For some applications, leaflet-engaging element 760 is similar in structure to a valve-anchoring element 64, such as a loop-shaped valve-anchoring element 200. Element 760 is positioned and configured so as to engage a single leaflet, typically the anterior leaflet, of native valve 23. The engagement of the leaflet is hypothesized to reduce undesired interference with blood flow. Specifically, holding the anterior leaflet clear of the LVOT is hypothesized to reduce interference with blood flowing from the left ventricle into the aorta.

Although element 760 is described with reference to FIG. 34 as being coupled to the primary structural element of prosthetic valve 42, it is to be noted that the scope of the present invention includes an element 760 being additionally or alternatively coupled to prosthetic valve support 40.

Figure 35A:
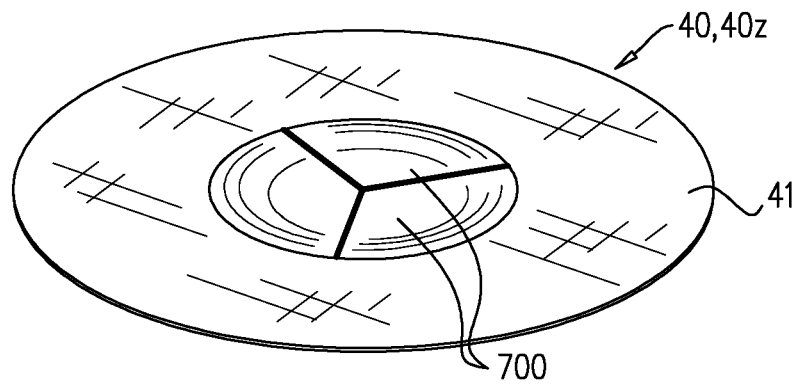
FIGS. 35A-C are schematic illustrations of a prosthetic valve support comprising temporary valve components, and sequential steps in the coupling of a prosthetic valve to the support, in accordance with some applications of the invention.
Figure 35B:
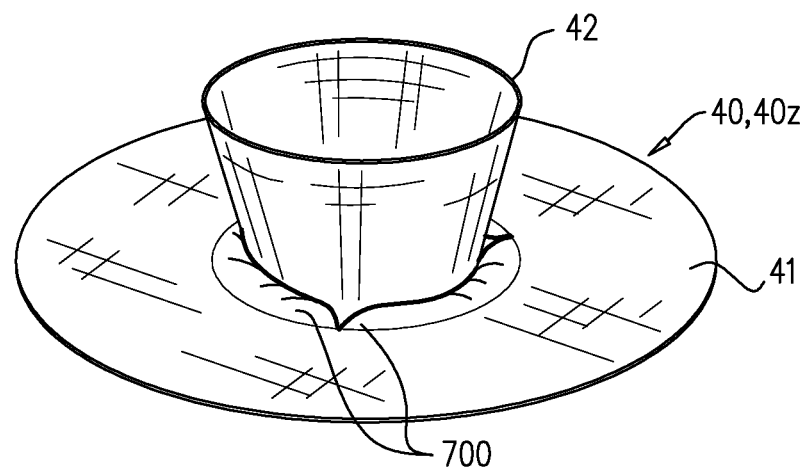
Figure 35C:
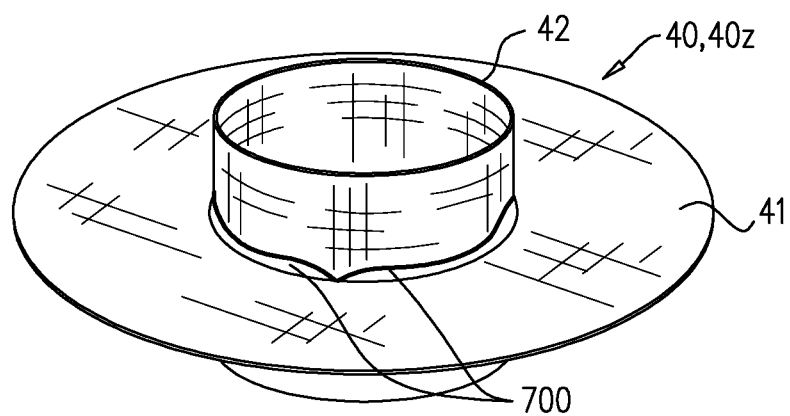

Reference is made to FIGS. 35A-C, which are schematic illustrations of sequential steps in the implantation of prosthetic valve 42, and prosthetic valve support 40, comprising prosthetic valve support 40z, in accordance with some applications of the invention. As described hereinabove, support 40 comprises an upstream support portion 41 which is shaped to define a lumen. During implantation of implant 30, prosthetic valve 42 is deployed in this lumen. As described herein, for some applications of the invention, support 40 is coupled to native valve 23 prior to delivery and/or deployment of prosthetic valve 42. For example, support 40 may comprise tissue-engaging elements 62, comprising support-anchoring elements 66 (not shown in FIGS. 35A-C). In some applications, support 40 and/or the coupling thereof to native valve 23, interferes with the functioning of leaflets 82 of the native valve. For example, in some applications, support 40 is coupled to the native valve via support-anchoring elements 66 engaging (i.e., coupling to) leaflets 82, thereby disrupting native valve function. For further example, in some applications, elements 66 move leaflets 82, so as to sandwich the leaflets against prosthetic valve 42. For applications such as these, there is typically a period after the coupling of support 40 to the native valve, and before deployment of prosthetic valve 42, that the native valve has significantly reduced functionality. Prosthetic valve support 40z comprises one or more temporary valve components, such as temporary leaflets 700, and advantageously provides temporary valve functionality during this period.

FIG. 35A shows prosthetic valve support 40z, which comprises one or more temporary valve components, such as temporary leaflets 700, typically disposed in the lumen defined by support 40z. Leaflets 700 provide temporary valve functionality to support 40z, thereby facilitating pumping of blood by the heart in the absence of native valve function. Temporary leaflets 700 may comprise a biological material, such as pericardial tissue, and/or a synthetic material, such as silicone, polyethylene terephthalate (e.g., polyester), and/or polytetrafluoroethylene (e.g., Teflon). Temporary leaflets are typically coupled to upstream support portion 41 using sutures. It is noted that, although prosthetic valve support 40z is illustrated in FIGS. 35A-C as not comprising tissue-engaging elements such as support-anchoring elements 66, prosthetic valve support 40z typically does comprise support-anchoring elements 66, such as those described elsewhere herein.

FIG. 35B shows prosthetic valve 42 being deployed in the lumen of support 40z. For some applications, prosthetic valve 42 is deployed as described with reference to FIGS. 1A-H, mutatis mutandis. For some applications, prosthetic valve 42 is deployed as described with reference to FIGS. 15A-L, mutatis mutandis. As it expands, prosthetic valve 42 typically pushes aside temporary leaflets 700.

FIG. 35C shows prosthetic valve 42 having been fully deployed (i.e., expanded) in the lumen of support 40z. In some applications, leaflets 700 are sandwiched between prosthetic valve 42 and support 40z. In some applications, leaflets 700 facilitate sealing between prosthetic valve 42 and support 40z. As prosthetic valve 42 is deployed, it begins to function, thereby replacing the temporary valve functionality of leaflets 700. Thereby, the techniques described with reference to FIGS. 35A-C provide ongoing valve functionality throughout the implantation of a prosthetic valve.

Reference is made to FIGS. 36A-D, which are schematic illustrations of prosthetic valve support 40, comprising a prosthetic valve support 1040, in accordance with some applications of the invention. For some applications of the invention, prosthetic valve support 1040 is analogous to other prosthetic valve supports described herein. For some applications of the invention, prosthetic valve support 1040 comprises prosthetic valve support 40. Support 1040 comprises upstream support portion 41, which is shaped to define a lumen. Support 1040 comprises one or more support-anchoring elements 900 and one or more stabilizing legs 910. Typically, support 1040 comprises two support-anchoring elements 900 and two stabilizing legs 910. Typically, support-anchoring elements 900 and stabilizing legs 910 are coupled to inner edge 68 of upstream support portion 41. For some applications of the invention, support-anchoring elements 900 are embodiments of support-anchoring elements 66, which are embodiments of tissue-engaging elements 62, as described hereinabove. For some applications of the invention, stabilizing legs 910 are embodiments of support-anchoring elements and/or of tissue-engaging elements 62, as described hereinabove.

FIG. 36A shows a lower side view of support 1040. Typically, support-anchoring elements 900 comprise clips and/or clip functionality. Elements 900 are illustrated in FIG. 36A as generic clips, and may comprise any of the clips described herein, and/or any other clips that are couplable to the leaflets of the native valve (e.g., support-anchoring elements 900a and 900b and the clip functionalities thereof, described hereinbelow with reference to FIGS. 37A-H, and 38A-H). For some applications of the invention, support-anchoring element 900 comprises two clip elements, (1) coupled at a coupling point, and (2) between which, during implantation, leaflets 82 of the native valve are typically clamped. Clamping of a leaflet between the two clip elements couples element 900 to the leaflet. Typically, one clip element is substantially immobile, and the other clip element is (1) biased to assume a first configuration, and (2) movable between the first configuration and another configuration.

Element 900 typically has (1) an open configuration, in which leaflets 82 of the native valve may be moved between the two clip elements, and (2) a closed configuration, in which the clip elements typically clamp (i.e., couple to) the leaflets. Element 900 is typically moved between the open and closed configurations thereof (i.e., is opened and closed) by moving at least one clip element between the first configuration thereof, and the other configuration thereof.

Typically, the clip elements are disposed at a distal portion of each support-anchoring element 900, and a proximal portion (e.g., a proximal end) of each element 900 is coupled to upstream support portion 41. Typically, support-anchoring elements 900 have a length (i.e., a distance from (1) the point of coupling of the element 900 to upstream support portion 41, to (2) a distal end of the element 900) of between 3 and 20 mm, (e.g., between 5 and 12 mm). Typically, the proximal portion has a length (i.e., a distance between (1) the point of coupling of element 900 to upstream support portion 41, and (2) a clip element) of between 2 and 10 mm, (e.g., between 2 and 8 mm).

Support 1040 typically comprises two support-anchoring elements 900 and two stabilizing legs 910. Typically, elements 900 and legs 910 are disposed at inner edge 68 in an alternating manner, i.e., such that each leg 910 is between two elements 900, and each element 900 is between two legs 910.

Typically, stabilizing leg 910 is longer than support-anchoring element 900. That is, a distance between (1) a coupling point 911 of upstream support portion 41 and a stabilizing leg 910 and (2) a distal end of the stabilizing leg, is typically greater than a distance between (1) a coupling point of upstream support portion 41 and an element 900 and (2) a distal end of the element 900. Typically, stabilizing leg 910 has a length of between 5 mm and 30 mm (e.g., between 5 mm and 20 mm), and a width of between 0.4 mm and 5.0 mm.

For some applications of the invention, each stabilizing leg 910 comprises a proximal portion 912 and a distal portion 914, whereby the proximal portion is coupled at coupling point 913 between the stabilizing leg and the distal portion. For some such applications, stabilizing leg 910 comprises a bend, such that an axis defined by distal portion 914 is divergent to an axis defined by the proximal portion. Typically, proximal portion 912 has a length of between 5 mm and 20 mm.

Typically, stabilizing legs 910 have a stabilizing configuration, in which they stabilize prosthetic valve support 1040 at the native valve. Typically, in the stabilizing configuration, the proximal portion 912 of each leg 910 is disposed on a plane between (1) a plane that is orthogonal to a plane defined by upstream support portion 41, and (2) a position in which the leg touches a part of upstream support portion 41 that is peripheral to inner edge 68. That is, in the stabilizing configuration, proximal portion 912 typically forms an acute angle with a portion of upstream support portion 41.

Stabilizing legs 910 are hypothesized to increase the stability of prosthetic valve support 1040 at the native valve. For example, legs 910 are hypothesized to at least partly inhibit (1) lateral rotation (i.e., rotation around an atrial-ventricular axis) of the prosthetic valve support, and/or (2) movement of the parts of upstream support portion 41 that are disposed against the proximal (e.g., atrial) side of the native valve, from moving away from, or through, the native valve. Following deployment (e.g., implantation) of prosthetic valve 42, legs 910 are further hypothesized to reduce rolling movement (e.g., movement around a lateral axis, e.g., an axis between two elements 900, such as an axis that is generally orthogonal to an axis between the stabilizing legs) of the prosthetic valve and/or implant 30, including inversion (e.g., 'flipping') of the implant.

For some applications of the invention, support 1040 is configured such that legs 910 and/or elements 900 are biased to reside in a particular (e.g., a pre-selected) configuration. For example, legs 910 and/or elements 900 and/or a coupling point (e.g., coupling point 911) may comprise a shape-memory material (e.g., nitinol, stainless steel, nickel cobalt, cobalt chrome, and/or titanium) or a spring mechanism. For some applications of the invention, the pre-selected configuration of legs 910 comprises the stabilizing configuration of legs 910.

For some applications of the invention, legs 910 and/or elements 900 are rotatable around coupling point 911. For example, legs 910 and/or elements 900 may be coupled to upstream support portion 41 via a hinge point (e.g., a hinge element), which may comprise a flexible material and/or moving components. For some applications of the invention, legs 910 and/or elements 900 rotate freely around coupling point 911 as far as their shape and juxtaposition allows.

For some applications where elements 900 rotate freely, following the coupling of elements 900 to leaflets 82 of the native valve, the leaflets continue to function, at least in part.

For some applications where stabilizing legs 910 rotate freely, the stabilizing legs have (1) a floating configuration, in which the stabilizing legs rotate freely, and (2) a stabilizing configuration, in which the stabilizing legs assume the pre-selected configuration, and are movable from the floating configuration to the pre-selected configuration. For some such applications, stabilizing legs assume the floating configuration when support 1040 is implanted, and are moved to the stabilizing configuration when the prosthetic valve is deployed in the lumen of the support.

FIG. 36B shows a top (i.e., atrial side) view of implant 30, comprising support 1040 and prosthetic valve 42, following implantation in native valve 23, comprising mitral valve 24, in accordance with some applications of the invention. Zones (scallops) P1, P2 and P3 of posterior leaflet 82*p*, and zones A1 and A3 of anterior leaflet 82*a* are labeled. As described hereinabove, elements 900 and legs 910 are disposed at inner edge 68 in an alternating manner. For the applications of the invention illustrated in FIG. 36B, elements 900 and legs 910 are typically arranged such that (1) the two elements 900 are disposed opposite each other, (2) the two legs 910 are disposed opposite each other, and (3) each leg 910 is generally midway between the two elements 900. That is, inner edge 68 is typically elliptical (e.g., circular), and each leg 910 is disposed at edge 68 generally between 80 degrees and 100 degrees (e.g., 90 degrees) to an element 900.

Typically, support-anchoring elements 900 are coupled to leaflets 82, i.e., one element 900 is coupled to anterior leaflet 82*a*, and one element 900 is coupled to posterior leaflet 82*p*. Typically, stabilizing legs 910 are oriented toward zones (scallops) P1 and P3 of the posterior leaflet. This configuration and orientation of elements 900 and legs 910 with respect to each other, and with respect to the native valve, is hypothesized to facilitate the stable placement and coupling (i.e., 1.0 implantation) of prosthetic valve support 1040 at/to the native valve, and thereby is hypothesized to facilitate the stable implantation of implant 30 at the native valve.

Figure 36C:
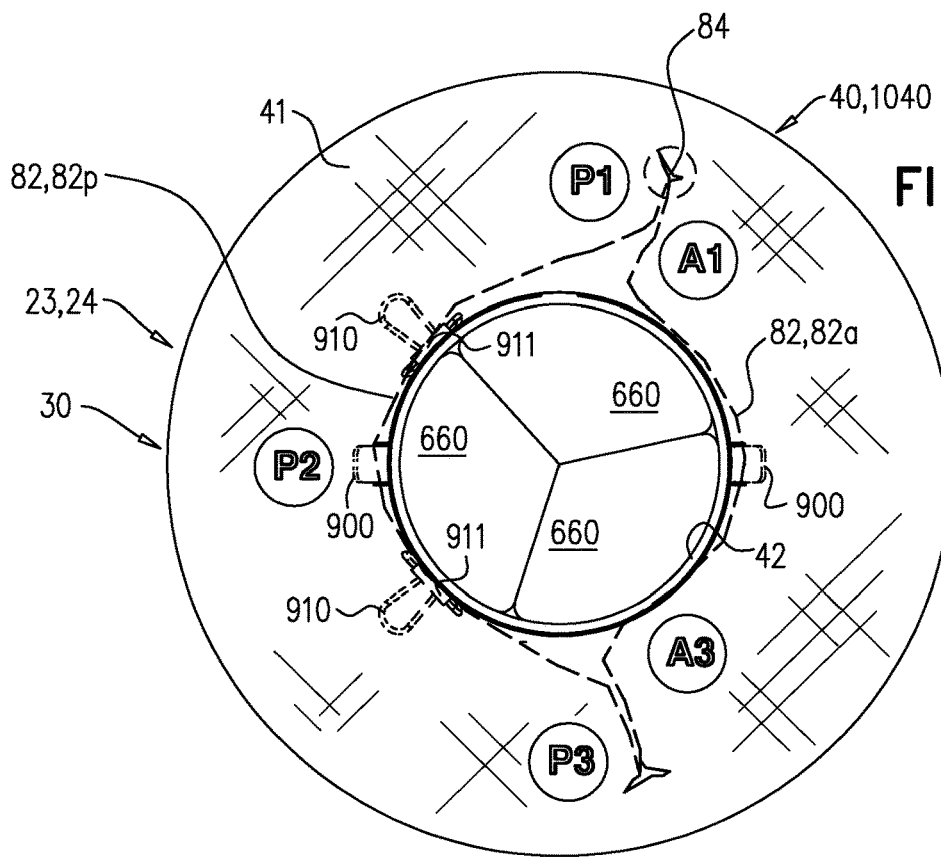

FIG. 36C shows a top (i.e., atrial side) view of implant 30, comprising support 1040 and prosthetic valve 42, following implantation in native valve 23, comprising mitral valve 24, in accordance with some applications of the invention. Zones (scallops) P1, P2 and P3 of posterior leaflet 82*p*, and zones A1 and A3 of anterior leaflet 82*a* are labeled. As described hereinabove, elements 900 and legs 910 are disposed at inner edge 68 in an alternating manner. For the applications of the invention illustrated in FIG. 36C, support-anchoring elements 900 are coupled to leaflets 82, i.e., one element 900 is coupled to anterior leaflet 82*a*, and one element 900 is coupled to posterior leaflet 82*p*. Elements 900 and legs 910 are typically arranged such that (1) the two elements 900 are disposed opposite each other, and (2) each leg 910 is disposed between 30 degrees and 120 degrees (e.g., between 60 degrees and 120 degrees) from the element 900 that is coupled to the posterior leaflet.

Stabilizing legs 910 are thereby typically oriented toward parts of posterior leaflet 82*p*. This configuration and orientation of elements 900 and legs 910 with respect to each other, and with respect to the native valve, is hypothesized to facilitate the stable placement and coupling (i.e., implantation) of prosthetic valve support 1040 at/to the native valve, and thereby is hypothesized to facilitate the stable implantation of implant 30 at the native valve.

Figure 36D:
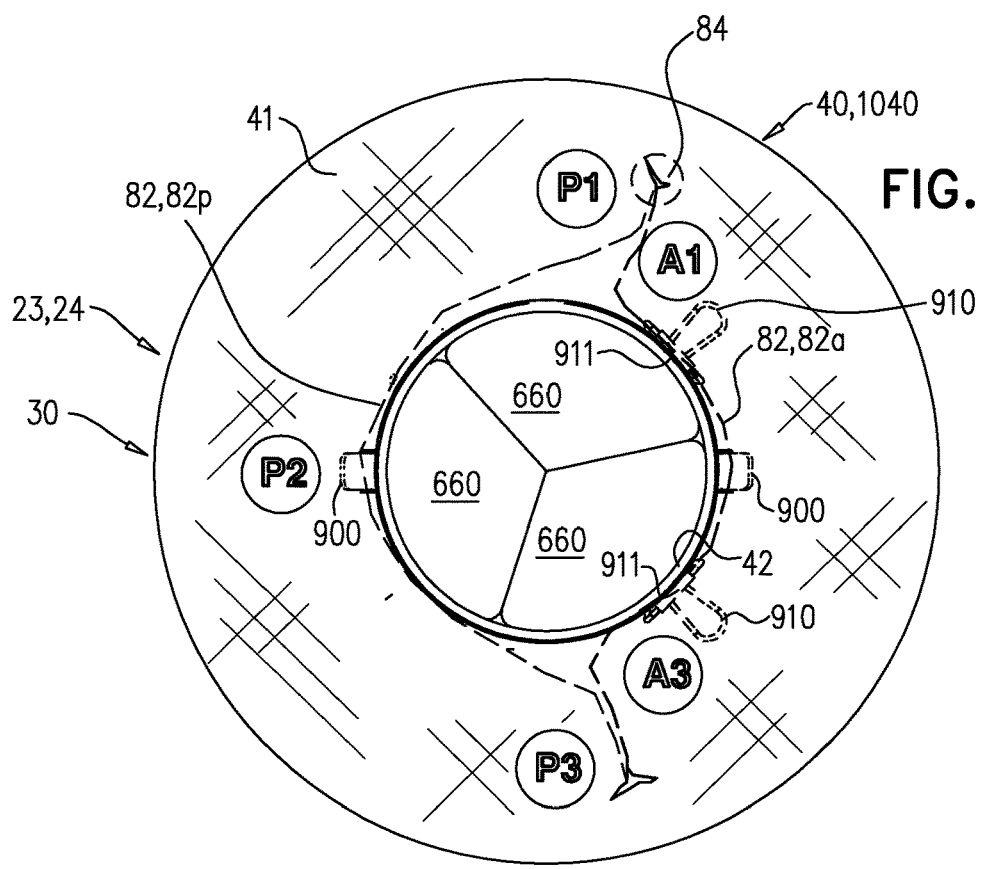

FIG. 36D shows a top (i.e., atrial side) view of implant 30, comprising support 1040 and prosthetic valve 42, following implantation in native valve 23, comprising mitral valve 24, in accordance with some applications of the invention. Zones (scallops) P1, P2 and P3 of posterior leaflet 82*p*, and zones A1 and A3 of anterior leaflet 82*a* are labeled. As described hereinabove, elements 900 and legs 910 are disposed at inner edge 68 in an alternating manner. For the applications of the invention illustrated in FIG. 36D, support-anchoring elements 900 are coupled to leaflets 82, i.e., one element 900 is coupled to anterior leaflet 82*a*, and one element 900 is coupled to posterior leaflet 82*p*. Elements 900 and legs 910 are typically arranged such that (1) the two elements 900 are disposed opposite each other, and (2) each leg 910 is disposed between 30 degrees and 120 degrees (e.g., between 60 degrees and 120 degrees) from the element 900 that is coupled to the anterior leaflet.

Stabilizing legs 910 are thereby typically oriented toward parts of anterior leaflet 82*a*. This configuration and orientation of elements 900 and legs 910 with respect to each other, and with respect to the native valve, is hypothesized to facilitate the stable placement and coupling (i.e., implantation) of prosthetic valve support 1040 at/to the native valve, and thereby is hypothesized to facilitate the stable implantation of implant 30 at the native valve.

Figure 37A:
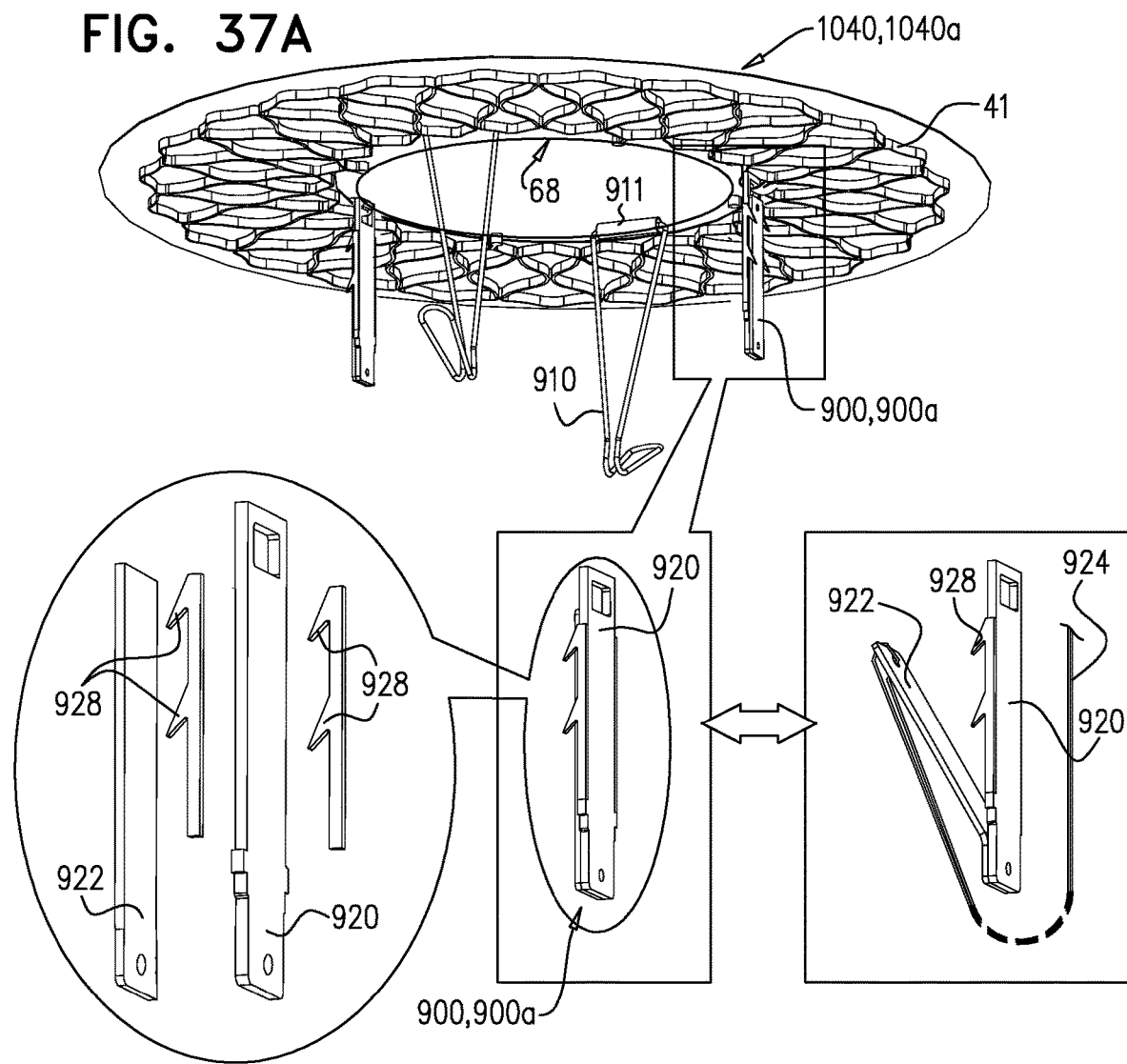

Reference is made to FIGS. 37A-H, which are schematic illustrations of prosthetic valve support 1040, comprising a prosthetic valve support 1040*a*, and the implantation thereof in a native valve, in accordance with some applications of the invention. For some applications of the invention, support 1040*a* is an embodiment of prosthetic valve support 40, described hereinabove. FIG. 37A shows a lower side view, and some detailed views, of support 1040*a*. Support 1040*a* comprises two support-anchoring elements 900, comprising support-anchoring elements 900*a*, and two stabilizing legs 910. Typically, elements 900*a* and legs 910 are disposed at inner edge 68 such that (1) the two elements 900*a* are disposed opposite each other, (2) the two legs 910 are disposed opposite each other, and (3) each leg 910 is generally midway between the two elements 900*a*. That is, inner edge 68 is typically elliptical (e.g., circular), and each leg 910 is disposed at edge 68 generally at a right angle (e.g., between 80 degrees and 100 degrees, such as 90 degrees) to an element 900*a*.

Support-anchoring element 900*a* comprises two clip elements, such as plate 920 and plate 922, (1) coupled at a coupling point, and (2) between which, during implantation, leaflets 82 of the native valve are clamped. Typically, plate 920 is substantially immobile, and plate 922 is (1) biased to assume a first configuration, and (2) movable between the first configuration and another configuration. Typically, the first configuration of plate 922 is a closed configuration. Typically, the other configuration of plate 922 is an open configuration, whereby a portion of plate 922 that is furthest from the coupling point is disposed (1) further from plate 920 than is the same portion in the first, closed configuration, and (2) further from plate 920 than a portion of plate 922 that is closest to the coupling point. When plate 922 is in the closed configuration thereof, element 900a is in a closed configuration thereof. When plate 922 is in the open configuration thereof, element 900a is in an open configuration thereof. That is, element 900a is movable between open and closed configurations thereof, by plate 922 moving between open and closed configurations thereof. FIG. 37A shows detailed illustrations of support-anchoring element 900a in the open and closed configurations, and further shows an exploded view of the components of element 900a.

Support-anchoring element 900a further comprises, or is coupled to, an actuator, typically comprising a pull-wire 924, which facilitates movement of plate 922 between the closed and open configurations. Pull-wire 924 is typically coupled to plate 922, and controlled from outside the subject. For example, pull-wire 924 may be coupled to plate 922, and extend to a control unit outside the body of the subject, for use by a physician. Typically, pull-wire 924 is coupled to the portion of plate 922 that is furthest from the coupling point, such that movement of the pull-wire proximally (e.g., by pulling) moves plate 922 toward the open configuration. For some applications of the invention, pull-wire 924 is slidably coupled to another part of element 900a, such as plate 920, and/or to another part of support 1040a, and/or to a part of delivery apparatus, such as core 926, as shown in FIGS. 37C-E. That is, plate 922, and thereby element 900a, are configured to be biased toward assuming a closed configuration, such that the user (1) actively opens element 900a to envelop a leaflet 82, and (2) releases element 900a to couple the element to the leaflet (i.e., to clamp the leaflet between plates 920 and 922).

For some applications of the invention, both support-coupling elements 900a are controlled simultaneously by a user (e.g., support-coupling elements 900a are configured to operate simultaneously). For some applications, each element 900a is controllable independently. For some applications, element 900a further comprises one or more grips, such as teeth 928, which facilitate the clamping of leaflets 82 when element 900a is closed.

Figure 37B:
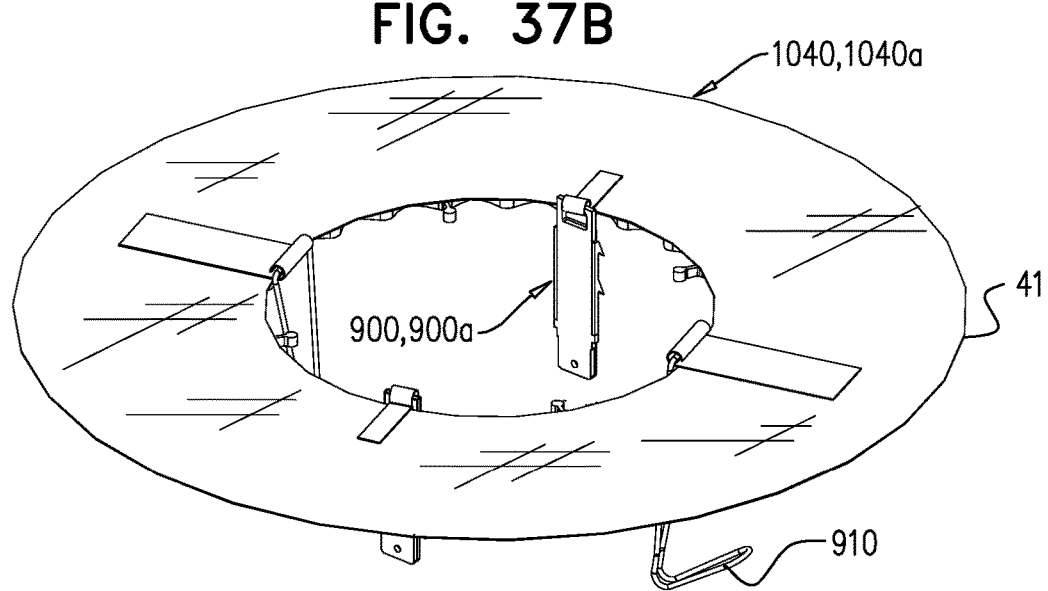
Figure 37E:
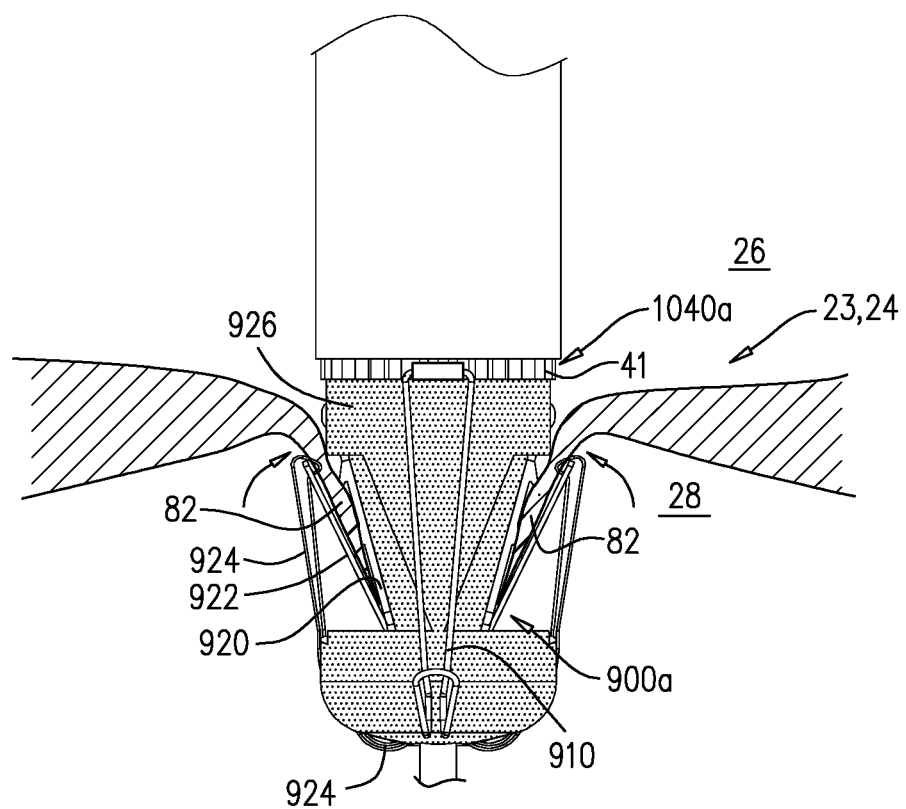

FIG. 37B shows a top side view of prosthetic valve support 1040a. Support-coupling elements 900a are shown in their closed configuration.

FIG. 37C shows prosthetic valve support 1040a being delivered to native valve 23, comprising mitral valve 24. Support 1040a is shown in a partially deployed configuration, whereby upstream support portion 41 is compressed within an overtube 1044, and support-anchoring elements 900a and stabilizing legs 910 are exposed from the distal end of the overtube. Support-anchoring elements 900a are shown in the closed configuration thereof. Typically, prior to deployment, at least part of support 1040a is coupled to (e.g., disposed around) a scaffold, such as a core 926. For some applications of the invention, core 926 is configured to facilitate the opening of elements 900a (i.e., movement of elements 900a and/or plate 922 to the open configuration), and/or to facilitate the enveloping of leaflets 82 of the native valve by elements 900a. For example, and as shown in FIG. 37C, core 926 may support elements 900a at an angle that facilitates the movement of plate 922 by pull-wire 924.

FIG. 37D shows, in cross-section, support 1040a in a partially-deployed configuration within native valve 23. Upstream support portion 41 of support 1040a is in a compressed configuration thereof, and is partially disposed within overtube 1044. Support-anchoring elements 900a and stabilizing legs 910 are exposed from the distal end of the overtube (i.e., have been deployed from the overtube). Arrows indicate the movement of pull-wire 924, caused by proximally pulling the pull-wire. Support-anchoring elements 900a are shown having been moved to the open configuration thereof, by the movement of pull-wire 924. A part of each leaflet 82 is shown within the 'clip' of a respective element 900a (i.e., enveloped by and/or disposed between plate 920 and plate 922 of a respective element 900a). For some applications, the entry of leaflets 82 between the plates is facilitated by the movement of the leaflets caused by the beating of heart 22. For some applications, the entry of leaflets 82 between the plates is facilitated by movement of support 1040a, and/or iterative opening and closing of elements 900a.

FIG. 37E shows support-anchoring elements 900a having moved to the closed configuration thereof, following the release of pull-wire 924. Arrows indicate the movement of pull-wire 924 following the release thereof. The part of each leaflet 82 that was previously disposed between plate 920 and plate 922 is thereby clamped between the two plates. That is, elements 900a are coupled to leaflets 82 of the native valve. Once elements 900a have been successfully coupled to leaflets 82 (e.g., once a physician is satisfied with the position and coupling of support 1040a), the remainder of the support (e.g., upstream support portion 41) is typically deployed.

Figure 37F:
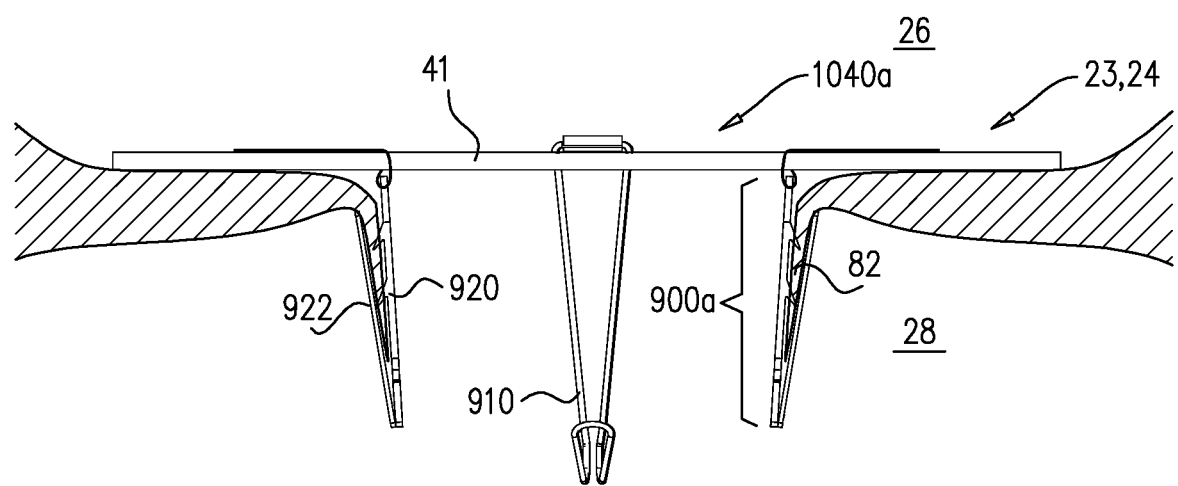

FIG. 37F shows prosthetic valve support 1040a in a fully-deployed configuration thereof. Following coupling of elements 900a to leaflets 82, overtube 1044 is retracted proximally, and/or support 1040a is moved distally, such that the support emerges from the overtube, and expands to its expanded configuration. For some applications, the expansion of support 1040a automatically decouples the support from the scaffold (e.g., core 926), which is subsequently removed from the subject. Annular portion 41 of support 1040a is shown disposed against the proximal side (e.g., the atrial surface) of the native valve, as described hereinabove with respect to upstream support portion 41 of other prosthetic valve supports. FIG. 37D shows native valve 23 in an open configuration thereof, whereby leaflets 82 generally extend into ventricle 28. As described hereinabove, mutatis mutandis, with reference to elements 900, illustrated in FIGS. 36A-D, for some applications, elements 900a are configured to allow leaflets 82 to continue to function, at least in part. For such applications, FIG. 37F illustrates a snapshot of the position of leaflets 82 during diastole. As also described hereinabove, mutatis mutandis, with reference to elements 900, illustrated in FIGS. 36A-D, for some applications, elements 900a are configured to be biased to assume a pre-selected position with respect to upstream support portion 41. For such applications, FIG. 37F illustrates leaflets 82 being held in the open configuration thereof, by elements 900a that are configured to be biased to assume the position shown.

For some applications, following deployment of support 1040a, pull-wire 924, or a portion thereof, is decoupled from the support, or a portion thereof, (e.g., from element 900a). For example, the pull-wire may be coupled to element 900a using a lock described herein (e.g., with reference to FIGS. 45A-C and/or 64A-C, mutatis mutandis), and decoupled from element 900a by moving the lock to the open configuration. Alternatively, the pull-wire may be coupled to element 900a by being looped around the element, and decoupled from the element by being unlooped from the element, e.g., by subsequent to a portion of the pull-wire being cut and/or released.

FIG. 37G shows prosthetic valve 42, having been deployed (e.g., delivered and expanded) in the lumen of prosthetic valve support 1040a, and coupled thereto, as described herein (e.g., with reference to other prosthetic valve supports).

FIG. 37H is a top (e.g., atrial) view of prosthetic valve 42, having been deployed (e.g., delivered and expanded) in the lumen of prosthetic valve support 1040a, and coupled thereto, as described herein (e.g., with reference to other prosthetic valve supports). Support-anchoring elements 900a are coupled to leaflets 82, i.e., one element 900a is coupled to anterior leaflet 82a, and one element 900a is coupled to posterior leaflet 82p. Elements 900a and legs 910 are typically arranged such that (1) the two elements 900a are disposed opposite each other, and (2) each leg 910 is disposed between 60 degrees and 120 degrees from the element 900a that is coupled to the posterior leaflet.

Figure 38E:
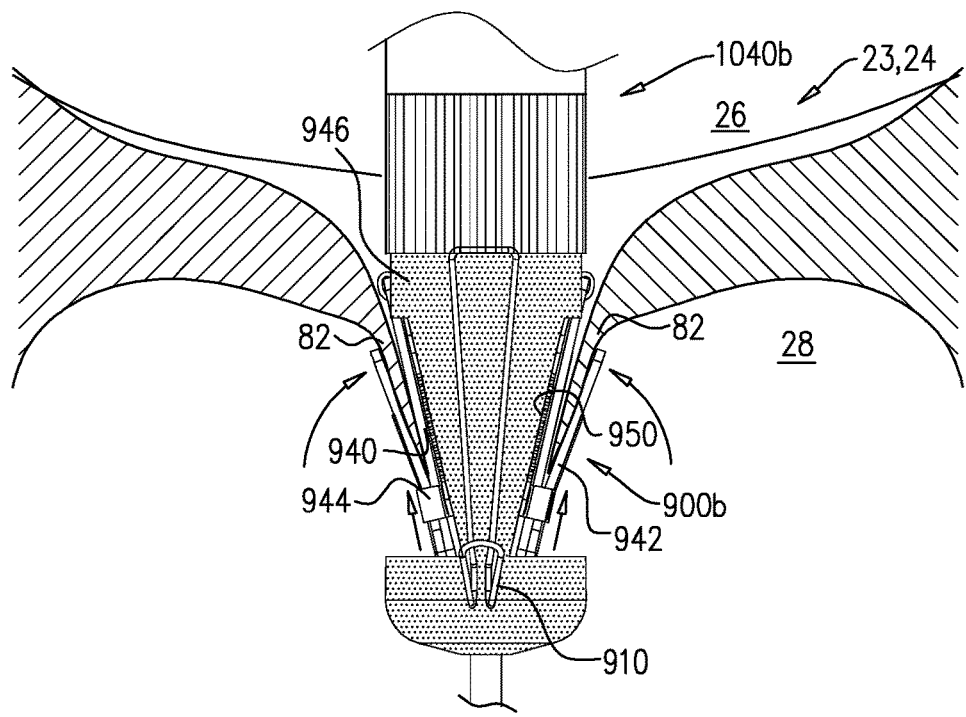

Reference is made to FIGS. 38A-H, which are schematic illustrations of prosthetic valve support 1040, comprising a prosthetic valve support 1040b, and the implantation thereof in a native valve, in accordance with some applications of the invention. For some applications of the invention, support 1040b is an embodiment of prosthetic valve support 40, described hereinabove. FIG. 38A shows a lower side view, and some detailed views, of support 1040b. Support 1040b comprises two support-anchoring elements 900, comprising support-anchoring elements 900b, and two stabilizing legs 910. Typically, elements 900b and legs 910 are disposed at inner edge 68 such that (1) the two elements 900b are disposed opposite each other, (2) the two legs 910 are disposed opposite each other, and (3) each leg 910 is generally midway between the two elements 900b.

Support-anchoring element 900b comprises two clip elements, such as plate 940 and plate 942, (1) coupled at a coupling point, and (2) between which, during implantation, leaflets 82 of the native valve are clamped. Typically, plate 940 is substantially immobile, and plate 942 is (1) biased to assume a first configuration, and (2) movable between the first configuration and another configuration. Typically, the first configuration of plate 942 is an open configuration, whereby a portion of plate 942 that is furthest from the coupling point is disposed further from plate 940 than a portion of plate 942 that is closest to the coupling point. Typically, the other configuration of plate 942 is a closed configuration, whereby a portion of plate 942 that is furthest from the coupling point is disposed closer to plate 940 than is the same portion in the first, open configuration. When plate 942 is in the closed configuration thereof, element 900b is in a closed configuration thereof. When plate 942 is in the open configuration thereof, element 900b is in an open configuration thereof. That is, element 900b is movable between open and closed configurations thereof, by plate 942 moving between open and closed configurations thereof.

FIG. 38A shows detailed illustrations of support-anchoring element 900b in the open and closed configurations, and further shows an exploded view of the components of element 900b. As shown in the exploded view, for some applications, plate 942 comprises more than one element, including a spring element 942a, and a face element 942b. Spring element 942a typically comprises a strip of shape-memory material (e.g., nitinol, stainless steel, nickel cobalt, cobalt chrome, and/or titanium), that is configured such that plate 942 is biased to assume the open configuration. Spring element 942a is typically configured to provide a force that is (1) sufficiently strong to provide this bias, but (2) sufficiently weak so as to facilitate (e.g., to not inhibit) sliding of cuff 944 over plate 942. Typically, this configuration is provided by selecting an appropriate thickness of the strip of shape-memory material of spring element 942a. Face element 942b is typically configured to increase the rigidity of at least part of plate 942, thereby facilitating clamping of the native leaflets when cuff 944 is slid over plate 942.

Support-anchoring element 900b further comprises an actuator, typically comprising a restraint, such as cuff 944, which facilitates movement of plate 922 between the closed and open configurations. Cuff 944 is typically coupled to plate 940 and/or plate 942, and controlled from outside the subject (e.g., controlled from outside the body of the subject by a physician, such as via a control unit). Typically, cuff 944 is coupled to plate 940 via a spring 950, and is slidable over (e.g., onto and off of) at least a portion of plate 942. Support-anchoring element 900b is configured such that (1) spring 950 applies a force (i.e., a first force) to cuff 944, that slides cuff 944 over plate 942, and (2) sliding of cuff 944 over plate 942 moves the portion of plate 942 that is furthest from the coupling point closer to plate 940 (i.e., moves plate 942, and thereby element 900b, into the closed configuration). A user typically opens element 900b (e.g., so as to clamp leaflets of the native valve, e.g., as described hereinbelow with reference to FIGS. 38D-E) by sliding cuff 944 off of plate 942. For example, a control rod 952 may be used to slide cuff 944 off of plate 942 (e.g., by distal movement of the control rod), and may be controlled, by a physician, via a control unit outside the body of the subject. That is, (1) plate 942 itself is configured to be biased toward assuming an open configuration, (2) cuff 944 and spring 950 are configured to move plate 942 toward a closed configuration, and (3) the user (a) actively opens element 900b by sliding cuff 944 off of plate 942, so as to envelop a leaflet 82, and (b) releases cuff 944 to couple the element to the leaflet (i.e., to clamp the leaflet between plates 940 and 942).

For some applications of the invention, both support-coupling elements 900b are controlled simultaneously by a user (e.g., support-coupling elements 900b are configured to operate simultaneously). For some applications, each element 900b is controllable independently. For some applications, element 900b further comprises one or more grips, such as teeth 948, which facilitate the clamping of leaflets 82 when element 900b is closed. For some applications, control rod 952 is moved distally using a pusher (not shown), disposed within delivery apparatus (e.g., overtube 1044), and typically not fixedly coupled to the control rod.

FIG. 38B shows a top side view of prosthetic valve support 1040b. Support-coupling elements 900b are shown in their open configuration.

FIG. 38C shows prosthetic valve support 1040b being delivered to native valve 23, comprising mitral valve 24. Support 1040b is shown in a partially deployed configuration, whereby upstream support portion 41 is compressed within overtube 1044, and support-anchoring elements 900b and stabilizing legs 910 are exposed from the distal end of the overtube. Support-anchoring elements 900b are shown in the closed configuration thereof. Typically, prior to deployment, at least part of support 1040b is coupled to (e.g., disposed around) a scaffold, such as a core 946. For some applications of the invention, core 946 is configured to facilitate the opening of elements 900b (i.e., movement of elements 900b and/or plate 942 to the open configuration), and/or to facilitate the enveloping of leaflets 82 of the native valve by elements 900b. For example, and as shown in FIG. 38C, core 946 may support elements 900b at a pre-selected angle.

FIG. 38D shows support 1040*b* in a partially-deployed configuration within native valve 23. Annular portion 41 of support 1040*b* is in a compressed configuration thereof, and is partially disposed within overtube 1044. Support-anchoring elements 900*b* and stabilizing legs 910 are exposed from the distal end of the overtube (i.e., have been deployed from the overtube). Arrows indicate the movement of cuff 944, caused by distal movement (e.g., pushing) of control rod 952. Support-anchoring elements 900*b* are shown having been moved to the open configuration thereof, by the movement of cuff 944. A part of each leaflet 82 is shown within the 'clip' of a respective element 900*b* (i.e., enveloped by and/or disposed between plate 940 and plate 942 of a respective element 900*b*). For some applications, the entry of leaflets 82 between the plates is facilitated by the movement of the leaflets caused by the beating of heart 22. For some applications, the entry of leaflets 82 between the plates is facilitated by movement of support 1040*b*, and/or iterative opening and closing of elements 900*b*.

FIG. 38E shows support-anchoring elements 900*b* having moved to the closed configuration thereof, following the release of cuff 944 (e.g., caused by the release of control rod 952). Arrows indicate the movement of cuff 944 following the release thereof. The part of each leaflet 82 that was previously enveloped by (i.e., disposed between) plate 940 and plate 942 is thereby clamped between the two plates. That is, elements 900*b* are coupled to leaflets 82 of the native valve. Once elements 900*b* have been successfully coupled to leaflets 82 (e.g., once a physician is satisfied with the position and coupling of support 1040*b*), the remainder of prosthetic valve support 1040*b* (e.g., upstream support portion 41) is typically deployed.

Figure 38F:
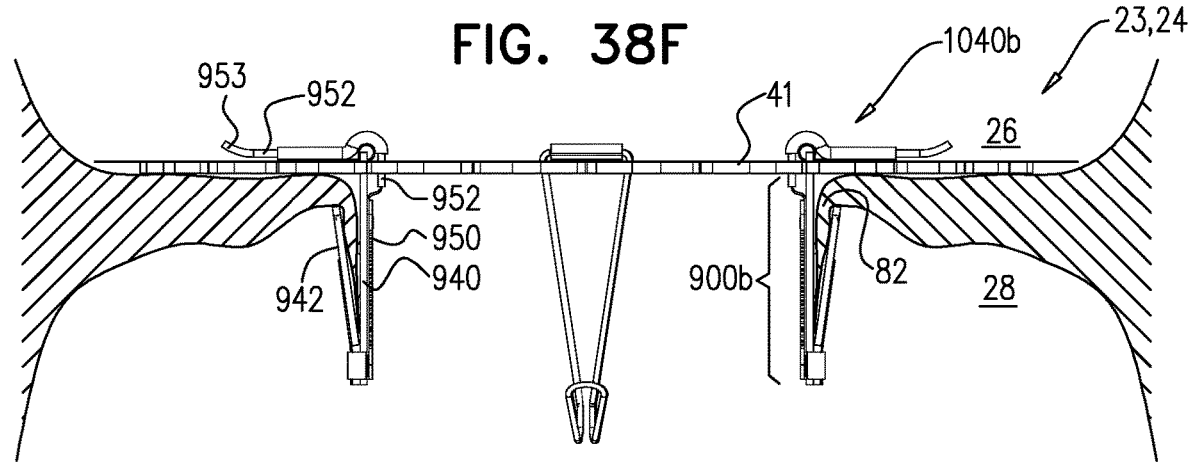

FIG. 38F shows prosthetic valve support 1040*b* in a fully-deployed configuration thereof. Following coupling of elements 900*b* to leaflets 82, overtube 1044 is retracted proximally, and/or support 1040*b* is moved distally, such that the support emerges from the overtube, and expands to its expanded configuration. For some applications, the expansion of support 1040*b* automatically decouples the support from the scaffold (e.g., core 946), which is subsequently removed from the subject. Annular portion 41 of support 1040*b* is shown disposed against the proximal side (e.g., the atrial surface) of the native valve, as described hereinabove with respect to upstream support portion 41 of other prosthetic valve supports. FIG. 38D shows native valve 23 in an open configuration thereof, whereby leaflets 82 generally extend into ventricle 28. As described hereinabove, mutatis mutandis, with reference to elements 900, illustrated in FIGS. 36A-D, for some applications, elements 900*b* are configured to allow leaflets 82 to continue to function, at least in part. For such applications, FIG. 38F illustrates a snapshot of the position of leaflets 82 during diastole. As also described hereinabove, mutatis mutandis, with reference to elements 900, illustrated in FIGS. 36A-D, for some applications, elements 900*b* are configured to be biased to assume a pre-selected position with respect to upstream support portion 41. For such applications, FIG. 38F illustrates leaflets 82 being held in the open configuration thereof, by elements 900*b* that are configured to be biased to assume the position shown.

As described hereinabove, for some applications, control rod 952 is moved distally using a pusher, disposed within delivery apparatus (e.g., overtube 1044), and typically not fixedly coupled to the control rod. For such applications, the pusher remains within the delivery apparatus, and is removed with the delivery apparatus, following full deployment of prosthetic valve support 1040*b*. FIG. 38F thus shows a proximal end 953 of each control rod 952, previously disposed within overtube 1044, now exposed and not in contact with the pusher, following removal of the overtube.

FIG. 38G shows prosthetic valve 42, having been deployed (e.g., delivered and expanded) in the lumen of prosthetic valve support 1040*b*, and coupled thereto, as described herein (e.g., with reference to other prosthetic valve supports).

FIG. 38H is a top (e.g., atrial) view of prosthetic valve 42, having been deployed (e.g., delivered and expanded) in the lumen of prosthetic valve support 1040*b*, and coupled thereto, as described herein (e.g., with reference to other prosthetic valve supports). Support-anchoring elements 900*b* are coupled to leaflets 82, i.e., one element 900*b* is coupled to anterior leaflet 82*a*, and one element 900*b* is coupled to posterior leaflet 82*p*. Elements 900*b* and legs 910 are typically arranged such that (1) the two elements 900*b* are disposed opposite each other, and (2) each leg 910 is disposed between 60 degrees and 120 degrees from the element 900*b* that is coupled to the posterior leaflet.

Reference is again made to FIGS. 36A-38H. Typically, support-anchoring elements 900 (e.g., elements 900*a* and 900*b*) and stabilizing legs 910 are configured to be movable independently from each other, and to be at least in part flexible and/or movable with respect to upstream support portion 41. That is, elements 900 and legs 910 are typically positionable according to the individual anatomy of the subject in which the implant is implanted. For some applications of the invention, this is conferred at least in part by the connection between (1) the element 900 and/or leg 910, and (2) upstream support portion 41. For some applications of the invention, this is conferred at least in part by the composition of the element 900 and/or leg 910 itself. For example, for some applications, techniques and/or elements described with reference to FIGS. 2-7 and 17A-20F, may be used in combination with those described with reference to FIGS. 36A-37H (e.g., in combination with support-anchoring elements 900, 900*a*, and/or 900*b*, and stabilizing legs 910).

For some applications of the invention, during the deployment (e.g., implantation) of prosthetic valve support 1040 (e.g., support 1040*a*, and/or support 1040*b*), the user (e.g., physician) may determine the quality (e.g., strength) of coupling of support-anchoring elements 900 (e.g., elements 900*a*, and/or 900*b*) by applying a force (e.g., pushing, pulling, twisting) to the device, and/or using imaging techniques to visualize the device in situ.

Typically, support-anchoring elements 900 (e.g., elements 900*a* and/or 900*b*) are operable (i.e., openable, and/or closable) repeatedly. Should coupling of elements 900 to leaflets 82 be determined to be suboptimal, elements 900 may be opened (e.g., decoupled from the leaflets) and reclosed (e.g., re-coupled to the leaflets), until optimal coupling has been achieved.

Should it be necessary and/or desirable during deployment, until prosthetic valve support 1040 (e.g., support 1040*a*, and/or support 1040*b*) is fully deployed (e.g., from overtube 1044), the deployed, expanded portions of the support (i.e., the portions of the support, including elements 900) that are exposed from the overtube may be drawn back into the overtube (e.g., for repositioning, or for withdrawal from the body of the subject).

It is to be noted that, although the support-anchoring elements described with reference to FIGS. 36A-38H (e.g., elements 900, 900*a* and 900*b*) are described and/or illustrated in the context of prosthetic valve supports that comprise two support-anchoring elements and two stabilizing legs (e.g., as described with reference to FIGS. 36A-D), the scope of the invention includes other contexts for these support-anchoring elements, and the clip functionality thereof. For example, for some applications of the invention, a prosthetic valve support comprises two support-anchoring elements 900a and/or support-anchoring elements 900b, and does not comprise stabilizing legs 910. For some applications of the invention, a prosthetic valve support comprises greater or fewer than two such support-anchoring elements. Furthermore, for some applications of the invention, the structure and/or function of element 900a and/or 900 may be incorporated in a valve-anchoring element (e.g., valve-anchoring element 64). That is, for some applications of the invention, a prosthetic valve comprises at least one valve-anchoring element, which is described as a support-anchoring element with reference to one or more of FIGS. 36A-38H, mutatis mutandis.

Figure 39A:
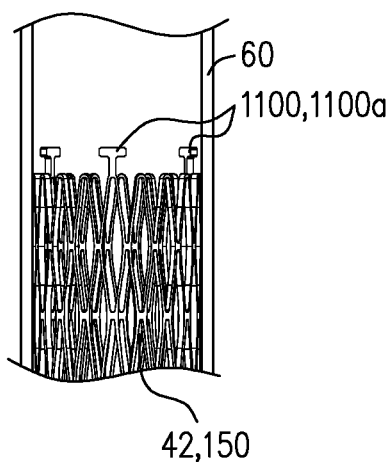
FIGS. 39A-D are schematic illustrations of a medical device, comprising one or more coupling tabs, in accordance with some applications of the invention.
Figure 39B:
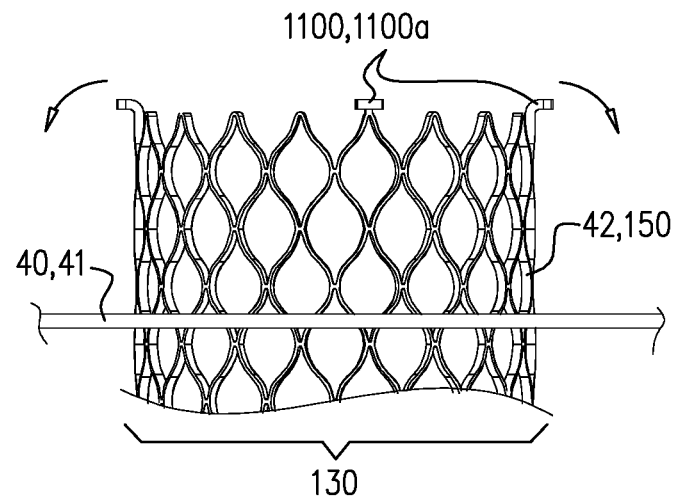
Figure 39C:
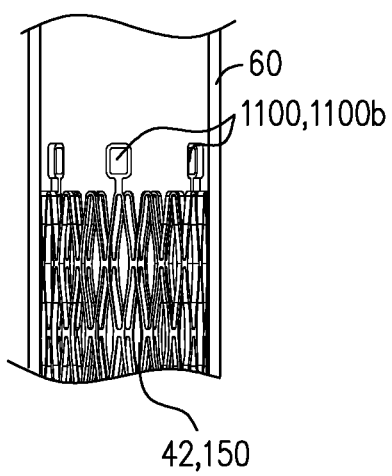
Figure 39D:
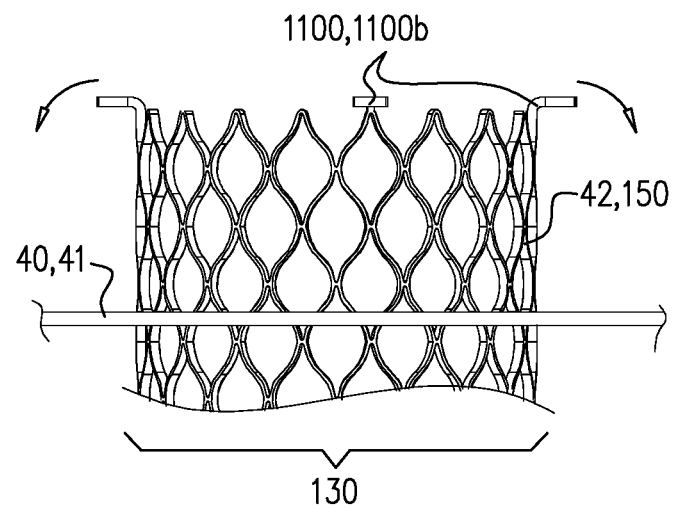

Reference is made to FIGS. 39A-D, which are schematic illustrations of a medical device 150, comprising one or more coupling tabs 1100, in accordance with some applications of the invention. Coupling tabs 1100 facilitate delivery of medical device 150, by facilitating reversible coupling of the medical device to a delivery apparatus, such as, but not limited to, delivery apparatus 880 (described with reference to FIGS. 27A-D). FIGS. 39A-D illustrate medical device 150 as comprising prosthetic valve 42. However, it should be noted that the scope of the invention includes coupling tabs 1100 that facilitate delivery of other medical devices (e.g., expandable medical devices). FIGS. 39A-B show coupling tabs 1100 comprising T-shaped coupling tabs 1100a, and FIG. 39C-D show coupling tabs 1100 comprising box-shaped coupling tabs 1100b. Tabs 1100a and 1100b are configured, respectively, to be reversibly couplable to delivery apparatus of a respective, complimentary configuration.

As described hereinabove, prosthetic valve 42 has (1) a compressed configuration, in which it is typically delivered, within a delivery tube (e.g., tube 60), to the implantation site (e.g., native valve 23), and (2) an expanded configuration, toward which the prosthetic valve moves during deployment. Coupling tabs 1100 are configured such that (1) in the compressed configuration of the prosthetic valve, the tabs assume a restrained configuration (FIGS. 39A and 39C), and (2) in the expanded configuration of the prosthetic valve, the tabs assume an unconstrained configuration, e.g., a preselected configuration (FIGS. 39B and 39D). Typically, in the restrained configuration, coupling tabs 1100 extend collinearly from an end of prosthetic valve 42. For example, and as illustrated in FIGS. 39A and 39C, coupling tabs 1100 extend proximally from the proximal end of the prosthetic valve. Typically, in the unconstrained configuration, at least part of each coupling tab 1100 protrudes radially from primary structural element 130 of the prosthetic valve. For some applications, and as illustrated in FIGS. 39B and 39D, in the unconstrained configuration, coupling tabs 1100 extend radially outward from primary structural element 130 of the prosthetic valve. The arrows indicate the direction of the movement of coupling tabs 1100 from the constrained to the unconstrained configuration. This movement is typically between 5 degrees and 180 degrees (e.g., between 80 degrees and 180 degrees). For some applications, this movement is greater than 180 degrees, whereby coupling tabs 1100 protrude into voids defined by prosthetic valve 42.

Typically, coupling tabs 1100 comprise a shape-memory material (e.g., nitinol, stainless steel, nickel cobalt, cobalt chrome, and/or titanium), and the unconstrained configuration is pre-selected by shape-setting the material.

It is hypothesized that, when prosthetic valve 42 is implanted in the native valve, coupling tabs 1100 (e.g., tabs 1100a and tabs 1100b), advantageously, disturb blood flow less than some coupling tabs that do not move into a configuration in which at least part of the tabs protrude radially from the prosthetic valve. For example, for some applications, coupling tabs 1100 protrude less far proximally into the atrium from the proximal part of primary structural element 130, and/or are disposed further peripherally to a flow of blood through the prosthetic valve. It is hypothesized that this reduced blood flow disturbance of tabs 1100 reduces the likelihood of inducing hemodynamic disorders such as thrombus formation. It is further hypothesized that this reduced proximal protrusion into the atrium, increases the available space in the atrium, thereby facilitating the delivery, removal and/or other movement of medical devices and/or delivery apparatus in the vicinity of the prosthetic valve.

For some applications of the invention, coupling tabs 1100 (e.g., coupling tabs 1100a, and/or coupling tabs 1100b) further facilitate coupling of the prosthetic valve to the prosthetic valve support (e.g., prosthetic valve support 40). As described herein, the size of the lumen of support 40 typically determines the size to which prosthetic valve 42 expands, when implanted in this lumen. Thus, when implanted and expanded in the lumen of prosthetic valve support 40, the primary structural element of prosthetic valve 42 typically has a longest transverse cross-sectional length that generally corresponds to a longest transverse cross-sectional length of the lumen of support 40. A transverse cross section of prosthetic valve 42 at the position of radially-protruding coupling tabs 1100, typically has a longest length that is greater than the longest transverse cross-sectional length of the lumen of support 40. That is, in the region of coupling tabs 1100, prosthetic valve 42 is typically wider than in other (e.g., more distal) regions of the prosthetic valve. This extra width provides axial resistance against undesired distal (e.g., ventricular) movement of prosthetic valve 42 with respect to support 40, in addition to the resistance typically provided by radially expansive forces of prosthetic valve against the support.

For some applications of the invention, coupling tabs 1100 (e.g., coupling tabs 1100a, and/or coupling tabs 1100b) increase the rigidity of prosthetic valve 42 (e.g., the rigidity of primary structural element 130 of the prosthetic valve). For example, for some applications, when primary structural element 130 is generally cylindrical, coupling tabs 1100 inhibit deformation of element 130.

Figure 40A:
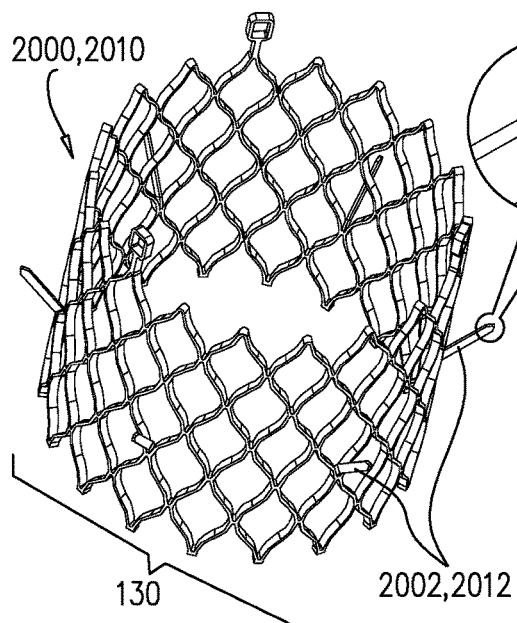
FIGS. 40A-C are schematic illustrations of a prosthetic valve, comprising tissue-engaging elements, in accordance with some applications of the invention.
Figure 40B:
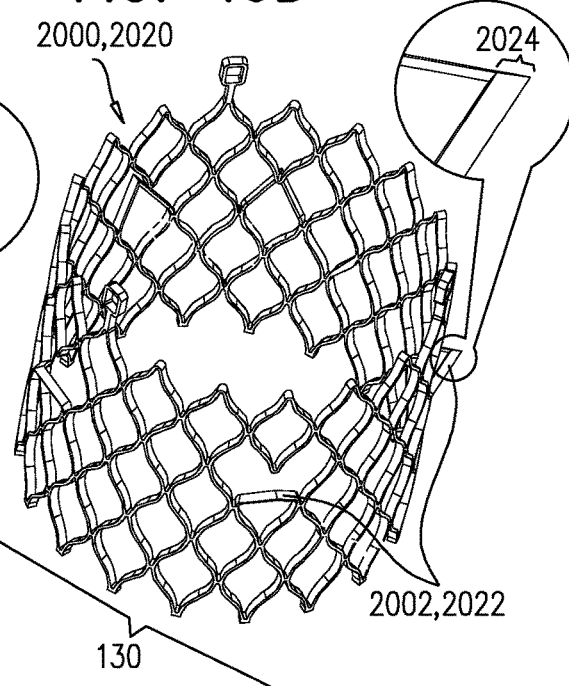
Figure 40C:
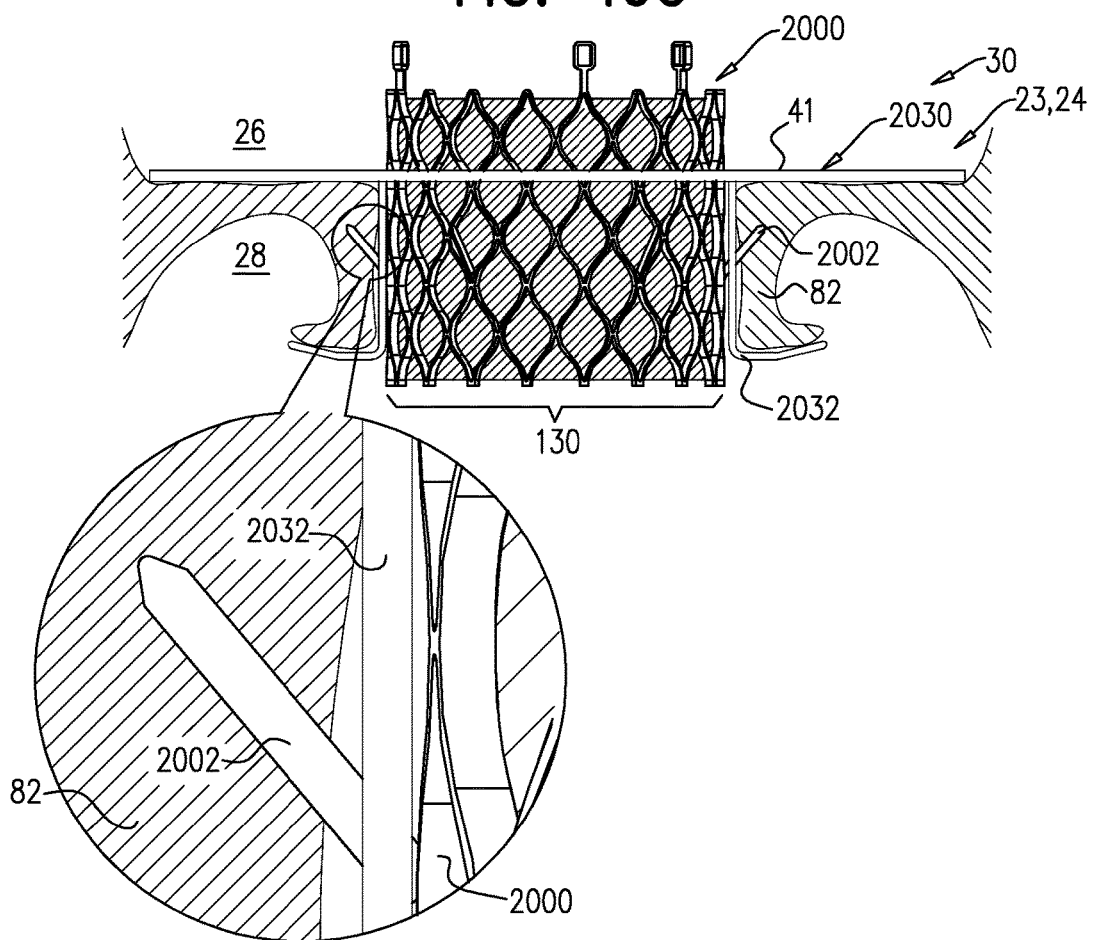

Reference is made to FIGS. 40A-C, which are schematic illustrations of prosthetic valve 42, comprising prosthetic valve 2000, which comprises one or more tissue-engaging elements 2002. For some applications, elements 2002 are embodiments of tissue-engaging elements 62. For some applications, elements 2002 are embodiments of valve-anchoring elements 64. Tissue-engaging elements 2002 protrude laterally from primary structural element 130 of prosthetic valve 2000.

Tissue-engaging elements 2002 are configured to couple to leaflets 82 of the native valve, subsequent to the deployment (e.g., implantation) of prosthetic valve 2000. Typically, elements 2002 are configured to couple to the leaflets by piercing the leaflets, at least in part.

For some applications, prosthetic valve 2000 comprises two elements 2002, that are disposed at sites on the circumference of primary structural element 130 that are generally opposite each other. For some applications of the invention, prosthetic valve 2000 comprises more than two (e.g., four or more, such as six or more) elements 2002, that are disposed circumferentially around primary structural element 130.

For some applications, tissue-engaging elements 2002 protrude generally orthogonally to the outer surface of primary structural element 130 (i.e., generally straight outward laterally from element 130). For some applications, elements 2002 protrude at an acute angle from the outer surface of primary structural element 130. For example, and as illustrated in FIGS. 40A-C, elements 2002 may protrude proximally, such that a portion (e.g., a tip) of elements 2002 that is further from a point of coupling between the element 2002 and primary structural element 130, is closer to the proximal end of element 130 than is a portion of elements 2002 that is closer to that point of coupling.

FIG. 40A shows prosthetic valve 2010, comprising a plurality of tissue-engaging elements 2012. Prosthetic valve 2010 is an embodiment of prosthetic valve 2000, and elements 2012 are embodiments of tissue-engaging elements 2002. Elements 2012 are typically configured to protrude at an acute angle from the outer surface of primary structural element 130 of prosthetic valve 2010. Tip 2014 is the portion of element 2012 that is furthest from a point of coupling between the element 2012 and element 130. For some applications of the invention, tip 2014 is sharp (e.g., pointed) so as to facilitate piercing of the native leaflets.

FIG. 40B shows prosthetic valve 2020, comprising a plurality of tissue-engaging elements 2022. Prosthetic valve 2020 is an embodiment of prosthetic valve 2000, and elements 2022 are embodiments of tissue-engaging elements 2002. For some applications of the invention, prosthetic valve 2020 and elements 2022 are analogous to, and/or comprise, prosthetic valve 2010 and elements 2012, respectively. Elements 2022 are typically configured to protrude at an acute angle from the outer surface of primary structural element 130 of prosthetic valve 2020. For some applications of the invention, elements 2022 are formed from a lattice structure that the prosthetic valve comprises. For example, a separation in the structure may allow a portion of the structure to be moved out of the plane of the structure, thereby protruding from element 130. Element 2022 thereby comprises the protruding portion of the structure. Tip 2024 is the portion of element 2022 that is furthest from a point of coupling between the element 2022 and element 130. For some applications of the invention, tip 2024 is sharp (e.g., pointed) so as to facilitate piercing of the native leaflets.

FIG. 40C shows implant 30, comprising prosthetic valve support 2030 and prosthetic valve 2000, following implantation thereof in native valve 23. Prosthetic valve support 2030 typically comprises support-anchoring elements 2032. For some applications of the invention, prosthetic valve support 2030 and/or support-anchoring elements 2032 are analogous, respectively, to other prosthetic valve supports and support-anchoring elements described herein. For some applications of the invention, prosthetic valve support 2030 comprises prosthetic valve support 40.

Immediately following the implantation of support 2030 and prosthetic valve 2000, leaflets 82 of the native valve typically continue to function, at least in part. For example, support-anchoring elements 2032 may be configured to rotate around a coupling point with upstream support portion 41 of the prosthetic valve, so as to allow the leaflets to continue to function, at least in part (e.g., as described herein for several support-anchoring elements). When leaflets 82 move against prosthetic valve 2000 (e.g., during systole), tissue-engaging elements 2002 couple to (e.g., by piercing) the leaflets.

For some applications of the invention, tissue-engaging elements 2032 are configured to move leaflets 82 against prosthetic valve 2000, and thereby onto tissue-engaging elements 2002. For example, elements 2032 may be configured to move toward each other, such that following implantation of prosthetic valve support 2030 and coupling of elements 2032 to leaflets 82, when prosthetic valve 2000 is deployed in the lumen of support 2030, elements 2032 push leaflets 82 against the prosthetic valve.

It is hypothesized that such coupling of leaflets 82 to elements 2002, and thereby to prosthetic valve 2000, facilitates (1) stable implantation of implant 30 in the native valve, and/or (2) sealing of leaflets 82 around the prosthetic valve, thereby inhibiting retrograde leakage of blood between the leaflets and the implant.

FIG. 40C shows, by way of illustration and not limitation, prosthetic valve 2000 being used in combination with a prosthetic valve support that comprises support-anchoring elements. It is to be noted that, for some applications, prosthetic valve 2000 is used in combination with other prosthetic valve supports that comprise support-anchoring elements, and/or with prosthetic valve supports that do not comprise support-anchoring elements.

Reference is made to FIGS. 41A-B, 42A-B, 43A-C, and 44A-B, which are schematic illustrations of prosthetic valves and prosthetic valve supports, comprising a coupling functionality for coupling support-anchoring elements of the prosthetic valve support to the prosthetic valve.

Figure 41A:
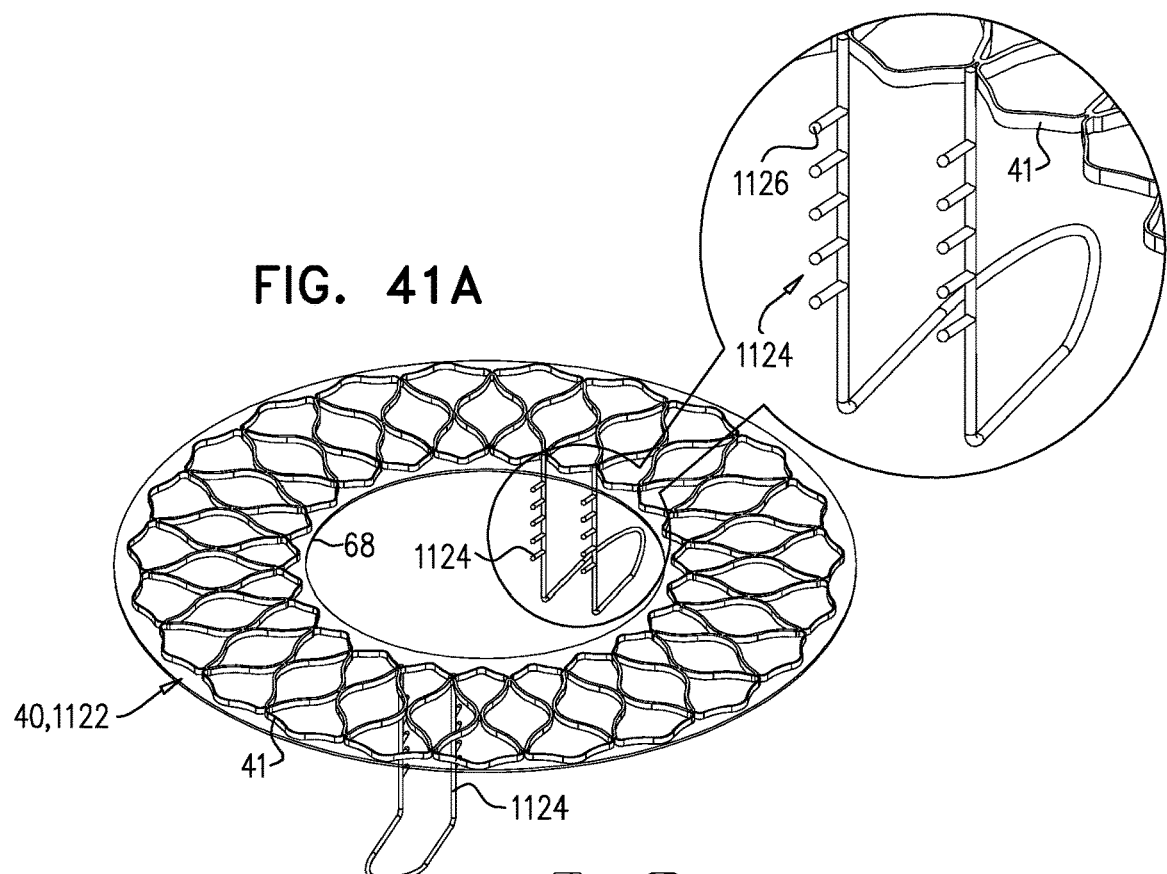
FIGS. 41A-B are schematic illustrations of a prosthetic valve, and a prosthetic valve support, comprising support-anchoring elements that are couplable to the prosthetic valve, in accordance with some applications of the invention.
Figure 41B:
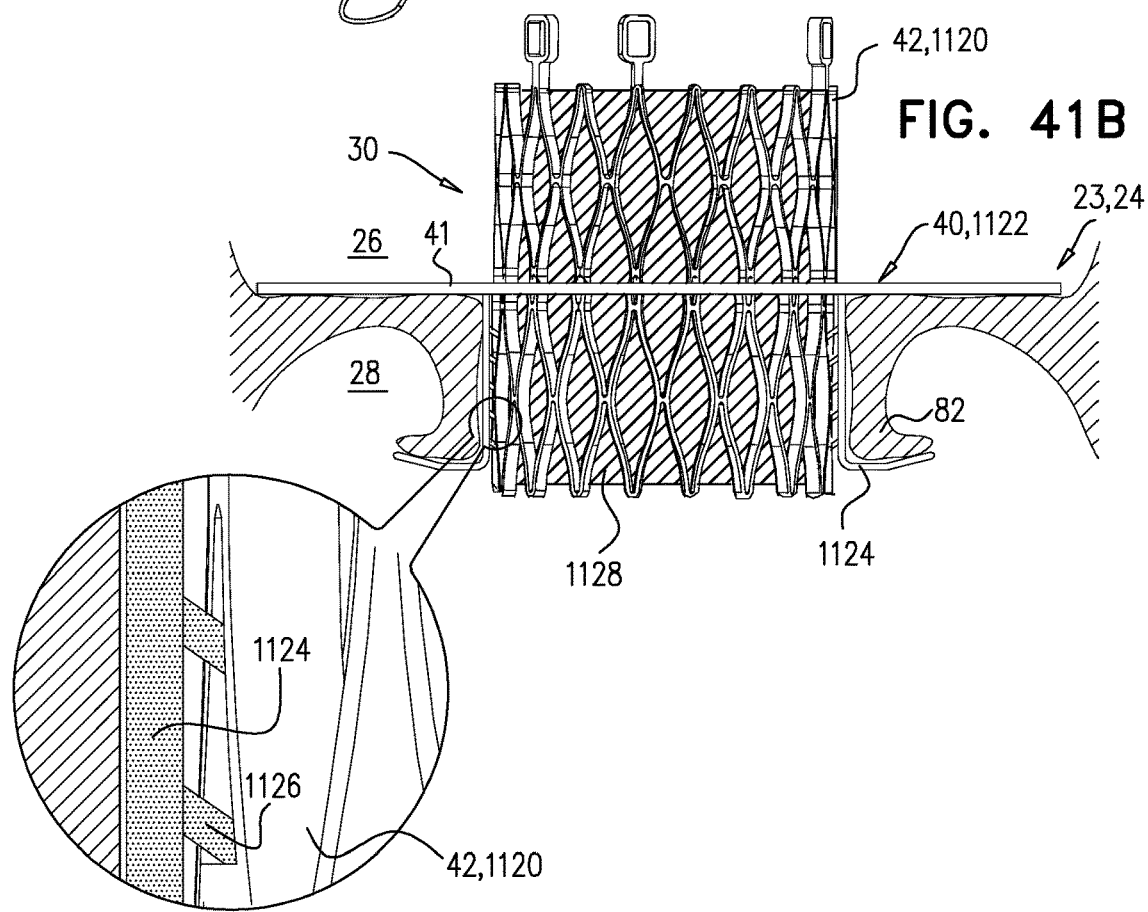

Reference is now made to FIGS. 41A-B, which are schematic illustrations of prosthetic valve support 40, comprising a prosthetic valve support 1122, which comprises one or more support-anchoring elements 1124, in accordance with some applications of the invention. FIG. 41A shows support 1122, and FIG. 41B shows, implanted in a native valve 23, an implant 30, which comprises support 1122 and prosthetic valve 42, comprising a prosthetic valve 1120. For some applications of the invention, support-anchoring elements 1124 comprise (1) other support-anchoring elements described herein (e.g., support-anchoring elements 66), and/or (tissue-engaging elements 62). Support-anchoring elements 1124 comprise one or more barbs 1126, which comprise the coupling functionality for coupling the support-anchoring elements of the prosthetic valve support to the prosthetic valve. Typically, each barb 1126 protrudes from another part of element 1124 at between 10 degrees and 80 degrees (e.g., between 15 degrees and 60 degrees). Typically, a tip of each barb is thereby disposed more distally (e.g., ventricularly) than a base of that barb. Typically, each barb 1136 has a length of between 0.5 and 5 mm.

Prosthetic valve support 1122 is typically delivered to, and deployed at, native valve 23, as described herein for other prosthetic valve supports. Support-anchoring elements 1124 are typically coupled to leaflets 82 of the native valve, as described herein for other support-anchoring elements. Subsequent to the deployment and coupling of support 1122 to the native valve, prosthetic valve 1120 is deployed in the lumen of the prosthetic valve support, as described herein for other prosthetic valves. As prosthetic valve 1120 expands, barbs 1126 engage and couple to the prosthetic valve, typically by protruding into voids defined by the prosthetic valve. For some applications of the invention, elements 1124 are configured to assume a pre-selected configuration, such as that shown in FIG. 41A, and to restrain leaflets 82. For some applications of the invention, elements 1124 are configured to allow leaflets 82 to continue to function, at least in part. For some such applications, movement of leaflets 82 and elements 1124, caused by the beating of the heart, is hypothesized to facilitate engagement of the prosthetic valve by barbs 1126.

Typically, barbs 1126 are configured to protrude into the voids defined by prosthetic valve 1120, but to not protrude further into the prosthetic valve, e.g., into the lumen defined by the prosthetic valve. Typically, prosthetic valve 1120 comprises a wire frame, and a covering 1128, which covers at least part of the inner surface of the prosthetic valve (i.e., the walls of the lumen), so as to facilitate blood flow through the prosthetic valve. Typically, barbs 1126 are dimensioned so as to protrude into the voids defined by the prosthetic valve, but to not protrude into and/or through covering 1128. That is, prosthetic valve 1120 and prosthetic valve support 1122 are configured so as to be couplable to each other using barbs 1126, without the barbs contacting (and possibly damaging) covering 1128.

For some applications of the invention, and as illustrated in FIG. 41B, the prosthetic valve is coupled to prosthetic valve support only by (1) a radially-expansive force exerted by the prosthetic valve on the prosthetic valve support, and (2) barbs 1126 protruding into the voids defined by the prosthetic valve. For such applications of the invention, the prosthetic valve (e.g., prosthetic valve 1120) is typically couplable to the prosthetic valve support at a plurality of relative positions. That is, the prosthetic valve is typically implantable in the native valve at a plurality of depths i.e., a physician may decide on the depth at which the prosthetic valve is implanted in the native valve.

Reference is now made to FIGS. 42A-B, which are schematic illustrations of prosthetic valve support 40, comprising a prosthetic valve support 1132, which comprises one or more support-anchoring elements 1134, in accordance with some applications of the invention. FIG. 42A shows support 1132, and FIG. 42B shows, implanted in a native valve 23, an implant 30, which comprises support 1132 and prosthetic valve 42, comprising a prosthetic valve 1130. For some applications of the invention, support-anchoring elements 1134 comprise (1) other support-anchoring elements described herein (e.g., support-anchoring elements 66), and/or (2) tissue-engaging elements 62. Support-anchoring elements 1134 comprise one or more barbs 1136, which comprise the coupling functionality for coupling the support-anchoring elements of the prosthetic valve support to the prosthetic valve. Typically, each barb 1136 protrudes from another part of element 1134 at between 10 degrees and 80 degrees (e.g., between 15 degrees and 60 degrees). Typically, a tip of each barb is thereby disposed more distally (e.g., ventricularly) than a base of that barb. Typically, each barb 1136 has a length of between 0.5 and 5 mm.

The structure, function and implantation method of prosthetic valve support 1132 and prosthetic valve 1130, are typically similar to those of prosthetic valve support 1122 and prosthetic valve 1120. However, each support-anchoring element 1134 of prosthetic valve support 1132 typically comprises no more than 4 barbs 1136 (e.g., 2 barbs 1136). Prosthetic valve 1130 comprises a wire frame, and a covering 1138, which covers at least part of the inner surface of the prosthetic valve (i.e., the walls of the lumen), so as to facilitate blood flow through the prosthetic valve. Typically, the inner surface of a portion (e.g., a distal portion 1139) of prosthetic valve 1130 is not covered with covering 1138. Typically, barbs 1136 are positioned and/or configured to engage and couple distal portion 1139. That is, prosthetic valve 1130 and prosthetic valve support 1132 are configured so as to be couplable to each other using barbs 1136, without the barbs contacting (and possibly damaging) covering 1138.

Figure 43A:
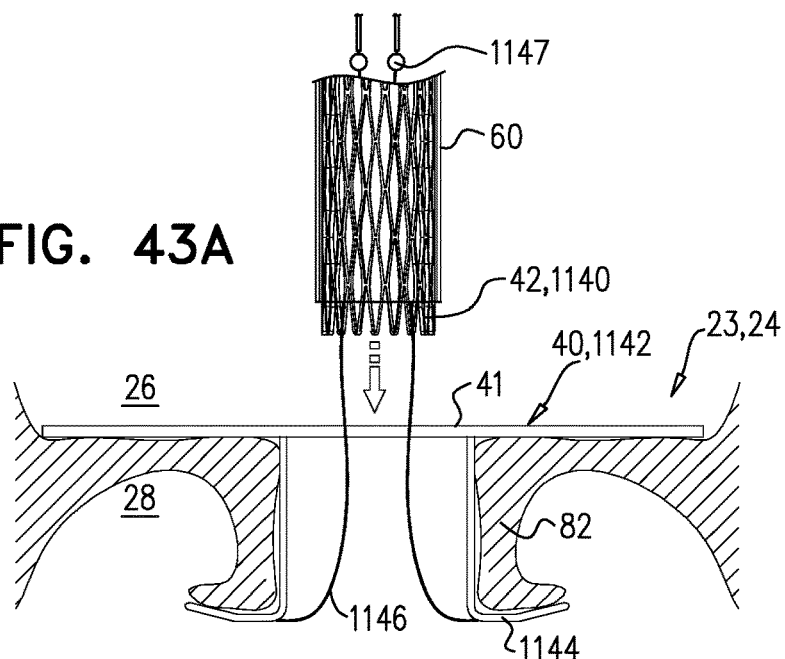
FIGS. 43A-C are schematic illustrations of a prosthetic valve, and a prosthetic valve support, comprising support-anchoring elements that are couplable to the prosthetic valve, in accordance with some applications of the invention.
Figure 43B:
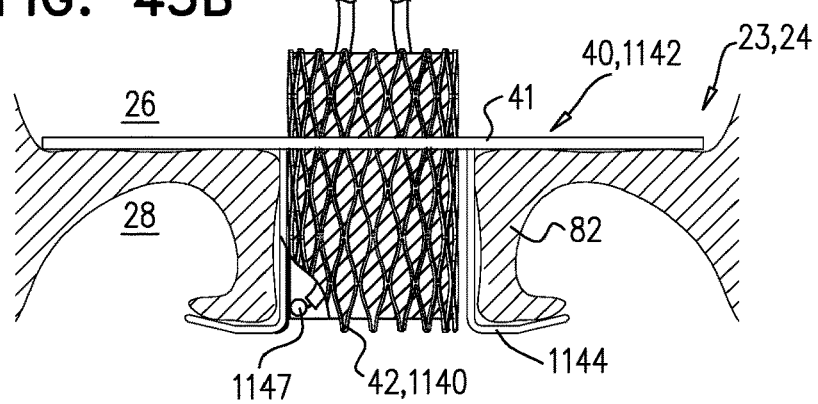
Figure 43C:
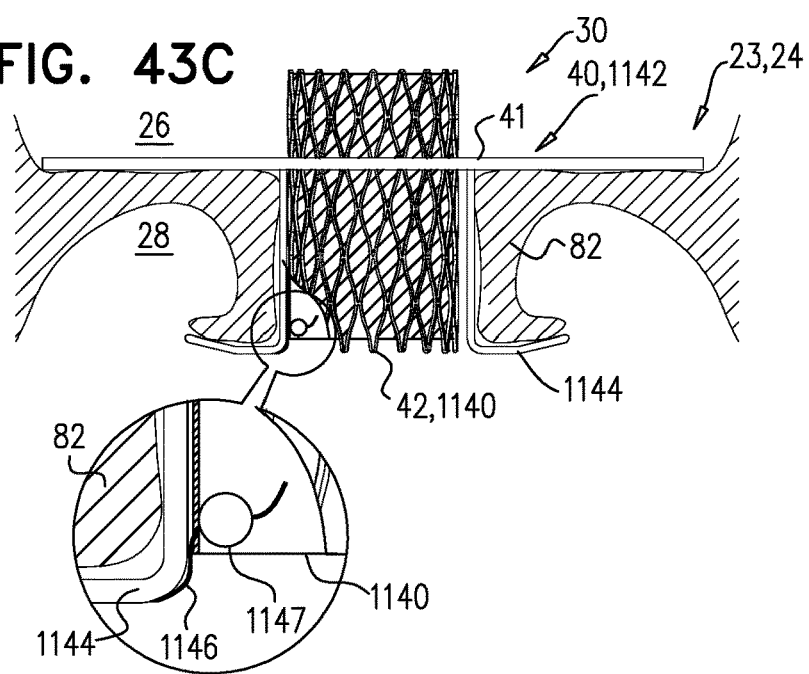

Reference is now made to FIGS. 43A-C, which are schematic illustrations of a prosthetic valve support 1142, comprising one or more support-anchoring elements 1144, which are couplable to a prosthetic valve 1140, in accordance with some applications of the invention. For some applications of the invention, prosthetic valve support 1142 comprises, and/or is analogous to, another prosthetic valve support described herein (e.g., prosthetic valve support 40). For some applications of the invention, prosthetic valve 1140 comprises, and/or is analogous to, another prosthetic valve described herein (e.g., prosthetic valve 42).

Prosthetic valve support 1142 comprises one or more support-anchoring elements 1144, which, for some applications of the invention, comprise, and/or are analogous to, (1) other support-anchoring elements described herein (e.g., support-anchoring elements 66), and/or (2) tissue-engaging elements 62. Support-anchoring elements 1144 comprise a coupling lead 1146 (e.g., a coupling wire) and a stopper 1147, which is slidably coupled to the coupling lead. Coupling lead 114 and stopper 1147 comprise the coupling functionality for coupling the support-anchoring elements of the prosthetic valve support to the prosthetic valve. One end (e.g., a distal end) of coupling lead 1146 is typically coupled to element 1144, and portion (e.g., a proximal portion) of the coupling lead is slidably coupled to prosthetic valve 1140. For some applications of the invention, prosthetic valve 1140 is shaped to define an eyelet (not shown), through which coupling lead is slidable.

FIG. 43A shows prosthetic valve support 1142 having been deployed (e.g., implanted) in native valve 23, and prosthetic valve 1140 in a compressed configuration within delivery tube 60, prior to deployment. A coupling lead 1146 is coupled to each support-anchoring element 1144, and extends proximally, through prosthetic valve 1140.

FIG. 43B shows prosthetic valve 1140 following deployment thereof in the lumen defined by prosthetic valve support 1142. Prosthetic valve 1140 has been slid over coupling leads 1146. That is, the length of each coupling lead that is disposed between an element 1144 and a closest portion of the prosthetic valve, has been shortened. Each stopper 1147 has been slid distally over coupling lead 1146 (e.g., using a pusher; not shown), thereby sandwiching a portion of the prosthetic valve between each stopper and a respective element 1144. Typically, coupling lead 1146 and stopper 1147 are configured to inhibit movement of the stopper in the opposite direction. For example, stopper 1147 may comprise a ratchet housing (e.g., may contain a ratchet mechanism), and coupling lead 1146 may comprise ratchet teeth. Thereby, sliding of stopper 1147 over coupling lead 1146 facilitates coupling of the prosthetic valve to the prosthetic valve support.

For some applications of the invention, coupling leads 1146 facilitate rotational orientation of prosthetic valve 1140 with respect to support 1142 during deployment of the prosthetic valve in the lumen of the support. For example, coupling leads 1146 may act as guidewires, along which the prosthetic valve is slid during deployment thereof.

For some applications of the invention, prosthetic valve 1140 is coupled to prosthetic valve support 1142 using coupling leads 1146 and stoppers 1147 (i.e., stoppers 1147 are slid distally, sandwiching the portions of the prosthetic valve between the stoppers and elements 1144) before the prosthetic valve is fully deployed. For example, this coupling may be performed when the prosthetic valve is semi-deployed from delivery tube 60, i.e., when a proximal portion of the prosthetic valve is still compressed within the delivery tube.

Coupling of prosthetic valve 1140 to elements 1144 with coupling lead 1146 is hypothesized to inhibit lateral rotation (e.g., rotation around an atrial-ventricular axis), and/or axial movement, of the prosthetic valve, with respect to the support.

Following coupling of prosthetic valve 1140 to support-anchoring elements 1144, a proximal portion of coupling lead 1146 is typically subsequently removed from the subject. FIG. 43C shows a distal portion of coupling lead 1146 having been decoupled from a proximal portion of the coupling lead. For some applications of the invention, coupling lead 1146 is cut. For some applications of the invention, the proximal portion of the coupling lead comprises a loop, which is (1) coupled to the distal portion of the coupling lead by being looped around an element of the distal portion of the coupling lead, and (2) decoupled from the distal portion of the coupling lead by being unlooped from the distal portion of the coupling lead. For some applications, the proximal portion of the coupling lead is (1) coupled to the distal portion of the guidewire using a lock described herein (e.g., with reference to FIGS. 45A-C and/or 64A-C, mutatis mutandis), and (2) decoupled from the distal portion of the coupling lead by moving the lock to the open configuration.

Reference is made to FIGS. 44A-B, which are schematic illustrations of (1) a prosthetic valve support 1162, comprising one or more support-anchoring elements 1164, and (2) a prosthetic valve 1160, comprising one or more valve-anchoring elements 1166, which are couplable to prosthetic valve support 1162, in accordance with some applications of the invention. Typically, valve-anchoring elements 1166 are couplable to the prosthetic valve support by being couplable to support-anchoring elements 1164. For some applications of the invention, prosthetic valve support 1142 comprises, and/or is analogous to, another prosthetic valve support described herein (e.g., prosthetic valve support 40). For some applications of the invention, prosthetic valve 1160 comprises, and/or is analogous to, another prosthetic valve described herein (e.g., prosthetic valve 42). For some applications of the invention, support-anchoring elements 1164 comprise, and/or are analogous to, (1) other support-anchoring elements described herein (e.g., support-anchoring elements 66), and/or (2) tissue-engaging elements 62. For some applications of the invention, valve-anchoring elements 1166 comprise, and/or are analogous to, other valve-anchoring elements described herein (e.g., valve-anchoring elements 64). For some applications of the invention, valve-anchoring elements 1166 comprise, and/or are analogous to, support-engaging elements, such as support-engaging elements 422.

FIG. 44A shows prosthetic valve support 1162 having been deployed (e.g., implanted) in native valve 23, and at least part of prosthetic valve 1160 in a compressed configuration within delivery tube 60, prior to deployment. Valve-anchoring elements 1166 are typically coupled to a distal portion (e.g., a distal end) of the primary structural element of prosthetic valve 1160, and, in the compressed configuration of the prosthetic valve, elements 1166 extending distally from the prosthetic valve. Elements 1166 are shown emerging from delivery tube 60. For some applications of the invention, valve-anchoring elements 1166 are formed from the regular repeating structure of the lattice that forms the prosthetic valve, e.g., as described with reference to support-engaging elements 424 (FIGS. 8A-B), mutatis mutandis.

FIG. 44B shows prosthetic valve 1160 following deployment thereof in the lumen defined by prosthetic valve support 1162. Valve-anchoring elements 1166 are deployed on the distal (e.g., ventricular) side of the native valve, and are coupled to support-anchoring elements 1164. Typically, support-anchoring elements 1164 are configured to facilitate coupling (1) of elements 1164 to the native valve (e.g., to leaflets 82), and (2) of valve-anchoring elements 1166 to support-anchoring elements 1164. Valve-anchoring elements 1166 thereby restrict proximal movement of prosthetic valve 1160, i.e., elements 1166 couple the prosthetic valve to support 1162, and to the native valve.

Figure 45A:
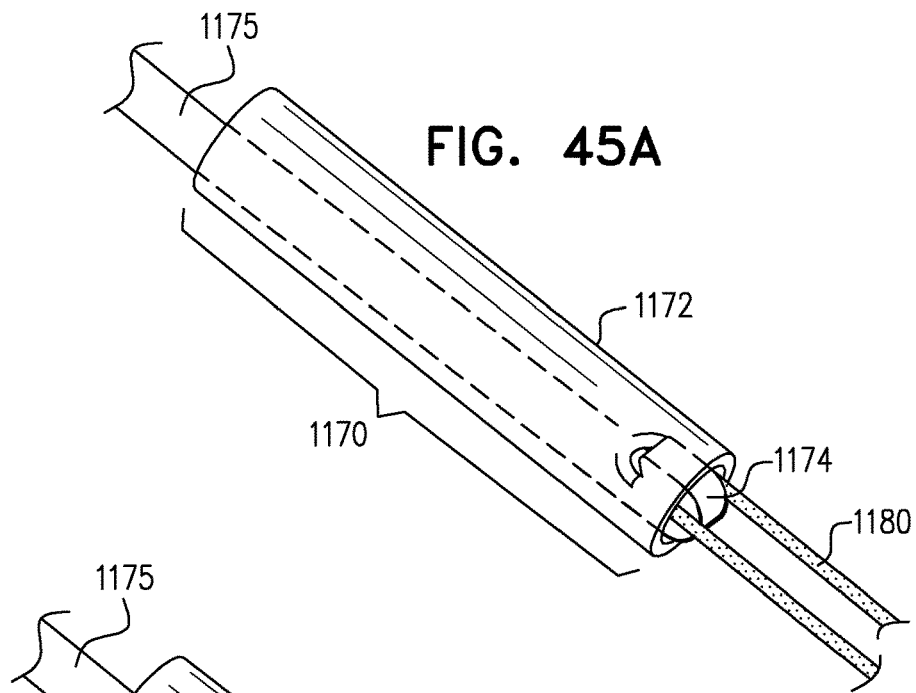
FIGS. 45A-C are schematic illustrations of a lock for facilitating delivery of a medical device, in accordance with some applications of the invention.
Figure 45B:
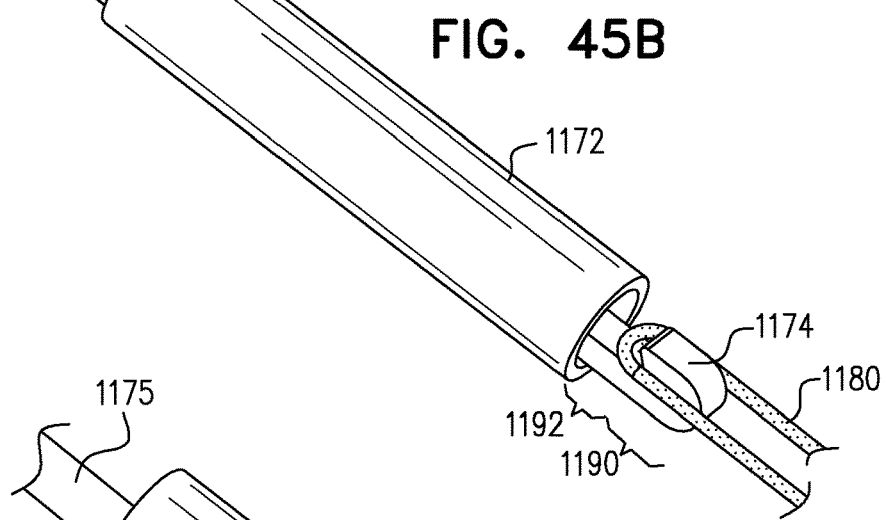
Figure 45C:
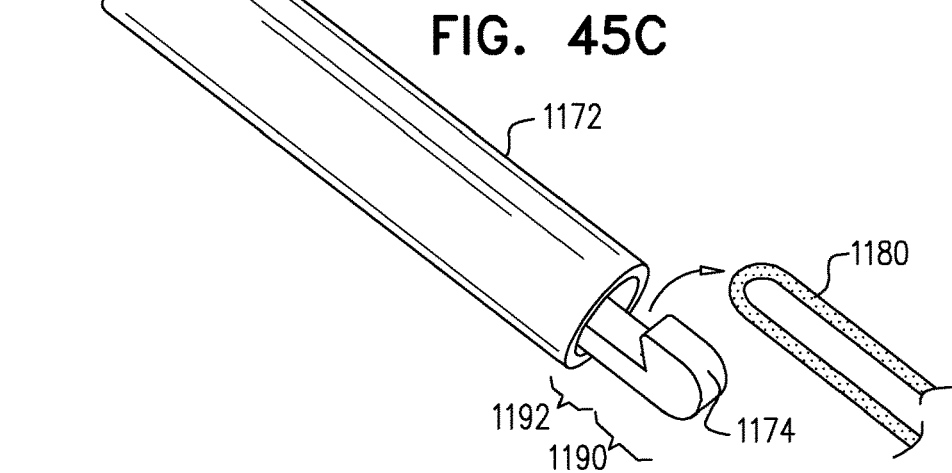

Reference is made to FIGS. 45A-C, which are schematic illustrations of a lock 1170 for facilitating delivery of a medical device, in accordance with some applications of the invention.

Reference is now made to FIG. 45A. Lock 1170 comprises a tubular member 1172 and a plug 1174. Plug 1174 is dimensioned such that it is disposable in, and slidable through (e.g., into and out of) the lumen of tubular member 1172. Plug 1174 comprises a restricting portion 1190 and a second portion 1192. Lock 1170 has a locking configuration, in which (1) at least part of restricting portion 1190 is disposed inside the lumen of tubular member 1172, and (2) a coupling lead 1180 (e.g., a coupling wire) that is coupled to the lock, is generally not decouplable from the lock. Lock 1170 further has an open configuration, in which (1) at least restricting portion 1190 is disposed outside the lumen of tubular member 1172, and (2) coupling lead 1180 is decouplable from the lock. Typically, at least part of plug 1174 (e.g., restricting portion 1190) is dimensioned so as to fit tightly in the lumen of tubular member 1172, in a manner in which an outer surface of plug 1174 (e.g., an outer surface of portion 1190) is disposed very close to an inner surface of tubular member 1172, i.e., such that little space exists between the at least part of the plug and the tubular member. Typically, a surface of second portion 1192 is disposed further from the inner surface of tubular member 1172, than is the surface of the at least part of portion 1190.

For some applications of the invention, second portion 1192 is shaped to define at least part of a trough, and the surface of the second portion that is disposed further from the inner surface of the tubular member, comprises a surface of the trough.

FIG. 45A shows coupling lead 1180 comprising a loop, and coupled to lock 1170 by at least part of the loop being disposed against second portion 1192 when the lock is in the locking configuration. Restricting portion 1190 inhibits axial movement of the coupling lead, and tubular member 1172 inhibits lateral movement of the coupling lead (e.g., the inner surface of tubular member holds the coupling lead against second portion 1192). Tubular member 172 thereby facilitates coupling of coupling lead 1180 to plug 1174, and thereby to lock 1170.

As is described hereinbelow, coupling lead 1180 is typically coupled to a medical device 150 and facilitates (1) coupling of medical device 150 to delivery apparatus during delivery of the medical device and (2) decoupling of medical device 150 from the delivery apparatus following implantation of device 150.

Reference is now made to FIG. 45B. Plug 1174 is slid distally through tubular member 1172, such that lock 1170 is in an open configuration. Typically, plug 1174 is moved using control wire 1175. In this open configuration, restricting portion 1190, and typically at least part of second portion 1192, are exposed from the tubular member (i.e., are outside the lumen of the tubular member). Coupling lead 1180 is shown in FIG. 45B as being disposed against a surface of second portion 1192, by way of illustration and not limitation, as a temporary configuration prior to disengagement of coupling lead 1180 from plug 1174 (i.e., decoupling of the coupling lead from lock 1170; disengagement of coupling lead 1180 is described hereinbelow).

FIG. 45C shows lock 1170 in the open configuration, and coupling lead 1180 decoupled from the lock. In the open configuration of the lock, coupling lead 1180 is allowed to move away from plug 1174 (e.g., tubular member 1172 does not restrict lateral movement of the coupling lead away from second portion 1192). That is, in the open configuration of the lock, coupling lead 1180 is decouplable from the lock. Typically, coupling lead 1180 is moved away from plug 1174 by moving the former with respect to the latter (e.g., by applying a moving force to coupling lead 1180 and/or to plug 1174). In some applications of the invention, at least a portion of coupling lead 1180 is configured such that it automatically moves out of the trough upon being exposed from the tubular member (i.e., when lock 1170 moves to the open configuration). For example, the coupling lead may comprise a shape-memory material such as nitinol, stainless steel, nickel cobalt, cobalt chrome, and/or titanium. In some applications of the invention, portions 1190 and 1192 are shaped to facilitate the decoupling of coupling lead 1180 from the lock. For example, a boundary between portions 1190 and 1192 may be sloped.

Figure 46A:
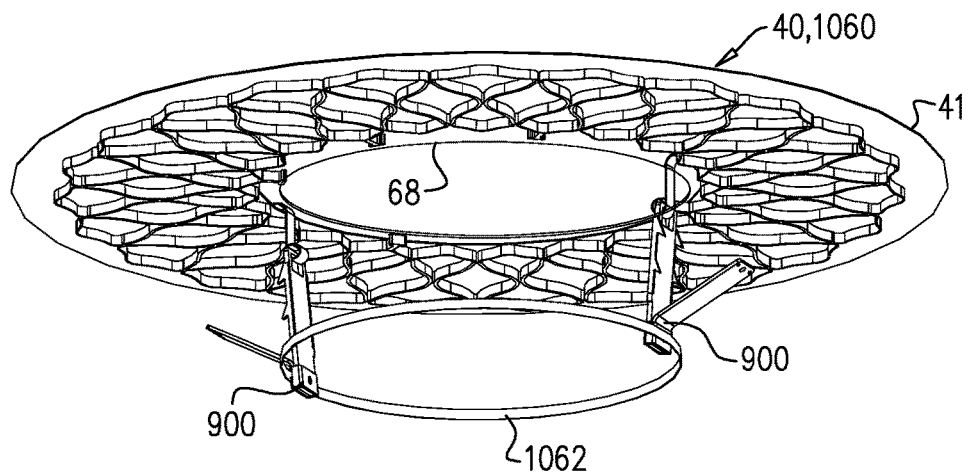
FIGS. 46A-B are schematic illustrations of a prosthetic valve support, comprising one or more support-anchoring elements, coupled to a stabilizing strip, in accordance with some applications of the invention.
Figure 46B:
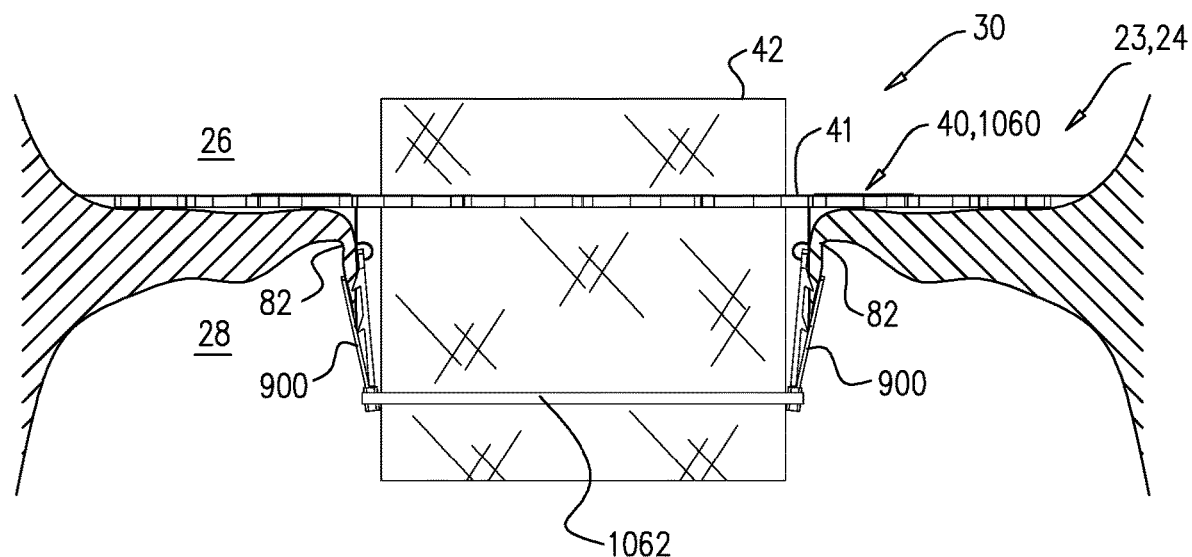

Reference is made to FIGS. 46A-B, which are schematic illustrations of prosthetic valve support 40, comprising prosthetic valve support 1060, which comprises one or more support-anchoring elements, such as support-anchoring elements 900, coupled to a stabilizing element 1062 (e.g., a stabilizing strip or a stabilizing element), in accordance with some applications of the invention. FIG. 46A shows a lower side view of support 1060. As described hereinabove, the support-anchoring elements are typically coupled to inner edge 68, which defines the lumen of upstream support portion 41. That is, a first portion (e.g., a proximal end) of each support-anchoring element is typically coupled to inner edge 68. A second portion of each support-anchoring element is typically coupled to stabilizing element 1062. Typically, stabilizing element 1062 comprises an annular band. Further typically, a distal portion of each support-anchoring elements is coupled to the stabilizing element. Stabilizing element 1062 defines an opening (e.g., an aperture), and is typically inelastic and at least partly flexible. Non-limiting examples of materials that stabilizing element 1062 may comprise include polyester, PTFE (e.g., ePTFE), nylon, cotton, nitinol, stainless steel, nickel cobalt, cobalt chrome, titanium, tantalum and palladium. The flexibility of element 1062 typically facilitates the compressibility of the prosthetic valve support (e.g., for transvascular delivery). For some applications of the invention, the support-anchoring elements are configured to rotate freely around the point at which they couple to upstream support portion 41, e.g., so as to allow leaflets of the native valve to continue to function (i.e., to move), at least in part. For some such applications, the flexibility of stabilizing element 1062 typically allows (i.e., does not generally inhibit) this movement of the support-anchoring elements and the leaflets.

Stabilizing element 1062 is hypothesized to increase the stability of prosthetic valve support 1060 at the native valve. For example, stabilizing element 1062 is hypothesized to at least partly inhibit lateral rotation (e.g., rotation around an atrial-ventricular axis, e.g., 'yaw') of the support and/or support-anchoring elements. Following deployment (e.g., implantation) of the prosthetic valve, stabilizing element 1062 is further hypothesized to reduce rolling movement (e.g., movement around a lateral axis, e.g., an axis between two elements 900, e.g., 'pitch' and 'roll') of the prosthetic valve and/or implant 30, including inversion (e.g., 'flipping') of the implant.

For some applications of the invention, stabilizing element 1062 is further hypothesized to stabilize elements 900 during deployment of the elements, e.g., by facilitating coupling thereof to delivery apparatus.

FIG. 46B shows implant 30, comprising prosthetic valve support 1060 and prosthetic valve 42, following implantation in native valve 23. The prosthetic valve support and the prosthetic valve are typically implanted as described hereinabove, mutatis mutandis. Prosthetic valve 42 is deployed (e.g., delivered and expanded) in the lumen of support 1060, and in the opening defined by stabilizing element 1062. That is, when prosthetic valve 42 is deployed at the native valve, it is expanded such that (1) a proximal portion of the prosthetic valve couples to inner edge 68 of support 1060, and (2) a distal portion of the prosthetic valve is disposed within the opening of the stabilizing element. For some applications of the invention, and as illustrated in FIG. 46B, the distal portion of the prosthetic valve makes contact with the stabilizing element.

For some applications of the invention, stabilizing element 1062 is configured (e.g., dimensioned) such that, when the prosthetic valve is expanded within the opening of the stabilizing element, the stabilizing element limits the expansion of the distal portion of primary structural element 130 of the prosthetic valve. That is, for some applications, the cross-sectional area defined by the primary structural element 130 of the prosthetic valve, upon expansion of the prosthetic valve, is determined by the cross-sectional area of the opening of the stabilizing element. For some applications, the cross-sectional area of the opening of the stabilizing element is substantially equal to the cross-sectional area of the lumen defined by upstream support portion 41, thereby the expansion of both the distal and proximal portions of the primary structural element are limited to the same diameter, thereby facilitating the primary structural element to assume a cylindrical shape.

For applications where stabilizing element 1062 limits the expansion of prosthetic valve 42, a radially-expansive force is thereby applied by prosthetic valve 42 to stabilizing element 1062. The radially-expansive force typically couples the prosthetic valve to the stabilizing element. That is, for some applications, prosthetic valve 42 is couplable to the stabilizing element. For some applications, the prosthetic valve is coupled to the stabilizing element by alternative or additional means. For example, the stabilizing element may comprise barbs and/or hooks, which facilitate coupling to the prosthetic valve.

For some applications of the invention, at least part (e.g., an inner surface) of stabilizing element 1062 comprises a friction coating, that is configured to increase friction, and thereby coupling, between the stabilizing element and the prosthetic valve.

For some applications of the invention, at least part of stabilizing element 1062 is shaped to define ridges, which are configured (e.g., dimensioned) to protrude between struts of the lattice structure of the prosthetic valve (i.e., into voids defined by the lattice structure). The protruding parts facilitate coupling of the stabilizing element to the prosthetic valve, e.g., by inhibiting axial movement of the prosthetic valve through the opening defined by the stabilizing element.

For some applications of the invention, a soft (e.g., crushable) material is disposed on the inner surface of stabilizing element 1062 (e.g., the stabilizing element comprises the soft material). When prosthetic valve 42 expands, and applies radially-expansive force to the stabilizing element, (1) the struts of the lattice structure of the prosthetic valve compress (e.g., crush) the parts of the soft material against which the struts apply the force, and (2) the parts of the soft material that are disposed between the struts (i.e., that are disposed at voids defined by the lattice structure), form ridges that protrude between the struts (i.e., protrude into the voids). The protruding parts of the soft material facilitate coupling of the stabilizing element to the prosthetic valve, e.g., by inhibiting axial movement of the prosthetic valve through the opening defined by the band, such as by increasing friction.

For some applications of the invention, prosthetic valve 42 (e.g., the primary structural element of prosthetic valve 42) is shaped to define a circumferential groove that is configured (e.g., dimensioned) to receive stabilizing element 1062. That is, for some applications of the invention, stabilizing element 1062 is configured (e.g., dimensioned) to be placeable in a circumferential groove defined by prosthetic valve 42. When prosthetic valve 42 is deployed, and expands in the opening defined by stabilizing element 1062, stabilizing element 1062 is disposed in the groove, thereby further facilitating coupling of the stabilizing element to the prosthetic valve, e.g., by inhibiting axial movement of the prosthetic valve through the opening defined by the stabilizing element.

It is to be noted that, although stabilizing element 1062 is described with reference to FIGS. 46A-B as being coupled to support-anchoring elements 900, the scope of the present invention includes stabilizing elements coupled to other support-anchoring elements described herein, such as support-anchoring elements 66.

Reference is made to FIGS. 47A-C, which are schematic illustrations of sequential steps in the implantation of implant 30, comprising prosthetic valve 42 and prosthetic valve support 1040, which comprises prosthetic valve support 1080, in accordance with some applications of the invention. Prosthetic valve support 1080 comprises two stabilizing legs 910, which comprise stabilizing legs 910a. Support 1080 and/or legs 910a are configured such that, during deployment of support 1080 (e.g., from an overtube), legs 910a automatically move toward a pre-defined stabilizing configuration thereof. For example, legs 910a may comprise a shape-memory material that is biased (e.g., shape-set) to move the legs toward the stabilizing configuration thereof.

FIG. 47A shows support 1080 during deployment thereof. Annular portion 41 is disposed against the proximal (e.g., atrial) side of native valve 23, and stabilizing legs 910a are moving toward the stabilizing configuration thereof. That is, FIG. 47A is a 'snapshot' of support 1080 immediately following the release thereof from a delivery tube.

FIG. 47B shows support 1080 following deployment thereof at native valve 23. Stabilizing legs 910a have moved into the stabilizing configuration thereof. As described hereinabove, mutatis mutandis, for stabilizing legs 910, with reference to FIG. 36A, proximal portion 912 of each leg is disposed on a plane between (1) a plane 999 that is orthogonal to a plane defined by upstream support portion 41, and (2) a position in which the leg touches a part of upstream support portion 41 that is peripheral to inner edge 68.

FIG. 47C shows prosthetic valve 42 following deployment thereof in the lumen of support 1080. Typically, and as shown in FIG. 47C, the primary structural element of prosthetic valve 42 defines plane 999, that is orthogonal to the plane defined by upstream support portion 41. That is, in the stabilizing configuration thereof, stabilizing legs 910a are typically disposed on a plane between (1) a plane defined by the primary structural element of prosthetic valve 42, and (2) a plane defined by upstream support portion 41.

Reference is made to FIGS. 48A-C, which are schematic illustrations of sequential steps in the implantation of implant 30, comprising prosthetic valve 42 and prosthetic valve support 1040, which comprises prosthetic valve support 1090, in accordance with some applications of the invention. Prosthetic valve support 1090 comprises two stabilizing legs 910, which comprise stabilizing legs 910b.

FIG. 48A shows prosthetic valve support 1090 in an at-rest configuration thereof, subsequent to deployment of the support at native valve 23. Support 1090 and/or legs 910b are configured such that, subsequent to deployment of support 1090 (e.g., from an overtube), legs 910b are disposed proximal to upstream support portion 41 (e.g., atrially). For example, legs 910b may comprise a shape-memory material that is biased (e.g., shape-set) to move the legs toward the at-rest configuration.

FIG. 48B shows prosthetic valve 42, in a compressed configuration thereof, disposed within a delivery tube 60, being delivered to native valve 23. Prosthetic valve 42 is moved distally into the lumen defined by upstream support portion 41. Stabilizing legs 910b move (e.g., rotate) through the lumen, responsively to the movement of the prosthetic valve. For example, distal movement of the prosthetic valve may directly push the stabilizing legs through the lumen. Alternatively or additionally, prosthetic valve 42 and/or stabilizing legs 910b may comprise engaging elements (e.g., barbs and/or levers) which facilitate the movement of the stabilizing legs in response to the movement of the prosthetic valve.

FIG. 48C shows prosthetic valve 42 following deployment thereof in the lumen of support 1090. Stabilizing legs 910b have moved into the stabilizing configuration thereof. Typically, and as shown in FIG. 48C, the primary structural element of prosthetic valve 42 defines plane 999, that is orthogonal to the plane defined by upstream support portion 41. That is, in the stabilizing configuration thereof, stabilizing legs 910b are typically disposed on a plane between (1) a plane defined by the primary structural element of prosthetic valve 42, and (2) a plane defined by upstream support portion 41.

Figure 49:
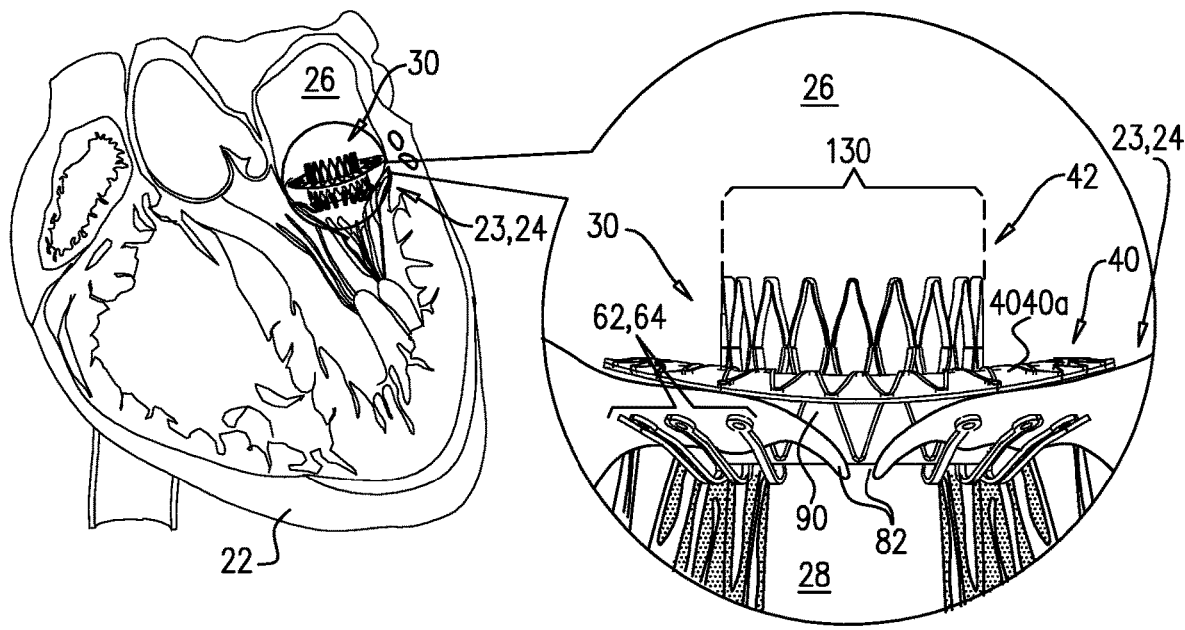
FIG. 49 is a schematic illustration of the prosthetic valve support, in accordance with some applications of the invention.

Reference is made to FIG. 49, which is a schematic illustration of prosthetic valve support 40, embodied as a prosthetic valve support 4040a, in accordance with some applications of the invention. Prosthetic valve support 4040a comprises a cylindrical element 90 that is configured to extend distally through native valve 23. Cylindrical element 90 is typically configured to (1) facilitate coupling of prosthetic valve support 4040a to the native valve, and/or sealing therebetween, (2) to facilitate coupling of prosthetic valve support 4040a to prosthetic valve 42 (or any other prosthetic valve described herein), and/or sealing therebetween, and/or (3) to push aside native leaflets 82 of native valve 23. For such applications of the present invention in which prosthetic valve support 40 (i.e., prosthetic valve support 4040a) comprises cylindrical element 90, support 40 and prosthetic valve 42 may be implanted in a manner as described hereinabove with reference to FIGS. 1A-H.

Figure 50:
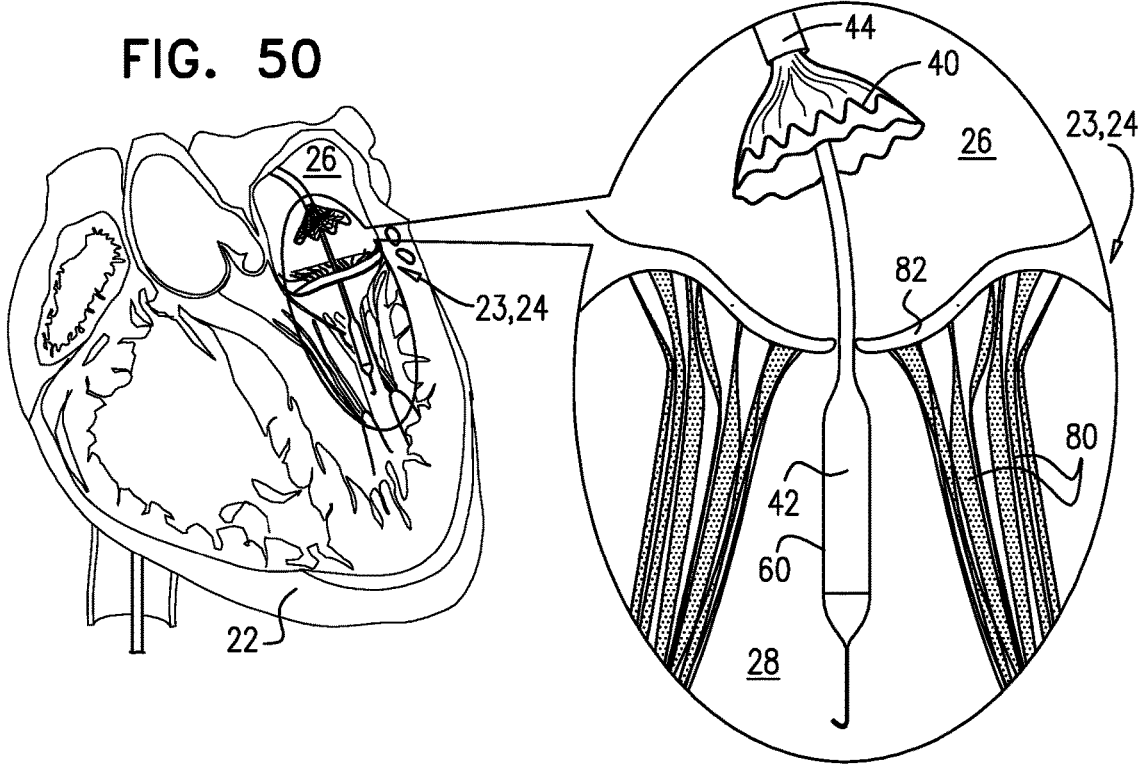
FIG. 50 is a schematic illustration of a step in the implantation of the implant, in accordance with some applications of the invention.

Reference is made to FIG. 50, which is a schematic illustration of an alternative technique for the implantation of implant 30, in accordance with some applications of the invention. FIG. 50 shows a technique in which prosthetic valve 42 (shown crimped within delivery tube 60) is advanced within ventricle 28 prior to and/or in conjunction with the deployment of support 40.

Reference is now made to FIGS. 1A-H and 50. FIGS. 1A-H illustrate the implantation of implant 30, whereby prosthetic valve support 40 is initially delivered and placed against the annulus of the native valve, and subsequently, prosthetic valve 42 is delivered to the native valve. In some applications of the invention, as shown in FIG. 50, these two components of implant 30 are delivered in reverse order. FIG. 50 illustrates (1) the undeployed prosthetic valve 42, having been initially delivered to ventricle 28, and (2) prosthetic valve support 40 being subsequently and/or in conjunction, delivered and deployed within atrium 26. In these applications of the invention, following deployment and positioning of prosthetic valve support 40 against the annulus of native valve 23, prosthetic valve 42 is moved atrially (i.e., proximally) into the respective lumens of the native valve and prosthetic valve support 40, and is deployed, as described hereinabove with reference to FIGS. 1G-H.

It is to be noted that implants 30 described herein may be implanted using the method described hereinabove with reference to FIGS. 1A-H, or using the method described hereinabove with reference to FIG. 50.

Figure 51A:
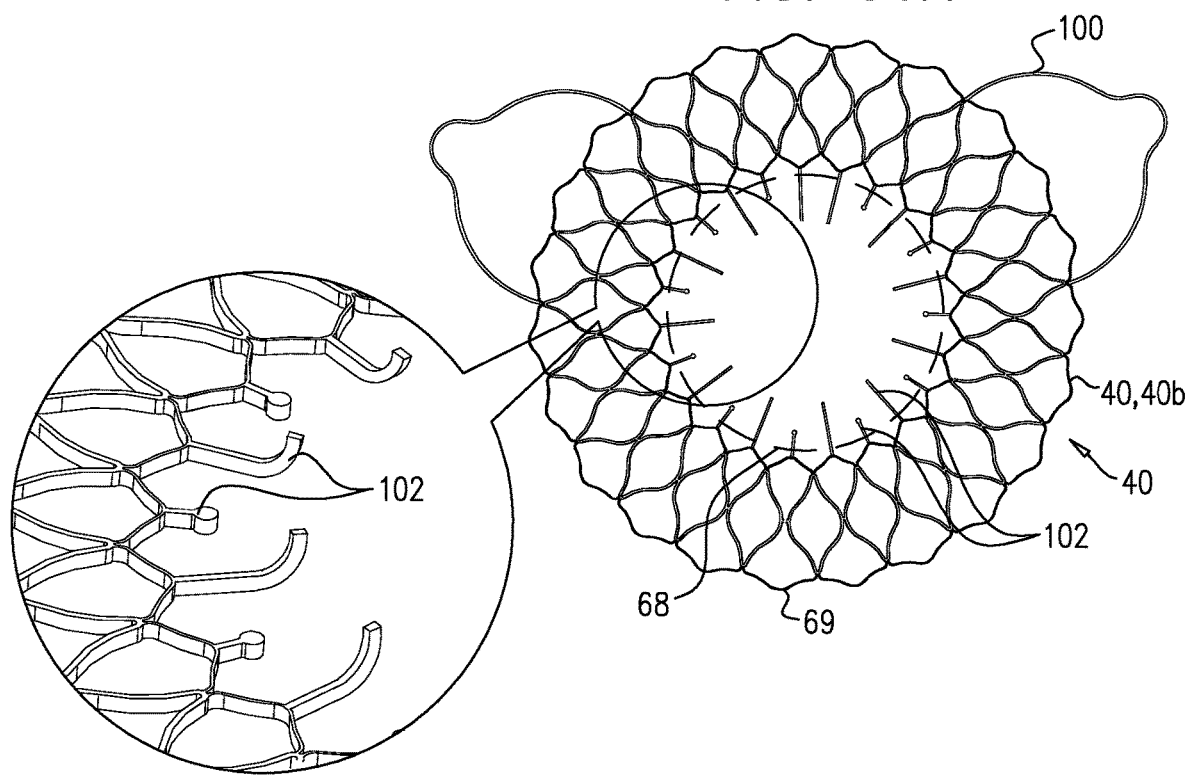
FIGS. 51A-B are schematic illustrations of the prosthetic valve support, in accordance with some applications of the invention.
Figure 51B:
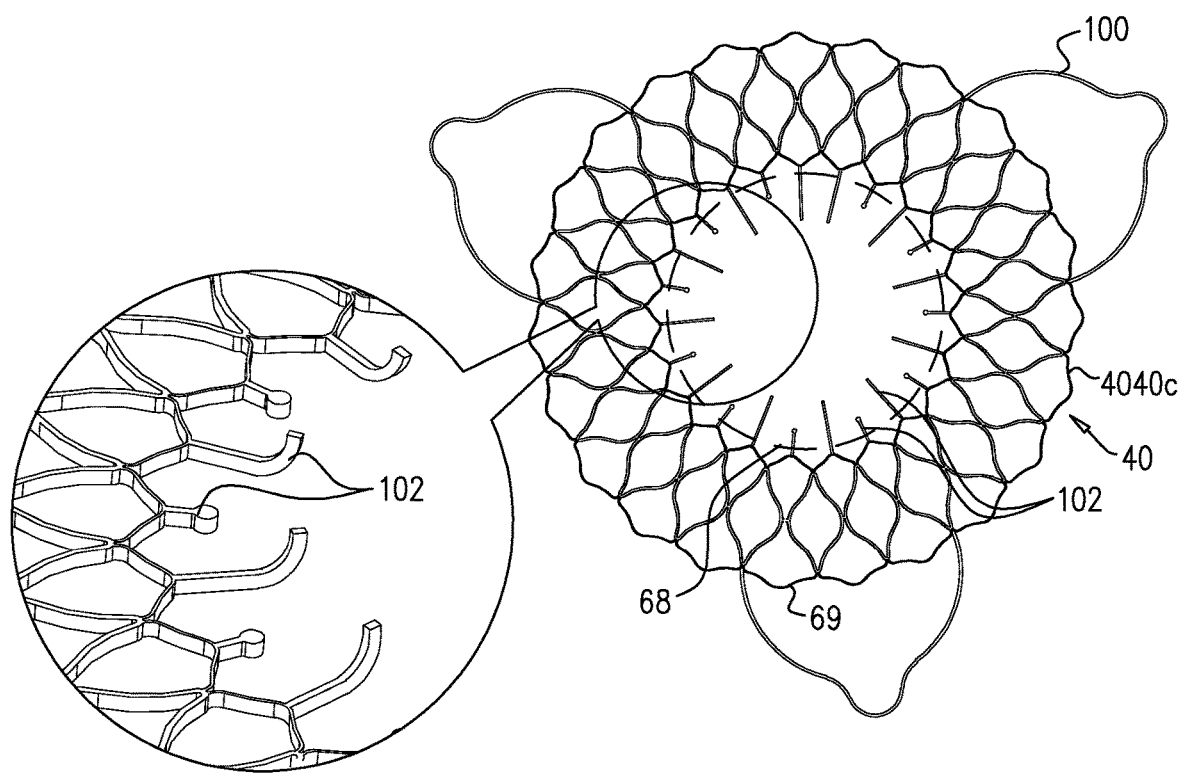

Reference is made to FIGS. 51A-B, which are schematic illustrations of prosthetic valve support 40, comprising respective prosthetic valve supports 4040*b* and 4040*c* which each comprise one or more wings 100, in accordance with respective applications of the invention. Prosthetic valve support 40 is generally annular and is shaped to define a lumen. Wings 100 are configured and positioned with respect to prosthetic valve supports 4040*b* and 4040*c* so as to provide one or more of the following advantages: (1) Increasing the stability of the support on the atrial surface of the native valve annulus during the implantation procedure and/or post-implantation. (2) Distributing forces more evenly across the annulus of the native valve. (3) Restricting movement of native valve leaflets. (4) Preventing tilting of support 40 and subsequent interference with the LVOT.

Wings 100 typically increase a ratio of surface area of the support to annular tissue. Wings 100 typically protrude between 5 mm and 40 mm (e.g., between 10 mm and 30 mm) from outer edge 69 of the support. Prosthetic valve support 4040*b* comprises two wings, as shown in FIG. 51A, typically positioned spaced apart from each other by 80-150 degrees, as shown. Prosthetic valve support 4040*c* comprises three wings, as shown in FIG. 51B, typically positioned spaced apart from each other by 80-150 degrees (e.g., by 120 degrees, as shown). Other quantities and configurations of wings 100 may be used in order to optimize the positioning and/or stability of prosthetic valve support 40.

In some applications of the invention, prosthetic valve support 40 (e.g., prosthetic valve supports 4040*a*, 4040*b*, 4040*c*) comprises barbs 102, which protrude into the lumen defined by support 40. During the expansion of prosthetic valve 42 within the lumen of support 40, as described hereinabove, barbs 102 protrude into and engage prosthetic valve 42. Barbs 102 thereby facilitate coupling between support 40 and prosthetic valve 42 in addition to the radial forces between support 40 and prosthetic valve 42. In some applications of the invention, some or all of barbs 102 may be curved, as shown in the enlarged images of FIGS. 51A-B. Typically, the curved barbs curve away from the transverse plane of prosthetic valve support 40, such that, when implanted, barbs 102 point proximally (i.e., into atrium 26). The applications of the invention described with reference to FIGS. 51A-B may be used in combination with other applications of the invention described herein (i.e., applications described herein in which prosthetic valve support 40 is used).

Reference is made to FIG. 52, which is a schematic illustration of prosthetic valve 42 which comprises a variable-dimensioned valve 4042*a*, in accordance with some applications of the present invention. As described hereinabove, expansion of prosthetic valve 42 in the lumen of prosthetic valve support 40 creates radial force between prosthetic valve support 40 and prosthetic valve 42, which facilitates coupling of prosthetic valve 42 to prosthetic valve support 40. In some applications of the present invention, a proximal portion 110 (e.g., the atrial end) of structural element 130 of prosthetic valve 4042*a* expands such that it assumes a dimension larger than the lumen defined by support 40 (i.e., such that portion 110 has a longest length measured from a first point of portion 110 to a second point of portion 110 opposite the first point of portion 110 at a transverse cross-section of portion 110, which is larger than a longest length of the lumen of support 40 measured from a first point on support 40 to a second point of support 40 opposite the first point of support 40 at the transverse cross-section). Typically, proximal portion 110 expands more than distal portions of prosthetic valve 4042*a*. For example, portion 110 expands more than at least the portion of prosthetic valve 4042*a* that is disposed within the lumen of support 40. For some applications of the present invention, portion 110 expands more than at least the distal end of valve 4042*a* (e.g., the portion of valve 42 designated for positioning within ventricle 28).

As illustrated in FIG. 52, proximal portion 110 may be trumpet-shaped. Alternatively, proximal portion 110 may be frustoconical, or may be any other configuration that has a dimension larger than the lumen defined by prosthetic valve support 40. The extra expansion of proximal portion 110 described hereinabove provides axial resistance against undesired distal (i.e., ventricular) movement of prosthetic valve 4042*a* with respect to support 40, in addition to the resistance provided by the radially expansive forces between prosthetic valve 42 (i.e., prosthetic valve 4042*a*) and prosthetic valve support 40, as described hereinabove. The extra expansion of proximal portion 110 is further hypothesized to facilitate release of proximal portion 110 from delivery apparatus (e. g., from a pushing member, from coupling tabs 4146, and/or from troughs 222, described hereinbelow with reference to FIGS. 62A-D and 63A-B) thereby facilitating deployment of prosthetic valve 4042*a*. Furthermore, the shape of prosthetic valve 4042*a* is hypothesized to facilitate its alignment with respect to prosthetic valve support 40 and/or native valve 23 (e.g., to be at least in part self-righting, at least during deployment).

In FIG. 52, prosthetic valve 4042*a* is illustrated by a solid surface for clarity of illustration. It is to be noted that, typically, prosthetic valve 42 comprises a lattice structure as described hereinabove. The application of the present invention described with reference to FIG. 52 may be used in combination with applications of the present invention described herein (i.e., applications for which prosthetic valve 42 is used).

Figure 53C:
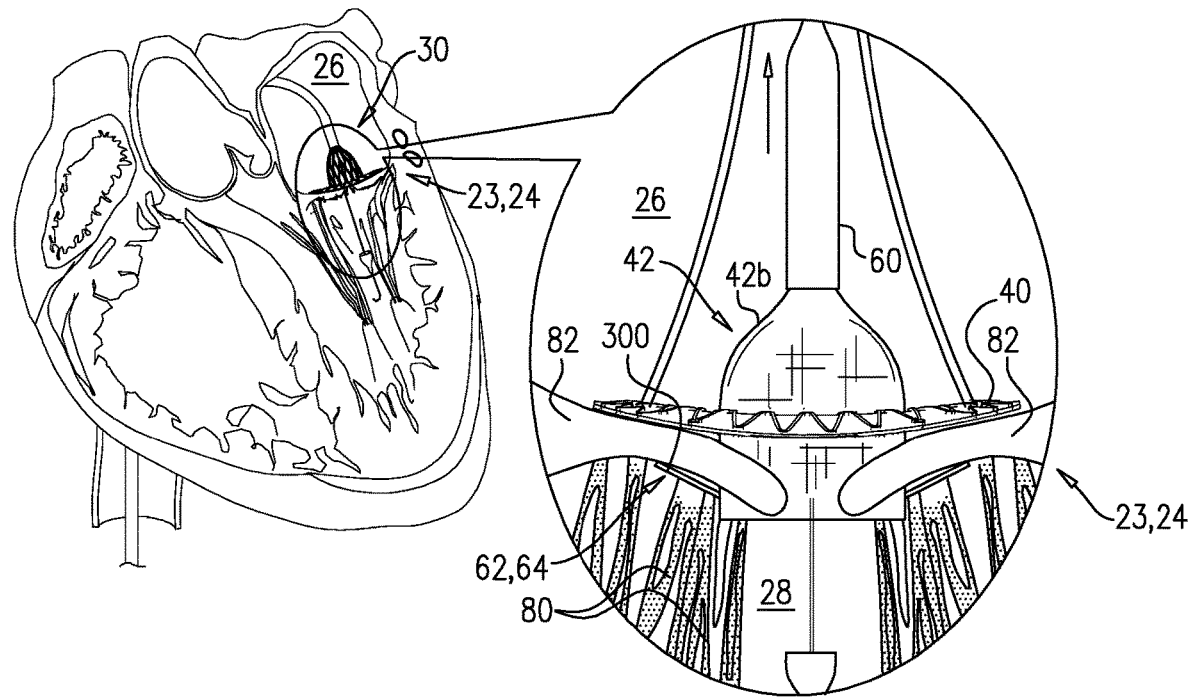

Reference is made to FIGS. 53A-C, which are schematic illustrations of prosthetic valve 42 comprising an integrally-anchoring prosthetic valve 42*b*, which comprises valve-anchoring elements 64 comprising a plurality of integral anchors 300, in accordance with some applications of the present invention.

Reference is now made to FIG. 53A, which is a schematic illustration of prosthetic valve 42*b*, in planar/flattened view in which prosthetic valve 42b is cut longitudinally and flattened, for clarity of illustration. It is to be noted, however, that the configuration shown in FIG. 53B defines the configuration of valve 42b in an assembled, crimped state. Prosthetic valve 42b comprises a lattice structure, comprising a plurality of struts which typically collectively define a tessellation of shapes 128, e.g., generally-quadrilateral shapes, as shown. In the application of the present invention illustrated in FIGS. 53A-C, the shapes 128 that form the lattice structure include crude diamonds 120 or crude kite-shapes (i.e., deltoids) 122, or a combination thereof. It is to be noted that the scope of the present invention includes prosthetic valves having a tessellation of one or a combination of other shapes.

The lattice structure of prosthetic valve 42b further defines a plurality of voids 126. Shapes 128 are typically arranged in columns 118, each shape connected to the next in each column. In some regions of the prosthetic valve, there is a separation 124 between a distal shape and an adjacent shape (e.g., between the final shape in a column and a respective penultimate shape in the column that is longitudinally proximal to the distal quadrilateral). This separation 124 allows a portion of the shape to move or be moved out of the plane of the lattice, thereby protruding from primary structural element 130 of prosthetic valve 42b when the distal portion of prosthetic valve 42b is expanded. The protruding portion of shapes 128 thereby form integral anchors 300, which are typically configured to anchor prosthetic valve 42b to native valve 23. Valve-anchoring elements 64 are thereby formed from integral parts of the lattice structure that forms prosthetic valve 42b, and are disposed between a proximal end 251 and a distal end 252 of primary structural element 130 of prosthetic valve 42b. That is, prosthetic valve 42b has a functional length (i.e., a length selected so as to facilitate prosthetic valve function), and integral anchors 300 typically do not increase the length of prosthetic valve 42b to be greater than the functional length.

Reference is made to FIGS. 53B-C, which are schematic illustrations of sequential steps of prosthetic valve 42b being implanted.

Reference is now made to FIG. 53B. Prosthetic valve 42b is compressible (e.g., crimpable) and expandable, and typically comprises a shape-memory material (e.g., nitinol). Prosthetic valve 42b is configured (e.g., shape-set) such that valve-anchoring elements 64, embodied as integral anchors 300, are biased to protrude from the surface of primary structural element 130. In this application of the present invention, primary structural element 130 of prosthetic valve 42b is generally cylindrical, and integral anchors 300 protrude radially from the surface of the cylinder. Because integral anchors 300 are formed from the regular repeating structure of the lattice that forms prosthetic valve 42b, anchors 300 fit back into the plane of structural element 130 when valve 42b is crimped into delivery tube 60, prior to and even during implantation. Integral anchors 300, thereby typically do not increase the length nor the transverse cross-sectional longest dimension of the crimped configuration of prosthetic valve 42, as compared to those of any other prosthetic valves that do not comprise valve-anchoring elements 64 or that comprise elements 64 at a distal end thereof.

As described hereinabove, prosthetic valve 42 is deployed by distal movement out of delivery tube 60. FIG. 53B shows prosthetic valve 42b in a partially-deployed state, such that integral anchors 300 have emerged from delivery tube 60, and have assumed an unconstrained, expanded, resting configuration in which the integral anchors 300 protrude from the surface of primary structural element 130 of the prosthetic valve. In an expanded state of at least the distal portion of valve 42b, as shown in FIG. 53B, integral anchors 300 typically protrude up to and including 110 degrees (e.g., between 45 and 90, such as between 45 and 60 degrees) from the surface of primary structural element 130, in a resting state of anchors 300. That is, in the protruded state, the proximal portions of anchors 300 are distanced further from structural element than the distal portions of anchors 300 which function as the pivot joints 4074 between anchors 300 and structural element 130, as shown in the enlarged image of FIG. 53B. Typically, this partial deployment of prosthetic valve 42 is performed on the distal side of native heart valve 23 (e.g., the ventricular side of mitral valve 24).

Reference is now made to FIG. 53C. Following the movement of integral anchors 300 into their unconstrained, protruding, configuration, prosthetic valve 42b is pulled proximally (i.e., toward atrium 26), along with delivery tube 60. This proximal movement causes integral anchors 300 to abut against and capture leaflets 82 of the native valve in order to anchor prosthetic valve 42b to the ventricular side of the native valve. Typically, integral anchors 300 capture leaflets 82 of the native valve by sandwiching leaflets 82 against primary structural element 130 of prosthetic valve 42b and/or against the wall of ventricle 28. Typically, but not necessarily, integral anchors 300 protrude between chordae tendineae 80 of the native valve.

Typically, the anchoring of the prosthetic valve and/or the capturing of leaflets of the native valve are performed while prosthetic valve 42b is partially deployed from delivery tube 60, as shown in FIG. 53C. Prosthetic valve 42b is then fully deployed by moving delivery tube 60 proximally with respect to valve 42b, thereby sliding the delivery tube off of the prosthetic valve and allowing the prosthetic valve to expand. Such expanding of prosthetic valve 42b facilitates coupling of the prosthetic valve to support 40, as described with reference to FIG. 1G.

Reference is made to FIGS. 54A-D, which are schematic illustrations of prosthetic valve 42 comprising an integrally-anchoring prosthetic valve 42c, which comprises valve-anchoring elements 64 comprising a plurality of integral anchors 310, in accordance with some applications of the present invention.

Integral anchors 310 are similar in form and function to integral anchors 300, and are typically formed by separations 124 in the lattice structure of structural element 130, as described with reference to FIGS. 53A-C. Integral anchors 310 are configured (e.g., shape-set) so as protrude from primary structural element 130 of prosthetic valve 42c, typically at a more acute angle than integral anchors 300 of FIGS. 53A-C protrude from prosthetic valve 42b. For example, integral anchors 310 may have an unconstrained, expanded, resting configuration in an expanded state of at least the distal portion of prosthetic valve 42c, in which anchors 310 protrude up to and including 110 degrees (e.g., up to and including 60 degrees, or between 5 and 80 degrees, or between 5 and 40 degrees) from the surface of primary structural element 130 in a resting state of anchors 310. Integral anchors 310 can be deformed by a deforming force (e.g., by pushing tube 60 distally against pivot joints 4074 between anchors 310 and structural element 130, as described hereinbelow) into a further-expanded configuration, in which anchors 310 protrude at a greater angle from the surface of primary structural element 130 than the angle of the resting configuration of anchors 310; thus, integral anchors 310 may be considered more open in this configuration than they are in their resting configuration. In this further-expanded, open configuration, integral anchors 310 typically are made to protrude up to and including 160 degrees (e.g., between 30 and 110 degrees, such as between 60 and 110 degrees) from the surface of structural element 130 of prosthetic valve 42c. Since anchors 310 have a shape memory of assuming the resting state in the absence of force applied thereto, integral anchors 310 return toward the resting state upon removal of the deforming force (e.g., once tube 60 is not pushed distally against pivot joints 4074).

Figure 54A:
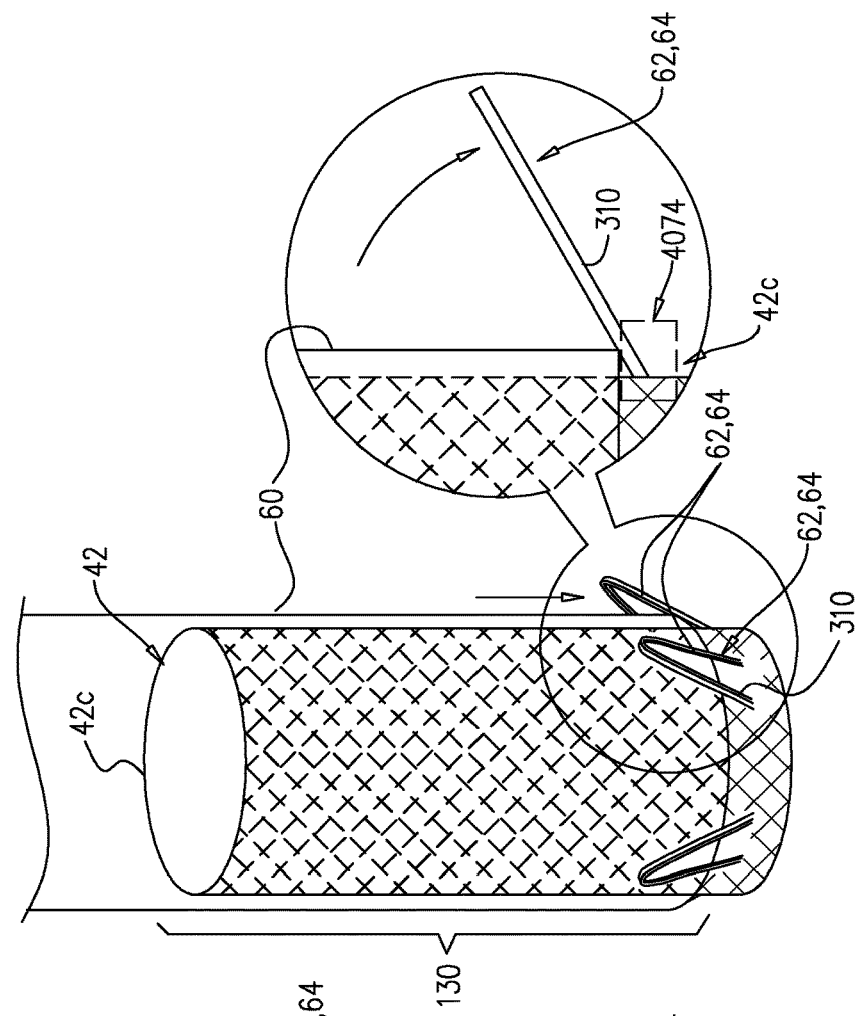
FIGS. 54A-D are schematic illustrations of the prosthetic valve, comprising tissue-engaging elements, in accordance with some applications of the invention.

As described hereinabove, prosthetic valve 42 is deployed by distal movement out of delivery tube 60. FIG. 54A shows prosthetic valve 42c in a partially-deployed state, such that integral anchors 310 have emerged from delivery tube 60, and have assumed the unconstrained, expanded resting configuration described hereinabove. Typically, this partial deployment of prosthetic valve 42 is performed on the distal side of native heart valve 23 (e.g., the ventricular side of mitral valve 24).

Figure 54B:
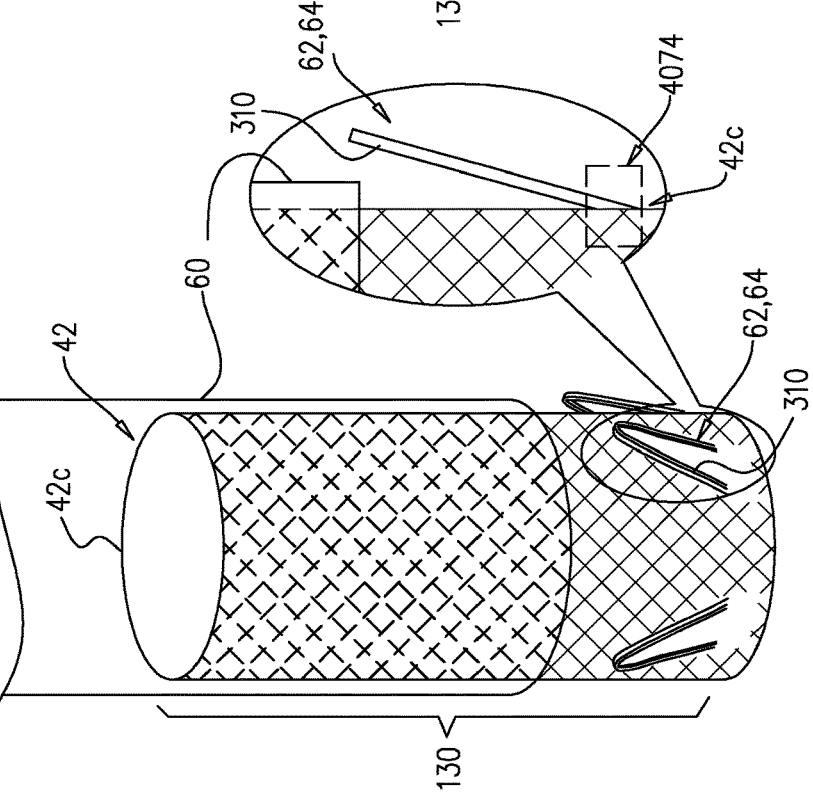

Reference is now made to FIG. 54B. Following partial deployment of prosthetic valve 42c, the prosthetic valve is moved proximally with respect to delivery tube 60 (e.g., prosthetic valve 42c is moved proximally while delivery tube 60 remains stationary, or prosthetic valve 42c remains stationary while delivery tube 60 is moved distally, or prosthetic valve 42c is moved proximally while delivery tube 60 is moved distally). The distal end of delivery tube 60 is thereby pushed between primary structural element 130 and integral anchors 310, and provides the deforming force that pushes the integral anchors toward their further-expanded open configuration, described hereinabove.

Figure 54C:
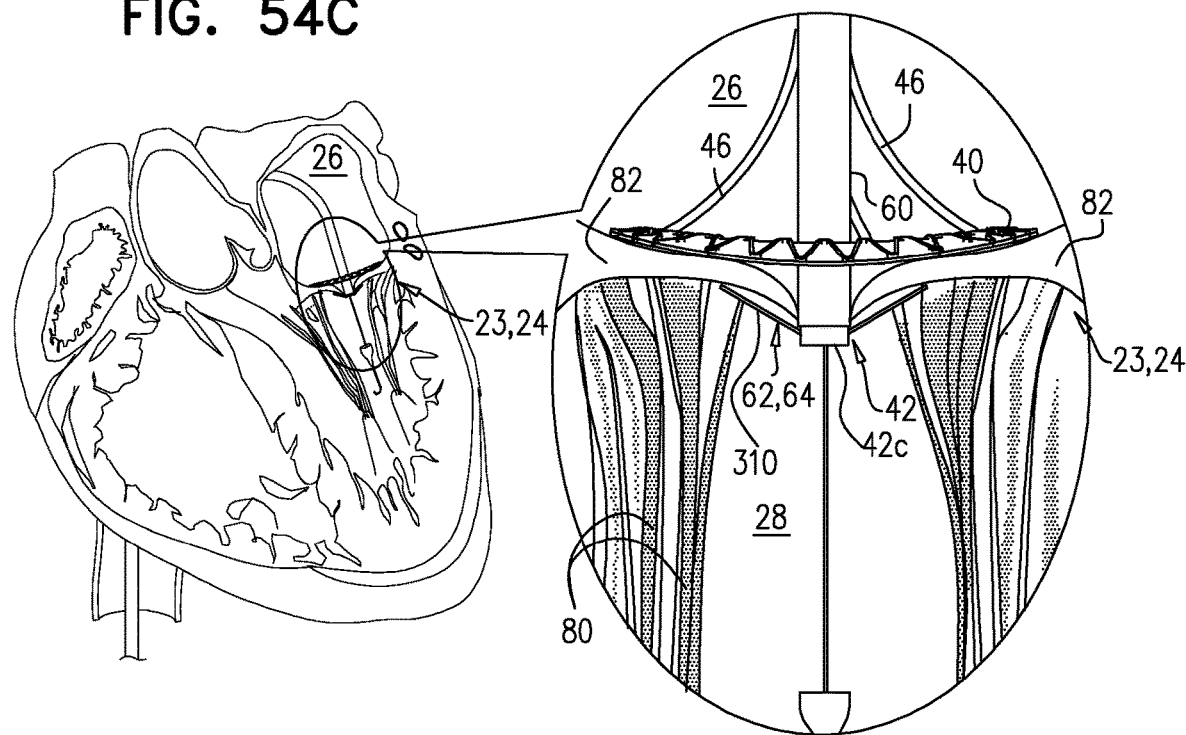

Reference is now made to FIG. 54C. Delivery tube 60 and prosthetic valve 42c are pulled proximally (i.e., toward atrium 26). This proximal movement causes the open integral anchors 310 to engage leaflets 82 of the native valve, as described hereinabove.

Figure 54D:
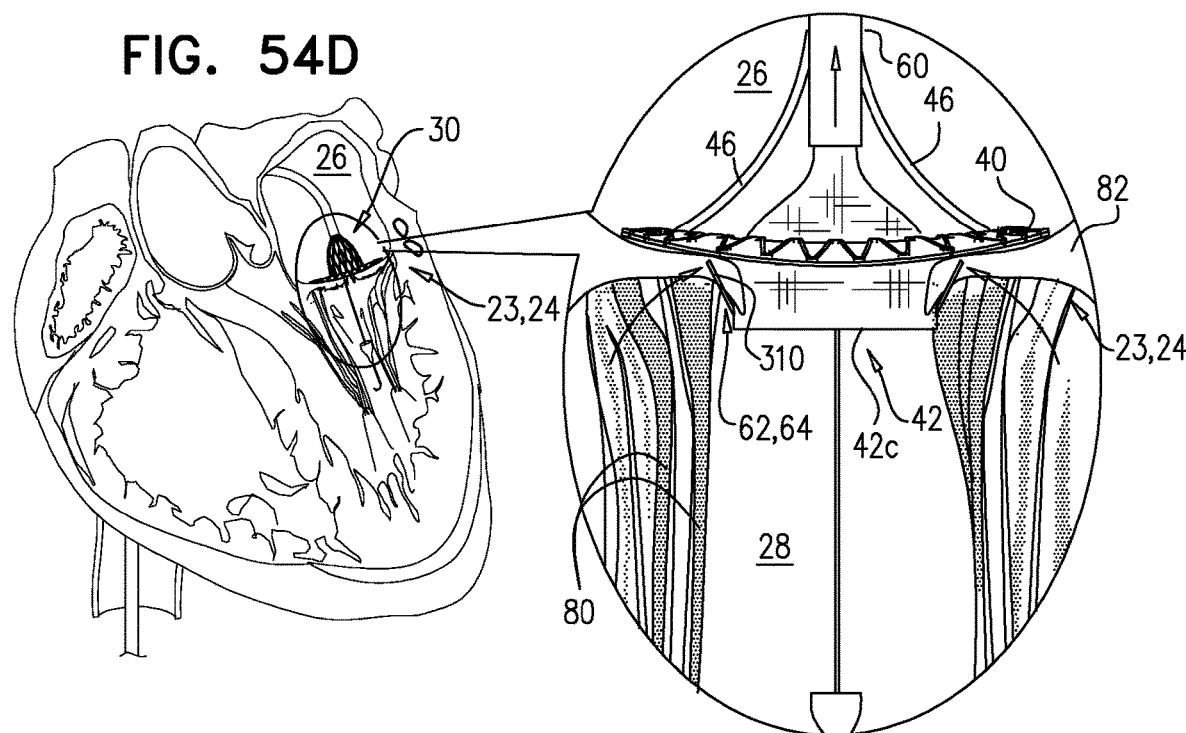

Reference is now made to FIG. 54D. Delivery tube 60 is moved proximally with respect to prosthetic valve 42c (e.g., by withdrawing delivery tube 60 proximally), thereby removing the deforming force on anchors 310. As described hereinabove, this removal of the deforming force releases integral anchors 310, which are thereby allowed to return toward their resting state, to (1) clamp the chordae tendineae 80 and/or leaflets 82 of native valve 23 against primary structural element 130 of prosthetic valve 42c, and (2) anchor the prosthetic valve to the ventricular side of the native valve. Typically, prosthetic valve 42 is then fully deployed from delivery tube 60 (e.g., by retracting tube 60 with respect to valve 42), thereby allowing radial expansion of the prosthetic valve to couple prosthetic valve 42 to prosthetic valve support 40, as described hereinabove.

Reference is now made to FIGS. 53A-C and 54A-C. For such applications of the present invention in which prosthetic valve 42 (i.e., prosthetic valves 42b and/or 42c) comprises integral anchors 300 and/or 310, prosthetic valve support 40 and prosthetic valve 42 may be implanted in a manner as described hereinabove with reference to FIGS. 1A-H. The scope of the present invention includes implantation of implant 30 in a manner whereby prosthetic valve 42 is delivered to native valve 23 and/or at least partially deployed, prior to the deployment of support 40 (e.g., as described hereinabove with reference to FIG. 50).

Reference is made to FIGS. 55A-E, which are schematic illustrations of prosthetic valve 42 comprising a twisted-anchor-based prosthetic valve 42d, which comprises valve-anchoring elements 64 comprising twisted anchors 320, in accordance with some application of the invention.

Figure 55A:
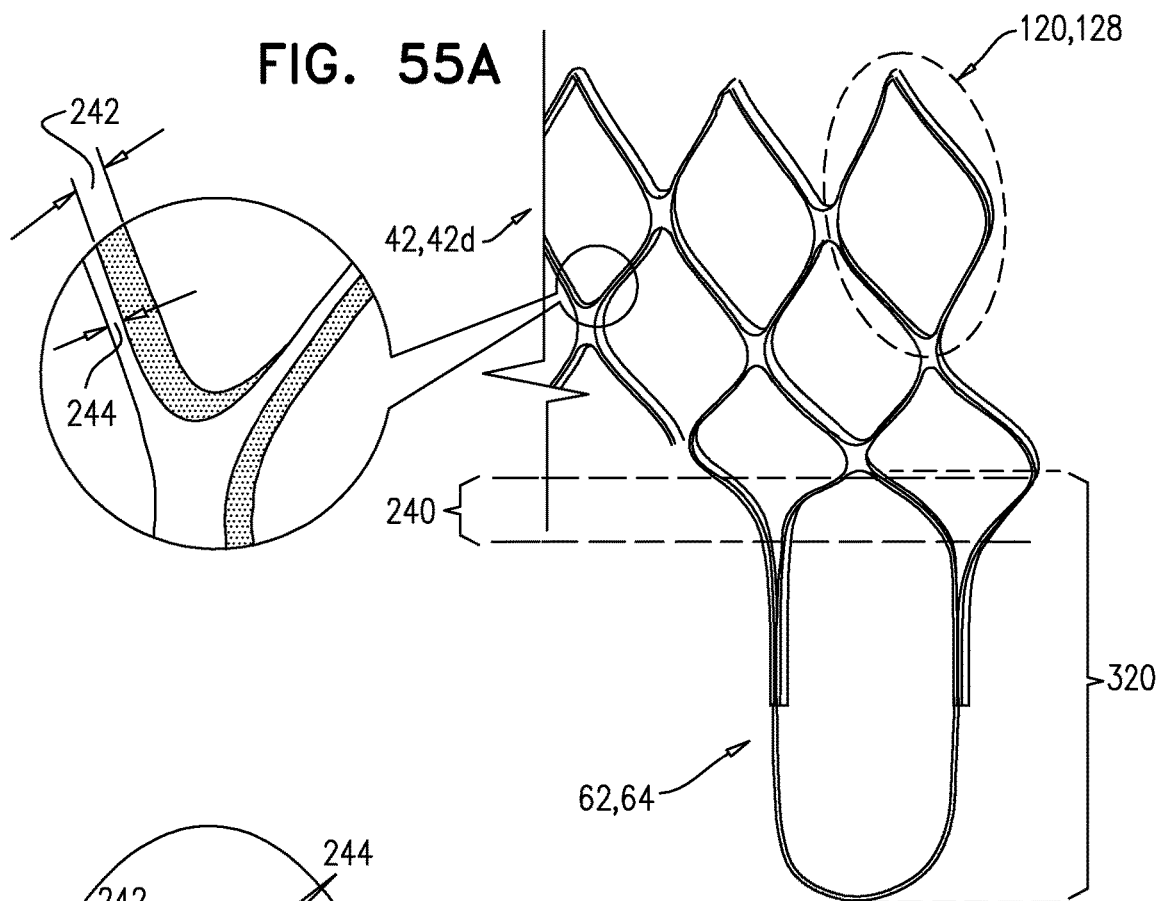
FIGS. 55A-E are schematic illustrations of the prosthetic valve, comprising tissue-engaging elements, in accordance with some applications of the invention.
Figure 55B:
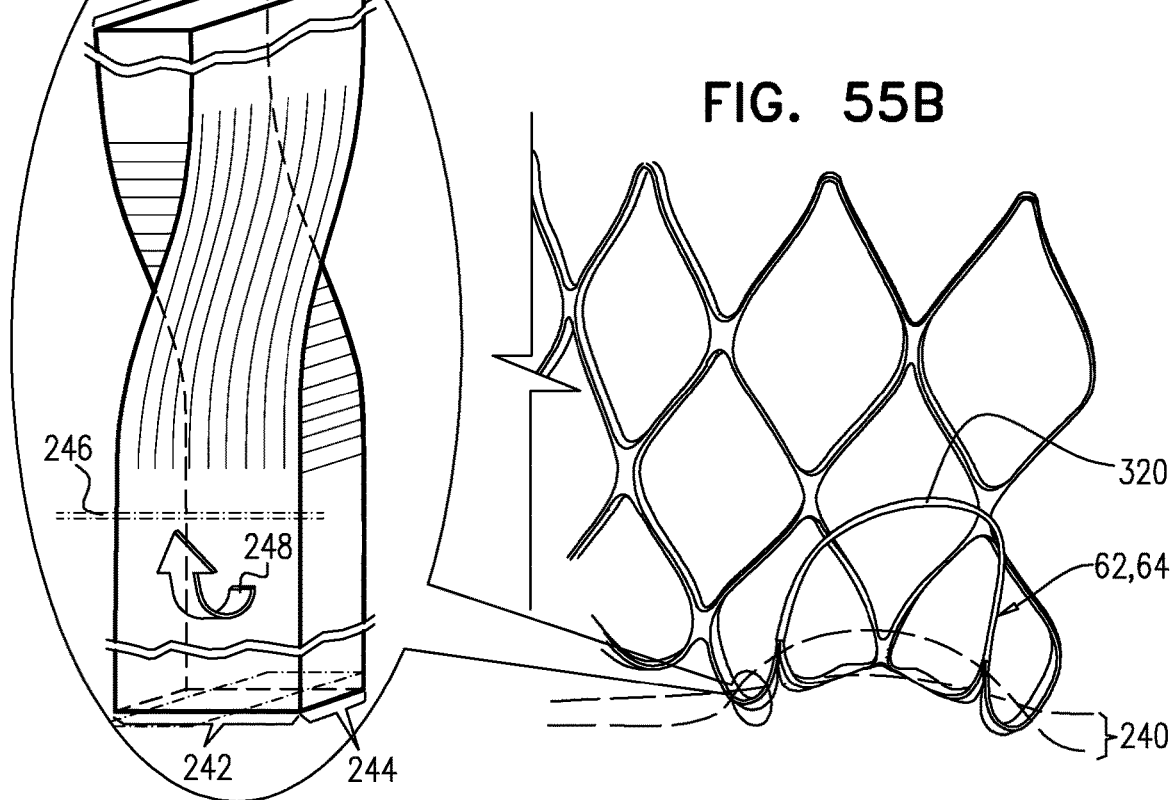

FIGS. 55A-B show valve-anchoring elements 64, comprising twisted anchors 320, in their constrained and unconstrained configurations, respectively. Prosthetic valve 42d typically comprises a shape-memory material (e.g., nitinol), shaped to define a lattice structure. The lattice structure comprises a plurality of struts which typically collectively define a tessellation of shapes 128 (e.g., crude diamonds 120). Prosthetic valve 42d comprises one or more twisted anchors 320, disposed at the distal end of prosthetic valve 42d.

As described hereinabove, valve-anchoring elements 64 typically have a constrained configuration for delivery, and an unconstrained configuration whereby they protrude radially from primary structural element 130 of prosthetic valve 42. For some applications, in the constrained configuration of elements 64, during delivery, elements 64 are typically but not necessarily disposed distal to the generally-cylindrical structure of valve 42 at an angle that is between 165 and 180 degrees with respect to the generally-cylindrical structure. In order to achieve these constrained and unconstrained configurations for prosthetic valve 42d, comprising twisted anchors 320, a distal portion of prosthetic valve 42d is typically torsionally bent to define twisted anchors 320. For some applications of the present invention, in order to achieve these configurations for prosthetic valve 42d comprising twisted anchors 320, a distal portion of prosthetic valve 42d is typically bent to define twisted anchors 320.

The material comprising the lattice structure of prosthetic valve 42 has a depth 242 and each strut of the lattice structure has a width 244 (shown in FIG. 55B). Typically, depth 242 is greater than width 244. Depth 242 is typically between 0.15 mm and 1.1 mm (e.g., between 0.3 mm and 0.6 mm) and width 244 is typically between 0.05 mm and 0.9 mm, (e.g., between 0.1 mm and 0.4 mm). In this application of the invention, the bending comprises twisting in the vicinity of a bending region 240, such that a bend axis 246 (shown in FIG. 55B) is substantially parallel to depth 242 in a vicinity of a distal portion of bending region 240. That is, a bend radius 248 lies on a plane that is substantially parallel to the relatively smaller width 244, thereby allowing a smaller thickness of material to be bent, compared to if bend radius 248 were parallel with the relatively greater depth 242.

It is hypothesized that this configuration allows a greater bend angle to be imparted, such that twisted anchors 320 can (1) be disposed distal to (e.g., planar with) primary structural element 130 of prosthetic valve 42d when the twisted anchors are in their constrained configuration (i.e., when compressed in delivery tube 60 for delivery) as shown in FIG. 55A, and (2) pivot greater than 90 degrees (e.g., greater than 110 degrees, greater than 120 degrees, or greater than 150 degrees), to protrude radially from primary structural element 130 when in their unconstrained configuration (i.e., following deployment of at least the distal portion of prosthetic valve 42d).

It is to be noted, that during delivery of prosthetic valve 42d toward mitral valve 24, valve 42d is crimped within delivery tube 60 such that anchors 320 assume a constrained and compressed state within tube 60.

Figure 55C:
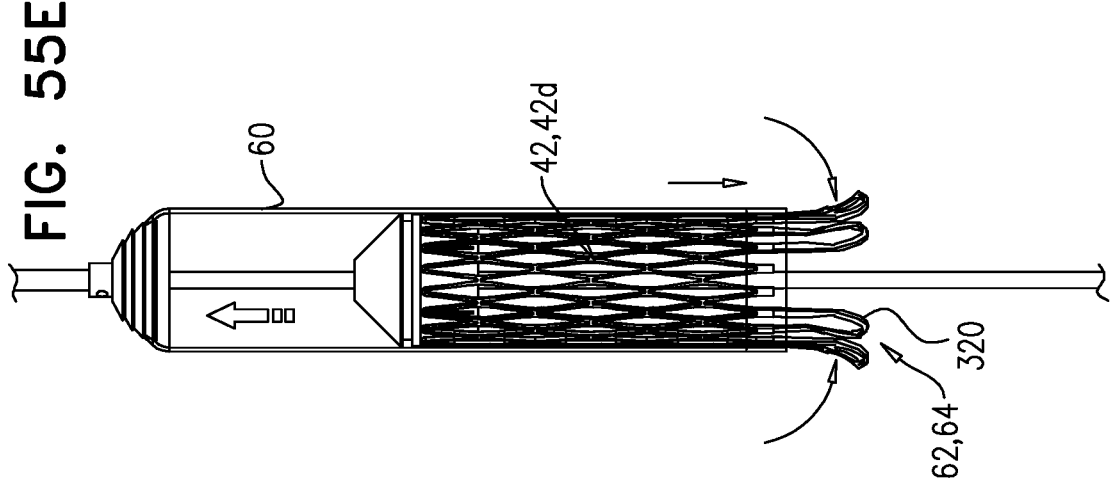
Figure 55D:
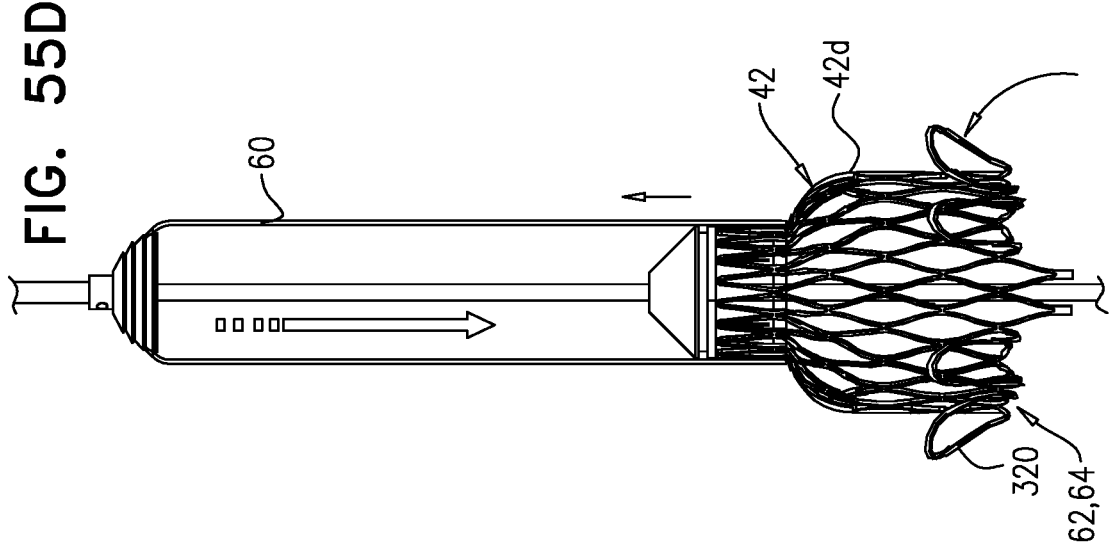
Figure 55E:
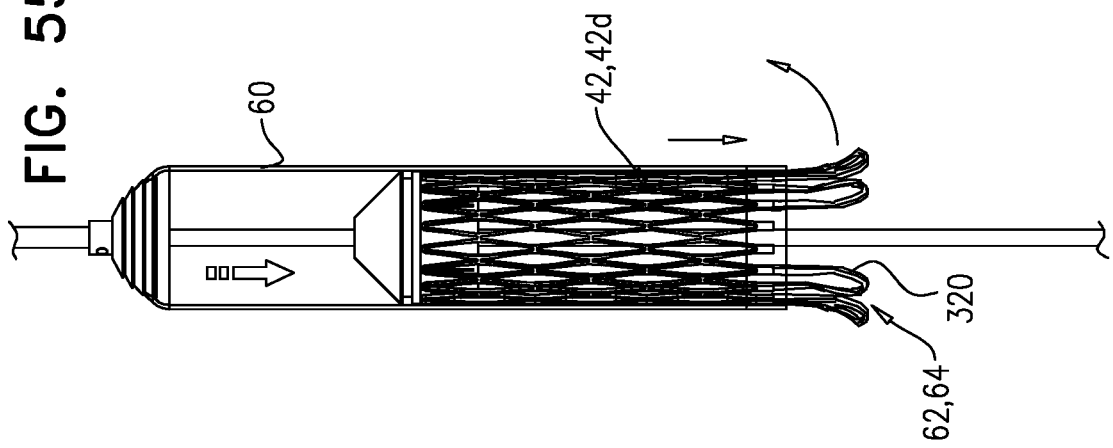

Reference is now made to FIGS. 55C-E, which are schematic illustrations of sequential steps in the deployment and retrieval of prosthetic valve 42d that comprises twisted anchors 320. FIG. 55C shows delivery tube 60 being moved proximally with respect to prosthetic valve 42d (e.g., prosthetic valve 42d is moved distally while delivery tube 60 remains stationary, or prosthetic valve 42d remains stationary while delivery tube 60 is moved proximally, or prosthetic valve 42*d* is moved distally while delivery tube 60 is moved proximally). Twisted anchors 320 (disposed at a distal portion of valve 42), emerge first from within tube 60 and begin to move from their constrained and compressed configuration toward their unconstrained and expanded configuration once exposed from within tube 60.

Reference is now made to FIG. 55D. Delivery tube 60 is moved further proximally, such that prosthetic valve 42*d* is partially deployed toward its expanded configuration. Because delivery tube 60 clears anchors 320, twisted anchors 320 typically assume their resting unconstrained configuration. The physician may proceed to couple prosthetic valve 42*d* to the native valve and/or to prosthetic valve support 40, as described with reference to FIGS. 1F-G.

Reference is now made to FIG. 55E. Valve-anchoring elements 64 comprising twisted anchors 320, facilitate retrieval of prosthetic valve 42*d* into delivery tube 60. Should it be necessary and/or desirable, while a proximal portion of valve 42*d* is still crimped within tube 60, delivery tube 60 may be moved distally with respect to prosthetic valve 42*d* (e.g., prosthetic valve 42*d* is moved proximally while delivery tube 60 remains stationary, prosthetic valve 42*d* remains stationary while delivery tube 60 is moved distally, or prosthetic valve 42*d* is moved proximally while delivery tube 60 is moved distally), thereby recompressing prosthetic valve 42*d* into the delivery tube. Twisted anchors 320 are pushed distally by delivery tube 60, such that they may also by straightened, as shown, and subsequently enter the delivery tube. Prosthetic valve 42*d* may then be repositioned and redeployed, or may be removed from the subject.

In some applications of the invention, twisted anchors 320 comprise more than one bending region 240. For such applications, the material comprising prosthetic valve 42*d* is bent and twisted in each respective bending region, as described with reference to FIGS. 55A-B. For example, one bending region may be longitudinally proximal (i.e., coaxial) with respect to another bending region. Twisted anchors 320 that comprise more than one bending region are hypothesized to have enhanced pivoting ability compared to valve-anchoring elements that comprise one bending region. That is, twisted anchors 320 having more than one bending region enable anchors 320 to move more than 90 degrees, e.g., more than 160 degrees, with respect to a surface of structural element 130. For example, twisted anchors 320 may pivot such that they clamp leaflets 82 of the native valve against primary structural element 130 of prosthetic valve 42, thereby anchoring the prosthetic valve to the native valve.

Reference is made to FIGS. 56A-D, which are schematic illustrations of prosthetic valve 42 comprising a clip-on prosthetic valve 42*e*, which comprises valve-anchoring elements 64 that comprise loop-shaped valve-anchoring elements 200 arranged in pairs 132 to form clips 65*a*, in accordance with some applications of the invention.

Figure 56A:
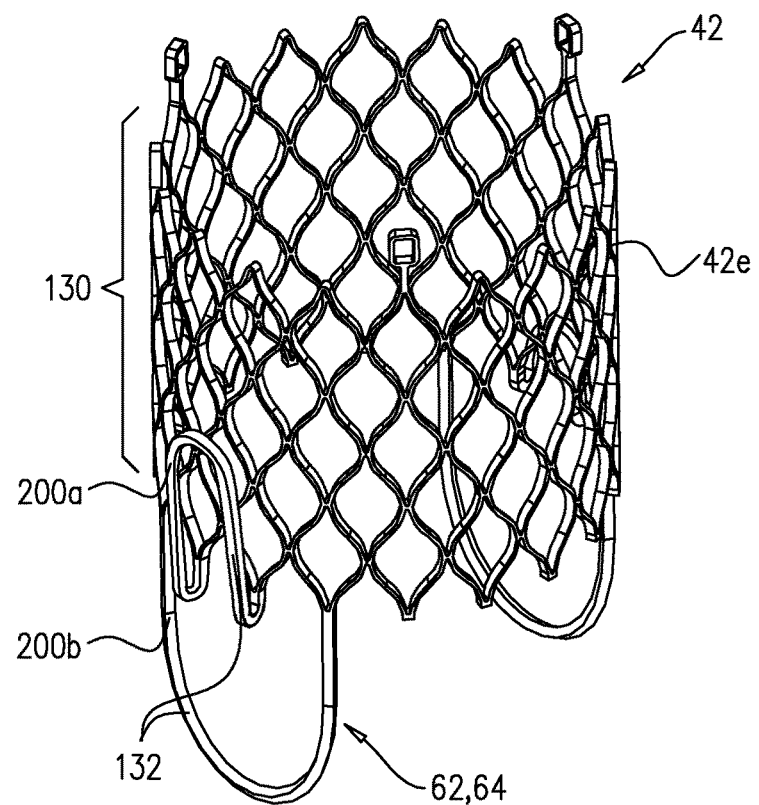
FIGS. 56A-D are schematic illustrations of the prosthetic valve, comprising tissue-engaging elements, in accordance with some applications of the invention.

Reference is now made to FIG. 56A. As described hereinabove, prosthetic valve 42 is compressible (e.g., crimpable) and expandable, and typically comprises a shape-memory material (e.g., nitinol). In this application of the invention, prosthetic valve 42*e* comprises loop-shaped valve-anchoring elements 200, arranged in pairs 132. Typically, a first loop-shaped valve-anchoring element 200*a* in each pair is smaller than a second loop-shaped valve-anchoring element 200*b*, such that first loop-shaped element 200*a* is disposable within and/or passable through a space defined by the larger loop shape of second loop-shaped valve-anchoring element 200*b*. It is to be noted that the scope of the present invention includes other configurations and arrangements of elements 200.

It is to be noted that the scope of the present invention includes a first loop-shaped valve-anchoring element 200*a* being larger than second loop-shaped valve-anchoring element 200*b*, such that second loop-shaped element 200*b* is disposable within and/or passable through a space defined by the larger loop shape of first loop-shaped valve-anchoring element 200*a*.

Figure 56B:
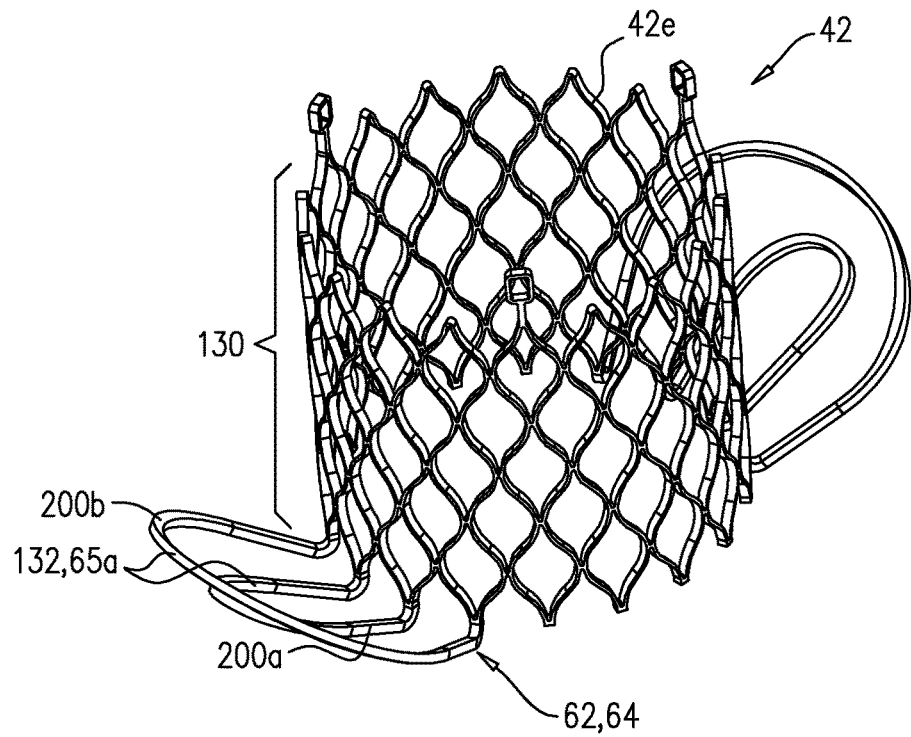

As described hereinabove, valve-anchoring elements 64 have a constrained and compressed configuration for delivery of prosthetic valve 42*e* (as shown in FIG. 56A), and an unconstrained, expanded configuration when prosthetic valve 42*e* is deployed (as shown in FIG. 56B).

Loop-shaped valve-anchoring elements 200 are shown in FIG. 56A in their constrained configuration in which second loop-shaped valve-anchoring element 200*b* of each pair 132 is typically disposed distal to primary structural element 130, and first loop-shaped valve-anchoring element 200*a* of each pair 132 is typically disposed against the surface of primary structural element 130. That is, in their constrained configuration, loop-shaped valve-anchoring elements 200 are typically longitudinally aligned.

FIG. 56B shows loop-shaped valve-anchoring elements 200 in their unconstrained, expanded configuration. Movement from the constrained configuration to the unconstrained configuration of elements 200 typically comprises (1) pivoting proximally of second valve-anchoring element 200*b* of each pair 132, and (2) pivoting distally of first valve-anchoring element 200*a* of each pair 132. In some applications of the invention, in the unconstrained configuration, the planes defined by the two valve-anchoring elements 200 of each pair 132 are generally aligned (e.g., within 20 degrees of each other).

In some applications of the invention, in the unconstrained configuration, a rounded end of second valve-anchoring element 200*b* of each pair 132 is disposed more proximally than a rounded end of first valve-anchoring element 200*a*. In such applications, movement of valve-anchoring elements 200 from the constrained configuration to the unconstrained configuration comprises movement of the rounded ends of the second valve-anchoring elements 200*b* of each pair 132 proximally past the respective rounded ends of the first valve anchoring elements 200*a* of each pair 132.

In either application, movement of valve-anchoring elements 200 from the constrained configuration to the unconstrained configuration allows elements 200*a* and 200*b* to capture material (e.g., leaflets 82 of the native valve) between them, i.e., in a manner in which elements 200*a* and 200*b* function together as a clip 65*a*.

Figure 56C:
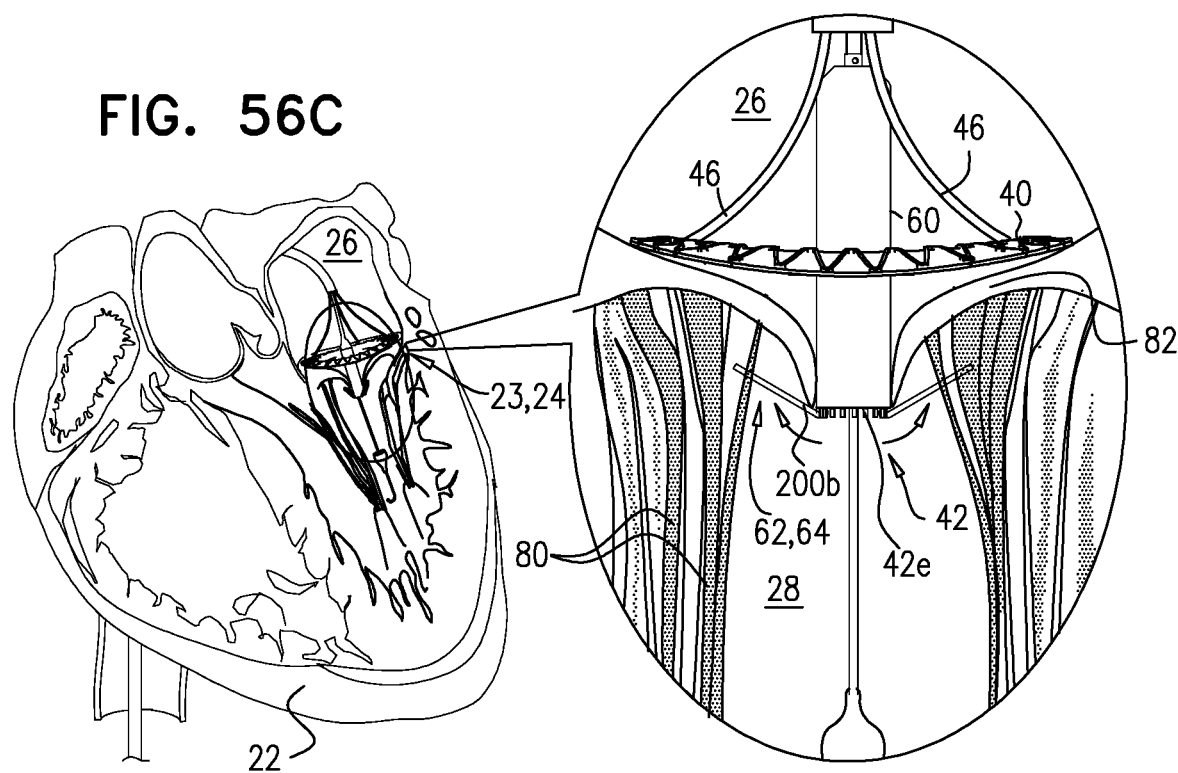
Figure 56D:
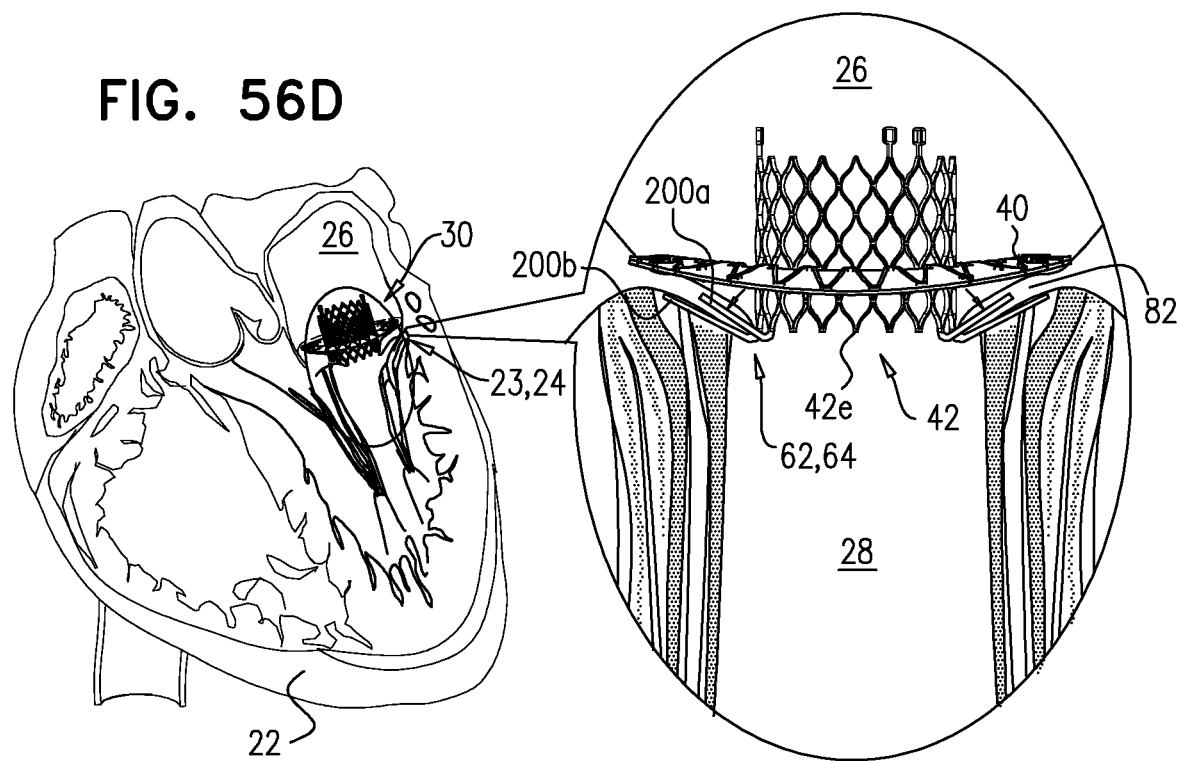

FIGS. 56C-D show sequential steps in the implantation of prosthetic valve 42*e*. FIG. 56C shows prosthetic valve 42*e* disposed in a crimped configuration in delivery tube 60. Delivery tube 60 is moved proximally with respect to prosthetic valve 42*e*, such that only loop-shaped valve-anchoring elements 200*b* (i.e., the first-deployed anchoring elements) of each pair 132 are released and move toward their unconstrained configuration, typically by pivoting in a proximal direction and in a direction toward the ventricular surface of respective leaflets 82.

Typically, following the deployment of elements 200*b* at the respective ventricular surfaces of leaflets 82, elements 200*a* are positioned within tube 60 in a manner in which during their expansion from within tube 60, elements 200*a* move toward respective atrial surfaces of leaflets 82. For some applications, following the deploying of elements

200b, valve 42e is pulled proximally (e.g., by pulling proximally on both valve 42e and tube 60) in order to adjust the positioning of valve 42e with respect to leaflets 82 and so as to ensure that, once deployed from within tube 60, elements 200a will press against respective atrial surfaces of leaflets 82.

FIG. 56D shows delivery tube 60 having been removed (i.e., by being retracted) from the body of the subject. During the retracting of tube 60 loop-shaped valve-anchoring elements 200a (i.e., the second-deployed anchoring elements) of each pair are deployed such that elements 200a move toward their unconstrained configuration, typically by pivoting in a distal direction and in a direction toward the atrial surfaces of respective leaflets 82. Leaflets 82 of the native valve are thereby clamped between the two loop-shaped valve-anchoring elements 200a and 200b of each pair 132, thereby anchoring prosthetic valve 42e to native valve 23. Thus, pairs 132 of loop-shaped valve-anchoring elements 200 function as clips 65a.

Reference is made to FIGS. 57A-D, which are schematic illustrations of prosthetic valve 42 comprising a clip-on prosthetic valve 42f, which comprises valve-anchoring elements 64 that comprise clips 65b, in accordance with some applications of the invention.

Figure 57A:
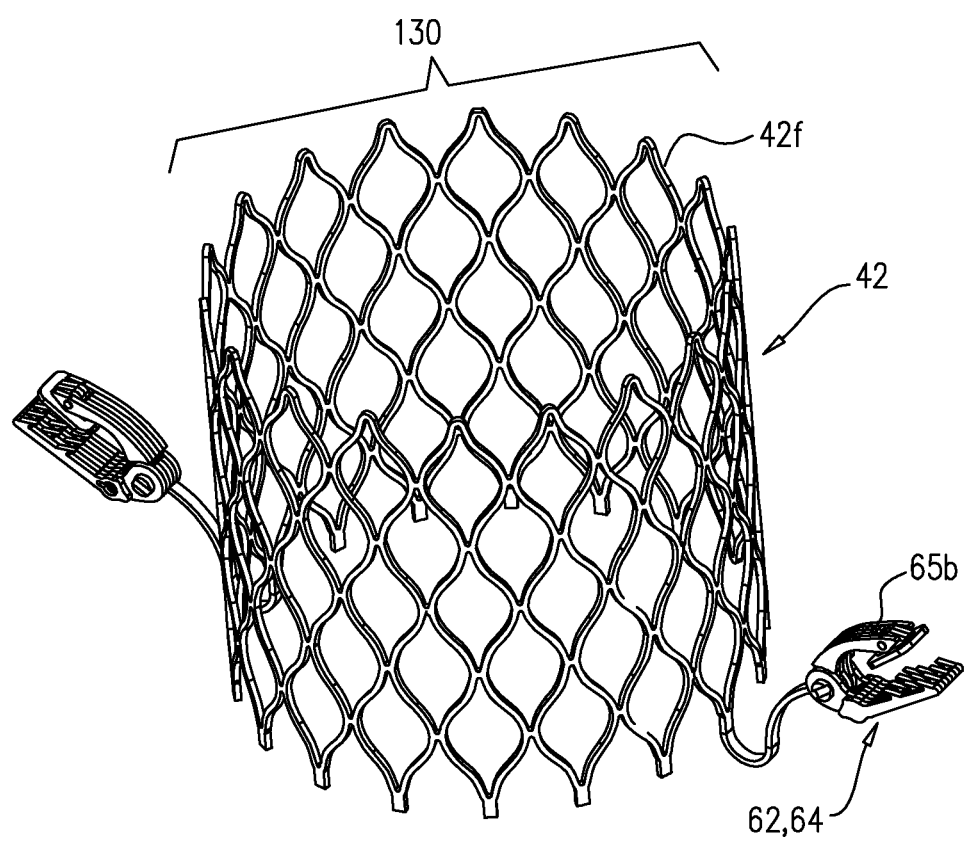

FIG. 57A shows clips 65b being typically coupled to the distal end of primary structural element 130 of prosthetic valve 42f. Typically, clips 65b are flexibly coupled to prosthetic valve 42f, i.e., valve-coupling elements 64 are configured such that clips 65b are able to move with respect to prosthetic valve 42f. During the implantation of prosthetic valve 42f, clips 65b are clipped to leaflets 82 and/or chordae tendineae 80 of the native valve, thereby anchoring the prosthetic valve to the native valve. FIG. 57A shows two valve-anchoring elements 64 comprising respective clips 65b, disposed on opposite sides of the distal end of prosthetic valve 42f. It is to be noted that the scope of the present invention includes prosthetic valves 42f having any suitable quantity and arrangement of clips 65b, depending on the technique used and the individual anatomy of the subject.

Typically, during advancement of valve 42f, valve 42f is crimped within delivery tube 60.

FIG. 57B shows prosthetic valve 42f being partially deployed from delivery tube 60, such that clips 65b are disposed outside of the delivery tube. Clips 65b are coupled to leaflets 82 of the native valve, holding the leaflets and drawing them close to the primary structural element 130 of prosthetic valve 42f. For some applications, clips 65b have a tendency to close, and are held open during delivery of valve 42f by a force applied to clips 65b (e.g., by a pull wire). In the absence of the force applied to clips 65b, clips 65b close around respective leaflets 82. For other applications, the opening and closing of clips 65b are remotely controlled by the operating physician. Typically, clips 65b may be opened and closed repeatedly until a firm grasping of leaflets 82 is achieved. Clips 65b are typically configured such that they do not cause substantial damage to leaflets 82.

FIG. 57C is a top-view schematic illustration of prosthetic valve 42f in the partially-deployed state, as described hereinabove with reference to FIG. 57B. While prosthetic valve 42f is in a compressed configuration within delivery tube 60, it has a cross-sectional diameter smaller than that of the lumen defined by prosthetic valve support 40. Typically, clips 65b couple parts of leaflets 82 (e.g., central parts, or part of leaflets 82 adjacent one another) to prosthetic valve 42f, the remaining portions of leaflets 82 remain relatively free. This arrangement typically results in a double-orifice configuration of native valve 23, whereby native valve 23 (comprising a pair of leaflets 82) can be considered to be divided into two orifices 86, on opposite sides of prosthetic valve 42f, each orifice 86 being surrounded by respective pairs of remaining portions of leaflets 82. It is hypothesized that, in this arrangement, the native valve can continue to function until prosthetic valve 42f is fully deployed. It is further hypothesized that this double-orifice state provides even greater advantage in applications of the invention where the prosthetic valve is delivered before prosthetic valve support 40 (such as the application of the invention described with reference to FIG. 50). In such applications in which the prosthetic valve is delivered before support 40, the interval between delivery and full deployment of the prosthetic valve is typically longer than in applications where prosthetic valve support 40 is delivered and deployed before delivery of the prosthetic valve. Thus, for these applications, the double orifice created by the prosthetic valve facilitates blood flow from the atrium to the ventricle during the implantation procedure.

Figure 57D:
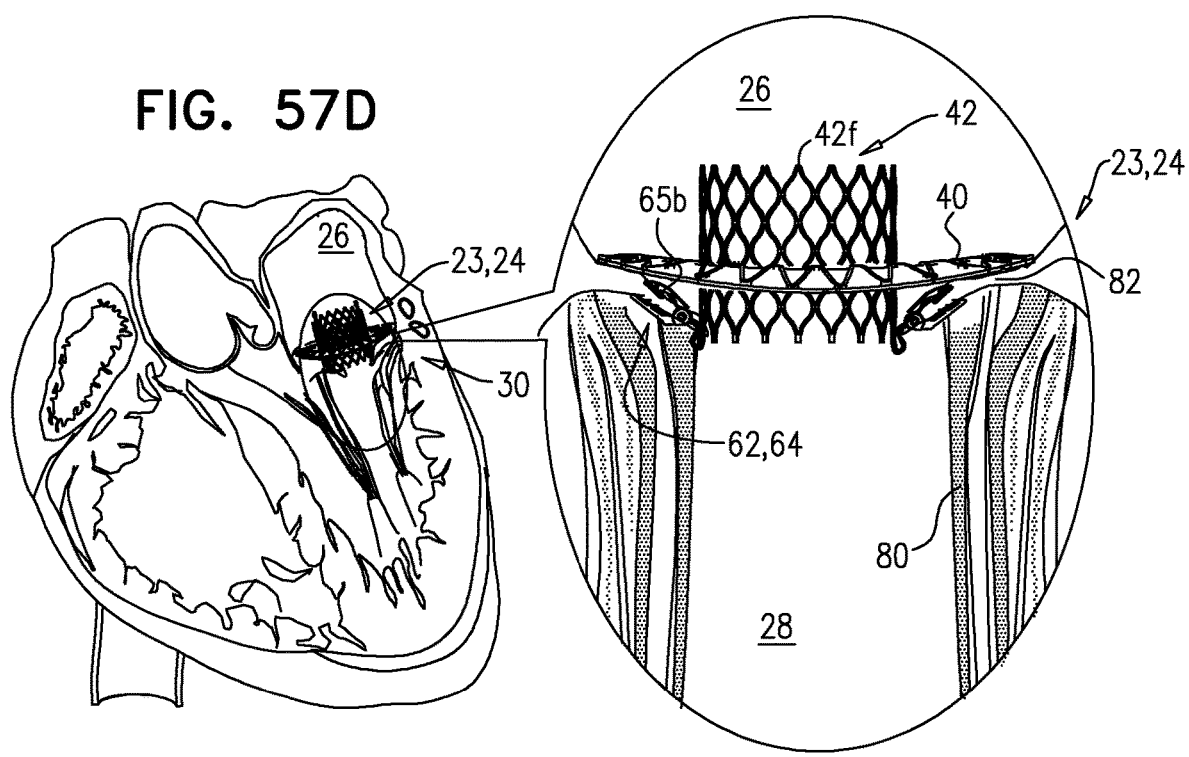

FIG. 57D is a side-view schematic illustration of prosthetic valve 42f, fully deployed in the annulus of the native valve. Valve-anchoring elements 64, comprising clips 65b, couple leaflets 82 of the native valve to the primary structural element 130 of prosthetic valve 42, thereby anchoring the prosthetic valve to the native valve.

It is to be noted that the technique described with reference to FIGS. 57A-D, in particular the 'double-orifice' configuration described with reference to FIG. 57C, may be used in combination with other prosthetic valves comprising tissue-engagement elements 62. In particular, the technique may be used where valve-anchoring elements 64 comprise clips 65 or clip functionality, such as integral anchors 310, described with reference to FIGS. 54A-D, and/or twisted anchors 320, described with reference to FIGS. 55A-E, and/or pairs 132 loop-shaped valve-anchoring elements 200, described with reference to FIGS. 56A-D.

Reference is now made to FIGS. 52, 53A-C, 54A-C, 55A-E, 56A-D, and 57A-D. It is to be noted that the scope of the present invention includes implanting the respective prosthetic valves 42 disclosed herein at native valve 23 prior to implanting support 40. In such applications of the present invention, anchoring elements 64 enable prosthetic valves 42 described herein to remain coupled to native valve 23 until support 40 is positioned at the annulus of native valve 23. In such applications, leaflets 82 are brought closer together, temporarily in a manner which forms a double orifice in native valve 23 for blood to pass from the atrium to the ventricle during the implantation procedure (as described hereinabove with reference to FIG. 57C). Following the coupling of prosthetic valve 42 to leaflets 82, support 40 is then positioned around the proximal portion of prosthetic valve 42 in order to facilitate coupling of support 40 to valve 42 and provide the radial force against valve 42 in order to maintain implanting of prosthetic valve 42 at native valve 23, as described hereinabove. In such applications, support 40 is positioned around the proximal portion of prosthetic valve 42 when the proximal portion of prosthetic valve 42 is crimped and compressed within tube 60 (for ease of positioning support 40 around the proximal portion of valve 42).

Reference is made to FIGS. 58A-61C, which are schematic illustrations of prosthetic valve support 40, embodied as anchoring prosthetic valve supports 4040d, 4040e, and 4040f, comprising tissue-engaging elements 62, in accordance with respective applications of the invention. In these applications of the invention, tissue-engaging elements 62 comprise support-anchoring elements 66, which anchor prosthetic valve support 40 to native valve 23. As described hereinabove, prosthetic valve support 40 is typically used in combination with prosthetic valve 42. The anchoring of prosthetic valve support 40 to the native valve provides one or more of the following advantages: (1) The delivery apparatus used to deploy the prosthetic valve support (e.g., holding members 46, described with reference to FIGS. 1C-F) may be removed following implantation of support 40 and prior to delivering and/or deploying prosthetic valve 42, thereby providing more space in atrium 26 for the delivery and/or deployment of the prosthetic valve; (2) Implant 30, comprising prosthetic valve 42 and prosthetic valve support 40, is anchored more securely to the native valve; and (3) Support-anchoring elements 66 contribute toward the capture of leaflets 82 of the native valve.

For some applications of the invention, it is hypothesized that the anchoring of support 40 to the native valve by support-anchoring elements 66 may be sufficient to anchor implant 30 to the native valve, thereby minimizing or even eliminating the need for supplemental anchoring of implant 30 by valve-securing elements 64. Therefore, for such applications of the invention, prosthetic valve 42 does not comprise valve-anchoring elements 64. In some such applications of the invention, leaflets 82 of the native valve are allowed to function, at least in part, following implantation of the prosthetic valve.

Reference is now made to FIGS. 58A-D, which are schematic illustrations of prosthetic valve support 40 comprising anchoring prosthetic valve support 4040d, which comprises support-anchoring elements 66 comprising fixed anchors 330, in accordance with some applications of the invention.

Figure 58A:
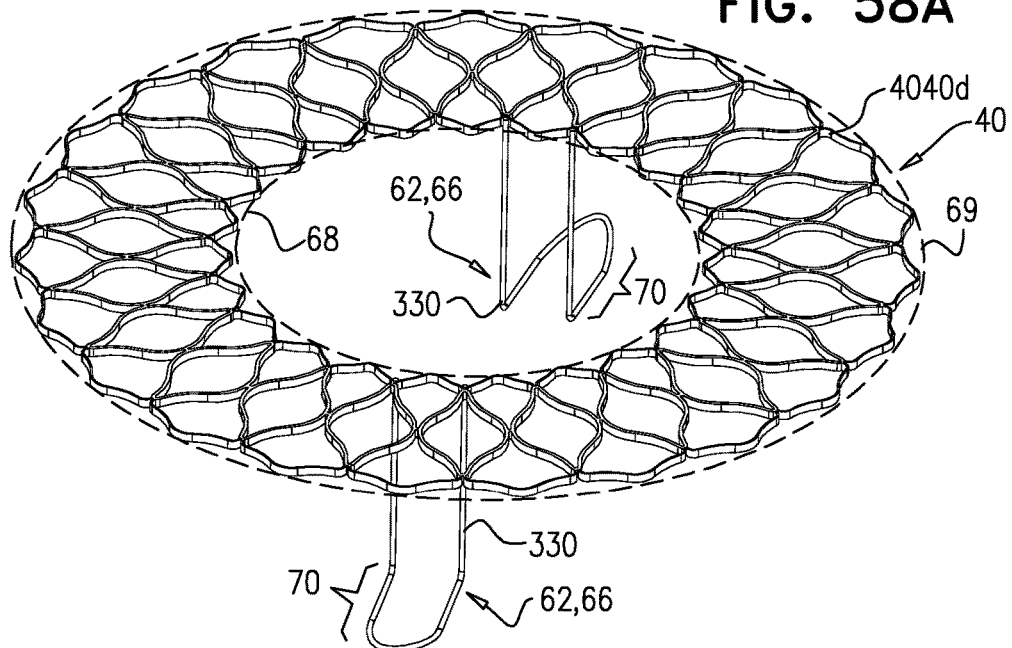
FIGS. 58A-D are schematic illustrations of the prosthetic valve support, comprising tissue-engaging elements, in accordance with some applications of the invention.

During delivery of support 4040d to the native valve, support 4040d is crimped within overtube 44, as described hereinabove with reference to support 40 of FIGS. 1B-C. FIG. 58A shows prosthetic valve support 4040d in its expanded configuration, as described hereinabove with reference to support 40 in FIG. 1B. Typically, prosthetic valve support 4040d is annular and is shaped to define an outer edge 69 and an inner edge 68. Outer edge 69 typically defines the diameter of the annular prosthetic valve support, and inner edge 68 typically defines the diameter of the lumen in which prosthetic valve 42 is typically disposed, as described hereinabove. Support-anchoring elements 66 comprising fixed anchors 330, are typically coupled to inner edge 68.

In some applications of the invention, fixed anchors 330 comprise coupling-portion 70 configured to engage tissue of the native valve. Coupling-portion 70 is illustrated as an extension of fixed anchors 330 such that fixed anchors 330 assume a generally L-shape. In other applications of the invention, coupling-portion 70 may be disposed differently (e.g., at an angle other than the angle as shown), or may comprise clips 65a or 65b, or another means for engaging native valve 23. In some applications of the invention, fixed anchors 330 do not comprise a coupling-portion.

Figure 58B:
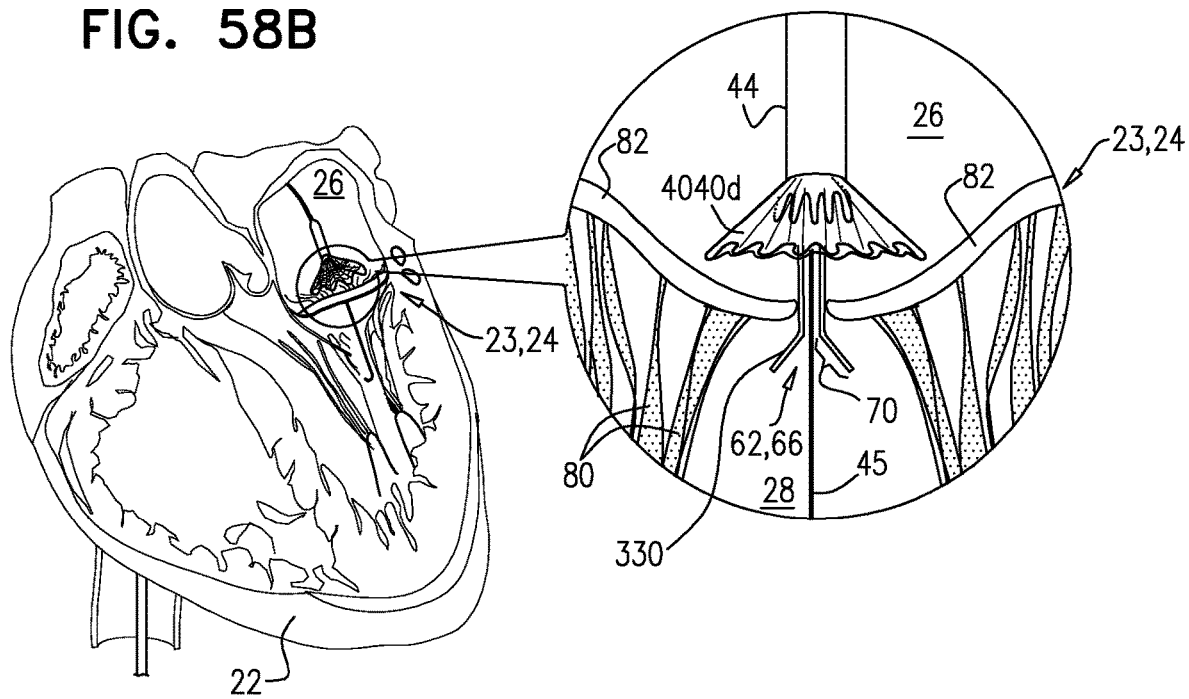

FIG. 58B shows prosthetic valve support 4040d, partially deployed proximal to native valve 23 (i.e., in atrium 26), as described hereinabove (e.g., with reference to FIG. 1B). Fixed anchors 330 extend distally from the semi-deployed prosthetic valve support, and are moved distally, between the leaflets of the native valve.

Figure 58C:
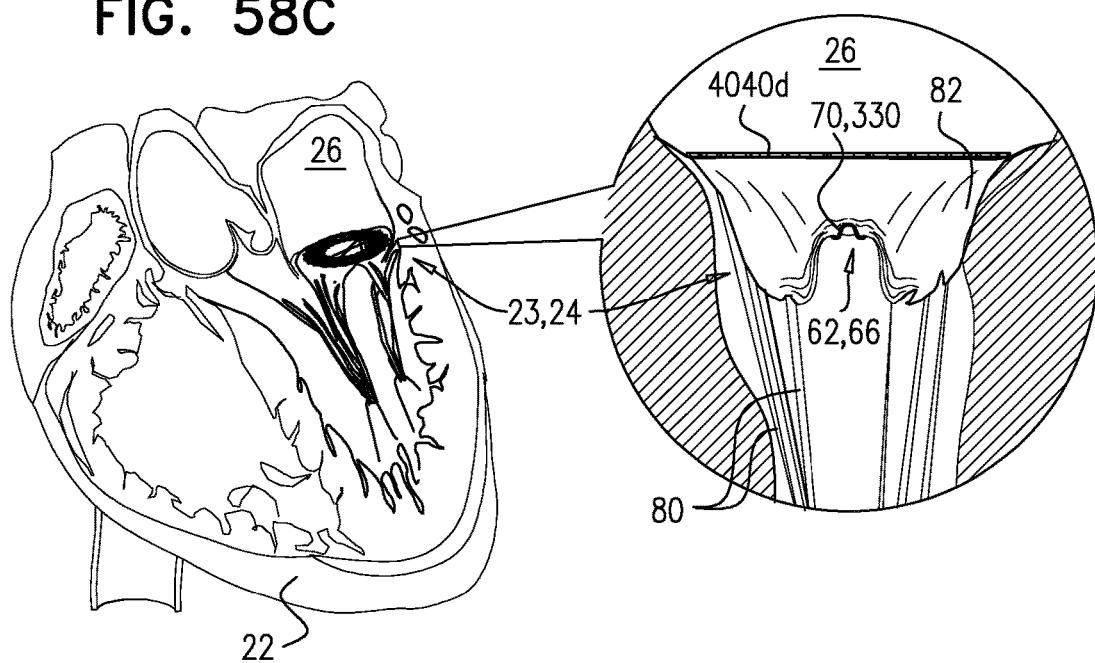

Reference is now made to FIG. 58C. Fixed anchors 330 move apart as prosthetic valve support 4040d expands to its fully-deployed, expanded configuration at native valve 23. That is, as inner edge 68 expands to assume its expanded state, the lumen of support 4040d expands thereby moving apart anchors 330. Fixed anchors 330 engage leaflets 82 of the native valve, thereby anchoring prosthetic valve support 4040d to the native valve. In some applications of the invention, fixed anchors 330 are configured such that native leaflets 82 continue to function, at least in part when support 4040d is implanted. For example, in some applications, the dimensions and relative positions of fixed anchors 330 do not substantially restrict the movement of leaflets 82. For example, the total width of each of the fixed anchors 330 elements may be less than 1 mm. Furthermore, in some applications of the invention, the forces exerted on leaflets 82 by the flow of blood are hypothesized to overcome at least some of the force applied to leaflets 82 by the rigidity of fixed anchors 330, i.e., in order to cause fixed anchors 330 to flex as leaflets 82 move.

Figure 58D:
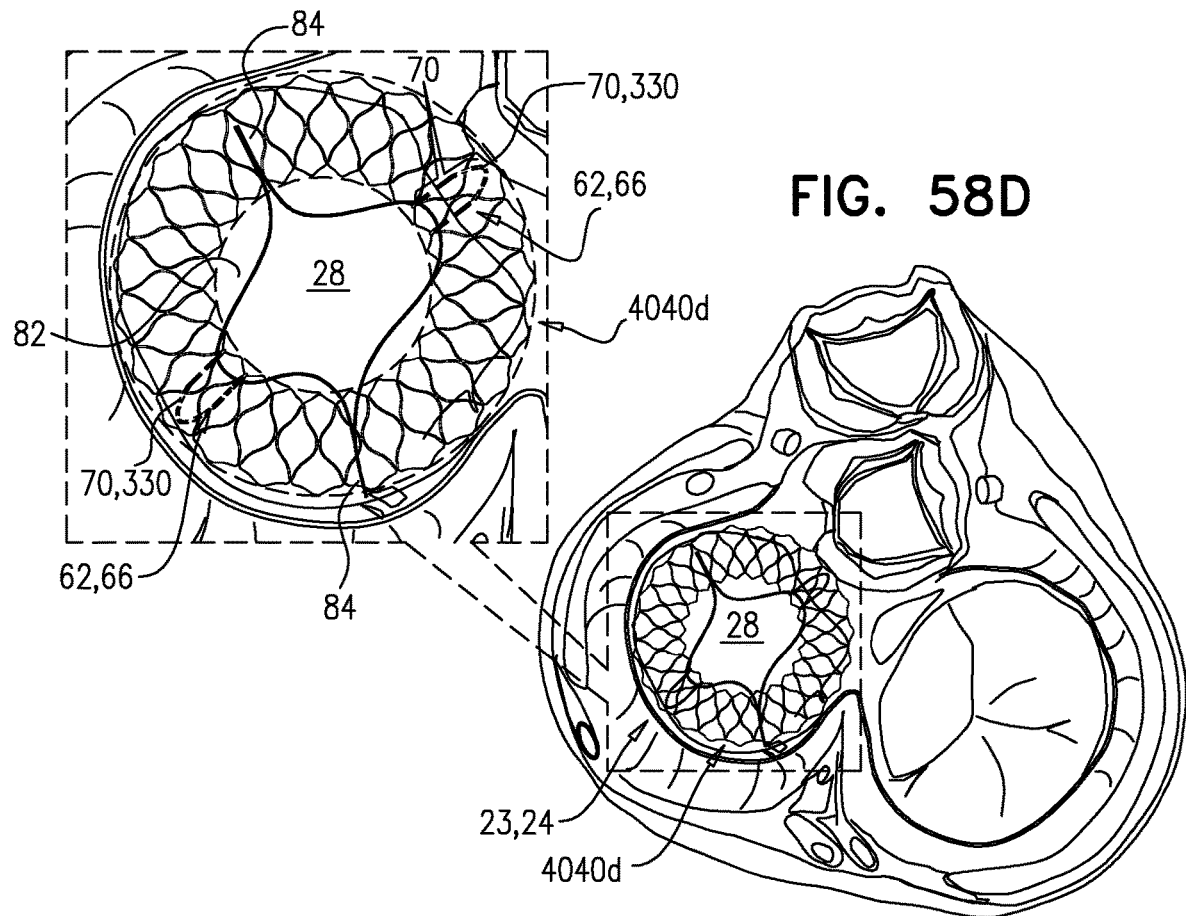

FIG. 58D is a schematic illustration of a transverse atrial cross-section of the fully-deployed prosthetic valve support described with reference to FIG. 58C. Fixed anchors 330 engage leaflets 82 of the native valve, thereby anchoring prosthetic valve support 4040d to the native valve. Coupling-portions 70 are disposed on the distal (i.e., ventricular) side of the native valve, and are therefore illustrated in phantom.

Reference is now made to FIGS. 59A-B, which are schematic illustrations of anchoring prosthetic valve support 4040d comprising support-anchoring elements 66 comprising fixed anchors 330, in accordance with some applications of the invention.

Anchoring prosthetic valve support 4040d is anchored to native valve 23 in a different orientation to that described with reference to FIGS. 58A-D. FIG. 59A shows prosthetic valve support 40 fully deployed and anchored to native valve 23. Fixed anchors 330 extend toward, and engage, commissures 84 of the native valve, thereby anchoring prosthetic valve support 4040d to the native valve.

FIG. 59B is a schematic illustration of a transverse atrial cross-section of the fully-deployed prosthetic valve support 4040d described with reference to FIG. 59A. Fixed anchors 330 engage commissures 84 of the native valve, holding the leaflets apart at commissures 84 and anchoring prosthetic valve support 4040d to the native valve. Coupling-portions 70 are disposed on the distal (i.e., ventricular) side of the native valve, and are therefore illustrated in phantom. It is hypothesized that the orientation of prosthetic valve support 4040d and positioning of fixed anchors 330, described with reference to FIGS. 59A-B, interferes less with leaflets 82, as compared to the orientation and positioning of fixed anchors 330 described with reference to FIGS. 58C-D (i.e., fixed anchors 330 engaging respective portions of leaflets 82). This positioning of anchors 330 at commissures 84, thereby allows the native valve to continue to function, at least in part, until prosthetic valve 42 is deployed.

Reference is made to FIGS. 60A-B and 61A-C, which are schematic illustrations of prosthetic valve support 40 comprising prosthetic valve support 4040e and 4040f, respectively, in accordance with some applications of the invention. Support-anchoring elements 66 in such applications comprise hinged anchors 340 that are typically coupled to inner edge 68 of support 40. In some applications of the invention, hinged anchors 340 comprise a coupling-portion 70, configured to engage tissue of the native valve. Coupling-portion 70 is illustrated as an extension of hinged anchors 340, thereby forming the hinged anchors into generally L-shapes. In other applications of the invention, coupling-portion 70 may be disposed differently (e.g., at an angle different to that as shown in FIGS. 60A-B and 61A-C), or may comprise clips 65a or 65b, or another means for engaging native valve 23. In some applications of the invention, hinged anchors 340 do not comprise a coupling-portion.

Hinged anchors 340 are typically coupled to prosthetic valve support 40 via a hinge point 72. Hinge point 72 may comprise a flexible material and/or moving components. For some applications of the invention, hinged anchors 340 rotate freely around hinge point 72 as far as their shape and juxtaposition allows. For some applications of the invention, hinged anchors 340 are biased to reside in a particular configuration. For example, hinged anchors 340 and/or hinge point 72 and/or prosthetic valve support 40 may comprise a shape-memory material (e.g., nitinol) or a spring mechanism, configured to push hinged anchors 340 radially outward.

The use of hinge points 72 for coupling support-anchoring elements 66 to prosthetic valve support 40 is hypothesized to provide one or more of the following advantages: (1) Improving compressibility of prosthetic valve support 40, for transcatheter delivery. (2) Improving movement of native leaflets 82 following deployment of prosthetic valve support 40 to the native valve. (3) Increasing adjustability of the dimensions and configuration of support-anchoring elements 66.

Figure 60A:
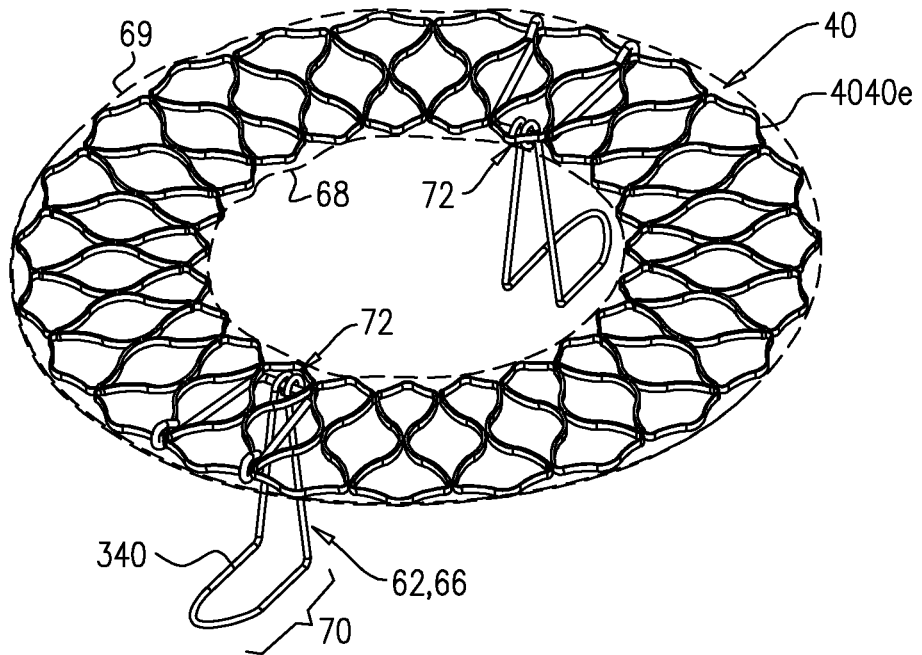
FIGS. 60A-B are schematic illustrations of the prosthetic valve support, comprising tissue-engaging elements, in accordance with some applications of the invention.
Figure 60B:
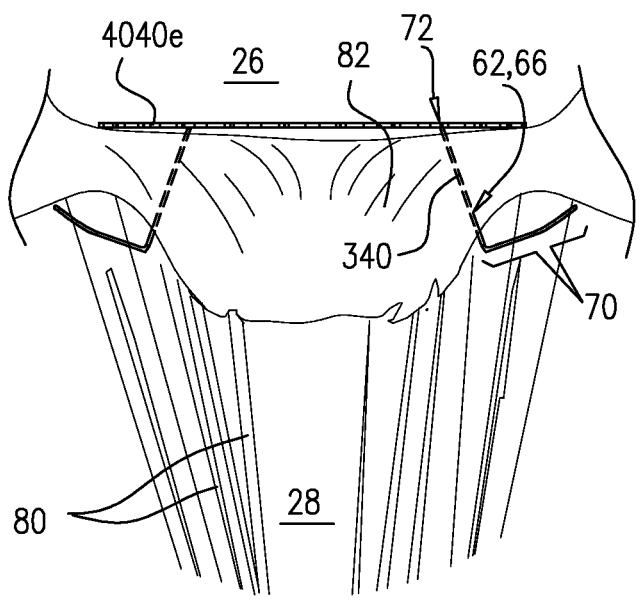

Reference is now made to FIGS. 60A-B, which are schematic illustrations of prosthetic valve support 40 comprising hinged prosthetic valve support 4040e, comprising hinged anchors 340, in accordance with some applications of the invention. FIG. 60A shows prosthetic valve support 4040e in a fully-expanded configuration. Prosthetic valve 4040e is configured such that hinged anchors 340 are biased to extend radially outward.

FIG. 60B shows prosthetic valve support 4040e fully deployed at native valve 23. As described with reference to FIGS. 58C-D and 59A-B, support-anchoring elements 66 may be positioned to engage commissures 84 (FIGS. 59A-B) and/or leaflets 82 of the native valve (FIGS. 58C-D). In the application of the invention illustrated in FIG. 60B, prosthetic valve support 4040e and hinged anchors 340 are configured such that the hinged anchors extend radially to engage the commissures 84 of the native valve. For other applications, hinged anchors 340 are freely rotatable, and are coupled to leaflets 82 such that support 40 is anchored to the native valve whilst allowing leaflets 82 to move.

Figure 61A:
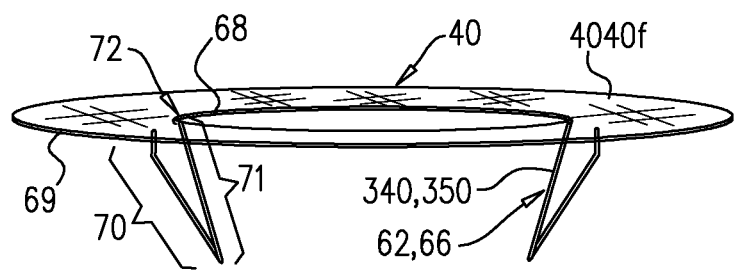
Figure 61B:
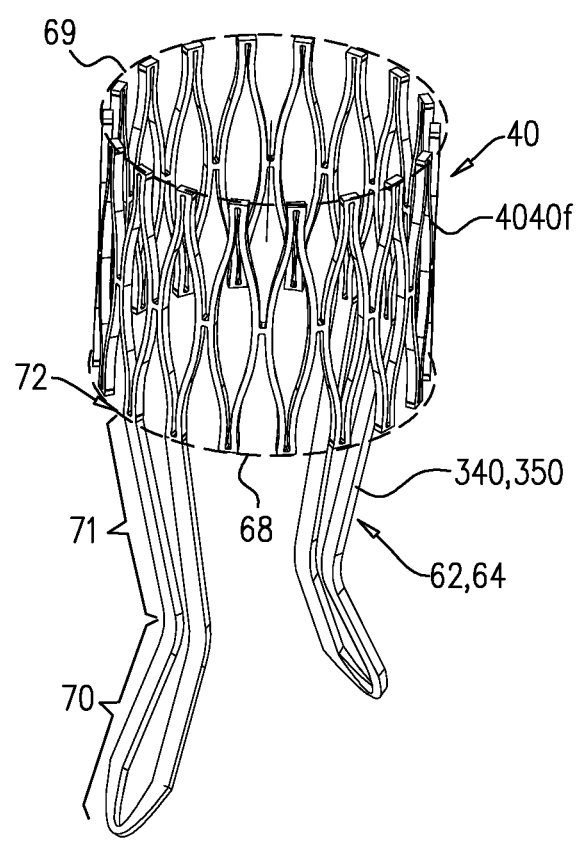

Reference is made to FIGS. 61A-C, which are schematic illustrations of prosthetic valve support 40 comprising free-hinged prosthetic valve support 40f, comprising hinged anchors 340 comprising clamping-hinged-anchors 350, in accordance with some applications of the invention.

FIG. 61A shows prosthetic valve support 4040f, comprising hinged anchors 350, in a fully-expanded configuration and a resting state thereof. Clamping-hinged-anchors 350 are coupled to prosthetic valve support 4040f via hinge point 72 and are typically free to pivot around the hinge point as far as their shape and juxtaposition allows. Coupling-portion 70 is shown in an unconstrained clamped configuration, in which it is typically configured to extend from structural component 71 of clamping-hinged-anchor 350, at an acute angle (e.g., less than 80 degrees, less than 45 degrees, or less than 20 degrees). In some applications of the invention, coupling-portion 70 may be configured to extend at less than 1 degree, i.e., to touch the structural component 71 of clamping-hinged-anchor 350. Clamping-hinged-anchors 350 typically comprise a shape-memory material (e.g., nitinol), such that they are compressible into a compressed (e.g., crimped) configuration for delivery, and are deformable and expandable at the site of implantation.

FIG. 61B shows clamping-hinged anchors 350 of prosthetic valve support 4040f, in a compressed configuration, e.g., for delivery toward the native valve within overtube 44 (e.g., as described hereinabove with reference to support 40 in FIG. 1B). It is to be noted that overtube 44 is not shown for clarity of illustration. Clamping-hinged-anchors 350 are disposed distally to other parts of prosthetic valve support 4040f. Prior to delivery, coupling-portions 70 are typically in an unclamped configuration, in which they extend further distally from prosthetic valve support 4040f and from structural component 71 of clamping-hinged-anchor 350. During deployment of prosthetic valve support 4040f from overtube 44, clamping-hinged-anchors 350 are extended from within overtube 44 (coupling-portion 70 first followed by structural component 71) and between leaflets 82 of native valve 23. As clamping-hinged-anchors 350 are fully exposed from within overtube 44, they move toward their clamped configuration, and are allowed to assume their resting state (as shown in FIG. 61A) in which coupling-portion 70 moves toward structural component 71 in order to clamp a portion of leaflet 82 therebetween and to thereby anchor prosthetic valve support 4040f to the native valve.

FIG. 61C shows prosthetic valve support 4040f fully deployed at native valve 23. Coupling-portions 70 clamp leaflets 82 against respective structural components 71 of clamping-hinged-anchors 350, as described hereinabove. Thus, clamping-hinged-anchors 350 function as clips 65c. As described hereinabove, clamping-hinged-anchors 350 are typically able to rotate freely about hinge point 72 as far as their shape and juxtaposition allows. Leaflets 82 are thereby able to move proximally and distally (i.e., atrially and ventricularly), as illustrated by the upper and lower panels of FIG. 61C. Clamping-hinged-anchors 350 thereby allow native valve 23 to continue to function until prosthetic valve 42 is deployed, as described hereinabove.

For some applications of the invention, prosthetic valve support 4040f is configured such that clamping hinged anchors 350 are biased to extend radially inward (i.e., toward each other). This configuration is illustrated by the upper panel of FIG. 61C. In such applications of the invention, leaflets 82 of the native valve are held together, forming a double-orifice configuration, as described herein (e.g., with reference to FIG. 57C). Clamping hinged anchors 350 thereby allow native valve 23 to continue to function, at least in part, until prosthetic valve 42 is deployed.

Reference is again made to FIGS. 58A-D, 59A-B, 60A-B and 61A-C. It is to be noted that supports 40 described herein comprise two support-anchoring elements 66 by way of illustration and not limitation. That is, the scope of the present invention includes the supports 40 comprising any suitable number and configuration of anchoring elements 66. For example, valve support 40 may comprise four support-anchoring elements 66 configured such that a pair of elements 66 are anchored to commissures 84 and a pair of elements 66 are anchored to leaflets 82 of the native valve.

Reference is now made to FIGS. 1, 49-61. It is to be noted that applications of tissue-engaging elements 62 described herein are interchangeable as valve-anchoring elements 64, and/or as support-anchoring elements 66. For example, pairs 132 of loop-shaped anchoring elements 200, described with reference to FIGS. 56A-D as valve-anchoring elements 64, may be coupled to prosthetic valve support 40 to the native valve (i.e., so as to function as support-anchoring elements 66). Similarly, clamping-hinged-anchors-350, for example, described with reference to FIGS. 61A-C as support-anchoring elements 66, may be employed to couple prosthetic valve 42 to the native valve (i.e., and function as valve-anchoring elements 64).

Reference is made to FIGS. 62A-D, which are schematic illustrations of delivery apparatus 4138a, used to deploy a medical device 150, in accordance with some applications of the invention. As shown in FIG. 62A, delivery apparatus 4138a comprises a delivery tube 154 and a pushing member 140a. Pushing member 140a comprises a support 4142a and one or more coupling tabs 4146, extending from the support. In the application of the invention shown in FIG. 62A, support 4142a comprises a core 144, and coupling tabs 4146 extend radially from the core. In some applications of the invention, support 4142a is shaped to define a plate 4148 at the proximal end of support 4142a. The dimensions and relative positions of support 4142a, tabs 4146, and plate 4148 may be adjusted for the specific medical device 150 to be deployed using delivery apparatus 4138a.

In the application of the invention described with respect to FIGS. 62A-D, medical device 150 comprises prosthetic valve 42 (e.g., any one of prosthetic valves 42 described herein).

FIG. 62B shows prosthetic valve 42 in a compressed (i.e., crimped) configuration for delivery and deployment using delivery apparatus 4138a. As described hereinabove, prosthetic valve 42 typically has a lattice structure that defines a plurality of shapes, and voids 4126, and has elastic memory. Prosthetic valve 42 is shown in a compressed (e.g., crimped) configuration, and as shown in the enlarged image, a proximal portion of valve 42 is disposed around core 144 of pushing member 140a such that each of coupling tabs 4146 is disposed within a respective void 4126 defined by the lattice structure of the prosthetic valve.

Prosthetic valve 42 and pushing member 140a are disposed within the lumen of delivery tube 154. Delivery tube 154 restricts expansion of prosthetic valve 42, thereby holding the proximal portion of prosthetic valve 42 around core 144 of pushing member 140a, in the configuration described herein. Coupling tabs 4146 restrict movement of prosthetic valve 42 with respect to pushing member 140a. Delivery tube 154 therefore facilitates coupling of prosthetic valve 42 to pushing member 140a via coupling tabs 4146. In applications of the invention where pushing member 140a is shaped to define plate 4148, the plate typically further facilitates this coupling by restricting proximal movement of prosthetic valve 42 with respect to the pushing member (e.g., by functioning as a cap).

FIG. 62C shows prosthetic valve 42 partially deployed from delivery tube 154. Pushing member 140a, and, thereby, prosthetic valve 42, are moved distally through delivery tube 154.

A control tube 4152 is coupled at a distal end thereof to pushing member 140a (e.g., control tube 4152 is coupled to support 4142a). Control tube 4152 is shaped so as to define a lumen through which a guidewire tube 4153 passes, and control tube 4152 is slidable with respect to and along guidewire tube 4153. Guidewire tube 4153 houses guidewire 45 described hereinabove. Control tube 4152 is slidably disposed within a lumen of an overtube 4155.

Reference is again made to FIG. 62C. Pushing member 140a is pushed distally by pushing control tube 4152 along guidewire tube 4153 such that pushing member 140a pushes prosthetic valve 42. As pushing member 140a pushes valve 42 distally, distal portions of the prosthetic valve expand toward the expanded configuration as they become exposed from delivery tube 154, while the proximal end of valve 42 remains coupled to pushing member 140a via tabs 4146.

FIG. 62D shows prosthetic valve 42 having been fully deployed from within delivery tube 154. Pushing member 140a and prosthetic valve 42 are moved further distally through delivery tube 154 by control tube 4152. When the proximal portion of prosthetic valve 42 emerges from within delivery tube 154, expansion of the proximal portion of prosthetic valve 42 uncouples the prosthetic valve from coupling tabs 4146 by expanding voids 4126 away from tabs 4146, thereby releasing the prosthetic valve from pushing member 140a.

Should it be necessary and/or desirable during the procedure, until medical device 150 (e.g., prosthetic valve 42) is released from pushing member 140a (i.e., while the proximal portion of medical device 150 is crimped within delivery tube 154), the remaining portions of medical device 150 may be drawn back into delivery tube 154 (e.g., for repositioning or withdrawal of the medical device).

Reference is now made to FIGS. 54A-D and 62A-D. It is to be noted that for some applications, withdrawing of a portion of prosthetic valve 42 within delivery tube 154 facilitates deforming of integral anchors 310 toward their constrained, further-expanded open configuration. This occurs when a distal end of tube 154 pushes against pivot joint 4074 between anchor 310 and structural element 130 as the portion of prosthetic valve 42 is withdrawn.

In the application of the invention described with reference to FIGS. 62A-D, voids 4126 are defined by the lattice structure of medical device 150 (i.e., prosthetic valve 42). In other applications of the invention, voids in medical device 150 may be defined by other structural features of the medical device and not necessarily by a lattice structure. Typically, as described herein, coupling tabs 4146 couple medical device 150 to pushing member 140a at a proximal portion of the medical device, thereby retaining coupling of the medical device to pushing member 140a until the medical device is fully deployed from delivery tube 154. It is to be noted that the scope of the present invention includes tabs which alternatively or additionally couple medical device 150 to pushing member 140a at portions of the medical device other than the proximal portion thereof.

It is hypothesized that utilization of pushing member 140a, comprising coupling tabs 4146 that are disposable in voids 4126 defined by an expandable medical device 150, (1) reduces the overall length of the apparatus (i.e., the combined lengths of medical device 150 and delivery tube 154) being advanced into the subject, and/or (2) reduces the requirement for additional components of medical device 150 which function as coupling structures of medical device 150. That is, medical device 150 has an integral coupling system by which voids 4126 are coupled to tabs 4146. The applications of the invention described with reference to FIGS. 62A-D may be used in combination with applications of the invention described hereinabove, as well as for the delivery of other expandable medical devices.

Reference is again made to FIGS. 1A-H, 9A-E, and 62A-D. It is to be noted that delivery tube 154 of FIGS. 9A-E and 62A-D may be similar to, may act as, and/or may comprise, overtube 44 and/or delivery tube 60 of FIGS. 1A-H.

Reference is made to FIGS. 63A-B, which are schematic illustrations of delivery apparatus 4138b, used to deploy an expandable medical device 150, in accordance with some applications of the invention. Reference is now made to FIG. 63A. Delivery apparatus 4138b comprises delivery tube 154 and a pushing member 140b, which comprises a support 4142b. In this application of the invention, pushing member 140b is shaped to define a plurality of troughs 222. Typically, troughs 222 run along the surface of pushing member 140*b*, from one end of the pushing member (e.g., a distal end) to a point along the length of the pushing member. Typically, troughs 222 are shaped so as to define a respective widened part 224 (e.g., at a proximal end of the trough) or is configured to open into a larger widened part 224 (as shown). In the application of the invention described with reference to FIGS. 63A-B, widened part 224 comprises a single circumferential groove surrounding the circumference of pushing member 140*b*, into which all troughs 222 open. Alternatively, each trough 222 may be shaped so as to define a respective widened part.

Reference is now made to FIG. 63B. Medical device 150, embodied in this application of the invention as expandable prosthetic valve 42, comprises a plurality of coupling tabs 220. Coupling tabs 220 are configured to be disposable in respective troughs 222 of pushing member 140*b*, such that troughs 222 restrict distal movement of medical device 150. In the application of the invention described with reference to FIGS. 63A-B, coupling tabs 220 are T-shaped, so as to be disposable in respective troughs 222 and in the circumferential groove that forms widened part 224. The disposition of coupling tabs 220 in troughs 222 couples prosthetic valve 42 to pushing member 140*b*. Coupling tabs 220, troughs 222, and widened part 224 may assume any shape that allows such coupling.

Prior to delivery, prosthetic valve 42 is compressed (e.g., crimped) such that all coupling tabs 220 are disposed in respective troughs 222. Prosthetic valve 42 and pushing member 140*b* are disposed within the lumen of delivery tube 154. Delivery tube 154 restricts expansion of prosthetic valve 42, thereby holding coupling tabs 220 in troughs 222, in the configuration described herein. Coupling tabs 220 restrict movement of prosthetic valve 42 with respect to pushing member 140*b*. Delivery tube 154 therefore facilitates coupling of prosthetic valve 42 to pushing member 140*b* via coupling tabs 220. As described with reference to FIGS. 62C-D, prosthetic valve 42 (or another medical device 150) is advanced to the site of implantation, where pushing member 140*b* pushes prosthetic valve 42 out of delivery tube 154. When coupling tabs 220 emerge from delivery tube 154, expansion of prosthetic valve 42 releases coupling tabs 220 from troughs 222, thereby releasing prosthetic valve 42 from the pushing member.

Reference is made to FIGS. 64A-C, which are schematic illustrations of a lock 170 for facilitating delivery of a medical device, in accordance with some applications of the invention.

Reference is now made to FIG. 64A. Lock 170 comprises a tubular member 4172 and a plug 174. Plug 174 is dimensioned such that it is disposable in, and slidable through the lumen of tubular member 4172. Typically, plug 174 is dimensioned so as to fit tightly in the lumen of tubular member 4172 in a manner in which an outer surface of plug 174 is disposed very close to an inner surface to tubular member 4172, i.e., such that little space exists between the plug and the tubular member. Plug 174 is shaped to define a trough 176. Trough 176 typically runs along the surface of the plug from one end of the plug to a point along the length of the plug. Typically, trough 176 is shaped so as to define a widened part 178.

A coupling lead 4180 (e.g., a coupling wire) is disposable in trough 176, and is reversibly couplable thereto (and thereby to lock 170), as described hereinbelow. As is described hereinbelow, coupling lead 4180 is coupled to a medical device 150 and facilitates (1) coupling of medical device 150 to a delivery mechanism during delivery of the medical device and (2) decoupling of medical device 150 from the delivery mechanism following implantation of device 150. Typically, a region at an end of coupling lead 4180 is shaped to define a stopper 182, which is thicker than other regions of the coupling lead, and is configured to be disposable in widened part 178 of trough 176, typically when tubular member 4172 surrounds plug 174. Alternatively, stopper 182 may comprise a distinct component that is coupled to coupling lead 4180. Trough 176, coupling lead 4180, widened part 178, and stopper 182 are dimensioned such that when the coupling lead and the stopper are disposed in trough 176, plug 174 remains disposable in, and slidable through, tubular member 4172. FIG. 64A shows trough 176 disposed within the lumen of tubular member 4172 such that lock 170 assumes a locking configuration. In this locking configuration, coupling lead 4180 is held in the trough by the inner surface of the tubular member. Tubular member 4172 therefore facilitates coupling of coupling lead 4180 to plug 174.

Reference is now made to FIG. 64B. Plug 174 is slid distally through tubular member 4172, such that lock 170 is in an open configuration. Typically, plug 174 is moved using control wire 175. In this open configuration, trough 176 and stopper 182 are exposed from the tubular member (i.e., are outside the tubular member). Coupling lead 4180 and stopper 182 are shown in FIG. 64B as being disposed within trough 176, by way of illustration and not limitation, as a temporary configuration prior to disengaging wire 4180 and stopper 182 from trough 176 (disengaging of wire 4180 and stopper 182 are described hereinbelow).

Reference is now made to FIG. 64C. In the open configuration, coupling lead 4180 (and stopper 182) are allowed to leave trough 176. Typically, coupling lead 4180 is released from trough 176 by moving the former with respect to the latter (e.g., by applying a moving force to either coupling lead 4180, directly or indirectly, or by applying a moving force to plug 174 away from wire 4180). In some applications of the invention, at least a portion of coupling lead 4180 is configured such that it automatically moves out of the trough upon being exposed from the tubular member (e.g., the coupling lead comprises a shape-memory material such as nitinol). In some applications of the invention, trough 176 and widened part 178 are shaped to facilitate release of coupling lead 4180 from trough 176. For example, a distal edge of widened part 178 may be sloped such that distal movement of coupling lead 4180 facilitates the release.

Figure 65A:
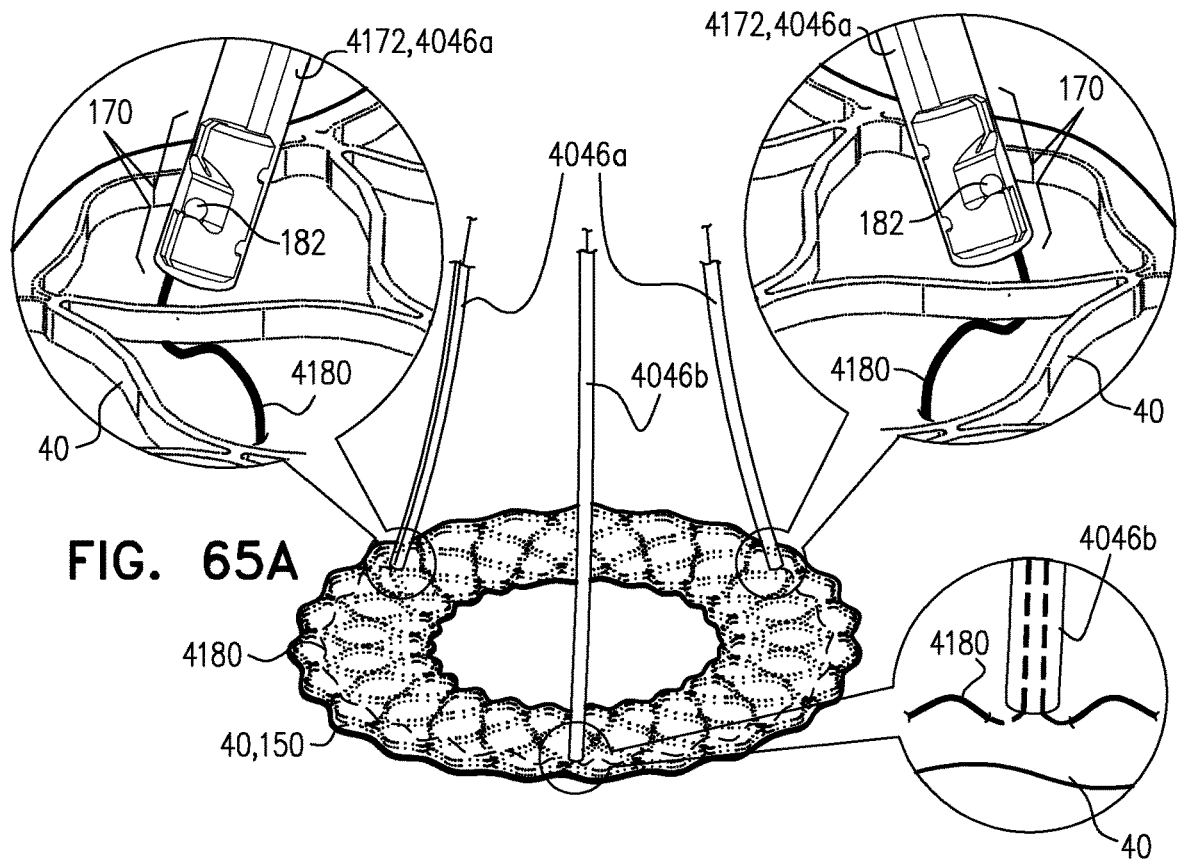
Figure 65B:
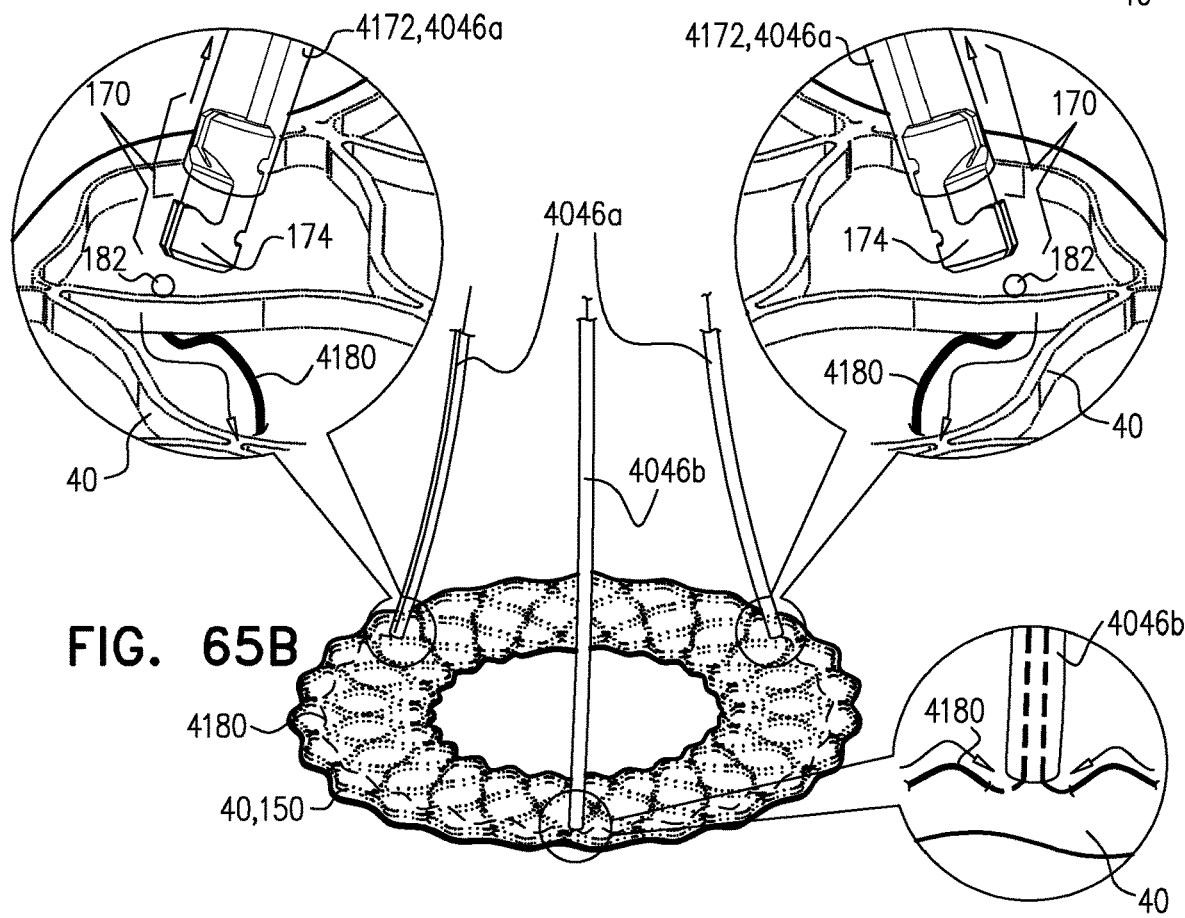

Reference is made to FIGS. 65A-B, which are schematic illustrations of sequential steps in lock 170 being used to facilitate the delivery of a medical device 150, the medical device embodied by prosthetic valve support 40, in accordance with some applications of the invention. FIG. 65A shows a coupling lead 4180 (e.g., a coupling wire) extending from a holding member 4046 (e.g., a holding member 4046*a*) to another holding member 4046 (e.g., a holding member 4046*b*). For some applications, holding members 4046 comprise holding members 46, described hereinabove with reference to FIGS. 1C-F. Coupling lead 4180 is coupled to medical device 150. For example, coupling lead 4180 may loop around a part of medical device 150. Alternatively, coupling lead 4180 may weave through at least a portion of medical device 150, as shown in FIG. 65A. At least one holding member 4046 (e.g., holding member 4046*a*) comprises lock 170 at a distal end of holding member 4046. Holding member 4046 is shaped to define a lumen and defines tubular member 4172 of lock 170. Holding member 4046*a* is reversibly coupled to a first portion of coupling lead 4180 (e.g., an end portion of wire 4180, as shown) via lock 170. The remaining portions of wire 4180 are threaded through support 40, as shown, and extend through a lumen, of holding member 4046b, as shown. Alternatively, a second portion of coupling lead 4180 is coupled to a portion of holding member 4046b.

In the application of the invention illustrated in FIG. 65A, two holding members 4046a are coupled to coupling lead 4180 via respective locks 170, and one holding member 4046b is coupled to coupling lead 4180 without a lock 170. That is, a first holding member 4046a holds a first end of wire 4180, and a second holding member 4046a holds a second end of wire 4180. Portions of wire 4180 extending from the first and second ends thereof are threaded through respective portions of support 40 and extend through a lumen of holding member 4046b, as shown. Alternatively, each holding member 4046a is coupled to respective first ends of respective first and second coupling leads 4180. Respective portions of the first and second coupling leads 4180 extending from the respective first ends thereof are threaded through respective portions of support 40, and extend through a lumen of holding member 4046b. Alternatively, respective second portions of the first and second coupling leads 4180 are coupled to a portion of holding member 4046b.

Reference is now made to FIG. 65B. At the site of implantation, lock 170 is moved into its open configuration, thereby releasing coupling lead 4180 from holding member 4046a. Coupling lead 4180 is then decoupled (e.g., unthreaded or unlooped) from medical device 150 (e.g., by pulling on a portion of coupling lead 4180). In some applications of the invention, holding member 4046b is slidably coupled to coupling lead 4180, and the decoupling of coupling lead 4180 from medical device 150 is performed by withdrawing coupling lead 4180 proximally, through holding member 4046b. In other applications of the invention, holding member 4046b is substantially attached to coupling lead 4180, and the decoupling of coupling lead 4180 from medical device 150 is performed by withdrawing holding members 4046 proximally following the decoupling of holding members 4042a from coupling lead 4180. Medical device 150 is typically left at the site of implantation following the decoupling.

Figure 66A:
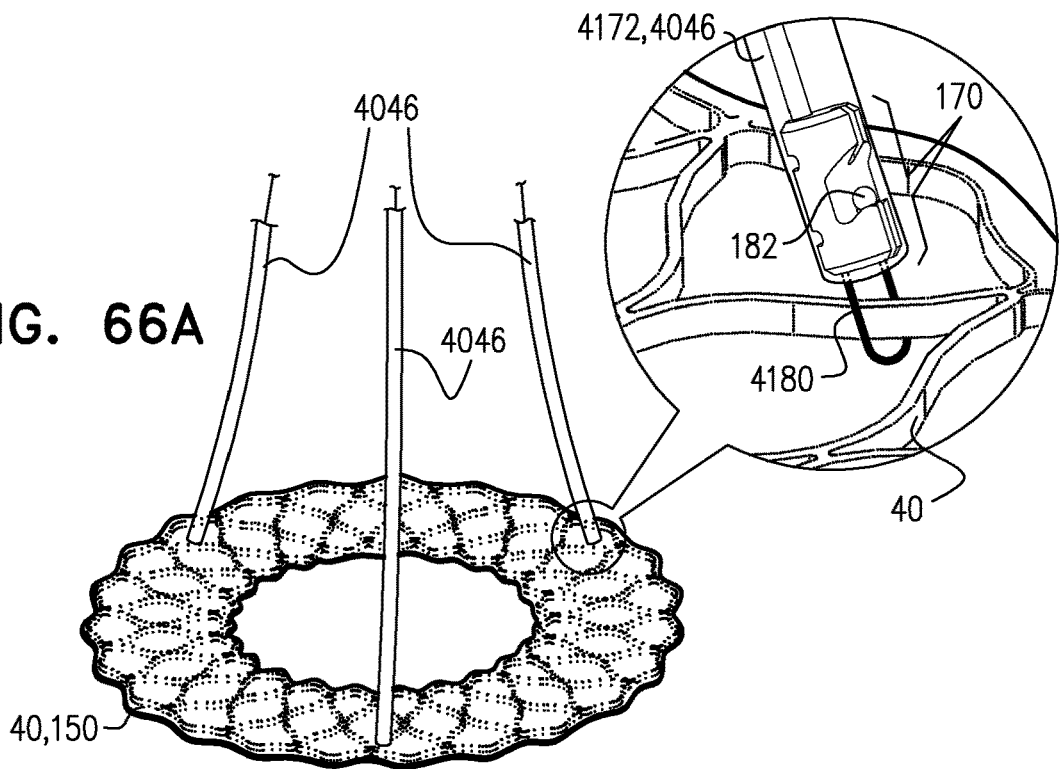
Figure 66B:
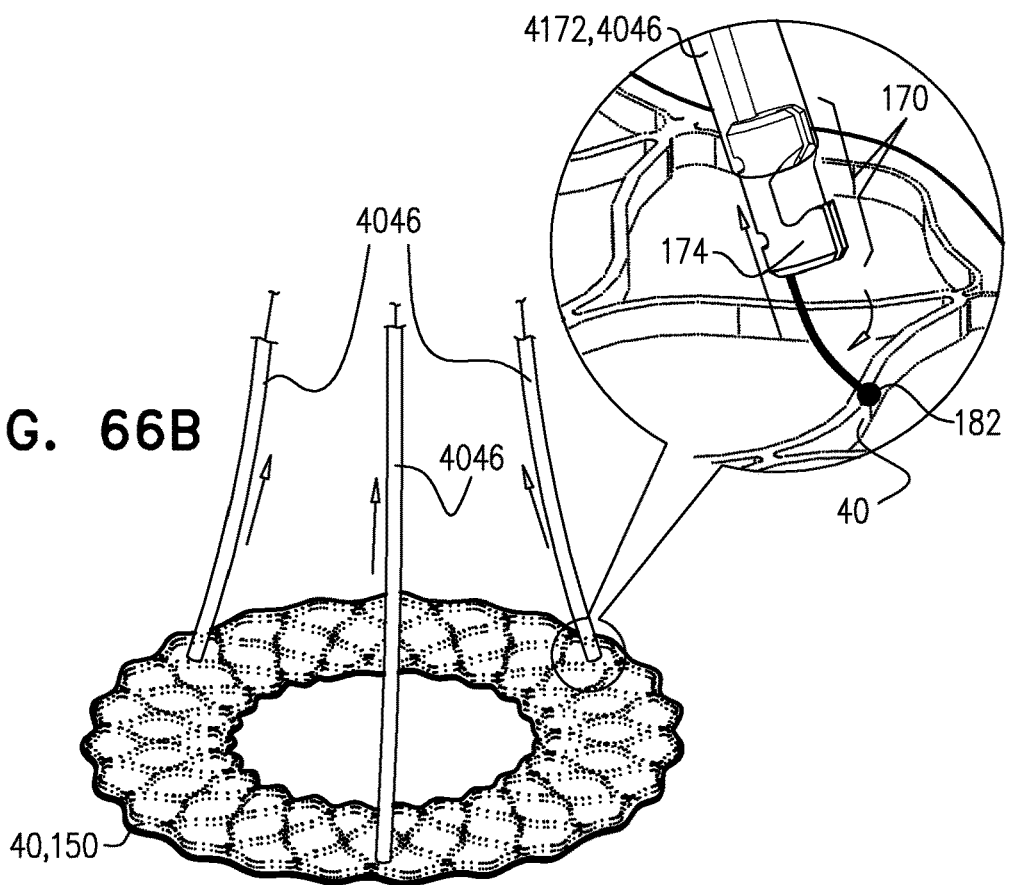

Reference is made to FIGS. 66A-B, which are schematic illustrations of sequential steps in lock 170 facilitating the delivery of a medical device 150, the medical device embodied by prosthetic valve support 40, in accordance with some applications of the invention. Reference is now made to FIG. 66A. In this application of the invention, both ends of each coupling lead 4180 are coupled to one respective holding member 4046. Each one of holding members 4046 comprises a respective lock 170. A respective coupling lead 4180 is coupled to each holding member 4046. For each holding member 4046, one end of coupling lead 4180 (i.e., the end of wire 4180 comprising stopper 182) is reversibly coupled to the holding member via lock 170, as described hereinabove with reference to FIG. 65A. The other end of the coupling lead is coupled to the holding member in a substantially fixed manner (e.g., attached to the holding member, or attached to a second part of lock, such as a second part of plug 174). In such a manner, each coupling lead 4180 forms a loop around a part of medical device 150 (as shown in the enlarged image of FIG. 66A), thereby coupling each coupling lead 4180, and thereby coupling each holding member 4046, to medical device 150.

Reference is now made to FIG. 66B. At the site of implantation, each lock 170 is moved into its open configuration (described hereinabove), thereby releasing one end of each coupling lead 4180 (i.e., the end of wire 4180 comprising stopper 182), and thereby opening the loop formed by coupling lead 4180. Each coupling lead 4180 is withdrawn proximally (i.e., by pulling proximally on each holding member 4046, as shown), thereby uncoupling (e.g., unthreading or unlooping) coupling lead 4180 from medical device 150.

For some applications of the present invention, the other end of coupling lead 4180 is attached to a portion of holding member 4046. In such applications, withdrawal of coupling lead 4180 typically comprises withdrawing holding member 4046 proximally.

For some applications of the invention, the other end of coupling lead 4180 is attached to a portion (e.g., an outer surface of) of plug 174. For such applications, withdrawal of coupling lead 4180 may comprise withdrawing the plug into tubular member 4172 (i.e., holding member 4046).

In either application, following the decoupling of holding members 4046 and wires 4180 from device 150, medical device 150 is typically left at the site of implantation.

Figure 67A:
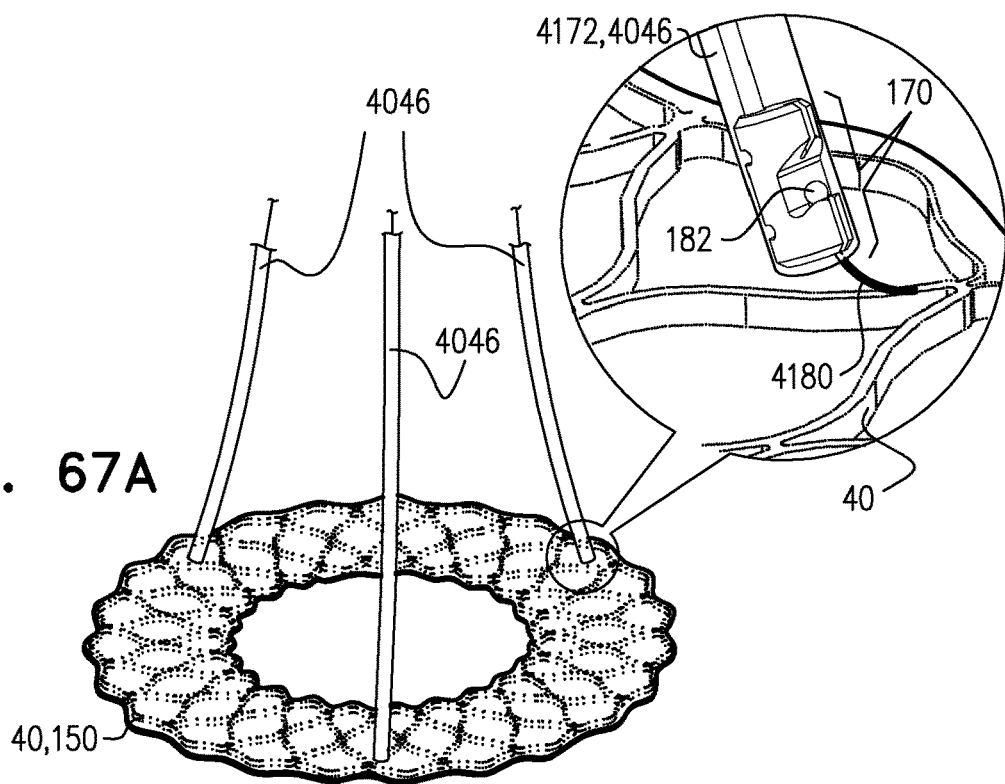
Figure 67B:
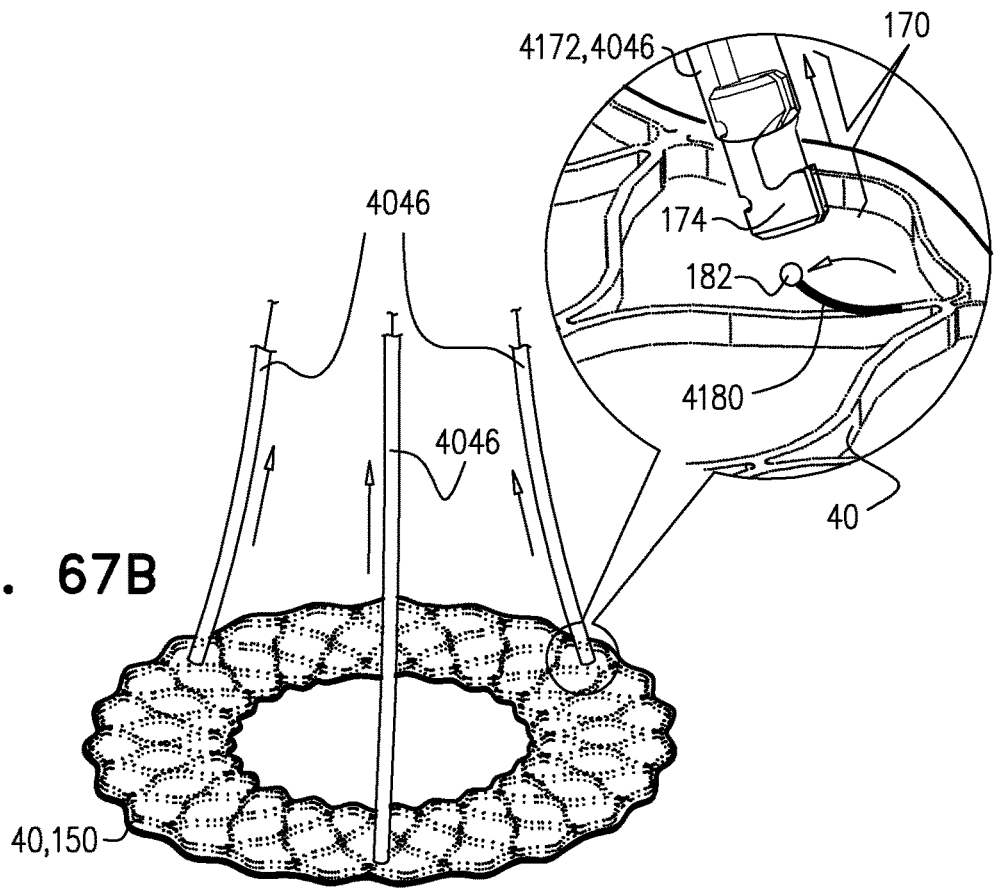

Reference is made to FIGS. 67A-B, which are schematic illustrations of sequential steps in lock 170 facilitating the delivery of a medical device 150, the medical device embodied by prosthetic valve support 40, in accordance with some applications of the invention. Reference is now made to FIG. 67A. One end of coupling lead 4180 (i.e., the end of wire 4180 comprising stopper 182) is reversibly coupled to holding member 4046 via lock 170, as described hereinabove with reference to FIG. 65A. The other end of the coupling lead is coupled to medical device 150 in a substantially fixed manner. Typically, but not necessarily, coupling lead 4180 is short in comparison to the coupling lead described with reference to FIGS. 65A-B and 66A-B.

Reference is now made to FIG. 67B. At the site of implantation, lock 170 is moved into its open configuration, releasing one end of coupling lead 4180 (i.e., the end of wire 4180 comprising stopper 182). Holding members 4046 are withdrawn proximally, releasing coupling lead 4180 and medical device 150 from holding members 4046. Following the decoupling of holding members 4046 from device 150, medical device 150 is typically left at the site of implantation. In this application of the invention, coupling leads 4180 typically remain coupled to medical device 150.

The applications of the invention described with reference to FIGS. 64A-C, 65A-B, 66A-B, and 67A-B may be used in combination with each other, and/or in combination with applications of the invention described herein, including those comprising delivery and/or deployment of prosthetic valve 42, prosthetic valve support 40, and/or medical device 150. These applications of the invention may also be used to deliver and/or deploy medical devices not described herein.

Reference is made to FIGS. 68A-B and 69A-E, which are schematic illustrations of prosthetic valve support 40 comprising a retrievability functionality, in accordance with some applications of the invention.

Figure 68A:
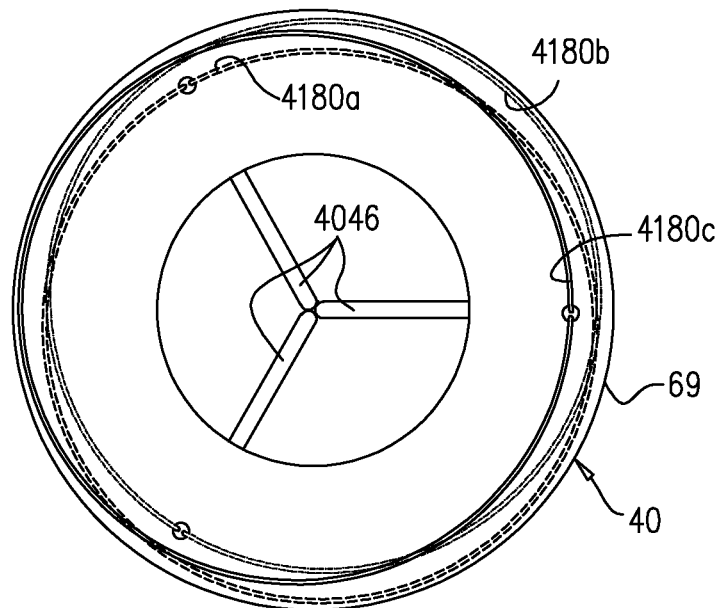
FIGS. 68A-B and 69A-E are schematic illustrations of a retrievable prosthetic valve support, and sequential steps in the retrieval of the retrievable prosthetic valve support, in accordance with some applications of the invention.
Figure 68B:
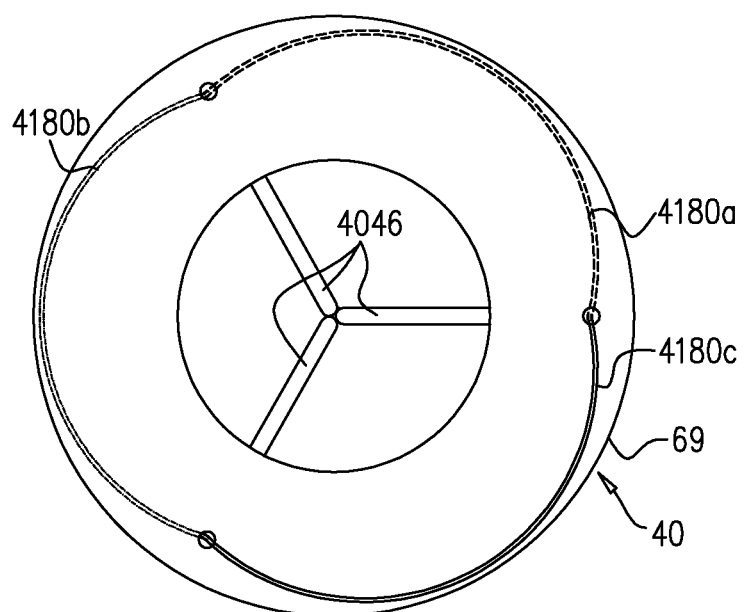

FIGS. 68A-B show prosthetic valve support 40 is coupled to one or more holding members 4046 via one or more coupling retrieving wires 4180, in accordance with respective applications of the invention. Typically, prosthetic valve support 40 is coupled to 2 or more (e.g., 3) holding members 4046 via 2 or more (e.g., 3) coupling leads 4180. Typically, the ends of each coupling lead 4180 are disposed within holding members 4046, or more proximally (e.g., outside a body of the subject). A portion (e.g., a middle portion) of each coupling lead is disposed through respective portions of prosthetic valve support 40 (e.g., threaded through support 40), thereby coupling the prosthetic valve support to holding members 4046. Since (1) the respective ends of coupling leads 4180 are coupled to or extend beyond a proximal end of holding members 4046, and (2) respective middle portions of wires 4180 are threaded through respective portions of support 40, each coupling lead forms a loop. Typically, this middle portion of each coupling lead is disposed through a peripheral region (e.g., close to an outer edge 69) of the prosthetic valve support.

FIGS. 68A-B show two configurations of coupling leads 4180, coupling holding members 4046 to prosthetic valve support 40, in accordance with respective applications of the invention. For these applications of the invention, three coupling leads 4180 (e.g., coupling wires) are used, and are illustrated as coupling leads 4180*a*, 4180*b*, and 4180*c*, for clarity. Prosthetic valve support 40 is typically deployed in the atrium 26 of the subject, e.g., as described with reference to FIGS. 1B-D.

FIG. 68A shows the middle portions of wires 4180*a-c* forming respective pulling loops (e.g., closed loops) around and threaded through support 40. That is, a respective pulling force is applied annularly to the entire support 40 by each one of wires 4180*a-c*.

FIG. 68B shows the middle portions of wires 4180*a-c* threaded through portions of support 40 in a manner in which the respective middle portions of wires 4180*a-c* collectively form a pulling loop. That is, a respective pulling force is applied to respective portions of support 40 (i.e., to respective thirds of support 40) corresponding to the portions of support 40 through which the respective middle portions of wires 4180*a-c* are threaded.

Figure 69A:
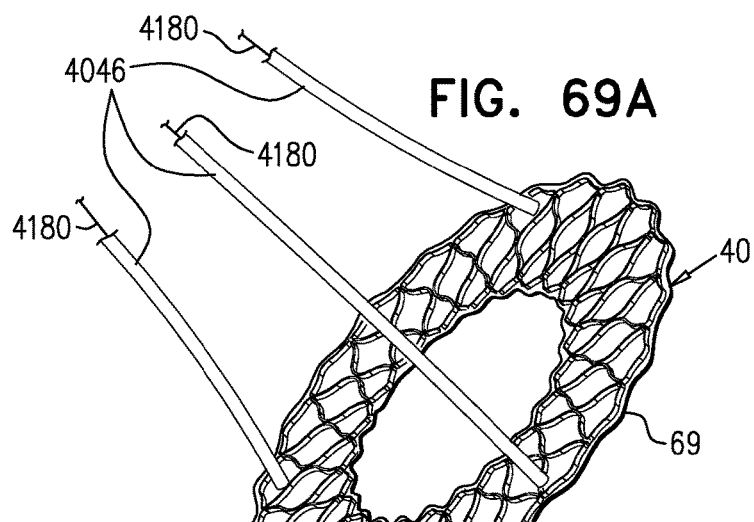

Reference is now made to FIGS. 69A-E, which are schematic illustrations of sequential steps in the retrieval of prosthetic valve support 40 described hereinabove with reference to FIGS. 68A-B, in accordance with some applications of the invention. Should it be required (e.g., for repositioning of the prosthetic valve support, or abortion of the procedure), the deployed prosthetic valve support may be retrieved into overtube 44. FIG. 69A shows prosthetic valve support 40 in a fully deployed configuration, still coupled to holding members 4046 via coupling leads 4180. In this configuration, prosthetic valve support 40 is typically flat, but may have a different shape (e.g., a saddle shape).

Figure 69B:
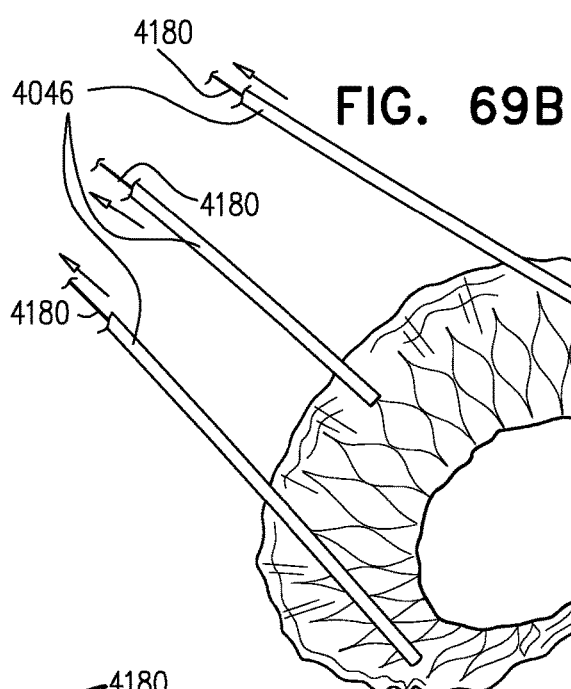

Reference is now made to FIG. 69B. A user moves coupling leads 4180 proximally with respect to holding members 4046 and prosthetic valve support 40 (e.g., the user pulls coupling leads 4180 through holding members 4046). Due to the configuration of coupling leads 4180 (as described with reference to FIGS. 68A-B) the portion of each coupling lead that passes through the prosthetic valve support becomes shortened, thereby reducing a perimeter of the peripheral region (e.g. of outer edge 69) of prosthetic valve support 40, through which coupling leads 4180 are disposed.

Figure 69C:
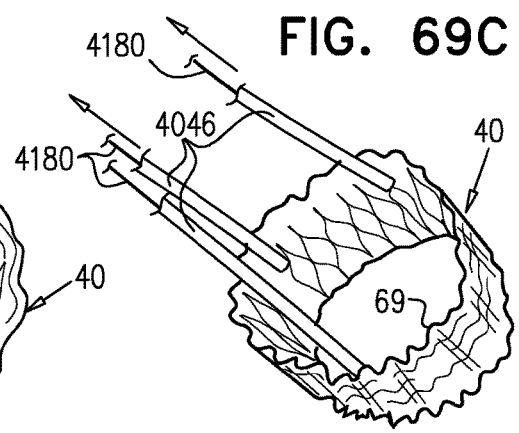
Figure 69D:
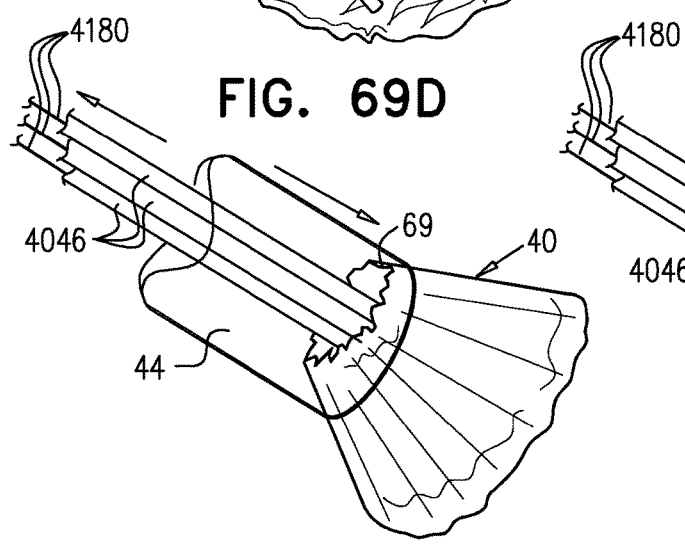
Figure 69E:
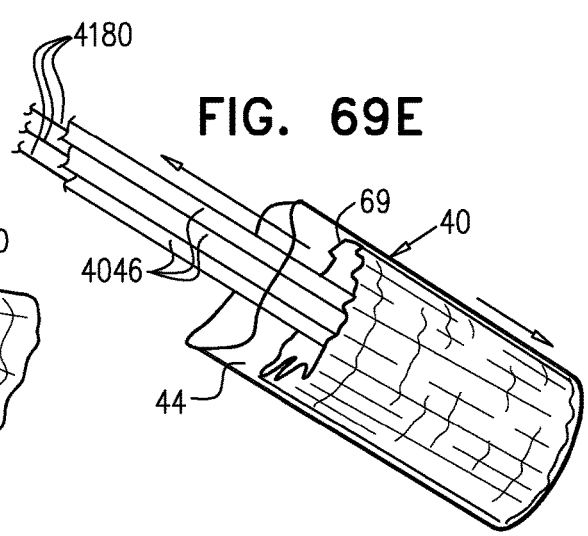

FIG. 69C shows the perimeter of outer edge 69 of prosthetic valve support 40 having been reduced further, thereby deforming prosthetic valve support toward a cylindrical shape, with outer edge 69 defining a proximal end of the further-reduced support 40. FIG. 69D shows the diameter of outer edge 69 having been reduced, such that the proximal end comprising outer edge 69 of prosthetic valve support 40 is slidable and disposable in overtube 44. As the user pulls coupling leads 4180, he/she pushes overtube 44 distally over successive portions of support 40. FIG. 69E shows holding members 4046 and prosthetic valve support 40 being moved proximally with respect to overtube 44 (e.g., the prosthetic valve support is moved proximally and/or the overtube is moved distally). As overtube 44 slides over prosthetic valve support 40, it compresses more distal portions of the prosthetic valve support, until the prosthetic valve support has been entirely retrieved into overtube 44. Prosthetic valve support 40 may be redeployed or may be removed from the subject. Retrieval and/or deployment may be halted and/or reversed at any stage in the process described with reference to FIGS. 69A-E.

The applications of the invention described with reference to FIGS. 68A-B and 69A-E may be used in combination with each other, and/or in combination with applications of the invention described herein, including those which include prosthetic valve support 40.

Figure 70A:
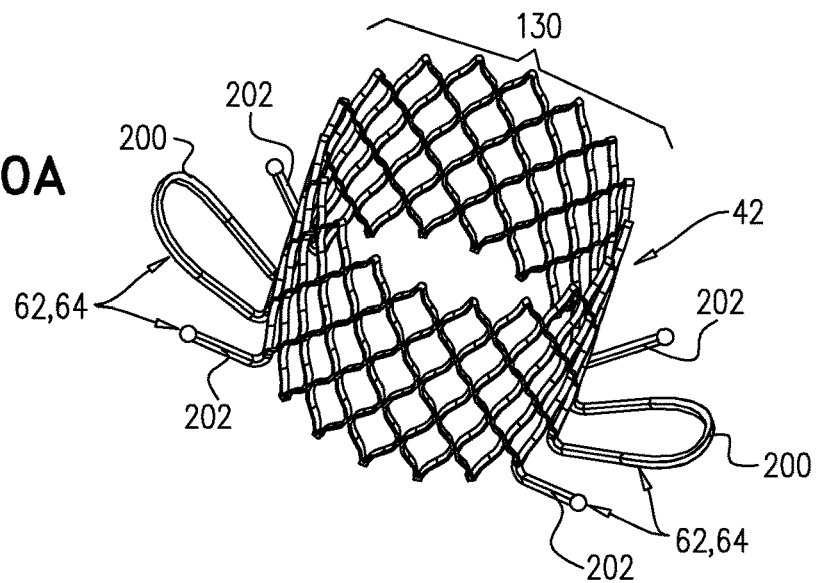
FIGS. 70A-C are schematic illustrations of the prosthetic valve, comprising tissue-engaging elements, in accordance with some applications of the invention.
Figure 70B:
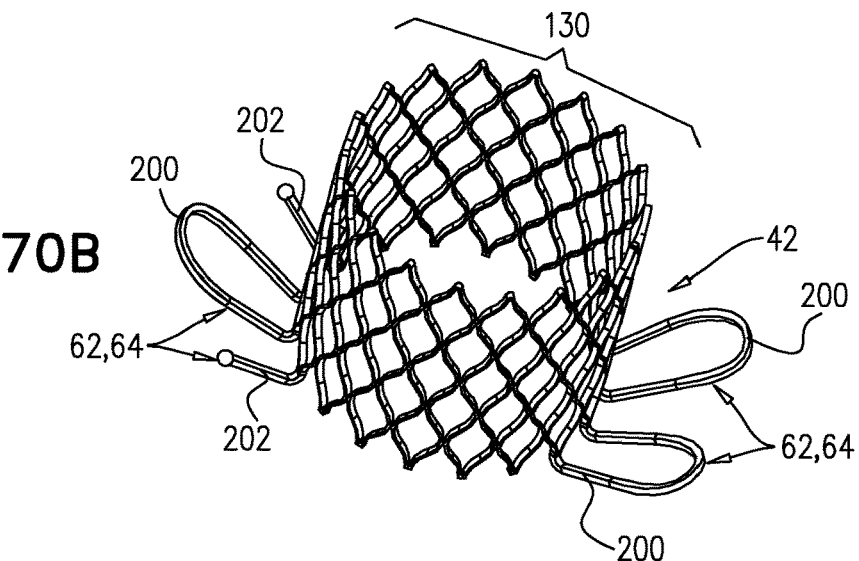
Figure 70C:
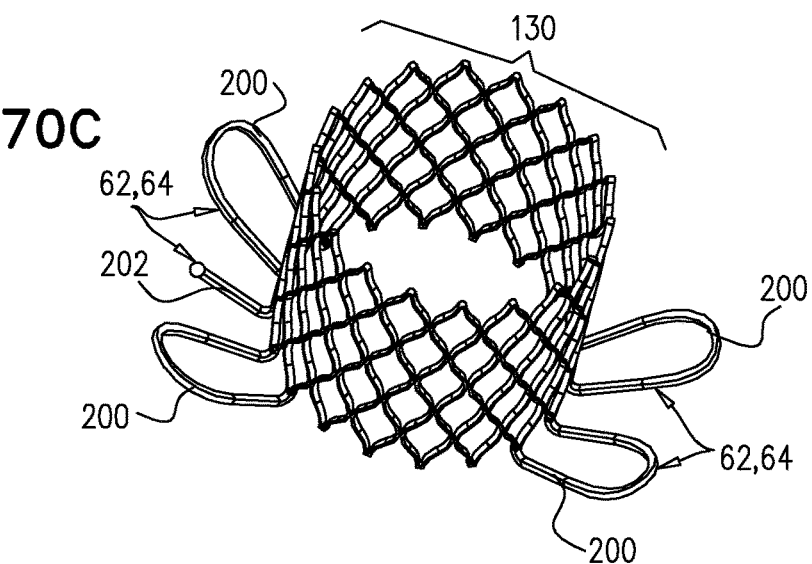

Reference is made to FIGS. 70A-C, which are schematic illustrations of prosthetic valve 42, comprising tissue-engagement elements 62, in accordance with some applications of the invention. In these applications of the invention, tissue-engagement elements 62 comprise valve-anchoring elements 64, disposed at the distal end of prosthetic valve 42. Each valve-anchoring element 64 may comprise a loop-shaped valve-anchoring element 200 or a stick-shaped valve-anchoring element 202. Loop-shaped valve-anchoring elements 200 have a larger surface area with which to grasp leaflets 82, and are hypothesized to be facilitate more atraumatic advancement with respect to tissue than are stick-shaped valve-anchoring elements 202. Stick-shaped valve-anchoring elements 202 are hypothesized to more easily, be insertable between chordae tendineae 80 (e.g., comb between chordae tendineae), than are loop-shaped valve-anchoring elements 200.

Prosthetic valve 42 may be coupled to one or more valve-anchoring elements 64, comprising loop-shaped valve-anchoring elements 200, stick-shaped valve-anchoring elements 202, or a combination thereof, in order to facilitate deployment of prosthetic valve 42 and coupling of the prosthetic valve to native heart valve 23. For example, stick-shaped valve-anchoring elements 202 may be used in areas of heart valve 23 in which chordae tendineae 80 are disposed more densely, whereas loop-shaped valve-anchoring elements 200 may be used to capture relatively exposed regions of leaflets 82. Loop-shaped valve-anchoring elements 200 and stick-shaped valve-anchoring elements 202 are illustrated here as fixed anchors. In some applications of the invention, elements 200 and 202 may be alternatively or additionally used as hinged anchors (e.g., hinged anchors 340) and/or clamping hinged anchors (e.g., clamping hinged anchors 350), as described hereinabove.

Figure 71:
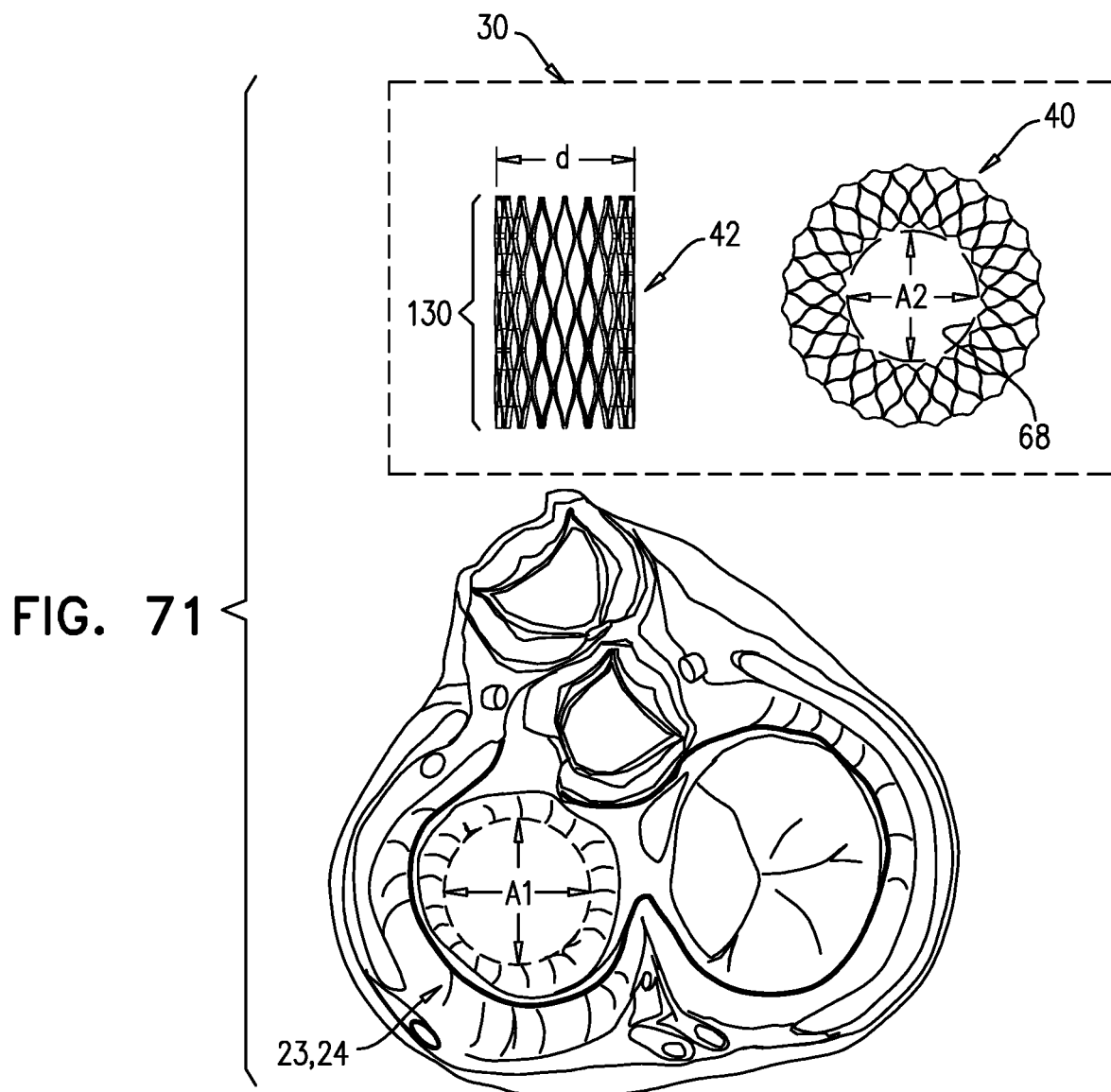
FIG. 71 is a schematic illustration of an implant comprising a prosthetic valve and a prosthetic valve support, in accordance with some applications of the present invention.

Reference is now made to FIG. 71, which is a schematic illustration of prosthetic valve 42, for placing inside native heart valve 23 of the patient, in accordance with some applications of the present invention. For this application of the invention, native valve 23 includes mitral valve 24. The primary structural element 130 of the prosthetic valve has a diameter d, and a corresponding cross-sectional area. The annulus of the native valve, which is typically saddle-shaped, defines an area A1, as shown. For some applications, area A1 is measured, e.g., using a measuring ring prior to deployment of valve 42. Taking this measuring into account, a suitably-sized prosthetic valve is chosen to be placed in the annulus, in a manner in which the cross-sectional area of the prosthetic valve in its deployed state is less than 90% (e.g., less than 80%, or less than 60%) of area A1.

For some applications, diameter d of the prosthetic valve is less than 25 mm, e.g., less than 20 mm, and/or more than 15 mm, e.g., 15-25 mm. For some applications, placing a prosthetic valve inside the native valve, with the dimensions of the native valve annulus and the prosthetic valve as described, facilitates sealing of the prosthetic valve with respect to the native valve, by the native valve leaflets closing around the outer surface of the prosthetic valve. In such applications, prosthetic valve 42 is implanted directly within native valve 23 (i.e., without support 40).

For some applications, a prosthetic valve support 40, that is shaped to define a lumen, is placed against the annulus of native valve 23 (e.g., as described with reference to FIGS. 1A-1H). The lumen of support 40 has a cross-sectional area A2 that is less than 90% (e.g., less than 80%, or less than 60%) of area A1 of native valve 23. As described hereinabove, prosthetic valve 42 is typically coupled to prosthetic valve support 40 and, thereby, to native valve 23, at least in part by expansion of the prosthetic valve such that primary structural element 130 exerts a radial force against inner edge 68 of prosthetic valve support 40. The cross-sectional area defined by the primary structural element 130 of the prosthetic valve, upon expansion of the prosthetic valve, is limited by the cross-sectional area A2 of the lumen of the prosthetic valve support 40 to less than 90% (e.g., less than 80%, or less than 60%) of area A1 of native valve 23. For some applications, placing a prosthetic valve support 40 at the native valve, as described, facilitates sealing of the prosthetic valve with respect to the native valve, by the native valve leaflets closing around the outer surface of the prosthetic valve.

Typically, placing a prosthetic valve inside the native valve with the dimensions of the native valve annulus, the prosthetic valve 42, and/or valve support 40 as described in the above paragraphs, facilitates sealing of the prosthetic valve with respect to the native valve. For some applications, the sealing is facilitated by the native leaflets being pushed against, and closing against, the outer surface of the frame of the valve during systole, in a similar manner to the manner in which native valve leaflets coapt during systole, in a healthy mitral valve.

Typically, as the diameter d of the prosthetic valve is increased, the proportion of the native leaflets that is pushed against the outer surface of the valve during systole is increased, thereby enhancing the sealing of the native leaflets with respect to the frame of the prosthetic valve. However, beyond a given diameter, as the diameter d of the prosthetic valve is increased, the native valve leaflets are pushed apart at the commissures, thereby causing retrograde leakage of blood through the commissures. Therefore, in accordance with some applications of the present invention, prosthetic valve 42, and/or valve support 40 are chosen such that the cross-sectional area of the prosthetic valve (when expanded inside the valve support) is less than 90% (e.g., less than 80%, or less than 60%) of area A1 of native valve 23. Thus, the valve support facilitates additional sealing of the prosthetic valve with respect to the native valve, by the native valve leaflets closing around the outer surface of the prosthetic valve, while not causing retrograde leakage of blood through the commissures.

For some applications, in order to facilitate the sealing of the native valve around the outer surface of the prosthetic valve, a material is placed on the outer surface of the prosthetic valve in order to provide a sealing interface between the prosthetic valve and the native valve. For example, a smooth material that prevents tissue growth (e.g., polytetrafluoroethylene (PTFE), and/or pericardium) may be placed on the outer surface of the prosthetic valve. Alternatively or additionally, a material that facilitates tissue growth (such as polyethylene terephthalate; PET) may be placed on the outer surface of the prosthetic valve, in order to (a) act as a sealing interface between the native valve and the prosthetic valve, and (b) facilitate tissue growth around the prosthetic valve to facilitate anchoring and/or sealing of the prosthetic valve.

Reference is made to FIGS. 72A-D, which are schematic illustrations of an implant 2030, comprising a prosthetic valve support 2040, and a prosthetic valve 2042, in accordance with some applications of the invention. Implant 2030 is configured to be implanted at a native heart valve of a subject, such as the mitral valve 2024 of the subject.

Figure 72A:
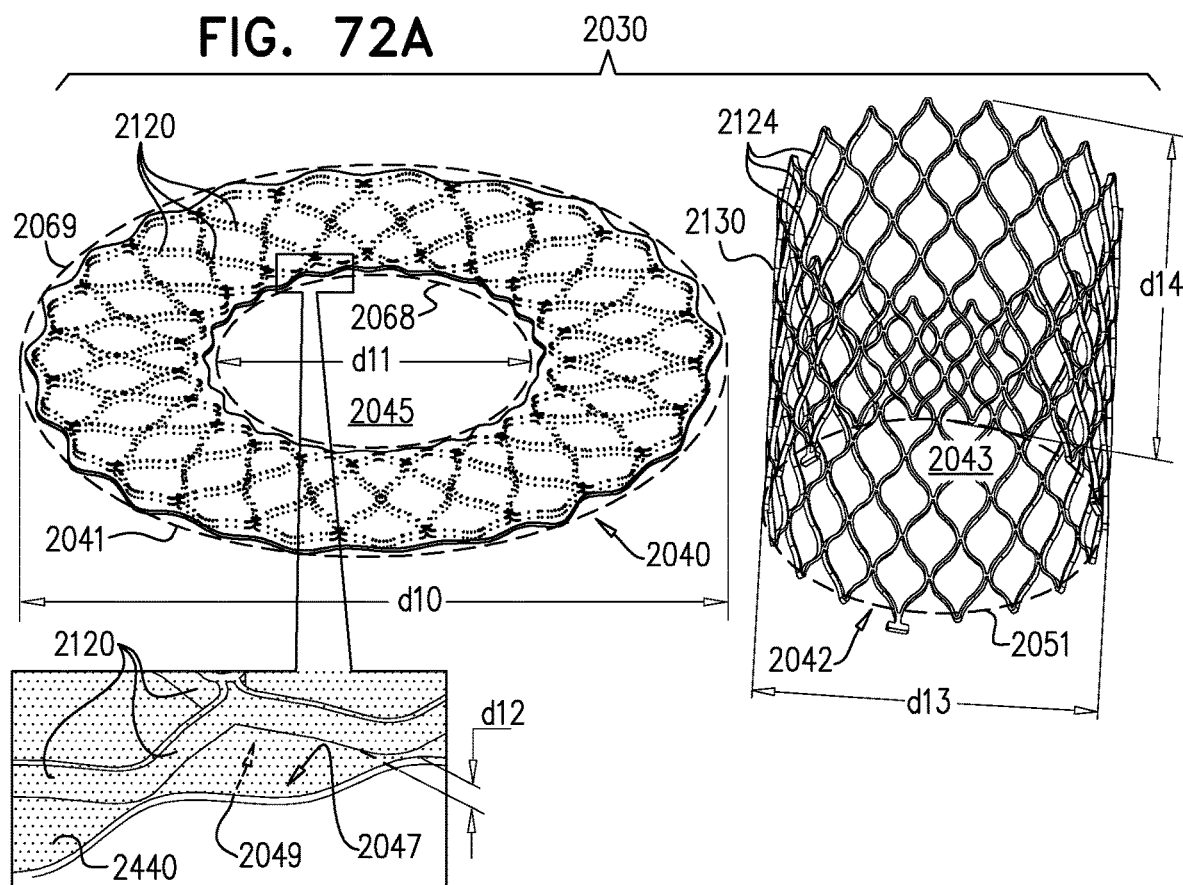

FIG. 72A shows support 2040 and prosthetic valve 2042 of implant 2030 in respective fully uncompressed configurations thereof. Support 2040 comprises an upstream support portion 2041, which is shaped to define an opening 2045, and configured to be placed against an upstream side of the native valve of the subject (e.g., against an atrial side of the mitral valve of the subject, such as against the annulus of the mitral valve of the subject). Typically, upstream support portion 2041 is configured to be placed against the upstream side of the native valve such that the entire of opening 2045 is disposed above (i.e., upstream and within a periphery defined by) the orifice of the native valve. Typically, upstream support portion 2041 is configured and/or selected such that opening 2045 has a greatest diameter that is less than 90% (e.g., less than 80%, e.g., as less than 60%, such as less than 50%) of a greatest diameter of the orifice of the native valve. Typically, upstream support portion 2041 is generally annular (e.g., portion 2041 and opening 2045 are generally elliptical, circular, and/or oval).

In the fully uncompressed configuration thereof, upstream support portion 2041 typically has an outer perimeter 2069 of length between 125 and 190 mm (e.g., between 140 and 170 mm, such as between 140 and 150 mm), and an inner perimeter 2068 (that defines opening 2045) of length between 62 and 105 mm (e.g., between 65 and 80 mm, such as between 75 and 80 mm). When upstream support portion 2041 is annular, the upstream support portion, in the fully uncompressed configuration thereof, typically has an outer diameter d10 (e.g., a greatest outer diameter) of between 40 and 80 mm (e.g., between 40 and 70 mm, such as between 40 and 60 mm), and an inner diameter d11 (e.g., a greatest inner diameter) of between 20 and 35 mm (e.g., between 23 and 32 mm, such as between 25 and 30 mm). That is, opening 2045 typically has a diameter of between 20 and 35 mm (e.g., between 23 and 32 mm, such as between 25 and 30 mm). Typically, outer perimeter 2069 has a length that is at least 10% (e.g., at least 50%, such as at least 80%) greater than inner perimeter 2068.

In the fully uncompressed configuration thereof, upstream support portion 2041 is typically (but not necessarily) generally flat (e.g., laminar, and/or planar). For some applications, in the fully uncompressed configuration, portion 2041 assumes a frustoconical shape, typically arranged from the generally flat composition of the portion. Portion 2041 has a thickness of less than 5 mm, such as less than 2 mm. Opening 2045 has a depth (e.g., a height) d12 from an upstream side 2047 of the upstream support portion to a downstream side 2049 of the upstream support portion. Depth d12 of opening 2045 is less than 5 mm, such as less than 2 mm. Typically, therefore, inner diameter d11 is more than 4 times (e.g., more than 6 times, such as more than 10 times) greater than depth d12. That is, opening 2045 is more than 4 times (e.g., more than 6 times, such as more than 10 times) wider than it is deep. Typically, in the fully uncompressed configuration, upstream support portion 2041 has a total height of less than 10 mm (e.g., less than 5 mm, such as less than 2 mm).

Typically, inner perimeter 2068 comprises, or is defined by, a free inner edge of upstream support portion 2041. That is, opening 2045 resembles a hole cut out of a lamina (e.g., out of a disc). For some applications, inner perimeter 2068 comprises, or is defined by, a curved and/or folded inner edge of upstream support portion 2041. If the inner perimeter of upstream support portion 2041 comprises, or is defined by, a curved or folded edge, then a radius of curvature of the curved or folded edge is typically less than 2.5 mm, such as less than 1 mm. That is, the curve or fold of the edge is generally sharp, such that when viewed from within opening 2045, the curved or folded edge looks generally like a free edge.

It is to be noted that, for simplicity, upstream support portion 2041 is generally described herein in terms of symmetrical geometric shapes (e.g., ellipse and frustum), but that the upstream support portion may assume a symmetrical or an unsymmetrical shape.

Prosthetic valve 2042 comprises a generally tubular (e.g., cylindrical) primary structural element 2130, shaped to define a lumen 2043 therethrough, and at least one check valve element (not shown), configured to regulate blood flow through the prosthetic valve. Typically, the check valve element comprises one or more prosthetic valve leaflets, disposed in lumen 2043, and coupled (e.g., sutured) to the primary structural element. For some applications of the invention, the check valve element comprises a ball, disc, or other check valve component. For some applications of the invention, prosthetic valve 2042 comprises a commercially-available stent-based prosthetic valve.

Prosthetic valve 2042 is configured to be placeable in opening 2045 of support 2040, and couplable to the support by being expandable within this opening, e.g., as described in more detail hereinbelow. Typically, support 2040 comprises tissue-engaging elements (e.g., support-anchoring elements), such as those described herein (not shown in FIGS. 72A-D), and is couplable to the native valve, such that coupling of prosthetic valve 2042 to the support, couples the prosthetic valve to the native valve. For some applications, prosthetic valve 2042 comprises tissue-engaging elements (e.g., valve-anchoring elements), such as those described herein (not shown in FIGS. 72A-D), and is alternatively or additionally directly couplable to the native valve.

In the fully uncompressed configuration thereof, prosthetic valve 2042 typically has a perimeter 2051 of length between 62 and 110 mm (e.g., between 70 and 90 mm, such as between 80 and 90 mm), and a height d14, (i.e., a length from an upstream end to a downstream end) of between 15 and 40 mm (e.g., between 20 and 35 mm, such as between 25 and 25 mm). When structural element 2130 is cylindrical, prosthetic valve 2042, in the fully uncompressed configuration thereof, typically has a diameter d13 of between 20 and 35 mm (e.g., between 25 and 35 mm, such as between 25 and 30 mm). Typically, support 2040 and prosthetic valve 2042 are configured and/or selected (e.g., paired), such that perimeter 2051 is slightly (e.g., between 1 and 15 mm, such as between 1 and 7 mm) greater than perimeter 2068, and/or that diameter d13 is slightly (e.g., between 1 and 5 mm, such as between 1 and 3 mm) greater than diameter d11.

In the respective fully uncompressed configurations thereof, height d14 of prosthetic valve 2042 is typically at least 1.5 times greater (e.g., at least 3 times greater, such as at least 5 times greater) than the total height of upstream support portion 2041.

Typically, support 2040 comprises a lattice structure which defines a plurality of struts 2120, typically in a repeating arrangement, and a plurality of voids between the struts. Typically, upstream support portion 2041 comprises the lattice structure of support 2040. Typically, prosthetic valve 2042 comprises a lattice structure which defines a plurality of struts 2124, and a plurality of voids between the struts. Support 2040 and prosthetic valve 2042 typically have shape-memory (e.g., resilient, pseudoelastic and/or superelastic) properties. Typically, struts 2120 and/or struts 2124 comprise a shape-memory (e.g., resilient, pseudoelastic and/or superelastic) material, such that support 2040 and/or prosthetic valve 2042 are compressible when a compressive force is applied (e.g., prior to implantation), and re-expandable when the compressive force is removed (e.g., during implantation), as described hereinbelow. Non-limiting examples of materials that the support (e.g., struts 2120) and/or prosthetic valve (e.g., struts 2124) may comprise include nickel-titanium (Nitinol), stainless steel, nickel cobalt, cobalt chrome, titanium, tantalum, and palladium.

Typically, support 2040 and/or prosthetic valve 2042 are at least in part covered with a covering 2440 (for clarity, covering 2440 is only shown on support 2040). Non-limiting examples of materials that covering 2440 may comprise include polyethylene terephthalate (e.g., polyester), polytetrafluoroethylene (e.g., Teflon, ePTFE), and pericardial tissue. For some applications, covering 2440 comprises a fabric. Typically, a thickness of the covering is less than 0.5 mm, such as less than 0.2 mm, e.g., less than 0.1 mm, or less than 0.05 mm. In FIG. 72A, struts 2120 are shown in phantom, as they are covered by covering 2440.

For some applications of the invention, covering 2440 is configured to facilitate blood flow through the prosthetic valve, e.g., to channel blood through lumen 2043 defined by prosthetic valve 2042, and/or to prevent leakage (1) between the prosthetic valve and support 2040, and/or (2) between implant 2030 and the native valve. For some applications of the invention, the covering is configured to mask sharp and/or hard surfaces (e.g., metal surfaces, such as surfaces of struts 2120 and/or 2124), and thereby to protect native tissues from being damaged by such surfaces. For some applications of the invention, the covering is configured to facilitate (e.g., to enhance) coupling between support 2040 and prosthetic valve 2042 (e.g., as described hereinbelow), such as by increasing friction. For some applications of the invention, the covering is configured to facilitate (e.g., to encourage) growth of tissue (e.g., fibrosis) over one or more components of implant 2030.

Figure 72B:
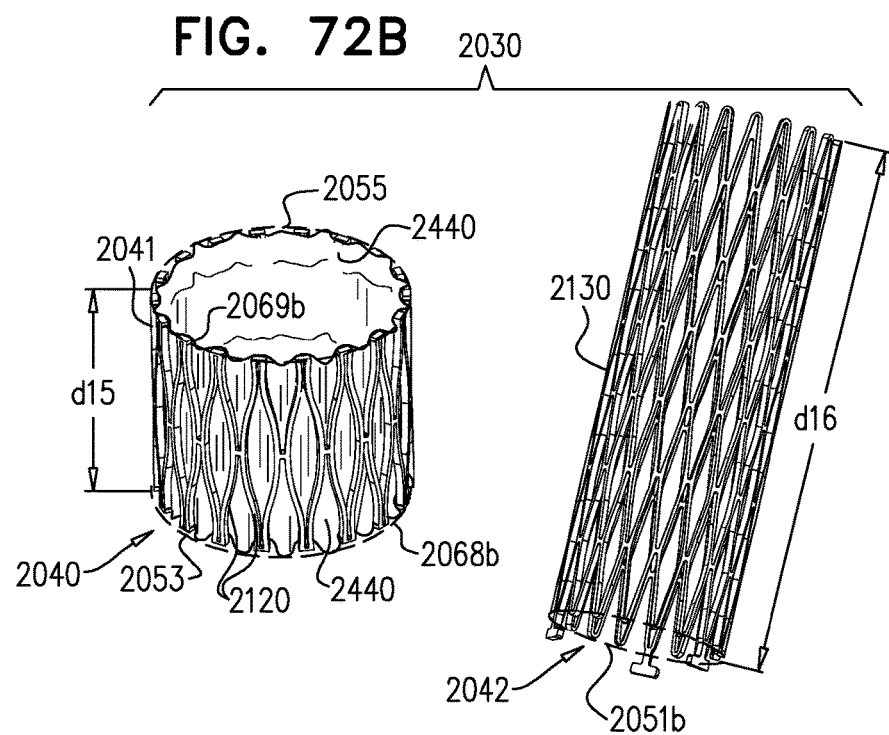

FIG. 72B shows support 2040 and prosthetic valve 2042 of implant 2030 in respective compressed configurations thereof, typically for delivery to the native valve. Typically, support 2040 and prosthetic valve 2042 are delivered percutaneously (e.g., transcatheterally). Typically, the support and the valve component are delivered to the native valve transluminally (e.g., transfemorally). For some applications, support 2040 and prosthetic valve 2042 are delivered to the native valve transatrially. For some applications, support 2040 and prosthetic valve 2042 are delivered to the native valve transapically. In the compressed configuration thereof, upstream support portion 2041 is typically generally cylindrical, and is typically delivered to a site that is upstream of the native valve of the subject (e.g., the left atrium, upstream of the mitral valve of the subject), such that a downstream (e.g., distal) end 2053 of the support has a perimeter 2068*b*, which is a compressed inner perimeter 2068, and an upstream end 2055 of the support comprises perimeter 2069*b*, which is a compressed outer perimeter 2069.

In the compressed configuration thereof, upstream support portion 2041 typically has (e.g., perimeters 2068*b* and 2069*b* have) a perimeter of length between 9 and 30 mm (e.g., between 15 and 25 mm, such as between 18 and 22 mm), and a height d15 of between 11 and 30 mm (e.g., between 15 and 30 mm, such as between 15 and 25 mm). When upstream support portion 2041, in the compressed configuration thereof, is cylindrical, portion 2041 typically has a diameter of between 3 and 9 mm (e.g., between 5 and 8 mm, such as between 6 and 7 mm).

In the compressed configuration thereof, prosthetic valve 2042 is typically generally cylindrical. Compression of the prosthetic valve typically comprises inwardly-radial compression, such that the component is narrower and taller in the compressed configuration than in the fully uncompressed configuration thereof. In the compressed configuration thereof, prosthetic valve 2042 typically has a perimeter 2051b (a compressed perimeter 2051) of between 9 and 30 mm (e.g., between 10 and 20 mm, such as between 15 and 20 mm), and a height d16 of between 16 and 41 mm (e.g., between 20 and 35 mm, such as between 20 and 30 mm). When prosthetic valve 2042, in the compressed configuration thereof, is cylindrical, prosthetic valve 2042 typically has a diameter of between 2 and 9 mm (e.g., between 3 and 8 mm, such as between 3 and 6 mm).

Support 2040 (e.g., portion 2041) and prosthetic valve 2042 typically have shape-memory properties, and are compressed (e.g., crimped) into their respective compressed configurations prior to (e.g., immediately prior to) the implantation procedure. Typically, the support and prosthetic valve are retained (e.g., 'constrained') in this configuration by a constraining member, such as an overtube, a delivery tube, and/or other delivery apparatus. Support 2040 and prosthetic valve 2042 are typically subsequently expanded (e.g., 'deployed') close to the site of implantation by releasing the constraining (e.g., compressive) force (e.g., by removing the constraining member). That is, the compressed configurations of prosthetic valve support 2040 (e.g., of upstream support portion 2041) and prosthetic valve 2042, described with reference to FIG. 72B, typically comprise constrained compressed configurations, and the fully uncompressed configurations, described with reference to FIG. 72A, are unconstrained uncompressed configurations.

FIG. 72C shows an end-view of implant 2030, with prosthetic valve 2042 coupled to prosthetic valve support 2040 by being disposed and expanded within opening 2045 (not shown in FIG. 72C) defined by portion 2041. FIG. 72C shows downstream side 2049 of support 2040, therefore struts 2120 are shown in solid form. Typically, prosthetic valve 2042 is delivered to opening 2045 in a constrained compressed configuration thereof (e.g., as described with reference to FIG. 72B), and expanded (e.g., released) in the opening, such that prosthetic valve 2042 applies a radially-expansive force against inner perimeter 2068 of portion 2041. Typically, this radially-expansive force facilitates coupling of prosthetic valve 2042 to portion 2041.

So as to provide the radially-expansive force, and as described hereinabove, prosthetic valve 2042 and support 2040 (e.g., portion 2041) are typically configured and/or selected (e.g., paired) such that perimeter 2051 of prosthetic valve 2042, in the fully uncompressed configuration thereof, is slightly greater than inner perimeter 2068 of portion 2041. When prosthetic valve 2042 is expanded within opening 2045, portion 2041 (e.g., inner perimeter 2068) thereby restricts the full expansion of prosthetic valve 2042. Therefore, in the coupled configuration shown in FIG. 72C, a perimeter 2051c of prosthetic valve 2042 is typically smaller than perimeter 2051 of the prosthetic valve in the fully uncompressed configuration thereof.

As described hereinabove (e.g., with reference to FIG. 72A), upstream support portion 2041 is configured to be placed against an upstream side of the native valve. As further discussed hereinbelow (e.g., with reference to FIG. 72K), it should be noted, that radial expansion of prosthetic valve 2042 against inner perimeter 2068 of upstream support portion 2041, thereby typically does not cause the prosthetic valve support to apply a radially-expansive force to the native valve.

For some applications, the prosthetic valve is couplable to the upstream support portion at a continuum of positions along the axial length of the prosthetic valve. That is, a physician can couple the prosthetic valve to the support at a continuum of depths within the support. For example, in applications in which the prosthetic valve is configured to be coupled to the upstream support portion solely by the radially-expansive force, the prosthetic valve may be coupled to the upstream support portion at a continuum of positions along the length of the prosthetic valve.

As described hereinabove, the lattice structures of prosthetic valve 2042 and portion 2041 typically define a repeating arrangement of struts, e.g., a repeating arrangement of shapes. For some applications, and as shown in FIG. 72C, prosthetic valve 2042 and portion 2041 comprise the same number of arrangement repeats. For some such applications, this matching number of repeats facilitates coupling of prosthetic valve 2042 and portion 2041. For example, and as shown in FIG. 72C, a number of inwardly-protruding ridges 2057 of portion 2041 protrude (e.g., interpose) within an equal number of corresponding circumferential voids defined by the lattice structure of prosthetic valve 2042. These ridges facilitate coupling of support 2040 and prosthetic valve 2042, e.g., by inhibiting axial movement of the prosthetic valve through opening 2045 of upstream support portion 2041.

Typically, the arrangement of repeating circumferential voids defined by the lattice structure of the prosthetic valve is repeated axially, thereby defining a prismatic (e.g., cylindrical) shape of the prosthetic valve. For some applications, the prosthetic valve is thereby couplable to the upstream support portion at a plurality of positions along the axial length of the prosthetic valve. That is, a physician can couple the prosthetic valve is couplable to the upstream support portion at a plurality of depths within the support. For example, in applications in which when a circumferential arrangement of voids is repeated four times along the axial length of the prosthetic valve, the prosthetic valve is typically couplable to the upstream support portion at four positions along the axial length of the prosthetic valve.

It is noted that, for some applications, the above descriptions of prosthetic valve 2042 and support 2040 are applicable to (e.g., the applications described above are combinable with) other embodiments of prosthetic valves and prosthetic valve supports described herein.

FIG. 72D shows an end view of an implant 2030a, comprising prosthetic valve 2042 coupled to a prosthetic valve support 2040a. For some applications of the invention, prosthetic valve support 2040a comprises, and/or is analogous to, another prosthetic valve support (e.g., prosthetic valve support 2040) described herein, and implant 2030a comprises, and/or is analogous to, other implants (e.g., implant 2030) described herein. Prosthetic valve support 2040a comprises an upstream support portion 2041a. For some applications of the invention, upstream support portion 2041a comprises, and/or is analogous to, other upstream support portions described herein. Upstream support portion 2041a comprises a plurality of inwardly-protruding barbs 2102, protruding from inner perimeter 2068 into opening 2045, such that, when prosthetic valve 2042 is expanded within opening 2045, barbs 2102 protrude (e.g., interpose) into voids defined by the lattice structure of prosthetic valve 2042. Similarly to the protrusion of ridges 2057 (described with reference to FIG. 72C) the protrusion of barbs 2102 further facilitates coupling of prosthetic valve support 2040a and prosthetic valve 2042. For some applications, barbs 2102 are disposed on (e.g., protrude from) ridges 2057. For some applications, barbs 2102 are disposed between ridges 2057 (e.g., protrude from sites between ridges 2057).

Reference is made to FIG. 73, which is a schematic illustration of a prosthetic valve support 2040b, in accordance with some applications of the invention. For some applications of the invention, prosthetic valve support 2040b comprises, and/or is analogous to, other prosthetic valve supports described herein. For some applications, prosthetic valve support 2040b comprises prosthetic valve support 2040, described hereinabove. Support 2040b comprises upstream support portion 2041, coupled to one or more clips 2900, configured to be couplable to one or more native leaflets 2082 of the native valve. For some applications of the invention, clips 2900 comprise tissue-engaging elements and/or support-anchoring elements (e.g., as described hereinabove). For some applications, prosthetic valve support 2040b alternatively or additionally comprises other tissue-engaging elements. Typically, support 2040b comprises two clips 2900, coupled to portion 2041 at or near inner perimeter 2068. Typically, clips 2900 are disposed opposite each other.

Typically, clips 2900 are articulatably coupled to portion 2041. That is, typically, clips 2900 can move, at least in part, with respect to portion 2041. Typically, each clip 2900 is coupled to portion 2041 via a connector 2540, which facilitates this movement. Typically, but not necessarily, connector 2540 comprises a flexible material, such as a fabric and/or polymer. For some applications, connector 2540 comprises one or more hinge points, to facilitate the movement of the clips.

Each clip 2900 typically comprises two or more clip elements, such as a clip arm 2920 and a clip arm 2922, movable with respect to each other. Typically, the clip arms are articulatably-coupled at an articulation point 2921, and are movable with respect to each other by the relative angular disposition of the clip arms being controllable. Typically, clip 2900 is configured to be biased (e.g., pre-set, such as shape-set) to be in a closed configuration, such that arms 2920 and 2922 are relatively disposed at a generally small angle (e.g., less than 45 degrees, such as less than 20 degrees, such as less than 5 degrees) to each other. For some applications, in the closed configuration of clip 2900, arms 2920 and 2922 touch each other at a site that other than the articulation point. Each clip 2900 is configured to be couplable to a native leaflet 2082 of the native valve by enveloping the native leaflet when the clip is in the open configuration thereof, and clipping the leaflet between the clip arms when the clip subsequently moves toward the closed configuration thereof.

Typically, arm 2920 is substantially immobile, and arm 2922 is (1) biased to assume a first configuration, and (2) movable between the first configuration and another configuration. Typically, the first configuration of arm 2922 is a closed configuration. Typically, the other configuration of arm 2922 is an open configuration, whereby a portion of arm 2922 that is furthest from articulation point 2921 is disposed (1) further from arm 2920 than is the same portion in the first, closed configuration, and (2) further from arm 2920 than a portion of arm 2922 that is closest to the articulation point. That is, an angular disposition of arm 2922 to arm 2920 is greater when arm 2922 is in the open configuration thereof, than when arm 2922 is in the closed configuration thereof. When arm 2922 is in the closed configuration thereof, clip 2900 is in the closed configuration thereof. When arm 2922 is in the open configuration thereof, clip 2900 is in the open configuration thereof. That is, clip 2900 is movable between open and closed configurations thereof, by arm 2922 moving between open and closed configurations thereof. FIG. 73 shows detailed illustrations of clip 2900 in the open and closed configurations, and further shows an exploded view of the components of clip 2900.

Clip 2900 further comprises a clip-controller interface, typically comprising a pull-wire 2924, which facilitates movement of arm 2922 between the closed and open configurations, i.e., relative angular movement of arms 2920 and 2922. Pull-wire 2924 is typically coupled to arm 2922, and controlled from outside the body of the subject. For example, pull-wire 2924 may be coupled to arm 2922, and extend to a clip controller (e.g., clip controller 2930, described with reference to FIGS. 74A-L) disposed within delivery apparatus, and ultimately controlled by a physician. Typically, pull-wire 2924 is coupled to arm 2922 such that (1) placing the pull-wire under tension (e.g., by pulling) moves arm 2922 toward the open configuration, and (2) releasing the tension, at least in part, allows the arm to return toward the closed configuration.

For some applications of the invention, both clips 2900 are controlled simultaneously by a user (e.g., clips 2900 are configured to operate simultaneously). For some applications, each clip 2900 is controllable independently. For some applications, clip 2900 further comprises one or more grips, such as teeth 2928, which facilitate the clamping of leaflets 2082 when clip 2900 is closed. For some applications, clips 2900 may alternatively or additionally be directly coupled to the prosthetic valve, and configured to couple the prosthetic valve directly to the native valve.

Reference is made to FIGS. 74A-L, which are schematic illustrations of steps in the implantation of implant 2030b, comprising prosthetic valve 2042 and prosthetic valve support 2040b, in a native heart valve, such as mitral valve 2024 of a subject, in accordance with some applications of the invention.

Figure 74A:
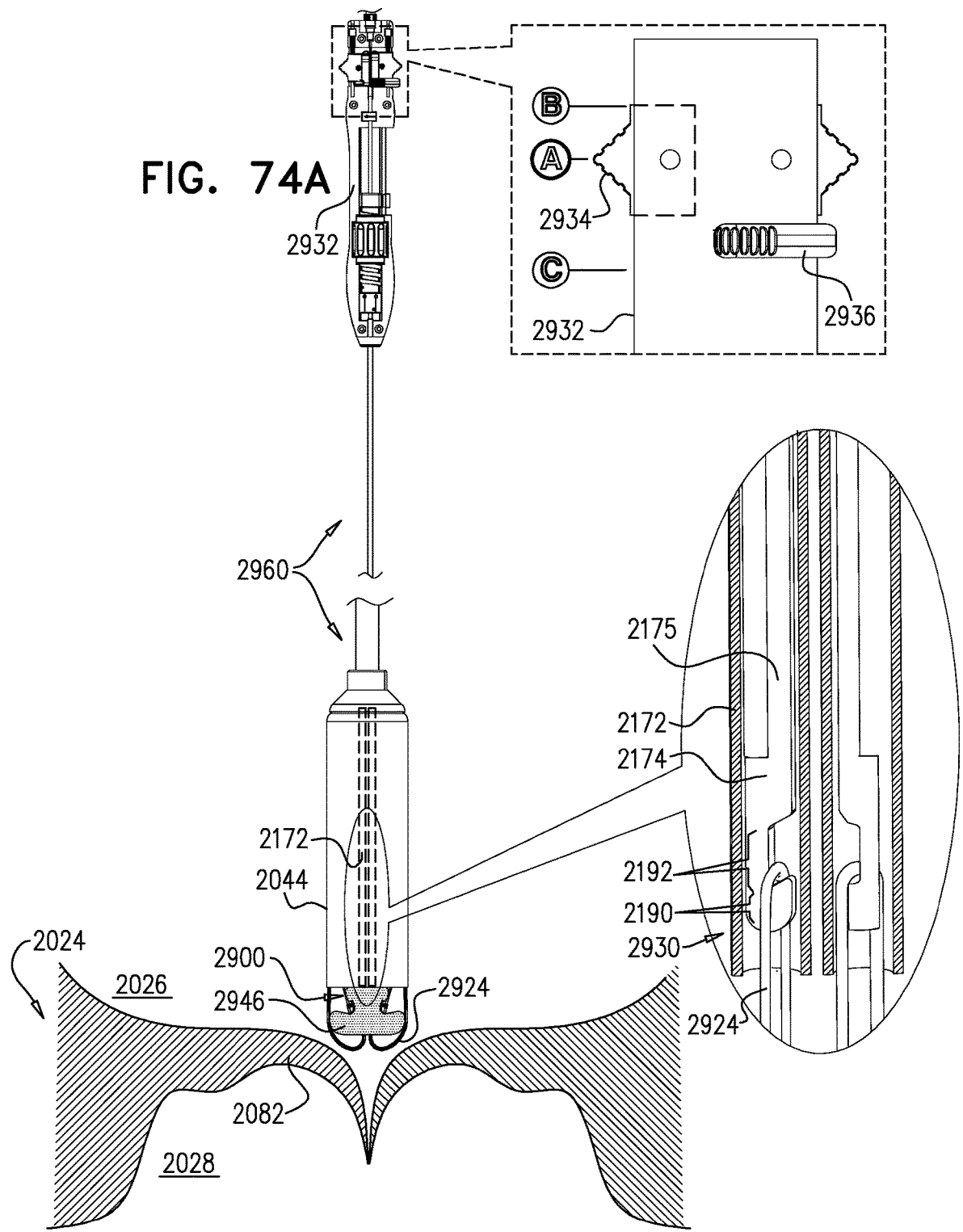

Prosthetic valve support 2040b is implanted using support-delivery apparatus, such as support-delivery apparatus 2960. As described hereinabove with reference to FIG. 73, each clip 2900 comprises a clip-controller interface, typically pull-wire 2924, which is configured to open the clip when pulled (i.e., placed under tension). For some applications of the invention, and as shown in FIG. 74A, support-delivery apparatus 2960 comprises at least one clip controller 2930, one end of pull-wire 2924 is coupled to clip arm 2922, and another end of the pull-wire is coupled to controller 2930. Controller 2930 comprises a tubular member 2172, shaped to define a lumen, and a plug 2174. Plug 2174 is dimensioned such that it is disposable in, and slidable through (e.g., within, into, and out of) the lumen of tubular member 2172. Plug 2174 comprises a restricting portion 2190 and a second portion 2192.

Typically, at least part of plug 2174 (e.g., restricting portion 2190) is dimensioned so as to fit tightly in the lumen of tubular member 2172, in a manner in which an outer surface of plug 2174 (e.g., an outer surface of portion 2190) is disposed very close to an inner surface of tubular member 2172, i.e., such that little space exists between the at least part of the plug and the tubular member. For example, the widest space between portion 2190 and member 2172 may be smaller than a thickness of pull-wire 2924. Typically, a surface of second portion 2192 is disposed further from the inner surface of tubular member 2172, than is the surface of the at least part of portion 2190.

Controller 2930 typically has at least three controller configurations, each configuration having a different relative disposition of plug 2174 within tubular member 2172. In a first controller configuration, plug 2174 is disposed at a first longitudinal position within tubular member 2172. In a second controller configuration, the plug is disposed at a second longitudinal position within the tubular member, the second position being more proximal (e.g., closer to a position outside the body; typically upstream) than the first longitudinal position. In a third controller configuration, the plug is disposed at a third longitudinal position, distal (e.g., downstream) to the first longitudinal position, such that at least restricting portion 2190 is disposed outside of (e.g., distal to) the tubular member.

Controller 2930 has at least one locking configuration, in which (1) at least part of restricting portion 2190 is disposed inside the lumen of tubular member 2172, and (2) pull-wire 2924, when coupled to the controller, is generally not decouplable from the controller. Typically, the first and second controller configurations, described hereinabove, are locking configurations. Controller 2930 further has at least one open configuration, in which (1) at least restricting portion 2190 is disposed outside the lumen of tubular member 2172, and (2) pull-wire 2924 is decouplable from the controller. Typically, the third controller configuration, described hereinabove, is an open configuration.

Typically, and as shown in FIG. 74A, pull-wire 2924 comprises, and/or is shaped to define, a loop, and is coupled to controller 2930 by at least part of the loop being disposed against second portion 2192 when the lock is in, or moves into, a locking configuration thereof. For some applications, pull-wire 2924 is generally flat (e.g., has an elongate transverse cross-section, e.g., is a strip), is shaped to define a hole, and is coupled to controller 2930 by at least part of restricting portion 2190 being disposed within the hole when the lock is in, or moves into, a locking configuration thereof. Restricting portion 2190 inhibits distal axial movement of the coupling lead, and tubular member 2172 inhibits lateral movement of the coupling lead (e.g., the inner surface of the tubular member holds the coupling lead against second portion 1192). Tubular member 2172 thereby facilitates coupling of pull-wire 2924 to plug 2174, and thereby to controller 2930.

Controller 2930 is typically controlled (e.g., the configurations of the controller, such as the disposition of plug 2174 within tubular member 2172, are typically selected), via a control rod 2175, using an extracorporeal controller, such as a control handle 2932, typically disposed at a proximal end of support-delivery apparatus 2960. Control handle 2932 comprises at least one adjuster 2934, each adjuster configured to control at least one clip 2900 of prosthetic valve support 2040*b*. Typically, control handle 2932 comprises two adjusters 2934, each adjuster configured to independently control one clip 2900. For clarity, however, adjusters 2934 are shown operating simultaneously. Typically, but not necessarily, adjuster 2934 has pre-defined positions in which it can reside, each pre-defined position of the adjuster corresponding to a respective configuration of controller 2930. That is, moving adjuster 2934 between the pre-defined positions thereof, moves controller 2930 between the configurations thereof. For illustrative purposes only, example pre-defined positions (A), (B) and (C) are indicated.

FIG. 74A shows support 2040*b* having been delivered, using support-delivery apparatus 2960, to left atrium 2026 of the heart of a subject (i.e., to a site upstream of native mitral valve 2024 of the subject). Support 2040*b* is typically delivered transcatheterally (e.g., transvascularly, such as transfemorally), while in a compressed configuration thereof (e.g., as described with reference to FIG. 72B for support 2040). Typically, support 2040*b* is delivered within an overtube 2044, which provides a constraining (e.g., compressive) force, to constrain the support in the compressed configuration thereof. Typically, upstream support portion 2041 of support 2040*b* is coupled to a scaffold, such as a core 2946, and constrained in the compressed configuration by being disposed within an overtube 2044 of the delivery apparatus. In the compressed configuration of support 2040*b*, clips 2900 are typically disposed downstream (e.g., distal) to the cylinder of upstream support portion 2041, and coupled to core 2946.

During delivery of support 2040*b*, and as shown in FIG. 74A, clips 2900 are typically in the closed configuration thereof. FIG. 74A shows clips 2900 exposed from the distal end of overtube 2044, overtube 2044 having been retracted (e.g., overtube 2044 having been moved proximally, and/or support 2040*b* having been moved distally). Adjuster 2934 of control handle 2932 is in a first position (A) (typically a middle position) thereof, and controller 2930 is in the first configuration thereof, whereby pull-wire 2924 is coupled to plug 2174, which is disposed within tubular member 2172.

Figure 74B:
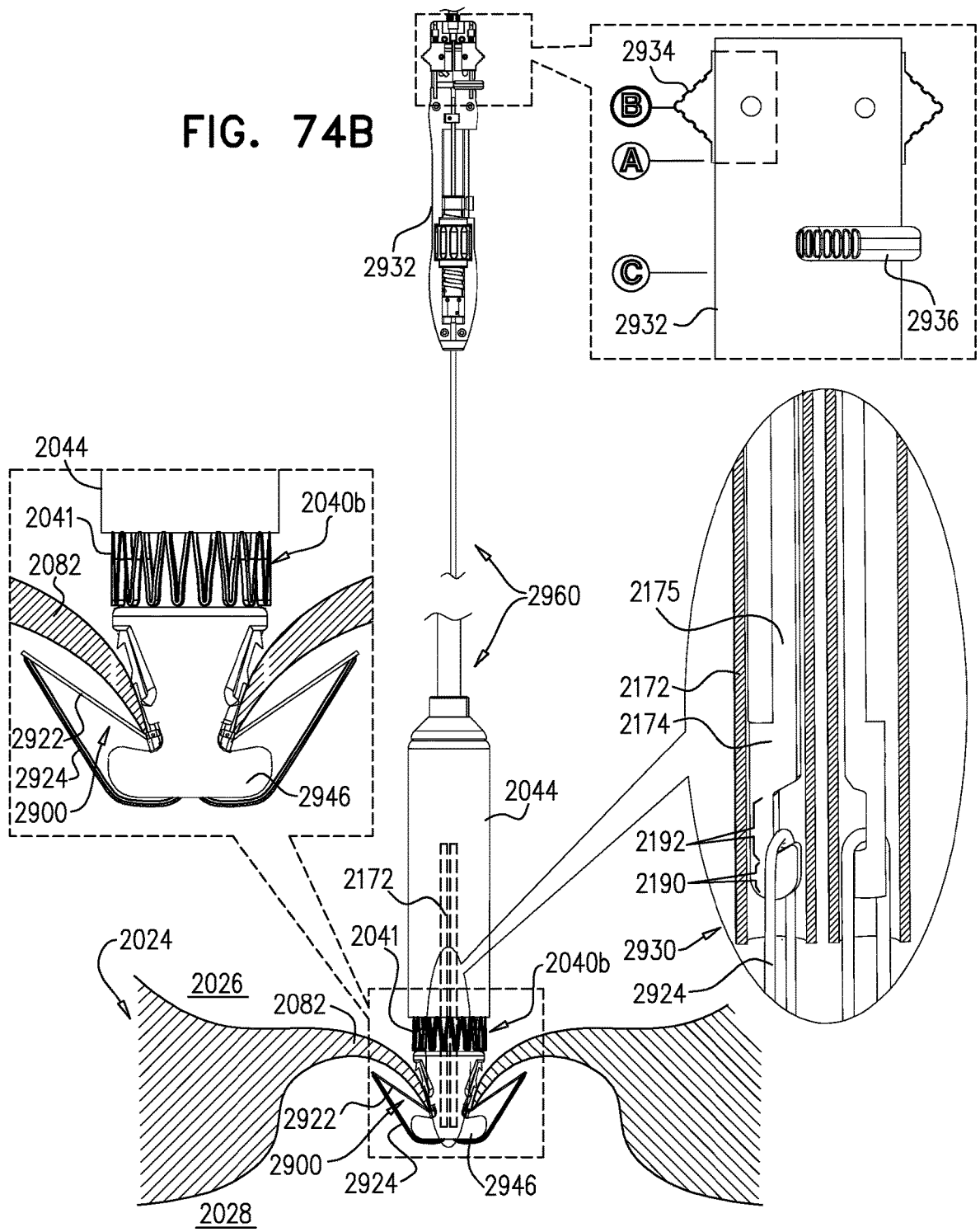

FIG. 74B shows support 2040*b* and core 2946 having been moved closer to the native valve, and clips 2900 enveloping leaflets 2082 of the native valve. Adjuster 2934 of control handle 2932 is in a second position (B) thereof (typically more proximal than the first position), and controller 2930 is in the second configuration thereof. Movement of controller 2930 into the second configuration thereof (i.e., moving plug 2174 proximally) places pull-wire 2924 under tension (i.e., pulls the pull-wire), thereby pulling clip arm 2922, and opening clip 2900. Using support-delivery apparatus 2960, the position of prosthetic valve support 2040*b* is adjusted, so as to envelope native leaflets 2082 between the clip arms of clips 2900.

FIG. 74C shows clips 2900, coupled (i.e., clipped) to native leaflets 2082. The user (e.g., the physician) couples the clips to the native leaflets by closing the clips while the leaflets are enveloped by the arms of the clips. Adjuster 2394 of control handle 2932 is in first position (A) thereof (i.e., has been returned to first position (A)), and controller 2930 is in the first configuration thereof (i.e., has been returned to the first configuration thereof). For some applications of the invention, control handle 2932 comprises a spring, which facilitates the return of adjuster 2394 to first position (A). For example, a user may apply a force to adjuster 2394 so as to move the adjuster to second position (B), and remove the force (e.g., release the adjuster) so as to return the adjuster to first position (A). Movement of controller 2930 into the first configuration thereof (i.e., moving plug 2174 distally) at least partly releases the tension on pull-wire 2924, allowing the bias of clip 2900 (e.g., of clip arm 2922) to return the clip toward the closed configuration. If a native leaflet 2082 is enveloped by the clip arms, the leaflet is sandwiched between the arms, thereby coupling the clip to the leaflet.

For some applications, visualization (e.g., imaging) techniques such as ultrasound are used to facilitate and/or confirm the coupling of clips 2900 to leaflets 2082. For example, an echocardiogram may be used to observe native leaflets 2082, and movement thereof. For some applications, coupling of both native leaflets by clips 2900 is accompanied by a generally lemniscate (e.g., 'FIG. 8') arrangement of the native leaflets, as shown in View A of FIG. 74C. Clips 2900 may be repeatedly opened and closed until coupling of the clips to leaflets 2082 has been achieved.

For some applications of the invention, clips 2900 further comprise a securing element (not shown), configured to secure the clips in the closed configuration, following coupling of the clips to the native leaflets. For some applications of the invention, the securing element is configured to secure the clips in one or a pre-defined selection of closed configurations (e.g., in a partially-closed configuration).

Figure 74D:
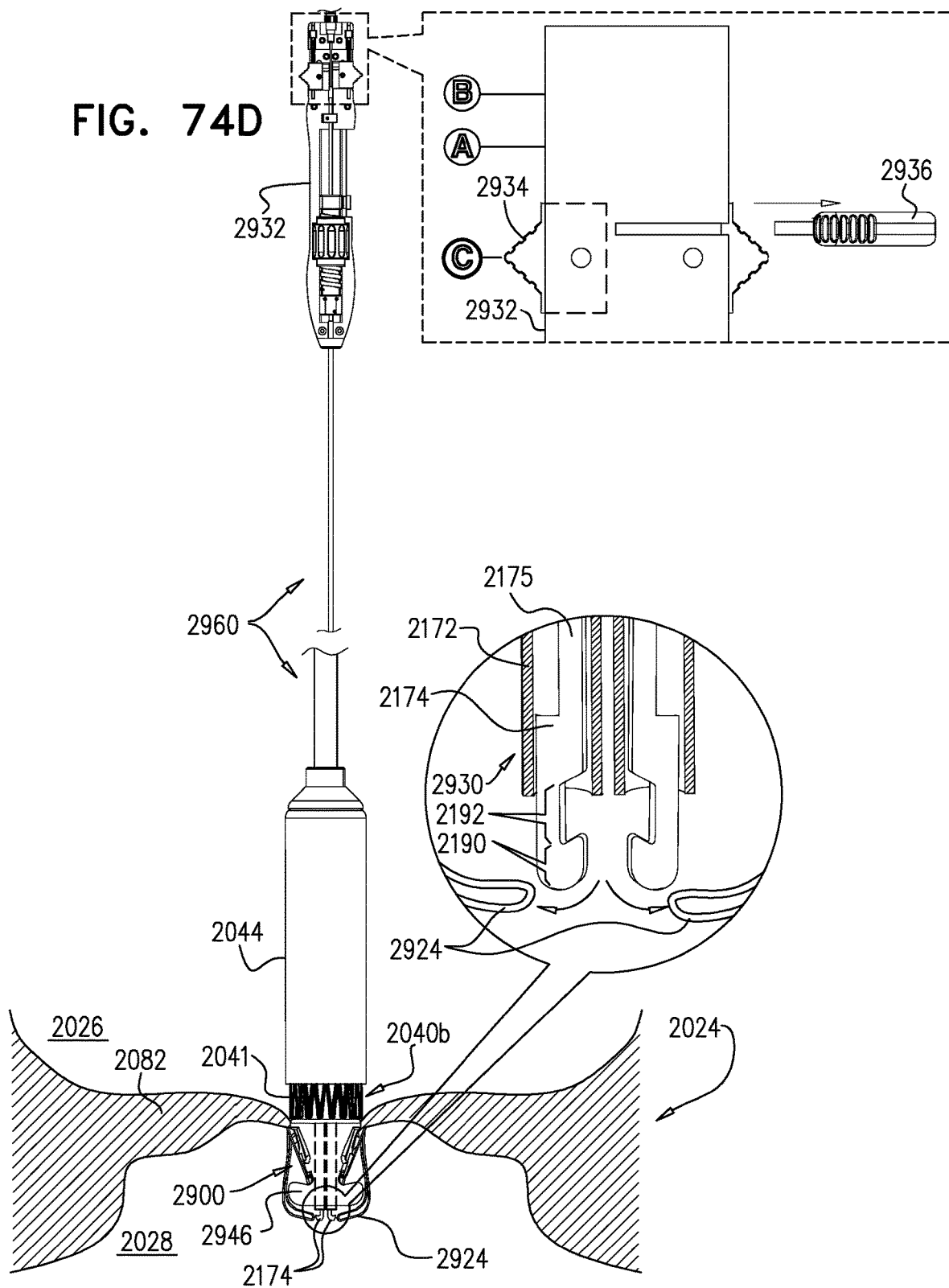

Reference is made to FIG. 74D. Following coupling of clips 2900 to native leaflets 2082, the clips are released (e.g., decoupled) from support-delivery apparatus 2960 (e.g., from core 2946) by decoupling pull-wire 2924 from controller 2930. To decouple the pull-wire from the controller, the user moves adjuster 2394 of control handle 2932 to third position (C) thereof (typically a distal position), thereby moving controller 2930 in the third configuration thereof, whereby at least restricting portion 2190 of plug 2174 is disposed outside of tubular member 2172. For some applications of the invention, control handle 2932 comprises a safety device, such as a safety lock 2936, configured to prevent inadvertent movement of adjuster 2394 into position (C), and thereby inadvertent release of clips 2900. For such applications, safety lock is disabled (e.g., removed) prior to releasing clips 2900.

Movement of controller 2930 into the third position thereof (i.e., moving at least part of plug 2174 outside of tubular member 2172) allows pull-wire 2924 to decouple from the controller. For some applications, pull-wire 2924 is configured to automatically decoupled from the controller when the controller moves into the third position. For example, the pull-wire may comprise a shape-memory (e.g., resilient, pseudoelastic and/or superelastic) material configured to lift the loop of the pull-wire away (e.g., laterally away) from plug 2174 when restricting portion 2190 moves outside of the tubular member. Non-limiting examples of materials that pull-wire 2924 may comprise include nickel-titanium (Nitinol), stainless steel, nickel cobalt, cobalt chrome, titanium, tantalum, palladium, polyester, PTFE, nylon, and cotton. For some applications of the invention, pull-wire 2924 is biodegradable (e.g., bioabsorbent).

Figure 74E:
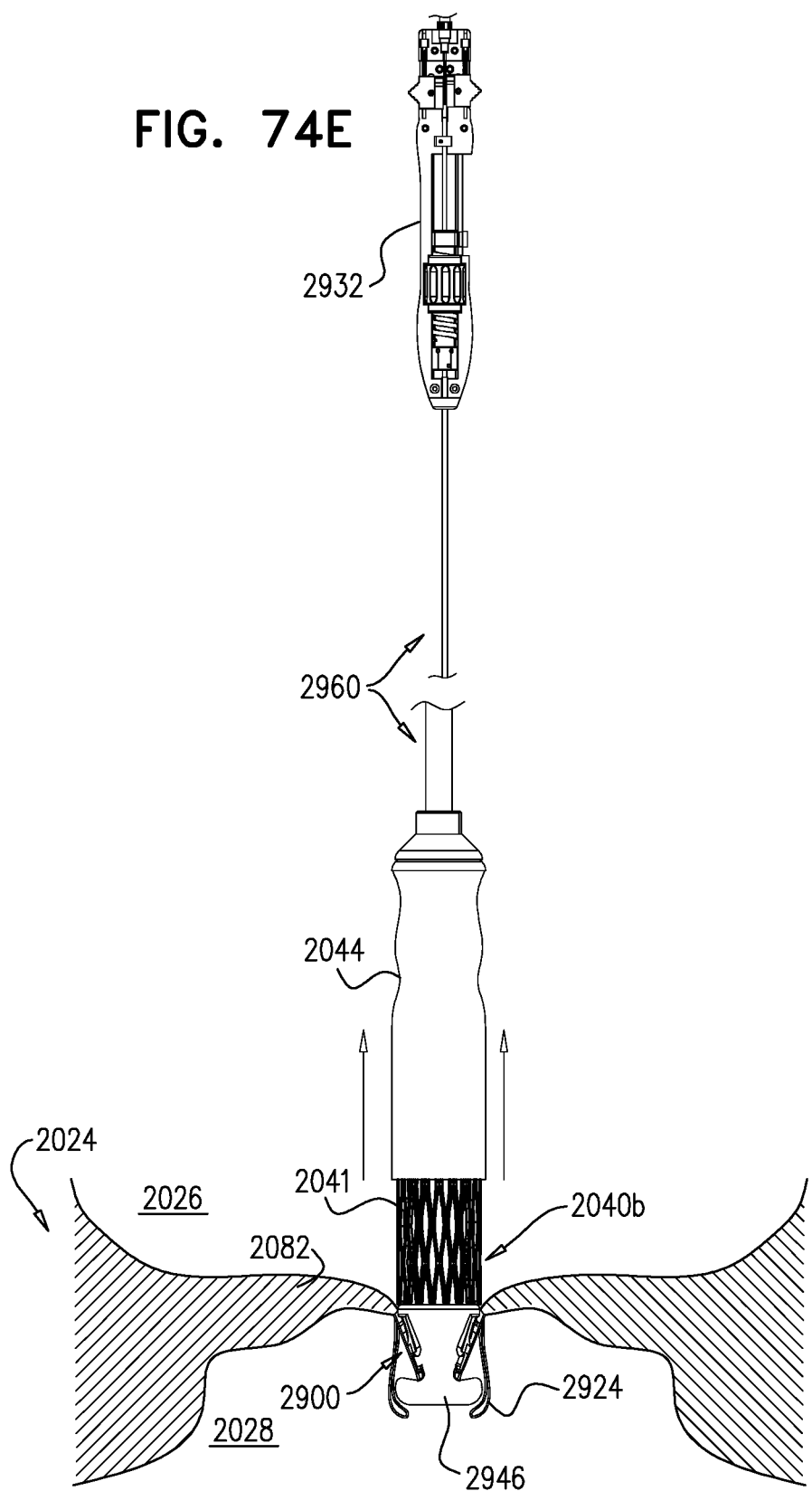

Reference is now made to FIG. 74E. Following the decoupling of clips 2900 from controller 2930, upstream support portion 2041 of prosthetic valve support 2040b is deployed (e.g., released from overtube 2044). Typically, overtube 2044 is withdrawn proximally, exposing successively more proximal (e.g., upstream) parts of portion 2041. As described hereinabove (e.g., with reference to FIG. 72A), portion 2041 typically comprises a shape-memory material, and is compressed prior to implantation. Portion 2041 thereby automatically expands upon removal of the constraining (e.g., compressive) force, i.e., when overtube 2044 is withdrawn.

Immediately prior to the release of prosthetic valve support 2040b from the overtube, the total length of overtube 2044 and support 2040b may be double or more than that of the overtube or support alone. For some applications, this extra length can hinder the movement and/or removal of the overtube from the body of the subject. For some applications, overtube 2044 comprises a flexible and/or soft material, such as a fabric or polymer, thereby becoming flexible as support 2040b is removed from within the overtube. It is hypothesized that this composition/configuration of overtube 2044 facilitates deployment of support 2040b, and removal of the overtube from the body of the subject.

Figure 74F:
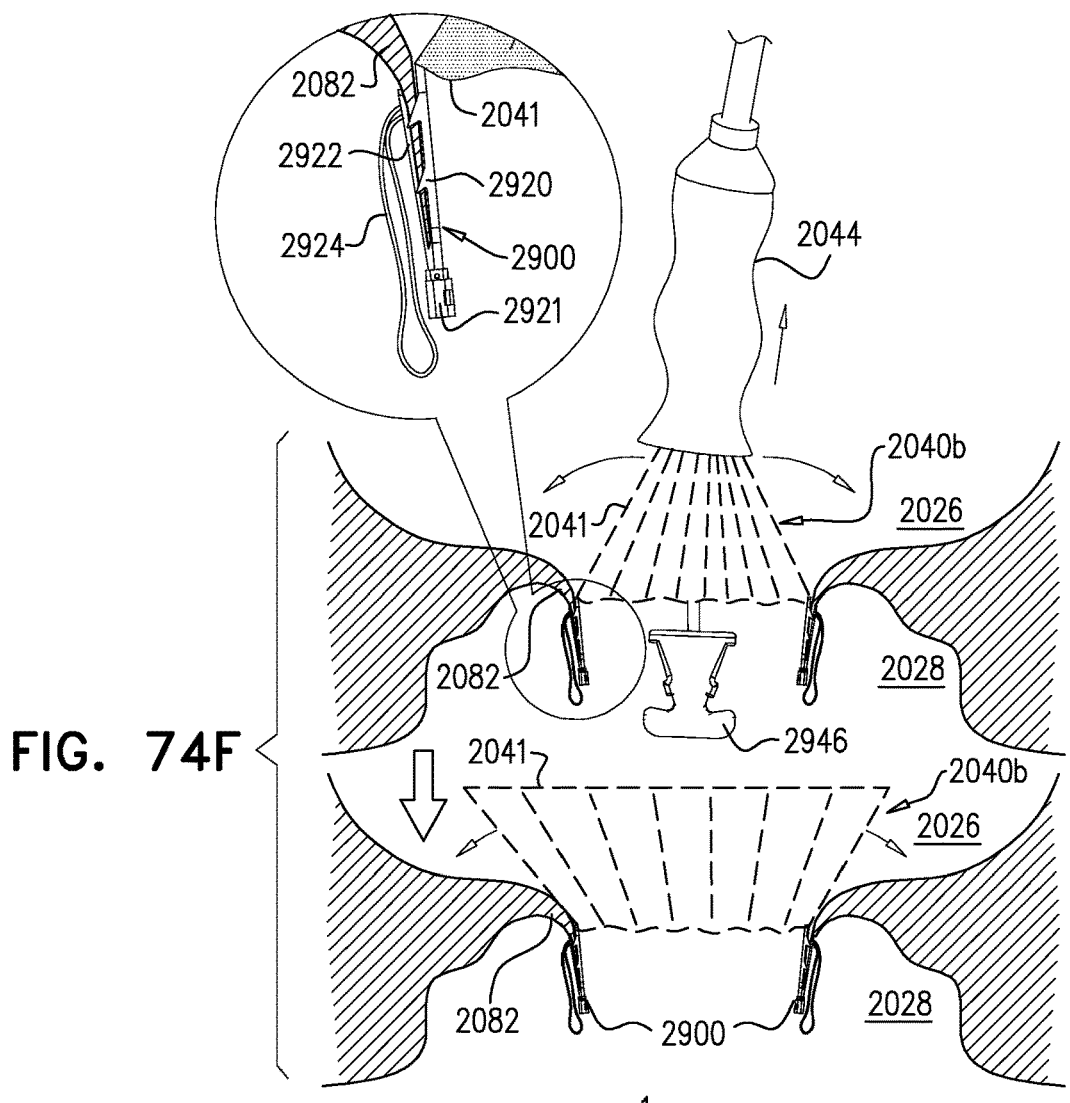

FIG. 74F shows prosthetic valve support 2040b during full deployment thereof. Typically, and as described hereinabove, when upstream support portion 2041 is delivered to the native valve in the cylindrical, compressed configuration, downstream (e.g., distal) end 2053 of the cylinder has perimeter 2068b, which is a compressed inner perimeter 2068. Distal end 2053, and therefore the inner perimeter of portion 2041, is thereby coupled to the native valve before deploying (e.g., expanding) upstream (e.g., proximal) end 2055, and therefore the outer perimeter of portion 2041. That is, the inner perimeter of portion 2041 typically engages the native valve before the outer perimeter.

The two phases illustrated in FIG. 74F illustrate typical behavior of upstream support portion 2041 during deployment thereof. As downstream end 2053, moves out of overtube 2044, it expands toward becoming and/or defining inner perimeter 2068 of portion 2041. As upstream end 2055 moves out of overtube 2044, it expands to become outer perimeter 2069. Due to this arrangement, during deployment, upstream end 2055 typically expands more than does downstream end 2053. For some applications, upstream end 2055 expands more than 1.5 times (e.g., more than twice) as much as does downstream end 2053.

Figure 74G:
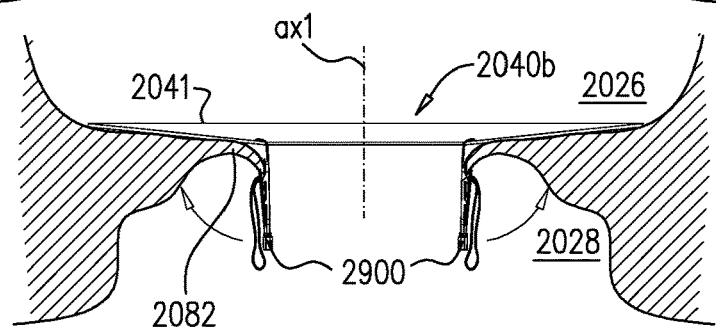
Figure 74H:
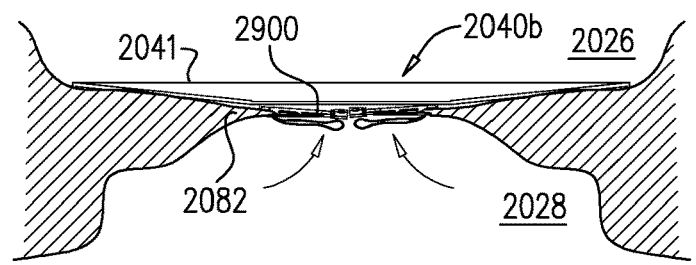
Figure 74I:
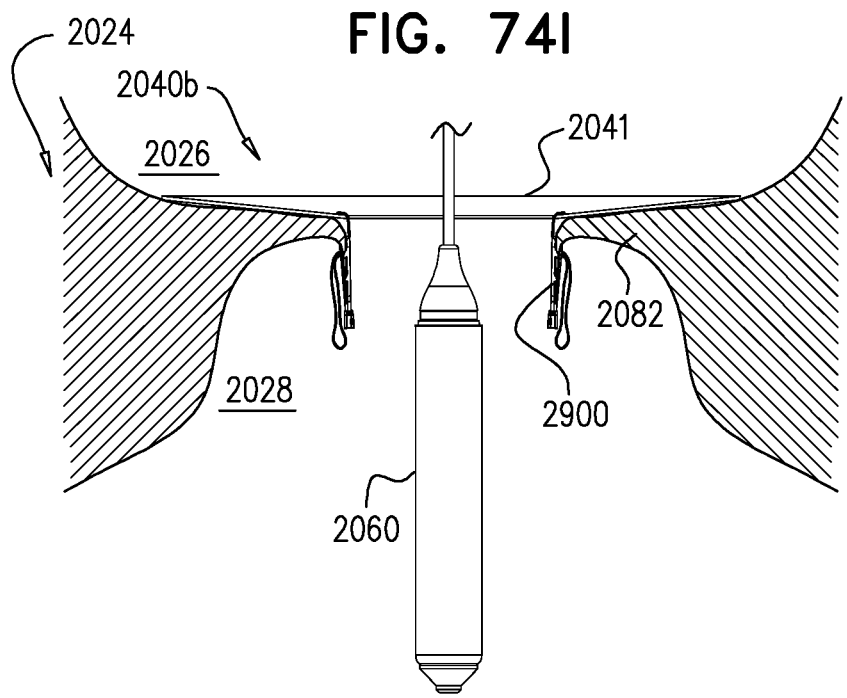

Reference is now made to FIGS. 74G-H, which show support 2040b in the implanted configuration thereof. Upstream support portion 2041 is described hereinabove (e.g., with reference to FIG. 72A) as being generally flat when in its fully uncompressed configuration. However, portion 2041 is typically at least partly resilient. For example, as described hereinabove, portion 2041 typically comprises a shape-memory material. Implanting support 2040b, as described with reference to FIGS. 74A-F, disposes portion 2041 against the upstream side of the native valve (e.g., the upstream side of the native valve annulus). Typically, portion 2041 is held tightly against the upstream side of the native valve by clips 2900, and deforms responsively to the contours of the native tissue (e.g., conforms to the native annulus), thereby assuming an implanted configuration. For some applications, portion 2041 repeatedly deforms responsively to the contours of the native tissue, as the native tissue repeatedly changes shape with the cardiac cycle.

Upstream support portion 2041 and clips 2900 are typically configured such that, when support 2040b is implanted at the native valve, upstream support portion inhibits downstream (e.g., ventricular) movement of support 2040b, and clips 2900 inhibit upstream (e.g., atrial) movement of the support. Typically, clips 2900 are configured to couple the prosthetic valve support to the native valve such that upstream support portion 2041 is in contact with the upstream side of the native valve (e.g., with the upstream side of the native annulus). For some applications, clips 2900 are the only component of prosthetic valve support 2040b that inhibits upstream movement of prosthetic valve support.

The dimensions of upstream support portion 2041 in the implanted configuration thereof are typically similar to those of the same portion in the fully uncompressed configuration thereof, with any difference between the configurations typically due to the portion being implanted. For example, in some applications in which upstream support portion 2041 is generally flat in the fully uncompressed (e.g., unconstrained uncompressed) configuration thereof, when support 2040b is implanted at the native valve, clips 2900 apply a downstream force to inner perimeter 2068 of upstream support portion 2041, thereby inducing portion 2041 to assume a frustoconical shape in the implanted configuration thereof. When upstream support portion 2041 is generally frustoconical in the implanted configuration thereof, a surface of portion 2041 typically has an angle of less than 60 degrees (e.g., less than 45 degrees) from a plane of the smaller base of the frustum. (As shown in FIG. 74G, for example, this angle is approximately 10 degrees.) That is, when upstream support portion 2041 is generally frustoconical in the implanted configuration thereof, portion 2041 is closer to being planar than it is to being cylindrical. Alternatively, the surface of portion 2041 has an angle of greater than 60 degrees from the smaller base of the frustum. It is to be noted that, although upstream support portion 2041 is generally described herein in terms of symmetrical geometric shapes (e.g., ellipse and frustum), when conforming to native tissue, the upstream support portion may assume a symmetrical or an unsymmetrical shape.

Thus, in general, as shown in and described with reference to FIGS. 72A-74L, (1) the fully uncompressed configurations of upstream support portion 2041 described with reference to FIG. 72A are typically unconstrained uncompressed configurations, (2) the compressed configurations of portion 2041 described with reference to FIG. 72B are typically constrained compressed configurations, and (3) the implanted configurations of portion 2041 described with reference to FIG. 74F are typically constrained uncompressed configurations.

When implanted at the native valve, and thereby in the implanted configuration thereof, no part of upstream support portion 2041 is disposed downstream of native leaflets 2082 (e.g., no part of portion 2041 is disposed in ventricle 2028). Typically, when prosthetic valve support 2040b is implanted at the native valve, no part of support 2040b that circumscribes a space (e.g., opening 2045) is disposed downstream of the native leaflets. For some applications, when prosthetic valve support 2040b is implanted at the native valve, no part of support 2040b that circumscribes a space is disposed downstream of the native annulus.

When implanted at the native valve, and thereby in the implanted configuration thereof, a height (i.e., a length along an upstream-to-downstream axis ax1 from a most upstream end to a most downstream end) of upstream support portion 2041, is typically less than 20 mm (e.g., less than 10 mm, such as less than 5 mm). Typically, when prosthetic valve support 2040b is implanted at the native valve, no part of the support that circumscribes a space has a height of more than 20 mm. For some applications, when prosthetic valve support 2040b is implanted at the native valve, no part of the support that circumscribes a space has a height of more than 10 mm. For some applications, when prosthetic valve support 2040b is implanted at the native valve, no part of the support that circumscribes a space has a height of more than 5 mm.

As described hereinabove with reference to FIG. 73, clips 2900 are articulatably-coupled to upstream support portion 41 of prosthetic valve support 2040b. Following the implantation (e.g., delivery, coupling and deployment) of prosthetic valve support 2040b, clips 2900 can move, at least in part, with respect to portion 2041, thereby allowing native leaflets 2082 to continue to function, at least in part. That is, implantation of prosthetic valve support 2040b at a native valve, does not eliminate the native blood flow regulation functionality of the native valve. FIGS. 74G-H show such movement of native leaflets 2082, and clips 2900. FIG. 74G shows support 2040b implanted at mitral valve 2024, with native leaflets 2082 open (e.g., during ventricular diastole), clips 2900 having moved away from each other. FIG. 74H shows support 2040b implanted at mitral valve 2024, with native leaflets 2082 closed (e.g., during ventricular systole), clips 2900 having moved toward each other. Typically, each clip moves through an arc of greater than 45 degrees (e.g., greater than 60 degrees, such as greater than 80 degrees) during each cardiac cycle.

Figure 74J:
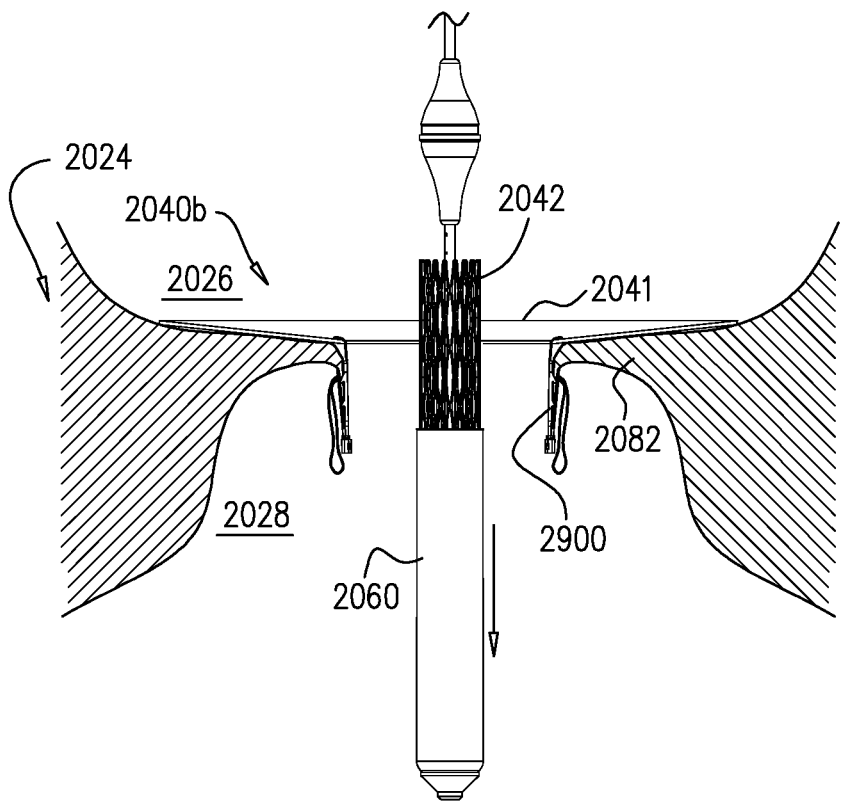

FIGS. 74I-L show steps in the implantation of prosthetic valve 2042 in opening 2045 of prosthetic valve support 2040b. As described hereinabove, prosthetic valve 2042 is typically delivered transcatheterally. Typically, prosthetic valve 2042 is delivered to the native valve from an upstream side (e.g., the atrial side of the mitral valve), in a compressed configuration, and constrained within a delivery tube 2060, as shown in 31. The prosthetic valve and delivery tube are typically placed within opening 2045. Delivery tube 2060 is then withdrawn from the prosthetic valve. Typically, the delivery tube is withdrawn in a downstream direction (e.g., distally and/or ventricularly), as shown in FIG. 74J. For some applications, the delivery tube is withdrawn in an upstream direction (e.g., proximally and/or atrially).

Figure 74K:
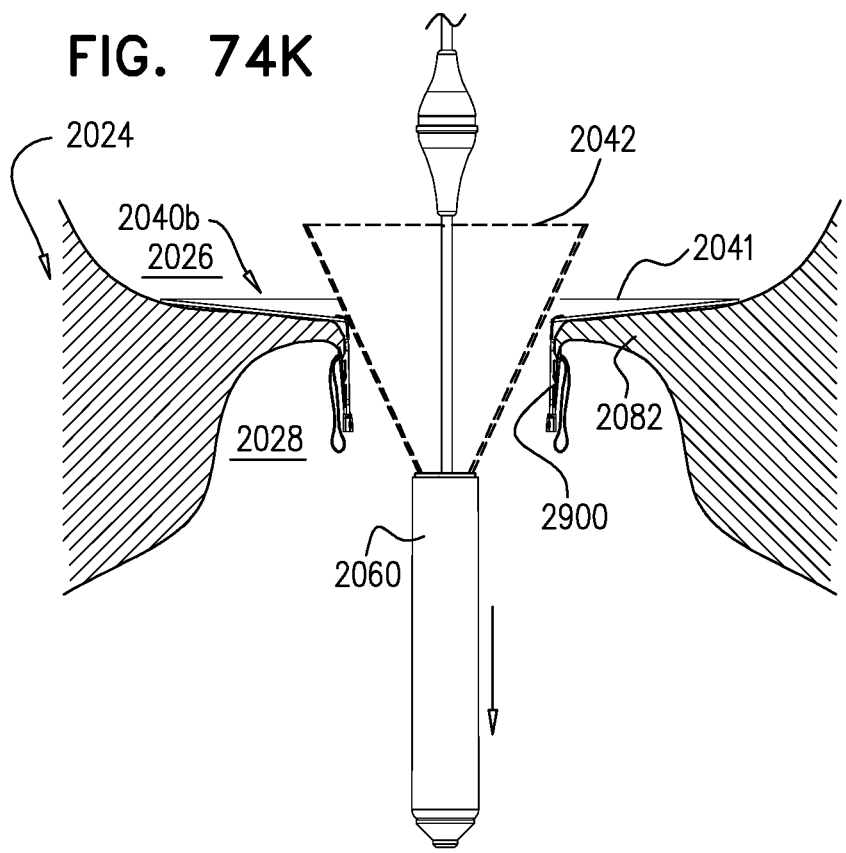

As regions of prosthetic valve 2042 are successively exposed as they exit delivery tube 2060, they expand (e.g., radially). When delivery tube 2060 is withdrawn in the downstream direction, the upstream end of the prosthetic valve is exposed, and expands, thereby coupling the prosthetic valve to the upstream support portion of prosthetic valve support 2040b, as shown in FIG. 74K (in which prosthetic valve 2042 is represented by a trapezoid/frustum). As described hereinabove (e.g., with reference to FIG. 72C), for some applications, the prosthetic valve is couplable to the upstream support portion at a plurality of positions along the axial length of the prosthetic valve. For such applications, a physician can typically implant (e.g., couple to support 2040b) the prosthetic valve at a plurality of depths with respect to upstream support portion 2041 and/or the native valve. For some such applications, the physician can implant the prosthetic valve prosthetic valve is implantable at a continuum of depths with respect to upstream support portion 2041 and/or the native valve.

As shown in FIG. 74K, upstream support portion 2041 is placed against the upstream side of the native valve, and prosthetic valve 2042 is radially expanded within opening 2045 defined by the upstream support portion. Radially-expansive force applied by prosthetic valve 2042 to upstream support portion 2041 (and which typically couples the prosthetic valve to the upstream support portion), is typically not transferred to the native valve via the prosthetic valve support. That is, and as described hereinabove (e.g., with reference to FIGS. 72A and 72C), radial expansion of prosthetic valve 2042 against inner perimeter 2068 of upstream support portion 2041, typically does not cause the prosthetic valve support to apply a radially-expansive force to the native valve.

Figure 74L:
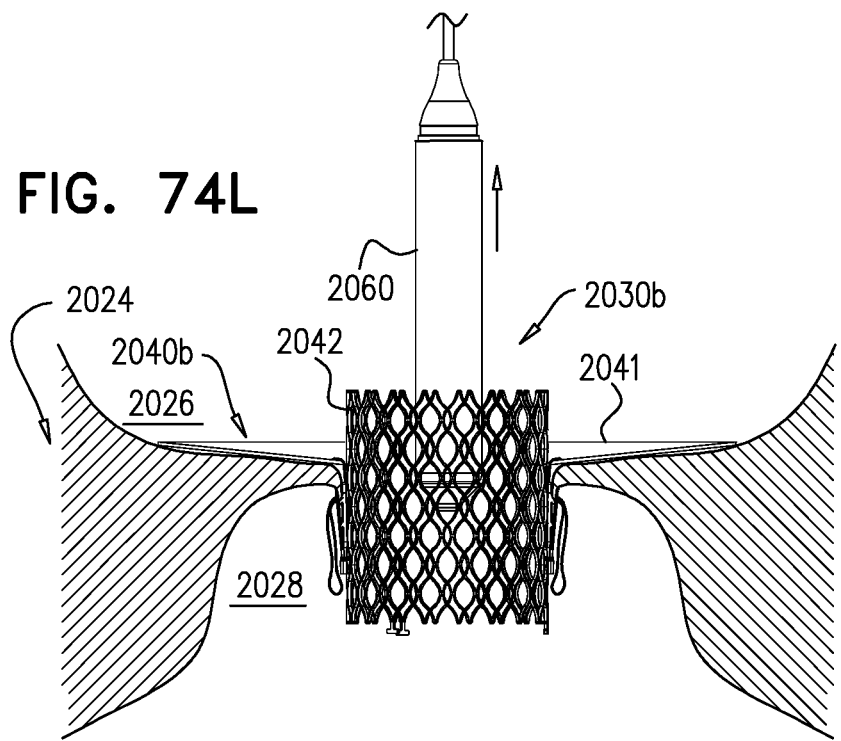

Once delivery tube 2060 is fully withdrawn from prosthetic valve 2042, and the prosthetic valve is fully deployed (e.g., in the implanted configuration thereof), delivery tube 2060 is removed from the body of the subject. For some applications, when the delivery tube is withdrawn in the downstream direction (e.g., ventricularly), it is removed from the body via the lumen of the prosthetic valve, as shown in FIG. 74L.

As described hereinabove (e.g., with reference to FIGS. 73, and 74G-H), following the implantation (e.g., delivery, coupling and deployment) of prosthetic valve support 2040b, clips 2900 and native leaflets 2082 can move, at least in part, thereby not eliminating the native blood flow regulation functionality of the native valve. In experiments conducted by the inventors, prosthetic valve support 2040b has been implanted in two pigs. Both animals remained alive and stable (e.g., had stable blood pressure, pulse, breathing rate and oxygen saturation) for a duration of sufficient length to withdraw the support-delivery apparatus, introduce a valve-delivery system (e.g., delivery tube 2060), and deploy (e.g., implant) prosthetic valve 2042 in opening 2045 of the support. The period between implanting support 2040b and implanting prosthetic valve 2042 was between 5 and 10 minutes.

It is thereby hypothesized that, following implantation of prosthetic valve support 2040b, the heart of the subject is able to continue pumping blood sufficiently to support the subject for longer than a minute, e.g., longer than 2 minutes, e.g., longer than 5 minutes, such as longer than an hour. It is thereby hypothesized that a period of generally normal physiological activity of the subject of up to a minute, e.g., up to 2 minutes, e.g., up to 5 minutes, such as up to an hour, between implantation of support 2040b and implantation of prosthetic valve 2042 (e.g., as described with reference to FIGS. 74I-L and/or 76D-E), is supported by prosthetic valve support 2040b. It is thereby hypothesized that the implantation of implant 2030b, comprising support 2040b and prosthetic valve 2042, may be performed without the use of cardiopulmonary bypass. It is thereby hypothesized that replacement of a native valve with implant 2030b, may be performed in a human, 'off-pump,' as was performed in the pig experiments.

Reference is again made to FIGS. 73 and 74A-L. It should be noted that clips 2900, clip-controller interface (e.g., pull-wire 2924), clip controller 2930), and/or the support-delivery apparatus (e.g., support-delivery apparatus 2960) are typically configured such that the clips are controllable independently of the deployment (e.g., expansion) of the prosthetic valve support (e.g., the withdrawal of overtube 2044 from upstream support portion 2041). That is, clips 2900 are typically configured to be controllable independently of a state of deployment of the prosthetic valve support (e.g., prosthetic valve support 2040b. Thus, a physician may independently control (1) the coupling (e.g., 'clipping') of clips 2900 to the leaflets of the native valve, and (2) the deployment of the prosthetic valve support (e.g., expansion of the upstream support portion).

Reference is made to FIGS. 75A-E, which are schematic illustrations of implant 2030c, comprising prosthetic valve 2042 and prosthetic valve support 2040c, and the implantation thereof, in accordance with some applications of the invention. For some applications of the invention, prosthetic valve support 2040c comprises, and/or is analogous to, other prosthetic valve supports (e.g., prosthetic valve support 2040), and implant 2030c comprises, and/or is analogous to, other implants (e.g., implant 2030) described herein. Support 2040c comprises upstream support portion 2041, coupled to one or more clips 2900, described hereinabove (e.g., with reference to FIGS. 73 and 74A-L), and configured to be couplable to one or more native leaflets 2082 of the native valve. Typically, support 2040c comprises two clips 2900, coupled to portion 2041 at or near inner perimeter 2068. Typically, clips 2900 are disposed opposite each other. Support 2040c further comprises a stabilizing element 3062 (e.g., a stabilizing strip or a stabilizing band), coupled to clips 2900.

Reference is now made to FIG. 75A, which shows a lower side view of support 2040c. Typically, stabilizing element 3062 is coupled to a downstream (e.g., distal) portion of clips 2900, and forms a ring shape downstream (e.g., distal) to upstream support portion 2041. Stabilizing element 3062 defines an opening 3064 (e.g., an aperture), and is typically inelastic and at least partly flexible. Non-limiting examples of materials that element 3062 may comprise include polyester, PTFE (e.g., ePTFE), nylon, cotton, nitinol, stainless steel, nickel cobalt, cobalt chrome, titanium, tantalum and palladium. The flexibility of element 3062 typically facilitates the compressibility of the prosthetic valve support (e.g., for delivery) and/or movement (e.g., articulation) of clips 2900 with respect to upstream support portion 2041.

Stabilizing element 3062 is hypothesized to increase the stability of prosthetic valve support 2040c at the native valve. For example, element 3062 is hypothesized to at least partly inhibit lateral movement (e.g., rotation around an atrial-ventricular axis, e.g., 'yaw') of the support and/or clips, when the support is implanted at the native valve. Element 3062 is further hypothesized to reduce rolling movement (e.g., movement around a lateral axis, e.g., an axis between two clips 2900, e.g., 'pitch' and 'roll') of implant 2030c, including inversion (e.g., 'flipping') of the implant, following deployment (e.g., implantation) of prosthetic valve 2042.

For some applications of the invention, stabilizing element 3062 is further hypothesized to stabilize clips 2900 during deployment of the elements, e.g., by facilitating coupling thereof to delivery apparatus, such as apparatus 2960.

FIGS. 75B-C show prosthetic valve support 2040c, following implantation thereof at mitral valve 2024. As described hereinabove, the upstream support portion is disposed upstream of the native valve. Stabilizing element is disposed downstream of the native valve (i.e., in ventricle 2028). Prosthetic valve support 2040c is typically implanted as described elsewhere herein for other prosthetic valve supports, mutatis mutandis. As described hereinabove, stabilizing element 3062 is typically at least partly flexible, such that clips 2900 are movable with respect to upstream support portion 2041. Typically, element 3062 is sufficiently flexible to allow native leaflets 2082 to continue to function, at least in part. FIG. 75B shows support 2040c implanted at mitral valve 2024, with native leaflets 2082 open (e.g., during ventricular diastole). FIG. 75C shows support 2040c implanted at mitral valve 2024, with native leaflets 2082 closed (e.g., during ventricular systole). For some applications, when the native leaflets close, stabilizing element 3062 deforms toward a generally lemniscate (e.g., 'figure-8' or 'butterfly') configuration (e.g., as shown in FIG. 75C).

For some applications of the invention, a similar generally lemniscate configuration is formed by element 3062 when prosthetic valve support 2040c is coupled to delivery apparatus, during delivery to the native valve (e.g., as described for support 2040b with reference to FIGS. 74A-B). For some such applications, stabilizing element 3062 protrudes from the compressed prosthetic valve support, and facilitates positioning and/or orientation of the support. For example, the 'limbs' of the lemniscate are typically oriented at right angles to clips 2900, and protrude from the compressed support. When the clips are in close proximity to the native leaflets, the 'limbs' are typically downstream of the leaflets, and interact (e.g., touch) chordae tendineae of the native valve. By orienting the prosthetic valve support such that the 'limbs' have the least interaction with chordae tendineae (typically when the 'limbs are oriented toward commissures of the native valve), a user automatically orients clips 2900 toward leaflets 2082 of the native valve.

Similarly to support 2040b (described with reference to FIGS. 74A-L), implantation of prosthetic valve support 2040c at a native valve does not eliminate the native blood flow regulation functionality of the native valve. It is thereby hypothesized that, following implantation of prosthetic valve support 2040c, the heart of the subject is able to continue pumping blood sufficiently well to support the physiological systems of the subject for longer than a minute, e.g., longer than 2 minutes, e.g., longer than 5 minutes, such as longer than an hour. It is thereby hypothesized that a period of up to a minute, e.g., up to 2 minutes, e.g., up to 5 minutes, such as up to an hour, between implantation of support 2040c and implantation of a prosthetic valve (e.g., prosthetic valve 2042), is supported by prosthetic valve support 2040c. It is thereby hypothesized that the implantation of implant 2030c, comprising support 2040c and prosthetic valve 2042, may be performed without the use of cardiopulmonary bypass. That is, it is hypothesized that replacement of a native valve with implant 2030c, may be performed 'off-pump'.

When implanted at the native valve, and thereby in the implanted configuration thereof, no part of stabilizing element 3062 is disposed upstream of native leaflets 2082 (e.g., no part of element 3062 is disposed in atrium 2026). Typically, when prosthetic valve support 2040c is implanted at the native valve, no part of support 2040c that circumscribes a space (e.g., portion 2041, which circumscribes opening 2045 and/or element 3062, which circumscribes opening 3064) traverses (e.g., fully traverses) the native annulus.

When implanted at the native valve, and thereby in the implanted configuration thereof, a height (i.e., a length along an upstream-to-downstream axis ax2 from a most upstream part to a most downstream part) of stabilizing element 3062, is typically less than 20 mm (e.g., less than 10 mm, such as less than 5 mm). For example, stabilizing element 3062 typically has a thickness of less than 20 min (e.g., less than 10 mm, e.g., less than 5 mm, such as less than 1 mm). Typically, when prosthetic valve support 2040c is implanted at the native valve, no part of the support that circumscribes a space has a height of more than 20 mm. For some applications, when prosthetic valve support 2040c is implanted at the native valve, no part of the support that circumscribes a space has a height of more than 10 mm. For some applications, when prosthetic valve support 2040c is implanted at the native valve, no part of the support that circumscribes a space has a height of more than 5 mm.

FIG. 75D shows implant 2030, comprising prosthetic valve support 2040c and prosthetic valve 2042, following implantation at mitral valve 2024. The prosthetic valve is typically implanted as described elsewhere herein (e.g., with reference to FIGS. 74I-L), mutatis mutandis. Prosthetic valve 2042 is deployed (e.g., delivered and expanded) in opening 2045, defined by upstream support portion 2041, and in opening 3064, defined by stabilizing element 3062. That is, when prosthetic valve 2042 is deployed at the native valve, it is expanded such that (1) an upstream (e.g., proximal) portion of the prosthetic valve engages (e.g., couples to) inner perimeter 2068 of support 2040c, and (2) a downstream (e.g., distal) portion of the prosthetic valve is disposed within the opening of the stabilizing element. For some applications of the invention, and as illustrated in FIG. 75D, the distal portion of the prosthetic valve engages (e.g., couples to) the stabilizing element.

For some applications of the invention, stabilizing element 3062 is configured (e.g., dimensioned) such that, when the prosthetic valve is expanded within the opening of the stabilizing element, the stabilizing element restricts the full expansion of the downstream portion of the prosthetic valve. That is, for some applications, upon expansion of the prosthetic valve, a transverse cross-sectional dimension (e.g., area) defined by a downstream portion of the prosthetic valve is determined (e.g., restricted) by a transverse cross-sectional dimension (e.g., area) of opening 3064 of the stabilizing element. For some applications, one or more dimensions of opening 3064, defined by stabilizing element 3062, are substantially equal to one or more dimensions of opening 2045, defined by upstream support portion 2041. For some such applications, the expansion of both the downstream and upstream portions of the prosthetic valve are restricted to substantially the same transverse cross-sectional dimensions, thereby facilitating the primary structural element of the prosthetic valve to assume a generally prismatic (e.g., generally cylindrical) shape.

For applications where stabilizing element 3062 limits the expansion of prosthetic valve 2042, a radially-expansive force is thereby applied by prosthetic valve 2042 to stabilizing element 3062. The radially-expansive force typically couples the prosthetic valve to the stabilizing element. That is, for some applications, prosthetic valve 2042 is couplable to the stabilizing element. For some applications, the prosthetic valve is coupled to the stabilizing element by alternative or additional means. For example, the stabilizing element may comprise barbs and/or hooks, which facilitate coupling to the prosthetic valve.

For some applications of the invention, at least part (e.g., an inner surface) of stabilizing element 3062 comprises a friction coating that is configured to increase friction and, thereby, coupling between the stabilizing element and the prosthetic valve.

For some applications of the invention, at least part of stabilizing element 3062 is shaped to define ridges, which are configured (e.g., dimensioned) to protrude (e.g., interpose) within corresponding voids defined by the lattice structure of the prosthetic valve. The ridges facilitate coupling of the stabilizing element to the prosthetic valve, e.g., by inhibiting axial movement of the prosthetic valve through opening 3064.

For some applications of the invention, a soft (e.g., crushable) material is disposed on the inner surface of stabilizing element 3062 (e.g., the stabilizing element comprises the soft material). When prosthetic valve 2042 expands, and applies radially-expansive force to the stabilizing element, (1) the struts of the lattice structure of the prosthetic valve compress (e.g., crush) the parts of the soft material against which the struts apply the force, and (2) the parts of the soft material that are disposed between the struts (i.e., that are disposed at voids defined by the lattice structure), form ridges that protrude between the struts (i.e., protrude into the voids). The protruding parts of the soft material facilitate coupling of the stabilizing element to the prosthetic valve, e.g., by inhibiting axial movement of the prosthetic valve through opening 3064, such as by increasing friction.

For some applications of the invention, prosthetic valve 2042 (e.g., the primary structural element of prosthetic valve 2042) is shaped to define a circumferential groove that is configured (e.g., dimensioned) to receive stabilizing element 3062. That is, for some applications of the invention, stabilizing element 3062 is configured (e.g., dimensioned) to be placeable in a circumferential groove defined by prosthetic valve 2042. When prosthetic valve 2042 is deployed, and expands within opening 3064, element 3062 is disposed in the groove, thereby further facilitating coupling of the stabilizing element to the prosthetic valve, e.g., by inhibiting axial movement of the prosthetic valve through the opening 3064.

Reference is made to FIGS. 76A-E, which are schematic illustrations of steps in the implantation of implant 2030h, comprising prosthetic valve 2042 and prosthetic valve support 2040h, in a native heart valve, such as mitral valve 2024 of a subject, in accordance with some applications of the invention. For some applications of the invention, prosthetic valve support 2040h comprises, and/or is analogous to, other prosthetic valve supports described herein. Prosthetic valve support 2040h comprises upstream support portion 2041 and clips 2900, and typically comprises, and/or is analogous to prosthetic valve support 2040b. FIGS. 76A-E show steps in the transapical implantation of implant 2030h.

Figure 76A:
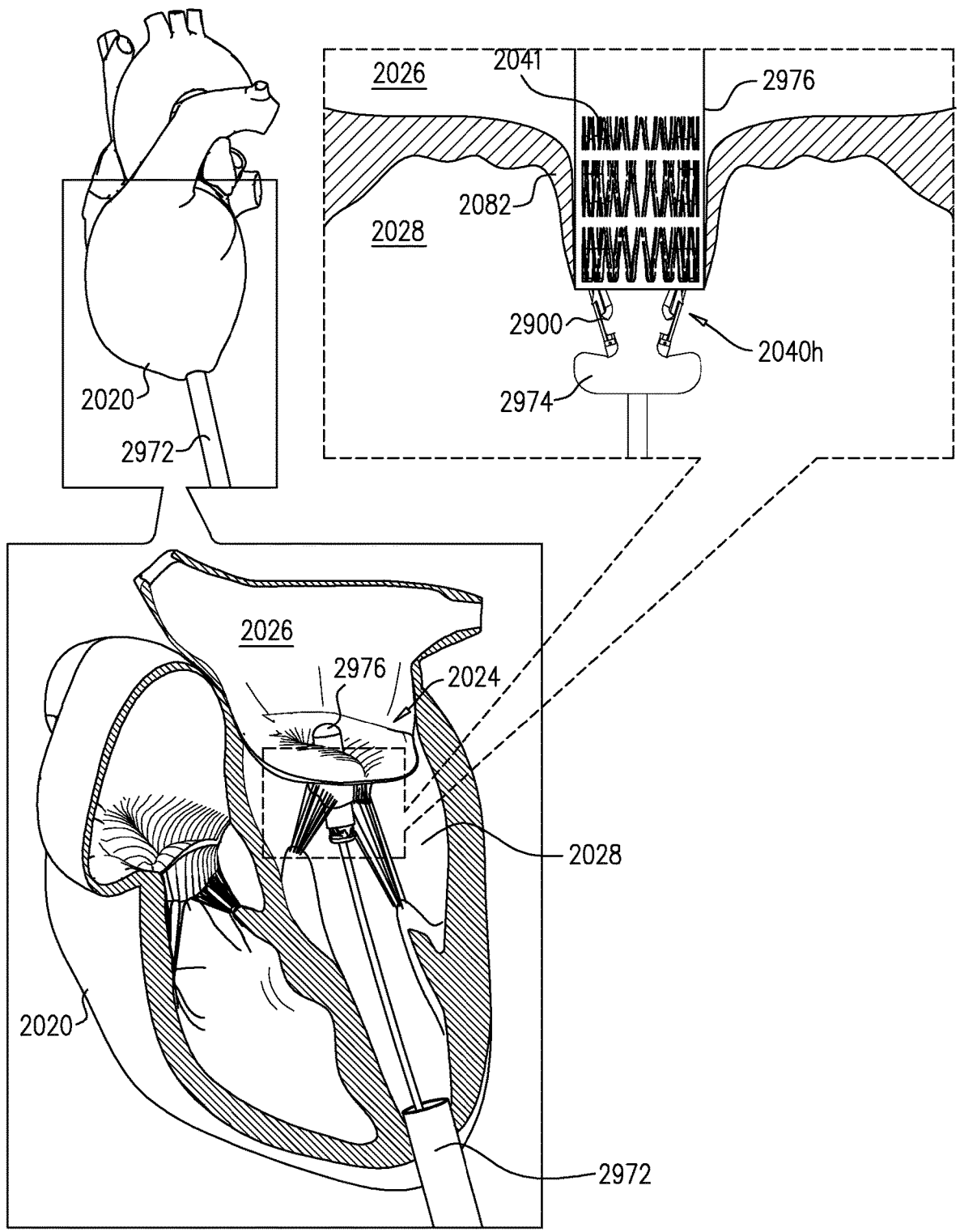

FIG. 76A shows support 2040h being delivered, using support-delivery apparatus 2970, via the apex of the heart, to left ventricle 2028 of the subject. During delivery, portion 2041 is disposed, in the compressed configuration thereof, within an overtube 2972 of the delivery apparatus. Typically, portion 2041 is disposed within a delivery tube 2976, which itself is disposed within the overtube.

Figure 76B:
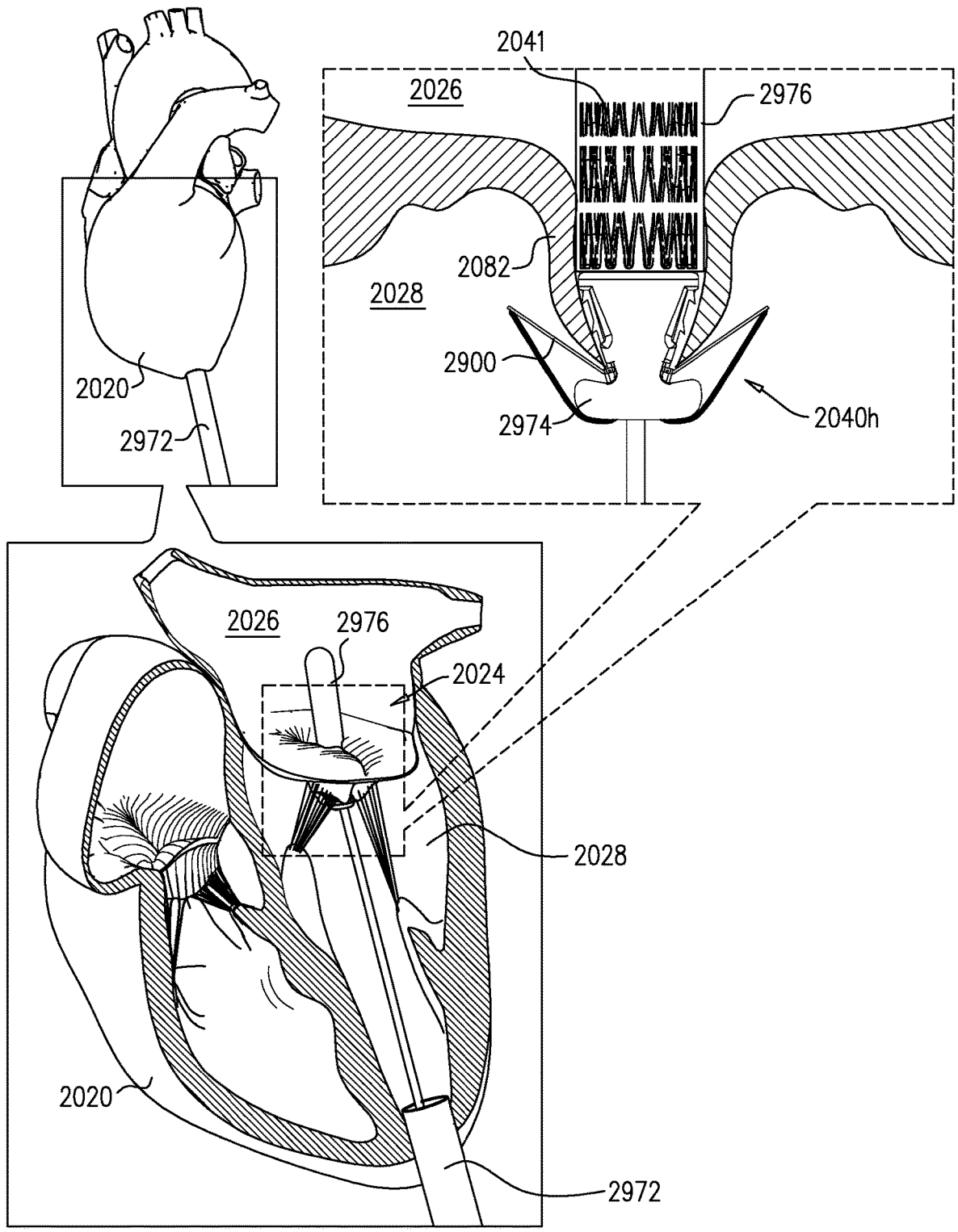
Figure 76C:
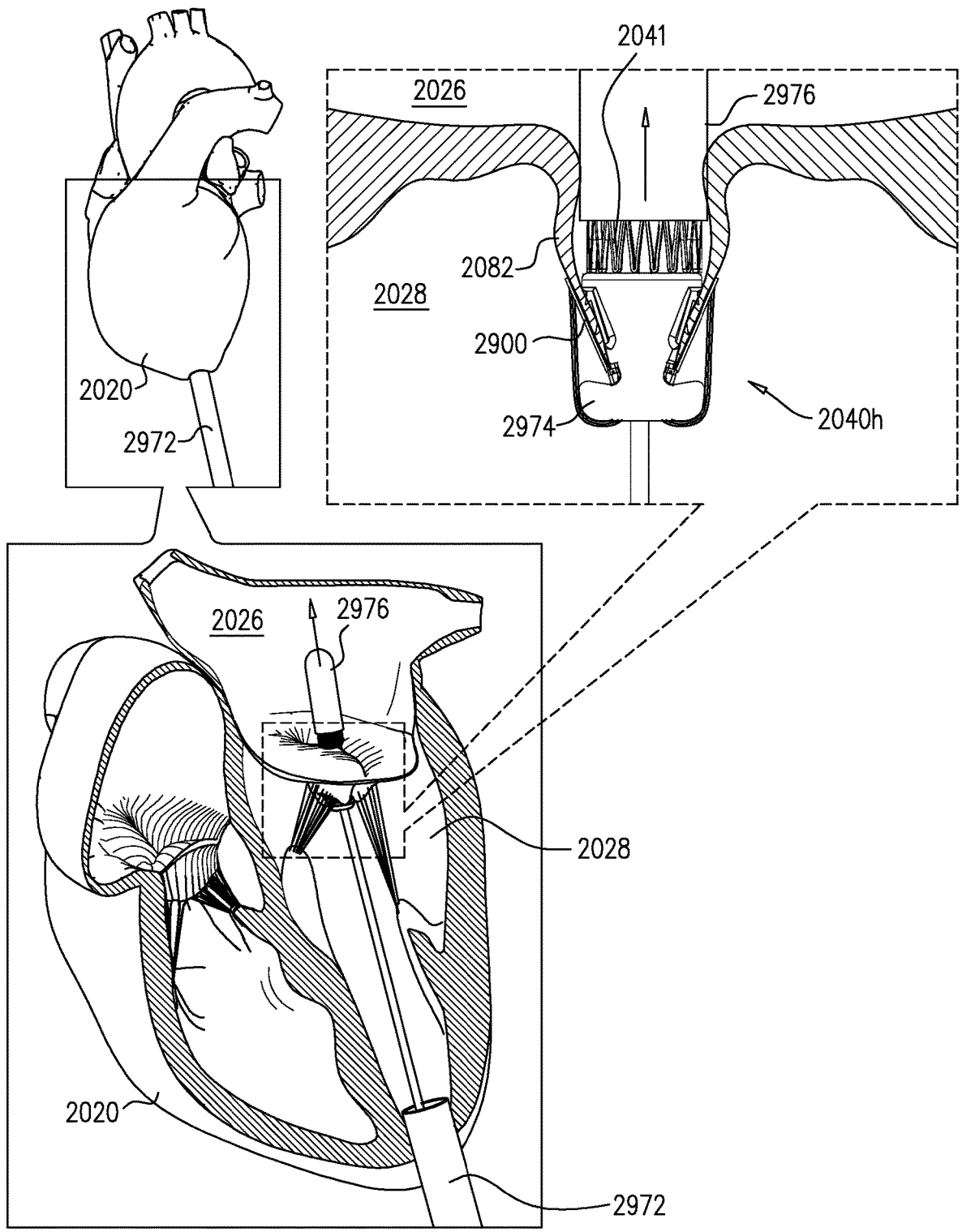

FIG. 76B shows clips 2900 in the open configuration thereof, and coupled to a scaffold, such as core 2974. Clips 2900 are typically operated and coupled to native leaflets 2082 as described hereinabove, mutatis mutandis. Upstream support portion 2041 is advanced, in the compressed configuration thereof, such that upstream end 2055 is upstream of downstream end 2053. Upstream end 2055 of portion 2041 is advanced between native leaflets 2082. Typically, coupling clips 2900 to leaflets 2082 automatically advances at least part of portion 2041 (e.g., upstream end 2055) between the native leaflets. FIG. 76C shows clips 2900 in the closed configuration thereof, coupled to native leaflets 2082.

Figure 76D:
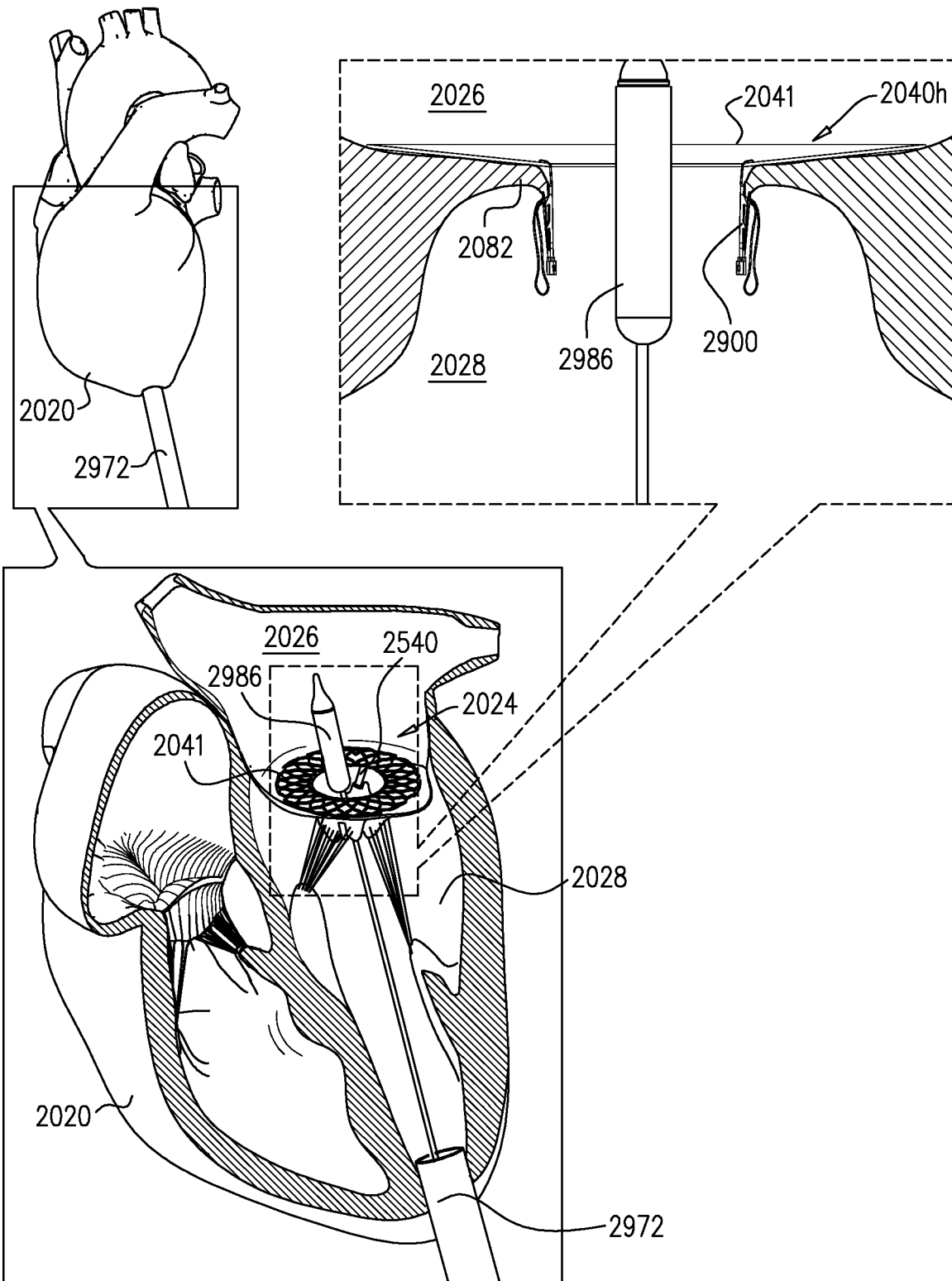

After clips 2900 have been coupled to native leaflets 2082, delivery tube 2976 is withdrawn distally (e.g., atrially) from upstream support portion 2041, such that downstream end 2053 of portion 2041 is exposed, and expands to define inner perimeter 2068 as described hereinabove, mutatis mutandis. As successively more distal (e.g., upstream) parts of portion 2041 are exposed as they exit delivery tube 2976, they expand (e.g., radially). When portion 2041 is sufficiently exposed from the delivery tube (e.g., when upstream end 2055 is exposed from the delivery tube), upstream end 2055 expands to define outer perimeter 2068, as described hereinabove, mutatis mutandis. As shown in FIG. 76D, support 2040h thereby assumes its implanted configuration, as described hereinabove, whereby clips 2900 are coupled to the native leaflets, and upstream support portion 2041 is disposed against the upstream side of the native valve (e.g., the upstream side of the native valve annulus). Delivery tube 2976 is subsequently withdrawn from atrium 2026 via opening 2045 of upstream support portion 2041, and support-delivery apparatus 2970 (including delivery tube 2976) is withdrawn from the body of the subject.

FIG. 76E shows prosthetic valve 2042 being coupled to support 2040h (i.e., implanted). Prosthetic valve 2042 is delivered transapically, to ventricle 2028 of the subject. During delivery, prosthetic valve 2042 is disposed, in a compressed configuration thereof, within a delivery tube 2986 of the delivery apparatus. The delivery tube containing the prosthetic valve is disposed in opening 2045 of upstream support portion 2041. The delivery tube is subsequently withdrawn proximally (e.g., ventricularly) from prosthetic valve 2042, such that the upstream end of the prosthetic valve is exposed. As successively more proximal (e.g., downstream) parts of prosthetic valve 2042 are exposed as they exit delivery tube 2986, they expand (e.g., radially). When prosthetic valve 2042 is sufficiently exposed from the delivery tube, the prosthetic valve engages inner perimeter 2068 of upstream support portion 2041 of support 2040h, and couples the prosthetic valve thereto, as described hereinabove, mutatis mutandis.

Once prosthetic valve 2042 is completely exposed (e.g., deployed), the prosthetic valve thereby assumes its implanted configuration, as described hereinabove. Support-delivery apparatus 2980 (including delivery tube 2986) is subsequently withdrawn from the body of the subject.

Reference is made to FIGS. 77-80, which are schematic illustrations of implants, each comprising a prosthetic valve support and a prosthetic valve, implanted at native valves of a heart 2020 of a subject, in accordance with some applications of the invention. FIGS. 77-80 are not intended to limit the scope of the invention, but to indicate some placements of the implants with respect to the anatomy of the heart and/or native valve, and to illustrate commonalities between such placements. Other prosthetic valves and prosthetic valve supports described herein may be implanted at the native valves, as described with reference to FIGS. 77-80, mutatis mutandis.

Figure 77:
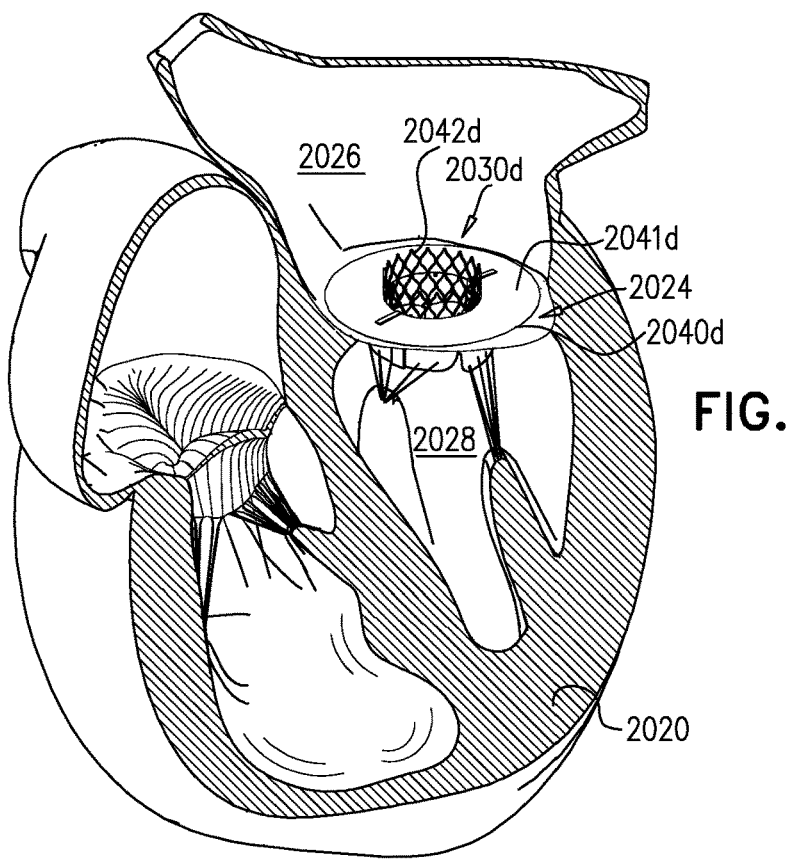
FIG. 77 is a schematic illustration of an implant, implanted at the mitral valve of a subject, in accordance with some applications of the invention.

FIG. 77 shows implant 2030d, comprising a prosthetic valve support 2040d and a prosthetic valve 2042d, implanted at mitral valve 2024 of heart 2020 of a subject, in accordance with some applications of the invention. For some applications of the invention, prosthetic valve support 2040d comprises, and/or is analogous to, other prosthetic valve supports described herein, and implant 2030d comprises, and/or is analogous to, other implants described herein. Implant 2030d (e.g., support 2040d and prosthetic valve 2042d) are configured (e.g., dimensioned) to be implanted at mitral valve 2024. Implant 2030d is typically implanted at mitral valve 2024 as described elsewhere herein (e.g., with reference to FIGS. 74A-L and/or 76A-E). An upstream support portion 2041d of support 2040d is disposed against the upstream (i.e., atrial) side of mitral valve 2024, and is coupled to the native valve, e.g., using clips or another support-anchoring element. Prosthetic valve 2042d is disposed and expanded in the opening defined by portion 2041d, thereby traversing the annulus of the native valve.

Figure 78:
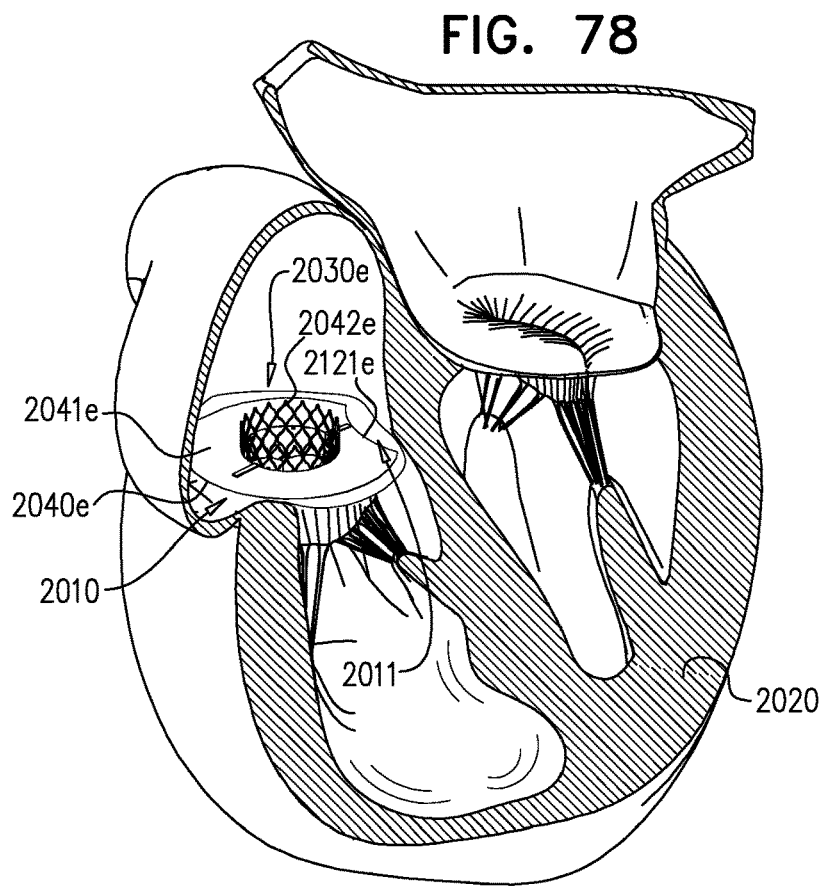
FIG. 78 is a schematic illustration of an implant, implanted at the tricuspid valve of a subject, in accordance with some applications of the invention.

FIG. 78 shows implant 2030e, comprising a prosthetic valve support 2040e and a prosthetic valve 2042e, implanted at tricuspid valve 2010 of heart 2020 of a subject, in accordance with some applications of the invention. For some applications of the invention, prosthetic valve support 2040e comprise, and/or is analogous to, other prosthetic valve supports described herein, and implant 2030e comprises, and/or is analogous to, other implants described herein. Implant 2030e (e.g., support 2040e and prosthetic valve 2042e) are configured (e.g., dimensioned) to be implanted at tricuspid valve 2010. For example, and as shown in FIG. 78, an upstream support portion 2041e of support 2040e typically defines a concavity 2121, configured to be oriented toward the atrioventricular (AV) node, so as to reduce a likelihood of support 2040e interfering with electrical activity of the heart. Upstream support portion 2041e of support 2040e is disposed against the upstream (i.e., atrial) side of tricuspid valve 2010, and is coupled to the native valve, e.g., using clips or another support-anchoring element. Prosthetic valve 2042e is disposed and expanded in the opening defined by portion 2041e, thereby traversing the annulus of the native valve.

Figure 79:
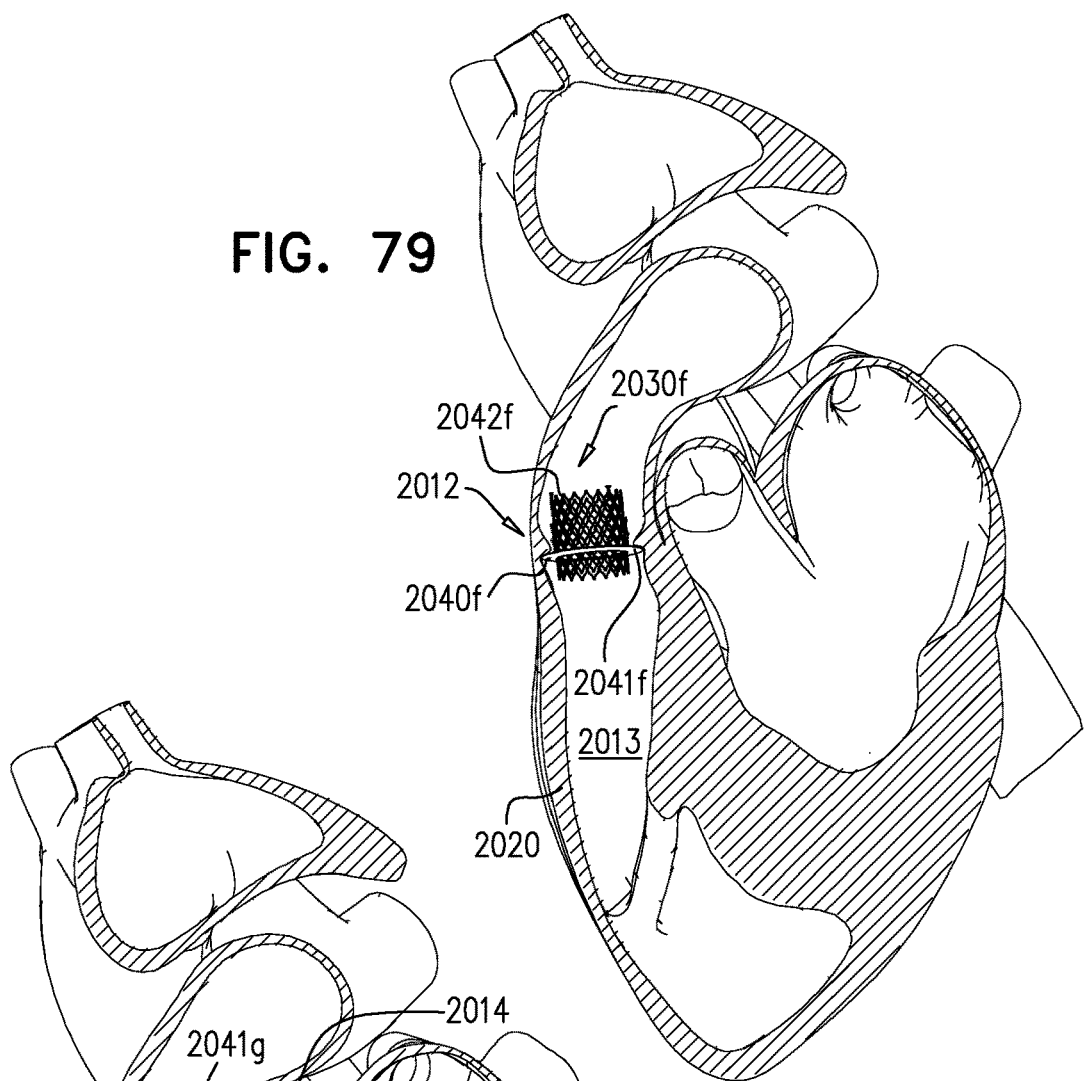
FIG. 79 is a schematic illustration of an implant, implanted at the pulmonary valve of a subject, in accordance with some applications of the invention.

FIG. 79 shows implant 2030f, comprising a prosthetic valve support 2040f and a prosthetic valve 2042f, implanted at pulmonary valve 2012 of heart 2020 of a subject, in accordance with some applications of the invention. For some applications of the invention, prosthetic valve support 2040f comprises, and/or is analogous to, other prosthetic valve supports described herein, and implant 2030f comprises, and/or is analogous to, other implants described herein. Implant 2030f (e.g., support 2040f and prosthetic valve 20420 are configured (e.g., dimensioned) to be implanted at pulmonary valve 2012. For example, and as shown in FIG. 79, an outer perimeter of upstream support portion 2041f of support 2040f may be dimensioned to be small enough to fit within the downstream portion of right ventricle 2013, but large enough to inhibit movement of implant 2030f downstream through the pulmonary valve. Upstream support portion 2041f of support 2040f is disposed against the upstream (i.e., ventricular) side of pulmonary valve 2012, and is coupled to the native valve, e.g., using clips or another support-anchoring element. Prosthetic valve 2042f is disposed and expanded in the opening defined by portion 2041f, thereby traversing the annulus of the native valve.

Figure 80:
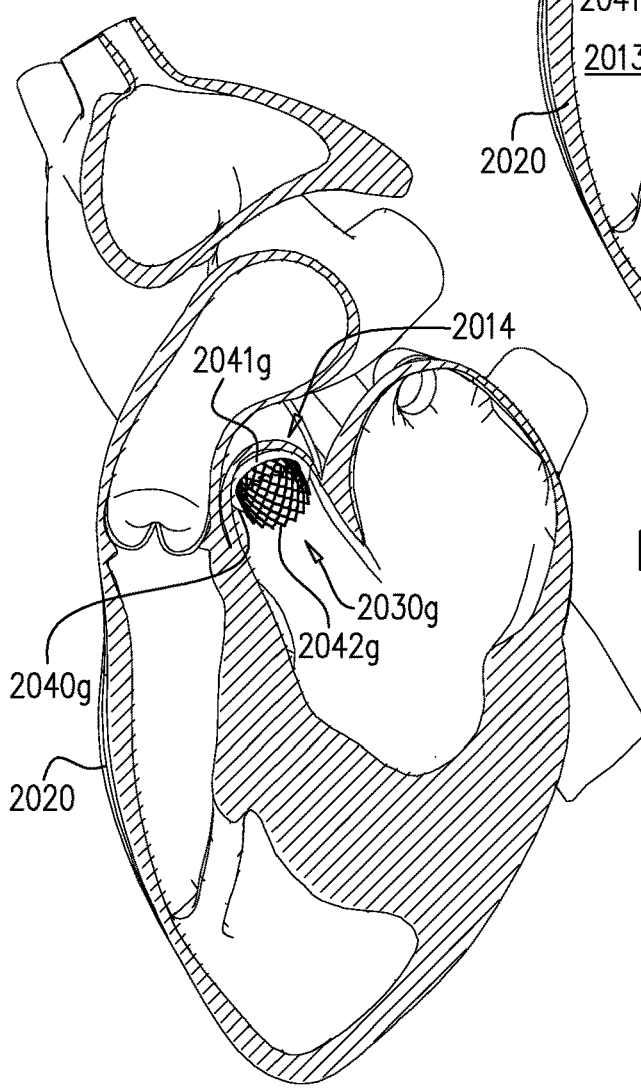
FIG. 80 is a schematic illustration of an implant, implanted at the aortic valve of a subject, in accordance with some applications of the invention.

FIG. 80 shows implant 2030g, comprising a prosthetic valve support 2040g and a prosthetic valve 2042g, implanted at aortic valve 2014 of heart 2020 of a subject, in accordance with some applications of the invention. For some applications of the invention, prosthetic valve support 2040g comprises, and/or is analogous to, other prosthetic valve supports described herein, and implant 2030g comprises, and/or is analogous to, other implants described herein. Implant 2030g (e.g., support 2040g and prosthetic valve 2042g) are configured (e.g., dimensioned) to be implanted at aortic valve 2014. For example, and as shown in FIG. 80, an outer perimeter of upstream support portion 2041g of support 2040g may be dimensioned to be sufficiently large to inhibit movement of implant 2030g downstream through the aortic valve, and/or prosthetic valve 2042g, and prosthetic valve 2042g may be dimensioned to reduce a likelihood of interference with (e.g., reduction of) blood flow into the coronary arteries of the subject. Upstream support portion 2041g of support 2040g is disposed against the upstream (i.e., ventricular) side of aortic valve 2014, and is coupled to the native valve, e.g., using clips or another support-anchoring element. Prosthetic valve 2042g is disposed and expanded in the opening defined by portion 2041g, thereby traversing the annulus of the native valve.

Reference is again made to FIGS. 77-80. It is thereby to be noted that although some apparatus and methods are described herein to facilitate replacement of a native mitral valve of the subject, apparatus (and subcomponents thereof) and methods described herein may also be used to replace a native cardiac valve other than the native mitral valve, such as the tricuspid valve, the aortic valve, and the pulmonary valve.

Reference is again made to FIGS. 1A-80. For each of the prosthetic valve supports described, at least a part of the prosthetic valve support circumscribes (e.g., encloses on all lateral sides) a space. For example, the upstream support portions and stabilizing elements described hereinabove, define respective openings (e.g., apertures). These openings are thereby spaces that the upstream support portions and stabilizing elements circumscribe.

For some applications of the invention, following implantation at the native valve, no part of the prosthetic valve support that circumscribes a space, traverses the native leaflets and/or annulus. For example, following implantation, the upstream support portions described hereinabove (e.g., upstream support portions 41 and 2041) are typically disposed only upstream of the native leaflets and/or annulus. Similarly, for applications in which the prosthetic valve support comprises a stabilizing element (e.g., stabilizing element 1062 or 3062), following implantation, the stabilizing element is typically disposed only downstream to the native leaflets and/or annulus. It is hypothesized that this advantageously facilitates continued function of the native leaflets following implantation of the prosthetic valve support, and prior to the implantation of a prosthetic valve, as described hereinabove.

Typically, the perimeter (e.g., the circumference) of the spaces defined by the upstream support portions and stabilizing elements described hereinabove, is greater than 60 mm. Typically, the upstream support portions and stabilizing elements have respective heights of less than 10 mm. For some applications of the invention, no part of the prosthetic valve support that circumscribes a space that has a perimeter that is greater than 60 mm, has a height (e.g., a depth) that is greater than 10 mm. For example, prosthetic valve supports that do not comprise a cylindrical element (e.g., cylindrical element 90 or 690), do not comprise a part that (1) circumscribes a space that has a perimeter that is greater than 60 mm, and (2) has a height (e.g., a depth) that is greater than 10 mm.

Reference is again made to FIGS. 1A-80. It is to be noted that the apparatus and techniques described hereinabove are not limited to the combinations described hereinabove. For example:

(1) Any of the prosthetic valves described hereinabove (including features and/or components thereof) may be used in combination with any of the prosthetic valve supports (including features and/or components thereof) described hereinabove (e.g., any of the prosthetic valve supports described hereinabove may be used to facilitate implantation of any of the prosthetic valves described hereinabove), mutatis mutandis;

(2) any of the prosthetic valve supports described hereinabove may comprise any of the upstream support portions, tissue-engaging elements (e.g., support-anchoring elements and/or clips), connectors (e.g., flexible and/or length-adjustable connectors), holding wires and/or stabilizing elements described hereinabove, mutatis mutandis;

(3) any of the prosthetic valves or prosthetic valve supports described hereinabove may comprise any of the coupling functionalities (e.g., barbs, coupling leads and/or support-engaging elements) described hereinabove, for coupling a prosthetic valve support (e.g., support-anchoring elements thereof) to a prosthetic valve, mutatis mutandis;

(4) any of the tissue-engaging elements, and/or elements thereof, described hereinabove may be used in combination with any one of prosthetic valve supports or prosthetic valves described herein, mutatis mutandis. For example, tissue-engaging elements (e.g., support-anchoring elements) that are described hereinabove for coupling a prosthetic valve support to the native valve, may be alternatively or additionally used to couple a prosthetic valve to the native valve (the tissue-engaging element thereby acting as a valve-anchoring element), mutatis mutandis. Similarly, tissue-engaging elements (e.g., valve-anchoring elements) that are described hereinabove for coupling a prosthetic valve to the native valve, may be alternatively or additionally used to couple a prosthetic valve support to the native valve (the tissue-engaging element thereby acting as a support-anchoring element), mutatis mutandis;

(5) any of the implantation techniques described hereinabove (e.g., those described with reference to FIGS. 1A-H, 15A-E, 16, 28A-30B, 37A-H, 38A-H, 50, 74A-L, 75A-D and 76A-F) may be used in combination with any of the implants (e.g., any of the prosthetic valves and/or prosthetic valve supports) described hereinabove, mutatis mutandis;

(6) any of the delivery apparatus described hereinabove (e.g., those described with reference to FIGS. 9A-E, 27A-D, 31A-33C, 37A-H, 38A-H, 62A-D, 63A-B, 64A-67B and 74A-L) may be used to facilitate delivery of any of the implants (e.g., any of the prosthetic valves and/or prosthetic valve supports) described hereinabove, mutatis mutandis; and (7) any of the techniques and apparatus described hereinabove (e.g., those described with reference to FIGS. 9A-F, 25A-E, 27A-D, and 68A-69E), for retrieval of a prosthetic valve or prosthetic valve support, may be used in combination with (e.g., may be used to retrieve) any of the prosthetic valves and/or prosthetic valve supports described hereinabove, mutatis mutandis.

Reference is again made to FIGS. 1A-80. It is to be noted that for some applications of the present invention that comprise tissue-engaging elements 62, movement of tissue-engaging elements 62 from their constrained configuration to their unconstrained configuration during deployment, comprises movement of over 180 degrees. For some applications, tissue-engaging elements, comprising valve-anchoring elements, move from a constrained configuration distal to the primary structural element of the prosthetic valve, to an unconstrained configuration wherein a portion of each valve-anchoring element is disposed inside the generally-cylindrical structure of the primary structural element of the prosthetic valve (e.g., valve-anchoring elements protrude through voids defined by the lattice structure of the primary structural element).

Reference is again made to FIGS. 1A-80. For some applications of the invention, apparatus such as the prosthetic valves and/or prosthetic valve supports described hereinabove (e.g., the primary structural elements, upstream support portions, and tissue-engaging elements thereof), are covered at least in part with a covering. The covering may comprise polyethylene terephthalate (e.g., polyester), polytetrafluoroethylene (e.g., Teflon, ePTFE), a fabric, and/or or pericardial tissue. Typically, a thickness of the covering is less than 0.2 mm, e.g., less than 0.1 mm, or less than 0.05 mm. The covering may be selected according to requirements. For example, for some applications, a surface of the apparatus that is placed in contact with the native valve is covered; the covering being configured to facilitate coupling of the prosthetic valve support to the native valve, by enhancing tissue growth at the interface between the prosthetic valve support and the native valve. Conversely, for some applications, the covering may be configured to inhibit tissue growth thereon. For some applications, a surface of the apparatus is covered with the covering so as to inhibit (e.g., prevent) leakage of blood between the prosthetic valve and the native valve, and/or between the prosthetic valve and the prosthetic valve support.

For some applications, the prosthetic valve support (e.g., the upstream support portion thereof) is not covered with the covering, and is configured to allow flow of blood therethrough. For example, the prosthetic valve support may be configured to allow flow of blood through the interface between the valve support and the prosthetic valve, in order to accommodate antegrade flow of blood between the subject's atrium and the subject's ventricle that is greater than can be accommodated by blood flowing through the prosthetic valve alone. For some such application of the invention, the prosthetic valve support is not covered with the covering and is configured to support prosthetic valve, such that the leaflets of the native valve (1) move in response to the beating of the heart, (2) coapt with each other and/or with the primary structural element of the prosthetic valve, and (3) inhibit (e.g., prevent) retrograde flow of blood through the prosthetic valve support.

Reference is yet again made to FIGS. 1A-80. It is to be noted that although some apparatus and methods are described herein to replace a native heart valve (e.g., a native mitral valve) of the subject, apparatus (and subcomponents thereof) and methods described herein may also be used at any other site in the body of the subject. For example, delivery apparatus and/or locks described herein may be used to facilitate implantation and/or adjustment of any suitable implant at a given implantation site of a body of the subject, e.g., the stomach.

Reference is made to FIGS. 1A-80. It is to be noted that for some applications of the present invention, medical device 150 comprises an implant that comprises a prosthetic valve support and a prosthetic valve. For other applications, medical device 150 comprises a prosthetic valve support. For yet other applications, medical device 150 comprises a prosthetic valve.

Reference is again made to FIGS. 1A-80. It is to be noted that at least some of the tissue-engaging elements that are described herein as adjustable (e.g., length-adjustable), may be adjusted prior to implantation, during the implantation procedure, or following implantation.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
advancing, toward a native heart valve of a heart of a patient, apparatus comprising:
(a) a core
(1) having a central longitudinal axis,
(2) having a first portion having a first perimeter in a first transverse plane to the central longitudinal axis,
(3) having a second portion having a second perimeter in a second transverse plane to the central longitudinal axis that is distal to the first transverse plane, the second perimeter being a smallest perimeter of the core, and
(4) tapering in a distal direction from the first portion to the second portion of the core;
(b) first and second ventricular arms; and
(c) first and second atrial arms, wherein:
the first ventricular arm is articulatable with respect to the first atrial arm at a first articulation site,
the second ventricular arm is articulatable with respect to the second atrial arm at a second articulation site,
the first and second articulation sites are adjacent to the smallest perimeter of the core, and
the tapering of the core defines a minimum nonzero angle of the first and second atrial arms with respect to the central longitudinal axis; and
subsequently to the advancing, clamping (i) a first native leaflet of the native heart valve between the first atrial arm and the first ventricular arm and (ii) a second native leaflet of the native heart valve between the second atrial arm and the second ventricular arm.

2. The method according to claim 1, wherein:
the core is shaped so as to define a conduit therethrough, and
the method further comprises controlling the first and second ventricular arms using an elongate controller that is slidably disposed within the conduit.

3. The method according to claim 1, wherein the step of clamping comprises forming the first and second native leaflets into a generally lemniscate arrangement.

4. The method according to claim 1, wherein the tapering of the core is such that: (i) the first articulation site is disposed closer to the central longitudinal axis of the core than a terminal end of the first atrial arm is to the central longitudinal axis of the core, and (ii) the second articulation site is disposed closer to the central longitudinal axis of the core than a terminal end of the second atrial arm is to the central longitudinal axis of the core.

5. The method according to claim 1, wherein the first atrial arm, the first ventricular arm, the second atrial arm, and the second ventricular arm are configured to allow the first and second native leaflets to function following the clamping, and wherein the step of clamping is performed in a manner that allows the first and second native leaflets to function following the clamping.

6. The method according to claim 1, wherein the step of clamping does not eliminate native blood flow regulation functionality of the native heart valve.

7. The method according to claim 1, further comprising, (i) subsequently to the advancing and (ii) prior to the step of clamping, moving the first and second ventricular arms with respect to the central longitudinal axis.

8. The method according to claim 7, wherein moving the first and second ventricular arms comprises:
articulating the first ventricular arm with respect to the first atrial arm; and
articulating the second ventricular arm with respect to the second atrial arm.

9. The method according to claim 7, wherein moving the first and second ventricular arms comprises moving the first and second ventricular arms while the first and second atrial arms are held in place.

10. The method according to claim 7, wherein moving the first and second ventricular arms comprises operating the first and second ventricular arms simultaneously.

11. The method according to claim 7, wherein moving the first and second ventricular arms comprises:
applying a distally-directed pulling force to the first ventricular arm from below the first ventricular arm; and
applying a distally-directed pulling force to the second ventricular arm from below the second ventricular arm.

12. The method according to claim 7, further comprising, (i) subsequently to the moving of the first and second ventricular arms and (ii) prior to the step of clamping, positioning the core between first and second native leaflets of the native heart valve such that:
the first atrial arm faces an atrial surface of the first native leaflet,
the first ventricular arm faces a ventricular surface of the first native leaflet,
the second atrial arm faces an atrial surface of the second native leaflet, and
the second ventricular arm-faces a ventricular surface of the second native leaflet.

13. The method according to claim 12, wherein positioning the core between the first and second native leaflets comprises positioning the core such that:
a proximal end portion of the core is disposed at an atrial side of the native heart valve, and
a distal end portion of the core is disposed at a ventricular side of the native heart valve.

14. The method according to claim 7, wherein moving the first and second ventricular arms with respect to the central longitudinal axis comprises moving the first and second ventricular arms with respect to the central longitudinal axis while the first and second ventricular arms, the first and second atrial arms, and a distal end of the core are disposed in an atrium of the heart.

15. The method according to claim 14, further comprising, subsequently to the moving:
advancing at least the first and second ventricular arms and the distal end of the core below respective ventricular surfaces of the first and second native leaflets; and
raising the first and second ventricular arms toward the central longitudinal axis.

16. The method according to claim 7, wherein the apparatus comprises a ventricular section that is distal to the second portion of the core, and wherein moving the first and second ventricular arms comprises moving the first and second ventricular arms via the ventricular section.

17. The method according to claim 16, wherein:
the core is shaped so as to define a conduit therethrough, and
the method further comprises controlling the first and second ventricular arms using an elongate controller that is slidably disposed within the conduit and passes through an opening in the ventricular section.

18. The method according to claim 16, wherein the ventricular section is wider than the second portion of the core.

* * * * *